US012384842B2

(12) United States Patent
Loew et al.

(10) Patent No.: US 12,384,842 B2
(45) Date of Patent: *Aug. 12, 2025

(54) ANTIBODY MOLECULES THAT BIND TO NKP30 AND USES THEREOF

(71) Applicant: Marengo Therapeutics, Inc., Cambridge, MA (US)

(72) Inventors: Andreas Loew, Boston, MA (US); Nidhi Malhotra, Boston, MA (US); Madan Katragadda, Acton, MA (US); Brian Edward Vash, Cambridge, MA (US); Stephanie J. Maiocco, Arlington, MA (US)

(73) Assignee: Marengo Therapeutics, Inc., Cambridge, MA (US)

( * ) Notice: Subject to any disclaimer, the term of this patent is extended or adjusted under 35 U.S.C. 154(b) by 1035 days.

This patent is subject to a terminal disclaimer.

(21) Appl. No.: 17/402,320

(22) Filed: Aug. 13, 2021

(65) Prior Publication Data
US 2021/0371523 A1 Dec. 2, 2021

Related U.S. Application Data

(63) Continuation of application No. PCT/US2020/019329, filed on Feb. 21, 2020.

(60) Provisional application No. 62/808,582, filed on Feb. 21, 2019.

(51) Int. Cl.
C07K 16/28 (2006.01)
A61K 39/395 (2006.01)
A61K 45/06 (2006.01)

(52) U.S. Cl.
CPC ...... C07K 16/2803 (2013.01); A61K 39/3955 (2013.01); C07K 2317/24 (2013.01); C07K 2317/31 (2013.01); C07K 2317/52 (2013.01); C07K 2317/565 (2013.01)

(58) Field of Classification Search
CPC ............ C07K 16/2803; C07K 2317/24; C07K 2317/31; C07K 2317/52; C07K 2317/565; C07K 2317/74; A61K 39/3955; A61K 45/06; A61P 31/00; A61P 35/00; A61P 37/00
See application file for complete search history.

(56) References Cited

U.S. PATENT DOCUMENTS

| | | |
|---|---|---|
| 861,745 A | 7/1907 | Maxwell |
| 4,433,059 A | 2/1984 | Chang et al. |
| 4,439,196 A | 3/1984 | Higuchi |
| 4,444,878 A | 4/1984 | Paulus |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,676,980 A | 6/1987 | Segal et al. |
| 4,737,456 A | 4/1988 | Weng et al. |
| 4,790,824 A | 12/1988 | Morrow et al. |
| 4,816,567 A | 3/1989 | Cabilly et al. |
| 4,941,880 A | 7/1990 | Burns |
| 5,057,423 A | 10/1991 | Hiserodt et al. |
| 5,064,413 A | 11/1991 | McKinnon et al. |
| 5,116,615 A | 5/1992 | Gokcen et al. |
| 5,208,020 A | 5/1993 | Chari et al. |
| 5,223,409 A | 6/1993 | Ladner et al. |
| 5,225,539 A | 7/1993 | Winter |
| 5,273,743 A | 12/1993 | Ahlem et al. |
| 5,312,335 A | 5/1994 | McKinnon et al. |
| 5,374,548 A | 12/1994 | Caras |
| 5,383,851 A | 1/1995 | McKinnon, Jr. et al. |
| 5,391,377 A | 2/1995 | Barnwell |
| 5,399,163 A | 3/1995 | Peterson et al. |
| 5,399,331 A | 3/1995 | Loughrey et al. |
| 5,416,016 A | 5/1995 | Low et al. |
| 5,416,064 A | 5/1995 | Chari et al. |
| 5,500,362 A | 3/1996 | Robinson et al. |
| 5,534,254 A | 7/1996 | Huston et al. |
| 5,571,894 A | 11/1996 | Wels et al. |
| 5,582,996 A | 12/1996 | Curtis |
| 5,585,089 A | 12/1996 | Queen et al. |
| 5,587,458 A | 12/1996 | King et al. |
| 5,591,828 A | 1/1997 | Bosslet et al. |
| 5,624,821 A | 4/1997 | Winter et al. |
| 5,626,561 A | 5/1997 | Butler et al. |
| 5,635,483 A | 6/1997 | Pettit et al. |

(Continued)

FOREIGN PATENT DOCUMENTS

| | | |
|---|---|---|
| AU | 2001278662 B2 | 9/2006 |
| CA | 3016563 A1 | 9/2017 |

(Continued)

OTHER PUBLICATIONS

Almagro et al., Front. Immunol. 2018; 8:1751 (Year: 2018).*
Chiu ML et al. Antibodies 2019 8, 55, 1-80 (Year: 2019).*
Adachi, Osamu, et al., Targeted Disruption of the MyD88 Gene Results in Loss of IL-1-and IL-8-Mediated Function. Immunity 9(1):143-150 (1998).
Agostinis, Patrizia, et al., Photodynamic Therapy of Cancer: An Update. Ca: A Cancer Journal for Clinicians 61(4):250-281 (2011).
Aigner et al.: An effective tumor vaccine optimized for costimulation via bispecific and trispecific fusion proteins. Int J Oncol. 32(4):777-789 (2008).

(Continued)

Primary Examiner — Janet L Epps-Smith
Assistant Examiner — Kathleen Cunningchen
(74) Attorney, Agent, or Firm — Wilson Sonsini Goodrich & Rosati

(57) ABSTRACT

Antibody molecules that specifically bind to NKp30 are disclosed. The anti-NKp30 antibody molecules can be used to treat, prevent and/or diagnose cancerous, autoimmune or infectious conditions and disorders.

23 Claims, 2 Drawing Sheets
Specification includes a Sequence Listing.

(56) References Cited

U.S. PATENT DOCUMENTS

| | | |
|---|---|---|
| 5,635,602 A | 6/1997 | Cantor et al. |
| 5,637,481 A | 6/1997 | Ledbetter et al. |
| 5,641,870 A | 6/1997 | Rinderknecht et al. |
| 5,648,237 A | 7/1997 | Carter |
| 5,648,260 A | 7/1997 | Winter et al. |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,731,116 A | 3/1998 | Matsuo et al. |
| 5,731,168 A | 3/1998 | Carter et al. |
| 5,739,116 A | 4/1998 | Hamann et al. |
| 5,747,036 A | 5/1998 | Brenner et al. |
| 5,750,373 A | 5/1998 | Garrard et al. |
| 5,766,947 A | 6/1998 | Rittershaus et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,787,900 A | 8/1998 | Butler et al. |
| 5,789,199 A | 8/1998 | Joly et al. |
| 5,811,097 A | 9/1998 | Allison et al. |
| 5,821,337 A | 10/1998 | Carter et al. |
| 5,831,012 A | 11/1998 | Nilsson et al. |
| 5,837,242 A | 11/1998 | Holliger et al. |
| 5,837,821 A | 11/1998 | Wu |
| 5,840,523 A | 11/1998 | Simmons et al. |
| 5,843,069 A | 12/1998 | Butler et al. |
| 5,844,094 A | 12/1998 | Hudson et al. |
| 5,849,500 A | 12/1998 | Breitling et al. |
| 5,849,589 A | 12/1998 | Tedder et al. |
| 5,861,155 A | 1/1999 | Lin |
| 5,864,019 A | 1/1999 | King et al. |
| 5,869,046 A | 2/1999 | Presta et al. |
| 5,869,620 A | 2/1999 | Whitlow et al. |
| 5,877,296 A | 3/1999 | Hamann et al. |
| 5,902,745 A | 5/1999 | Butler et al. |
| 5,910,573 A | 6/1999 | Pluckthun et al. |
| 5,913,998 A | 6/1999 | Butler et al. |
| 5,932,448 A | 8/1999 | Tso et al. |
| 5,959,083 A | 9/1999 | Bosslet et al. |
| 5,959,177 A | 9/1999 | Hein et al. |
| 5,968,753 A | 10/1999 | Tseng-Law et al. |
| 5,980,889 A | 11/1999 | Butler et al. |
| 5,989,830 A | 11/1999 | Davis et al. |
| 6,005,079 A | 12/1999 | Casterman et al. |
| 6,040,498 A | 3/2000 | Stomp et al. |
| 6,075,181 A | 6/2000 | Kucherlapati et al. |
| 6,120,766 A | 9/2000 | Hale et al. |
| 6,150,584 A | 11/2000 | Kucherlapati et al. |
| 6,171,586 B1 | 1/2001 | Lam et al. |
| 6,171,799 B1 | 1/2001 | Skibbens et al. |
| 6,172,197 B1 | 1/2001 | McCafferty et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,291,158 B1 | 9/2001 | Winter et al. |
| 6,294,353 B1 | 9/2001 | Pack et al. |
| 6,333,396 B1 | 12/2001 | Filpula et al. |
| 6,352,694 B1 | 3/2002 | June et al. |
| 6,417,429 B1 | 7/2002 | Hein et al. |
| 6,420,548 B1 | 7/2002 | Vezina et al. |
| 6,476,198 B1 | 11/2002 | Kang |
| 6,511,663 B1 | 1/2003 | King et al. |
| 6,534,055 B1 | 3/2003 | June et al. |
| 6,582,915 B1 | 6/2003 | Griffiths et al. |
| 6,593,081 B1 | 7/2003 | Griffiths et al. |
| 6,602,684 B1 | 8/2003 | Umana et al. |
| 6,630,579 B2 | 10/2003 | Chari et al. |
| 6,632,427 B1 | 10/2003 | Finiels et al. |
| 6,670,453 B2 | 12/2003 | Frenken et al. |
| 6,696,245 B2 | 2/2004 | Winter et al. |
| 6,703,199 B1 | 3/2004 | Koide |
| 6,737,056 B1 | 5/2004 | Presta |
| 6,743,896 B2 | 6/2004 | Filpula et al. |
| 6,756,523 B1 | 6/2004 | Kahn et al. |
| 6,765,087 B1 | 7/2004 | Casterman et al. |
| 6,809,185 B1 | 10/2004 | Schoonjans et al. |
| 6,818,418 B1 | 11/2004 | Lipovsek et al. |
| 6,833,441 B2 | 12/2004 | Wang et al. |
| 6,838,254 B1 | 1/2005 | Hamers et al. |
| 6,905,680 B2 | 6/2005 | June et al. |
| 6,979,546 B2 | 12/2005 | Moretta et al. |
| 6,982,321 B2 | 1/2006 | Winter |
| 7,041,870 B2 | 5/2006 | Tomizuka et al. |
| 7,083,785 B2 | 8/2006 | Browning et al. |
| 7,087,409 B2 | 8/2006 | Barbas, III et al. |
| 7,105,149 B1 | 9/2006 | Dalla-Favera |
| 7,125,978 B1 | 10/2006 | Vezina et al. |
| 7,129,330 B1 | 10/2006 | Little et al. |
| 7,183,076 B2 | 2/2007 | Arathoon et al. |
| 7,186,804 B2 | 3/2007 | Gillies et al. |
| 7,189,826 B2 | 3/2007 | Rodman |
| 7,250,297 B1 | 7/2007 | Beste et al. |
| 7,276,241 B2 | 10/2007 | Schneider et al. |
| 7,332,581 B2 | 2/2008 | Presta |
| 7,361,360 B2 | 4/2008 | Kitabwalla et al. |
| 7,371,826 B2 | 5/2008 | Presta |
| 7,402,314 B2 | 7/2008 | Sherman |
| 7,431,380 B1 | 10/2008 | Buresh |
| 7,476,724 B2 | 1/2009 | Dennis et al. |
| 7,498,298 B2 | 3/2009 | Doronina et al. |
| 7,501,121 B2 | 3/2009 | Tchistiakova et al. |
| 7,517,966 B2 | 4/2009 | Moretta et al. |
| 7,521,056 B2 | 4/2009 | Chang et al. |
| 7,521,541 B2 | 4/2009 | Eigenbrot et al. |
| 7,527,787 B2 | 5/2009 | Chang et al. |
| 7,527,791 B2 | 5/2009 | Adams et al. |
| 7,534,866 B2 | 5/2009 | Chang et al. |
| 7,563,441 B2 | 7/2009 | Graus et al. |
| 7,601,803 B1 | 10/2009 | Fiedler et al. |
| 7,612,181 B2 | 11/2009 | Wu et al. |
| 7,642,228 B2 | 1/2010 | Carter et al. |
| 7,700,739 B2 | 4/2010 | Lacy et al. |
| 7,741,446 B2 | 6/2010 | Pardridge et al. |
| 7,750,128 B2 | 7/2010 | Gegg et al. |
| 7,767,429 B2 | 8/2010 | Bookbinder et al. |
| 7,799,902 B2 | 9/2010 | Browning et al. |
| 7,803,376 B2 | 9/2010 | Velardi et al. |
| 7,807,160 B2 | 10/2010 | Presta et al. |
| 7,829,289 B2 | 11/2010 | Lantz et al. |
| 7,855,275 B2 | 12/2010 | Eigenbrot et al. |
| 7,858,759 B2 | 12/2010 | Brandt et al. |
| 7,906,118 B2 | 3/2011 | Chang et al. |
| 7,919,257 B2 | 4/2011 | Hoogenboom et al. |
| 7,943,743 B2 | 5/2011 | Korman et al. |
| 7,999,077 B2 | 8/2011 | Pastan et al. |
| 8,003,774 B2 | 8/2011 | Stavenhagen et al. |
| 8,008,449 B2 | 8/2011 | Korman et al. |
| 8,012,465 B2 | 9/2011 | Elias et al. |
| 8,034,326 B2 | 10/2011 | Hjorth et al. |
| 8,202,517 B2 | 6/2012 | Bookbinder et al. |
| 8,216,805 B2 | 7/2012 | Carter et al. |
| 8,227,577 B2 | 7/2012 | Klein et al. |
| 8,299,220 B2 | 10/2012 | Dalla-Favera |
| 8,354,509 B2 | 1/2013 | Carven et al. |
| 8,362,213 B2 | 1/2013 | Elkins et al. |
| 8,450,470 B2 | 5/2013 | Bookbinder et al. |
| 8,466,260 B2 | 6/2013 | Elkins et al. |
| 8,552,156 B2 | 10/2013 | Takayanagi et al. |
| 8,580,252 B2 | 11/2013 | Bookbinder et al. |
| 8,586,713 B2 | 11/2013 | Davis et al. |
| 8,592,562 B2 | 11/2013 | Kannan et al. |
| 8,609,089 B2 | 12/2013 | Langermann et al. |
| 8,617,545 B2 | 12/2013 | Hsu et al. |
| 8,617,559 B2 | 12/2013 | Elkins et al. |
| 8,658,135 B2 | 2/2014 | O'Connor-McCourt et al. |
| 8,703,132 B2 | 4/2014 | Imhof-Jung et al. |
| 8,772,246 B2 | 7/2014 | Bookbinder et al. |
| 8,790,895 B2 | 7/2014 | Fiedler et al. |
| 8,821,883 B2 | 9/2014 | Ambrose et al. |

(56) References Cited

U.S. PATENT DOCUMENTS

| | | |
|---|---|---|
| 8,846,042 B2 | 9/2014 | Zhou |
| 8,871,912 B2 | 10/2014 | Davis et al. |
| 8,920,776 B2 | 12/2014 | Gaiger et al. |
| 8,945,571 B2 | 2/2015 | Mössner et al. |
| 8,993,524 B2 | 3/2015 | Bedi et al. |
| 9,000,130 B2 | 4/2015 | Bhakta et al. |
| 9,034,324 B2 | 5/2015 | Kalled et al. |
| 9,056,905 B2 | 6/2015 | Olson et al. |
| 9,145,588 B2 | 9/2015 | Throsby et al. |
| 9,200,060 B2 | 12/2015 | Kannan et al. |
| 9,243,058 B2 | 1/2016 | Armitage et al. |
| 9,309,311 B2 | 4/2016 | Gurney et al. |
| 9,340,621 B2 | 5/2016 | Kufer et al. |
| 9,358,286 B2 | 6/2016 | De et al. |
| 9,359,437 B2 | 6/2016 | Davis et al. |
| 9,382,323 B2 | 7/2016 | Brinkmann et al. |
| 9,387,237 B2 | 7/2016 | Kalled et al. |
| 9,416,187 B2 | 8/2016 | Tedder et al. |
| 9,447,159 B2 | 9/2016 | Ast et al. |
| 9,447,185 B2 | 9/2016 | Romagne et al. |
| 9,545,086 B2 | 1/2017 | Mackay et al. |
| 9,593,376 B2 | 3/2017 | Zitvogel et al. |
| 9,663,577 B2 | 5/2017 | Pierres et al. |
| 9,676,863 B2 | 6/2017 | Lo |
| 9,833,476 B2 | 12/2017 | Zhang et al. |
| 10,150,816 B2 | 12/2018 | Abbot et al. |
| 10,294,300 B2 | 5/2019 | Raum et al. |
| 10,308,721 B2 | 6/2019 | Williams et al. |
| 10,478,509 B2 | 11/2019 | Torgov et al. |
| 10,610,571 B2 | 4/2020 | Ptacin et al. |
| 10,676,516 B2 | 6/2020 | Viney et al. |
| 10,730,942 B2 | 8/2020 | Pule et al. |
| 10,815,311 B2 | 10/2020 | Wesche et al. |
| 11,033,634 B2 | 6/2021 | Stull et al. |
| 11,291,721 B2 | 4/2022 | Loew et al. |
| 11,292,838 B2 | 4/2022 | Schendel et al. |
| 11,673,953 B2 | 6/2023 | Zhang et al. |
| 11,692,031 B2 | 7/2023 | Dahlhoff et al. |
| 11,845,797 B2 | 12/2023 | Tan et al. |
| 11,965,025 B2 | 4/2024 | Tan et al. |
| 12,152,073 B2 | 11/2024 | Loew et al. |
| 2002/0004587 A1 | 1/2002 | Miller et al. |
| 2002/0041865 A1 | 4/2002 | Austin et al. |
| 2002/0062010 A1 | 5/2002 | Arathoon et al. |
| 2002/0076406 A1 | 6/2002 | Leung |
| 2002/0103345 A1 | 8/2002 | Zhu |
| 2002/0164328 A1 | 11/2002 | Shinkawa et al. |
| 2003/0099647 A1 * | 5/2003 | Deshpande .......... C07K 16/249 530/388.25 |
| 2003/0115614 A1 | 6/2003 | Kanda et al. |
| 2003/0130496 A1 | 7/2003 | Winter et al. |
| 2003/0157108 A1 | 8/2003 | Presta |
| 2003/0175884 A1 | 9/2003 | Umana et al. |
| 2003/0207346 A1 | 11/2003 | Arathoon et al. |
| 2003/0211078 A1 | 11/2003 | Heavner |
| 2004/0009530 A1 | 1/2004 | Wilson et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0175756 A1 | 9/2004 | Kolkman et al. |
| 2004/0219643 A1 | 11/2004 | Winter et al. |
| 2004/0220388 A1 | 11/2004 | Mertens et al. |
| 2004/0241817 A1 | 12/2004 | Umana et al. |
| 2004/0242847 A1 | 12/2004 | Fukushima et al. |
| 2005/0003403 A1 | 1/2005 | Rossi et al. |
| 2005/0004352 A1 | 1/2005 | Kontermann et al. |
| 2005/0014934 A1 | 1/2005 | Hinton et al. |
| 2005/0048512 A1 | 3/2005 | Kolkman et al. |
| 2005/0053973 A1 | 3/2005 | Kolkman et al. |
| 2005/0069552 A1 | 3/2005 | Bleck et al. |
| 2005/0079170 A1 | 4/2005 | Le Gall et al. |
| 2005/0079574 A1 | 4/2005 | Bond |
| 2005/0090648 A1 | 4/2005 | Tsurushita et al. |
| 2005/0100543 A1 | 5/2005 | Hansen et al. |
| 2005/0119455 A1 | 6/2005 | Fuh et al. |
| 2005/0123546 A1 | 6/2005 | Umana et al. |
| 2005/0136049 A1 | 6/2005 | Ledbetter et al. |
| 2005/0136051 A1 | 6/2005 | Scallon |
| 2005/0163782 A1 | 7/2005 | Glaser et al. |
| 2005/0260186 A1 | 11/2005 | Bookbinder et al. |
| 2005/0266000 A1 | 12/2005 | Bond et al. |
| 2005/0266425 A1 | 12/2005 | Zauderer et al. |
| 2006/0008844 A1 | 1/2006 | Stemmer et al. |
| 2006/0025576 A1 | 2/2006 | Miller et al. |
| 2006/0083747 A1 | 4/2006 | Winter et al. |
| 2006/0104968 A1 | 5/2006 | Bookbinder et al. |
| 2006/0120960 A1 | 6/2006 | Deyev et al. |
| 2006/0141581 A1 | 6/2006 | Gillies et al. |
| 2006/0204493 A1 | 9/2006 | Huang et al. |
| 2006/0263367 A1 | 11/2006 | Fey et al. |
| 2007/0004909 A1 | 1/2007 | Johnson et al. |
| 2007/0036783 A1 | 2/2007 | Humeau et al. |
| 2007/0061900 A1 | 3/2007 | Murphy et al. |
| 2007/0087381 A1 | 4/2007 | Kojima |
| 2007/0105105 A1 | 5/2007 | Clelland et al. |
| 2007/0117126 A1 | 5/2007 | Sidhu et al. |
| 2007/0128150 A1 | 6/2007 | Norman |
| 2007/0141049 A1 | 6/2007 | Bredehorst et al. |
| 2007/0154901 A1 | 7/2007 | Thogersen et al. |
| 2007/0160598 A1 | 7/2007 | Dennis et al. |
| 2007/0178106 A1 | 8/2007 | Romagne |
| 2007/0184052 A1 | 8/2007 | Lin et al. |
| 2007/0231322 A1 | 10/2007 | Romagne et al. |
| 2007/0237764 A1 | 10/2007 | Birtalan et al. |
| 2007/0274985 A1 | 11/2007 | Dubel et al. |
| 2007/0292936 A1 | 12/2007 | Barthelemy et al. |
| 2008/0050370 A1 | 2/2008 | Glaser et al. |
| 2008/0063717 A1 | 3/2008 | Romagne et al. |
| 2008/0069820 A1 | 3/2008 | Fuh et al. |
| 2008/0152645 A1 | 6/2008 | Pardridge et al. |
| 2008/0171855 A1 | 7/2008 | Rossi et al. |
| 2008/0241884 A1 | 10/2008 | Shitara et al. |
| 2008/0247944 A1 | 10/2008 | Graziano et al. |
| 2008/0254512 A1 | 10/2008 | Capon |
| 2008/0260738 A1 | 10/2008 | Moore et al. |
| 2008/0299137 A1 | 12/2008 | Svendsen et al. |
| 2009/0002360 A1 | 1/2009 | Chen et al. |
| 2009/0010843 A1 | 1/2009 | Spee et al. |
| 2009/0130106 A1 | 5/2009 | Christopherson et al. |
| 2009/0148905 A1 | 6/2009 | Ashman et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0175867 A1 | 7/2009 | Thompson et al. |
| 2009/0214533 A1 | 8/2009 | Clynes |
| 2009/0232811 A1 | 9/2009 | Klein et al. |
| 2009/0234105 A1 | 9/2009 | Gervay-Hague et al. |
| 2009/0263392 A1 | 10/2009 | Igawa et al. |
| 2009/0274649 A1 | 11/2009 | Qu et al. |
| 2009/0280116 A1 | 11/2009 | Smith et al. |
| 2009/0324538 A1 | 12/2009 | Wong et al. |
| 2010/0015133 A1 | 1/2010 | Igawa et al. |
| 2010/0015153 A1 | 1/2010 | Moretta et al. |
| 2010/0028330 A1 | 2/2010 | Collins et al. |
| 2010/0047169 A1 | 2/2010 | Mandelboim et al. |
| 2010/0168393 A1 | 7/2010 | Clube et al. |
| 2010/0260704 A1 | 10/2010 | Berenguer et al. |
| 2010/0316645 A1 | 12/2010 | Imhof-Jung et al. |
| 2011/0014659 A1 | 1/2011 | Balazs et al. |
| 2011/0054151 A1 | 3/2011 | Lazar et al. |
| 2011/0091372 A1 | 4/2011 | Ghayur et al. |
| 2011/0150892 A1 | 6/2011 | Thudium et al. |
| 2011/0177073 A1 | 7/2011 | Van Berkel et al. |
| 2011/0177093 A1 | 7/2011 | Kalled et al. |
| 2011/0250170 A1 | 10/2011 | Pedretti et al. |
| 2011/0287056 A1 | 11/2011 | Gu et al. |
| 2011/0293613 A1 | 12/2011 | Brinkmann et al. |
| 2012/0034221 A1 | 2/2012 | Bonvini et al. |
| 2012/0039906 A1 | 2/2012 | Olive |
| 2012/0114649 A1 | 5/2012 | Langermann et al. |
| 2012/0149876 A1 | 6/2012 | Von Kreudenstein et al. |

(56) References Cited

U.S. PATENT DOCUMENTS

| | | |
|---|---|---|
| 2012/0184716 A1 | 7/2012 | Fischer et al. |
| 2012/0201746 A1 | 8/2012 | Liu et al. |
| 2012/0213768 A1 | 8/2012 | Oh et al. |
| 2012/0294857 A1 | 11/2012 | Sentman et al. |
| 2013/0017200 A1 | 1/2013 | Scheer et al. |
| 2013/0022601 A1 | 1/2013 | Brinkmann et al. |
| 2013/0078249 A1 | 3/2013 | Ast et al. |
| 2013/0129723 A1 | 5/2013 | Blankenship et al. |
| 2013/0164293 A1 | 6/2013 | Florio et al. |
| 2013/0165638 A1 | 6/2013 | Hsu et al. |
| 2013/0178605 A1 | 7/2013 | Blein et al. |
| 2013/0195849 A1 | 8/2013 | Spreter Von Kreudenstein et al. |
| 2013/0243775 A1 | 9/2013 | Papadopoulos et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0273089 A1 | 10/2013 | Getts et al. |
| 2013/0280208 A1 | 10/2013 | Stepkowski et al. |
| 2013/0303396 A1 | 11/2013 | Igawa et al. |
| 2013/0317200 A1 | 11/2013 | Elson et al. |
| 2014/0037621 A1 | 2/2014 | Tsurushita et al. |
| 2014/0044728 A1 | 2/2014 | Takayanagi et al. |
| 2014/0051833 A1 | 2/2014 | Fischer et al. |
| 2014/0051835 A1 | 2/2014 | Dixit et al. |
| 2014/0072528 A1 | 3/2014 | Gerdes et al. |
| 2014/0072581 A1 | 3/2014 | Dixit et al. |
| 2014/0079689 A1 | 3/2014 | Elliott et al. |
| 2014/0079691 A1 | 3/2014 | McConnell et al. |
| 2014/0099254 A1 | 4/2014 | Chang et al. |
| 2014/0154254 A1 | 6/2014 | Kannan et al. |
| 2014/0199294 A1 | 7/2014 | Mimoto et al. |
| 2014/0200331 A1 | 7/2014 | Corper et al. |
| 2014/0227265 A1 | 8/2014 | Wu et al. |
| 2014/0242075 A1 | 8/2014 | Parren et al. |
| 2014/0242077 A1 | 8/2014 | Choi et al. |
| 2014/0256916 A1 | 9/2014 | Kruip et al. |
| 2014/0308285 A1 | 10/2014 | Yan et al. |
| 2014/0322212 A1 | 10/2014 | Brogdon et al. |
| 2014/0322221 A1 | 10/2014 | Miller et al. |
| 2014/0348839 A1 | 11/2014 | Chowdhury et al. |
| 2014/0363426 A1 | 12/2014 | Moore et al. |
| 2014/0377269 A1 | 12/2014 | Mabry et al. |
| 2015/0017187 A1 | 1/2015 | Thanos et al. |
| 2015/0018529 A1 | 1/2015 | Humphreys et al. |
| 2015/0056199 A1 | 2/2015 | Kumar et al. |
| 2015/0098900 A1 | 4/2015 | Ebens et al. |
| 2015/0133638 A1 | 5/2015 | Wranik et al. |
| 2015/0166661 A1 | 6/2015 | Chen et al. |
| 2015/0166670 A1 | 6/2015 | Castoldi et al. |
| 2015/0175707 A1 | 6/2015 | De Jong et al. |
| 2015/0203591 A1 | 7/2015 | Yancopoulos et al. |
| 2015/0211001 A1 | 7/2015 | Ohrn et al. |
| 2015/0218260 A1 | 8/2015 | Klein et al. |
| 2015/0232560 A1 | 8/2015 | Heindl et al. |
| 2015/0315296 A1 | 11/2015 | Schaefer et al. |
| 2015/0337049 A1 | 11/2015 | Labrijn et al. |
| 2015/0344570 A1 | 12/2015 | Igawa et al. |
| 2015/0353636 A1 | 12/2015 | Parren et al. |
| 2015/0368351 A1 | 12/2015 | Vu et al. |
| 2015/0368352 A1 | 12/2015 | Liu |
| 2015/0376287 A1 | 12/2015 | Vu et al. |
| 2016/0015749 A1 | 1/2016 | Gottschalk et al. |
| 2016/0039947 A1 | 2/2016 | Demarest et al. |
| 2016/0075785 A1 | 3/2016 | Ast et al. |
| 2016/0102135 A1 | 4/2016 | Escobar-Cabrera |
| 2016/0114057 A1 | 4/2016 | Dixit et al. |
| 2016/0130347 A1 | 5/2016 | Bruenker et al. |
| 2016/0131654 A1 | 5/2016 | Berenson et al. |
| 2016/0145340 A1 | 5/2016 | Borges et al. |
| 2016/0145354 A1 | 5/2016 | Bacac et al. |
| 2016/0176973 A1 | 6/2016 | Kufer et al. |
| 2016/0194389 A1 | 7/2016 | Regula et al. |
| 2016/0229915 A1 | 8/2016 | Igawa et al. |
| 2016/0244523 A1 | 8/2016 | Blank et al. |
| 2016/0257763 A1 | 9/2016 | Von Kreudenstein et al. |
| 2016/0264685 A1 | 9/2016 | Fouque et al. |
| 2016/0297885 A1 | 10/2016 | Kuo et al. |
| 2016/0311915 A1 | 10/2016 | Pulé et al. |
| 2016/0368985 A1 | 12/2016 | Hotzel et al. |
| 2016/0368988 A1 | 12/2016 | Bakker et al. |
| 2017/0022284 A1 | 1/2017 | Timmer et al. |
| 2017/0035905 A1 | 2/2017 | Abrams et al. |
| 2017/0037128 A1 | 2/2017 | Little et al. |
| 2017/0051068 A1 | 2/2017 | Pillarisetti et al. |
| 2017/0066827 A1 | 3/2017 | Pulé et al. |
| 2017/0151281 A1 | 6/2017 | Wagner et al. |
| 2017/0204176 A1 | 7/2017 | Bonvini et al. |
| 2017/0269092 A1 | 9/2017 | Kralovics |
| 2017/0275362 A1 | 9/2017 | Brentjens et al. |
| 2017/0298445 A1 | 10/2017 | Ogg |
| 2017/0334998 A1 | 11/2017 | Pulé et al. |
| 2017/0368169 A1 | 12/2017 | Loew et al. |
| 2018/0153938 A1 | 6/2018 | Keating et al. |
| 2018/0235887 A1 | 8/2018 | Garidel et al. |
| 2018/0256716 A1 | 9/2018 | Schendel et al. |
| 2019/0062448 A1 | 2/2019 | Soros et al. |
| 2019/0209612 A1 | 7/2019 | Pulé et al. |
| 2019/0315883 A1 | 10/2019 | Ast et al. |
| 2019/0322763 A1 | 10/2019 | Ast et al. |
| 2020/0071417 A1 | 3/2020 | Loew et al. |
| 2020/0109195 A1 | 4/2020 | Watkins et al. |
| 2020/0129638 A1 | 4/2020 | Van Berkel et al. |
| 2020/0140549 A1 | 5/2020 | Cordoba et al. |
| 2020/0172591 A1 | 6/2020 | Hosse et al. |
| 2020/0172868 A1 | 6/2020 | Wickham et al. |
| 2020/0200756 A1 | 6/2020 | Pulé et al. |
| 2020/0230208 A1 | 7/2020 | Wang et al. |
| 2020/0277384 A1 | 9/2020 | Chang et al. |
| 2020/0291089 A1 | 9/2020 | Loew et al. |
| 2020/0299349 A1 | 9/2020 | Garcia et al. |
| 2020/0306301 A1 | 10/2020 | Andresen et al. |
| 2020/0308242 A1 | 10/2020 | Lowe et al. |
| 2020/0317787 A1 | 10/2020 | Li et al. |
| 2020/0332003 A1 | 10/2020 | Britanova et al. |
| 2020/0377571 A1 | 12/2020 | Loew et al. |
| 2020/0385472 A1 | 12/2020 | Loew et al. |
| 2021/0009711 A1 | 1/2021 | Loew et al. |
| 2021/0024631 A1 | 1/2021 | Kley et al. |
| 2021/0079114 A1 | 3/2021 | Hudson |
| 2021/0137982 A1 | 5/2021 | Loew et al. |
| 2021/0198369 A1 | 7/2021 | Chang et al. |
| 2021/0221863 A1 | 7/2021 | Kang et al. |
| 2021/0230311 A1 | 7/2021 | Nezu et al. |
| 2021/0238280 A1 | 8/2021 | Loew et al. |
| 2021/0246227 A1 | 8/2021 | Loew et al. |
| 2021/0277119 A1 | 9/2021 | Tan et al. |
| 2021/0363250 A1 | 11/2021 | Kamikawaji et al. |
| 2021/0380670 A1 | 12/2021 | Loew et al. |
| 2021/0380682 A1 | 12/2021 | Loew et al. |
| 2021/0380691 A1 | 12/2021 | Loew et al. |
| 2021/0380692 A1 | 12/2021 | Loew et al. |
| 2021/0380715 A1 | 12/2021 | Yoshida et al. |
| 2022/0064255 A1 | 3/2022 | Loew et al. |
| 2022/0064297 A1 | 3/2022 | Tan et al. |
| 2022/0112286 A1 | 4/2022 | Britanova et al. |
| 2022/0288200 A1 | 9/2022 | Loew et al. |
| 2023/0025484 A1 | 1/2023 | Tan et al. |
| 2023/0031734 A1 | 2/2023 | Tan et al. |
| 2023/0034161 A1 | 2/2023 | Tan et al. |
| 2023/0048244 A1 | 2/2023 | Loew |
| 2023/0102344 A1 | 3/2023 | Katragadda et al. |
| 2023/0127740 A1 | 4/2023 | Tan et al. |
| 2023/0142522 A1 | 5/2023 | Tan et al. |
| 2023/0174650 A1 | 6/2023 | Tan et al. |
| 2023/0192848 A1 | 6/2023 | Loew |
| 2023/0227552 A1 | 7/2023 | Tan et al. |
| 2023/0333112 A1 | 10/2023 | Loew et al. |
| 2023/0348593 A1 | 11/2023 | Loew et al. |
| 2023/0357395 A1 | 11/2023 | Loew et al. |
| 2023/0374133 A1 | 11/2023 | Tan et al. |
| 2024/0002543 A1 | 1/2024 | Loew et al. |

(56) References Cited

U.S. PATENT DOCUMENTS

| | | |
|---|---|---|
| 2024/0076377 A1 | 3/2024 | Tan et al. |
| 2024/0301060 A1 | 9/2024 | Tan et al. |

FOREIGN PATENT DOCUMENTS

| | | |
|---|---|---|
| CA | 3214757 A1 | 10/2022 |
| CN | 101802010 A | 8/2010 |
| CN | 101985476 A | 3/2011 |
| CN | 104203981 A | 12/2014 |
| CN | 104769103 A | 7/2015 |
| CN | 105916876 A | 8/2016 |
| CN | 106103475 A | 11/2016 |
| CN | 106163547 A | 11/2016 |
| CN | 107206024 A | 9/2017 |
| CN | 107903325 A | 4/2018 |
| CN | 108026171 A | 5/2018 |
| CN | 108949698 A | 12/2018 |
| CN | 109153728 A | 1/2019 |
| CN | 114026122 A | 2/2022 |
| DE | 10261223 A1 | 7/2004 |
| EP | 0125023 A1 | 11/1984 |
| EP | 0171496 A2 | 2/1986 |
| EP | 0173494 A2 | 3/1986 |
| EP | 0184187 A2 | 6/1986 |
| EP | 0346087 A2 | 12/1989 |
| EP | 0368684 A1 | 5/1990 |
| EP | 0388151 A1 | 9/1990 |
| EP | 0404097 A2 | 12/1990 |
| EP | 0519596 A1 | 12/1992 |
| EP | 0171496 B1 | 5/1993 |
| EP | 0616640 A1 | 9/1994 |
| EP | 0425235 B1 | 9/1996 |
| EP | 0403156 B1 | 9/1997 |
| EP | 1176195 A1 | 1/2002 |
| EP | 0125023 B2 | 3/2002 |
| EP | 0368684 B2 | 9/2004 |
| EP | 0616640 B1 | 9/2004 |
| EP | 1301605 B1 | 11/2005 |
| EP | 1870459 A1 | 12/2007 |
| EP | 2581113 A1 | 4/2013 |
| EP | 1846020 B1 | 8/2013 |
| EP | 2699259 A1 | 2/2014 |
| EP | 2467165 B1 | 1/2015 |
| EP | 2847231 A1 | 3/2015 |
| EP | 2982694 A1 | 2/2016 |
| EP | 3023437 A1 | 5/2016 |
| EP | 1870459 B1 | 6/2016 |
| EP | 2982694 B1 | 6/2016 |
| EP | 3029068 A1 | 6/2016 |
| EP | 2699259 B1 | 7/2016 |
| EP | 3055329 A1 | 8/2016 |
| EP | 3137500 A1 | 3/2017 |
| EP | 3059246 B1 | 7/2018 |
| EP | 2723380 B1 | 8/2019 |
| EP | 3294768 B1 | 8/2019 |
| EP | 3149031 B1 | 12/2019 |
| EP | 3590967 A1 | 1/2020 |
| EP | 3626739 A1 | 3/2020 |
| EP | 3642228 A1 | 4/2020 |
| EP | 3189132 B1 | 6/2020 |
| EP | 3303392 B1 | 8/2020 |
| EP | 4087871 A1 | 11/2022 |
| GB | 2188638 A | 10/1987 |
| GB | 2599228 A | 3/2022 |
| GB | 2616354 A | 9/2023 |
| JP | H0787994 A | 4/1995 |
| JP | H08502246 A | 3/1996 |
| JP | H09509307 A | 9/1997 |
| JP | 2011524743 A | 9/2011 |
| JP | 2013515509 A | 5/2013 |
| JP | 2014527802 A | 10/2014 |
| JP | 2016512557 A | 4/2016 |
| JP | 6153947 B2 | 6/2017 |
| JP | 2017143838 A | 8/2017 |
| JP | 2018517712 A | 7/2018 |
| JP | 2018531939 A | 11/2018 |
| WO | WO-8500817 A1 | 2/1985 |
| WO | WO-8601533 A1 | 3/1986 |
| WO | WO-8702671 A1 | 5/1987 |
| WO | WO-9002809 A1 | 3/1990 |
| WO | WO-9100906 A1 | 1/1991 |
| WO | WO-9103493 A1 | 3/1991 |
| WO | WO-9110741 A1 | 7/1991 |
| WO | WO-9117271 A1 | 11/1991 |
| WO | WO-9201047 A1 | 1/1992 |
| WO | WO-9203917 A1 | 3/1992 |
| WO | WO-9203918 A1 | 3/1992 |
| WO | WO-9209690 A2 | 6/1992 |
| WO | WO-9215679 A1 | 9/1992 |
| WO | WO-9218619 A1 | 10/1992 |
| WO | WO-9220791 A1 | 11/1992 |
| WO | WO-9209690 A3 | 12/1992 |
| WO | WO-9301161 A1 | 1/1993 |
| WO | WO-9301288 A1 | 1/1993 |
| WO | WO-9308829 A1 | 5/1993 |
| WO | WO-9311161 A1 | 6/1993 |
| WO | WO-9311236 A1 | 6/1993 |
| WO | WO-9323537 A1 | 11/1993 |
| WO | WO-9404678 A1 | 3/1994 |
| WO | WO-9405801 A1 | 3/1994 |
| WO | WO-9409131 A1 | 4/1994 |
| WO | WO-9411026 A2 | 5/1994 |
| WO | WO-9412625 A2 | 6/1994 |
| WO | WO-9425591 A1 | 11/1994 |
| WO | WO-9429351 A2 | 12/1994 |
| WO | WO-9509917 A1 | 4/1995 |
| WO | WO-9516038 A2 | 6/1995 |
| WO | WO-9637621 A2 | 11/1996 |
| WO | WO-9730087 A1 | 8/1997 |
| WO | WO-9814206 A1 | 4/1998 |
| WO | WO-9856915 A2 | 12/1998 |
| WO | WO-9858964 A1 | 12/1998 |
| WO | WO-9904820 A2 | 2/1999 |
| WO | WO-9916873 A1 | 4/1999 |
| WO | WO-9922764 A1 | 5/1999 |
| WO | WO-9945110 A1 | 9/1999 |
| WO | WO-9951642 A1 | 10/1999 |
| WO | WO-9964460 A2 | 12/1999 |
| WO | WO-0006605 A2 | 2/2000 |
| WO | WO-0034784 A1 | 6/2000 |
| WO | WO-0060070 A1 | 10/2000 |
| WO | WO-0061739 A1 | 10/2000 |
| WO | WO-0104144 A2 | 1/2001 |
| WO | WO-0129246 A1 | 4/2001 |
| WO | WO-0136630 A2 | 5/2001 |
| WO | WO-0164942 A1 | 9/2001 |
| WO | WO-0198357 A2 | 12/2001 |
| WO | WO-0231140 A1 | 4/2002 |
| WO | WO-02070647 A2 | 9/2002 |
| WO | WO-02072635 A2 | 9/2002 |
| WO | WO-03002609 A2 | 1/2003 |
| WO | WO-03011878 A2 | 2/2003 |
| WO | WO-03014161 A2 | 2/2003 |
| WO | WO-03056914 A1 | 7/2003 |
| WO | WO-03084570 A1 | 10/2003 |
| WO | WO-03085107 A1 | 10/2003 |
| WO | WO-03085119 A1 | 10/2003 |
| WO | WO-03093318 A1 | 11/2003 |
| WO | WO-2004003019 A2 | 1/2004 |
| WO | WO-2004024927 A1 | 3/2004 |
| WO | WO-2004033685 A1 | 4/2004 |
| WO | WO-2004056312 A2 | 7/2004 |
| WO | WO-2004056392 A1 | 7/2004 |
| WO | WO-2004056873 A1 | 7/2004 |
| WO | WO-2004057002 A2 | 7/2004 |
| WO | WO-2004058821 A2 | 7/2004 |
| WO | WO-2004065540 A2 | 8/2004 |
| WO | WO-2004081026 A2 | 9/2004 |
| WO | WO-2004081051 A1 | 9/2004 |
| WO | WO-2004101790 A1 | 11/2004 |
| WO | WO-2004106368 A1 | 12/2004 |
| WO | WO-2005035572 A2 | 4/2005 |
| WO | WO-2005035586 A1 | 4/2005 |
| WO | WO-2005035778 A1 | 4/2005 |

(56) References Cited

FOREIGN PATENT DOCUMENTS

| | | |
|---|---|---|
| WO | WO-2005053742 A1 | 6/2005 |
| WO | WO-2005100402 A1 | 10/2005 |
| WO | WO-2006000830 A2 | 1/2006 |
| WO | WO-2006020258 A2 | 2/2006 |
| WO | WO-2006029879 A2 | 3/2006 |
| WO | WO-2006044908 A2 | 4/2006 |
| WO | WO-2006079372 A1 | 8/2006 |
| WO | WO-2006106905 A1 | 10/2006 |
| WO | WO-2006121168 A1 | 11/2006 |
| WO | WO-2006135886 A2 | 12/2006 |
| WO | WO-2007005874 A2 | 1/2007 |
| WO | WO-2007044887 A2 | 4/2007 |
| WO | WO-2007059782 A1 | 5/2007 |
| WO | WO-2007005874 A3 | 7/2007 |
| WO | WO-2007095338 A2 | 8/2007 |
| WO | WO-2007110205 A2 | 10/2007 |
| WO | WO-2007137760 A2 | 12/2007 |
| WO | WO-2008017859 A2 | 2/2008 |
| WO | WO-2008077546 A1 | 7/2008 |
| WO | WO-2008087219 A1 | 7/2008 |
| WO | WO-2008119353 A1 | 10/2008 |
| WO | WO-2009021754 A2 | 2/2009 |
| WO | WO-2009068630 A1 | 6/2009 |
| WO | WO-2009077993 A2 | 6/2009 |
| WO | WO-2009089004 A1 | 7/2009 |
| WO | WO-2009101611 A1 | 8/2009 |
| WO | WO-2009103538 A1 | 8/2009 |
| WO | WO-2009114335 A2 | 9/2009 |
| WO | WO-2009147137 A1 | 12/2009 |
| WO | WO-2010019570 A2 | 2/2010 |
| WO | WO-2010027797 A1 | 3/2010 |
| WO | WO-2010027827 A2 | 3/2010 |
| WO | WO-2010029513 A2 | 3/2010 |
| WO | WO-2010077634 A1 | 7/2010 |
| WO | WO-2010129304 A2 | 11/2010 |
| WO | WO-2011066342 A2 | 6/2011 |
| WO | WO-2011090762 A1 | 7/2011 |
| WO | WO-2011131746 A2 | 10/2011 |
| WO | WO-2011155607 A1 | 12/2011 |
| WO | WO-2012079000 A1 | 6/2012 |
| WO | WO-2012088309 A1 | 6/2012 |
| WO | WO-2012107417 A1 | 8/2012 |
| WO | WO-2012131555 A2 | 10/2012 |
| WO | WO-2012138475 A1 | 10/2012 |
| WO | WO-2012143498 A1 | 10/2012 |
| WO | WO-2012170438 A2 * | 12/2012 ................ A61P 3/00 |
| WO | WO-2013019615 A2 | 2/2013 |
| WO | WO-2013033626 A2 | 3/2013 |
| WO | WO-2013037484 A2 | 3/2013 |
| WO | WO-2013060867 A2 | 5/2013 |
| WO | WO-2013079174 A1 | 6/2013 |
| WO | WO-2013103912 A1 | 7/2013 |
| WO | WO-2013170168 A1 | 11/2013 |
| WO | WO-2014008218 A1 | 1/2014 |
| WO | WO-2014100823 A1 | 6/2014 |
| WO | WO-2014159940 A1 | 10/2014 |
| WO | WO-2015052230 A1 | 4/2015 |
| WO | WO-2015066379 A2 | 5/2015 |
| WO | WO-2015095811 A2 | 6/2015 |
| WO | WO-2015107015 A1 | 7/2015 |
| WO | WO-2015107025 A1 | 7/2015 |
| WO | WO-2015107026 A1 | 7/2015 |
| WO | WO-2015121383 A1 | 8/2015 |
| WO | WO-2015127158 A1 | 8/2015 |
| WO | WO-2015132598 A1 | 9/2015 |
| WO | WO-2015164815 A1 | 10/2015 |
| WO | WO-2015166073 A1 | 11/2015 |
| WO | WO-2015181805 A1 | 12/2015 |
| WO | WO-2015197582 A1 | 12/2015 |
| WO | WO-2015197593 A1 | 12/2015 |
| WO | WO-2015197598 A2 | 12/2015 |
| WO | WO-2016016299 A1 | 2/2016 |
| WO | WO-2016019969 A1 | 2/2016 |
| WO | WO-2016026943 A1 | 2/2016 |
| WO | WO-2016033555 A1 | 3/2016 |
| WO | WO-2016071376 A2 | 5/2016 |
| WO | WO-2016071377 A1 | 5/2016 |
| WO | WO-2016079081 A1 | 5/2016 |
| WO | WO-2016087416 A1 | 6/2016 |
| WO | WO-2016087514 A1 | 6/2016 |
| WO | WO-2016087650 A1 | 6/2016 |
| WO | WO-2016090327 A2 | 6/2016 |
| WO | WO-2016110468 A1 | 7/2016 |
| WO | WO-2016110584 A1 | 7/2016 |
| WO | WO-2016115274 A1 | 7/2016 |
| WO | WO-2016118641 A1 | 7/2016 |
| WO | WO-2016168149 A1 | 10/2016 |
| WO | WO-2016180969 A1 | 11/2016 |
| WO | WO-2016193301 A1 | 12/2016 |
| WO | WO-2017021349 A1 | 2/2017 |
| WO | WO-2017021450 A1 | 2/2017 |
| WO | WO-2017037634 A1 | 3/2017 |
| WO | WO-2017040930 A2 | 3/2017 |
| WO | WO-2017055391 A1 | 4/2017 |
| WO | WO-2017059551 A1 | 4/2017 |
| WO | WO-2017062604 A1 | 4/2017 |
| WO | WO-2017077382 A1 | 5/2017 |
| WO | WO-2017134140 A1 | 8/2017 |
| WO | WO-2017165464 A1 | 9/2017 |
| WO | WO-2017167919 A1 | 10/2017 |
| WO | WO-2017180913 A2 | 10/2017 |
| WO | WO-2018057955 A1 | 3/2018 |
| WO | WO-2018067992 A1 | 4/2018 |
| WO | WO-2018098365 A2 | 5/2018 |
| WO | WO-2018144777 A2 | 8/2018 |
| WO | WO-2018201047 A1 | 11/2018 |
| WO | WO-2018224844 A1 | 12/2018 |
| WO | WO-2018237192 A1 | 12/2018 |
| WO | WO-2019005641 A1 | 1/2019 |
| WO | WO-2019035938 A1 | 2/2019 |
| WO | WO-2019040700 A1 | 2/2019 |
| WO | WO-2019040780 A1 | 2/2019 |
| WO | WO-2019055677 A1 | 3/2019 |
| WO | WO-2019067805 A1 | 4/2019 |
| WO | WO-2019086865 A1 | 5/2019 |
| WO | WO-2019101695 A1 | 5/2019 |
| WO | WO-2019132738 A1 | 7/2019 |
| WO | WO-2019139987 A1 | 7/2019 |
| WO | WO-2019158764 A1 | 8/2019 |
| WO | WO-2019178362 A1 | 9/2019 |
| WO | WO-2019178364 A2 | 9/2019 |
| WO | WO-2019178364 A3 | 10/2019 |
| WO | WO-2019191519 A1 | 10/2019 |
| WO | WO-2019226617 A1 | 11/2019 |
| WO | WO-2019231920 A1 | 12/2019 |
| WO | WO-2020005819 A1 | 1/2020 |
| WO | WO-2020010250 A2 | 1/2020 |
| WO | WO-2020018708 A1 | 1/2020 |
| WO | WO-2020010250 A3 | 2/2020 |
| WO | WO-2020025928 A1 | 2/2020 |
| WO | WO-2020057646 A1 | 3/2020 |
| WO | WO-2020082048 A1 | 4/2020 |
| WO | WO-2020084290 A1 | 4/2020 |
| WO | WO-2020086758 A1 | 4/2020 |
| WO | WO-2020088459 A1 | 5/2020 |
| WO | WO-2020089644 A1 | 5/2020 |
| WO | WO-2020091635 A2 | 5/2020 |
| WO | WO-2020106708 A1 | 5/2020 |
| WO | WO-2020139171 A1 | 7/2020 |
| WO | WO-2020139175 A2 | 7/2020 |
| WO | WO-2020142672 A2 | 7/2020 |
| WO | WO-2020142672 A3 | 8/2020 |
| WO | WO-2020172571 A1 | 8/2020 |
| WO | WO-2020172596 A1 | 8/2020 |
| WO | WO-2020172598 A1 | 8/2020 |
| WO | WO-2020172601 A1 | 8/2020 |
| WO | WO-2020172605 A1 | 8/2020 |
| WO | WO-2020183245 A2 | 9/2020 |
| WO | WO-2020249757 A1 | 12/2020 |
| WO | WO-2021089704 A1 | 5/2021 |
| WO | WO-2021097325 | 5/2021 |
| WO | WO-2021138407 A2 | 7/2021 |
| WO | WO-2021138474 A2 | 7/2021 |
| WO | WO-2021140190 A1 | 7/2021 |

(56) References Cited

FOREIGN PATENT DOCUMENTS

| | | |
|---|---|---|
| WO | WO-2021138474 A3 | 9/2021 |
| WO | WO-2021188454 A1 | 9/2021 |
| WO | WO-2021217085 A1 | 10/2021 |
| WO | WO-2022046920 A2 | 3/2022 |
| WO | WO-2022046922 A2 | 3/2022 |
| WO | WO-2022047046 A1 | 3/2022 |
| WO | WO-2022046920 A3 | 4/2022 |
| WO | WO-2022046922 A3 | 4/2022 |
| WO | WO-2022175413 A1 | 8/2022 |
| WO | WO-2022179580 * 9/2022 ............ C07K 16/28 |
| WO | WO-2022216993 A2 | 10/2022 |
| WO | WO-2022216993 A3 | 11/2022 |
| WO | WO-2022240688 A1 | 11/2022 |
| WO | WO-2023081412 A2 | 5/2023 |
| WO | WO-2023122206 A2 | 6/2023 |
| WO | WO-2023141297 A2 | 7/2023 |
| WO | WO-2023081412 A3 | 8/2023 |
| WO | WO-2023122206 A3 | 8/2023 |
| WO | WO-2023141297 A3 | 8/2023 |
| WO | WO-2024081329 A1 | 4/2024 |
| WO | WO-2024081381 A1 | 4/2024 |
| WO | WO-2024197082 A2 | 9/2024 |
| WO | WO-2024226532 A2 | 10/2024 |
| WO | WO-2024227109 A1 | 10/2024 |
| WO | WO-2024197082 A3 | 11/2024 |
| WO | WO-2024254611 A2 | 12/2024 |
| WO | WO-2024226532 A3 | 1/2025 |

OTHER PUBLICATIONS

Akiyama et al.: TNFalpha induces rapid activation and nuclear translocation of telomerase in human lymphocytes. Biochem Biophys Res Commun. 316(2):528-532 (2004).
Ala-Aho, Risto, et al., Collagenases in Cancer. Biochimie 87(3-4):273-286 (2005).
Al-Aghbar, M.A. et al., "High-affinity ligands can trigger T cell receptor signaling without CD45 segregation," Frontiers in Immunology, 2018;9(713):1-18.
Ali et al.: Modulation of human natural killer cytotoxicity by influenza virus and its subunit protein. Immunology 52(4):687-695 (1984).
Al-Lazikani, B. et al., "Standard Conformations for Canonical Structures of Immunoglobulins", J. Mol. Biol., 1997, vol. 273 ,pp. 927-948.
Altschul et al.: Basic Local Alignment Search Tool. Journal of Molecular Biology 215(3):403-410 (1990).
Altschul, et al. Gapped BLAST and PSI-BLAST: A New Generation Of Protein Database Search Programs. Nucleic Acids Research. 25(17):3389-3402 (1997).
Amarante-Mendes GP, Griffith TS. Therapeutic applications of TRAIL receptor agonists in cancer and beyond. Pharmacol Ther. Nov. 2015;155:117-31. Epub Sep. 5, 2015.
Arai, R. et al., "Design of the linkers which effectively separate domains of a bifunctional fusion protein", Protein Engineering, 2001, vol. 14, No. 8, pp. 529-532.
Arenas-Ramirez et al.: Interleukin-2: Biology, Design and Application. Trends in Immunology 36(12):763-777 (2015).
Arnon, T.I. et al., "Recognition of viral hemagglutinins by NKp44 but not by NKp30", Eur J. Immunol., 2001, vol. 31, No. 9, pp. 2680-2689.
Aslan, J.E et al., "S6K1 and mTOR regulate Rac1-driven platelet activation and aggregation", Blood, 2011, vol. 118, No. 11, pp. 3129-3136.
Aversa, Ilenia, et al., Molecular T-Cell Repertoire Analysis as Source of Prognostic and Predictive Biomarkers for Checkpoint blockade Immunotherapy. International Journal of Molecular Sciences 21(7):2378, 1-19 (2020).
Banerjee, Hridesh, et al., 33rd Annual Meeting & Pre-Conference Programs of the Society for Immunotherapy of Cancer (SITC). Journal for Immunotherapy of Cancer 6(1):1-192 (2018).

Barbas, Carlos, et al., Assembly of Combinatorial Antibody Libraries on Phage Surfaces: The Gene III Site. Proceedings of the National Academy of Sciences of the United States of America 88(18):7978-7982 (1991).
Beidler, C B, et al., Cloning and High Level Expression of a Chimeric Antibody With Specificity for Human Carcinoembryonic Antigen. Journal of Immunology 141(11):4053-4060 (1988).
Berge, Ten, et al., Selective Expansion of a Peripheral Blood Cd8+ Memory T Cell Subset Expressing Both Granzyme B and L-selectin During Primary Viral Infection in Renal Allograft Recipients. Transplantation Proceedings 30(8):3975-3977 (1998).
Better, M. et al., "*Escherichia coli* Secretion of an Active Chimeric Antibody Fragment", Science, 1988, vol. 240, No. 4855, pp. 1041-1043.
Beun, G. et al., "T cell Retargeting Using Bispecific Monoclonal Antibodies in a Rat Colon Carcinoma Model", The Journal of Immunology, 1993, vol. 150, No. 6, pp. 2305-2315.
Bierer, B E, et al., Cyclosporin a and Fk506: Molecular Mechanisms of Immunosuppression and Probes for Transplantation Biology. Current Opinion in Immunology 5(5):763-773 (1993).
Bird et al., Single-Chain Antigen-binding Proteins. Science 242(4877):423-426 (1988).
Bluemel, C. et al., "Epitope distance to the target cell membrane and antigen size determine the potency of T cell-mediated lysis by BiTE antibodies specific for a large melanoma surface antigen", Cancer Immunology, Immunotherapy, 2010, vol. 59, No. 8, pp. 1197-1209.
Bolt, S. et al., "The generation of a humanized, non-mitogenic CD3 monoclonal antibody which retains in vitro immunosuppressive properties," Eur. J. Immunol., 1993;23:403-411.
Breman, E. et al., "Overcoming target driven fratricide for T Cell Therapy," Frontiers in Immunology, 2018;9(2940):1-11.
Bruggemann, M. et al., Designer Mice: The Production of Human Antibody Repertoires in Transgenic Animals, Terhorst C. Malavasi F, Albertini A (eds): Generation of Antibodies by Cell and Gene Immortalization, Year Immunol, 1993, vol. 7, pp. 33-40.
Bruggemann, M. et al., "Human antibody production in transgenic mice: expression from 100kb of the human IgH locus", Eur J. Immunol, 1991, vol. 21, pp. 1323-1326.
Buchwald et al. Long-term, continuous intravenous heparin administration by an implantable infusion pump in ambulatory patients with recurrent venous thrombosis. Surgery 88:507-516 (1980).
Cadwell, R. C. et al., "Randomization of Genes by PCR Mutagenesis", PCR Methods Appl., 1992, vol. 2, No. 1, pp. 28-33.
Cain, Chris, et al., Crossing over to Bispecificity. SciBX 4(28):1-3 (2011).
Chang et al.: A therapeutic T cell receptor mimic antibody targets tumor-associated PRAME peptide/HLA-I antigens. J Clin Invest. 127(7):2705-2718 (2017).
Chao, G. et al., "Isolating and engineering human antibodies using yeast surface display", Nature Protocols, 2006, vol. 1, No. 2, pp. 755-768.
Chaudry, et al. EpCAM an immunotherapeutic target for gastrointestinal malignancy: current experience and future challenges. Br J Cancer. Apr. 10, 2007;96(7):1013-9. Epub Feb. 27, 2007.
Chen et al.: Chromosome X-encoded cancer/testis antigens show distinctive expression patterns in developing gonads and in testicular seminoma. Hum Reprod. 26(12):3232-3243 doi:10.1093/humrep/der330 (2011).
Chen et al.: The nuclear localization sequences of the BRCA1 protein interact with the importin-alpha subunit of the nuclear transport signal receptor. J Biol Chem. 271(51):32863-32868 (1996).
Chiang, E. et al., "Abstract 3527: Potent anti-tumor activity of AbGn-100, an anti-CD326 x anti-TCR bispecific antibody to CD326-expressing solid tumors," Cancer Res., 2012;72(8_supplement):3527.
Chichili, V.P.R. et al., "Linkers in the structural biology of protein-protein interactions," Protein Science, 2013;22:153-167.
Chinese Patent Application No. 201780028089.4 2nd Office Action dated Apr. 18, 2022.
Cho, B.K. et al., "Single-Chain Fv/Folate Conjugates Mediate Efficient Lysis of Folate-Receptor-Positive Tumor Cells," Bioconjugate Chem., 1997;8:338-346.

(56) References Cited

OTHER PUBLICATIONS

Chothia, C. et al., "Canonical Structures for the Hypervariable Regions of Immunoglobulins", J. Mol. Biol, 1987, vol. 196, pp. 901-917.
Chothia et al., Structural repertoire of the human VH segments. J Mol Biol 227:799-817 (1992).
Ciccone, E. et al., "A monoclonal antibody specific for a common determinant of the human T cell receptor gamma/delta directly activates CD3+WT31-lymphocytes to express their functional program(s)," J Exp Med., 1988; 168(1):1-11.
Clackson, T. et al., Making antibody fragments using phage display libraries, Nature, 1991, vol. 352, pp. 624-628.
Colcher, David, et al., Single-Chain Antibodies in Pancreatic Cancer. Annals of the New York Academy of Sciences 880:263-280 (1999).
Coloma, J. et al., "Design and production of novel tetravalent bispecific antibodies", Nature Biotech, 1997, vol. 15, pp. 159-163.
Costa-Mattioli, Mauro, et al., RAPping Production of type I Interferon in pDCs through mTOR. Nature Immunology 9(10):1097-1099 (2008).
Cui, et al., "T cell receptor B-chain repertoire analysis of tumor-infiltrating lymphocytes in pancreatic cancer" Cancer Science (2018) 60-71.
Dao, Tao, et al., Targeting the Intracellular Wt1 Oncogene Product With a Therapeutic Human Antibody. Science Translational Medicine 5(176):176ra33, 1-22 (2013).
Davis, J. et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection, 2010, vol. 23, No. 4, pp. 195-202.
Dela Cruz et al.: Anti-HER2/neu lgG3-(IL-2) and anti-HER2/neu lgG3-(GM-CSF) promote HER2/neu processing and presentation by dendritic cells: Implications in immunotherapy and vaccination strategies. Molecular Immunology 43(6):667-676 (2006).
Dickopf, S. et a., "Formal and geometries matter: Structure-based design defines the functionality of bispecific antibodies", Computational and Structural Biotechnology Journal, 2020, vol. 18, pp. 1221-1227.
Dimasi et al. Development of a trispecific antibody designed to simultaneously and efficiently target three different antigens on tumor cells. Mol Pharm 12(9):3490-3501 (2015).
Doyle, Sean, et al., IRF3 Mediates a TLR3/TLR4-Specific Antiviral Gene Program. Immunity 17(3):251-263 (2002).
Duhen et al., Co-expression of $CD_{39}$ and $CD_{103}$ identifies tumor-reactive CD8 T cells in human solid tumors. Nat Commun. 9(1):2724, pp. 1-13 (2018).
During, M J, et al., Controlled Release of Dopamine From a Polymeric Brain Implant: in Vivo Characterization. American Neurological Association 25(4):351-356 (1989).
El Achi, H. et al., "CD123 as a Biomarker in Hematolymphoid Malignancies: Principles of Detection and Targeted Therapies," Cancers, 2020;12(11):3087.
European Patent Application No. 17 718 441.3 Office Action dated Jan. 24, 2022.
European Search Report issued in EP20736073, dated Aug. 2, 2022.
Falini et al.: Cytoplasmic nucleophosmin in acute myelogenous leukemia with a normal karyotype. N Engl J Med. 352(3):254-266 doi:10.1056/NEJMoa041974 (2005).
Farrar et al.: The Molecular Cell Biology Of Interferon-gamma And Its Receptor. Annu Rev Immunol 11:571-611 (1993).
Fernandez-Malave, Edgar, et al., An Natural Anti-T-Cell Receptor Monoclonal Antibody Protects Against Experimental Autoimmune Encephalomyelitis. Journal of Neuroimmunology 234(1-2):63-70 (2011).
Foley, K.. et al., Combination immunotherapies implementing adoptive T-cell transfer for advanced-stage melanoma, Melanoma Research, vol. 28, 3 (2018):171-184.
Frost, Gregory, et al., A Microtiter-Based Assay for Hyaluronidase Activity Not Requiring Specialized Reagents. Analytical Biochemistry 251(2):263-269 (1997).
Fuchs, P. et al., "Targeting Recombinant Antibodies to the surface of *Escherichia coli*: Fusion to the Peptidoglycan associated Lipoprotein", Nature Publishing Group, 1991, vol. 9, No. 12, pp. 1369-1372.
Funayama et al.: Embryonic axis induction by the armadillo repeat domain of beta-catenin: evidence for intracellular signaling. J Cell Biol. 128(5):959-968 (1995).
Gao et al.: Alg14 recruits Alg13 to the cytoplasmic face of the endoplasmic reticulum to form a novel bipartite UDP-N-acetylglucosamine transferase required for the second step of N-linked glycosylation. J Biol Chem. 280(43):36254-36262 doi:10.1074/jbc.M507569200 (2005).
Garland, R.J., et al., "The use of Teflon cell culture bags to expand functionally active CD8+ cytotoxic T lymphocytes", Journal of Immunological Methods, 1999, vol. 227, pp. 53-63.
Garrard, L. et al., "FAB Assembly and Enrichment in a Monovalent Phage Display System", Nature Publishing Group, 1991, vol. 9, pp. 1373-1377.
Garrity, David, et al., The Activating NKG2D Receptor Assembles in the Membrane With Two Signaling Dimers Into a Hexameric Structure. Proceedings of the National Academy of Sciences of the United States of America 102(21):7641-7646 (2005).
GB Exam Report for GB2109794.4 dated Jun. 21, 2020.
Geissinger, E. et al., "Identification of the Tumor Cells in Peripheral T-Cell Lymphomas by Combined Polymerase Chain Reaction-Based T-Cell Receptor [3 Spectrotyping and Immunohistological Detection with T-Cell Receptor [3 Chain Variable Region Segment-Specific Antibodies," J. of Mol Diag., 2005;7(4):455-464.
Gillies, S.D. et al., "Bi-functional cytokine fusion proteins for gene therapy and antibody-targeted treatment of cancer," Cancer Immunol Immunotherapy, 2002;51:449-460.
Gjerstorff et al.: GAGE cancer-germline antigens are recruited to the nuclear envelope by germ cell-less (GCL). PLoS One 7(9):e45819:1-12 doi:10.1371/journal.pone.0045819 (2012).
Goel, M. et a., "Plasticity within the Antigen-Combining site may manifest as molecular mimicry in the humoral immune response," J Immunology, 2004;173(12):7358-7367.
Gohal, G, et al., "T-cell receptor phenotype pattern in atopic children using commercial fluorescently labeled antibodies against 21 human class-specific v segments for the tcrβ chain (vβ) of peripheral blood: a cross sectional study," Allergy Asthma Clin Immunol., 2016;12:10.
Gokden et al.: Diagnostic utility of renal cell carcinoma marker in cytopathology. Appl Immunohistochem Mol Morphol. Abstract Only. 11(2):116-119 doi:10.1097/00129039-200306000-00004 (2003).
Gordon, E.D. et al., "Alternative splicing of interleukin-33 and type 2 inflammation in asthma," PNAS, 2016;113(31):8765-8770.
Gram, H. et al., In vitro selection and affinity maturation of antibodies from a naïve combinatorial immunoglobulin library, PNAS, 1992, vol. 89, pp. 3576-3580.
Green, Edward, et al., TCR Validation Toward Gene Therapy for Cancer. Methods in Enzymology 629(21):419-441 (2019).
Green, L.L. et al., "Antigen-specific human monoclonal antibodies from mice engineered with human Ig heavy and light chain YACS", Nature Genet, 1994, vol. 7, pp. 13-21.
Griffiths, A.D. et al., "Human anti-self antibodies with high specificity from phage display libraries", The EMBO Journal, 1993, vol. 12, No. 2, pp. 725-734.
Gulley, J.L. et al., "New drugs on the horizon," Eur J Cancer, 2022;174(S1):S5.
Gupta, S. et al., "T cell activation via the T cell receptor: a comparison between WT31 (defining alpha/beta TcR)-induced and anti-CD3-induced activation of human T lymphocytes," Cell Immunol., 1991;132(1):26-44.
Haanen, J. et al., "Selective Expansion of Cross-reactive CD8+ Memory T Cells by Viral Variants", J. Exp. Med., 1999, vol. 190, No. 9, pp. 1319-1328.
Halin, C. et al., "Synergistic Therapeutic Effects of a Tumor Targeting Antibody Fragment, Fused to Interleukin 12 and to Tumor Necrosis Factor a1," Cancer Research, 2003;63:3202-3210.

(56) References Cited

OTHER PUBLICATIONS

Hall, MacLean, et al., Expansion of Tumor-Infiltrating Lymphocytes (TIL) from Human Pancreatic Tumors. Journal for Immuno Therapy of Cancer 4:61, 1-12 (2016).
Hamid, O. et al., "Safety and Tumor Responses with Lambrolizumab (Anti-PD-1) in Melanoma", The New England Journal of Medicine, 2013, vol. 369, No. 2, pp. 134-144.
Hamming et al. Crystal Structure of Interleukin-21 Receptor (IL-21R) Bound to IL-21 Reveals That Sugar Chain Interacting with WSXWS Motif Is Integral Part of IL-21R. The Journal of Biological Chemistry 287(12):9454-9460 (2012).
Hawkins, R. et al., "Selection of phage antibodies by binding affinity. Mimicking affinity maturation", J. Mol. Biol., 1992, vol. 226, No. 3, pp. 889-896.
Hay, B. et al., "Bacteriophage cloning and *Escherichia coli* expression of a human IgM Fab" Hum Antibodies Hybridomas, 1992, vol. 3, No. 2, pp. 81-85.
Henderson, D J, et al., Comparison of the Effects of FK-506, Cyclosporin A and Rapamycin on IL-2 Production. Immunology 73(3):316-321 (1991).
Herskovitz, O. et al., "NKp44 receptor mediates interaction of the envelope glycoproteins from the West-Nile and dengue viruses with Natural Killer cells," The Journal of Immunology, 2009;183(4):2610-2621.
Hirai et al.: Nucleolar scaffold protein, WDR46, determines the granular compartmental localization of nucleolin and DDX21. Genes Cells 18(9):780-797 (2013).
Hiyama, K, et al., Action of Chondroitinases. I. The Mode of Action of Two Chondroitinase-AC Preparations of Different Origin. Journal of Biochemistry 80(6):1201-1207 (1976).
Hiyama, K, et al., Crystallization and Some Properties of Chondroitinase from Arthrobacter Aurescens. The Journal of Biological Chemistry 250(5):1824-1828 (1975).
Hollinger, Philipp, et al., Engineered Antibody Fragments and the Rise of Single Domains. Nature Biotechnology 23(9):1126-1136 (2005).
Hombach, A.A. et al., "Antibody-IL2 Fusion Proteins for Tumor Targeting," Antibody Engineering, 2012:611-626.
"Hongyan, et al., "Fc Engineering for Developing Therapeutic Bispecific Antibodies and Novel Scaffolds" Frontiers In Immunology, (2017) vol. 8".
Hoogenboom, H.R. et al., "Multi-subunit proteins on the surface of filamentous phage: methodologies for displaying antibody (Fab) heavy and light chains", Nuc Acid Res, 1991, vol. 19, No. 15, pp. 4133-4137.
Howard, M A, et al., Intracerebral Drug Delivery in Rats with Lesion-induced Memory Deficits. Journal of Neurosurgery 71(1):105-112 (1989).
Hudson, K.R. et al., "Two Adjacent Residues in Staphylococcal EnterotoxIns A and E Determine T Cell Receptor Vbeta Specificity," J.Exp. Med., 1993;177:175-184.
Hudspeth et al.: Natural cytotoxicity receptors: broader expression patterns and functions in innate and adaptive immune cells. Frontiers in Immunology 4(69):1-15 (2013).
Hunig, T. et al., "A monoclonal antibody to a constant determinant of the rat t cell antigen receptor that induces t cell activation", J. Exp. Med., 1989, vol. 169, pp. 73-86.
Huse, W. et al., "Generation of a large combinatorial library of the immunoglobulin repertoire in phage lambda" Science, 1989, vol. 246, No. 4935, pp. 1275-1281.
Huston, James, et al., Protein Engineering Of Antibody Binding Sites: Recovery Of Specific Activity In An Anti-digoxin Single-chain Fv Analogue Produced In *Escherichia coli*. Proceedings of the National Academy of Sciences of the United States of America 85(16):5879-5883 (1988).
International Preliminary Report on Patentability issued in PCT/US2017/023483, dated Sep. 25, 2018.
International Preliminary Report on Patentability issued in PCT/US2019/040592, dated Jan. 5, 2021.
International Preliminary Report on Patentability issued in PCT/US2020/012162, dated Jun. 16, 2021.
International Preliminary Report on Patentability issued in PCT/US2020/019291, dated Aug. 10, 2021.
International Preliminary Report on Patentability issued in PCT/US2020/019319, dated Aug. 10, 2021.
International Preliminary Report on Patentability issued in PCT/US2020/019321, dated Aug. 10, 2021.
International Preliminary Report on Patentability issued in PCT/US2020/060557 dated May 17, 2022.
International Preliminary Report on Patentability issued in PCT/US/2020/067543, dated Jul. 5, 2022.
International Preliminary Report on Patentability issued in PCT/US2021/022408, dated Sep. 20, 2022.
International Preliminary Report on Patentability issued in PCT/US2021/028970, dated Oct. 25, 2022.
"International Search Report and Written Opinion for corresponding PCT Application No. PCT/US2019/012900 dated Jul. 5, 2019".
International Search Report and Written Opinion for corresponding PCT Application No. PCT/US2019/022282 issued Jul. 1, 2019.
International Search Report and Written Opinion issued in PCT/US2017/023483, mailed Aug. 29, 2017.
International Search Report and Written Opinion issued in PCT/US2019/040592, mailed Jan. 9, 2020.
International Search Report and Written Opinion issued in PCT/US2020/012162 mailed Jun. 26, 2020.
International Search Report and Written Opinion issued in PCT/US2020/019291, mailed Jun. 15, 2020.
International Search Report and Written Opinion issued in PCT/US2020/019319, mailed Jun. 26, 2020.
International Search Report and Written Opinion issued in PCT/US2020/019321, mailed Aug. 10, 2020.
International Search Report and Written Opinion issued in PCT/US2020/060557, mailed Mar. 30, 2021.
International Search Report and Written Opinion issued in PCT/US2020/067543, mailed Jul. 7, 2021.
International Search Report and Written Opinion issued in PCT/US2021/022408, mailed Aug. 31, 2021.
International Search Report and Written Opinion issued in PCT/US2021/028970 mailed Oct. 4, 2021.
International Search Report and Written Opinion issued in PCT/US2021/047571, dated Feb. 14, 2022.
International Search Report and Written Opinion issued in PCT/US2022/023922, mailed Oct. 17, 2022.
Islam, D, et al., Changes in the Peripheral Blood T-Cell Receptor V Beta Repertoire in Vivo and in Vitro During Shigellosis. Infection and Immunity 64(4):1391-1399 (1996).
Jameson, Stephen C., "T cell receptor antagonism in vivo, at last", Proc. Natl. Acad. Sci., 1998, vol. 95, pp. 14001-14002.
Jiang, B. et al., "A novel peptide isolated from a phage display peptide library with trastuzumab can mimic antigen epitope of HER-2*," The Journal of Biological Chemistry, 2005;280(6):4656-4662.
Jiang et al.: Nuclear expression of CDK4 correlates with disease progression and poor prognosis in human nasopharyngeal carcinoma. Histopathology 64(5):722-730 doi:10.1111/his.12319 (2013).
Jones et al., Replacing The Complementarity-determining Regions In A Human Antibody With Those From A Mouse. Nature 321(6069):522-525 (1986).
Ju et al.: Structure-function analysis of human interleukin-2. Identification of amino acid residues required for biological activity. The Journal of Biological Chemistry 262(12):5723-5731 (1987).
Kanagawa, et al., "In Vivo T Cell Tumor Therapy With Monoclonal Antibody Directed to the VB chain of T Cell Antigen Receptor" J. Exp. Med., vol. 170, (1989) p. 1513-1519.
Kanagawa, O, et al., The T Cell Receptor VB6 Domain Imparts Reactivity to the Mls-1a Antigen. Cellular Immunology 119(2):412-426 (1989).
Kato et al.: The structure and binding mode of interleukin-18. Nature Structural Biology 10(11):366-971 (2003).

(56) References Cited

OTHER PUBLICATIONS

Kato, Y. et al., "Molecular analysis of the pathophysiological binding of the platelet aggregation-inducing factor podoplanin to the C-type lectin-like receptor CLEC-2", Cancer Sci, Jan. 2008, vol. 99, No. 1, pp. 54-61.

Kawaguchi, M, et al., Differential Activation Through the TCR-CD3 Complex Affects the Requirement for Costimulation of Human T Cells. Human immunology 43(2):136-148 (1995).

Kellner et al.: Enhancing natural killer cell-mediated lysis of lymphoma cells by combining therapeutic antibodies with CD20-specific immunoligands engaging NKG2D or NKp30. Oncoimmunology 5(1 )e1058459 [1-12] (2016).

Kerkela, E, et al., Expression of Human Macrophage Metalloelastase (MMP-12) by Tumor Cells in Skin Cancer. Journal of Investigative Dermatology 114(6):1113-1119 (2000).

Kiefer, J.D. et al., "Immunocytokines and bispecific antibodies: two complementary strategies for the selective activation of immune cells at the tumor site," Immunol Rev., 2016;270(1):178-192.

Kim, E.J. et al., "Interleukin-2 fusion protein with anti-CD3 single-chain Fv (sFv) selectively protects T cells from dexamethasone-induced apoptosis," Vaccine, 2002;20:608-615.

Kirkin, et al. Melanoma-associated antigens recognized by cytotoxic T lymphocytes. APMIS. Jul. 1998;106(7):665-79.

Kitaura, K. et al., "A new high-throughput sequencing method for determining diversity and similarity of T cell receptor (TCR) α and β repertoires and identifying potential new invariant TCR α chains," BMC Immunology, 2016, vol. 17, No. 38, pp. 1-16.

Klampfl, T. et al., "Somatic Mutations of Calreticulin in Myeloproliferative Neoplasms", N Engl J Med., 2013, vol. 369, No. 25, pp. 2379-2390.

Klein, Christian, et al., Progress in Overcoming the Chain Association Issue in Bispecific Heterodimeric IgG Antibodies. mAbs 4(6):653-663 (2012).

Koch et al.: Activating natural cytotoxicity receptors of natural killer cells in cancer and infection. Trends Immunol. 34(4):182-191 doi:10.1016/j.it.2013.01.003 (2013).

Kunkel, Thomas A., "Rapid and efficient site-specific mutagenesis without phenotypic selection", Proc Natl Acad Sci, 1985, vol. 82, No. 2, pp. 488-492.

Kushner et al.: Aberrant expression of cyclin A and cyclin B1 proteins in oral carcinoma. J Oral Pathol Med. 28(2):77-81 (1999).

Labrijn, Aran, et al., Controlled Fab-arm Exchange for the Generation of Stable Bispecific IgG1. Nature Protocols 9(10):2450-2463 (2014).

Labrijn, Aran, et al., Efficient Generation of Stable Bispecific IgG1 by Controlled Fab-arm Exchange. Proceedings of the National Academy of Sciences of the United States of America 110(13):5145-5150 (2013).

Lain et al.: Accumulating active p53 in the nucleus by inhibition of nuclear export: a novel strategy to promote the p53 tumor suppressor function. Exp Cell Res. 253(2):315-324 (1999).

Langer, Robert, et al., Chemical and Physical Structure of Polymers as Carriers for Controlled Release of Bioactive Agents: A Review. Journal of Macromolecular Science—Reviews in Macromolecular Chemistry and Physics 23(1):61-126 (1983).

Langer, Robert, et al., Medical Applications of Controlled Release. 2:115-138 (1984).

Langer, Robert, New Methods of Drug Delivery. Science 249(4976):1527-1533 (1990).

Lanier, L.L. et al., "Distinct epitopes on the t cell antigen receptor of HPB-ALL tumor cells identified by monoclonal antibodies," 1986;137(7):2286-2292.

Leclercq, G. et al., "Dissecting the mechanism of cytokine release induced by T-cell engagers highlights the contribution of neutrophils," Oncoimmunology, 2022;11(1):e2039432.

Lee, C. M. et al., "Selection of human antibody fragments by phage display", Nat Protoc., 2007, vol. 2, No. 11, pp. 3001-3008.

Lee, K.D. et al., "Construction and characterization of a novel fusion protein consisting of anti-CD3 antibody fused to recombinant interleukin-2," Oncology Reports, 2006;15:1211-1216.

Leonard, E.K. et al., "Engineered cytokine/antibody fusion proteins improve delivery of IL-2 to pro-inflammatory cells and promote antitumor activity," bioRxiv, 2023:1-36.

Leong et al.: Optimized expression and specific activity of IL-12 by directed molecular evolution. Proc. Natl. Acad. Sci. USA; 100(3): 1163-1168 (2003).

Leutkens et al.: Functional autoantibodies against SSX-2 and NY-ESO-1 in multiple myeloma patients after allogeneic stem cell transplantation. Cancer Immunol Immunother. 63(11):1151-1162 (2014).

Levy, R J, et al., Inhibition of Calcification of Bioprosthetic Heart Valves by Local Controlled-Release Diphosphonate. Science 228(4696):190-192 (1985).

Li, B. et al., "Landscape of tumor-infiltrating T cell repertoire of human cancers," Nature Genetics, 2016, vol. 48, No. 7, pp. 725-735.

Li, F. et al., "T cell receptor B-chain-targeting chimeric antigen receptor T cells against T cell malignancies," Nature Communications, 2022;13:4334.

Li, Hanchen, et al., Tumor Microenvironment: The Role of the Tumor Stroma in Cancer. Journal of Cellular Biochemistry 101(4):805-815 (2007).

Li, Peng, et al., Design and Synthesis of Paclitaxel Conjugated with an ErbB2-recognizing Peptide, EC-1. Biopolymers 87(4):225-230 (2007).

Liddy et al.: Monoclonal TCR-redirected tumor cell killing. Nat Med. 18(6):980-987 doi:10.1038/nm.2764 (2012).

Liu, Alvin, et al., Chimeric Mouse-human IgG1 Antibody that can Mediate Lysis of Cancer Cells. Proceedings of the National Academy of Sciences of the United States of America 84(10):3439-3443 (1987).

Liu, Alvin, et al., Production of a Mouse-human Chimeric Monoclonal Antibody to CD20 With Potent Fc-dependent Biologic Activity. Journal of Immunology 139(10):3521-3526 (1987).

Liu, Der-Zen, et al., Synthesis of 2'-paclitaxel Methyl 2-glucopyranosyl Succinate for Specific Targeted Delivery to Cancer Cells. Bioorganic & Medicinal Chemistry Letters 17(3):617-620 (2007).

Liu, D.V. et al., "Engineered Interleukin-2 Antagonists for the Inhibition of Regulatory T Cells," J. Immunother., 2009;32(9):887-894.

Liu, J, et al., Calcineurin is a Common Target of Cyclophilin-Cyclosporin A and FKBP-FK506 Complexes. Cell 66(4):807-815 (1991).

Liu, K. et al., "CD123 and its potential clinical application in leukemias," Life Sciences, 2015;122:59-64.

Lloyd et al., Modelling the Human Immune Response: Performance of a 10" Human Antibody Repertoire Against a Broad Panel of Therapeutically Relevant Antigens. Protein Engineering Design & Selection. 22(3):159-168 (2009).

Lobuglio, Albert, et al., Phase I Clinical Trial of CO17-1A Monoclonal Antibody. Hybridomia 5(1):S117-S123 (1986).

Lonberg, Nils, et al., Antigen-Specific Human Antibodies From Mice Comprising Four Distinct Genetic Modifications. Nature 368(6474):856-859 (1994).

Luo, S. et al., "Worldwide genetic variation of the IGHV and TRBV immune receptor gene families in humans" (2019) Life Sciences Alliance, vol. 2, No. 2, p. 1-9.

Lustgarten, J. et al., "Redirecting Effector T Cells through their IL-2 receptors," J Immunology, 1999;162:359-365.

Maciocia, P. M. et al., "Targeting the T cell receptor B-chain constant region for immunotherapy of T cell malignancies", Nature Medicine, 2017, vol. 23, No. 12, pp. 1416-1423.

Mackay, C.R. et al., "Gamma/delta T cells express a unique surface molecule appearing late during thymic development," Eur J Immunol., 1989;19(8):1477-1483.

Macor, P. et al., "Bispecific antibodies targeting tumor-associated antigens and neutralizing complement regulators increase the efficacy of antibody-based immunotherapy in mice", Leukemia, 2015, vol. 29, pp. 406-414.

Mandelboim, O. et al., "Recognition of hemagglutinins on virus-infected cells by NKp46 activates lysis by human NK cells", Nature, 2001, vol. 409, No. 6823, pp. 1055-1060.

(56) References Cited

OTHER PUBLICATIONS

Mao et al.: Inhibition of human natural killer cell activity by influenza virions and hemagglutinin. Journal of Virology 84(9 ):4148-4157 (2010).
Martens, Tobias, et al., A Novel One-Armed Anti-c-Met Antibody Inhibits Glioblastoma Growth In Vivo. Clinical Cancer Research 12(20 Pt 1):6144-6152 (2006).
Martin, A. et al., "Chapter 3: Protein Sequence and Structure Analysis of Antibody Variable Domains", In: Antibody Engineering Lab Manual (Ed: Duebel, S. and Kontermann, R., Springer- Verlag, Heidelberg), 2010, vol. 2, pp. 33-51.
Martin, F. et al., "The affinity-selection of a minibody polypeptide inhibitor of human interleukin-6", EMBO J., 1994, vol. 13, No. 22, pp. 5303-5309.
McConnell, Stephen, et al., Tendamistat as a Scaffold for Conformationally Constrained Phage Peptide Libraries. Journal of Molecular Biology 250(4):460-470 (1995).
McElroy et al.: Structural and Biophysical Studies of the Human IL-7/IL-7R alpha Complex. Structure 17(1):54-65 (2009).
Merchant, A.M. et al., "An efficient route to human bispecific IgG," Nature Biotechnology, 1998;16(7):677-681.
Meschendoerfer, W. et al., "SPR-based assays enable the full functional analysis of bispecific molecules," Journal of Pharmaceutical and Biomedical Analysis, 2017, vol. 5, No. 132, pp. 141-147.
Meyers, E. et al., "Optimal alignments in linear space", CABIOS,1988, vol. 4, No. 1, pp. 11-17.
Michelacci, Y M, et al., A Comparative Study Between a Chondroitinase B and a Chondroitinase AC From Flavobacterium Heparinum: Isolation of a Chondroitinase AC-Susceptible Dodecasaccharide From Chondroitin Sulphate B. The Biochemical Journal 151(1):121-129 (1975).
Michelacci, Yara, et al., Isolation and Partial Characterization of an Induced Chondroitinase B from Flavobacterium Heparinum. Biochemical and Biophysical Research Communications 56(4):973-980 (1974).
Miller et al.: Trispecific Killer Engagers (TrikEs) that contain IL-15 to make NK cells antigen specific and to sustain their persistence and expansion. Blood 126(23):232-232 (2015).
Milone, Michael, et al., Chimeric Receptors Containing CD137 Signal Transduction Domains Mediate Enhanced Survival of T Cells and Increased Antileukemic Efficacy in Vivo. Molecular Therapy 17(8):1453-1464 (2009).
Mitra, S. et al., "Interleukin-2 Activity can be Fine-Tuned with Engineering Receptor Signaling Clamps," Immunity, 2015;42(5):826-838.
Miyahara, Y et al., Anti-TCRβ mAb induces long-term allograft survival by reducing antigen-reactive T cells and sparing regulatory T cells, American journal of transplantation: official Journal of the American Society of Transplantation and the American Society of Transplant Surgeons, vol. 12, 6 (2012): 1409-18.
Modak et al.: Disialoganglioside GD2 and a novel tumor antigen: potential targets for immunotherapy of desmoplastic small round cell tumor. Med Pediatr Oncol. 39(6):547-551 (2002).
Moore, Gregory, et al., A Novel Bispecific Antibody Format Enables Simultaneous Bivalent and Monovalent Co-engagement of Distinct Target Antigens. mAbs 3(6):546-557 (2011).
Morel et al.: Processing of some antigens by the standard proteasome but not by the immunoproteasome results in poor presentation by dendritic cells. Immunity. 12(1):107-117 doi:10.1016/s1074-7613(00)80163-6 (2000).
Morrison, Sherie, et al., Chimeric Human Antibody Molecules: Mouse Antigen-binding Domains With Human Constant Region Domains. Proceedings of the National Academy of Sciences of the United States of America 81(21):6851-6855 (1984).
Morrison, Sherie, Transfectomas Provide Novel Chimeric Antibodies. Science 229(4719):1202-1207 (1985).
Muller, K.P. et al., "T cell receptor targeting to thymic cortical epithelial cells in vivo induces survival, activation and differentiation of immature thymocytes," Eur. J. Immunol., 1993;23(7):1661-1670.
Murer, P. et al., "Antibody-cytokine fusion proteins: A novel class of biopharmaceuticals for the therapy of cancer and of chronic inflammation", New Biotechnology, 2019, vol. 52, pp. 42-53.
Murzin, A G, et al., SCOP: A Structural Classification of Proteins Database for the Investigation of Sequences and Structures. Journal of Molecular Biology 247(4):536-540 (1995).
Nagarajan et al.: Ligand binding and phagocytosis by CD16 (Fc gamma receptor III) isoforms. Phagocytic signaling by associated zeta and gamma subunits in Chinese hamster ovary cells. Journal of Biological Chemistry J Biol Chem. 270(43):25762-25770 (1995).
Naing, et al., "Strategies for improving the management of immune-related adverse events" Journal for ImmunoTherapy of Cancer, (2020) p. 1-9.
Nandi et al.: CD28-mediated costimulation is necessary for optimal proliferation of murine NK cells. J Immunol. 152(7):3361-3369 (1994).
Nangalia, J. et al., "Somatic CALR Mutations in Myeloproliferative Neoplasms with Nonmutated JAK2", N Engl J Med., 2013, vol. 369, No. 25, pp. 2391-2405.
Needleman, Saul, et al., A General Method Applicable to the Search for Similarities in the Amino Acid Sequence of Two Proteins. Journal of Molecular Biology 48(3):444-453 (1970).
Newman et al.: Combining Early Heat Shock Protein Vaccination with Directed IL-2 Leads to Effective Anti-Tumor Immunity in Autologous Hematopoietic Cell Transplantation Recipients. 118(21):998-998 (2011).
Niederberger, N. et al., "Thymocyte stimulation by anti-TCR-b, but not by anti-TCR-a, leads to induction of developmental transcription program," Journal of Leukoeyte Biology, 2005;77(5):830-841.
Nishimura, Yushi, et al., Recombinant Human-Mouse Chimeric Monoclonal Antibody Specific for Common Acute Lymphocytic Leukemia Antigen. Cancer Research 47(4):999-1005 (1987).
No Author "PE anti-human TCR VB23 Antibody" (2012).
No Author "PE anti-mouse TCR VB6 Antibody" (2012).
Nolo, R. et al., "Targeting P-selection blocks neuroblastoma growth", Oncotarget, 2017, vol. 8, No. 49, pp. 86657-86670.
Novellino et al.: A listing of human tumor antigens recognized by T cells: Mar. 2004 update. Cancer Immunol Immunother. 54(3):187-207 doi:10.1007/s00262-004-0560-6 (2005).
Oh, Julyun, et al., Single Variable Domains From the T Cell Receptor B Chain Function as Mono- and Bifunctional CARs and TCRs. Scientific Reports 9(1):17291, 1-12 (2019).
Oi, Vernon, et al., Chimeric Antibodies. BioTechniques 4(3):214-221 (1986).
Ortiz-Sanchez, Elizabeth, et al., Antibody-Cytokine Fusion Proteins: Applications in Cancer Therapy. Expert Opinion on Biological Therapy 8(5):609-632 (2008).
Page, David, et al., Deep Sequencing of T-cell Receptor DNA as a Biomarker of Clonally Expanded TILs in Breast Cancer after Immunotherapy. Cancer Immunology Research 4(10):835-844 (2016).
Pardoll, D.M., "The blockade of immune checkpoints in cancer immunotherapy", Nat Rev Cancer, 2012, Vo. 12, pp. 252-264.
Park, Y.P. et al., "Complex Regulation of human NKG2D-DAP10 cell surface expression: opposing roles of the yc cytokines and TGF-β1", Blood, 2011, vol. 118, No. 11, pp. 3019-3027.
Pasche, N. et al., "Immunocytokines: a novel class of potent armed antibodies, " Drug Discovery Today, 2012;17(11):583-590.
Paul, S. et al., "TCR beta chain-directed bispecific antibodies for the treatment of T-cell cancers," Science Translational Medicine, 2021, pp. 1-21.
Payne, J. et al., "Two Monoclonal Rat Antibodies with Specificity for the β-Chain Variable Region Vβ6 of the Murine T-Cell Receptor", Proc. Natl. Acad. Sci., 1988, vol. 85, pp. 7695-7698.
PCT/US2017/023483 International Search Report and Written Opinion dated Aug. 29, 2017.
PCT/US2018/029951 International Preliminary Report on Patentability dated Oct. 29, 2019.
PCT/US2018/029951 International Search Report and Written Opinion dated Mar. 7, 2018.
PCT/US2019/022284 International Preliminary Report on Patentability dated Sep. 15, 2020.
PCT/US2019/022284 International Search Report and Written Opinion dated Sep. 10, 2019.

(56) References Cited

OTHER PUBLICATIONS

PCT/US2020/019324 International Preliminary Report on Patentability dated Aug. 10, 2021.
PCT/US2020/019324 International Search Report and Written Opinion dated Jun. 10, 2020.
Pettit et al.: Structure-function studies of interleukin 15 using site-specific mutagenesis, polyethylene glycol conjugation, and homology modeling. J Biol Chem. 272(4):2312-2318 (1997).
Pilch, H, et al., Improved Assessment of T-Cell Receptor (TCR) VB Repertoire in Clinical Specimens: Combination of TCR-CDR3 Spectratyping with Flow Cytometry-Based TCR VB Frequency Analysis. Clinical and Diagnostic Laboratory Immunology 9(2):257-266 (2002).
Posnett, D.N. et al., "Inherited polymorphism of the human T-cell antigen receptor detected by a monoclonal antibody," PNAS, 1986;83:7888-7892.
Presta, Leonard, Antibody Engineering. Current Opinion in Structural Biology 2(4):593-596 (1992).
Provenzano et al.: Enzymatic targeting of the stroma ablates physical barriers to treatment of pancreatic ductal adenocarcinoma. Cancer Cell. 21(3):418-429 doi:10.1016/j.ccr.2012.01.007 (2012).
Qi, et al., "Potent and selective antitumor activity of a T cell-engaging bispecific antibody targeting a membrane-proximal epitope of ROR1," PNAS, 2018;115(24):E5467-E5476.
Rabia, L. et al., "Understanding and overcoming trade-offs between antibody affinity, specificity, stability and solubility," Biochemical Engineering Journal, 2018;137:365-374.
Rakoff-Nahoum, Seth, et al., Toll-like Receptors and Cancer. Nature Reviews Cancer 9(1):57-63 (2009).
Rath, et al., "Engineering Strategies to Enhance TCR-Based Adoptive T Cell Therapy" (2020) Cells, 9, 1485, p. 1-34.
Reiter, Yoram, et al., Antibody Engineering of Recombinant Fv Immunotoxins for Improved Targeting of Cancer: Disulfide-stabilized Fv Immunotoxins. Clin Cancer Res 2(2):245-252 (1996).
Ridgway, John, et al., Knobs-Into-Holes Engineering of Antibody CH3 Domains for Heavy Chain Heterodimerization. Protein Engineering 9(7):617-621 (1996).
Riechmann, L, et al., Reshaping Human Antibodies for Therapy. Nature 332(6162):323-327 (1988).
Riemer, A.B. et al., "Matching of trastuzumab (Herceptin) epitope mimics onto the surface of Her-2/neu—a new method of epitope definition," Molecular Immunology, 2005;42:1121-1124.
Ring et al.: Mechanistic and structural insight into the functional dichotomy between interleukin-2 and interleukin-15. Nat Immunol. 13(12):1187-1195 (2012).
Roda-Navarro, P. et al., "Understanding the Spatial Topology of Artificial Immunology Synapses Assembled in T Cell-Redirecting Strategies: A Major Issue in Cancer Immunotherapy", Frontiers in Cell and Developmental Biology, 2020, vol. 7, No. 370.
Rohena-Rivera et al.: IL-15 regulates migration, invasion, angiogenesis and genes associated with lipid metabolism and inflammation in prostate cancer. PloS one 12(4):e0172786:1-27 (2017).
Rosenberg, Steven, et al., Use of Tumor-Infiltrating Lymphocytes and Interleukin-2 in the Immunotherapy of Patients with Metastatic Melanoma. The New England Journal of Medicine 319(25):1676-1680 (1988).
Rudikoff et al.: Single Amino Acid Substitution Altering Antigen-binding Specificity. Pnas USA 79(6):1979-1983 (1982).
Ruggiero, Eliana, et al., High-resolution Analysis of the Human T-Cell Receptor Repertoire. Nature Communication 6:8081, 1-7 (2014).
Salameire, et al., "Accurate detection of the tumor clone in peripheral T-cell lymphoma biopsies by flow cytometric analysis of TCR-V B repertoire" Modern Pathology (2012) 25, p. 1246-1257.
Saleh, Mansoor, et al., A Phase II Trial of Murine Monoclonal Antibody 17-1A and Interferon-gamma: Clinical and Immunological Data. Cancer Immunology, Immunotherapy 32(3):185-190 (1990).

Sano, Y. et al., "Properties of Blocking and Non-blocking Monoclonal Antibodies Specific for Human Macrophage Galactose-type C-type Lectin (MGL/ClecSF10A/CD301)," J. Biochem., 2007;127-136.
Sastry, Konduru, et al., Targeting Hepatitis B virus-infected cells with a T-Cell Receptor-like Antibody. Journal of Virology 85(5):1935-1942 (2011).
Saudek et al. A preliminary trial of the programmable implantable medication system for insulin delivery. N. Engl. J. Med. 321(9):574-579 (1989).
Saunders, Kevin, Conceptual Approaches to Modulating Antibody Effector Functions and Circulation Half-Life. Frontiers in Immunology 10:1296, 1-20 (2019).
Schleinitz, N. et al., "Natural killer cells in human autoimmune diseases," Immunology, 2010;131(4):451-458.
Schliemann et al.: Targeting interleukin-2 to the bone marrow stroma for therapy of acute myeloid leukemia relapsing after allogeneic hematopoietic stem cell transplantation. Cancer immunology research 3(5 ):547-556 (2015).
Schmittnaegel, Martina, et al., Activation of Cytomegalovirus-Specific CD8+ T-cell response by Antibody-Mediated peptide-major Histocompatibility class I Complexes. OncoImmunology 5(1):e1052930, 1-3 (2015).
Scodeller, Pablo, Hyaluronidase and Other Extracellular Matrix Degrading Enzymes for Cancer Therapy: New Uses and Nano-Formulations, Journal of Carcinogenesis & Mutagenesis 5(4):1-5 (2014).
Sefton, Michael, Implantable Pumps. Critical Reviews in Biomedical Engineering 14(3):201-240 (1987).
Seidel, U. et al., "Natural killer cell mediated antibody-dependent cellular cytotoxicity in tumor immunotherapy with therapeutic antibodies", frontiers in Immunology, 2013, vol. 4, No. 76, pp. 1-8.
Sekine, T. et al., "A feasible method for expansion of peripheral blood lymphocytes by culture with immobilized anti-CD3 monoclonal antibody and interleukin-2 for use in adoptive immunotherapy of cancer patients," Biomed & Pharmacother, 1993;47:73-78.
Sen, S. et al., "Expression of epithelial cell adhesion molecule (EpCAM) in oral squamous cell carcinoma," Histopathology, 2015:6:897-904. Abstract only.
Sergeeva, Anna, et al., An Anti-PR1/HLA-A2 T-cell Receptor-like Antibody Mediates Complement-Dependent Cytotoxicity Against Acute Myeloid Leukemia Progenitor Cells. Blood 117(16):4262-4272 (2011).
Shaw, Denise, et al., Mouse/Human Chimeric Antibodies to a Tumor-Associated Antigen: Biologic Activity of the Four Human IgG Subclasses. Journal of the National Cancer Institute 80(19):1553-1559 (1988).
Shi, M. et al., "A recombinant anti-erbB2, scFv-Fc-IL-2 fusion protein retains antigen specificity and cytokine function," Biotechnology letters, 2003;25:815-819.
Shimabukuro-Vornhagen, Alexander, et al., Cytokine Release Syndrome. Journal for Immuno Therapy of Cancer 6(56):1-14 (2018).
Shitaoka, Kiyomi, et al., Identification of Tumoricidal TCRs from Tumor-Infiltrating Lymphocytes by Single-Cell Analysis. Cancer Immunology Research 6(4):378-388 (2018).
Shpilberg, O, et al., Subcutaneous Administration of Rituximab (MabThera) and Trastuzumab (Herceptin) using Hyaluronidase. British Journal of Cancer 109(6):1556-1561 (2013).
Skegro, D. et al., "Immunoglobulin domain interface exchange as a platform technology for the generation of Fc heterodimers and bispecific antibodies," J Biol Chem, 2017, vol. 292, No. 23, pp. 9745-9759.
Spiess, C. et al., "Alternative molecular formats and therapeutic applications for bispecific antibodies", Molecular Immunology, 2015, vol. 67, pp. 95-106.
Stauber, D.J. et al., "Crystal structure of the IL-2 signaling complex: Paradigm for a heterotrimeric cytokine receptor," PNAS, 2006;103(8):2788-2793.
Stauber et al.: Nuclear and cytoplasmic survivin: molecular mechanism, prognostic, and therapeutic potential. Cancer Res. 67(13):5999-6002 (2007).
Stivala, Alex, et al., Automatic Generation of Protein Structure Cartoons With Pro-origami. Bioinformatics 27(23):3315-3316 (2011).

(56) References Cited

OTHER PUBLICATIONS

Sun, Lee, et al., Chimeric Antibody With Human Constant Regions and Mouse Variable Regions Directed Against Carcinoma-Associated Antigen 17-1A. Proceedings of the National Academy of Sciences of the United States of America 84(1):214-218 (1987).
Suzuki, Sakaru, et al., Formation of Three Types of Disulfated Disaccharides from Chondroitin Sulfates by Chondroitinase Digestion. The Journal of Biological Chemistry 243(7):1543-1550 (1968).
Swencki-Underwood, B. et al., "Engineering human IL-18 with increased bioactivity and bioavailability," Cytokine, 2006, vol. 34, pp. 114-124.
Tang, et al., "Anti-TCR Antibody Treatment Activates a Novel Population of Nonintestinal CD8aa+TCRaB+ Regulatory T Cells and Prevents Experimental Autoimmune Encephalomyelitis" The Journal of Immunology (2007) p. 1-9.
Tassev, D V, et al., Retargeting NK92 Cells using an HLA-A2-Restricted, EBNA3C-Specific Chimeric Antigen Receptor. Cancer Gene Ther 19(2):84-100 (2012).
"Stein, et al., "A new monoclonal antibody (CAL2) detects CALRETICULIN mutations in formalin-fixed and paraffin-embedded bone marrow biopsies," Leukemia, Jul. 23, 2015, vol. 30, No. 1, pp. 131-135".
"Ten Hacken, et al., "Calreticulin as a novel B-cell receptor antigen in chronic lymphocytic leukemia," Haematologica, Oct. 31, 2017, vol. 102, No. 10, pp. E394-e396".
Thorpe, Philip, Vascular Targeting Agents as Cancer Therapeutics. Clinical Cancer Research 10(2):415-427 (2004).
Tomlinson, Ian, et al., The Repertoire of Human Germline VH Sequences Reveals About Fifty Groups of VH Segments With Different Hypervariable Loops. Journal of Molecular Biology 227(3):776-798 (1992).
Tomonari, K. et al., "Epitope-specific binding of CD8 regulates activation of T cells and induction of cytotoxicity," International Immunology, 1990;2(12):1189-1194.
Tramontano et al.: The making of the minibody: an engineered beta-protein for the display of conformationally constrained peptides. J. Mol. Recognition. 7:9-24 (1994).
Trenevska et al.: Therapeutic Antibodies against Intracellular Tumor Antigens. Front Immunol. 8:1001 doi:10.3389/fimmu.2017.01001 [1-12] (2017).
Tsytsikov, V.N. et al., "Identification and Characterization of Two Alternative Splice Variants of Human Interleukin-2*" The Journal of Biological Chemistry, 1996;71(38):23055-23060.
Tuaillon, Nadine, et al., Human Immunoglobulin Heavy-Chain Minilocus Recombination in Transgenic Mice: Gene-Segment Use in Mu and Gamma Transcripts. Proceedings of the National Academy of Sciences of the United States of America 90(8):3720-3724 (1993).
U.S. Appl. No. 17/529,017 Non-Final Office Action dated Apr. 27, 2022.
Vallera et al.: Heterodimeric bispecific single-chain variable-fragment antibodies against EpCAM and CD16 induce effective antibody-dependent cellular cytotoxicity against human carcinoma cells. Cancer Biother Radiopharm. 28(4):274-282 doi:10.1089/cbr.2012.1329 (2013).
Vannucchi, et al., "Calreticulin mutation-specific immunostaining in myeloproliferative neoplasms: pathogenetic insight and diagnostic value" Leukemia (2014) 28, p. 1811-1818.
Verhoeyen, M. et al., "Reshaping Human Antibodies: Grafting an Antilysozyme Activity", Science, 1988, vol. 239, pp. 1534-1536.
Verma, Bhavna, et al., TCR Mimic Monoclonal Antibody Targets a Specific Peptide/HLA Class I Complex and Significantly Impedes Tumor Growth In Vivo Using Breast Cancer Models. J Immunol 184(4):2156-2165 (2010).
Verwilghen, J. et al., "Differences in the stimulating capacity of immobilized anti-CD3 monoclonal antibodies: variable dependence on interleukin-1 as a helper signal for T-cell activation," 1991;72:269-276.

Vonderheid, Eric, et al., Evidence for Restricted VB Usage in the Leukemic Phase of Cutaneous T Cell Lymphoma. The Journal of Investigative Dermatology 124(3):650-661 (2005).
Vyas, M. et al., "Natural ligands and antibody-based fusion proteins: harnessing the immune system against cancer", Trends in Molecular Medicine, 2014, vol. 20, No. 2, pp. 72-82.
Wadia, P. et al., "Impaired lymphocyte responses and their restoration in oral cancer patients expressing distinct TCR variable region," Cancer Investigation, 2008;26:471-480.
Wagner, E.K. et al., "Engineering therapeutics antibodies to combat infectious disease," Current Opinion in Chemical Engineering, 2018:19;131-141.
Wan, Y.Y. et al., "'Yin-Yang' functions of TGF-b and tregs in immune regulation," Immunol Rev., 2007;220:199-213.
Wang, Chun-Yan, et al., $\alpha\beta$ T-Cell Receptor Bias in Disease and Therapy (Review). International Journal of Oncology 48(6):2247-2256 (2016).
Wang et al.: Cloning genes encoding MHC class II-restricted antigens: mutated CDC27 as a tumor antigen. Science 284(5418):1351-1354 doi:10.1126/science.284.5418.1351 (1999).
Wang et al.: RNA interference targeting CML66, a novel tumor antigen, inhibits proliferation, invasion and metastasis of HeLa cells. Cancer Lett. 269(1):127-138 (2008).
Wang, H. et al., "Preparation and functional identification of a monoclonal antibody against the recombinant soluble human NKp30 receptor," Internal Immunopharmacology, 2011;11(11):1732-1739.
Warren, H.S. et al., "Evidence that the cellular ligand for the Human NK Cell Activation Receptor NKp30 is not a Heparan Sulfate Glycosaminoglycan," The Journal of Immunology, 2005;175(1):207-212.
Wei, Shan, et al., Identification of a Novel Human T-cell Receptor V$\beta$ Subfamily by Genomic Cloning. Human Immunology 41(3):201-206 (1994).
Weidle, U. et al., "The Intriguing Options of Multispecific Antibody Formats for Treatment of Cancer", Cancer Genomics & Proteomics, 2013, vol. 1, pp. 1-18.
Weidle, U.H. et al., "Tumor-Antigen-Binding Bispecific Antibodies for Cancer Treatment", Seminars in Oncology, 2014, vol. 41, No. 5, pp. 653-660.
Williemsen, R A, et al., A Phage Display Selected Fab Fragment with MHC Class I-Restricted Specificity for MAGE-A1 allows for Retargeting of Primary Human T Lymphocytes. Gene Therapy 8(21):1601-1608 (2001).
Wood, Clive, et al., The Synthesis and in Vivo Assembly of Functional Antibodies in Yeast. Nature 314(6010):446-449 (1985).
Wu, M.R. et al., "B7H6-Specific Bispecific T Cell Engagers Lead to Tumor Elimination and Host Antitumor Immunity", The Journal of Immunology, 2015, vol. 194, No. 11, pp. 5305-5311.
Wurzer et al.: Nuclear Ras: unexpected subcellular distribution of oncogenic forms.J Cell Biochem Suppl. Suppl 36:1-11 doi:10.1002/jcb.1070 (2001).
Xiao, Y.F. et al., "Peptide-based treatment: A promising cancer therapy", Journal of Immunology Research, 2015, pp. 1-14.
Xiaoying, C. et al., "Fusion protein linkers: Property, design and functionality", Advanced Drug Delivery Reviews, 2012, vol. 65, No. 10, pp. 1357-1369.
Xu, Xiao-Jun, et al., Cytokine Release Syndrome in Cancer Immunotherapy with Chimeric Antigen Receptor Engineered T Cells. Cancer Letters 343(2):172-178 (2014).
Yamagata, Tatsuya, et al., Purification and Properties of Bacterial Chondroitinases and Chondrosulfatases. The Journal of Biological Chemistry 243(7):1523-1535 (1968).
Yassai, Maryam, et al., A Clonotype Nomenclature for T Cell Receptors. Immunogenetics 61(7):493-502 (2009).
Yoon et al.: Charged residues dominate a unique interlocking topography in the heterodimeric cytokine interleukin-12. The EMBO J. 19(14):3530-3541 (2000).
Yoon, S.T. et al., "Both high and low avidity antibodies to the T cell receptor can have agonist or antagonist activity," Immunity, 1994;1(7):563-569.
Zhang, T. et al., "Cancer Immunotherapy Using a Bispecific NK Receptor Fusion Protein that Engages both T Cells and Tumor Cells", Cancer Research, 2011, vol. 71, No. 6, pp. 2066-2076.

(56) References Cited

OTHER PUBLICATIONS

Agata, Yasutoshi et al. Expression of the PD-1 Antigen on the Surface of Stimulated Mouse T and B Lymphocytes. International Immunology 8(5):765-772 (1996).

Aggen, DH et al. Single-chain VαVβ T-cell Receptors Function Without Mispairing With Endogenous TCR Chains. Gene Therapy 19(4):365-374 (2012).

Akers, Michael J. et al. Formulation Development of Protein Dosage Forms. Pharmaceutical Biotechnology 14:47-127 (2002).

Akers, Michael J., et al. Peptides and proteins as parenteral solutions. Pharmaceutical formulation development of peptides and proteins. London: Taylor & Francis. pp. 145-77.(2000).

Allison, A C. The Mode of Action of Immunological Adjuvants. Developments in Biological Standardization 92:3-11 (1998).

Almagro, Juan C, and Johan Fransson. Humanization of Antibodies. Frontiers in Bioscience 13:1619-1633 (2008).

Anderson, et al. Anti-CD3 + IL-2-stimulated murine killer cells. In vitro generation and in vivo antitumor activity. J Immunol 142 (4): 1383-1394 (1989).

Baca, Manuel et al. Antibody Humanization Using Monovalent Phage Display. The Journal of Biological Chemistry 272(16):10678-10684 (1997).

Batzer, Mark A. et al. Enhanced Evolutionary PCR Using Oligonucleotides With Inosine At The 3'-Terminus. Nucleic Acids Research 19(18):5081 (1991).

Baxter, et al. Acquired mutation of the tyrosine kinase JAK2 in human myeloproliferative disorders. The Lancet. 2005. 365(9464):1054-1061.

Benati, Daniela et al. Public T Cell Receptors Confer High-avidity CD4 Responses to HIV Controllers. Journal of Clinical Investigation 126(6):2093-2108 (2016).

Bendig. Humanization of rodent monoclonal antibodies by CDR grafting. Methods: A Companion to Methods in Enzymology 8:83-93 (1995).

Berge, Stephen M. et al. Pharmaceutical Salts. Journal of Pharmaceutical Sciences 66(1):1-19 (1977).

Biomunex Pharmaceuticals, "Disruptive biological approaches in immunotherapy, based on next generation BiXAb® bi-and multi-specific antibody platform for cancer treatment," Mar. 2023 [PowerPoint Slides].

Blank, Christian et al. Interaction of PD-L1 on Tumor Cells with PD-1 on Tumor-Specific T cells as a Mechanism of Immune Evasion: Implications for Tumor Immunotherapy. Cancer Immunology, Immunotherapy 54(4):307-314 (2005). Published Online on Dec. 15, 2004.

Bloeman, PGM. et al. Adhesion Molecules: A New Target for Immunoliposome-mediated Drug Delivery. FEBS Letters 357:140-144 (1995).

Boerner, Paula et al. Production Of Antigen-Specific Human Monoclonal Antibodies From In Vitro-primed Human Splenocytes. Journal of Immunology 147(1):86-95 (1991).

Bonsignori et al. Maturation Pathway from Germline to Broad HIV-1 Neutralizer of a CD4-Mimic Antibody. Cell 165(2):449-463 (2016).

Borrebaeck, Carl A K. Antibody Engineering, Second Edition. Oxford University Press: 1-11 (1995).

Bovay, Amandine et al. T Cell Receptor Alpha Variable 12-2 Bias in the Immunodominant Response to Yellow Fever Virus. European Journal of Immunology 48(2):258-272 (2018).

Brennan, Maureen et al. Preparation of Bispecific Antibodies by Chemical Recombination of Monoclonal Immunoglobulin G1 Fragments. Science 229(4708):81-83 (1985).

Brennan, Rebekah M. et al. Predictable Alphabeta T-cell Receptor Selection Toward an HLA-B*3501-restricted Human Cytomegalovirus Epitope. Journal of Virology 81(13):7269-7273 (2007).

Brey, et al. A gB/CD3 bispecific BiTE antibody construct for targeting Human Cytomegalovirus-infected cells. Sci Rep 28;8(1):17453 (2018). 12 pages.

Briscoe, Page et al. Delivery of Superoxide Dismutase to Pulmonary Epithelium via pH-sensitive Liposomes. American Journal of Physiology 268(3 Pt 1):L374-L380 (1995).

Brodeur, Bernard R. et al. Monoclonal Antibody Production Techniques and Applications. New York: Marcel Dekker:51-63 (1987).

Buckland, et al. Fusion glycoprotein of measles virus: nucleotide sequence of the gene and comparison with other paramyxoviruses. Journal of General Virology 68(6):1695-1703 (1987).

Bulek, Anna M. et al. Structural Basis of Human B-cell Killing by CD8+ T cells in Type 1 Diabetes. Nature Immunology 13(3):283-289 (2012).

Cadwell, Craig R, and Gerald F. Joyce. Randomization of Genes by PCR Mutagenesis. PCR Methods and Applications 2(1):28-33 (1992).

Caldas, Cristina et al. Humanization of the anti-CD18 antibody 6.7: an unexpected effect of a framework residue in binding to antigen. Molecular immunology 39(15):941-952 (2003).

Campbell, Peter J. The long-term outlook for essential thrombocythemia. Mayo Clin Proc 81(2):157-8 (2006).

Campbell, Peter J. The myeloproliferative disorders. N Engl J Med 355(23):2452-66 (2006).

Campisi, Laura et al. Clonally Expanded CD8 T Cells Characterize Amyotrophic Lateral Sclerosis-4. Nature 606(7916):945-952 (2022).

Carnero Contentti, Edgar, et al. Mucosal-Associated Invariant T Cell Features and TCR Repertoire Characteristics During the Course of Multiple Sclerosis. Frontiers in Immunology 10:1-17 (2019).

Carter, Laura L et al. PD-1: PD-L Inhibitory Pathway Affects both CD4(+) and CD8(+) T Cells and is Overcome by IL-2. European Journal of Immunology 32(3):634-643 (2002).

Carter, Paul et al. Humanization of an Anti-p185HER2 Antibody for Human Cancer Therapy. PNAS USA 89(10):4285-4289 (1992).

Cazzola, Mario, and Robert Kralovics. From Janus Kinase 2 to Calreticulin: The Clinically Relevant Genomic Landscape of Myeloproliferative Neoplasms. Blood 123(24):3714-3719 (2014).

Chancellor, A. et al., "CD1b-restricted Gem T cell responses are modulated by *Mycobacterium tuberculosis* mycolic acid meromycolate chains," PNAS, 2017;114(51):E10956-E10964.

Chang, et al. Opportunities and challenges for TCR mimic antibodies in cancer therapy. Expert Opinion on Biological Therapy 16(8):979-987 (2016).

Chari, Ravi V.J. et al. Immunoconjugates Containing Novel Maytansinoids: Promising Anticancer Drugs. Cancer Research 52(1):127-131 (1992).

Charlton, Keith A. Expression and Isolation of Recombinant Antibody Fragments in *E. coli*. Chapter 14. Methods in Molecular Biology 248:245-254 (2003).

Chen, Lan et al. The T Cell Repertoires from Nickel Sensitized Joint Implant Failure Patients. International Journal of Molecular Sciences 22(5):2428, 1-13 (2021).

Chen, Yvonne et al. Selection and Analysis of an Optimized Anti-VEGF Antibody: Crystal Structure of an Affinity-matured Fab in Complex With Antigen. Journal of Molecular Biology 293(4):865-881 (1999).

Choi, Yangwon et al. A method for production of antibodies to human T-cell receptor beta-chain variable regions. Proc Natl Acad Sci USA 88(19):8357-8361 (1991).

Chowdhury, Partha S. Engineering Hot Spots for Affinity Enhancement of Antibodies. Methods in Molecular Biology 207:179-196 (2003).

ClinicalTrials.gov Identifier: NCT00001846. Collection and Distribution of Blood Components From Healthy Donors for In Vitro Research Use, Record created Nov. 3, 1999. pp. 1-10. [retrieved on Aug. 22, 2024] Available at URL: https://clinicaltrials.gov/study/NCT00001846.

ClinicalTrials.gov Identifier: NCT01004822. A Safety, Tolerability, And Pharmacokinetic Trial With CVX-241 In Patients With Advanced Solid Tumors, Record created Oct. 28, 2009. pp. 1-17. [retrieved on Jul. 12, 2024] Available at URL: https://clinicaltrials.gov/study/NCT01004822?cond=NCT01004822&rank=1.

ClinicalTrials.gov Identifier: NCT03427411. M7824 in Subjects With HPV Associated Malignancies, Record created Feb. 8, 2018. pp. 1-19. [retrieved on Aug. 22, 2024] Available at URL: https://clinicaltrials.gov/study/NCT03427411?term=NCT03427411&rank=1.

(56) References Cited

OTHER PUBLICATIONS

Clynes, Raphael et al. Fc Receptors Are Required in Passive and Active Immunity to Melanoma. Proceedings of the National Academy of Sciences of the United States of America 95(2):652-656 (1998).
Cole, David K. et al. Germ Line-governed Recognition of a Cancer Epitope by an Immunodominant Human T-cell Receptor. Journal of Biological Chemistry 284(40):27281-27289 (2009).
Connolly, James L. et al. Tumor Structure and Tumor Stroma Generation. 6th Edition. Holland-Frei Cancer Medicine :1-5 (2003).
Consonni, M. et al., "Human T cells engineered with a leukemia lipid-specific TCR enables donor-unrestricted recognition of CD1c-expressing leukemia," Nat Commun., 2021; 12(1):4844.
Co-pending U.S. Appl. No. 18/286,062, inventors Andreas; Loew et al., filed Oct. 6, 2023.
Co-pending U.S. Appl. No. 18/431,634, inventors Seng-Lai; Tan et al., filed Feb. 2, 2024.
Co-pending U.S. Appl. No. 18/654,860, inventors Hayday; Adrian et al., filed May 3, 2024.
Co-pending U.S. Appl. No. 18/659,544, inventors Andreas; Loew et al., filed May 9, 2024.
Co-pending U.S. Appl. No. 18/749,969, inventors Hsu; Jonathan et al., filed Jun. 21, 2024.
Co-pending U.S. Appl. No. 18/779,692, inventor Andreas; Loew, filed Jul. 22, 2024.
Cragg, Mark S, and Martin J Glennie et al. Antibody Specificity Controls in Vivo Effector Mechanisms of anti-CD20 Reagents. Blood 103(7):2738-2743 (2004).
Cragg, Mark S. et al. Complement-mediated Lysis by Anti-CD20 mAb Correlates with Segregation into Lipid Rafts. Blood 101(3):1045-1052 (2003).
Crowther, Michael D. et al. Genome-wide CRISPR-Cas9 Screening Reveals Ubiquitous T Cell Cancer Targeting via the Monomorphic MHC Class I-related Protein MR1. Nature Immunology 21(2):178-185 (2020).
Cunningham, Brian C, and James A. Wells. High-resolution Epitope Mapping of hGH-receptor Interactions by Alanine-scanning Mutagenesis. Science 244(4908):1081-1085 (1989).
Dahal-Koirala, S. et al. TCR Sequencing of Single Cells Reactive to DQ2.5-glia-α2 and DQ2.5-glia-ω2 Reveals Clonal Expansion and Epitope-specific V-gene Usage. 9(3):587-596 (2016).
Dall'Acqua, William F. et al. Antibody Humanization by Framework Shuffling. Methods 36(1):43-60 (2005).
Deak, Laura Codarri, et al., PD-1-cis IL-2R Agonism Yields Better Effectors from Stem-like CD8+ T Cells. Nature 610(7930):161-172 (2022).
Delhommeau, François et al. Mutation in TET2 in Myeloid Cancers. N Engl J Med 360(22):2289-2301 (2009).
Dimasi, Nazzareno et al. The Design and Characterization of Oligospecific Antibodies for Simultaneous Targeting of Multiple Disease Mediators. Journal of Molecular Biology 393(3):672-692 (2009).
Diskin, Ron et al. Increasing the Potency and Breadth of an HIV Antibody by Using Structure-based Rational Design. Science 334(6060):1289-1293 (2011).
Dong, Haidong, and Lieping Chen. B7-H1 Pathway and its Role in the Evasion of Tumor Immunity. Journal of Molecular Medicine 81(5):281-287 (2003).
Draghi, et al. P530 Novel bispecific antibody targeting NKp30 receptor enhances NK-mediated killing activity against multiple myeloma cells and overcomes CD16A deficiency. Abstract. In Meeting Abstracts: 33rd Annual Meeting & Pre-Conference Programs of the Society for Immunotherapy of Cancer (STIC 2018). 8 pages.
Du, Jiamu et al. Molecular basis of recognition of human osteopontin by 23C3, a potential therapeutic antibody for treatment of rheumatoid arthritis. Journal of molecular biology 382(4):835-842 (2008).
Dubowchik, Gene M. et al. Doxorubicin Immunoconjugates Containing Bivalent, Lysosomally-cleavable Dipeptide Linkages. Bioorganic & Medicinal Chemistry Letters 12(11):1529-1532 (2002).
Duncan, Alexander R, and Greg Winter. The Binding Site for C1q on IgG. Nature 332(6166):738-740 (1988).
Dupuis, Marc et al. Dendritic Cells Internalize Vaccine Adjuvant After Intramuscular Injection. Cell Immunology 186(1):18-27 (1998).
Edwards, Bryan M. et al. The Remarkable Flexibility of the Human Antibody Repertoire; Isolation of Over One Thousand Different Antibodies to a Single Protein, BLyS. Journal of Molecular Biology 334(1):103-118 (2003).
Ernst, et al. Inactivating mutations of the histone methyltransferase gene EZH2 in myeloid disorders. Nat Genet 42(8):722-6 (2010).
Fellouse, Frederic A. et al. Synthetic Antibodies From a Four-amino-acid Code: a Dominant Role for Tyrosine in Antigen Recognition. Proceedings of the National Academy of Sciences 24:101(34):12467-12472 (2004).
Fernandez-Sesma, Ana et al. A bispecific antibody recognizing influenza A virus M2 protein redirects effector cells to inhibit virus replication in vitro. Journal of virology 70(7):4800-4804 (1996).
Ferrari De Andrade, et al. Natural killer cells are essential for the ability of BRAF inhibitors to control BRAFV600E-mutant metastatic melanoma. Cancer research 74(24):7298-7308 (2014).
Fix, J A et al. Oral Controlled Release Technology for Peptides: Status and Future Prospects. Pharmaceutical research 13(12):1760-1764 (1996).
Flatman, Stephen et al. Process Analytics for Purification of Monoclonal Antibodies. Journal of Chromatography 848:79-87 (2007). Published Online on Dec. 11, 2006.
Fontana, Angelo et al. Probing the Partly Folded States of Proteins by Limited Proteolysis. Folding & Design 2(2):R17-R26 (1997).
Freeman, Gordon et al. Engagement of the PD-1 Immunoinhibitory Receptor by a Novel B7 Family Member Leads To Negative Regulation Of Lymphocyte Activation. Journal Of Experimental Medicine 192(7):1027-1034 (2000).
Frick, Rahel et al. A TRAV26-1-encoded Recognition Motif Focuses the Biased T Cell Response in Celiac Disease. European Journal of Immunology 50(1):142-145 (2020).
Gabrilovich, D I. et al. IL-12 And Mutant P53 Peptide-Pulsed Dendritic Cells For The Specific Immunotherapy Of Cancer. Journal of Immunotherapy with Emphasis on Tumor Immunology 19(6):414-418 (1996).
Gacerez, Albert T. et al. How Chimeric Antigen Receptor Design Affects Adoptive T Cell Therapy. Journal of cellular physiology 231(12):2590-2598 (2016).
Galvin, Teresa A. Effect of different promoters on immune responses elicited by HIV-1 gag/env multigenic DNA vaccine in Macaca mulatta and Macaca nemestrina. Vaccine 18(23):2566-2583 (2000).
Gamvrellis, Anita et al. Vaccines That Facilitate Antigen Entry Into Dendritic Cells. Immunology & Cell Biology 82(5):506-516 (2004).
Gazzano-Santoro, Helene et al. A Non-radioactive Complement-dependent Cytotoxicity Assay For Anti-cd20 Monoclonal Antibody. Journal Of Immunological Methods 202(2):163-171 (1996).
Gedda, Mallikarjuna R. et al. Longitudinal transcriptional analysis of peripheral blood leukocytes in COVID-19 convalescent donors. J Transl Med 20(1):587, 1-16 (2022).
GenBank Accession No. 2ERJ_D. Version 2ERJ_D. Chain D, Interleukin-2. Record created Mar. 21, 2006. 2 pages. Retrieved Jul. 15, 2024 at URL: https://www.ncbi.nlm.nih.gov/protein/90109213.
GenBank Accession No. AAA62478.2. Version No. AAA62478.2. induced by lymphocyte activation; similar to Human receptor protein encoded by GenBank Accession No. U03397 [*Homo sapiens*]. Record created Jun. 12, 1993. 2 Pages. Retrieved Aug. 1, 2024 at URL: https://www.ncbi.nlm.nih.gov/protein/AAA62478.
GenBank Accession No. AAH66254. Version No. AAH66254.1. Interleukin 2 [*Homo sapiens*]. Record created Feb. 12, 2004. 2 Pages. Retrieved Jul. 12, 2024 at URL: https://www.ncbi.nlm.nih.gov/protein/AAH66254.
GenBank Accession No. BAG36664. Version No. BAG36664.1. unnamed protein product [*Homo sapiens*]. Record created May 23, 2008. 2 Pages. Retrieved Aug. 1, 2024 at URL: https://www.ncbi.nlm.nih.gov/protein/BAG36664.
GenBank Accession No. NM_005191. Version No. NM_005191.4. *Homo sapiens* CD80 Molecule (CD80), mRNA. Record created May 24, 1999. Retrieved Aug. 2, 2024. Retrieved from: https://www.ncbi.nlm.nih.gov/nuccore/NM_005191.

(56) References Cited

OTHER PUBLICATIONS

GenBank Accession No. NP002174. Version No. NP_002174.1. interleukin-3 receptor subunit alpha isoform 1 precursor [*Homo sapiens*]. Record created Mar. 14, 2021. 3 Pages. Retrieved Aug. 1, 2024 at URL: https://www.ncbi.nlm.nih.gov/protein/NP_002174.
Gerngross, Tillman U. Advances In The Production Of Human Therapeutic Proteins In Yeasts and Filamentous Fungi. Nature Biotechnology 22(11):1409-1414 (2004).
Giaccone, Giuseppe. et al. A phase I study of the natural killer T-cell ligand alpha-galactosylceramide (KRN7000) in patients with solid tumors. Clinical cancer research 8(12):3702-3709 (2002).
Godfrey, Dale I. et al. The Burgeoning Family of Unconventional T Cells. Nature Immunology 16(11):1114-1123 (2015).
Graham, Frank L. et al. Characteristics of a Human Cell line Transformed by DNA from Human Adenovirus type 5. Journal of General Virology 36(1):59-72 (1977).
Gruber, Meegan et al. Efficient Tumor Cell Lysis Mediated By A Bispecific Single Chain Antibody Expressed In *Escherichia coli*. Journal Of Immunology 152(11):5368-5374 (1994).
Gussow et al., Chapter 5: Humanization of Monoclonal Antibodies. Methods in Enzymology. 203:99-121 (1991).
Hamers-Casterman, C. et al. Naturally Occurring Antibodies Devoid of Light Chains. Nature 363(6428):446-448 (1993).
Harutyunyan, et al. p53 lesions in leukemic transformation. N Engl J Med 364(5):488-90 (2011).
Harutyunyan, et al. Rare germline variants in regions of loss of heterozygosity may influence clinical course of hematological malignancies. Leukemia 25(11):1782-4 (2011).
Hashimoto, M, et al., PD-1 Combination Therapy with IL-2 Modifies CD8+ T Cell Exhaustion Program. Nature 610(7930):173-181 (2022).
He, X.Y. et al. TRAV gene expression in PBMCs and TILs in patients with breast cancer analyzed by a DNA melting curve (FQ-PCR) technique for TCR a chain CDR3 spectratyping. Neoplasma 59(6):693-699 (2012).
Helliwell, P S, and W J Taylor. Classification and Diagnostic Criteria for Psoriatic Arthritis. Annals of the Rheumatic Diseases 64(Suppl 2):ii3-ii8 (2005).
Hinks, Timothy S. C. and Xia-Wei Zhang. MAIT Cell Activation and Functions. Frontiers in Immunology 11:1014, 1-10 (2020).
Hinman, Lois M. et al. Preparation And Characterization Of Monoclonal Antibody Conjugates Of The Calicheamicins: A Novel And Potent Family Of Antitumor Antibiotics. Cancer Research 53(14):3336-3342 (1993).
Holliger, Philipp et al. "Diabodies": Small Bivalent and Bispecific Antibody Fragments. Proceedings of the National Academy of Sciences of the United States of America 90(14):6444-6448 (1993).
Holmström, M O. et al. The calreticulin (CALR) exon 9 mutations are promising targets for cancer immune therapy. Leukemia 32(2):429-437 (2018).
Holmström, Morten Orebo, and Hans Carl Hasselbalch. Cancer immune therapy for myeloid malignancies: present and future. Seminars in Immunopathology 41(1):97-109 (2019).
Holmstrom, M O. et al. The CALR Exon 9 Mutations Are Shared Neoantigens in Patients With Calr Mutant Chronic Myeloproliferative Neoplasms. Leukemia 30(12):2413-2416 (2016).
Hong, Sung Noh et al. Reduced diversity of intestinal T-cell receptor repertoire in patients with Crohn's disease. Frontiers in Cellular and Infection Microbiology 12:1-12 (2022).
Hoogenboom, Hennie R, and Greg Winter. By-Passing Immunisation: Human Antibodies From Synthetic Repertoires Of Germline VH Gene Segments Rearranged In Vitro. Journal of Molecular Biology 227(2):381-388 (1992).
Hoogenboom, Hennie R. Overview Of Antibody Phage-display Technology And Its Applications. Methods In Molecular Biology 178:1-37 (2002).
Horna, Pedro et al. Utility of TRBC1 expression in the diagnosis of peripheral blood involvement by cutaneous T-cell lymphoma. Journal of Investigative Dermatology 141(4):821-829.e2 (2021).

Howson, Lauren J. et al. MAIT cell clonal expansion and TCR repertoire shaping in human volunteers challenged with Salmonella Paratyphi A. Nat Commun 9(1):253, 1-11 (2018).
Hsu, Jonathan et al. AT cell receptor β chain-directed antibody fusion molecule activates and expands subsets of T cells to promote antitumor activity. Science translational medicine 15(724):eadi0258, 1-18 (2023).
Hsu, Jonathan et al. Supplementary Materials for: A T Cell Receptor β Chain-directed Antibody Fusion Molecule Activates and Expands Subsets of T Cells to Promote Antitumor Activity. Science Translational Medicine 15(724):eadi0258, 1-39 (2023).
Huang, Huang et al. Select sequencing of clonally expanded CD8+ T cells reveals limits to clonal expansion. Proc Natl Acad Sci U S A 116(18):8995-9001 (2019).
Huda, Taha I. et al. Specific HLA Alleles, Paired With TCR V- and J-gene Segment Usage, Link to Distinct Multiple Myeloma Survival Rates. Leukemia & Lymphoma 62(7):1711-1720 (2021).
Hudson, Peter J, and Christelle Souriau. Engineered Antibodies. Nature Medicine 9(1):129-134 (2003).
Human NKp30/NCR3 Antibody. Catalog No. MAB1849. Clone 210845 was used by HLDA to establish CD designation. [Website] R&D Systems. Retrieved Jul. 27, 2024 at URL: https://www.rndsystems.com/products/human-nkp30-ncr3-antibody-210845_mab1849. 7 pages.
Human NKp30/NCR3 Antibody. Catalog No. MAB18491. Source: Monoclonal Mouse IgG2A Clone No. 210847. [Website] R&D Systems. Retrieved Nov. 23, 2023 at URL: https://www.rndsystems.com/products/human-nkp30-ncr3-antibody-210847_mab18491#productdetails. 6 pages.
Hussain, Khiyam et al. 1392 An Atypical Central Memory like Phenotype Can be Induced in Human T Cells by Innate TCRa Engagement. J. Immuno Ther. Cancer 10(suppl 2):A1447 (2022).
Idusogie, Eshoe E. et al. Mapping of the C1q Binding Site on Rituxan, A Chimeric Antibody with a Human IgG1 Fc. The Journal of Immunology 164(8):4178-4184 (2000).
Imai-Nishiya, Harue et al. Double Knockdown of Alpha1,6-fucosyltransferase (FUT8) And GDP-mannose 4,6-dehydratase (GMD) In Antibody-producing Cells: A New Strategy For Generating Fully Non-fucosylated Therapeutic Antibodies With Enhanced ADCC. BMC Biotechnology 7:84, 1-13 (2007).
Ipilimumab. CAS 477202-00-9. chemicalbook.com [Website] Retrieved Oct. 8, 2024 at: https://www.chemicalbook.com/CASEN_477202-00-9.htm. 3 pages.
James, et al. A JAK2 mutation in myeloproliferative disorders: pathogenesis and therapeutic and scientific prospects. Trends Mol Med 11(12):546-54 (2005).
James, et al. A unique clonal JAK2 mutation leading to constitutive signalling causes polycythaemia vera. Nature. 2005;434:1144-1148.
Jeffrey, Scott C. et al. Dipeptide-based Highly Potent Doxorubicin Antibody Conjugates. Bioorganic Medicinal Chemistry Letters 16(2):358-362 (2006).
Johnsson, Bo. et al. Comparison Of Methods for Immobilization To Carboxymethyl Dextran Sensor Surfaces By Analysis Of The Specific Activity Of Monoclonal Antibodies. Journal of Molecular Recognition 8(1-2):125-131 (1995).
Johnsson, Bo. et al. Immobilization of Proteins To A Carboxymethyldextran-modified Gold Surface For Biospecific Interaction Analysis In Surface Plasmon Resonance Sensors. Analytical Biochemistry 198(2):268-277 (1991).
Jonsson, U. et al. Introducing a Biosensor Based Technology for Real-time Biospecific Interaction Analysis. Annals of Clinical Biology 51(1):19-26 (1993).
Jonsson, U. et al. Real-time Biospecific Interaction Analysis Using Surface Plasmon Resonance and a Sensor Chip Technology. BioTechniques 11(5):620-627 (1991).
Jung, S. et al. Prevention and therapy of experimental autoimmune neuritis by an antibody against T cell receptors-alpha/beta. Journal of immunology 148(12):3768-3775 (1992).
Kabat, Elvin A. et al. Sequences of Proteins of Immunological Interest. Fifth Edition, NIH Pub. No. 91-3242. Public Health Service, U.S. Department of Health and Human Services, National Institutes of Health: 647-669 (1991).

(56) References Cited

OTHER PUBLICATIONS

Kam, Nadine Wong Shi et al. Carbon Nanotubes as Multifunctional Biological Transporters and Near-infrared Agents for Selective Cancer Cell Destruction. Proceedings of the National Academy of Sciences of the United States of America 102(33):11600-11605 (2005).
Kanda, Yutaka et al. Comparison of Cell Lines for Stable Production of Fucose-negative Antibodies With Enhanced ADCC. Biotechnology and Bioengineering 94(4):680-688 (2006).
Karlin, S, and S F Altschul. Applications and Statistics for Multiple High-scoring Segments in Molecular Sequences. Proceedings of the National Academy of Sciences of the United States of America 90(12):5873-5877 (1993).
Kashmiri, Syed V S. et al. SDR Grafting—a New Approach to Antibody Humanization. Methods 36(1):25-34 (2005).
Kasmar, A.G. et al., "CD1b tetramers bind αβ T cell receptors to identify a mycobacterial glycolipid-reactive T cell repertoire in humans," J Exp Med., 2011;208(9):1741-1747.
Keinanen, A, and M L Laukkanen. Biosynthetic Lipid-tagging of Antibodies. FEBS letters 346(1):123-126 (1994).
Killion, J J, and I J Fidler. Systemic Targeting of Liposome-encapsulated Immunomodulators to Macrophages for Treatment of Cancer Metastasis. ImmunoMethods 4(3):273-279 (1994).
King, H Dalton et al. Monoclonal Antibody Conjugates of Doxorubicin Prepared With Branched Peptide Linkers: Inhibition of Aggregation by Methoxytriethyleneglycol Chains. Journal of Medicinal Chemistry 45(19):4336-4343 (2002).
Klampfl, Thorsten et al. Genome Integrity of Myeloproliferative Neoplasms in Chronic Phase and During Disease Progression. Blood 118(1): 167-176 (2011).
Klimka, A et al. Human Anti-CD30 Recombinant Antibodies by Guided Phage Antibody Selection Using Cell Panning. British Journal of Cancer 83(2):252-260 (2000).
Knappik, et al. Fully synthetic human combinatorial antibody libraries (HuCAL) based on modular consensus frameworks and CDRs randomized with trinucleotides. J Mol Biol. Feb. 11, 2000;296(1):57-86.
Konishi, Jun et al. B7-H1 Expression on Non-small Cell Lung Cancer Cells and Its Relationship With Tumor-infiltrating Lymphocytes and Their PD-1 Expression. Clinical Cancer Research 10(15):5094-5100 (2004).
Kostelny, S A. et al. Formation of a Bispecific Antibody by the Use of Leucine Zippers. Journal of Immunology 148(5):1547-1553 (1992).
Kozbor, D. et al. A Human Hybrid Myeloma for Production of Human Monoclonal Antibodies. Journal of Immunology 133(6):3001-3005 (1984).
Kralovics, et al. Altered gene expression in myeloproliferative disorders correlates with activation of signaling by the V617F mutation of Jak2. Blood 106(10):3374-6 (2005).
Kralovics, et al. Molecular pathogenesis of Philadelphia chromosome negative myeloproliferative disorders. Blood Rev 19(1):1-13 (2005).
Kralovics, Robert et al. A Gain-of-function Mutation of JAK2 in Myeloproliferative Disorders. The New England Journal of Medicine 352(17):1779-1790 (2005).
Kralovics, Robert. Genetic Complexity of Myeloproliferative Neoplasms. Leukemia 22(10):1841-1848 (2008).
Kratz, F. et al. Prodrugs of Anthracyclines in Cancer Chemotherapy. Current Medicinal Chemistry 13(5):477-523 (2006).
Kronenberg, M. et al., "A 'Gem' of a cell," Nat Immunol., 2013;14(7):694-695.
Kunik, Vered et al. Structural consensus among antibodies defines the antigen binding site. PLoS computational biology 8(2):e1002388, 1-12 (2012).
Latchman, Yvette et al. PD-L2 is a Second Ligand for PD-1 and Inhibits T Cell Activation. Nature Immunology 2(3):261-268 (2001).
Lee, Chingwei V. et al. Bivalent Antibody Phage Display Mimics Natural Immunoglobulin. Journal of Immunological Methods 284(1-2):119-132 (2004).
Lee, Chingwei V. et al. High-affinity Human Antibodies From Phage-displayed Synthetic Fab Libraries With a Single Framework Scaffold. Journal of Molecular Biology 340(5):1073-1093 (2004).
Lepore, Marco et al. Functionally Diverse Human T cells Recognize non-microbial Antigens Presented by MR1.Elife 6:e24476, 1-22 (2017).
Levine, et al. The JAK2V617F activating mutation occurs in chronic myelomonocytic leukemia and acute myeloid leukemia, but not in acute lymphoblastic leukemia or chronic lymphocytic leukemia. Blood 106(10):3377-9 (2005).
Levine, Ross L. et al. Activating Mutation in the Tyrosine Kinase JAK2 in Polycythemia Vera, Essential Thrombocythemia, and Myeloid Metaplasia With Myelofibrosis. Cancer Cell 7(4):387-397 (2005).
Li, Huijuan et al. Optimization of Humanized IgGs in Glycoengineered Pichia Pastoris. Nature Biotechnology 24(2):210-215 (2006).
Li, Jian. et al. Human Antibodies for Immunotherapy Development Generated via a Human B Cell Hybridoma Technology. Proceedings of the National Academy of Sciences of the United States of America 103(10):3557-3562 (2006).
Li, Yangqiu et al. Restricted TRBV repertoire in CD4+ and CD8+ T-cell subsets from CML patients. Hematology 16(1):43-49 (2011).
Lifely, M R. et al. Glycosylation and biological activity of CAMPATH-1H Expressed in different Cell lines and Grown under different Culture Conditions. Glycobiology 5(8):813-822 (1995).
Lode, Holger N. et al. Targeted Therapy With a Novel Enediyene Antibiotic Calicheamicin Theta(I)1 Effectively Suppresses Growth and Dissemination of Liver Metastases in a Syngeneic Model of Murine Neuroblastoma. Cancer Research 58(14):2925-2928 (1998).
Lonberg, Nils. Fully Human Antibodies From Transgenic Mouse and Phage Display Platforms. Current Opinion in Immunology 20(4):450-459 (2008).
Lonberg, Nils. Human Antibodies From Transgenic Animals. Nature Biotechnology 23(9):1117-1125 (2005).
Lopez, K. et al., "CD1b Tetramers Broadly Detect T Cells That Correlate With Mycobacterial Exposure but Not Tuberculosis Disease State," Front Immunol., 2020; 11:199.
Lossius, Andreas. et al. High-throughput Sequencing of TCR Repertoires in Multiple Sclerosis Reveals Intrathecal Enrichment of EBV-reactive CD8+ T Cells. European Of Journal Immunnology 44(11):3439-3452 (2014).
Lu, Chenyang et al. Clinical Significance of T Cell Receptor Repertoire in Primary Sjogren's Syndrome. EBioMedicine 84:104252, 1-12 (2022).
Maciocia, Paul M. et al. Supplemental Figures: Targeting the T cell receptor β-chain constant region for immunotherapy of T cell malignancies. Nature Medicine 23(12):1416-1423 (2017). Retrieved Oct. 8, 2024 at URL: https://static-content.springer.com/esm/art%3A10.1038%2Fnm.4444/MediaObjects/41591_2017_BFnm4444_MOESM1_ESM.pdf. 6 pages.
Maeda, T. et al. Amelioration of acute graft-versus-host disease and re-establishment of tolerance by short-term treatment with an anti-TCR antibody. Journal of immunology 153(9):4311-4320 (1994).
Marks, James D, and Andrew Bradbury. Selection of Human Antibodies From Phage Display Libraries. Methods in Molecular Biology 48:161-176 (2004).
Marks, James D. et al. By-passing Immunization Human Antibodies from V-gene Libraries Displayed on Phage. Journal of Molecular Biology 222(3):581-597 (1991).
Martin, Andrew C. et al., Chapter 3: Protein Sequence and Structure Analysis of Antibody Variable Domains. In: Antibody Engineering Lab Manual (Ed: Duebel, S. and Kontermann, R., Springer-Verlag, Heidelberg) 2:33-51 (2010).
Martin, Andrew CR. Protein Sequence and Structure Analysis of Antibody Variable Domains. Antibody Engineering:422-439 (2001).
Matsumoto, Y. et al. Successful prevention and treatment of autoimmune encephalomyelitis by short-term administration of anti-T-cell receptor alpha beta antibody. Immunology 81(1):1-7 (1994).
Mayer, Gene et al. Chapter 10: Major Histocompatibility Complex (MHC) And T-Cell Receptors—Role In Immune Responses. In: Microbiology and Immunology on-line, University of South Carolina School of Medicine: 1-6 (2010).
McCafferty, J. et al. Phage Antibodies: Filamentous Phage Displaying Antibody Variable Domains. Nature 348(6301):552-554 (1990).

(56) References Cited

OTHER PUBLICATIONS

McGoff, Paul, and David S. Scher. Solution Formulation of Proteins/Peptides:In McNally EJ., ed, Protein Formulation and Delivery:139-158 (2000).
McLellan, Jason S. et al. Structure of HIV-1 gp120 V1/V2 Domain with Broadly Neutralizing Antibody PG9. Nature 480(7377):336-343 (2011).
Meermeier, Erin W. et al. Human TRAV1-2-negative MR1-restricted T cells detect S. pyogenes and alternatives to MAIT riboflavin-based antigens. Nat Commun 7:12506, 1-12 (2016).
Meeting Abstracts. 33rd Annual Meeting & Pre-Conference Programs of the Society for Immunotherapy of Cancer (SITC 2018). Journal for Immunotherapy of Cancer 6(Suppl 1):207-398 (2018).
Meilleur, Courtney et al. Bacterial Superantigens Expand and Activate, Rather than Delete or Incapacitate, Preexisting Antigen-Specific Memory CD8+ T Cells. J Infect Dis 219(8):1307-1317 (2019). Published online Nov. 12, 2018.
Milosevic, Jelena D, and Robert Kralovics. Genetic and Epigenetic Alterations of Myeloproliferative Disorders. International Journal of Hematology 97(2):183-197 (2013). Published Online Dec. 12, 2012.
Milstein, C, and A C Cuello. Hybrid Hybridomas and Their Use in Immunohistochemistry. Nature 305(5934):537-540 (1983).
Moore, et al. Abstract C180: A novel bispecific platform for potent redirected killing of B-cell lymphoma. Mol Cancer Ther 8 (12_Supplement): C180 (2009).
Mosca, Paul J. et al. Dendritic cell vaccines. Frontiers in Bioscience 12:4050-4060 (2007).
Motozono, Chihiro et al. Molecular Basis of a Dominant T Cell Response to an HIV Reverse Transcriptase 8-mer Epitope Presented by the Protective Allele HLA-B*51:01. Journal of Immunology 192(7):3428-3434 (2014).
Myers, et al. Optimal alignments in linear space. CABIOS 4(1):11-17 (1988).
Nagy, Attila et al. Stability of Cytotoxic Luteinizing Hormone-releasing Hormone Conjugate (AN-152) Containing Doxorubicin 14-O-Hemiglutarate in Mouse and Human Serum in vitro: Implications for the Design of Preclinical Studies. Proc Natl Acad Sci U S A 97(2):829-834 (2000).
Nair et al., Epitope Recognition by Diverse Antibodies Suggests Conformational Convergence in an Antibody Response. The Journal of Immunology, 168:2371-2382 (2002).
Natsume, Akito et al. Engineered Antibodies of IgG1/IgG3 Mixed Isotype with Enhanced Cytotoxic Activities. Cancer Research 68(10):3863-3872 (2008).
Ni, Jian. Research Progress and Prospects of Antibodymoics and Antibody-Based Drugs, Modern Immunology 26(4):265-268 (2006). Abstract Only. One page.
No Author, "33rd Annual Meeting & Pre-Conference Programs of the Society for Immunotherapy of Cancer (SITC 2018)", Journal for Immuno Therapy of Cancer, 2018, vol. 6(1), No. 115, pp. 1-192.
Nomoto, K. et al. Tolerance induction in a fully allogeneic combination using anti-T cell receptor-alpha beta monoclonal antibody, low dose irradiation, and donor bone marrow transfusion. Transplantation 59(3):395-401 (1995).
Ohtsuka, Eiko et al. An Alternative Approach to Deoxyoligonucleotides as Hybridization Probes by Insertion of Deoxyinosine at Ambiguous Codon Positions. Journal of Biological Chemistry 260(5):2605-2608 (1985).
Okazaki, Akira et al. Fucose Depletion From Human IgG1 Oligosaccharide Enhances Binding Enthalpy and Association Rate Between IgG1 and FcgammaRIIIa. Journal of Molecular Biology 336(5):1239-1249 (2004).
Osbourn, Jane et al. From Rodent Reagents to Human Therapeutics Using Antibody Guided Selection. Methods 36(1):61-68 (2005).
Owais, Mohammad et al. Chloroquine Encapsulated in Malaria-infected Erythrocyte-specific Antibody-bearing Liposomes Effectively Controls Chloroquine-resistant Plasmodium Berghei Infections in Mice. Antimicrobial Agents and Chemotherapy 39(1):180-184 (1995).

Padlan, Eduardo A. A Possible Procedure for Reducing the Immunogenicity of Antibody Variable Domains While Preserving Their Ligand-binding Properties. Molecular Immunology 28(4-5):489-498 (1991).
Panka et al. Variable region framework differences result in decreased or increased affinity of variant anti-digoxin antibodies. PNAS USA 85:3080-3084 (1988).
Pardanani, Animesh D. et al. MPL515 Mutations in Myeloproliferative and Other Myeloid Disorders: a Study of 1182 Patients. Blood 108(10):3472-3476 (2006).
Pardanani, et al. Discordant distribution of JAK2V617F mutation in siblings with familial myeloproliferative disorders. Blood 107(11):4572-3 (2006).
Paul: Fundamental Immunology. 3rd Edition. 292-295 (1993).
PCT/US2020/019329 International Search Report and Written Opinion dated Jun. 26, 2020.
PCT/US2020/060557 International Search Report and Written Opinion dated Mar. 30, 2021.
PCT/US2021/047574 International Search Report and Written Opinion dated Feb. 17, 2022.
PCT/US2021/047773 International Search Report and Written Opinion dated Dec. 23, 2021.
PCT/US2022/023922 International Search Report and Written Opinion dated Oct. 6, 2022.
PCT/US2022/049039 International Search Report and Written Opinion dated May 10, 2023.
PCT/US2022/053705 International Search Report and Written Opinion dated Jul. 7, 2023.
PCT/US2023/011280 International Search Report and Written Opinion dated Jun. 28, 2023.
PCT/US2023/034966 International Search Report and Written Opinion dated Mar. 29, 2024.
PCT/US2023/035056 International Search Report and Written Opinion dated Mar. 5, 2024.
PCT/US2024/026686 International Search Report and Written Opinion dated Sep. 23, 2024.
Pearson, William R, and David J Lipman. Improved Tools For Biological Sequence Comparison. PNAS USA 85(8):2444-2448 (1988).
Pejchal, Robert et al. A Potent and Broad Neutralizing Antibody Recognizes and Penetrates the HIV Glycan Shield. Science 334(6059):1097-1103 (2011).
Petersen, Jan. et al. Diverse T Cell Receptor Gene Usage in HLA-DQ8-associated Celiac Disease Converges Into a Consensus Binding Solution. Structure 24(10):1643-1657 (2016).
Petkova, Stefka B. et al. Enhanced Half-life of Genetically Engineered Human IgG1 Antibodies in a Humanized FcRn Mouse Model: Potential Application in Humorally Mediated Autoimmune Disease. International Immunology 18(12):1759-1769 (2006).
Pikman, et al. MPLW515L Is a Novel Somatic Activating Mutation in Myelofibrosis with Myeloid Metaplasia. PLoS Med. 2006;3(7):e270.
Pluckthun, A. Chapter 11: Antibodies From *Escherichia coli*. The Pharmacology of Monoclonal Antibodies 113:269-315 (1994).
Porritt, Rebecca A. et al. HLA Class I-associated Expansion of TRBV11-2 T Cells in Multisystem Inflammatory Syndrome in Children. The Journal of Clinical Investigation 131(10):e146614, 1-13 (2021).
Presta, Leonard G. et al. Humanization of an Antibody Directed Against IgE. Journal of Immunology 151(5): 2623-2632 (1993).
Presta, Leonard G. et al. Humanization of an Anti-vascular Endothelial Growth Factor Monoclonal Antibody for the Therapy of Solid Tumors and Other Disorders. Cancer Research 57(20):4593-4599 (1997).
Queen, Cary et al. A Humanized Antibody That Binds to the Interleukin 2 Receptor. Proceedings of the National Academy of Sciences 86(24):10029-10033 (1989).
Ranade, Vasant V. Drug Delivery Systems. 1. Site-specific Drug Delivery Using Liposomes as Carriers. Journal of Clinical Pharmacology 29(8):685-694 (1989).
Reinink, P. et al., "A Tcr β-Chain Motif Biases toward Recognition of Human CD1 Proteins," J Immunol., 2019;203(12):3395-3406.

(56) References Cited

OTHER PUBLICATIONS

Ripka, James et al. Two Chinese Hamster Ovary Glycosylation Mutants Affected in the Conversion of GDP-mannose to GDP-fucose. Archives of Biochemistry and Biophysics 249(2):533-545 (1986).
Rosok, Mae Joanne et al. A Combinatorial Library Strategy for the Rapid Humanization of Anticarcinoma BR96 Fab. The Journal of Biological Chemistry 271(37):22611-22618 (1996).
Rossolini, Gian Maria et al. Use of Deoxyinosine-containing Primers vs Degenerate Primers for Polymerase Chain Reaction Based on Ambiguous Sequence Information. Molecular and Cellular Probes 8(2):91-98 (1994).
Rowntree, Louise C. et al. A Shared TCR Bias Toward an Immunogenic EBV Epitope Dominates in HLA-B*07:02-Expressing Individuals. Journal of Immunology 205(6):1524-1534 (2020).
Samanen, James. et al. Chemical Approaches to Improve the Oral Bioavailability of Peptidergic Molecules. Journal of Pharmacy and Pharmacology 48(2):119-135 (1996).
Sanchez-Ruiz, Jose M. et al. Differential Scanning Calorimetry of the Irreversible Thermal Denaturation of Thermolysin. Biochemistry 27(5):1648-1652 (1988).
Schachter, Harry. et al. Biosynthetic Controls that Determine the Branching and Microheterogeneity of Protein-bound Oligosaccharides. Biochemistry and Cell Biology 64(3):163-181 (1986).
Scheid, Johannes F. et al. Sequence and Structural Convergence of Broad and Potent HIV Antibodies that Mimic CD4 Binding. Science 333(6049):1633-1637 (2011).
Scheuermann, R.H. and Racila, E. CD19 Antigen in Leukemia and Lymphoma Diagnosis and Immunotherapy. Leukemia & Lymphoma 18(5-6):385-397 (1995).
Schreier, Hans et al. Targeting of Liposomes to Cells Expressing CD4 Using Glycosylphosphatidylinositol-anchored gp120. Influence of Liposome Composition on Intracellular Trafficking. The Journal of Biological Chemistry 269(12):9090-9098 (1994).
Scott, et al. JAK2 exon 12 mutations in polycythemia vera and idiopathic erythrocytosis. N Engl J Med 356(5):459-68 (2007).
Shields, Robert L. et al. High Resolution Mapping of the Binding Site on Human IgG1 for Fc Gamma RI, Fc Gamma RII, Fc Gamma RIII, and FcRn and design of IgG1 Variants with Improved Binding to the Fc Gamma R. Journal of Biological Chemistry 276(9):6591-6604 (2001).
Sidhu, Sachdev S. et al. Phage-displayed Antibody Libraries of Synthetic Heavy Chain Complementarity Determining Regions. Journal of Molecular Biology 338(2):299-310 (2004).
Sim, Gek Kee et al. Primary Structure Of Human T-Cell Receptor Alpha-chain. Nature 312(5996):771-775 (1984).
Sims, Martin J. et al. A Humanized CD18 Antibody Can Block Function Without Cell Destruction. Journal of Immunology 151(4):2296-2308 (1993).
Smith, et al. T cell inactivation and cytokine deviation promoted by anti-CD3 mAbs. Curr Opin Immunol 9(5):648-54 (1997).
Smith, Temple F, and Waterman Michael S. Comparison of Biosequences. Advances in applied mathematics 2(4):482-489 (1981).
Song, De-Gang et al. CD27 Costimulation Augments the Survival and Antitumor Activity of Redirected Human T cells in vivo. Blood 119(3):696-706 (2012).
Srivastava, Shivani, and Stanley R Riddell. Engineering CAR-T cells: Design concepts. Trends in immunology 36(8):494-502 (2015).
Staerz, Uwe D, and Michael J. Bevan. Activation of resting T lymphocytes by a monoclonal antibody directed against an allotypic determinant on the T cell receptor. Eur. J. Immunol 16:263-270 (1986).
Stegelmann, F. et al. DNMT3a Mutations in Myeloproliferative Neoplasms. Leukemia 25(7):1217-1219 (2011).
Stein, et al. Disruption of the ASXL1 gene is frequent in primary, post-essential thrombocytosis and post-polycythemia vera myelofibrosis, but not essential thrombocytosis or polycythemia vera: analysis of molecular genetics and clinical phenotypes. Haematologica 96(10):1462-9 (2011).
Stein, et al. Natural Killer (NK)- and T-Cell Engaging Antibody-Derived Therapeutics. Antibodies 1(1):88-123 (2012).
Stein, Sokrates et al. Protective Roles of SIRT1 in Atherosclerosis. Cell Cycle 10(4):640-647 (2011).
Streltsov, Victor A. et al. Structure of a Shark IgNAR Antibody Variable Domain and Modeling of an Early-developmental Isotype. Protein Science 14(11):2901-2909 (2005).
Surman, Sherri L. et al. Clonally Related CD8+ T Cells Responsible for Rapid Population of Both Diffuse Nasal-associated Lymphoid Tissue and Lung After Respiratory Virus Infection. Journal of Immunology 187(2):835-841 (2011).
Suzuki-Inoue, et al. Involvement of the Snake Toxin Receptor CLEC-2, in Podoplanin-mediated Platelet Activation, by Cancer Cells. The Journal of Biological Chemistry, 282(36):25993-26001 (2007).
Szeto, Christopher et al. Molecular Basis of a Dominant SARS-CoV-2 Spike-Derived Epitope Presented by HLA-A*02:01 Recognised by a Public TCR. Cells 10(10):2646, 1-15 (2021).
Tan, Huo et al. Clonal expanded TRA and TRB subfamily T cells in peripheral blood from patients with diffuse large B-cell lymphoma. Hematology 15(2):81-87 (2010).
Tang, Yong. et al. Regulation of Antibody-dependent Cellular Cytotoxicity by IgG Intrinsic and Apparent Affinity for Target Antigen. Journal of Immunology 179(5):2815-2823 (2007).
Tastan, Cihan et al. Tuning of human MAIT cell activation by commensal bacteria species and MR1-dependent T-cell presentation. Mucosal Immunol 11(6):1591-1605 (2018).
Torgov, Michael Y. et al. Generation of an Intensely Potent Anthracycline by a Monoclonal Antibody-beta-galactosidase Conjugate. Bioconjugate Chemistry 16(3):717-721 (2005).
Traunecker, André et al. Bispecific Single Chain Molecules (Janusins) Target Cytotoxic Lymphocytes on HIV Infected Cells. The EMBO Journal 10(12):3655-3659 (1991).
Tutt, Alison et al. Trispecific F(ab')3 Derivatives that Use Cooperative Signaling via the TCR/CD3 Complex and CD2 to Activate and Redirect Resting Cytotoxic T cells. Journal of Immunology 147(1):60-69 (1991).
Umezawa, F, and Y Eto. Liposome Targeting to Mouse Brain: Mannose as a Recognition Marker. Biochemical and Biophysical Research Communications 153(3):1038-1044 (1988).
UniProt reference No. P04626. Receptor Tyrosine-Protein Kinase erbB-2. Record created Nov. 1, 1988. pp. 1-19. Retrieved Sep. 27, 2024 at URL: https://www.uniprot.org/uniprotkb/P04626/entry.
UniProt reference No. Q9HBE4. Interleukin-21. Record created Mar. 1, 2001. pp. 1-9. Retrieved Sep. 27, 2024 at URL: https://www.uniprot.org/uniprotkb/Q9HBE4/entry.
UniProtKB Accession No. A0A075B6N4. T cell receptor beta variable 25-1. Record created Oct. 1, 2014. pp. 1-9. Retrieved Sep. 9, 2024 at URL: https://www.uniprot.org/uniprotkb/A0A075B6N4/entry.
UniProtKB Accession No. A0A0B4J240. T cell receptor alpha variable 10. Record created Mar. 11, 2015. pp. 1-9. Retrieved Sep. 9, 2024 at URL: https://www.uniprot.org/uniprotkb/A0A0B4J240/entry.
UniProtKB Accession No. A0A1G7UTW6_9SPHI. Uncharacterized protein Pedobacter terrae (Nov. 22, 2017). Retrieved Jul. 16, 2024 at URL: https://rest.uniprot.org/unisave/A0A1G7UTW6?format=txt&versions=1. One page.
UniProtKB Accession No. A0A2V7GPM2_9BACT. Uncharacterized protein Gemmatimonadetes bacterium (Sep. 12, 2018). Retrieved Jul. 16, 2024 at URL: https://rest.uniprot.org/unisave/A0A2V7GPM2?format=txt&versions=1. One page.
UniProtKB Accession No. O00220. Tumor necrosis factor receptor superfamily member 10A. Record created Jul. 1, 1997. Retrieved Aug. 16, 2024 at URL: https://www.uniprot.org/uniprotkb/O00220/entry pp. 1-9.
UniProtKB Accession No. O14763. Tumor necrosis factor receptor superfamily member 10B. Record created Jan. 1, 1998. Retrieved Aug. 16, 2024 at URL: https://www.uniprot.org/uniprotkb/O14763/entry pp. 1-10.
UniProtKB Accession No. O95760. Interleukin-33. Record created May 1, 1999. pp. 1-10. Retrieved Sep. 9, 2024 at URL: https://www.uniprot.org/uniprotkb/O95760/entry.

(56) References Cited

OTHER PUBLICATIONS

UniProtKB Accession No. O95866. Megakaryocyte and platelet inhibitory receptor G6b. Record created May 1, 1999. Retrieved Aug. 16, 2024 at URL: https://www.uniprot.org/uniprotkb/O95866/entry pp. 1-11.
UniProtKB Accession No. P01137. Transforming growth factor beta-1 proprotein. Record created Nov. 1, 1988. Retrieved Aug. 16, 2024 at URL: https://www.uniprot.org/uniprotkb/P01137/entry pp. 1-17.
UniProtKB Accession No. P01562. Interferon alpha-1/13. Record created Nov. 1, 1988. pp. 1-10. Retrieved Sep. 9, 2024 at URL: https://www.uniprot.org/uniprotkb/P01562/entry.
UniProtKB Accession No. P01563. Interferon alpha-2. Record created Nov. 1, 1988. pp. 1-12. Retrieved Oct. 9, 2024 at URL: https://www.uniprot.org/uniprotkb/P01563/entry.
UniProtKB Accession No. P01566. Interferon alpha-10. Record created Nov. 1, 1988. pp. 1-10. Retrieved Sep. 9, 2024 at URL: https://www.uniprot.org/uniprotkb/P01566/entry.
UniProtKB Accession No. P01567. Interferon alpha-7. Record created Nov. 1, 1988. pp. 1-7. Retrieved Sep. 9, 2024 at URL: https://www.uniprot.org/uniprotkb/P01567/entry.
UniProtKB Accession No. P01568. IFN21_HUMAN. Record created Nov. 1, 1988. pp. 1-7. Retrieved Sep. 9, 2024 at URL: https://www.uniprot.org/uniprotkb/P01568/entry.
UniProtKB Accession No. P01569. Interferon alpha-5. Record created Nov. 1, 1988. pp. 1-10. Retrieved Sep. 9, 2024 at URL: https://www.uniprot.org/uniprotkb/P01569/entry.
UniProtKB Accession No. P01570. IFN14_HUMAN. Record created Nov. 1, 1988. pp. 1-7. Retrieved Sep. 9, 2024 at URL: https://www.uniprot.org/uniprotkb/P01570/entry.
UniProtKB Accession No. P01574. Interferon beta. Record created Nov. 1, 1988. pp. 1-9. Retrieved Sep. 9, 2024 at URL: https://www.uniprot.org/uniprotkb/P01574/entry.
UniProtKB Accession No. P05013. Interferon alpha-6. Record created Nov. 1, 1988. pp. 1-11. Retrieved Sep. 9, 2024 at URL: https://www.uniprot.org/uniprotkb/P05013/entry.
UniProtKB Accession No. P05014. Interferon alpha-4. Record created Nov. 1, 1988. pp. 1-11. Retrieved Sep. 9, 2024 at URL: https://www.uniprot.org/uniprotkb/P05014/entry.
UniProtKB Accession No. P05106. Integrin beta-3. Record created Nov. 1, 1988. Retrieved Aug. 16, 2024 at URL: https://www.uniprot.org/uniprotkb/P05106/entry pp. 1-20.
UniProtKB Accession No. P05107. Integrin beta-2. Record created Nov. 1, 1988. Retrieved Aug. 16, 2024 at URL: https://www.uniprot.org/uniprotkb/P05107/entry pp. 1-15.
UniProtKB Accession No. P07359. Platelet glycoprotein Ib alpha chain. Record created Nov. 1, 1988. Retrieved Aug. 16, 2024 at URL: https://www.uniprot.org/uniprotkb/P07359/entry pp. 1-15.
UniProtKB Accession No. P08514. Integrin alpha-IIb. Record created Nov. 1, 1988. Retrieved Aug. 16, 2024 at URL: https://www.uniprot.org/uniprotkb/P08514/entry pp. 1-15.
UniProtKB Accession No. P0DOX5. Immunoglobulin gamma-1 heavy chain. Record created Mar. 15, 2017. Retrieved Nov. 6, 2024 at URL: https://www.uniprot.org/uniprotkb/P0DOX5/entry pp. 1-4.
UniProtKB Accession No. P10600. Transforming growth factor beta-3 proprotein. Record created Jul. 1, 1989. Retrieved Aug. 16, 2024 at URL: https://www.uniprot.org/uniprotkb/P10600/entry pp. 1-11.
UniProtKB Accession No. P10721. Mast/stem cell growth factor receptor Kit. Record created Jul. 1, 1989. Retrieved Aug. 16, 2024 at URL: https://www.uniprot.org/uniprotkb/P10721/entry pp. 1-20.
UniProtKB Accession No. P12318. Low affinity immunoglobulin gamma Fc region receptor II-a. Record created Oct. 1, 1989. Retrieved Aug. 16, 2024 at URL: https://www.uniprot.org/uniprotkb/P12318/entry pp. 1-9.
UniProtKB Accession No. P16109. P-selectin. Record created Apr. 1, 1990. Retrieved Aug. 16, 2024 at URL: https://www.uniprot.org/uniprotkb/P16109/entry pp. 1-12.
UniProtKB Accession No. P28906. Hematopoietic progenitor cell antigen CD34. Record created Dec. 1, 1992. Retrieved Aug. 16, 2024 at URL: https://www.uniprot.org/uniprotkb/P28906/entry pp. 1-10.
UniProtKB Accession No. P29459. Interleukin-12 subunit alpha. Record created Apr. 1, 1993. pp. 1-13. Retrieved Sep. 9, 2024 at URL: https://www.uniprot.org/uniprotkb/P29459/entry.
UniProtKB Accession No. P29460. Interleukin-12 subunit beta. Record created Apr. 1, 1993. pp. 1-10. Retrieved Sep. 9, 2024 at URL: https://www.uniprot.org/uniprotkb/P29460/entry.
UniProtKB Accession No. P30408. Transmembrane 4 L6 family member 1. Record created Apr. 1, 1993. Retrieved Aug. 16, 2024 at URL: https://www.uniprot.org/uniprotkb/P30408/entry pp. 1-7.
UniProtKB Accession No. P32881. Interferon alpha-8. Record created Oct. 1, 1993. pp. 1-7. Retrieved Sep. 9, 2024 at URL: https://www.uniprot.org/uniprotkb/P32881/entry.
UniProtKB Accession No. P36888. Receptor-type tyrosine-protein kinase FLT3. Record created Jun. 1, 1994. Retrieved Aug. 16, 2024 at URL: https://www.uniprot.org/uniprotkb/P36888/entry pp. 1-13.
UniProtKB Accession No. P36897. TGF-beta receptor type-1. Record created Jun. 1, 1994. Retrieved Aug. 16, 2024 at URL: https://www.uniprot.org/uniprotkb/P36897/entry pp. 1-16.
UniProtKB Accession No. P37173. TGF-beta receptor type-2. Record created Oct. 1, 1994. Retrieved Aug. 16, 2024 at URL: https://www.uniprot.org/uniprotkb/P37173/entry pp. 1-18.
UniProtKB Accession No. P40238. Thrombopoietin receptor. Record created Feb. 1, 1995. Retrieved Aug. 16, 2024 at URL: https://www.uniprot.org/uniprotkb/P40238/entry pp. 1-11.
UniProtKB Accession No. P40933. Interleukin-15. Record created Feb. 1, 1995. pp. 1-9. Retrieved Sep. 9, 2024 at URL: https://www.uniprot.org/uniprotkb/P40933/entry.
UniProtKB Accession No. P56856. Cld_Human. 14 pages. Retrieved Oct. 7, 2024 at URL: https://www.uniprot.org/uniprotkb/P56856/entry.
UniProtKB Accession No. P60568. Interleukin-2. Record created Mar. 15, 2004. pp. 1-12. Retrieved Jul. 12, 2024 at URL: https://www.uniprot.org/uniprotkb/P60568/entry.
UniProtKB Accession No. P61812. Transforming growth factor beta-2 proprotein. Record created Jun. 7, 2004. Retrieved Aug. 16, 2024 at URL: https://www.uniprot.org/uniprotkb/P61812/entry pp. 1-12.
UniProtKB Accession No. Q02487. Desmocollin-2. Record created Feb. 1, 1994. Retrieved Aug. 16, 2024 at URL: https://www.uniprot.org/uniprotkb/Q02487/entry pp. 1-15.
UniProtKB Accession No. Q03167. Transforming growth factor beta receptor type 3. Record created Feb. 1, 1994. Retrieved Aug. 16, 2024 at URL: https://www.uniprot.org/uniprotkb/Q03167/entry pp. 1-10.
UniProtKB Accession No. Q14116. Interleukin-18. Record created Nov. 1, 1996. pp. 1-10. Retrieved Sep. 9, 2024 at URL: https://www.uniprot.org/uniprotkb/Q14116/entry.
UniProtKB Accession No. Q9H293. Interleukin-25. Record created Mar. 1, 2001. pp. 1-11. Retrieved Sep. 9, 2024 at URL: https://www.uniprot.org/uniprotkb/Q9H293/entry.
UniProtKB Accession No. Q9NPF7. Interleukin-23 subunit alpha. Record created Oct. 1, 2000. pp. 1-13. Retrieved Sep. 9, 2024 at URL: https://www.uniprot.org/uniprotkb/Q9NPF7/entry.
UniProtKB Accession No. Q9NYJ7. Delta-like protein 3. Record created Oct. 1, 2000. pp. 1-9. Retrieved Oct. 10, 2024 at URL: https://www.uniprot.org/uniprotkb/Q9NYJ7/entry.
Urakami, Akane et al. An Envelope-Modified Tetravalent Dengue Virus-Like-Particle Vaccine Has Implications for Flavivirus Vaccine Design. Journal of virology 91(23):e00090-17, 1-16 (2017).
U.S. Appl. No. 15/465,564 Notice of Allowance dated Nov. 10, 2021.
U.S. Appl. No. 15/465,564 Notice of Allowance dated Oct. 29, 2021.
U.S. Appl. No. 15/465,564 Office Action dated Apr. 29, 2020.
U.S. Appl. No. 15/465,564 Office Action dated May 26, 2021.
U.S. Appl. No. 15/465,564 Office Action dated Oct. 13, 2020.
U.S. Appl. No. 15/465,564 Office Action dated Sep. 9, 2019.
U.S. Appl. No. 16/960,704 Office Action dated Dec. 22, 2023.
U.S. Appl. No. 16/960,704 Office Action dated Jul. 5, 2024.

(56) References Cited

OTHER PUBLICATIONS

U.S. Appl. No. 16/980,730 Notice of Allowance dated Jun. 13, 2024.
U.S. Appl. No. 16/980,730 Office Action dated Feb. 12, 2024.
U.S. Appl. No. 16/980,771 Office Action dated Jan. 10, 2024.
U.S. Appl. No. 17/256,917 Notice of Allowance dated Sep. 7, 2023.
U.S. Appl. No. 17/366,638 Office Action dated Apr. 25, 2024.
U.S. Appl. No. 17/366,638 Office Action dated Aug. 27, 2024.
U.S. Appl. No. 17/402,325 Office Action dated Sep. 24, 2024.
U.S. Appl. No. 17/402,329 Office Action dated Nov. 5, 2024.
U.S. Appl. No. 17/529,017 Office Action dated Nov. 18, 2022.
U.S. Appl. No. 17/820,634 Office Action dated Apr. 19, 2023.
U.S. Appl. No. 17/820,634 Office Action dated Aug. 11, 2023.
U.S. Appl. No. 17/820,634 Office Action dated Aug. 15, 2023.
U.S. Appl. No. 17/820,794 Notice of Allowance dated Feb. 1, 2024.
U.S. Appl. No. 17/820,794 Office Action dated Dec. 29, 2023.
U.S. Appl. No. 17/820,794 Office Action dated Mar. 31, 2023.
U.S. Appl. No. 17/820,794 Office Action dated Sep. 15, 2023.
U.S. Appl. No. 17/820,800 Office Action dated Feb. 21, 2023.
U.S. Appl. No. 17/820,800 Office Action dated Jun. 1, 2023.
U.S. Appl. No. 17/820,805 Office Action dated Apr. 26, 2024.
U.S. Appl. No. 17/820,805 Office Action dated Aug. 14, 2023.
U.S. Appl. No. 17/820,805 Office Action dated Oct. 31, 2024.
U.S. Appl. No. 17/820,806 Office Action dated Apr. 12, 2023.
U.S. Appl. No. 17/820,806 Office Action dated Aug. 15, 2023.
U.S. Appl. No. 17/820,811 Office Action dated May 25, 2023.
U.S. Appl. No. 17/820,818 Office Action dated Jun. 1, 2023.
U.S. Appl. No. 17/820,818 Office Action dated Mar. 12, 2024.
U.S. Appl. No. 18/341,688 Office Action dated Jan. 25, 2024.
U.S. Appl. No. 18/341,688 Office Action dated May 10, 2024.
U.S. Appl. No. 18/472,920 Office Action dated Nov. 4, 2024.
Valkenburg, Sophie A. et al. Molecular Basis for Universal HLA-A*0201-restricted CD8+ T-cell Immunity Against Influenza Viruses. Proceedings of the National Academy of Sciences of the United States of America 113(16):4440-4445 (2016).
Van Dijk, Marc A. et al. Human Antibodies as Next Generation Therapeutics. Current Opinion in Chemical Biology 5(4):368-374 (2001).
Van Mierlo, Carlo PM, and Elles Steensma. Protein Folding and Stability Investigated by Fluorescence, Circular Dichroism (CD), and Nuclear Magnetic Resonance (NMR) Spectroscopy: the Flavodoxin Story. Journal of Biotechnology 79(3):281-298 (2000).
Van Rhijn, I. et al., "A conserved human T cell population targets mycobacterial antigens presented by CD1b," Nat Immunol., 2013;14(7):706-713.
Van Rhijn, I. et al., "TCR bias and affinity define two compartments of the CD1b-glycolipid-specific T Cell repertoire," J Immunol., 2014;192(9):4054-4060.
Vantourout, Pierre et al. Innate TCRβ-chain engagement drives human T cells toward distinct memory-like effector phenotypes with immunotherapeutic potentials. Science Advances 9(49):eadj6174, 1-19 (2023).
Viney, Joanne L. et al. Generation of Monoclonal Antibodies Against a Human T Cell Receptor Beta Chain Expressed in Transgenic Mice. Hybridoma 11(6):701-713 (1992).
Vitetta, Ellen S. et al. Redesigning Nature's Poisons to Create Anti-tumor Reagents. Science 238(4830):1098-1104 (1987).
Vollmers, H P. et al. Death by Stress: Natural IgM-induced Apoptosis. Methods and Findings in Experimental and Clinical Pharmacology 27(3):185-191 (2005).
Vollmers, H P. et al. The "Early Birds": Natural IgM Antibodies and Immune Surveillance. Histology and Histopathology 20(3):927-937 (2005).
Walker, Laura M. et al. Broad and Potent Neutralizing Antibodies from an African Donor Reveal a New HIV-1 Vaccine Target. Science 326(5950):285-289 (2009).
Walker, Laura M. et al. Broad Neutralization Coverage of Hiv by Multiple Highly Potent Antibodies. Nature 477(7365):466-470 (2011).
Wang, Zhenguang et al. Current status and perspectives of chimeric antigen receptor modified T cells for cancer treatment. Protein and Cell 8(12):896-925 (2017).
Watanabe, M. et al. Interleukin-21 Can Efficiently Restore Impaired Antibody-dependent Cell- mediated Cytotoxicity in Patients With Oesophageal Squamous Cell Carcinoma. British Journal of Cancer 102(3):520-529 (2010).
Willemsen, R A. et al. Grafting Primary Human T Lymphocytes With Cancer-specific Chimeric Single Chain and Two Chain TCR. Gene Therapy 7(16):1369-1377 (2000).
Winkler et al., Changing the Antigen Binding Specificity by Single Point Mutations of an Anti-p24 (HIV-1) Antibody. Journal of Immunology 165(8):4505-4514 (2000).
Winter, Greg. et al. Making Antibodies by Phage Display Technology. Annual Review of Immunology 12(1):433-455 (1994).
Wright, Ann, and Sherie L. Morrison et al. Effect of Glycosylation on Antibody Function: Implications for Genetic Engineering. Trends in Biotechnology 15(1):26-32 (1997).
Xiang, Jianhua H. et al. Modification in Framework Region I Results in a Decreased Affinity of Chimeric Anti-TAG72 antibody. Molecular Immunology 28(1-2):141-148 (1991).
Xu, Jian et al. MIR548P and TRAV39 Are Potential Indicators of Tumor Microenvironment and Novel Prognostic Biomarkers of Esophageal Squamous Cell Carcinoma. Journal of Clinical Oncology 2022:3152114, 1-20 (2022).
Yamane-Ohnuki, Naoko. et al. Establishment of FUT8 Knockout Chinese Hamster Ovary Cells: an Ideal Host Cell Line for Producing Completely Defucosylated Antibodies With Enhanced Antibody-dependent Cellular Cytotoxicity. Biotechnology and Bioengineering 87(5):614-622 (2004).
Yang, Xinbo et al. Structural basis for clonal diversity of the human T-cell response to a dominant influenza virus epitope. J Biol Chem 292(45):18618-18627 (2017).
Yazaki, Paul J, and Anna M Wu. Expression of Recombinant Antibodies in Mammalian Cell Lines. Methods in Molecular Biology 248:255-268 (2004).
Yohannes, Dawit A. et al. Deep Sequencing of Blood and Gut T-cell Receptor B-chains Reveals Gluten-induced Immune Signatures in Celiac Disease. Scientific Reports 7(1):17977, 1-12 (2017).
Zhang, Tong. et al. An NKp30-Based Chimeric Antigen Receptor Promotes T cell Effector Functions and Antitumor Efficacy In Vivo. Journal of Immunology 189(5):2290-2299 (2012).
Zhang, Tong. et al. Transgenic TCR Expression: Comparison of Single Chain With Full-length Receptor Constructs for T-cell Function. Cancer Gene Therapy 11(7):487-496 (2004).
Zhou, Hongyu. et al. A Novel Risk Score System of Immune Genes Associated With Prognosis in Endometrial Cancer. Cancer Cell International 20:240, 1-12 (2020).
Zitti, et al. Natural killer cells in inflammation and autoimmunity. Cytokine & Growth Factor Reviews 42:37-46 (2018).
Barthelemy, Pierre A. et al. Comprehensive analysis of the factors contributing the stability and solubility of autonomous human VH domains. The Journal of biological chemistry 283(6):3639-3654 (2008).
Beiboer, Sigrid HW. et al. Guided selection of a pan carcinoma specific antibody reveals similar binding characteristics yet structural divergence between the original murine antibody and its human equivalent. Journal of Molecular Biology 296(3):833-849 (2000).
Blythe, Martin J, and Darren R Flower. Benchmarking B cell epitope prediction: underperformance of existing methods. Protein science 14(1):246-248 (2005). Published online Dec. 2, 2004.
British Medical Association. Definition of Polypeptide. p. 457. The British Medical Association Illustrated Medical Dictionary, First UK Edition, 2002, Dorling Kindersley, London, England.
Choi, Yoonjoo, and Charlotte M Deane. Predicting antibody complementarity determining region structures without classification. Molecular bioSystems 7(12):3327-3334 (2011).
Couzi, Lionel et al. Antibody-dependent anti-cytomegalovirus activity of human Gamma delta T cells expressing CD16 (FcgammaRIIIa). Blood 119(6):1418-1427 (2012).
De Genst, Erwin et al. Antibody Repertoire Development in Camelids. Developmental and Comparative Immunology 30(1-2):187-198 (2006).

(56) References Cited

OTHER PUBLICATIONS

Desmyter, Aline. et al. Camelid Nanobodies: Killing Two Birds with One Stone. Current Opinion in Structural Biology 32:1-8 (2015).
Dondelinger, Mathieu et al. Understanding the Significance and Implications of Antibody Numbering and Antigen-Binding Surface/Residue Definition. Frontiers in Immunology 9:2278, 1-15 (2018).
Gershoni, Jonathan M. et al. Epitope mapping: the first step in developing epitope-based vaccines. BioDrugs 21(3):145-156 (2007).
Gherardin, Nicholas A. et al. Human blood MAIT cell subsets defined using MR1 tetramers. Immunology and cell biology 96(5):507-525 (2018).
Grabstein, et al. Cloning of a T cell growth factor that interacts with the ß chain of the interleukin-2 receptor. Science 264(5161): 965-968 (1994).
International Search Report and Written Opinion issued in PCT/US2019/040592, mailed Jan. 3, 2020.
Janeway Jr, Charles A. et al. The rearrangement of antigen-receptor gene segments controls lymphocyte development. Immunobiology: The Immune System in Health and Disease. 5th Edition. New York: Garland Science. 1-17 (2001).
Ladner, Robert C. Mapping the epitopes of antibodies. Biotechnology and genetic engineering reviews 24(1):1-30 (2007).
Lin, Yuan et al. Improved Affinity of a Chicken Single-chain Antibody to Avian Infectious Bronchitis Virus by Site-directed Mutagenesis of Complementarity-determining Region H3. African Journal of Biotechnology 10(79):18294-18302 (2011).
Lydard, Peter. et al. In Antibodies: Generation of diversity. Immunology :76-85 (2011).
Makins, Marian, ed. Definition of Polypeptide. p. 1207. Collins English Dictionary, Third Edition, Updated 1995, HarperCollins Publishers, Glasgow, Scotland.
McLaughlin-Taylor, Elizabeth et al. Identification of the major late human cytomegalovirus matrix protein pp65 as a target antigen for CD8+ virus-specific cytotoxic T lymphocytes. Journal of medical virology 43(1):103-110 (1994).
PCT/US2018/029951 International Search Report and Written Opinion dated Jul. 3, 2018.
PCT/US2024/025875 International Search Report and Written Opinion dated Dec. 17, 2024.
PCT/US2024/033300 International Search Report and Written Opinion dated Jan. 29, 2025.
PCT/US2024/044469 International Search Report and Written Opinion dated Feb. 14, 2025.
Riechmann, Lutz et al. Reshaping Human Antibodies For Therapy. Nature 332(6162):323-327 (1988).
Rosenberg, Steven A. et al. Use of Tumor-infiltrating Lymphocytes and Interleukin-2 in the Immunotherapy of Patients with Metastatic Melanoma. The New England Journal of Medicine 319(25):1676-1680 (1988).
Schreiber, Andreas et al. 3D-Epitope-Explorer (3DEX): localization of conformational epitopes within three-dimensional structures of proteins. Journal of computational chemistry 26(9):879-887 (2005).
Sze, Daniel M. et al. Clonal cytotoxic T cells are expanded in myeloma and reside in the CD8(+)CD57(+)CD28(−) compartment. Blood 98(9):2817-2827 (2001).
Tutt, Alison L. et al. Activation and preferential expansion of rat cytotoxic (CD8) T cells in vitro and in vivo with a bispecific (anti-TCR alpha/beta x anti-CD2) F(ab')2 antibody. Journal of immunology 155(6):2960-2971 (1995).
UniProtKB Accession No. O14931. Natural cytotoxicity triggering receptor 3. Record created Jan. 1, 1998. Retrieved Nov. 14, 2024 at URL: https://www.uniprot.org/uniprotkb/014931/entry pp. 1-10.
UniProtKB Accession No. P01854. Immunoglobulin heavy constant epsilon. Record created Nov. 1, 1988. Retrieved Nov. 15, 2024 at URL: https://www.uniprot.org/uniprotkb/P01854/entry pp. 1-10.
UniProtKB Accession No. P01859. Immunoglobulin heavy constant gamma 2. Record created Nov. 1, 1988. pp. 1-9. Retrieved Oct. 11, 2024 at URL: https://www.uniprot.org/uniprotkb/P01859/entry.
UniProtKB Accession No. P01860. Immunoglobulin heavy constant gamma 3. Record created Nov. 1, 1988. pp. 1-14. Retrieved Oct. 11, 2024 at URL: https://www.uniprot.org/uniprotkb/P01860/entry.
UniProtKB Accession No. P01861. Immunoglobulin heavy constant gamma 4. Record created Nov. 1, 1988. pp. 1-13. Retrieved Oct. 11, 2024 at URL: https://www.uniprot.org/uniprotkb/P01861/entry.
UniProtKB Accession No. P01871. Immunoglobulin heavy constant mu. Record created Nov. 1, 1988. Retrieved Nov. 15, 2024 at URL: https://www.uniprot.org/uniprotkb/P01871/entry pp. 1-12.
UniProtKB Accession No. P01876. Immunoglobulin heavy constant alpha 1. Record created Nov. 1, 1988. Retrieved Nov. 15, 2024 at URL: https://www.uniprot.org/uniprotkb/P01876/entry pp. 1-9.
UniProtKB Accession No. P01877. Immunoglobulin heavy constant alpha 2. Record created Nov. 1, 1988. Retrieved Nov. 15, 2024 at URL: https://www.uniprot.org/uniprotkb/P01877/entry pp. 1-9.
UniProtKB Accession No. Q9H293. Interleukin-25. Record created Mar. 1, 2001. pp. 1-7. Retrieved Sep. 9, 2024 at URL: https://www.uniprot.org/uniprotkb/Q9H293/entry.
U.S. Appl. No. 16/960,704 Corrected Notice of Allowability dated Dec. 20, 2024.
U.S. Appl. No. 16/960,704 Notice of Allowance dated Dec. 19, 2024.
U.S. Appl. No. 17/402,322 Office Action dated Nov. 19, 2024.
U.S. Appl. No. 17/584,892 Office Action dated Feb. 3, 2025.
U.S. Appl. No. 17/820,805 Notice of Allowance dated Jan. 24, 2025.
U.S. Appl. No. 18/341,688 Office Action dated Mar. 5, 2025.
Ward, E Sally et al. Binding Activities of a Repertoire of Single Immunoglobulin Variable Domains Secreted from *Escherichia coli*. Nature 341(6242):544-546 (1989).
Weisser, Nina E, and J Christopher Hall. Applications of single-chain variable fragment antibodies in therapeutics and diagnostics. Biotechnology advances 27(4):502-520 (2009).
Wu, Zhihua. et al. T cell receptor beta-chain CDR3 spectratyping and cytomegalovirus activation in allogeneic hematopoietic stem cell transplant recipients. Journal of Zhejiang University Medical Sciences 45(5):515-521 (2016). With English abstract.

\* cited by examiner

```
                        SEQUENCE LISTING

<160> NUMBER OF SEQ ID NOS: 7385

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000
```

```
<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
```

```
<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33
```

000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 42

Gly Gly Gly Gly Ser
1               5

<210> SEQ ID NO 43
<211> LENGTH: 10
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 43

Gly Gly Gly Gly Ser Gly Gly Gly Gly Ser
1               5                   10

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Gly Gly Ser Gly Gly Gly Gly Ser Gly Gly Gly Gly Ser
1               5                   10                  15

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asp Val Pro Ser Gly Pro Gly Gly Gly Gly Ser Gly Gly Gly Gly
1               5                   10                  15

Ser

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
```

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74

<400> SEQUENCE: 74

000

<210> SEQ ID NO 75
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ala Glu Ala Ala Ala Lys Glu Ala Ala Ala Lys Ala Ala Ala
1               5                   10

<210> SEQ ID NO 76
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Ala Glu Ala Ala Ala Lys Glu Ala Ala Ala Lys Glu Ala Ala Ala Lys
1               5                   10                  15

Ala Ala Ala

<210> SEQ ID NO 77
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ala Glu Ala Ala Ala Lys Glu Ala Ala Ala Lys Glu Ala Ala Ala Lys
1               5                   10                  15

Glu Ala Ala Ala Lys Ala Ala Ala
            20

<210> SEQ ID NO 78
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 79

```
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
```

000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

```
<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
000

<210> SEQ ID NO 107
<400> SEQUENCE: 107
000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
```

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

```
<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000
```

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

```
<400> SEQUENCE: 158
000

<210> SEQ ID NO 159
<400> SEQUENCE: 159
000

<210> SEQ ID NO 160
<400> SEQUENCE: 160
000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
```

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

```
<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203
```

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

-continued

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

```
<400> SEQUENCE: 271
000

<210> SEQ ID NO 272
<400> SEQUENCE: 272
000

<210> SEQ ID NO 273
<400> SEQUENCE: 273
000

<210> SEQ ID NO 274
<400> SEQUENCE: 274
000

<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
```

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

```
<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<400> SEQUENCE: 300
000

<210> SEQ ID NO 301
<400> SEQUENCE: 301
000

<210> SEQ ID NO 302
<400> SEQUENCE: 302
000

<210> SEQ ID NO 303
<400> SEQUENCE: 303
000

<210> SEQ ID NO 304
<400> SEQUENCE: 304
000
```

```
<210> SEQ ID NO 305
<400> SEQUENCE: 305
000

<210> SEQ ID NO 306
<400> SEQUENCE: 306
000

<210> SEQ ID NO 307
<400> SEQUENCE: 307
000

<210> SEQ ID NO 308
<400> SEQUENCE: 308
000

<210> SEQ ID NO 309
<400> SEQUENCE: 309
000

<210> SEQ ID NO 310
<400> SEQUENCE: 310
000

<210> SEQ ID NO 311
<400> SEQUENCE: 311
000

<210> SEQ ID NO 312
<400> SEQUENCE: 312
000

<210> SEQ ID NO 313
<400> SEQUENCE: 313
000

<210> SEQ ID NO 314
<400> SEQUENCE: 314
000

<210> SEQ ID NO 315
<400> SEQUENCE: 315
000

<210> SEQ ID NO 316
```

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

-continued

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339
<400> SEQUENCE: 339
000

<210> SEQ ID NO 340
<400> SEQUENCE: 340
000

<210> SEQ ID NO 341
<400> SEQUENCE: 341
000

<210> SEQ ID NO 342
<400> SEQUENCE: 342
000

<210> SEQ ID NO 343
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
000

<210> SEQ ID NO 350

```
<400> SEQUENCE: 350
000

<210> SEQ ID NO 351
<400> SEQUENCE: 351
000

<210> SEQ ID NO 352
<400> SEQUENCE: 352
000

<210> SEQ ID NO 353
<400> SEQUENCE: 353
000

<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
```

000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

```
<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406
```

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

-continued

<210> SEQ ID NO 418
<400> SEQUENCE: 418
000

<210> SEQ ID NO 419
<400> SEQUENCE: 419
000

<210> SEQ ID NO 420
<400> SEQUENCE: 420
000

<210> SEQ ID NO 421
<400> SEQUENCE: 421
000

<210> SEQ ID NO 422
<400> SEQUENCE: 422
000

<210> SEQ ID NO 423
<400> SEQUENCE: 423
000

<210> SEQ ID NO 424
<400> SEQUENCE: 424
000

<210> SEQ ID NO 425
<400> SEQUENCE: 425
000

<210> SEQ ID NO 426
<400> SEQUENCE: 426
000

<210> SEQ ID NO 427
<400> SEQUENCE: 427
000

<210> SEQ ID NO 428
<400> SEQUENCE: 428
000

<210> SEQ ID NO 429

```
<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440
```

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

-continued

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

```
<210> SEQ ID NO 463
<400> SEQUENCE: 463
000

<210> SEQ ID NO 464
<400> SEQUENCE: 464
000

<210> SEQ ID NO 465
<400> SEQUENCE: 465
000

<210> SEQ ID NO 466
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000

<210> SEQ ID NO 472
<400> SEQUENCE: 472
000

<210> SEQ ID NO 473
<400> SEQUENCE: 473
000

<210> SEQ ID NO 474
```

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486
<400> SEQUENCE: 486
000

<210> SEQ ID NO 487
<400> SEQUENCE: 487
000

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723
<400> SEQUENCE: 723
000

<210> SEQ ID NO 724
<400> SEQUENCE: 724
000

<210> SEQ ID NO 725
<400> SEQUENCE: 725
000

<210> SEQ ID NO 726
<400> SEQUENCE: 726
000

<210> SEQ ID NO 727
<400> SEQUENCE: 727
000

<210> SEQ ID NO 728
<400> SEQUENCE: 728
000

<210> SEQ ID NO 729
<400> SEQUENCE: 729
000

<210> SEQ ID NO 730
<400> SEQUENCE: 730
000

<210> SEQ ID NO 731
<400> SEQUENCE: 731
000

<210> SEQ ID NO 732
<400> SEQUENCE: 732
000

<210> SEQ ID NO 733
<400> SEQUENCE: 733
000

-continued

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757
<400> SEQUENCE: 757
000

<210> SEQ ID NO 758
<400> SEQUENCE: 758
000

<210> SEQ ID NO 759
<400> SEQUENCE: 759
000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

-continued

<210> SEQ ID NO 779
<400> SEQUENCE: 779
000

<210> SEQ ID NO 780
<400> SEQUENCE: 780
000

<210> SEQ ID NO 781
<400> SEQUENCE: 781
000

<210> SEQ ID NO 782
<400> SEQUENCE: 782
000

<210> SEQ ID NO 783
<400> SEQUENCE: 783
000

<210> SEQ ID NO 784
<400> SEQUENCE: 784
000

<210> SEQ ID NO 785
<400> SEQUENCE: 785
000

<210> SEQ ID NO 786
<400> SEQUENCE: 786
000

<210> SEQ ID NO 787
<400> SEQUENCE: 787
000

<210> SEQ ID NO 788
<400> SEQUENCE: 788
000

<210> SEQ ID NO 789
<400> SEQUENCE: 789
000

<210> SEQ ID NO 790

```
<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801

<400> SEQUENCE: 801
```

000

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813
<400> SEQUENCE: 813
000

<210> SEQ ID NO 814
<400> SEQUENCE: 814
000

<210> SEQ ID NO 815
<400> SEQUENCE: 815
000

<210> SEQ ID NO 816
<400> SEQUENCE: 816
000

<210> SEQ ID NO 817
<400> SEQUENCE: 817
000

<210> SEQ ID NO 818
<400> SEQUENCE: 818
000

<210> SEQ ID NO 819
<400> SEQUENCE: 819
000

<210> SEQ ID NO 820
<400> SEQUENCE: 820
000

<210> SEQ ID NO 821
<400> SEQUENCE: 821
000

<210> SEQ ID NO 822
<400> SEQUENCE: 822
000

<210> SEQ ID NO 823
<400> SEQUENCE: 823
000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

```
<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880
```

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

<400> SEQUENCE: 913

000

<210> SEQ ID NO 914

<400> SEQUENCE: 914

000

<210> SEQ ID NO 915
<400> SEQUENCE: 915
000

<210> SEQ ID NO 916
<400> SEQUENCE: 916
000

<210> SEQ ID NO 917
<400> SEQUENCE: 917
000

<210> SEQ ID NO 918
<400> SEQUENCE: 918
000

<210> SEQ ID NO 919
<400> SEQUENCE: 919
000

<210> SEQ ID NO 920
<400> SEQUENCE: 920
000

<210> SEQ ID NO 921
<400> SEQUENCE: 921
000

<210> SEQ ID NO 922
<400> SEQUENCE: 922
000

<210> SEQ ID NO 923
<400> SEQUENCE: 923
000

<210> SEQ ID NO 924
<400> SEQUENCE: 924
000

<210> SEQ ID NO 925
<400> SEQUENCE: 925
000

-continued

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994
<400> SEQUENCE: 994
000

<210> SEQ ID NO 995
<400> SEQUENCE: 995
000

<210> SEQ ID NO 996
<400> SEQUENCE: 996
000

<210> SEQ ID NO 997
<400> SEQUENCE: 997
000

<210> SEQ ID NO 998
<400> SEQUENCE: 998
000

<210> SEQ ID NO 999
<400> SEQUENCE: 999
000

<210> SEQ ID NO 1000
<400> SEQUENCE: 1000
000

<210> SEQ ID NO 1001
<400> SEQUENCE: 1001
000

<210> SEQ ID NO 1002
<400> SEQUENCE: 1002
000

<210> SEQ ID NO 1003
<400> SEQUENCE: 1003
000

<210> SEQ ID NO 1004
<400> SEQUENCE: 1004
000

-continued

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

```
<210> SEQ ID NO 1016
<400> SEQUENCE: 1016
000

<210> SEQ ID NO 1017
<400> SEQUENCE: 1017
000

<210> SEQ ID NO 1018
<400> SEQUENCE: 1018
000

<210> SEQ ID NO 1019
<400> SEQUENCE: 1019
000

<210> SEQ ID NO 1020
<400> SEQUENCE: 1020
000

<210> SEQ ID NO 1021
<400> SEQUENCE: 1021
000

<210> SEQ ID NO 1022
<400> SEQUENCE: 1022
000

<210> SEQ ID NO 1023
<400> SEQUENCE: 1023
000

<210> SEQ ID NO 1024
<400> SEQUENCE: 1024
000

<210> SEQ ID NO 1025
<400> SEQUENCE: 1025
000

<210> SEQ ID NO 1026
<400> SEQUENCE: 1026
000

<210> SEQ ID NO 1027
```

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

-continued

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

-continued

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

```
<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106
```

```
<400> SEQUENCE: 1106
000

<210> SEQ ID NO 1107
<400> SEQUENCE: 1107
000

<210> SEQ ID NO 1108
<400> SEQUENCE: 1108
000

<210> SEQ ID NO 1109
<400> SEQUENCE: 1109
000

<210> SEQ ID NO 1110
<400> SEQUENCE: 1110
000

<210> SEQ ID NO 1111
<400> SEQUENCE: 1111
000

<210> SEQ ID NO 1112
<400> SEQUENCE: 1112
000

<210> SEQ ID NO 1113
<400> SEQUENCE: 1113
000

<210> SEQ ID NO 1114
<400> SEQUENCE: 1114
000

<210> SEQ ID NO 1115
<400> SEQUENCE: 1115
000

<210> SEQ ID NO 1116
<400> SEQUENCE: 1116
000

<210> SEQ ID NO 1117
<400> SEQUENCE: 1117
```

000

<210> SEQ ID NO 1118

<400> SEQUENCE: 1118

000

<210> SEQ ID NO 1119

<400> SEQUENCE: 1119

000

<210> SEQ ID NO 1120

<400> SEQUENCE: 1120

000

<210> SEQ ID NO 1121

<400> SEQUENCE: 1121

000

<210> SEQ ID NO 1122

<400> SEQUENCE: 1122

000

<210> SEQ ID NO 1123

<400> SEQUENCE: 1123

000

<210> SEQ ID NO 1124

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

<400> SEQUENCE: 1128

000

<210> SEQ ID NO 1129
<400> SEQUENCE: 1129
000

<210> SEQ ID NO 1130
<400> SEQUENCE: 1130
000

<210> SEQ ID NO 1131
<400> SEQUENCE: 1131
000

<210> SEQ ID NO 1132
<400> SEQUENCE: 1132
000

<210> SEQ ID NO 1133
<400> SEQUENCE: 1133
000

<210> SEQ ID NO 1134
<400> SEQUENCE: 1134
000

<210> SEQ ID NO 1135
<400> SEQUENCE: 1135
000

<210> SEQ ID NO 1136
<400> SEQUENCE: 1136
000

<210> SEQ ID NO 1137
<400> SEQUENCE: 1137
000

<210> SEQ ID NO 1138
<400> SEQUENCE: 1138
000

<210> SEQ ID NO 1139
<400> SEQUENCE: 1139
000

<210> SEQ ID NO 1140

```
<400> SEQUENCE: 1140
000

<210> SEQ ID NO 1141
<400> SEQUENCE: 1141
000

<210> SEQ ID NO 1142
<400> SEQUENCE: 1142
000

<210> SEQ ID NO 1143
<400> SEQUENCE: 1143
000

<210> SEQ ID NO 1144
<400> SEQUENCE: 1144
000

<210> SEQ ID NO 1145
<400> SEQUENCE: 1145
000

<210> SEQ ID NO 1146
<400> SEQUENCE: 1146
000

<210> SEQ ID NO 1147
<400> SEQUENCE: 1147
000

<210> SEQ ID NO 1148
<400> SEQUENCE: 1148
000

<210> SEQ ID NO 1149
<400> SEQUENCE: 1149
000

<210> SEQ ID NO 1150
<400> SEQUENCE: 1150
000

<210> SEQ ID NO 1151
<400> SEQUENCE: 1151
```

000

<210> SEQ ID NO 1152

<400> SEQUENCE: 1152

000

<210> SEQ ID NO 1153

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000

<210> SEQ ID NO 1185

<400> SEQUENCE: 1185

000

<210> SEQ ID NO 1186

<400> SEQUENCE: 1186

000

<210> SEQ ID NO 1187

<400> SEQUENCE: 1187

000

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199

<400> SEQUENCE: 1199

000

<210> SEQ ID NO 1200

<400> SEQUENCE: 1200

000

<210> SEQ ID NO 1201

<400> SEQUENCE: 1201

000

<210> SEQ ID NO 1202

<400> SEQUENCE: 1202

000

<210> SEQ ID NO 1203

<400> SEQUENCE: 1203

000

<210> SEQ ID NO 1204

<400> SEQUENCE: 1204

000

<210> SEQ ID NO 1205

<400> SEQUENCE: 1205

000

<210> SEQ ID NO 1206

<400> SEQUENCE: 1206

000

<210> SEQ ID NO 1207

<400> SEQUENCE: 1207

000

```
<210> SEQ ID NO 1208
<400> SEQUENCE: 1208
000

<210> SEQ ID NO 1209
<400> SEQUENCE: 1209
000

<210> SEQ ID NO 1210
<400> SEQUENCE: 1210
000

<210> SEQ ID NO 1211
<400> SEQUENCE: 1211
000

<210> SEQ ID NO 1212
<400> SEQUENCE: 1212
000

<210> SEQ ID NO 1213
<400> SEQUENCE: 1213
000

<210> SEQ ID NO 1214
<400> SEQUENCE: 1214
000

<210> SEQ ID NO 1215
<400> SEQUENCE: 1215
000

<210> SEQ ID NO 1216
<400> SEQUENCE: 1216
000

<210> SEQ ID NO 1217
<400> SEQUENCE: 1217
000

<210> SEQ ID NO 1218
<400> SEQUENCE: 1218
000

<210> SEQ ID NO 1219
```

```
<400> SEQUENCE: 1219
000

<210> SEQ ID NO 1220
<400> SEQUENCE: 1220
000

<210> SEQ ID NO 1221
<400> SEQUENCE: 1221
000

<210> SEQ ID NO 1222
<400> SEQUENCE: 1222
000

<210> SEQ ID NO 1223
<400> SEQUENCE: 1223
000

<210> SEQ ID NO 1224
<400> SEQUENCE: 1224
000

<210> SEQ ID NO 1225
<400> SEQUENCE: 1225
000

<210> SEQ ID NO 1226
<400> SEQUENCE: 1226
000

<210> SEQ ID NO 1227
<400> SEQUENCE: 1227
000

<210> SEQ ID NO 1228
<400> SEQUENCE: 1228
000

<210> SEQ ID NO 1229
<400> SEQUENCE: 1229
000

<210> SEQ ID NO 1230
<400> SEQUENCE: 1230
```

000

<210> SEQ ID NO 1231

<400> SEQUENCE: 1231

000

<210> SEQ ID NO 1232

<400> SEQUENCE: 1232

000

<210> SEQ ID NO 1233

<400> SEQUENCE: 1233

000

<210> SEQ ID NO 1234

<400> SEQUENCE: 1234

000

<210> SEQ ID NO 1235

<400> SEQUENCE: 1235

000

<210> SEQ ID NO 1236

<400> SEQUENCE: 1236

000

<210> SEQ ID NO 1237

<400> SEQUENCE: 1237

000

<210> SEQ ID NO 1238

<400> SEQUENCE: 1238

000

<210> SEQ ID NO 1239

<400> SEQUENCE: 1239

000

<210> SEQ ID NO 1240

<400> SEQUENCE: 1240

000

<210> SEQ ID NO 1241

<400> SEQUENCE: 1241

000

<210> SEQ ID NO 1242

<400> SEQUENCE: 1242

000

<210> SEQ ID NO 1243

<400> SEQUENCE: 1243

000

<210> SEQ ID NO 1244

<400> SEQUENCE: 1244

000

<210> SEQ ID NO 1245

<400> SEQUENCE: 1245

000

<210> SEQ ID NO 1246

<400> SEQUENCE: 1246

000

<210> SEQ ID NO 1247

<400> SEQUENCE: 1247

000

<210> SEQ ID NO 1248

<400> SEQUENCE: 1248

000

<210> SEQ ID NO 1249

<400> SEQUENCE: 1249

000

<210> SEQ ID NO 1250

<400> SEQUENCE: 1250

000

<210> SEQ ID NO 1251

<400> SEQUENCE: 1251

000

<210> SEQ ID NO 1252

<400> SEQUENCE: 1252

000

<210> SEQ ID NO 1253

<400> SEQUENCE: 1253

000

<210> SEQ ID NO 1254

<400> SEQUENCE: 1254

000

<210> SEQ ID NO 1255

<400> SEQUENCE: 1255

000

<210> SEQ ID NO 1256

<400> SEQUENCE: 1256

000

<210> SEQ ID NO 1257

<400> SEQUENCE: 1257

000

<210> SEQ ID NO 1258

<400> SEQUENCE: 1258

000

<210> SEQ ID NO 1259

<400> SEQUENCE: 1259

000

<210> SEQ ID NO 1260

<400> SEQUENCE: 1260

000

<210> SEQ ID NO 1261

<400> SEQUENCE: 1261

000

<210> SEQ ID NO 1262

<400> SEQUENCE: 1262

000

<210> SEQ ID NO 1263

<400> SEQUENCE: 1263

000

<210> SEQ ID NO 1264

<400> SEQUENCE: 1264

000

<210> SEQ ID NO 1265

<400> SEQUENCE: 1265

000

<210> SEQ ID NO 1266

<400> SEQUENCE: 1266

000

<210> SEQ ID NO 1267

<400> SEQUENCE: 1267

000

<210> SEQ ID NO 1268

<400> SEQUENCE: 1268

000

<210> SEQ ID NO 1269

<400> SEQUENCE: 1269

000

<210> SEQ ID NO 1270

<400> SEQUENCE: 1270

000

<210> SEQ ID NO 1271

<400> SEQUENCE: 1271

000

<210> SEQ ID NO 1272

<400> SEQUENCE: 1272

000

<210> SEQ ID NO 1273

<400> SEQUENCE: 1273

000

<210> SEQ ID NO 1274

<400> SEQUENCE: 1274

000

<210> SEQ ID NO 1275

<400> SEQUENCE: 1275

000

<210> SEQ ID NO 1276
<400> SEQUENCE: 1276
000

<210> SEQ ID NO 1277
<400> SEQUENCE: 1277
000

<210> SEQ ID NO 1278
<400> SEQUENCE: 1278
000

<210> SEQ ID NO 1279
<400> SEQUENCE: 1279
000

<210> SEQ ID NO 1280
<400> SEQUENCE: 1280
000

<210> SEQ ID NO 1281
<400> SEQUENCE: 1281
000

<210> SEQ ID NO 1282
<400> SEQUENCE: 1282
000

<210> SEQ ID NO 1283
<400> SEQUENCE: 1283
000

<210> SEQ ID NO 1284
<400> SEQUENCE: 1284
000

<210> SEQ ID NO 1285
<400> SEQUENCE: 1285
000

<210> SEQ ID NO 1286
<400> SEQUENCE: 1286
000

<210> SEQ ID NO 1287

<400> SEQUENCE: 1287

000

<210> SEQ ID NO 1288

<400> SEQUENCE: 1288

000

<210> SEQ ID NO 1289

<400> SEQUENCE: 1289

000

<210> SEQ ID NO 1290

<400> SEQUENCE: 1290

000

<210> SEQ ID NO 1291

<400> SEQUENCE: 1291

000

<210> SEQ ID NO 1292

<400> SEQUENCE: 1292

000

<210> SEQ ID NO 1293

<400> SEQUENCE: 1293

000

<210> SEQ ID NO 1294

<400> SEQUENCE: 1294

000

<210> SEQ ID NO 1295

<400> SEQUENCE: 1295

000

<210> SEQ ID NO 1296

<400> SEQUENCE: 1296

000

<210> SEQ ID NO 1297

<400> SEQUENCE: 1297

000

<210> SEQ ID NO 1298

<210> SEQ ID NO 1298

<400> SEQUENCE: 1298

000

<210> SEQ ID NO 1299

<400> SEQUENCE: 1299

000

<210> SEQ ID NO 1300

<400> SEQUENCE: 1300

000

<210> SEQ ID NO 1301

<400> SEQUENCE: 1301

000

<210> SEQ ID NO 1302

<400> SEQUENCE: 1302

000

<210> SEQ ID NO 1303

<400> SEQUENCE: 1303

000

<210> SEQ ID NO 1304

<400> SEQUENCE: 1304

000

<210> SEQ ID NO 1305

<400> SEQUENCE: 1305

000

<210> SEQ ID NO 1306

<400> SEQUENCE: 1306

000

<210> SEQ ID NO 1307

<400> SEQUENCE: 1307

000

<210> SEQ ID NO 1308

<400> SEQUENCE: 1308

000

<210> SEQ ID NO 1309

<400> SEQUENCE: 1309

000

<210> SEQ ID NO 1310
<400> SEQUENCE: 1310
000

<210> SEQ ID NO 1311
<400> SEQUENCE: 1311
000

<210> SEQ ID NO 1312
<400> SEQUENCE: 1312
000

<210> SEQ ID NO 1313
<400> SEQUENCE: 1313
000

<210> SEQ ID NO 1314
<400> SEQUENCE: 1314
000

<210> SEQ ID NO 1315
<400> SEQUENCE: 1315
000

<210> SEQ ID NO 1316
<400> SEQUENCE: 1316
000

<210> SEQ ID NO 1317
<400> SEQUENCE: 1317
000

<210> SEQ ID NO 1318
<400> SEQUENCE: 1318
000

<210> SEQ ID NO 1319
<400> SEQUENCE: 1319
000

<210> SEQ ID NO 1320
<400> SEQUENCE: 1320
000

<210> SEQ ID NO 1321

<400> SEQUENCE: 1321

000

<210> SEQ ID NO 1322

<400> SEQUENCE: 1322

000

<210> SEQ ID NO 1323

<400> SEQUENCE: 1323

000

<210> SEQ ID NO 1324

<400> SEQUENCE: 1324

000

<210> SEQ ID NO 1325

<400> SEQUENCE: 1325

000

<210> SEQ ID NO 1326

<400> SEQUENCE: 1326

000

<210> SEQ ID NO 1327

<400> SEQUENCE: 1327

000

<210> SEQ ID NO 1328

<400> SEQUENCE: 1328

000

<210> SEQ ID NO 1329

<400> SEQUENCE: 1329

000

<210> SEQ ID NO 1330

<400> SEQUENCE: 1330

000

<210> SEQ ID NO 1331

<400> SEQUENCE: 1331

000

<210> SEQ ID NO 1332

<400> SEQUENCE: 1332

000

<210> SEQ ID NO 1333

<400> SEQUENCE: 1333

000

<210> SEQ ID NO 1334

<400> SEQUENCE: 1334

000

<210> SEQ ID NO 1335

<400> SEQUENCE: 1335

000

<210> SEQ ID NO 1336

<400> SEQUENCE: 1336

000

<210> SEQ ID NO 1337

<400> SEQUENCE: 1337

000

<210> SEQ ID NO 1338

<400> SEQUENCE: 1338

000

<210> SEQ ID NO 1339

<400> SEQUENCE: 1339

000

<210> SEQ ID NO 1340

<400> SEQUENCE: 1340

000

<210> SEQ ID NO 1341

<400> SEQUENCE: 1341

000

<210> SEQ ID NO 1342

<400> SEQUENCE: 1342

000

<210> SEQ ID NO 1343

<400> SEQUENCE: 1343

000

<210> SEQ ID NO 1344

<400> SEQUENCE: 1344

000

<210> SEQ ID NO 1345

<400> SEQUENCE: 1345

000

<210> SEQ ID NO 1346

<400> SEQUENCE: 1346

000

<210> SEQ ID NO 1347

<400> SEQUENCE: 1347

000

<210> SEQ ID NO 1348

<400> SEQUENCE: 1348

000

<210> SEQ ID NO 1349

<400> SEQUENCE: 1349

000

<210> SEQ ID NO 1350

<400> SEQUENCE: 1350

000

<210> SEQ ID NO 1351

<400> SEQUENCE: 1351

000

<210> SEQ ID NO 1352

<400> SEQUENCE: 1352

000

<210> SEQ ID NO 1353

<400> SEQUENCE: 1353

000

<210> SEQ ID NO 1354

<400> SEQUENCE: 1354

000

<210> SEQ ID NO 1355

<400> SEQUENCE: 1355

000

<210> SEQ ID NO 1356

<400> SEQUENCE: 1356

000

<210> SEQ ID NO 1357

<400> SEQUENCE: 1357

000

<210> SEQ ID NO 1358

<400> SEQUENCE: 1358

000

<210> SEQ ID NO 1359

<400> SEQUENCE: 1359

000

<210> SEQ ID NO 1360

<400> SEQUENCE: 1360

000

<210> SEQ ID NO 1361

<400> SEQUENCE: 1361

000

<210> SEQ ID NO 1362

<400> SEQUENCE: 1362

000

<210> SEQ ID NO 1363

<400> SEQUENCE: 1363

000

<210> SEQ ID NO 1364

<400> SEQUENCE: 1364

000

<210> SEQ ID NO 1365

<400> SEQUENCE: 1365

000

<210> SEQ ID NO 1366

<400> SEQUENCE: 1366

000

<210> SEQ ID NO 1367

<400> SEQUENCE: 1367

000

<210> SEQ ID NO 1368

<400> SEQUENCE: 1368

000

<210> SEQ ID NO 1369

<400> SEQUENCE: 1369

000

<210> SEQ ID NO 1370

<400> SEQUENCE: 1370

000

<210> SEQ ID NO 1371

<400> SEQUENCE: 1371

000

<210> SEQ ID NO 1372

<400> SEQUENCE: 1372

000

<210> SEQ ID NO 1373

<400> SEQUENCE: 1373

000

<210> SEQ ID NO 1374

<400> SEQUENCE: 1374

000

<210> SEQ ID NO 1375

<400> SEQUENCE: 1375

000

<210> SEQ ID NO 1376

<400> SEQUENCE: 1376

000

<210> SEQ ID NO 1377

```
<400> SEQUENCE: 1377
000

<210> SEQ ID NO 1378
<400> SEQUENCE: 1378
000

<210> SEQ ID NO 1379
<400> SEQUENCE: 1379
000

<210> SEQ ID NO 1380
<400> SEQUENCE: 1380
000

<210> SEQ ID NO 1381
<400> SEQUENCE: 1381
000

<210> SEQ ID NO 1382
<400> SEQUENCE: 1382
000

<210> SEQ ID NO 1383
<400> SEQUENCE: 1383
000

<210> SEQ ID NO 1384
<400> SEQUENCE: 1384
000

<210> SEQ ID NO 1385
<400> SEQUENCE: 1385
000

<210> SEQ ID NO 1386
<400> SEQUENCE: 1386
000

<210> SEQ ID NO 1387
<400> SEQUENCE: 1387
000

<210> SEQ ID NO 1388
<400> SEQUENCE: 1388
```

000

<210> SEQ ID NO 1389

<400> SEQUENCE: 1389

000

<210> SEQ ID NO 1390

<400> SEQUENCE: 1390

000

<210> SEQ ID NO 1391

<400> SEQUENCE: 1391

000

<210> SEQ ID NO 1392

<400> SEQUENCE: 1392

000

<210> SEQ ID NO 1393

<400> SEQUENCE: 1393

000

<210> SEQ ID NO 1394

<400> SEQUENCE: 1394

000

<210> SEQ ID NO 1395

<400> SEQUENCE: 1395

000

<210> SEQ ID NO 1396

<400> SEQUENCE: 1396

000

<210> SEQ ID NO 1397

<400> SEQUENCE: 1397

000

<210> SEQ ID NO 1398

<400> SEQUENCE: 1398

000

<210> SEQ ID NO 1399

<400> SEQUENCE: 1399

000

<210> SEQ ID NO 1400

<400> SEQUENCE: 1400

000

<210> SEQ ID NO 1401

<400> SEQUENCE: 1401

000

<210> SEQ ID NO 1402

<400> SEQUENCE: 1402

000

<210> SEQ ID NO 1403

<400> SEQUENCE: 1403

000

<210> SEQ ID NO 1404

<400> SEQUENCE: 1404

000

<210> SEQ ID NO 1405

<400> SEQUENCE: 1405

000

<210> SEQ ID NO 1406

<400> SEQUENCE: 1406

000

<210> SEQ ID NO 1407

<400> SEQUENCE: 1407

000

<210> SEQ ID NO 1408

<400> SEQUENCE: 1408

000

<210> SEQ ID NO 1409

<400> SEQUENCE: 1409

000

<210> SEQ ID NO 1410

<400> SEQUENCE: 1410

000

```
<210> SEQ ID NO 1411
<400> SEQUENCE: 1411
000

<210> SEQ ID NO 1412
<400> SEQUENCE: 1412
000

<210> SEQ ID NO 1413
<400> SEQUENCE: 1413
000

<210> SEQ ID NO 1414
<400> SEQUENCE: 1414
000

<210> SEQ ID NO 1415
<400> SEQUENCE: 1415
000

<210> SEQ ID NO 1416
<400> SEQUENCE: 1416
000

<210> SEQ ID NO 1417
<400> SEQUENCE: 1417
000

<210> SEQ ID NO 1418
<400> SEQUENCE: 1418
000

<210> SEQ ID NO 1419
<400> SEQUENCE: 1419
000

<210> SEQ ID NO 1420
<400> SEQUENCE: 1420
000

<210> SEQ ID NO 1421
<400> SEQUENCE: 1421
000

<210> SEQ ID NO 1422
```

-continued

<400> SEQUENCE: 1422

000

<210> SEQ ID NO 1423

<400> SEQUENCE: 1423

000

<210> SEQ ID NO 1424

<400> SEQUENCE: 1424

000

<210> SEQ ID NO 1425

<400> SEQUENCE: 1425

000

<210> SEQ ID NO 1426

<400> SEQUENCE: 1426

000

<210> SEQ ID NO 1427

<400> SEQUENCE: 1427

000

<210> SEQ ID NO 1428

<400> SEQUENCE: 1428

000

<210> SEQ ID NO 1429

<400> SEQUENCE: 1429

000

<210> SEQ ID NO 1430

<400> SEQUENCE: 1430

000

<210> SEQ ID NO 1431

<400> SEQUENCE: 1431

000

<210> SEQ ID NO 1432

<400> SEQUENCE: 1432

000

<210> SEQ ID NO 1433

<400> SEQUENCE: 1433

000

<210> SEQ ID NO 1434

<400> SEQUENCE: 1434

000

<210> SEQ ID NO 1435

<400> SEQUENCE: 1435

000

<210> SEQ ID NO 1436

<400> SEQUENCE: 1436

000

<210> SEQ ID NO 1437

<400> SEQUENCE: 1437

000

<210> SEQ ID NO 1438

<400> SEQUENCE: 1438

000

<210> SEQ ID NO 1439

<400> SEQUENCE: 1439

000

<210> SEQ ID NO 1440

<400> SEQUENCE: 1440

000

<210> SEQ ID NO 1441

<400> SEQUENCE: 1441

000

<210> SEQ ID NO 1442

<400> SEQUENCE: 1442

000

<210> SEQ ID NO 1443

<400> SEQUENCE: 1443

000

<210> SEQ ID NO 1444

<400> SEQUENCE: 1444

000

<210> SEQ ID NO 1445

<400> SEQUENCE: 1445

000

<210> SEQ ID NO 1446

<400> SEQUENCE: 1446

000

<210> SEQ ID NO 1447

<400> SEQUENCE: 1447

000

<210> SEQ ID NO 1448

<400> SEQUENCE: 1448

000

<210> SEQ ID NO 1449

<400> SEQUENCE: 1449

000

<210> SEQ ID NO 1450

<400> SEQUENCE: 1450

000

<210> SEQ ID NO 1451

<400> SEQUENCE: 1451

000

<210> SEQ ID NO 1452

<400> SEQUENCE: 1452

000

<210> SEQ ID NO 1453

<400> SEQUENCE: 1453

000

<210> SEQ ID NO 1454

<400> SEQUENCE: 1454

000

<210> SEQ ID NO 1455

<400> SEQUENCE: 1455

000

<210> SEQ ID NO 1456

<400> SEQUENCE: 1456

000

<210> SEQ ID NO 1457

<400> SEQUENCE: 1457

000

<210> SEQ ID NO 1458

<400> SEQUENCE: 1458

000

<210> SEQ ID NO 1459

<400> SEQUENCE: 1459

000

<210> SEQ ID NO 1460

<400> SEQUENCE: 1460

000

<210> SEQ ID NO 1461

<400> SEQUENCE: 1461

000

<210> SEQ ID NO 1462

<400> SEQUENCE: 1462

000

<210> SEQ ID NO 1463

<400> SEQUENCE: 1463

000

<210> SEQ ID NO 1464

<400> SEQUENCE: 1464

000

<210> SEQ ID NO 1465

<400> SEQUENCE: 1465

000

<210> SEQ ID NO 1466

<400> SEQUENCE: 1466

000

<210> SEQ ID NO 1467

<400> SEQUENCE: 1467

000

<210> SEQ ID NO 1468

<400> SEQUENCE: 1468

000

<210> SEQ ID NO 1469

<400> SEQUENCE: 1469

000

<210> SEQ ID NO 1470

<400> SEQUENCE: 1470

000

<210> SEQ ID NO 1471

<400> SEQUENCE: 1471

000

<210> SEQ ID NO 1472

<400> SEQUENCE: 1472

000

<210> SEQ ID NO 1473

<400> SEQUENCE: 1473

000

<210> SEQ ID NO 1474

<400> SEQUENCE: 1474

000

<210> SEQ ID NO 1475

<400> SEQUENCE: 1475

000

<210> SEQ ID NO 1476

<400> SEQUENCE: 1476

000

<210> SEQ ID NO 1477

<400> SEQUENCE: 1477

000

<210> SEQ ID NO 1478

<400> SEQUENCE: 1478

000

<210> SEQ ID NO 1479

<400> SEQUENCE: 1479

000

<210> SEQ ID NO 1480

<400> SEQUENCE: 1480

000

<210> SEQ ID NO 1481

<400> SEQUENCE: 1481

000

<210> SEQ ID NO 1482

<400> SEQUENCE: 1482

000

<210> SEQ ID NO 1483

<400> SEQUENCE: 1483

000

<210> SEQ ID NO 1484

<400> SEQUENCE: 1484

000

<210> SEQ ID NO 1485

<400> SEQUENCE: 1485

000

<210> SEQ ID NO 1486

<400> SEQUENCE: 1486

000

<210> SEQ ID NO 1487

<400> SEQUENCE: 1487

000

<210> SEQ ID NO 1488

<400> SEQUENCE: 1488

000

<210> SEQ ID NO 1489

<400> SEQUENCE: 1489

000

```
<210> SEQ ID NO 1490
<400> SEQUENCE: 1490
000

<210> SEQ ID NO 1491
<400> SEQUENCE: 1491
000

<210> SEQ ID NO 1492
<400> SEQUENCE: 1492
000

<210> SEQ ID NO 1493
<400> SEQUENCE: 1493
000

<210> SEQ ID NO 1494
<400> SEQUENCE: 1494
000

<210> SEQ ID NO 1495
<400> SEQUENCE: 1495
000

<210> SEQ ID NO 1496
<400> SEQUENCE: 1496
000

<210> SEQ ID NO 1497
<400> SEQUENCE: 1497
000

<210> SEQ ID NO 1498
<400> SEQUENCE: 1498
000

<210> SEQ ID NO 1499
<400> SEQUENCE: 1499
000

<210> SEQ ID NO 1500
<400> SEQUENCE: 1500
000

<210> SEQ ID NO 1501
```

<400> SEQUENCE: 1501

000

<210> SEQ ID NO 1502

<400> SEQUENCE: 1502

000

<210> SEQ ID NO 1503

<400> SEQUENCE: 1503

000

<210> SEQ ID NO 1504

<400> SEQUENCE: 1504

000

<210> SEQ ID NO 1505

<400> SEQUENCE: 1505

000

<210> SEQ ID NO 1506

<400> SEQUENCE: 1506

000

<210> SEQ ID NO 1507

<400> SEQUENCE: 1507

000

<210> SEQ ID NO 1508

<400> SEQUENCE: 1508

000

<210> SEQ ID NO 1509

<400> SEQUENCE: 1509

000

<210> SEQ ID NO 1510

<400> SEQUENCE: 1510

000

<210> SEQ ID NO 1511

<400> SEQUENCE: 1511

000

<210> SEQ ID NO 1512

<400> SEQUENCE: 1512

000

<210> SEQ ID NO 1513

<400> SEQUENCE: 1513

000

<210> SEQ ID NO 1514

<400> SEQUENCE: 1514

000

<210> SEQ ID NO 1515

<400> SEQUENCE: 1515

000

<210> SEQ ID NO 1516

<400> SEQUENCE: 1516

000

<210> SEQ ID NO 1517

<400> SEQUENCE: 1517

000

<210> SEQ ID NO 1518

<400> SEQUENCE: 1518

000

<210> SEQ ID NO 1519

<400> SEQUENCE: 1519

000

<210> SEQ ID NO 1520

<400> SEQUENCE: 1520

000

<210> SEQ ID NO 1521

<400> SEQUENCE: 1521

000

<210> SEQ ID NO 1522

<400> SEQUENCE: 1522

000

<210> SEQ ID NO 1523

<400> SEQUENCE: 1523

000

<210> SEQ ID NO 1524

<400> SEQUENCE: 1524

000

<210> SEQ ID NO 1525

<400> SEQUENCE: 1525

000

<210> SEQ ID NO 1526

<400> SEQUENCE: 1526

000

<210> SEQ ID NO 1527

<400> SEQUENCE: 1527

000

<210> SEQ ID NO 1528

<400> SEQUENCE: 1528

000

<210> SEQ ID NO 1529

<400> SEQUENCE: 1529

000

<210> SEQ ID NO 1530

<400> SEQUENCE: 1530

000

<210> SEQ ID NO 1531

<400> SEQUENCE: 1531

000

<210> SEQ ID NO 1532

<400> SEQUENCE: 1532

000

<210> SEQ ID NO 1533

<400> SEQUENCE: 1533

000

<210> SEQ ID NO 1534

<400> SEQUENCE: 1534

000

<210> SEQ ID NO 1535

<400> SEQUENCE: 1535

000

<210> SEQ ID NO 1536

<400> SEQUENCE: 1536

000

<210> SEQ ID NO 1537

<400> SEQUENCE: 1537

000

<210> SEQ ID NO 1538

<400> SEQUENCE: 1538

000

<210> SEQ ID NO 1539

<400> SEQUENCE: 1539

000

<210> SEQ ID NO 1540

<400> SEQUENCE: 1540

000

<210> SEQ ID NO 1541

<400> SEQUENCE: 1541

000

<210> SEQ ID NO 1542

<400> SEQUENCE: 1542

000

<210> SEQ ID NO 1543

<400> SEQUENCE: 1543

000

<210> SEQ ID NO 1544

<400> SEQUENCE: 1544

000

<210> SEQ ID NO 1545

<400> SEQUENCE: 1545

000

<210> SEQ ID NO 1546

<400> SEQUENCE: 1546

000

<210> SEQ ID NO 1547

<400> SEQUENCE: 1547

000

<210> SEQ ID NO 1548

<400> SEQUENCE: 1548

000

<210> SEQ ID NO 1549

<400> SEQUENCE: 1549

000

<210> SEQ ID NO 1550

<400> SEQUENCE: 1550

000

<210> SEQ ID NO 1551

<400> SEQUENCE: 1551

000

<210> SEQ ID NO 1552

<400> SEQUENCE: 1552

000

<210> SEQ ID NO 1553

<400> SEQUENCE: 1553

000

<210> SEQ ID NO 1554

<400> SEQUENCE: 1554

000

<210> SEQ ID NO 1555

<400> SEQUENCE: 1555

000

<210> SEQ ID NO 1556

<400> SEQUENCE: 1556

000

<210> SEQ ID NO 1557

<400> SEQUENCE: 1557

000

<210> SEQ ID NO 1558

<400> SEQUENCE: 1558

000

<210> SEQ ID NO 1559

<400> SEQUENCE: 1559

000

<210> SEQ ID NO 1560

<400> SEQUENCE: 1560

000

<210> SEQ ID NO 1561

<400> SEQUENCE: 1561

000

<210> SEQ ID NO 1562

<400> SEQUENCE: 1562

000

<210> SEQ ID NO 1563

<400> SEQUENCE: 1563

000

<210> SEQ ID NO 1564

<400> SEQUENCE: 1564

000

<210> SEQ ID NO 1565

<400> SEQUENCE: 1565

000

<210> SEQ ID NO 1566

<400> SEQUENCE: 1566

000

<210> SEQ ID NO 1567

<400> SEQUENCE: 1567

000

<210> SEQ ID NO 1568

<400> SEQUENCE: 1568

000

<210> SEQ ID NO 1569

<400> SEQUENCE: 1569

000

<210> SEQ ID NO 1570

<400> SEQUENCE: 1570

000

<210> SEQ ID NO 1571

<400> SEQUENCE: 1571

000

<210> SEQ ID NO 1572

<400> SEQUENCE: 1572

000

<210> SEQ ID NO 1573

<400> SEQUENCE: 1573

000

<210> SEQ ID NO 1574

<400> SEQUENCE: 1574

000

<210> SEQ ID NO 1575

<400> SEQUENCE: 1575

000

<210> SEQ ID NO 1576

<400> SEQUENCE: 1576

000

<210> SEQ ID NO 1577

<400> SEQUENCE: 1577

000

<210> SEQ ID NO 1578

<400> SEQUENCE: 1578

000

<210> SEQ ID NO 1579

<400> SEQUENCE: 1579

000

<210> SEQ ID NO 1580

<400> SEQUENCE: 1580

000

<210> SEQ ID NO 1581

<400> SEQUENCE: 1581

000

<210> SEQ ID NO 1582

<400> SEQUENCE: 1582

000

<210> SEQ ID NO 1583

<400> SEQUENCE: 1583

000

<210> SEQ ID NO 1584

<400> SEQUENCE: 1584

000

<210> SEQ ID NO 1585

<400> SEQUENCE: 1585

000

<210> SEQ ID NO 1586

<400> SEQUENCE: 1586

000

<210> SEQ ID NO 1587

<400> SEQUENCE: 1587

000

<210> SEQ ID NO 1588

<400> SEQUENCE: 1588

000

<210> SEQ ID NO 1589

<400> SEQUENCE: 1589

000

<210> SEQ ID NO 1590

<400> SEQUENCE: 1590

000

<210> SEQ ID NO 1591

<400> SEQUENCE: 1591

000

<210> SEQ ID NO 1592
<400> SEQUENCE: 1592
000

<210> SEQ ID NO 1593
<400> SEQUENCE: 1593
000

<210> SEQ ID NO 1594
<400> SEQUENCE: 1594
000

<210> SEQ ID NO 1595
<400> SEQUENCE: 1595
000

<210> SEQ ID NO 1596
<400> SEQUENCE: 1596
000

<210> SEQ ID NO 1597
<400> SEQUENCE: 1597
000

<210> SEQ ID NO 1598
<400> SEQUENCE: 1598
000

<210> SEQ ID NO 1599
<400> SEQUENCE: 1599
000

<210> SEQ ID NO 1600
<400> SEQUENCE: 1600
000

<210> SEQ ID NO 1601
<400> SEQUENCE: 1601
000

<210> SEQ ID NO 1602
<400> SEQUENCE: 1602
000

<210> SEQ ID NO 1603

<400> SEQUENCE: 1603

000

<210> SEQ ID NO 1604

<400> SEQUENCE: 1604

000

<210> SEQ ID NO 1605

<400> SEQUENCE: 1605

000

<210> SEQ ID NO 1606

<400> SEQUENCE: 1606

000

<210> SEQ ID NO 1607

<400> SEQUENCE: 1607

000

<210> SEQ ID NO 1608

<400> SEQUENCE: 1608

000

<210> SEQ ID NO 1609

<400> SEQUENCE: 1609

000

<210> SEQ ID NO 1610

<400> SEQUENCE: 1610

000

<210> SEQ ID NO 1611

<400> SEQUENCE: 1611

000

<210> SEQ ID NO 1612

<400> SEQUENCE: 1612

000

<210> SEQ ID NO 1613

<400> SEQUENCE: 1613

000

<210> SEQ ID NO 1614

-continued

<400> SEQUENCE: 1614

000

<210> SEQ ID NO 1615

<400> SEQUENCE: 1615

000

<210> SEQ ID NO 1616

<400> SEQUENCE: 1616

000

<210> SEQ ID NO 1617

<400> SEQUENCE: 1617

000

<210> SEQ ID NO 1618

<400> SEQUENCE: 1618

000

<210> SEQ ID NO 1619

<400> SEQUENCE: 1619

000

<210> SEQ ID NO 1620

<400> SEQUENCE: 1620

000

<210> SEQ ID NO 1621

<400> SEQUENCE: 1621

000

<210> SEQ ID NO 1622

<400> SEQUENCE: 1622

000

<210> SEQ ID NO 1623

<400> SEQUENCE: 1623

000

<210> SEQ ID NO 1624

<400> SEQUENCE: 1624

000

<210> SEQ ID NO 1625

<400> SEQUENCE: 1625

000

<210> SEQ ID NO 1626

<400> SEQUENCE: 1626

000

<210> SEQ ID NO 1627

<400> SEQUENCE: 1627

000

<210> SEQ ID NO 1628

<400> SEQUENCE: 1628

000

<210> SEQ ID NO 1629

<400> SEQUENCE: 1629

000

<210> SEQ ID NO 1630

<400> SEQUENCE: 1630

000

<210> SEQ ID NO 1631

<400> SEQUENCE: 1631

000

<210> SEQ ID NO 1632

<400> SEQUENCE: 1632

000

<210> SEQ ID NO 1633

<400> SEQUENCE: 1633

000

<210> SEQ ID NO 1634

<400> SEQUENCE: 1634

000

<210> SEQ ID NO 1635

<400> SEQUENCE: 1635

000

<210> SEQ ID NO 1636

<400> SEQUENCE: 1636

000

<210> SEQ ID NO 1637

<400> SEQUENCE: 1637

000

<210> SEQ ID NO 1638

<400> SEQUENCE: 1638

000

<210> SEQ ID NO 1639

<400> SEQUENCE: 1639

000

<210> SEQ ID NO 1640

<400> SEQUENCE: 1640

000

<210> SEQ ID NO 1641

<400> SEQUENCE: 1641

000

<210> SEQ ID NO 1642

<400> SEQUENCE: 1642

000

<210> SEQ ID NO 1643

<400> SEQUENCE: 1643

000

<210> SEQ ID NO 1644

<400> SEQUENCE: 1644

000

<210> SEQ ID NO 1645

<400> SEQUENCE: 1645

000

<210> SEQ ID NO 1646

<400> SEQUENCE: 1646

000

<210> SEQ ID NO 1647

<400> SEQUENCE: 1647

000

<210> SEQ ID NO 1648

<400> SEQUENCE: 1648

000

<210> SEQ ID NO 1649

<400> SEQUENCE: 1649

000

<210> SEQ ID NO 1650

<400> SEQUENCE: 1650

000

<210> SEQ ID NO 1651

<400> SEQUENCE: 1651

000

<210> SEQ ID NO 1652

<400> SEQUENCE: 1652

000

<210> SEQ ID NO 1653

<400> SEQUENCE: 1653

000

<210> SEQ ID NO 1654

<400> SEQUENCE: 1654

000

<210> SEQ ID NO 1655

<400> SEQUENCE: 1655

000

<210> SEQ ID NO 1656

<400> SEQUENCE: 1656

000

<210> SEQ ID NO 1657

<400> SEQUENCE: 1657

000

<210> SEQ ID NO 1658

<400> SEQUENCE: 1658

000

<210> SEQ ID NO 1659

<400> SEQUENCE: 1659

000

<210> SEQ ID NO 1660

<400> SEQUENCE: 1660

000

<210> SEQ ID NO 1661

<400> SEQUENCE: 1661

000

<210> SEQ ID NO 1662

<400> SEQUENCE: 1662

000

<210> SEQ ID NO 1663

<400> SEQUENCE: 1663

000

<210> SEQ ID NO 1664

<400> SEQUENCE: 1664

000

<210> SEQ ID NO 1665

<400> SEQUENCE: 1665

000

<210> SEQ ID NO 1666

<400> SEQUENCE: 1666

000

<210> SEQ ID NO 1667

<400> SEQUENCE: 1667

000

<210> SEQ ID NO 1668

<400> SEQUENCE: 1668

000

<210> SEQ ID NO 1669

<400> SEQUENCE: 1669

000

<210> SEQ ID NO 1670

<400> SEQUENCE: 1670

000

<210> SEQ ID NO 1671
<400> SEQUENCE: 1671
000

<210> SEQ ID NO 1672
<400> SEQUENCE: 1672
000

<210> SEQ ID NO 1673
<400> SEQUENCE: 1673
000

<210> SEQ ID NO 1674
<400> SEQUENCE: 1674
000

<210> SEQ ID NO 1675
<400> SEQUENCE: 1675
000

<210> SEQ ID NO 1676
<400> SEQUENCE: 1676
000

<210> SEQ ID NO 1677
<400> SEQUENCE: 1677
000

<210> SEQ ID NO 1678
<400> SEQUENCE: 1678
000

<210> SEQ ID NO 1679
<400> SEQUENCE: 1679
000

<210> SEQ ID NO 1680
<400> SEQUENCE: 1680
000

<210> SEQ ID NO 1681
<400> SEQUENCE: 1681
000

-continued

<210> SEQ ID NO 1682

<400> SEQUENCE: 1682

000

<210> SEQ ID NO 1683

<400> SEQUENCE: 1683

000

<210> SEQ ID NO 1684

<400> SEQUENCE: 1684

000

<210> SEQ ID NO 1685

<400> SEQUENCE: 1685

000

<210> SEQ ID NO 1686

<400> SEQUENCE: 1686

000

<210> SEQ ID NO 1687

<400> SEQUENCE: 1687

000

<210> SEQ ID NO 1688

<400> SEQUENCE: 1688

000

<210> SEQ ID NO 1689

<400> SEQUENCE: 1689

000

<210> SEQ ID NO 1690

<400> SEQUENCE: 1690

000

<210> SEQ ID NO 1691

<400> SEQUENCE: 1691

000

<210> SEQ ID NO 1692

<400> SEQUENCE: 1692

000

<210> SEQ ID NO 1693

<400> SEQUENCE: 1693

000

<210> SEQ ID NO 1694

<400> SEQUENCE: 1694

000

<210> SEQ ID NO 1695

<400> SEQUENCE: 1695

000

<210> SEQ ID NO 1696

<400> SEQUENCE: 1696

000

<210> SEQ ID NO 1697

<400> SEQUENCE: 1697

000

<210> SEQ ID NO 1698

<400> SEQUENCE: 1698

000

<210> SEQ ID NO 1699

<400> SEQUENCE: 1699

000

<210> SEQ ID NO 1700

<400> SEQUENCE: 1700

000

<210> SEQ ID NO 1701

<400> SEQUENCE: 1701

000

<210> SEQ ID NO 1702

<400> SEQUENCE: 1702

000

<210> SEQ ID NO 1703

<400> SEQUENCE: 1703

000

<210> SEQ ID NO 1704

<400> SEQUENCE: 1704

000

<210> SEQ ID NO 1705

<400> SEQUENCE: 1705

000

<210> SEQ ID NO 1706

<400> SEQUENCE: 1706

000

<210> SEQ ID NO 1707

<400> SEQUENCE: 1707

000

<210> SEQ ID NO 1708

<400> SEQUENCE: 1708

000

<210> SEQ ID NO 1709

<400> SEQUENCE: 1709

000

<210> SEQ ID NO 1710

<400> SEQUENCE: 1710

000

<210> SEQ ID NO 1711

<400> SEQUENCE: 1711

000

<210> SEQ ID NO 1712

<400> SEQUENCE: 1712

000

<210> SEQ ID NO 1713

<400> SEQUENCE: 1713

000

<210> SEQ ID NO 1714

<400> SEQUENCE: 1714

000

<210> SEQ ID NO 1715

<400> SEQUENCE: 1715

000

<210> SEQ ID NO 1716

<400> SEQUENCE: 1716

000

<210> SEQ ID NO 1717

<400> SEQUENCE: 1717

000

<210> SEQ ID NO 1718

<400> SEQUENCE: 1718

000

<210> SEQ ID NO 1719

<400> SEQUENCE: 1719

000

<210> SEQ ID NO 1720

<400> SEQUENCE: 1720

000

<210> SEQ ID NO 1721

<400> SEQUENCE: 1721

000

<210> SEQ ID NO 1722

<400> SEQUENCE: 1722

000

<210> SEQ ID NO 1723

<400> SEQUENCE: 1723

000

<210> SEQ ID NO 1724

<400> SEQUENCE: 1724

000

<210> SEQ ID NO 1725

<400> SEQUENCE: 1725

000

<210> SEQ ID NO 1726

<400> SEQUENCE: 1726

000

-continued

<210> SEQ ID NO 1727

<400> SEQUENCE: 1727

000

<210> SEQ ID NO 1728

<400> SEQUENCE: 1728

000

<210> SEQ ID NO 1729

<400> SEQUENCE: 1729

000

<210> SEQ ID NO 1730

<400> SEQUENCE: 1730

000

<210> SEQ ID NO 1731

<400> SEQUENCE: 1731

000

<210> SEQ ID NO 1732

<400> SEQUENCE: 1732

000

<210> SEQ ID NO 1733

<400> SEQUENCE: 1733

000

<210> SEQ ID NO 1734

<400> SEQUENCE: 1734

000

<210> SEQ ID NO 1735

<400> SEQUENCE: 1735

000

<210> SEQ ID NO 1736

<400> SEQUENCE: 1736

000

<210> SEQ ID NO 1737

<400> SEQUENCE: 1737

000

<210> SEQ ID NO 1738

<400> SEQUENCE: 1738

000

<210> SEQ ID NO 1739

<400> SEQUENCE: 1739

000

<210> SEQ ID NO 1740

<400> SEQUENCE: 1740

000

<210> SEQ ID NO 1741

<400> SEQUENCE: 1741

000

<210> SEQ ID NO 1742

<400> SEQUENCE: 1742

000

<210> SEQ ID NO 1743

<400> SEQUENCE: 1743

000

<210> SEQ ID NO 1744

<400> SEQUENCE: 1744

000

<210> SEQ ID NO 1745

<400> SEQUENCE: 1745

000

<210> SEQ ID NO 1746

<400> SEQUENCE: 1746

000

<210> SEQ ID NO 1747

<400> SEQUENCE: 1747

000

<210> SEQ ID NO 1748

<400> SEQUENCE: 1748

000

<210> SEQ ID NO 1749

<400> SEQUENCE: 1749

000

<210> SEQ ID NO 1750
<400> SEQUENCE: 1750
000

<210> SEQ ID NO 1751
<400> SEQUENCE: 1751
000

<210> SEQ ID NO 1752
<400> SEQUENCE: 1752
000

<210> SEQ ID NO 1753
<400> SEQUENCE: 1753
000

<210> SEQ ID NO 1754
<400> SEQUENCE: 1754
000

<210> SEQ ID NO 1755
<400> SEQUENCE: 1755
000

<210> SEQ ID NO 1756
<400> SEQUENCE: 1756
000

<210> SEQ ID NO 1757
<400> SEQUENCE: 1757
000

<210> SEQ ID NO 1758
<400> SEQUENCE: 1758
000

<210> SEQ ID NO 1759
<400> SEQUENCE: 1759
000

<210> SEQ ID NO 1760
<400> SEQUENCE: 1760
000

-continued

<210> SEQ ID NO 1761

<400> SEQUENCE: 1761

000

<210> SEQ ID NO 1762

<400> SEQUENCE: 1762

000

<210> SEQ ID NO 1763

<400> SEQUENCE: 1763

000

<210> SEQ ID NO 1764

<400> SEQUENCE: 1764

000

<210> SEQ ID NO 1765

<400> SEQUENCE: 1765

000

<210> SEQ ID NO 1766

<400> SEQUENCE: 1766

000

<210> SEQ ID NO 1767

<400> SEQUENCE: 1767

000

<210> SEQ ID NO 1768

<400> SEQUENCE: 1768

000

<210> SEQ ID NO 1769

<400> SEQUENCE: 1769

000

<210> SEQ ID NO 1770

<400> SEQUENCE: 1770

000

<210> SEQ ID NO 1771

<400> SEQUENCE: 1771

000

<210> SEQ ID NO 1772

<400> SEQUENCE: 1772

000

<210> SEQ ID NO 1773

<400> SEQUENCE: 1773

000

<210> SEQ ID NO 1774

<400> SEQUENCE: 1774

000

<210> SEQ ID NO 1775

<400> SEQUENCE: 1775

000

<210> SEQ ID NO 1776

<400> SEQUENCE: 1776

000

<210> SEQ ID NO 1777

<400> SEQUENCE: 1777

000

<210> SEQ ID NO 1778

<400> SEQUENCE: 1778

000

<210> SEQ ID NO 1779

<400> SEQUENCE: 1779

000

<210> SEQ ID NO 1780

<400> SEQUENCE: 1780

000

<210> SEQ ID NO 1781

<400> SEQUENCE: 1781

000

<210> SEQ ID NO 1782

<400> SEQUENCE: 1782

000

<210> SEQ ID NO 1783

<400> SEQUENCE: 1783

000

<210> SEQ ID NO 1784

<400> SEQUENCE: 1784

000

<210> SEQ ID NO 1785

<400> SEQUENCE: 1785

000

<210> SEQ ID NO 1786

<400> SEQUENCE: 1786

000

<210> SEQ ID NO 1787

<400> SEQUENCE: 1787

000

<210> SEQ ID NO 1788

<400> SEQUENCE: 1788

000

<210> SEQ ID NO 1789

<400> SEQUENCE: 1789

000

<210> SEQ ID NO 1790

<400> SEQUENCE: 1790

000

<210> SEQ ID NO 1791

<400> SEQUENCE: 1791

000

<210> SEQ ID NO 1792

<400> SEQUENCE: 1792

000

<210> SEQ ID NO 1793

<400> SEQUENCE: 1793

000

<210> SEQ ID NO 1794

<400> SEQUENCE: 1794

000

<210> SEQ ID NO 1795

<400> SEQUENCE: 1795

000

<210> SEQ ID NO 1796

<400> SEQUENCE: 1796

000

<210> SEQ ID NO 1797

<400> SEQUENCE: 1797

000

<210> SEQ ID NO 1798

<400> SEQUENCE: 1798

000

<210> SEQ ID NO 1799

<400> SEQUENCE: 1799

000

<210> SEQ ID NO 1800

<400> SEQUENCE: 1800

000

<210> SEQ ID NO 1801

<400> SEQUENCE: 1801

000

<210> SEQ ID NO 1802

<400> SEQUENCE: 1802

000

<210> SEQ ID NO 1803

<400> SEQUENCE: 1803

000

<210> SEQ ID NO 1804

<400> SEQUENCE: 1804

000

<210> SEQ ID NO 1805

<400> SEQUENCE: 1805

000

<210> SEQ ID NO 1806

<400> SEQUENCE: 1806

000

<210> SEQ ID NO 1807

<400> SEQUENCE: 1807

000

<210> SEQ ID NO 1808

<400> SEQUENCE: 1808

000

<210> SEQ ID NO 1809

<400> SEQUENCE: 1809

000

<210> SEQ ID NO 1810

<400> SEQUENCE: 1810

000

<210> SEQ ID NO 1811

<400> SEQUENCE: 1811

000

<210> SEQ ID NO 1812

<400> SEQUENCE: 1812

000

<210> SEQ ID NO 1813

<400> SEQUENCE: 1813

000

<210> SEQ ID NO 1814

<400> SEQUENCE: 1814

000

<210> SEQ ID NO 1815

<400> SEQUENCE: 1815

000

<210> SEQ ID NO 1816

<400> SEQUENCE: 1816

000

<210> SEQ ID NO 1817

```
<400> SEQUENCE: 1817

000

<210> SEQ ID NO 1818

<400> SEQUENCE: 1818

000

<210> SEQ ID NO 1819

<400> SEQUENCE: 1819

000

<210> SEQ ID NO 1820

<400> SEQUENCE: 1820

000

<210> SEQ ID NO 1821

<400> SEQUENCE: 1821

000

<210> SEQ ID NO 1822

<400> SEQUENCE: 1822

000

<210> SEQ ID NO 1823

<400> SEQUENCE: 1823

000

<210> SEQ ID NO 1824

<400> SEQUENCE: 1824

000

<210> SEQ ID NO 1825

<400> SEQUENCE: 1825

000

<210> SEQ ID NO 1826

<400> SEQUENCE: 1826

000

<210> SEQ ID NO 1827

<400> SEQUENCE: 1827

000

<210> SEQ ID NO 1828

<400> SEQUENCE: 1828
```

000

<210> SEQ ID NO 1829

<400> SEQUENCE: 1829

000

<210> SEQ ID NO 1830

<400> SEQUENCE: 1830

000

<210> SEQ ID NO 1831

<400> SEQUENCE: 1831

000

<210> SEQ ID NO 1832

<400> SEQUENCE: 1832

000

<210> SEQ ID NO 1833

<400> SEQUENCE: 1833

000

<210> SEQ ID NO 1834

<400> SEQUENCE: 1834

000

<210> SEQ ID NO 1835

<400> SEQUENCE: 1835

000

<210> SEQ ID NO 1836

<400> SEQUENCE: 1836

000

<210> SEQ ID NO 1837

<400> SEQUENCE: 1837

000

<210> SEQ ID NO 1838

<400> SEQUENCE: 1838

000

<210> SEQ ID NO 1839

<400> SEQUENCE: 1839

000

```
<210> SEQ ID NO 1840
<400> SEQUENCE: 1840
000

<210> SEQ ID NO 1841
<400> SEQUENCE: 1841
000

<210> SEQ ID NO 1842
<400> SEQUENCE: 1842
000

<210> SEQ ID NO 1843
<400> SEQUENCE: 1843
000

<210> SEQ ID NO 1844
<400> SEQUENCE: 1844
000

<210> SEQ ID NO 1845
<400> SEQUENCE: 1845
000

<210> SEQ ID NO 1846
<400> SEQUENCE: 1846
000

<210> SEQ ID NO 1847
<400> SEQUENCE: 1847
000

<210> SEQ ID NO 1848
<400> SEQUENCE: 1848
000

<210> SEQ ID NO 1849
<400> SEQUENCE: 1849
000

<210> SEQ ID NO 1850
<400> SEQUENCE: 1850
000

<210> SEQ ID NO 1851
```

<400> SEQUENCE: 1851

000

<210> SEQ ID NO 1852

<400> SEQUENCE: 1852

000

<210> SEQ ID NO 1853

<400> SEQUENCE: 1853

000

<210> SEQ ID NO 1854

<400> SEQUENCE: 1854

000

<210> SEQ ID NO 1855

<400> SEQUENCE: 1855

000

<210> SEQ ID NO 1856

<400> SEQUENCE: 1856

000

<210> SEQ ID NO 1857

<400> SEQUENCE: 1857

000

<210> SEQ ID NO 1858

<400> SEQUENCE: 1858

000

<210> SEQ ID NO 1859

<400> SEQUENCE: 1859

000

<210> SEQ ID NO 1860

<400> SEQUENCE: 1860

000

<210> SEQ ID NO 1861

<400> SEQUENCE: 1861

000

<210> SEQ ID NO 1862

<400> SEQUENCE: 1862

000

<210> SEQ ID NO 1863

<400> SEQUENCE: 1863

000

<210> SEQ ID NO 1864

<400> SEQUENCE: 1864

000

<210> SEQ ID NO 1865

<400> SEQUENCE: 1865

000

<210> SEQ ID NO 1866

<400> SEQUENCE: 1866

000

<210> SEQ ID NO 1867

<400> SEQUENCE: 1867

000

<210> SEQ ID NO 1868

<400> SEQUENCE: 1868

000

<210> SEQ ID NO 1869

<400> SEQUENCE: 1869

000

<210> SEQ ID NO 1870

<400> SEQUENCE: 1870

000

<210> SEQ ID NO 1871

<400> SEQUENCE: 1871

000

<210> SEQ ID NO 1872

<400> SEQUENCE: 1872

000

<210> SEQ ID NO 1873

<400> SEQUENCE: 1873

000

<210> SEQ ID NO 1874

<400> SEQUENCE: 1874

000

<210> SEQ ID NO 1875

<400> SEQUENCE: 1875

000

<210> SEQ ID NO 1876

<400> SEQUENCE: 1876

000

<210> SEQ ID NO 1877

<400> SEQUENCE: 1877

000

<210> SEQ ID NO 1878

<400> SEQUENCE: 1878

000

<210> SEQ ID NO 1879

<400> SEQUENCE: 1879

000

<210> SEQ ID NO 1880

<400> SEQUENCE: 1880

000

<210> SEQ ID NO 1881

<400> SEQUENCE: 1881

000

<210> SEQ ID NO 1882

<400> SEQUENCE: 1882

000

<210> SEQ ID NO 1883

<400> SEQUENCE: 1883

000

<210> SEQ ID NO 1884

<400> SEQUENCE: 1884

000

```
<210> SEQ ID NO 1885
<400> SEQUENCE: 1885
000

<210> SEQ ID NO 1886
<400> SEQUENCE: 1886
000

<210> SEQ ID NO 1887
<400> SEQUENCE: 1887
000

<210> SEQ ID NO 1888
<400> SEQUENCE: 1888
000

<210> SEQ ID NO 1889
<400> SEQUENCE: 1889
000

<210> SEQ ID NO 1890
<400> SEQUENCE: 1890
000

<210> SEQ ID NO 1891
<400> SEQUENCE: 1891
000

<210> SEQ ID NO 1892
<400> SEQUENCE: 1892
000

<210> SEQ ID NO 1893
<400> SEQUENCE: 1893
000

<210> SEQ ID NO 1894
<400> SEQUENCE: 1894
000

<210> SEQ ID NO 1895
<400> SEQUENCE: 1895
000

<210> SEQ ID NO 1896
```

<400> SEQUENCE: 1896

000

<210> SEQ ID NO 1897

<400> SEQUENCE: 1897

000

<210> SEQ ID NO 1898

<400> SEQUENCE: 1898

000

<210> SEQ ID NO 1899

<400> SEQUENCE: 1899

000

<210> SEQ ID NO 1900

<400> SEQUENCE: 1900

000

<210> SEQ ID NO 1901

<400> SEQUENCE: 1901

000

<210> SEQ ID NO 1902

<400> SEQUENCE: 1902

000

<210> SEQ ID NO 1903

<400> SEQUENCE: 1903

000

<210> SEQ ID NO 1904

<400> SEQUENCE: 1904

000

<210> SEQ ID NO 1905

<400> SEQUENCE: 1905

000

<210> SEQ ID NO 1906

<400> SEQUENCE: 1906

000

<210> SEQ ID NO 1907

<400> SEQUENCE: 1907

000

<210> SEQ ID NO 1908

<400> SEQUENCE: 1908

000

<210> SEQ ID NO 1909

<400> SEQUENCE: 1909

000

<210> SEQ ID NO 1910

<400> SEQUENCE: 1910

000

<210> SEQ ID NO 1911

<400> SEQUENCE: 1911

000

<210> SEQ ID NO 1912

<400> SEQUENCE: 1912

000

<210> SEQ ID NO 1913

<400> SEQUENCE: 1913

000

<210> SEQ ID NO 1914

<400> SEQUENCE: 1914

000

<210> SEQ ID NO 1915

<400> SEQUENCE: 1915

000

<210> SEQ ID NO 1916

<400> SEQUENCE: 1916

000

<210> SEQ ID NO 1917

<400> SEQUENCE: 1917

000

<210> SEQ ID NO 1918

<400> SEQUENCE: 1918

000

<210> SEQ ID NO 1919

<400> SEQUENCE: 1919

000

<210> SEQ ID NO 1920

<400> SEQUENCE: 1920

000

<210> SEQ ID NO 1921

<400> SEQUENCE: 1921

000

<210> SEQ ID NO 1922

<400> SEQUENCE: 1922

000

<210> SEQ ID NO 1923

<400> SEQUENCE: 1923

000

<210> SEQ ID NO 1924

<400> SEQUENCE: 1924

000

<210> SEQ ID NO 1925

<400> SEQUENCE: 1925

000

<210> SEQ ID NO 1926

<400> SEQUENCE: 1926

000

<210> SEQ ID NO 1927

<400> SEQUENCE: 1927

000

<210> SEQ ID NO 1928

<400> SEQUENCE: 1928

000

<210> SEQ ID NO 1929

<400> SEQUENCE: 1929

000

<210> SEQ ID NO 1930

<400> SEQUENCE: 1930

000

<210> SEQ ID NO 1931

<400> SEQUENCE: 1931

000

<210> SEQ ID NO 1932

<400> SEQUENCE: 1932

000

<210> SEQ ID NO 1933

<400> SEQUENCE: 1933

000

<210> SEQ ID NO 1934

<400> SEQUENCE: 1934

000

<210> SEQ ID NO 1935

<400> SEQUENCE: 1935

000

<210> SEQ ID NO 1936

<400> SEQUENCE: 1936

000

<210> SEQ ID NO 1937

<400> SEQUENCE: 1937

000

<210> SEQ ID NO 1938

<400> SEQUENCE: 1938

000

<210> SEQ ID NO 1939

<400> SEQUENCE: 1939

000

<210> SEQ ID NO 1940

<400> SEQUENCE: 1940

000

<210> SEQ ID NO 1941

<400> SEQUENCE: 1941

000

<210> SEQ ID NO 1942

<400> SEQUENCE: 1942

000

<210> SEQ ID NO 1943

<400> SEQUENCE: 1943

000

<210> SEQ ID NO 1944

<400> SEQUENCE: 1944

000

<210> SEQ ID NO 1945

<400> SEQUENCE: 1945

000

<210> SEQ ID NO 1946

<400> SEQUENCE: 1946

000

<210> SEQ ID NO 1947

<400> SEQUENCE: 1947

000

<210> SEQ ID NO 1948

<400> SEQUENCE: 1948

000

<210> SEQ ID NO 1949

<400> SEQUENCE: 1949

000

<210> SEQ ID NO 1950

<400> SEQUENCE: 1950

000

<210> SEQ ID NO 1951

<400> SEQUENCE: 1951

000

<210> SEQ ID NO 1952

<400> SEQUENCE: 1952

000

<210> SEQ ID NO 1953

<400> SEQUENCE: 1953

000

<210> SEQ ID NO 1954

<400> SEQUENCE: 1954

000

<210> SEQ ID NO 1955

<400> SEQUENCE: 1955

000

<210> SEQ ID NO 1956

<400> SEQUENCE: 1956

000

<210> SEQ ID NO 1957

<400> SEQUENCE: 1957

000

<210> SEQ ID NO 1958

<400> SEQUENCE: 1958

000

<210> SEQ ID NO 1959

<400> SEQUENCE: 1959

000

<210> SEQ ID NO 1960

<400> SEQUENCE: 1960

000

<210> SEQ ID NO 1961

<400> SEQUENCE: 1961

000

<210> SEQ ID NO 1962

<400> SEQUENCE: 1962

000

<210> SEQ ID NO 1963

<400> SEQUENCE: 1963

000

```
<210> SEQ ID NO 1964
<400> SEQUENCE: 1964
000

<210> SEQ ID NO 1965
<400> SEQUENCE: 1965
000

<210> SEQ ID NO 1966
<400> SEQUENCE: 1966
000

<210> SEQ ID NO 1967
<400> SEQUENCE: 1967
000

<210> SEQ ID NO 1968
<400> SEQUENCE: 1968
000

<210> SEQ ID NO 1969
<400> SEQUENCE: 1969
000

<210> SEQ ID NO 1970
<400> SEQUENCE: 1970
000

<210> SEQ ID NO 1971
<400> SEQUENCE: 1971
000

<210> SEQ ID NO 1972
<400> SEQUENCE: 1972
000

<210> SEQ ID NO 1973
<400> SEQUENCE: 1973
000

<210> SEQ ID NO 1974
<400> SEQUENCE: 1974
000

<210> SEQ ID NO 1975
```

```
<400> SEQUENCE: 1975

000

<210> SEQ ID NO 1976

<400> SEQUENCE: 1976

000

<210> SEQ ID NO 1977

<400> SEQUENCE: 1977

000

<210> SEQ ID NO 1978

<400> SEQUENCE: 1978

000

<210> SEQ ID NO 1979

<400> SEQUENCE: 1979

000

<210> SEQ ID NO 1980

<400> SEQUENCE: 1980

000

<210> SEQ ID NO 1981

<400> SEQUENCE: 1981

000

<210> SEQ ID NO 1982

<400> SEQUENCE: 1982

000

<210> SEQ ID NO 1983

<400> SEQUENCE: 1983

000

<210> SEQ ID NO 1984

<400> SEQUENCE: 1984

000

<210> SEQ ID NO 1985

<400> SEQUENCE: 1985

000

<210> SEQ ID NO 1986

<400> SEQUENCE: 1986
```

000

<210> SEQ ID NO 1987

<400> SEQUENCE: 1987

000

<210> SEQ ID NO 1988

<400> SEQUENCE: 1988

000

<210> SEQ ID NO 1989

<400> SEQUENCE: 1989

000

<210> SEQ ID NO 1990

<400> SEQUENCE: 1990

000

<210> SEQ ID NO 1991

<400> SEQUENCE: 1991

000

<210> SEQ ID NO 1992

<400> SEQUENCE: 1992

000

<210> SEQ ID NO 1993

<400> SEQUENCE: 1993

000

<210> SEQ ID NO 1994

<400> SEQUENCE: 1994

000

<210> SEQ ID NO 1995

<400> SEQUENCE: 1995

000

<210> SEQ ID NO 1996

<400> SEQUENCE: 1996

000

<210> SEQ ID NO 1997

<400> SEQUENCE: 1997

000

<210> SEQ ID NO 1998

<400> SEQUENCE: 1998

000

<210> SEQ ID NO 1999

<400> SEQUENCE: 1999

000

<210> SEQ ID NO 2000

<400> SEQUENCE: 2000

000

<210> SEQ ID NO 2001

<400> SEQUENCE: 2001

000

<210> SEQ ID NO 2002

<400> SEQUENCE: 2002

000

<210> SEQ ID NO 2003

<400> SEQUENCE: 2003

000

<210> SEQ ID NO 2004

<400> SEQUENCE: 2004

000

<210> SEQ ID NO 2005

<400> SEQUENCE: 2005

000

<210> SEQ ID NO 2006

<400> SEQUENCE: 2006

000

<210> SEQ ID NO 2007

<400> SEQUENCE: 2007

000

<210> SEQ ID NO 2008

<400> SEQUENCE: 2008

000

<210> SEQ ID NO 2009

```
<400> SEQUENCE: 2009
000

<210> SEQ ID NO 2010
<400> SEQUENCE: 2010
000

<210> SEQ ID NO 2011
<400> SEQUENCE: 2011
000

<210> SEQ ID NO 2012
<400> SEQUENCE: 2012
000

<210> SEQ ID NO 2013
<400> SEQUENCE: 2013
000

<210> SEQ ID NO 2014
<400> SEQUENCE: 2014
000

<210> SEQ ID NO 2015
<400> SEQUENCE: 2015
000

<210> SEQ ID NO 2016
<400> SEQUENCE: 2016
000

<210> SEQ ID NO 2017
<400> SEQUENCE: 2017
000

<210> SEQ ID NO 2018
<400> SEQUENCE: 2018
000

<210> SEQ ID NO 2019
<400> SEQUENCE: 2019
000

<210> SEQ ID NO 2020
<400> SEQUENCE: 2020
```

000

<210> SEQ ID NO 2021

<400> SEQUENCE: 2021

000

<210> SEQ ID NO 2022

<400> SEQUENCE: 2022

000

<210> SEQ ID NO 2023

<400> SEQUENCE: 2023

000

<210> SEQ ID NO 2024

<400> SEQUENCE: 2024

000

<210> SEQ ID NO 2025

<400> SEQUENCE: 2025

000

<210> SEQ ID NO 2026

<400> SEQUENCE: 2026

000

<210> SEQ ID NO 2027

<400> SEQUENCE: 2027

000

<210> SEQ ID NO 2028

<400> SEQUENCE: 2028

000

<210> SEQ ID NO 2029

<400> SEQUENCE: 2029

000

<210> SEQ ID NO 2030

<400> SEQUENCE: 2030

000

<210> SEQ ID NO 2031

<400> SEQUENCE: 2031

000

<210> SEQ ID NO 2032

<400> SEQUENCE: 2032

000

<210> SEQ ID NO 2033

<400> SEQUENCE: 2033

000

<210> SEQ ID NO 2034

<400> SEQUENCE: 2034

000

<210> SEQ ID NO 2035

<400> SEQUENCE: 2035

000

<210> SEQ ID NO 2036

<400> SEQUENCE: 2036

000

<210> SEQ ID NO 2037

<400> SEQUENCE: 2037

000

<210> SEQ ID NO 2038

<400> SEQUENCE: 2038

000

<210> SEQ ID NO 2039

<400> SEQUENCE: 2039

000

<210> SEQ ID NO 2040

<400> SEQUENCE: 2040

000

<210> SEQ ID NO 2041

<400> SEQUENCE: 2041

000

<210> SEQ ID NO 2042

<400> SEQUENCE: 2042

000

-continued

<210> SEQ ID NO 2043

<400> SEQUENCE: 2043

000

<210> SEQ ID NO 2044

<400> SEQUENCE: 2044

000

<210> SEQ ID NO 2045

<400> SEQUENCE: 2045

000

<210> SEQ ID NO 2046

<400> SEQUENCE: 2046

000

<210> SEQ ID NO 2047

<400> SEQUENCE: 2047

000

<210> SEQ ID NO 2048

<400> SEQUENCE: 2048

000

<210> SEQ ID NO 2049

<400> SEQUENCE: 2049

000

<210> SEQ ID NO 2050

<400> SEQUENCE: 2050

000

<210> SEQ ID NO 2051

<400> SEQUENCE: 2051

000

<210> SEQ ID NO 2052

<400> SEQUENCE: 2052

000

<210> SEQ ID NO 2053

<400> SEQUENCE: 2053

000

<210> SEQ ID NO 2054

<400> SEQUENCE: 2054

000

<210> SEQ ID NO 2055

<400> SEQUENCE: 2055

000

<210> SEQ ID NO 2056

<400> SEQUENCE: 2056

000

<210> SEQ ID NO 2057

<400> SEQUENCE: 2057

000

<210> SEQ ID NO 2058

<400> SEQUENCE: 2058

000

<210> SEQ ID NO 2059

<400> SEQUENCE: 2059

000

<210> SEQ ID NO 2060

<400> SEQUENCE: 2060

000

<210> SEQ ID NO 2061

<400> SEQUENCE: 2061

000

<210> SEQ ID NO 2062

<400> SEQUENCE: 2062

000

<210> SEQ ID NO 2063

<400> SEQUENCE: 2063

000

<210> SEQ ID NO 2064

<400> SEQUENCE: 2064

000

<210> SEQ ID NO 2065

<400> SEQUENCE: 2065

-continued

000

<210> SEQ ID NO 2066

<400> SEQUENCE: 2066

000

<210> SEQ ID NO 2067

<400> SEQUENCE: 2067

000

<210> SEQ ID NO 2068

<400> SEQUENCE: 2068

000

<210> SEQ ID NO 2069

<400> SEQUENCE: 2069

000

<210> SEQ ID NO 2070

<400> SEQUENCE: 2070

000

<210> SEQ ID NO 2071

<400> SEQUENCE: 2071

000

<210> SEQ ID NO 2072

<400> SEQUENCE: 2072

000

<210> SEQ ID NO 2073

<400> SEQUENCE: 2073

000

<210> SEQ ID NO 2074

<400> SEQUENCE: 2074

000

<210> SEQ ID NO 2075

<400> SEQUENCE: 2075

000

<210> SEQ ID NO 2076

<400> SEQUENCE: 2076

000

<210> SEQ ID NO 2077
<400> SEQUENCE: 2077
000

<210> SEQ ID NO 2078
<400> SEQUENCE: 2078
000

<210> SEQ ID NO 2079
<400> SEQUENCE: 2079
000

<210> SEQ ID NO 2080
<400> SEQUENCE: 2080
000

<210> SEQ ID NO 2081
<400> SEQUENCE: 2081
000

<210> SEQ ID NO 2082
<400> SEQUENCE: 2082
000

<210> SEQ ID NO 2083
<400> SEQUENCE: 2083
000

<210> SEQ ID NO 2084
<400> SEQUENCE: 2084
000

<210> SEQ ID NO 2085
<400> SEQUENCE: 2085
000

<210> SEQ ID NO 2086
<400> SEQUENCE: 2086
000

<210> SEQ ID NO 2087
<400> SEQUENCE: 2087
000

<210> SEQ ID NO 2088

<400> SEQUENCE: 2088

000

<210> SEQ ID NO 2089

<400> SEQUENCE: 2089

000

<210> SEQ ID NO 2090

<400> SEQUENCE: 2090

000

<210> SEQ ID NO 2091

<400> SEQUENCE: 2091

000

<210> SEQ ID NO 2092

<400> SEQUENCE: 2092

000

<210> SEQ ID NO 2093

<400> SEQUENCE: 2093

000

<210> SEQ ID NO 2094

<400> SEQUENCE: 2094

000

<210> SEQ ID NO 2095

<400> SEQUENCE: 2095

000

<210> SEQ ID NO 2096

<400> SEQUENCE: 2096

000

<210> SEQ ID NO 2097

<400> SEQUENCE: 2097

000

<210> SEQ ID NO 2098

<400> SEQUENCE: 2098

000

<210> SEQ ID NO 2099

<400> SEQUENCE: 2099

-continued

000

<210> SEQ ID NO 2100
<400> SEQUENCE: 2100
000

<210> SEQ ID NO 2101
<400> SEQUENCE: 2101
000

<210> SEQ ID NO 2102
<400> SEQUENCE: 2102
000

<210> SEQ ID NO 2103
<400> SEQUENCE: 2103
000

<210> SEQ ID NO 2104
<400> SEQUENCE: 2104
000

<210> SEQ ID NO 2105
<400> SEQUENCE: 2105
000

<210> SEQ ID NO 2106
<400> SEQUENCE: 2106
000

<210> SEQ ID NO 2107
<400> SEQUENCE: 2107
000

<210> SEQ ID NO 2108
<400> SEQUENCE: 2108
000

<210> SEQ ID NO 2109
<400> SEQUENCE: 2109
000

<210> SEQ ID NO 2110
<400> SEQUENCE: 2110
000

<210> SEQ ID NO 2111

<400> SEQUENCE: 2111

000

<210> SEQ ID NO 2112

<400> SEQUENCE: 2112

000

<210> SEQ ID NO 2113

<400> SEQUENCE: 2113

000

<210> SEQ ID NO 2114

<400> SEQUENCE: 2114

000

<210> SEQ ID NO 2115

<400> SEQUENCE: 2115

000

<210> SEQ ID NO 2116

<400> SEQUENCE: 2116

000

<210> SEQ ID NO 2117

<400> SEQUENCE: 2117

000

<210> SEQ ID NO 2118

<400> SEQUENCE: 2118

000

<210> SEQ ID NO 2119

<400> SEQUENCE: 2119

000

<210> SEQ ID NO 2120

<400> SEQUENCE: 2120

000

<210> SEQ ID NO 2121

<400> SEQUENCE: 2121

000

<210> SEQ ID NO 2122

<400> SEQUENCE: 2122

000

<210> SEQ ID NO 2123

<400> SEQUENCE: 2123

000

<210> SEQ ID NO 2124

<400> SEQUENCE: 2124

000

<210> SEQ ID NO 2125

<400> SEQUENCE: 2125

000

<210> SEQ ID NO 2126

<400> SEQUENCE: 2126

000

<210> SEQ ID NO 2127

<400> SEQUENCE: 2127

000

<210> SEQ ID NO 2128

<400> SEQUENCE: 2128

000

<210> SEQ ID NO 2129

<400> SEQUENCE: 2129

000

<210> SEQ ID NO 2130

<400> SEQUENCE: 2130

000

<210> SEQ ID NO 2131

<400> SEQUENCE: 2131

000

<210> SEQ ID NO 2132

<400> SEQUENCE: 2132

000

<210> SEQ ID NO 2133

```
<400> SEQUENCE: 2133
000

<210> SEQ ID NO 2134
<400> SEQUENCE: 2134
000

<210> SEQ ID NO 2135
<400> SEQUENCE: 2135
000

<210> SEQ ID NO 2136
<400> SEQUENCE: 2136
000

<210> SEQ ID NO 2137
<400> SEQUENCE: 2137
000

<210> SEQ ID NO 2138
<400> SEQUENCE: 2138
000

<210> SEQ ID NO 2139
<400> SEQUENCE: 2139
000

<210> SEQ ID NO 2140
<400> SEQUENCE: 2140
000

<210> SEQ ID NO 2141
<400> SEQUENCE: 2141
000

<210> SEQ ID NO 2142
<400> SEQUENCE: 2142
000

<210> SEQ ID NO 2143
<400> SEQUENCE: 2143
000

<210> SEQ ID NO 2144
<400> SEQUENCE: 2144
```

000

<210> SEQ ID NO 2145

<400> SEQUENCE: 2145

000

<210> SEQ ID NO 2146

<400> SEQUENCE: 2146

000

<210> SEQ ID NO 2147

<400> SEQUENCE: 2147

000

<210> SEQ ID NO 2148

<400> SEQUENCE: 2148

000

<210> SEQ ID NO 2149

<400> SEQUENCE: 2149

000

<210> SEQ ID NO 2150

<400> SEQUENCE: 2150

000

<210> SEQ ID NO 2151

<400> SEQUENCE: 2151

000

<210> SEQ ID NO 2152

<400> SEQUENCE: 2152

000

<210> SEQ ID NO 2153

<400> SEQUENCE: 2153

000

<210> SEQ ID NO 2154

<400> SEQUENCE: 2154

000

<210> SEQ ID NO 2155

<400> SEQUENCE: 2155

000

<210> SEQ ID NO 2156

<400> SEQUENCE: 2156

000

<210> SEQ ID NO 2157

<400> SEQUENCE: 2157

000

<210> SEQ ID NO 2158

<400> SEQUENCE: 2158

000

<210> SEQ ID NO 2159

<400> SEQUENCE: 2159

000

<210> SEQ ID NO 2160

<400> SEQUENCE: 2160

000

<210> SEQ ID NO 2161

<400> SEQUENCE: 2161

000

<210> SEQ ID NO 2162

<400> SEQUENCE: 2162

000

<210> SEQ ID NO 2163

<400> SEQUENCE: 2163

000

<210> SEQ ID NO 2164

<400> SEQUENCE: 2164

000

<210> SEQ ID NO 2165

<400> SEQUENCE: 2165

000

<210> SEQ ID NO 2166

<400> SEQUENCE: 2166

000

<210> SEQ ID NO 2167

<400> SEQUENCE: 2167

000

<210> SEQ ID NO 2168

<400> SEQUENCE: 2168

000

<210> SEQ ID NO 2169

<400> SEQUENCE: 2169

000

<210> SEQ ID NO 2170

<400> SEQUENCE: 2170

000

<210> SEQ ID NO 2171

<400> SEQUENCE: 2171

000

<210> SEQ ID NO 2172

<400> SEQUENCE: 2172

000

<210> SEQ ID NO 2173

<400> SEQUENCE: 2173

000

<210> SEQ ID NO 2174

<400> SEQUENCE: 2174

000

<210> SEQ ID NO 2175

<400> SEQUENCE: 2175

000

<210> SEQ ID NO 2176

<400> SEQUENCE: 2176

000

<210> SEQ ID NO 2177

<400> SEQUENCE: 2177

000

<210> SEQ ID NO 2178

<400> SEQUENCE: 2178

000

<210> SEQ ID NO 2179

<400> SEQUENCE: 2179

000

<210> SEQ ID NO 2180

<400> SEQUENCE: 2180

000

<210> SEQ ID NO 2181

<400> SEQUENCE: 2181

000

<210> SEQ ID NO 2182

<400> SEQUENCE: 2182

000

<210> SEQ ID NO 2183

<400> SEQUENCE: 2183

000

<210> SEQ ID NO 2184

<400> SEQUENCE: 2184

000

<210> SEQ ID NO 2185

<400> SEQUENCE: 2185

000

<210> SEQ ID NO 2186

<400> SEQUENCE: 2186

000

<210> SEQ ID NO 2187

<400> SEQUENCE: 2187

000

<210> SEQ ID NO 2188

<400> SEQUENCE: 2188

000

<210> SEQ ID NO 2189

<400> SEQUENCE: 2189

000

```
<210> SEQ ID NO 2190
<400> SEQUENCE: 2190
000

<210> SEQ ID NO 2191
<400> SEQUENCE: 2191
000

<210> SEQ ID NO 2192
<400> SEQUENCE: 2192
000

<210> SEQ ID NO 2193
<400> SEQUENCE: 2193
000

<210> SEQ ID NO 2194
<400> SEQUENCE: 2194
000

<210> SEQ ID NO 2195
<400> SEQUENCE: 2195
000

<210> SEQ ID NO 2196
<400> SEQUENCE: 2196
000

<210> SEQ ID NO 2197
<400> SEQUENCE: 2197
000

<210> SEQ ID NO 2198
<400> SEQUENCE: 2198
000

<210> SEQ ID NO 2199
<400> SEQUENCE: 2199
000

<210> SEQ ID NO 2200
<400> SEQUENCE: 2200
000
```

<210> SEQ ID NO 2201

<400> SEQUENCE: 2201

000

<210> SEQ ID NO 2202

<400> SEQUENCE: 2202

000

<210> SEQ ID NO 2203

<400> SEQUENCE: 2203

000

<210> SEQ ID NO 2204

<400> SEQUENCE: 2204

000

<210> SEQ ID NO 2205

<400> SEQUENCE: 2205

000

<210> SEQ ID NO 2206

<400> SEQUENCE: 2206

000

<210> SEQ ID NO 2207

<400> SEQUENCE: 2207

000

<210> SEQ ID NO 2208

<400> SEQUENCE: 2208

000

<210> SEQ ID NO 2209

<400> SEQUENCE: 2209

000

<210> SEQ ID NO 2210

<400> SEQUENCE: 2210

000

<210> SEQ ID NO 2211

<400> SEQUENCE: 2211

000

<210> SEQ ID NO 2212

<400> SEQUENCE: 2212

000

<210> SEQ ID NO 2213

<400> SEQUENCE: 2213

000

<210> SEQ ID NO 2214

<400> SEQUENCE: 2214

000

<210> SEQ ID NO 2215

<400> SEQUENCE: 2215

000

<210> SEQ ID NO 2216

<400> SEQUENCE: 2216

000

<210> SEQ ID NO 2217

<400> SEQUENCE: 2217

000

<210> SEQ ID NO 2218

<400> SEQUENCE: 2218

000

<210> SEQ ID NO 2219

<400> SEQUENCE: 2219

000

<210> SEQ ID NO 2220

<400> SEQUENCE: 2220

000

<210> SEQ ID NO 2221

<400> SEQUENCE: 2221

000

<210> SEQ ID NO 2222

<400> SEQUENCE: 2222

000

<210> SEQ ID NO 2223

<400> SEQUENCE: 2223

000

<210> SEQ ID NO 2224

<400> SEQUENCE: 2224

000

<210> SEQ ID NO 2225

<400> SEQUENCE: 2225

000

<210> SEQ ID NO 2226

<400> SEQUENCE: 2226

000

<210> SEQ ID NO 2227

<400> SEQUENCE: 2227

000

<210> SEQ ID NO 2228

<400> SEQUENCE: 2228

000

<210> SEQ ID NO 2229

<400> SEQUENCE: 2229

000

<210> SEQ ID NO 2230

<400> SEQUENCE: 2230

000

<210> SEQ ID NO 2231

<400> SEQUENCE: 2231

000

<210> SEQ ID NO 2232

<400> SEQUENCE: 2232

000

<210> SEQ ID NO 2233

<400> SEQUENCE: 2233

000

<210> SEQ ID NO 2234

<400> SEQUENCE: 2234

000

<210> SEQ ID NO 2235

<400> SEQUENCE: 2235

000

<210> SEQ ID NO 2236

<400> SEQUENCE: 2236

000

<210> SEQ ID NO 2237

<400> SEQUENCE: 2237

000

<210> SEQ ID NO 2238

<400> SEQUENCE: 2238

000

<210> SEQ ID NO 2239

<400> SEQUENCE: 2239

000

<210> SEQ ID NO 2240

<400> SEQUENCE: 2240

000

<210> SEQ ID NO 2241

<400> SEQUENCE: 2241

000

<210> SEQ ID NO 2242

<400> SEQUENCE: 2242

000

<210> SEQ ID NO 2243

<400> SEQUENCE: 2243

000

<210> SEQ ID NO 2244

<400> SEQUENCE: 2244

000

<210> SEQ ID NO 2245

<400> SEQUENCE: 2245

000

<210> SEQ ID NO 2246

<400> SEQUENCE: 2246

000

<210> SEQ ID NO 2247

<400> SEQUENCE: 2247

000

<210> SEQ ID NO 2248

<400> SEQUENCE: 2248

000

<210> SEQ ID NO 2249

<400> SEQUENCE: 2249

000

<210> SEQ ID NO 2250

<400> SEQUENCE: 2250

000

<210> SEQ ID NO 2251

<400> SEQUENCE: 2251

000

<210> SEQ ID NO 2252

<400> SEQUENCE: 2252

000

<210> SEQ ID NO 2253

<400> SEQUENCE: 2253

000

<210> SEQ ID NO 2254

<400> SEQUENCE: 2254

000

<210> SEQ ID NO 2255

<400> SEQUENCE: 2255

000

<210> SEQ ID NO 2256

<400> SEQUENCE: 2256

000

<210> SEQ ID NO 2257

<400> SEQUENCE: 2257

000

<210> SEQ ID NO 2258

<400> SEQUENCE: 2258

000

<210> SEQ ID NO 2259

<400> SEQUENCE: 2259

000

<210> SEQ ID NO 2260

<400> SEQUENCE: 2260

000

<210> SEQ ID NO 2261

<400> SEQUENCE: 2261

000

<210> SEQ ID NO 2262

<400> SEQUENCE: 2262

000

<210> SEQ ID NO 2263

<400> SEQUENCE: 2263

000

<210> SEQ ID NO 2264

<400> SEQUENCE: 2264

000

<210> SEQ ID NO 2265

<400> SEQUENCE: 2265

000

<210> SEQ ID NO 2266

<400> SEQUENCE: 2266

000

<210> SEQ ID NO 2267

<400> SEQUENCE: 2267

000

<210> SEQ ID NO 2268

<400> SEQUENCE: 2268

000

```
<210> SEQ ID NO 2269
<400> SEQUENCE: 2269
000

<210> SEQ ID NO 2270
<400> SEQUENCE: 2270
000

<210> SEQ ID NO 2271
<400> SEQUENCE: 2271
000

<210> SEQ ID NO 2272
<400> SEQUENCE: 2272
000

<210> SEQ ID NO 2273
<400> SEQUENCE: 2273
000

<210> SEQ ID NO 2274
<400> SEQUENCE: 2274
000

<210> SEQ ID NO 2275
<400> SEQUENCE: 2275
000

<210> SEQ ID NO 2276
<400> SEQUENCE: 2276
000

<210> SEQ ID NO 2277
<400> SEQUENCE: 2277
000

<210> SEQ ID NO 2278
<400> SEQUENCE: 2278
000

<210> SEQ ID NO 2279
<400> SEQUENCE: 2279
000
```

```
<210> SEQ ID NO 2280
<400> SEQUENCE: 2280
000

<210> SEQ ID NO 2281
<400> SEQUENCE: 2281
000

<210> SEQ ID NO 2282
<400> SEQUENCE: 2282
000

<210> SEQ ID NO 2283
<400> SEQUENCE: 2283
000

<210> SEQ ID NO 2284
<400> SEQUENCE: 2284
000

<210> SEQ ID NO 2285
<400> SEQUENCE: 2285
000

<210> SEQ ID NO 2286
<400> SEQUENCE: 2286
000

<210> SEQ ID NO 2287
<400> SEQUENCE: 2287
000

<210> SEQ ID NO 2288
<400> SEQUENCE: 2288
000

<210> SEQ ID NO 2289
<400> SEQUENCE: 2289
000

<210> SEQ ID NO 2290
<400> SEQUENCE: 2290
000

<210> SEQ ID NO 2291
```

```
<400> SEQUENCE: 2291
000

<210> SEQ ID NO 2292
<400> SEQUENCE: 2292
000

<210> SEQ ID NO 2293
<400> SEQUENCE: 2293
000

<210> SEQ ID NO 2294
<400> SEQUENCE: 2294
000

<210> SEQ ID NO 2295
<400> SEQUENCE: 2295
000

<210> SEQ ID NO 2296
<400> SEQUENCE: 2296
000

<210> SEQ ID NO 2297
<400> SEQUENCE: 2297
000

<210> SEQ ID NO 2298
<400> SEQUENCE: 2298
000

<210> SEQ ID NO 2299
<400> SEQUENCE: 2299
000

<210> SEQ ID NO 2300
<400> SEQUENCE: 2300
000

<210> SEQ ID NO 2301
<400> SEQUENCE: 2301
000

<210> SEQ ID NO 2302
<400> SEQUENCE: 2302
```

000

<210> SEQ ID NO 2303

<400> SEQUENCE: 2303

000

<210> SEQ ID NO 2304

<400> SEQUENCE: 2304

000

<210> SEQ ID NO 2305

<400> SEQUENCE: 2305

000

<210> SEQ ID NO 2306

<400> SEQUENCE: 2306

000

<210> SEQ ID NO 2307

<400> SEQUENCE: 2307

000

<210> SEQ ID NO 2308

<400> SEQUENCE: 2308

000

<210> SEQ ID NO 2309

<400> SEQUENCE: 2309

000

<210> SEQ ID NO 2310

<400> SEQUENCE: 2310

000

<210> SEQ ID NO 2311

<400> SEQUENCE: 2311

000

<210> SEQ ID NO 2312

<400> SEQUENCE: 2312

000

<210> SEQ ID NO 2313

<400> SEQUENCE: 2313

000

<210> SEQ ID NO 2314

<400> SEQUENCE: 2314

000

<210> SEQ ID NO 2315

<400> SEQUENCE: 2315

000

<210> SEQ ID NO 2316

<400> SEQUENCE: 2316

000

<210> SEQ ID NO 2317

<400> SEQUENCE: 2317

000

<210> SEQ ID NO 2318

<400> SEQUENCE: 2318

000

<210> SEQ ID NO 2319

<400> SEQUENCE: 2319

000

<210> SEQ ID NO 2320

<400> SEQUENCE: 2320

000

<210> SEQ ID NO 2321

<400> SEQUENCE: 2321

000

<210> SEQ ID NO 2322

<400> SEQUENCE: 2322

000

<210> SEQ ID NO 2323

<400> SEQUENCE: 2323

000

<210> SEQ ID NO 2324

<400> SEQUENCE: 2324

000

<210> SEQ ID NO 2325

<400> SEQUENCE: 2325

000

<210> SEQ ID NO 2326

<400> SEQUENCE: 2326

000

<210> SEQ ID NO 2327

<400> SEQUENCE: 2327

000

<210> SEQ ID NO 2328

<400> SEQUENCE: 2328

000

<210> SEQ ID NO 2329

<400> SEQUENCE: 2329

000

<210> SEQ ID NO 2330

<400> SEQUENCE: 2330

000

<210> SEQ ID NO 2331

<400> SEQUENCE: 2331

000

<210> SEQ ID NO 2332

<400> SEQUENCE: 2332

000

<210> SEQ ID NO 2333

<400> SEQUENCE: 2333

000

<210> SEQ ID NO 2334

<400> SEQUENCE: 2334

000

<210> SEQ ID NO 2335

<400> SEQUENCE: 2335

000

<210> SEQ ID NO 2336

<400> SEQUENCE: 2336

-continued

000

<210> SEQ ID NO 2337

<400> SEQUENCE: 2337

000

<210> SEQ ID NO 2338

<400> SEQUENCE: 2338

000

<210> SEQ ID NO 2339

<400> SEQUENCE: 2339

000

<210> SEQ ID NO 2340

<400> SEQUENCE: 2340

000

<210> SEQ ID NO 2341

<400> SEQUENCE: 2341

000

<210> SEQ ID NO 2342

<400> SEQUENCE: 2342

000

<210> SEQ ID NO 2343

<400> SEQUENCE: 2343

000

<210> SEQ ID NO 2344

<400> SEQUENCE: 2344

000

<210> SEQ ID NO 2345

<400> SEQUENCE: 2345

000

<210> SEQ ID NO 2346

<400> SEQUENCE: 2346

000

<210> SEQ ID NO 2347

<400> SEQUENCE: 2347

000

<210> SEQ ID NO 2348

<400> SEQUENCE: 2348

000

<210> SEQ ID NO 2349

<400> SEQUENCE: 2349

000

<210> SEQ ID NO 2350

<400> SEQUENCE: 2350

000

<210> SEQ ID NO 2351

<400> SEQUENCE: 2351

000

<210> SEQ ID NO 2352

<400> SEQUENCE: 2352

000

<210> SEQ ID NO 2353

<400> SEQUENCE: 2353

000

<210> SEQ ID NO 2354

<400> SEQUENCE: 2354

000

<210> SEQ ID NO 2355

<400> SEQUENCE: 2355

000

<210> SEQ ID NO 2356

<400> SEQUENCE: 2356

000

<210> SEQ ID NO 2357

<400> SEQUENCE: 2357

000

<210> SEQ ID NO 2358

<400> SEQUENCE: 2358

000

<210> SEQ ID NO 2359

<400> SEQUENCE: 2359

000

<210> SEQ ID NO 2360

<400> SEQUENCE: 2360

000

<210> SEQ ID NO 2361

<400> SEQUENCE: 2361

000

<210> SEQ ID NO 2362

<400> SEQUENCE: 2362

000

<210> SEQ ID NO 2363

<400> SEQUENCE: 2363

000

<210> SEQ ID NO 2364

<400> SEQUENCE: 2364

000

<210> SEQ ID NO 2365

<400> SEQUENCE: 2365

000

<210> SEQ ID NO 2366

<400> SEQUENCE: 2366

000

<210> SEQ ID NO 2367

<400> SEQUENCE: 2367

000

<210> SEQ ID NO 2368

<400> SEQUENCE: 2368

000

<210> SEQ ID NO 2369

<400> SEQUENCE: 2369

000

<210> SEQ ID NO 2370

<400> SEQUENCE: 2370

000

<210> SEQ ID NO 2371

<400> SEQUENCE: 2371

000

<210> SEQ ID NO 2372

<400> SEQUENCE: 2372

000

<210> SEQ ID NO 2373

<400> SEQUENCE: 2373

000

<210> SEQ ID NO 2374

<400> SEQUENCE: 2374

000

<210> SEQ ID NO 2375

<400> SEQUENCE: 2375

000

<210> SEQ ID NO 2376

<400> SEQUENCE: 2376

000

<210> SEQ ID NO 2377

<400> SEQUENCE: 2377

000

<210> SEQ ID NO 2378

<400> SEQUENCE: 2378

000

<210> SEQ ID NO 2379

<400> SEQUENCE: 2379

000

<210> SEQ ID NO 2380

<400> SEQUENCE: 2380

000

<210> SEQ ID NO 2381

<400> SEQUENCE: 2381

000

<210> SEQ ID NO 2382

<400> SEQUENCE: 2382

000

<210> SEQ ID NO 2383

<400> SEQUENCE: 2383

000

<210> SEQ ID NO 2384

<400> SEQUENCE: 2384

000

<210> SEQ ID NO 2385

<400> SEQUENCE: 2385

000

<210> SEQ ID NO 2386

<400> SEQUENCE: 2386

000

<210> SEQ ID NO 2387

<400> SEQUENCE: 2387

000

<210> SEQ ID NO 2388

<400> SEQUENCE: 2388

000

<210> SEQ ID NO 2389

<400> SEQUENCE: 2389

000

<210> SEQ ID NO 2390

<400> SEQUENCE: 2390

000

<210> SEQ ID NO 2391

<400> SEQUENCE: 2391

000

<210> SEQ ID NO 2392

<400> SEQUENCE: 2392

000

-continued

<210> SEQ ID NO 2393

<400> SEQUENCE: 2393

000

<210> SEQ ID NO 2394

<400> SEQUENCE: 2394

000

<210> SEQ ID NO 2395

<400> SEQUENCE: 2395

000

<210> SEQ ID NO 2396

<400> SEQUENCE: 2396

000

<210> SEQ ID NO 2397

<400> SEQUENCE: 2397

000

<210> SEQ ID NO 2398

<400> SEQUENCE: 2398

000

<210> SEQ ID NO 2399

<400> SEQUENCE: 2399

000

<210> SEQ ID NO 2400

<400> SEQUENCE: 2400

000

<210> SEQ ID NO 2401

<400> SEQUENCE: 2401

000

<210> SEQ ID NO 2402

<400> SEQUENCE: 2402

000

<210> SEQ ID NO 2403

<400> SEQUENCE: 2403

000

<210> SEQ ID NO 2404

<400> SEQUENCE: 2404

000

<210> SEQ ID NO 2405

<400> SEQUENCE: 2405

000

<210> SEQ ID NO 2406

<400> SEQUENCE: 2406

000

<210> SEQ ID NO 2407

<400> SEQUENCE: 2407

000

<210> SEQ ID NO 2408

<400> SEQUENCE: 2408

000

<210> SEQ ID NO 2409

<400> SEQUENCE: 2409

000

<210> SEQ ID NO 2410

<400> SEQUENCE: 2410

000

<210> SEQ ID NO 2411

<400> SEQUENCE: 2411

000

<210> SEQ ID NO 2412

<400> SEQUENCE: 2412

000

<210> SEQ ID NO 2413

<400> SEQUENCE: 2413

000

<210> SEQ ID NO 2414

<400> SEQUENCE: 2414

000

<210> SEQ ID NO 2415

<400> SEQUENCE: 2415

000

<210> SEQ ID NO 2416

<400> SEQUENCE: 2416

000

<210> SEQ ID NO 2417

<400> SEQUENCE: 2417

000

<210> SEQ ID NO 2418

<400> SEQUENCE: 2418

000

<210> SEQ ID NO 2419

<400> SEQUENCE: 2419

000

<210> SEQ ID NO 2420

<400> SEQUENCE: 2420

000

<210> SEQ ID NO 2421

<400> SEQUENCE: 2421

000

<210> SEQ ID NO 2422

<400> SEQUENCE: 2422

000

<210> SEQ ID NO 2423

<400> SEQUENCE: 2423

000

<210> SEQ ID NO 2424

<400> SEQUENCE: 2424

000

<210> SEQ ID NO 2425

<400> SEQUENCE: 2425

000

<210> SEQ ID NO 2426

<400> SEQUENCE: 2426

000

<210> SEQ ID NO 2427

<400> SEQUENCE: 2427

000

<210> SEQ ID NO 2428

<400> SEQUENCE: 2428

000

<210> SEQ ID NO 2429

<400> SEQUENCE: 2429

000

<210> SEQ ID NO 2430

<400> SEQUENCE: 2430

000

<210> SEQ ID NO 2431

<400> SEQUENCE: 2431

000

<210> SEQ ID NO 2432

<400> SEQUENCE: 2432

000

<210> SEQ ID NO 2433

<400> SEQUENCE: 2433

000

<210> SEQ ID NO 2434

<400> SEQUENCE: 2434

000

<210> SEQ ID NO 2435

<400> SEQUENCE: 2435

000

<210> SEQ ID NO 2436

<400> SEQUENCE: 2436

000

<210> SEQ ID NO 2437

<400> SEQUENCE: 2437

000

<210> SEQ ID NO 2438

<400> SEQUENCE: 2438

000

<210> SEQ ID NO 2439

<400> SEQUENCE: 2439

000

<210> SEQ ID NO 2440

<400> SEQUENCE: 2440

000

<210> SEQ ID NO 2441

<400> SEQUENCE: 2441

000

<210> SEQ ID NO 2442

<400> SEQUENCE: 2442

000

<210> SEQ ID NO 2443

<400> SEQUENCE: 2443

000

<210> SEQ ID NO 2444

<400> SEQUENCE: 2444

000

<210> SEQ ID NO 2445

<400> SEQUENCE: 2445

000

<210> SEQ ID NO 2446

<400> SEQUENCE: 2446

000

<210> SEQ ID NO 2447

<400> SEQUENCE: 2447

000

<210> SEQ ID NO 2448

<400> SEQUENCE: 2448

000

<210> SEQ ID NO 2449

<400> SEQUENCE: 2449

000

<210> SEQ ID NO 2450

<400> SEQUENCE: 2450

000

<210> SEQ ID NO 2451

<400> SEQUENCE: 2451

000

<210> SEQ ID NO 2452

<400> SEQUENCE: 2452

000

<210> SEQ ID NO 2453

<400> SEQUENCE: 2453

000

<210> SEQ ID NO 2454

<400> SEQUENCE: 2454

000

<210> SEQ ID NO 2455

<400> SEQUENCE: 2455

000

<210> SEQ ID NO 2456

<400> SEQUENCE: 2456

000

<210> SEQ ID NO 2457

<400> SEQUENCE: 2457

000

<210> SEQ ID NO 2458

<400> SEQUENCE: 2458

000

<210> SEQ ID NO 2459

<400> SEQUENCE: 2459

000

<210> SEQ ID NO 2460

<400> SEQUENCE: 2460

000

<210> SEQ ID NO 2461

<400> SEQUENCE: 2461

000

<210> SEQ ID NO 2462

<400> SEQUENCE: 2462

000

<210> SEQ ID NO 2463

<400> SEQUENCE: 2463

000

<210> SEQ ID NO 2464

<400> SEQUENCE: 2464

000

<210> SEQ ID NO 2465

<400> SEQUENCE: 2465

000

<210> SEQ ID NO 2466

<400> SEQUENCE: 2466

000

<210> SEQ ID NO 2467

<400> SEQUENCE: 2467

000

<210> SEQ ID NO 2468

<400> SEQUENCE: 2468

000

<210> SEQ ID NO 2469

<400> SEQUENCE: 2469

000

<210> SEQ ID NO 2470

<400> SEQUENCE: 2470

000

<210> SEQ ID NO 2471

<400> SEQUENCE: 2471

000

-continued

<210> SEQ ID NO 2472

<400> SEQUENCE: 2472

000

<210> SEQ ID NO 2473

<400> SEQUENCE: 2473

000

<210> SEQ ID NO 2474

<400> SEQUENCE: 2474

000

<210> SEQ ID NO 2475

<400> SEQUENCE: 2475

000

<210> SEQ ID NO 2476

<400> SEQUENCE: 2476

000

<210> SEQ ID NO 2477

<400> SEQUENCE: 2477

000

<210> SEQ ID NO 2478

<400> SEQUENCE: 2478

000

<210> SEQ ID NO 2479

<400> SEQUENCE: 2479

000

<210> SEQ ID NO 2480

<400> SEQUENCE: 2480

000

<210> SEQ ID NO 2481

<400> SEQUENCE: 2481

000

<210> SEQ ID NO 2482

<400> SEQUENCE: 2482

000

<210> SEQ ID NO 2483

<400> SEQUENCE: 2483

000

<210> SEQ ID NO 2484

<400> SEQUENCE: 2484

000

<210> SEQ ID NO 2485

<400> SEQUENCE: 2485

000

<210> SEQ ID NO 2486

<400> SEQUENCE: 2486

000

<210> SEQ ID NO 2487

<400> SEQUENCE: 2487

000

<210> SEQ ID NO 2488

<400> SEQUENCE: 2488

000

<210> SEQ ID NO 2489

<400> SEQUENCE: 2489

000

<210> SEQ ID NO 2490

<400> SEQUENCE: 2490

000

<210> SEQ ID NO 2491

<400> SEQUENCE: 2491

000

<210> SEQ ID NO 2492

<400> SEQUENCE: 2492

000

<210> SEQ ID NO 2493

<400> SEQUENCE: 2493

000

<210> SEQ ID NO 2494

<400> SEQUENCE: 2494

000

<210> SEQ ID NO 2495

<400> SEQUENCE: 2495

000

<210> SEQ ID NO 2496

<400> SEQUENCE: 2496

000

<210> SEQ ID NO 2497

<400> SEQUENCE: 2497

000

<210> SEQ ID NO 2498

<400> SEQUENCE: 2498

000

<210> SEQ ID NO 2499

<400> SEQUENCE: 2499

000

<210> SEQ ID NO 2500

<400> SEQUENCE: 2500

000

<210> SEQ ID NO 2501

<400> SEQUENCE: 2501

000

<210> SEQ ID NO 2502

<400> SEQUENCE: 2502

000

<210> SEQ ID NO 2503

<400> SEQUENCE: 2503

000

<210> SEQ ID NO 2504

<400> SEQUENCE: 2504

000

<210> SEQ ID NO 2505

<400> SEQUENCE: 2505

000

<210> SEQ ID NO 2506

<400> SEQUENCE: 2506

000

<210> SEQ ID NO 2507

<400> SEQUENCE: 2507

000

<210> SEQ ID NO 2508

<400> SEQUENCE: 2508

000

<210> SEQ ID NO 2509

<400> SEQUENCE: 2509

000

<210> SEQ ID NO 2510

<400> SEQUENCE: 2510

000

<210> SEQ ID NO 2511

<400> SEQUENCE: 2511

000

<210> SEQ ID NO 2512

<400> SEQUENCE: 2512

000

<210> SEQ ID NO 2513

<400> SEQUENCE: 2513

000

<210> SEQ ID NO 2514

<400> SEQUENCE: 2514

000

<210> SEQ ID NO 2515

<400> SEQUENCE: 2515

000

<210> SEQ ID NO 2516

<400> SEQUENCE: 2516

000

<210> SEQ ID NO 2517

<400> SEQUENCE: 2517

000

<210> SEQ ID NO 2518

<400> SEQUENCE: 2518

000

<210> SEQ ID NO 2519

<400> SEQUENCE: 2519

000

<210> SEQ ID NO 2520

<400> SEQUENCE: 2520

000

<210> SEQ ID NO 2521

<400> SEQUENCE: 2521

000

<210> SEQ ID NO 2522

<400> SEQUENCE: 2522

000

<210> SEQ ID NO 2523

<400> SEQUENCE: 2523

000

<210> SEQ ID NO 2524

<400> SEQUENCE: 2524

000

<210> SEQ ID NO 2525

<400> SEQUENCE: 2525

000

<210> SEQ ID NO 2526

<400> SEQUENCE: 2526

000

<210> SEQ ID NO 2527

<400> SEQUENCE: 2527

000

<210> SEQ ID NO 2528

```
<400> SEQUENCE: 2528

000

<210> SEQ ID NO 2529
<400> SEQUENCE: 2529

000

<210> SEQ ID NO 2530
<400> SEQUENCE: 2530

000

<210> SEQ ID NO 2531
<400> SEQUENCE: 2531

000

<210> SEQ ID NO 2532
<400> SEQUENCE: 2532

000

<210> SEQ ID NO 2533
<400> SEQUENCE: 2533

000

<210> SEQ ID NO 2534
<400> SEQUENCE: 2534

000

<210> SEQ ID NO 2535
<400> SEQUENCE: 2535

000

<210> SEQ ID NO 2536
<400> SEQUENCE: 2536

000

<210> SEQ ID NO 2537
<400> SEQUENCE: 2537

000

<210> SEQ ID NO 2538
<400> SEQUENCE: 2538

000

<210> SEQ ID NO 2539
<400> SEQUENCE: 2539
```

000

<210> SEQ ID NO 2540

<400> SEQUENCE: 2540

000

<210> SEQ ID NO 2541

<400> SEQUENCE: 2541

000

<210> SEQ ID NO 2542

<400> SEQUENCE: 2542

000

<210> SEQ ID NO 2543

<400> SEQUENCE: 2543

000

<210> SEQ ID NO 2544

<400> SEQUENCE: 2544

000

<210> SEQ ID NO 2545

<400> SEQUENCE: 2545

000

<210> SEQ ID NO 2546

<400> SEQUENCE: 2546

000

<210> SEQ ID NO 2547

<400> SEQUENCE: 2547

000

<210> SEQ ID NO 2548

<400> SEQUENCE: 2548

000

<210> SEQ ID NO 2549

<400> SEQUENCE: 2549

000

<210> SEQ ID NO 2550

<400> SEQUENCE: 2550

000

```
<210> SEQ ID NO 2551
<400> SEQUENCE: 2551
000

<210> SEQ ID NO 2552
<400> SEQUENCE: 2552
000

<210> SEQ ID NO 2553
<400> SEQUENCE: 2553
000

<210> SEQ ID NO 2554
<400> SEQUENCE: 2554
000

<210> SEQ ID NO 2555
<400> SEQUENCE: 2555
000

<210> SEQ ID NO 2556
<400> SEQUENCE: 2556
000

<210> SEQ ID NO 2557
<400> SEQUENCE: 2557
000

<210> SEQ ID NO 2558
<400> SEQUENCE: 2558
000

<210> SEQ ID NO 2559
<400> SEQUENCE: 2559
000

<210> SEQ ID NO 2560
<400> SEQUENCE: 2560
000

<210> SEQ ID NO 2561
<400> SEQUENCE: 2561
000

<210> SEQ ID NO 2562
```

<400> SEQUENCE: 2562

000

<210> SEQ ID NO 2563

<400> SEQUENCE: 2563

000

<210> SEQ ID NO 2564

<400> SEQUENCE: 2564

000

<210> SEQ ID NO 2565

<400> SEQUENCE: 2565

000

<210> SEQ ID NO 2566

<400> SEQUENCE: 2566

000

<210> SEQ ID NO 2567

<400> SEQUENCE: 2567

000

<210> SEQ ID NO 2568

<400> SEQUENCE: 2568

000

<210> SEQ ID NO 2569

<400> SEQUENCE: 2569

000

<210> SEQ ID NO 2570

<400> SEQUENCE: 2570

000

<210> SEQ ID NO 2571

<400> SEQUENCE: 2571

000

<210> SEQ ID NO 2572

<400> SEQUENCE: 2572

000

<210> SEQ ID NO 2573

<400> SEQUENCE: 2573

000

<210> SEQ ID NO 2574

<400> SEQUENCE: 2574

000

<210> SEQ ID NO 2575

<400> SEQUENCE: 2575

000

<210> SEQ ID NO 2576

<400> SEQUENCE: 2576

000

<210> SEQ ID NO 2577

<400> SEQUENCE: 2577

000

<210> SEQ ID NO 2578

<400> SEQUENCE: 2578

000

<210> SEQ ID NO 2579

<400> SEQUENCE: 2579

000

<210> SEQ ID NO 2580

<400> SEQUENCE: 2580

000

<210> SEQ ID NO 2581

<400> SEQUENCE: 2581

000

<210> SEQ ID NO 2582

<400> SEQUENCE: 2582

000

<210> SEQ ID NO 2583

<400> SEQUENCE: 2583

000

<210> SEQ ID NO 2584

<400> SEQUENCE: 2584

000

<210> SEQ ID NO 2585

<400> SEQUENCE: 2585

000

<210> SEQ ID NO 2586

<400> SEQUENCE: 2586

000

<210> SEQ ID NO 2587

<400> SEQUENCE: 2587

000

<210> SEQ ID NO 2588

<400> SEQUENCE: 2588

000

<210> SEQ ID NO 2589

<400> SEQUENCE: 2589

000

<210> SEQ ID NO 2590

<400> SEQUENCE: 2590

000

<210> SEQ ID NO 2591

<400> SEQUENCE: 2591

000

<210> SEQ ID NO 2592

<400> SEQUENCE: 2592

000

<210> SEQ ID NO 2593

<400> SEQUENCE: 2593

000

<210> SEQ ID NO 2594

<400> SEQUENCE: 2594

000

<210> SEQ ID NO 2595

<400> SEQUENCE: 2595

000

<210> SEQ ID NO 2596

<400> SEQUENCE: 2596

000

<210> SEQ ID NO 2597

<400> SEQUENCE: 2597

000

<210> SEQ ID NO 2598

<400> SEQUENCE: 2598

000

<210> SEQ ID NO 2599

<400> SEQUENCE: 2599

000

<210> SEQ ID NO 2600

<400> SEQUENCE: 2600

000

<210> SEQ ID NO 2601

<400> SEQUENCE: 2601

000

<210> SEQ ID NO 2602

<400> SEQUENCE: 2602

000

<210> SEQ ID NO 2603

<400> SEQUENCE: 2603

000

<210> SEQ ID NO 2604

<400> SEQUENCE: 2604

000

<210> SEQ ID NO 2605

<400> SEQUENCE: 2605

000

<210> SEQ ID NO 2606

<400> SEQUENCE: 2606

000

<210> SEQ ID NO 2607

```
<400> SEQUENCE: 2607
000

<210> SEQ ID NO 2608
<400> SEQUENCE: 2608
000

<210> SEQ ID NO 2609
<400> SEQUENCE: 2609
000

<210> SEQ ID NO 2610
<400> SEQUENCE: 2610
000

<210> SEQ ID NO 2611
<400> SEQUENCE: 2611
000

<210> SEQ ID NO 2612
<400> SEQUENCE: 2612
000

<210> SEQ ID NO 2613
<400> SEQUENCE: 2613
000

<210> SEQ ID NO 2614
<400> SEQUENCE: 2614
000

<210> SEQ ID NO 2615
<400> SEQUENCE: 2615
000

<210> SEQ ID NO 2616
<400> SEQUENCE: 2616
000

<210> SEQ ID NO 2617
<400> SEQUENCE: 2617
000

<210> SEQ ID NO 2618
<400> SEQUENCE: 2618
```

000

<210> SEQ ID NO 2619

<400> SEQUENCE: 2619

000

<210> SEQ ID NO 2620

<400> SEQUENCE: 2620

000

<210> SEQ ID NO 2621

<400> SEQUENCE: 2621

000

<210> SEQ ID NO 2622

<400> SEQUENCE: 2622

000

<210> SEQ ID NO 2623

<400> SEQUENCE: 2623

000

<210> SEQ ID NO 2624

<400> SEQUENCE: 2624

000

<210> SEQ ID NO 2625

<400> SEQUENCE: 2625

000

<210> SEQ ID NO 2626

<400> SEQUENCE: 2626

000

<210> SEQ ID NO 2627

<400> SEQUENCE: 2627

000

<210> SEQ ID NO 2628

<400> SEQUENCE: 2628

000

<210> SEQ ID NO 2629

<400> SEQUENCE: 2629

000

```
<210> SEQ ID NO 2630
<400> SEQUENCE: 2630
000

<210> SEQ ID NO 2631
<400> SEQUENCE: 2631
000

<210> SEQ ID NO 2632
<400> SEQUENCE: 2632
000

<210> SEQ ID NO 2633
<400> SEQUENCE: 2633
000

<210> SEQ ID NO 2634
<400> SEQUENCE: 2634
000

<210> SEQ ID NO 2635
<400> SEQUENCE: 2635
000

<210> SEQ ID NO 2636
<400> SEQUENCE: 2636
000

<210> SEQ ID NO 2637
<400> SEQUENCE: 2637
000

<210> SEQ ID NO 2638
<400> SEQUENCE: 2638
000

<210> SEQ ID NO 2639
<400> SEQUENCE: 2639
000

<210> SEQ ID NO 2640
<400> SEQUENCE: 2640
000

<210> SEQ ID NO 2641
```

```
<400> SEQUENCE: 2641
000

<210> SEQ ID NO 2642
<400> SEQUENCE: 2642
000

<210> SEQ ID NO 2643
<400> SEQUENCE: 2643
000

<210> SEQ ID NO 2644
<400> SEQUENCE: 2644
000

<210> SEQ ID NO 2645
<400> SEQUENCE: 2645
000

<210> SEQ ID NO 2646
<400> SEQUENCE: 2646
000

<210> SEQ ID NO 2647
<400> SEQUENCE: 2647
000

<210> SEQ ID NO 2648
<400> SEQUENCE: 2648
000

<210> SEQ ID NO 2649
<400> SEQUENCE: 2649
000

<210> SEQ ID NO 2650
<400> SEQUENCE: 2650
000

<210> SEQ ID NO 2651
<400> SEQUENCE: 2651
000

<210> SEQ ID NO 2652
<400> SEQUENCE: 2652
```

000

<210> SEQ ID NO 2653

<400> SEQUENCE: 2653

000

<210> SEQ ID NO 2654

<400> SEQUENCE: 2654

000

<210> SEQ ID NO 2655

<400> SEQUENCE: 2655

000

<210> SEQ ID NO 2656

<400> SEQUENCE: 2656

000

<210> SEQ ID NO 2657

<400> SEQUENCE: 2657

000

<210> SEQ ID NO 2658

<400> SEQUENCE: 2658

000

<210> SEQ ID NO 2659

<400> SEQUENCE: 2659

000

<210> SEQ ID NO 2660

<400> SEQUENCE: 2660

000

<210> SEQ ID NO 2661

<400> SEQUENCE: 2661

000

<210> SEQ ID NO 2662

<400> SEQUENCE: 2662

000

<210> SEQ ID NO 2663

<400> SEQUENCE: 2663

000

<210> SEQ ID NO 2664

<400> SEQUENCE: 2664

000

<210> SEQ ID NO 2665

<400> SEQUENCE: 2665

000

<210> SEQ ID NO 2666

<400> SEQUENCE: 2666

000

<210> SEQ ID NO 2667

<400> SEQUENCE: 2667

000

<210> SEQ ID NO 2668

<400> SEQUENCE: 2668

000

<210> SEQ ID NO 2669

<400> SEQUENCE: 2669

000

<210> SEQ ID NO 2670

<400> SEQUENCE: 2670

000

<210> SEQ ID NO 2671

<400> SEQUENCE: 2671

000

<210> SEQ ID NO 2672

<400> SEQUENCE: 2672

000

<210> SEQ ID NO 2673

<400> SEQUENCE: 2673

000

<210> SEQ ID NO 2674

<400> SEQUENCE: 2674

000

<210> SEQ ID NO 2675

<400> SEQUENCE: 2675

000

<210> SEQ ID NO 2676

<400> SEQUENCE: 2676

000

<210> SEQ ID NO 2677

<400> SEQUENCE: 2677

000

<210> SEQ ID NO 2678

<400> SEQUENCE: 2678

000

<210> SEQ ID NO 2679

<400> SEQUENCE: 2679

000

<210> SEQ ID NO 2680

<400> SEQUENCE: 2680

000

<210> SEQ ID NO 2681

<400> SEQUENCE: 2681

000

<210> SEQ ID NO 2682

<400> SEQUENCE: 2682

000

<210> SEQ ID NO 2683

<400> SEQUENCE: 2683

000

<210> SEQ ID NO 2684

<400> SEQUENCE: 2684

000

<210> SEQ ID NO 2685

<400> SEQUENCE: 2685

000

<210> SEQ ID NO 2686

<400> SEQUENCE: 2686

000

<210> SEQ ID NO 2687

<400> SEQUENCE: 2687

000

<210> SEQ ID NO 2688

<400> SEQUENCE: 2688

000

<210> SEQ ID NO 2689

<400> SEQUENCE: 2689

000

<210> SEQ ID NO 2690

<400> SEQUENCE: 2690

000

<210> SEQ ID NO 2691

<400> SEQUENCE: 2691

000

<210> SEQ ID NO 2692

<400> SEQUENCE: 2692

000

<210> SEQ ID NO 2693

<400> SEQUENCE: 2693

000

<210> SEQ ID NO 2694

<400> SEQUENCE: 2694

000

<210> SEQ ID NO 2695

<400> SEQUENCE: 2695

000

<210> SEQ ID NO 2696

<400> SEQUENCE: 2696

000

<210> SEQ ID NO 2697

<400> SEQUENCE: 2697

000

<210> SEQ ID NO 2698

<400> SEQUENCE: 2698

000

<210> SEQ ID NO 2699

<400> SEQUENCE: 2699

000

<210> SEQ ID NO 2700

<400> SEQUENCE: 2700

000

<210> SEQ ID NO 2701

<400> SEQUENCE: 2701

000

<210> SEQ ID NO 2702

<400> SEQUENCE: 2702

000

<210> SEQ ID NO 2703

<400> SEQUENCE: 2703

000

<210> SEQ ID NO 2704

<400> SEQUENCE: 2704

000

<210> SEQ ID NO 2705

<400> SEQUENCE: 2705

000

<210> SEQ ID NO 2706

<400> SEQUENCE: 2706

000

<210> SEQ ID NO 2707

<400> SEQUENCE: 2707

000

<210> SEQ ID NO 2708

<400> SEQUENCE: 2708

000

```
<210> SEQ ID NO 2709
<400> SEQUENCE: 2709
000

<210> SEQ ID NO 2710
<400> SEQUENCE: 2710
000

<210> SEQ ID NO 2711
<400> SEQUENCE: 2711
000

<210> SEQ ID NO 2712
<400> SEQUENCE: 2712
000

<210> SEQ ID NO 2713
<400> SEQUENCE: 2713
000

<210> SEQ ID NO 2714
<400> SEQUENCE: 2714
000

<210> SEQ ID NO 2715
<400> SEQUENCE: 2715
000

<210> SEQ ID NO 2716
<400> SEQUENCE: 2716
000

<210> SEQ ID NO 2717
<400> SEQUENCE: 2717
000

<210> SEQ ID NO 2718
<400> SEQUENCE: 2718
000

<210> SEQ ID NO 2719
<400> SEQUENCE: 2719
000

<210> SEQ ID NO 2720
```

-continued

<400> SEQUENCE: 2720

000

<210> SEQ ID NO 2721

<400> SEQUENCE: 2721

000

<210> SEQ ID NO 2722

<400> SEQUENCE: 2722

000

<210> SEQ ID NO 2723

<400> SEQUENCE: 2723

000

<210> SEQ ID NO 2724

<400> SEQUENCE: 2724

000

<210> SEQ ID NO 2725

<400> SEQUENCE: 2725

000

<210> SEQ ID NO 2726

<400> SEQUENCE: 2726

000

<210> SEQ ID NO 2727

<400> SEQUENCE: 2727

000

<210> SEQ ID NO 2728

<400> SEQUENCE: 2728

000

<210> SEQ ID NO 2729

<400> SEQUENCE: 2729

000

<210> SEQ ID NO 2730

<400> SEQUENCE: 2730

000

<210> SEQ ID NO 2731

<400> SEQUENCE: 2731

000

<210> SEQ ID NO 2732

<400> SEQUENCE: 2732

000

<210> SEQ ID NO 2733

<400> SEQUENCE: 2733

000

<210> SEQ ID NO 2734

<400> SEQUENCE: 2734

000

<210> SEQ ID NO 2735

<400> SEQUENCE: 2735

000

<210> SEQ ID NO 2736

<400> SEQUENCE: 2736

000

<210> SEQ ID NO 2737

<400> SEQUENCE: 2737

000

<210> SEQ ID NO 2738

<400> SEQUENCE: 2738

000

<210> SEQ ID NO 2739

<400> SEQUENCE: 2739

000

<210> SEQ ID NO 2740

<400> SEQUENCE: 2740

000

<210> SEQ ID NO 2741

<400> SEQUENCE: 2741

000

<210> SEQ ID NO 2742

<400> SEQUENCE: 2742

000

<210> SEQ ID NO 2743

<400> SEQUENCE: 2743

000

<210> SEQ ID NO 2744

<400> SEQUENCE: 2744

000

<210> SEQ ID NO 2745

<400> SEQUENCE: 2745

000

<210> SEQ ID NO 2746

<400> SEQUENCE: 2746

000

<210> SEQ ID NO 2747

<400> SEQUENCE: 2747

000

<210> SEQ ID NO 2748

<400> SEQUENCE: 2748

000

<210> SEQ ID NO 2749

<400> SEQUENCE: 2749

000

<210> SEQ ID NO 2750

<400> SEQUENCE: 2750

000

<210> SEQ ID NO 2751

<400> SEQUENCE: 2751

000

<210> SEQ ID NO 2752

<400> SEQUENCE: 2752

000

<210> SEQ ID NO 2753

<400> SEQUENCE: 2753

000

<210> SEQ ID NO 2754
<400> SEQUENCE: 2754
000

<210> SEQ ID NO 2755
<400> SEQUENCE: 2755
000

<210> SEQ ID NO 2756
<400> SEQUENCE: 2756
000

<210> SEQ ID NO 2757
<400> SEQUENCE: 2757
000

<210> SEQ ID NO 2758
<400> SEQUENCE: 2758
000

<210> SEQ ID NO 2759
<400> SEQUENCE: 2759
000

<210> SEQ ID NO 2760
<400> SEQUENCE: 2760
000

<210> SEQ ID NO 2761
<400> SEQUENCE: 2761
000

<210> SEQ ID NO 2762
<400> SEQUENCE: 2762
000

<210> SEQ ID NO 2763
<400> SEQUENCE: 2763
000

<210> SEQ ID NO 2764
<400> SEQUENCE: 2764
000

<210> SEQ ID NO 2765

```
<400> SEQUENCE: 2765
000

<210> SEQ ID NO 2766
<400> SEQUENCE: 2766
000

<210> SEQ ID NO 2767
<400> SEQUENCE: 2767
000

<210> SEQ ID NO 2768
<400> SEQUENCE: 2768
000

<210> SEQ ID NO 2769
<400> SEQUENCE: 2769
000

<210> SEQ ID NO 2770
<400> SEQUENCE: 2770
000

<210> SEQ ID NO 2771
<400> SEQUENCE: 2771
000

<210> SEQ ID NO 2772
<400> SEQUENCE: 2772
000

<210> SEQ ID NO 2773
<400> SEQUENCE: 2773
000

<210> SEQ ID NO 2774
<400> SEQUENCE: 2774
000

<210> SEQ ID NO 2775
<400> SEQUENCE: 2775
000

<210> SEQ ID NO 2776
<400> SEQUENCE: 2776
```

000

<210> SEQ ID NO 2777
<400> SEQUENCE: 2777
000

<210> SEQ ID NO 2778
<400> SEQUENCE: 2778
000

<210> SEQ ID NO 2779
<400> SEQUENCE: 2779
000

<210> SEQ ID NO 2780
<400> SEQUENCE: 2780
000

<210> SEQ ID NO 2781
<400> SEQUENCE: 2781
000

<210> SEQ ID NO 2782
<400> SEQUENCE: 2782
000

<210> SEQ ID NO 2783
<400> SEQUENCE: 2783
000

<210> SEQ ID NO 2784
<400> SEQUENCE: 2784
000

<210> SEQ ID NO 2785
<400> SEQUENCE: 2785
000

<210> SEQ ID NO 2786
<400> SEQUENCE: 2786
000

<210> SEQ ID NO 2787
<400> SEQUENCE: 2787
000

<210> SEQ ID NO 2788

<400> SEQUENCE: 2788

000

<210> SEQ ID NO 2789

<400> SEQUENCE: 2789

000

<210> SEQ ID NO 2790

<400> SEQUENCE: 2790

000

<210> SEQ ID NO 2791

<400> SEQUENCE: 2791

000

<210> SEQ ID NO 2792

<400> SEQUENCE: 2792

000

<210> SEQ ID NO 2793

<400> SEQUENCE: 2793

000

<210> SEQ ID NO 2794

<400> SEQUENCE: 2794

000

<210> SEQ ID NO 2795

<400> SEQUENCE: 2795

000

<210> SEQ ID NO 2796

<400> SEQUENCE: 2796

000

<210> SEQ ID NO 2797

<400> SEQUENCE: 2797

000

<210> SEQ ID NO 2798

<400> SEQUENCE: 2798

000

<210> SEQ ID NO 2799

<400> SEQUENCE: 2799

000

<210> SEQ ID NO 2800

<400> SEQUENCE: 2800

000

<210> SEQ ID NO 2801

<400> SEQUENCE: 2801

000

<210> SEQ ID NO 2802

<400> SEQUENCE: 2802

000

<210> SEQ ID NO 2803

<400> SEQUENCE: 2803

000

<210> SEQ ID NO 2804

<400> SEQUENCE: 2804

000

<210> SEQ ID NO 2805

<400> SEQUENCE: 2805

000

<210> SEQ ID NO 2806

<400> SEQUENCE: 2806

000

<210> SEQ ID NO 2807

<400> SEQUENCE: 2807

000

<210> SEQ ID NO 2808

<400> SEQUENCE: 2808

000

<210> SEQ ID NO 2809

<400> SEQUENCE: 2809

000

<210> SEQ ID NO 2810

<400> SEQUENCE: 2810

000

<210> SEQ ID NO 2811

<400> SEQUENCE: 2811

000

<210> SEQ ID NO 2812

<400> SEQUENCE: 2812

000

<210> SEQ ID NO 2813

<400> SEQUENCE: 2813

000

<210> SEQ ID NO 2814

<400> SEQUENCE: 2814

000

<210> SEQ ID NO 2815

<400> SEQUENCE: 2815

000

<210> SEQ ID NO 2816

<400> SEQUENCE: 2816

000

<210> SEQ ID NO 2817

<400> SEQUENCE: 2817

000

<210> SEQ ID NO 2818

<400> SEQUENCE: 2818

000

<210> SEQ ID NO 2819

<400> SEQUENCE: 2819

000

<210> SEQ ID NO 2820

<400> SEQUENCE: 2820

000

<210> SEQ ID NO 2821

<400> SEQUENCE: 2821

000

```
<210> SEQ ID NO 2822
<400> SEQUENCE: 2822
000

<210> SEQ ID NO 2823
<400> SEQUENCE: 2823
000

<210> SEQ ID NO 2824
<400> SEQUENCE: 2824
000

<210> SEQ ID NO 2825
<400> SEQUENCE: 2825
000

<210> SEQ ID NO 2826
<400> SEQUENCE: 2826
000

<210> SEQ ID NO 2827
<400> SEQUENCE: 2827
000

<210> SEQ ID NO 2828
<400> SEQUENCE: 2828
000

<210> SEQ ID NO 2829
<400> SEQUENCE: 2829
000

<210> SEQ ID NO 2830
<400> SEQUENCE: 2830
000

<210> SEQ ID NO 2831
<400> SEQUENCE: 2831
000

<210> SEQ ID NO 2832
<400> SEQUENCE: 2832
000
```

<210> SEQ ID NO 2833

<400> SEQUENCE: 2833

000

<210> SEQ ID NO 2834

<400> SEQUENCE: 2834

000

<210> SEQ ID NO 2835

<400> SEQUENCE: 2835

000

<210> SEQ ID NO 2836

<400> SEQUENCE: 2836

000

<210> SEQ ID NO 2837

<400> SEQUENCE: 2837

000

<210> SEQ ID NO 2838

<400> SEQUENCE: 2838

000

<210> SEQ ID NO 2839

<400> SEQUENCE: 2839

000

<210> SEQ ID NO 2840

<400> SEQUENCE: 2840

000

<210> SEQ ID NO 2841

<400> SEQUENCE: 2841

000

<210> SEQ ID NO 2842

<400> SEQUENCE: 2842

000

<210> SEQ ID NO 2843

<400> SEQUENCE: 2843

000

<210> SEQ ID NO 2844

<400> SEQUENCE: 2844

000

<210> SEQ ID NO 2845

<400> SEQUENCE: 2845

000

<210> SEQ ID NO 2846

<400> SEQUENCE: 2846

000

<210> SEQ ID NO 2847

<400> SEQUENCE: 2847

000

<210> SEQ ID NO 2848

<400> SEQUENCE: 2848

000

<210> SEQ ID NO 2849

<400> SEQUENCE: 2849

000

<210> SEQ ID NO 2850

<400> SEQUENCE: 2850

000

<210> SEQ ID NO 2851

<400> SEQUENCE: 2851

000

<210> SEQ ID NO 2852

<400> SEQUENCE: 2852

000

<210> SEQ ID NO 2853

<400> SEQUENCE: 2853

000

<210> SEQ ID NO 2854

<400> SEQUENCE: 2854

000

<210> SEQ ID NO 2855

<400> SEQUENCE: 2855

000

<210> SEQ ID NO 2856

<400> SEQUENCE: 2856

000

<210> SEQ ID NO 2857

<400> SEQUENCE: 2857

000

<210> SEQ ID NO 2858

<400> SEQUENCE: 2858

000

<210> SEQ ID NO 2859

<400> SEQUENCE: 2859

000

<210> SEQ ID NO 2860

<400> SEQUENCE: 2860

000

<210> SEQ ID NO 2861

<400> SEQUENCE: 2861

000

<210> SEQ ID NO 2862

<400> SEQUENCE: 2862

000

<210> SEQ ID NO 2863

<400> SEQUENCE: 2863

000

<210> SEQ ID NO 2864

<400> SEQUENCE: 2864

000

<210> SEQ ID NO 2865

<400> SEQUENCE: 2865

000

<210> SEQ ID NO 2866

<400> SEQUENCE: 2866

000

```
<210> SEQ ID NO 2867
<400> SEQUENCE: 2867
000

<210> SEQ ID NO 2868
<400> SEQUENCE: 2868
000

<210> SEQ ID NO 2869
<400> SEQUENCE: 2869
000

<210> SEQ ID NO 2870
<400> SEQUENCE: 2870
000

<210> SEQ ID NO 2871
<400> SEQUENCE: 2871
000

<210> SEQ ID NO 2872
<400> SEQUENCE: 2872
000

<210> SEQ ID NO 2873
<400> SEQUENCE: 2873
000

<210> SEQ ID NO 2874
<400> SEQUENCE: 2874
000

<210> SEQ ID NO 2875
<400> SEQUENCE: 2875
000

<210> SEQ ID NO 2876
<400> SEQUENCE: 2876
000

<210> SEQ ID NO 2877
<400> SEQUENCE: 2877
000

<210> SEQ ID NO 2878
```

```
<400> SEQUENCE: 2878
000

<210> SEQ ID NO 2879
<400> SEQUENCE: 2879
000

<210> SEQ ID NO 2880
<400> SEQUENCE: 2880
000

<210> SEQ ID NO 2881
<400> SEQUENCE: 2881
000

<210> SEQ ID NO 2882
<400> SEQUENCE: 2882
000

<210> SEQ ID NO 2883
<400> SEQUENCE: 2883
000

<210> SEQ ID NO 2884
<400> SEQUENCE: 2884
000

<210> SEQ ID NO 2885
<400> SEQUENCE: 2885
000

<210> SEQ ID NO 2886
<400> SEQUENCE: 2886
000

<210> SEQ ID NO 2887
<400> SEQUENCE: 2887
000

<210> SEQ ID NO 2888
<400> SEQUENCE: 2888
000

<210> SEQ ID NO 2889
<400> SEQUENCE: 2889
```

000

<210> SEQ ID NO 2890

<400> SEQUENCE: 2890

000

<210> SEQ ID NO 2891

<400> SEQUENCE: 2891

000

<210> SEQ ID NO 2892

<400> SEQUENCE: 2892

000

<210> SEQ ID NO 2893

<400> SEQUENCE: 2893

000

<210> SEQ ID NO 2894

<400> SEQUENCE: 2894

000

<210> SEQ ID NO 2895

<400> SEQUENCE: 2895

000

<210> SEQ ID NO 2896

<400> SEQUENCE: 2896

000

<210> SEQ ID NO 2897

<400> SEQUENCE: 2897

000

<210> SEQ ID NO 2898

<400> SEQUENCE: 2898

000

<210> SEQ ID NO 2899

<400> SEQUENCE: 2899

000

<210> SEQ ID NO 2900

<400> SEQUENCE: 2900

000

<210> SEQ ID NO 2901

<400> SEQUENCE: 2901

000

<210> SEQ ID NO 2902

<400> SEQUENCE: 2902

000

<210> SEQ ID NO 2903

<400> SEQUENCE: 2903

000

<210> SEQ ID NO 2904

<400> SEQUENCE: 2904

000

<210> SEQ ID NO 2905

<400> SEQUENCE: 2905

000

<210> SEQ ID NO 2906

<400> SEQUENCE: 2906

000

<210> SEQ ID NO 2907

<400> SEQUENCE: 2907

000

<210> SEQ ID NO 2908

<400> SEQUENCE: 2908

000

<210> SEQ ID NO 2909

<400> SEQUENCE: 2909

000

<210> SEQ ID NO 2910

<400> SEQUENCE: 2910

000

<210> SEQ ID NO 2911

<400> SEQUENCE: 2911

000

<210> SEQ ID NO 2912

<400> SEQUENCE: 2912

000

<210> SEQ ID NO 2913

<400> SEQUENCE: 2913

000

<210> SEQ ID NO 2914

<400> SEQUENCE: 2914

000

<210> SEQ ID NO 2915

<400> SEQUENCE: 2915

000

<210> SEQ ID NO 2916

<400> SEQUENCE: 2916

000

<210> SEQ ID NO 2917

<400> SEQUENCE: 2917

000

<210> SEQ ID NO 2918

<400> SEQUENCE: 2918

000

<210> SEQ ID NO 2919

<400> SEQUENCE: 2919

000

<210> SEQ ID NO 2920

<400> SEQUENCE: 2920

000

<210> SEQ ID NO 2921

<400> SEQUENCE: 2921

000

<210> SEQ ID NO 2922

<400> SEQUENCE: 2922

000

<210> SEQ ID NO 2923

```
<400> SEQUENCE: 2923

000

<210> SEQ ID NO 2924

<400> SEQUENCE: 2924

000

<210> SEQ ID NO 2925

<400> SEQUENCE: 2925

000

<210> SEQ ID NO 2926

<400> SEQUENCE: 2926

000

<210> SEQ ID NO 2927

<400> SEQUENCE: 2927

000

<210> SEQ ID NO 2928

<400> SEQUENCE: 2928

000

<210> SEQ ID NO 2929

<400> SEQUENCE: 2929

000

<210> SEQ ID NO 2930

<400> SEQUENCE: 2930

000

<210> SEQ ID NO 2931

<400> SEQUENCE: 2931

000

<210> SEQ ID NO 2932

<400> SEQUENCE: 2932

000

<210> SEQ ID NO 2933

<400> SEQUENCE: 2933

000

<210> SEQ ID NO 2934

<400> SEQUENCE: 2934
```

000

<210> SEQ ID NO 2935
<400> SEQUENCE: 2935
000

<210> SEQ ID NO 2936
<400> SEQUENCE: 2936
000

<210> SEQ ID NO 2937
<400> SEQUENCE: 2937
000

<210> SEQ ID NO 2938
<400> SEQUENCE: 2938
000

<210> SEQ ID NO 2939
<400> SEQUENCE: 2939
000

<210> SEQ ID NO 2940
<400> SEQUENCE: 2940
000

<210> SEQ ID NO 2941
<400> SEQUENCE: 2941
000

<210> SEQ ID NO 2942
<400> SEQUENCE: 2942
000

<210> SEQ ID NO 2943
<400> SEQUENCE: 2943
000

<210> SEQ ID NO 2944
<400> SEQUENCE: 2944
000

<210> SEQ ID NO 2945
<400> SEQUENCE: 2945
000

-continued

<210> SEQ ID NO 2946

<400> SEQUENCE: 2946

000

<210> SEQ ID NO 2947

<400> SEQUENCE: 2947

000

<210> SEQ ID NO 2948

<400> SEQUENCE: 2948

000

<210> SEQ ID NO 2949

<400> SEQUENCE: 2949

000

<210> SEQ ID NO 2950

<400> SEQUENCE: 2950

000

<210> SEQ ID NO 2951

<400> SEQUENCE: 2951

000

<210> SEQ ID NO 2952

<400> SEQUENCE: 2952

000

<210> SEQ ID NO 2953

<400> SEQUENCE: 2953

000

<210> SEQ ID NO 2954

<400> SEQUENCE: 2954

000

<210> SEQ ID NO 2955

<400> SEQUENCE: 2955

000

<210> SEQ ID NO 2956

<400> SEQUENCE: 2956

000

<210> SEQ ID NO 2957

```
<400> SEQUENCE: 2957
000

<210> SEQ ID NO 2958
<400> SEQUENCE: 2958
000

<210> SEQ ID NO 2959
<400> SEQUENCE: 2959
000

<210> SEQ ID NO 2960
<400> SEQUENCE: 2960
000

<210> SEQ ID NO 2961
<400> SEQUENCE: 2961
000

<210> SEQ ID NO 2962
<400> SEQUENCE: 2962
000

<210> SEQ ID NO 2963
<400> SEQUENCE: 2963
000

<210> SEQ ID NO 2964
<400> SEQUENCE: 2964
000

<210> SEQ ID NO 2965
<400> SEQUENCE: 2965
000

<210> SEQ ID NO 2966
<400> SEQUENCE: 2966
000

<210> SEQ ID NO 2967
<400> SEQUENCE: 2967
000

<210> SEQ ID NO 2968
<400> SEQUENCE: 2968
```

000

<210> SEQ ID NO 2969

<400> SEQUENCE: 2969

000

<210> SEQ ID NO 2970

<400> SEQUENCE: 2970

000

<210> SEQ ID NO 2971

<400> SEQUENCE: 2971

000

<210> SEQ ID NO 2972

<400> SEQUENCE: 2972

000

<210> SEQ ID NO 2973

<400> SEQUENCE: 2973

000

<210> SEQ ID NO 2974

<400> SEQUENCE: 2974

000

<210> SEQ ID NO 2975

<400> SEQUENCE: 2975

000

<210> SEQ ID NO 2976

<400> SEQUENCE: 2976

000

<210> SEQ ID NO 2977

<400> SEQUENCE: 2977

000

<210> SEQ ID NO 2978

<400> SEQUENCE: 2978

000

<210> SEQ ID NO 2979

<400> SEQUENCE: 2979

000

-continued

<210> SEQ ID NO 2980

<400> SEQUENCE: 2980

000

<210> SEQ ID NO 2981

<400> SEQUENCE: 2981

000

<210> SEQ ID NO 2982

<400> SEQUENCE: 2982

000

<210> SEQ ID NO 2983

<400> SEQUENCE: 2983

000

<210> SEQ ID NO 2984

<400> SEQUENCE: 2984

000

<210> SEQ ID NO 2985

<400> SEQUENCE: 2985

000

<210> SEQ ID NO 2986

<400> SEQUENCE: 2986

000

<210> SEQ ID NO 2987

<400> SEQUENCE: 2987

000

<210> SEQ ID NO 2988

<400> SEQUENCE: 2988

000

<210> SEQ ID NO 2989

<400> SEQUENCE: 2989

000

<210> SEQ ID NO 2990

<400> SEQUENCE: 2990

000

```
<210> SEQ ID NO 2991
<400> SEQUENCE: 2991
000

<210> SEQ ID NO 2992
<400> SEQUENCE: 2992
000

<210> SEQ ID NO 2993
<400> SEQUENCE: 2993
000

<210> SEQ ID NO 2994
<400> SEQUENCE: 2994
000

<210> SEQ ID NO 2995
<400> SEQUENCE: 2995
000

<210> SEQ ID NO 2996
<400> SEQUENCE: 2996
000

<210> SEQ ID NO 2997
<400> SEQUENCE: 2997
000

<210> SEQ ID NO 2998
<400> SEQUENCE: 2998
000

<210> SEQ ID NO 2999
<400> SEQUENCE: 2999
000

<210> SEQ ID NO 3000
<400> SEQUENCE: 3000
000

<210> SEQ ID NO 3001
<400> SEQUENCE: 3001
000

<210> SEQ ID NO 3002
```

<400> SEQUENCE: 3002

000

<210> SEQ ID NO 3003

<400> SEQUENCE: 3003

000

<210> SEQ ID NO 3004

<400> SEQUENCE: 3004

000

<210> SEQ ID NO 3005

<400> SEQUENCE: 3005

000

<210> SEQ ID NO 3006

<400> SEQUENCE: 3006

000

<210> SEQ ID NO 3007

<400> SEQUENCE: 3007

000

<210> SEQ ID NO 3008

<400> SEQUENCE: 3008

000

<210> SEQ ID NO 3009

<400> SEQUENCE: 3009

000

<210> SEQ ID NO 3010

<400> SEQUENCE: 3010

000

<210> SEQ ID NO 3011

<400> SEQUENCE: 3011

000

<210> SEQ ID NO 3012

<400> SEQUENCE: 3012

000

<210> SEQ ID NO 3013

<400> SEQUENCE: 3013

000

<210> SEQ ID NO 3014

<400> SEQUENCE: 3014

000

<210> SEQ ID NO 3015

<400> SEQUENCE: 3015

000

<210> SEQ ID NO 3016

<400> SEQUENCE: 3016

000

<210> SEQ ID NO 3017

<400> SEQUENCE: 3017

000

<210> SEQ ID NO 3018

<400> SEQUENCE: 3018

000

<210> SEQ ID NO 3019

<400> SEQUENCE: 3019

000

<210> SEQ ID NO 3020

<400> SEQUENCE: 3020

000

<210> SEQ ID NO 3021

<400> SEQUENCE: 3021

000

<210> SEQ ID NO 3022

<400> SEQUENCE: 3022

000

<210> SEQ ID NO 3023

<400> SEQUENCE: 3023

000

<210> SEQ ID NO 3024

<400> SEQUENCE: 3024

000

```
<210> SEQ ID NO 3025
<400> SEQUENCE: 3025
000

<210> SEQ ID NO 3026
<400> SEQUENCE: 3026
000

<210> SEQ ID NO 3027
<400> SEQUENCE: 3027
000

<210> SEQ ID NO 3028
<400> SEQUENCE: 3028
000

<210> SEQ ID NO 3029
<400> SEQUENCE: 3029
000

<210> SEQ ID NO 3030
<400> SEQUENCE: 3030
000

<210> SEQ ID NO 3031
<400> SEQUENCE: 3031
000

<210> SEQ ID NO 3032
<400> SEQUENCE: 3032
000

<210> SEQ ID NO 3033
<400> SEQUENCE: 3033
000

<210> SEQ ID NO 3034
<400> SEQUENCE: 3034
000

<210> SEQ ID NO 3035
<400> SEQUENCE: 3035
000

<210> SEQ ID NO 3036
```

```
<400> SEQUENCE: 3036
000

<210> SEQ ID NO 3037
<400> SEQUENCE: 3037
000

<210> SEQ ID NO 3038
<400> SEQUENCE: 3038
000

<210> SEQ ID NO 3039
<400> SEQUENCE: 3039
000

<210> SEQ ID NO 3040
<400> SEQUENCE: 3040
000

<210> SEQ ID NO 3041
<400> SEQUENCE: 3041
000

<210> SEQ ID NO 3042
<400> SEQUENCE: 3042
000

<210> SEQ ID NO 3043
<400> SEQUENCE: 3043
000

<210> SEQ ID NO 3044
<400> SEQUENCE: 3044
000

<210> SEQ ID NO 3045
<400> SEQUENCE: 3045
000

<210> SEQ ID NO 3046
<400> SEQUENCE: 3046
000

<210> SEQ ID NO 3047
<400> SEQUENCE: 3047
```

000

<210> SEQ ID NO 3048

<400> SEQUENCE: 3048

000

<210> SEQ ID NO 3049

<400> SEQUENCE: 3049

000

<210> SEQ ID NO 3050

<400> SEQUENCE: 3050

000

<210> SEQ ID NO 3051

<400> SEQUENCE: 3051

000

<210> SEQ ID NO 3052

<400> SEQUENCE: 3052

000

<210> SEQ ID NO 3053

<400> SEQUENCE: 3053

000

<210> SEQ ID NO 3054

<400> SEQUENCE: 3054

000

<210> SEQ ID NO 3055

<400> SEQUENCE: 3055

000

<210> SEQ ID NO 3056

<400> SEQUENCE: 3056

000

<210> SEQ ID NO 3057

<400> SEQUENCE: 3057

000

<210> SEQ ID NO 3058

<400> SEQUENCE: 3058

000

<210> SEQ ID NO 3059

<400> SEQUENCE: 3059

000

<210> SEQ ID NO 3060

<400> SEQUENCE: 3060

000

<210> SEQ ID NO 3061

<400> SEQUENCE: 3061

000

<210> SEQ ID NO 3062

<400> SEQUENCE: 3062

000

<210> SEQ ID NO 3063

<400> SEQUENCE: 3063

000

<210> SEQ ID NO 3064

<400> SEQUENCE: 3064

000

<210> SEQ ID NO 3065

<400> SEQUENCE: 3065

000

<210> SEQ ID NO 3066

<400> SEQUENCE: 3066

000

<210> SEQ ID NO 3067

<400> SEQUENCE: 3067

000

<210> SEQ ID NO 3068

<400> SEQUENCE: 3068

000

<210> SEQ ID NO 3069

<400> SEQUENCE: 3069

000

<210> SEQ ID NO 3070

<400> SEQUENCE: 3070

000

<210> SEQ ID NO 3071

<400> SEQUENCE: 3071

000

<210> SEQ ID NO 3072

<400> SEQUENCE: 3072

000

<210> SEQ ID NO 3073

<400> SEQUENCE: 3073

000

<210> SEQ ID NO 3074

<400> SEQUENCE: 3074

000

<210> SEQ ID NO 3075

<400> SEQUENCE: 3075

000

<210> SEQ ID NO 3076

<400> SEQUENCE: 3076

000

<210> SEQ ID NO 3077

<400> SEQUENCE: 3077

000

<210> SEQ ID NO 3078

<400> SEQUENCE: 3078

000

<210> SEQ ID NO 3079

<400> SEQUENCE: 3079

000

<210> SEQ ID NO 3080

<400> SEQUENCE: 3080

000

<210> SEQ ID NO 3081

<400> SEQUENCE: 3081

000

<210> SEQ ID NO 3082

<400> SEQUENCE: 3082

000

<210> SEQ ID NO 3083

<400> SEQUENCE: 3083

000

<210> SEQ ID NO 3084

<400> SEQUENCE: 3084

000

<210> SEQ ID NO 3085

<400> SEQUENCE: 3085

000

<210> SEQ ID NO 3086

<400> SEQUENCE: 3086

000

<210> SEQ ID NO 3087

<400> SEQUENCE: 3087

000

<210> SEQ ID NO 3088

<400> SEQUENCE: 3088

000

<210> SEQ ID NO 3089

<400> SEQUENCE: 3089

000

<210> SEQ ID NO 3090

<400> SEQUENCE: 3090

000

<210> SEQ ID NO 3091

<400> SEQUENCE: 3091

000

<210> SEQ ID NO 3092
<211> LENGTH: 390
<212> TYPE: PRT
<213> ORGANISM: Homo sapiens

<400> SEQUENCE: 3092

```
Met Pro Pro Ser Gly Leu Arg Leu Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
370                 375                 380

Arg Ser Cys Lys Cys Ser
385                 390
```

<210> SEQ ID NO 3093
<211> LENGTH: 414
<212> TYPE: PRT
<213> ORGANISM: Homo sapiens

<400> SEQUENCE: 3093

```
Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
    210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
        275                 280                 285

Tyr Arg Leu Glu Ser Gln Gln Thr Asn Arg Arg Lys Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
        355                 360                 365

Thr Ile Asn Pro Glu Ala Ser Ala Ser Pro Cys Cys Val Ser Gln Asp
    370                 375                 380
```

```
Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
            405                 410

<210> SEQ ID NO 3094
<211> LENGTH: 412
<212> TYPE: PRT
<213> ORGANISM: Homo sapiens

<400> SEQUENCE: 3094

Met Lys Met His Leu Gln Arg Ala Leu Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
                115                 120                 125

Ser Lys Val Phe Arg Phe Asn Val Ser Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
                180                 185                 190

Thr Arg Gly Thr Ala Glu Trp Leu Ser Phe Asp Val Thr Asp Thr Val
                195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
                260                 265                 270

His His Asn Pro His Leu Ile Leu Met Met Ile Pro Pro His Arg Leu
            275                 280                 285

Asp Asn Pro Gly Gln Gly Gly Gln Arg Lys Lys Arg Ala Leu Asp Thr
290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350
```

```
Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 3095
<211> LENGTH: 503
<212> TYPE: PRT
<213> ORGANISM: Homo sapiens

<400> SEQUENCE: 3095

Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
                35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
    210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
```

```
            305                 310                 315                 320
        Val Gly Thr Gln Gly Lys Pro Ala Ile Ala His Arg Asp Leu Lys Ser
                        325                 330                 335

Lys Asn Ile Leu Val Lys Lys Asn Gly Thr Cys Cys Ile Ala Asp Leu
                        340                 345                 350

Gly Leu Ala Val Arg His Asp Ser Ala Thr Asp Thr Ile Asp Ile Ala
                        355                 360                 365

Pro Asn His Arg Val Gly Thr Lys Arg Tyr Met Ala Pro Glu Val Leu
                    370                 375                 380

Asp Asp Ser Ile Asn Met Lys His Phe Glu Ser Phe Lys Arg Ala Asp
        385                 390                 395                 400

Ile Tyr Ala Met Gly Leu Val Phe Trp Glu Ile Ala Arg Arg Cys Ser
                        405                 410                 415

Ile Gly Gly Ile His Glu Asp Tyr Gln Leu Pro Tyr Tyr Asp Leu Val
                        420                 425                 430

Pro Ser Asp Pro Ser Val Glu Glu Met Arg Lys Val Val Cys Glu Gln
                    435                 440                 445

Lys Leu Arg Pro Asn Ile Pro Asn Arg Trp Gln Ser Cys Glu Ala Leu
                    450                 455                 460

Arg Val Met Ala Lys Ile Met Arg Glu Cys Trp Tyr Ala Asn Gly Ala
        465                 470                 475                 480

Ala Arg Leu Thr Ala Leu Arg Ile Lys Lys Thr Leu Ser Gln Leu Ser
                        485                 490                 495

Gln Gln Glu Gly Ile Lys Met
                    500

<210> SEQ ID NO 3096
<211> LENGTH: 507
<212> TYPE: PRT
<213> ORGANISM: Homo sapiens

<400> SEQUENCE: 3096

Met Glu Ala Ala Val Ala Ala Pro Arg Pro Arg Leu Leu Leu Leu Val
        1               5                   10                  15

Leu Ala Ala Ala Ala Ala Ala Ala Leu Leu Pro Gly Ala Thr
                        20                  25                  30

Ala Leu Gln Cys Phe Cys His Leu Cys Thr Lys Asp Asn Phe Thr Cys
                        35                  40                  45

Val Thr Asp Gly Leu Cys Phe Val Ser Val Thr Glu Thr Thr Asp Lys
                    50                  55                  60

Val Ile His Asn Ser Met Cys Ile Ala Glu Ile Asp Leu Ile Pro Arg
        65                  70                  75                  80

Asp Arg Pro Phe Val Cys Ala Pro Ser Ser Lys Thr Gly Ser Val Thr
                        85                  90                  95

Thr Thr Tyr Cys Cys Asn Gln Asp His Cys Asn Lys Ile Glu Leu Pro
                        100                 105                 110

Thr Thr Gly Pro Phe Ser Val Lys Ser Ser Pro Gly Leu Gly Pro Val
                    115                 120                 125

Glu Leu Ala Ala Val Ile Ala Gly Pro Val Cys Phe Val Cys Ile Ser
        130                 135                 140

Leu Met Leu Met Val Tyr Ile Cys His Asn Arg Thr Val Ile His His
        145                 150                 155                 160

Arg Val Pro Asn Glu Glu Asp Pro Ser Leu Asp Arg Pro Phe Ile Ser
                        165                 170                 175
```

Glu Gly Thr Thr Leu Lys Asp Leu Ile Tyr Asp Met Thr Ser Gly
            180                 185                 190

Ser Gly Ser Gly Leu Pro Leu Leu Val Gln Arg Thr Ile Ala Arg Thr
        195                 200                 205

Ile Val Leu Gln Glu Ser Ile Gly Lys Gly Arg Phe Gly Glu Val Trp
    210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                245                 250                 255

Met Leu Arg His Glu Asn Ile Leu Gly Phe Ile Ala Ala Asp Asn Lys
            260                 265                 270

Asp Asn Gly Thr Trp Thr Gln Leu Trp Leu Val Ser Asp Tyr His Glu
        275                 280                 285

His Gly Ser Leu Phe Asp Tyr Leu Asn Arg Tyr Thr Val Thr Val Glu
    290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
            340                 345                 350

Ile Ala Asp Leu Gly Leu Ala Val Arg His Asp Ser Ala Thr Asp Thr
        355                 360                 365

Ile Asp Ile Ala Pro Asn His Arg Val Gly Thr Lys Arg Tyr Met Ala
    370                 375                 380

Pro Glu Val Leu Asp Asp Ser Ile Asn Met Lys His Phe Glu Ser Phe
385                 390                 395                 400

Lys Arg Ala Asp Ile Tyr Ala Met Gly Leu Val Phe Trp Glu Ile Ala
                405                 410                 415

Arg Arg Cys Ser Ile Gly Gly Ile His Glu Asp Tyr Gln Leu Pro Tyr
            420                 425                 430

Tyr Asp Leu Val Pro Ser Asp Pro Ser Val Glu Glu Met Arg Lys Val
        435                 440                 445

Val Cys Glu Gln Lys Leu Arg Pro Asn Ile Pro Asn Arg Trp Gln Ser
    450                 455                 460

Cys Glu Ala Leu Arg Val Met Ala Lys Ile Met Arg Glu Cys Trp Tyr
465                 470                 475                 480

Ala Asn Gly Ala Ala Arg Leu Thr Ala Leu Arg Ile Lys Lys Thr Leu
                485                 490                 495

Ser Gln Leu Ser Gln Gln Glu Gly Ile Lys Met
            500                 505

<210> SEQ ID NO 3097
<211> LENGTH: 426
<212> TYPE: PRT
<213> ORGANISM: Homo sapiens

<400> SEQUENCE: 3097

Met Glu Ala Ala Val Ala Ala Pro Arg Pro Arg Leu Leu Leu Leu Val
1               5                   10                  15

Leu Ala Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

```
Val Thr Asp Gly Leu Cys Phe Val Ser Val Thr Glu Thr Thr Asp Lys
 50                  55                  60

Val Ile His Asn Ser Met Cys Ile Ala Glu Ile Asp Leu Ile Pro Arg
 65                  70                  75                  80

Asp Arg Pro Phe Val Cys Ala Pro Ser Ser Lys Thr Gly Ser Val Thr
                 85                  90                  95

Thr Thr Tyr Cys Cys Asn Gln Asp His Cys Asn Lys Ile Glu Leu Pro
            100                 105                 110

Thr Thr Gly Leu Pro Leu Leu Val Gln Arg Thr Ile Ala Arg Thr Ile
        115                 120                 125

Val Leu Gln Glu Ser Ile Gly Lys Gly Arg Phe Gly Glu Val Trp Arg
130                 135                 140

Gly Lys Trp Arg Gly Glu Glu Val Ala Val Lys Ile Phe Ser Ser Arg
145                 150                 155                 160

Glu Glu Arg Ser Trp Phe Arg Glu Ala Glu Ile Tyr Gln Thr Val Met
                165                 170                 175

Leu Arg His Glu Asn Ile Leu Gly Phe Ile Ala Ala Asp Asn Lys Asp
            180                 185                 190

Asn Gly Thr Trp Thr Gln Leu Trp Leu Val Ser Asp Tyr His Glu His
        195                 200                 205

Gly Ser Leu Phe Asp Tyr Leu Asn Arg Tyr Thr Val Thr Val Glu Gly
210                 215                 220

Met Ile Lys Leu Ala Leu Ser Thr Ala Ser Gly Leu Ala His Leu His
225                 230                 235                 240

Met Glu Ile Val Gly Thr Gln Gly Lys Pro Ala Ile Ala His Arg Asp
                245                 250                 255

Leu Lys Ser Lys Asn Ile Leu Val Lys Lys Asn Gly Thr Cys Cys Ile
            260                 265                 270

Ala Asp Leu Gly Leu Ala Val Arg His Asp Ser Ala Thr Asp Thr Ile
        275                 280                 285

Asp Ile Ala Pro Asn His Arg Val Gly Thr Lys Arg Tyr Met Ala Pro
290                 295                 300

Glu Val Leu Asp Asp Ser Ile Asn Met Lys His Phe Glu Ser Phe Lys
305                 310                 315                 320

Arg Ala Asp Ile Tyr Ala Met Gly Leu Val Phe Trp Glu Ile Ala Arg
                325                 330                 335

Arg Cys Ser Ile Gly Gly Ile His Glu Asp Tyr Gln Leu Pro Tyr Tyr
            340                 345                 350

Asp Leu Val Pro Ser Asp Pro Ser Val Glu Glu Met Arg Lys Val Val
        355                 360                 365

Cys Glu Gln Lys Leu Arg Pro Asn Ile Pro Asn Arg Trp Gln Ser Cys
370                 375                 380

Glu Ala Leu Arg Val Met Ala Lys Ile Met Arg Glu Cys Trp Tyr Ala
385                 390                 395                 400

Asn Gly Ala Ala Arg Leu Thr Ala Leu Arg Ile Lys Lys Thr Leu Ser
                405                 410                 415

Gln Leu Ser Gln Gln Glu Gly Ile Lys Met
            420                 425

<210> SEQ ID NO 3098
<211> LENGTH: 567
<212> TYPE: PRT
<213> ORGANISM: Homo sapiens
```

```
<400> SEQUENCE: 3098

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415
```

-continued

Gly Gln Val Gly Thr Ala Arg Tyr Met Ala Pro Val Leu Glu Ser
                420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
        450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 3099
<211> LENGTH: 592
<212> TYPE: PRT
<213> ORGANISM: Homo sapiens

<400> SEQUENCE: 3099

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser

```
                210                 215                 220
Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
                275                 280                 285

Lys Gln Asn Thr Ser Glu Gln Phe Glu Thr Val Ala Val Lys Ile Phe
                290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
                340                 345                 350

His Ala Lys Gly Asn Leu Gln Glu Tyr Leu Thr Arg His Val Ile Ser
                355                 360                 365

Trp Glu Asp Leu Arg Lys Leu Gly Ser Ser Leu Ala Arg Gly Ile Ala
370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
                420                 425                 430

Leu Ser Val Asp Asp Leu Ala Asn Ser Gly Gln Val Gly Thr Ala Arg
                435                 440                 445

Tyr Met Ala Pro Glu Val Leu Glu Ser Arg Met Asn Leu Glu Asn Val
450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
                500                 505                 510

Lys Asp Asn Val Leu Arg Asp Arg Gly Arg Pro Glu Ile Pro Ser Phe
                515                 520                 525

Trp Leu Asn His Gln Gly Ile Gln Met Val Cys Glu Thr Leu Thr Glu
530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
                580                 585                 590

<210> SEQ ID NO 3100
<211> LENGTH: 137
<212> TYPE: PRT
<213> ORGANISM: Homo sapiens

<400> SEQUENCE: 3100
```

```
Thr Ile Pro Pro His Val Gln Lys Ser Val Asn Asn Asp Met Ile Val
  1               5                  10                  15

Thr Asp Asn Asn Gly Ala Val Lys Phe Pro Gln Leu Cys Lys Phe Cys
             20                  25                  30

Asp Val Arg Phe Ser Thr Cys Asp Asn Gln Lys Ser Cys Met Ser Asn
         35                  40                  45

Cys Ser Ile Thr Ser Ile Cys Glu Lys Pro Gln Glu Val Cys Val Ala
 50                  55                  60

Val Trp Arg Lys Asn Asp Glu Asn Ile Thr Leu Glu Thr Val Cys His
 65                  70                  75                  80

Asp Pro Lys Leu Pro Tyr His Asp Phe Ile Leu Glu Asp Ala Ala Ser
             85                  90                  95

Pro Lys Cys Ile Met Lys Glu Lys Lys Pro Gly Glu Thr Phe Phe
        100                 105                 110

Met Cys Ser Cys Ser Ser Asp Glu Cys Asn Asp Asn Ile Ile Phe Ser
             115                 120                 125

Glu Glu Tyr Asn Thr Ser Asn Pro Asp
        130                 135

<210> SEQ ID NO 3101
<211> LENGTH: 136
<212> TYPE: PRT
<213> ORGANISM: Homo sapiens

<400> SEQUENCE: 3101

Ile Pro Pro His Val Gln Lys Ser Val Asn Asn Asp Met Ile Val Thr
  1               5                  10                  15

Asp Asn Asn Gly Ala Val Lys Phe Pro Gln Leu Cys Lys Phe Cys Asp
             20                  25                  30

Val Arg Phe Ser Thr Cys Asp Asn Gln Lys Ser Cys Met Ser Asn Cys
         35                  40                  45

Ser Ile Thr Ser Ile Cys Glu Lys Pro Gln Glu Val Cys Val Ala Val
 50                  55                  60

Trp Arg Lys Asn Asp Glu Asn Ile Thr Leu Glu Thr Val Cys His Asp
65                   70                  75                  80

Pro Lys Leu Pro Tyr His Asp Phe Ile Leu Glu Asp Ala Ala Ser Pro
             85                  90                  95

Lys Cys Ile Met Lys Glu Lys Lys Pro Gly Glu Thr Phe Phe Met
        100                 105                 110

Cys Ser Cys Ser Ser Asp Glu Cys Asn Asp Asn Ile Ile Phe Ser Glu
             115                 120                 125

Glu Tyr Asn Thr Ser Asn Pro Asp
        130                 135

<210> SEQ ID NO 3102
<211> LENGTH: 162
<212> TYPE: PRT
<213> ORGANISM: Homo sapiens

<400> SEQUENCE: 3102

Thr Ile Pro Pro His Val Gln Lys Ser Asp Val Glu Met Glu Ala Gln
  1               5                  10                  15

Lys Asp Glu Ile Ile Cys Pro Ser Cys Asn Arg Thr Ala His Pro Leu
             20                  25                  30

Arg His Ile Asn Asn Asp Met Ile Val Thr Asp Asn Asn Gly Ala Val
         35                  40                  45
```

```
Lys Phe Pro Gln Leu Cys Lys Phe Cys Asp Val Arg Phe Ser Thr Cys
 50                  55                  60
Asp Asn Gln Lys Ser Cys Met Ser Asn Cys Ser Ile Thr Ser Ile Cys
 65                  70                  75                  80
Glu Lys Pro Gln Glu Val Cys Val Ala Val Trp Arg Lys Asn Asp Glu
                 85                  90                  95
Asn Ile Thr Leu Glu Thr Val Cys His Asp Pro Lys Leu Pro Tyr His
            100                 105                 110
Asp Phe Ile Leu Glu Asp Ala Ala Ser Pro Lys Cys Ile Met Lys Glu
            115                 120                 125
Lys Lys Lys Pro Gly Glu Thr Phe Phe Met Cys Ser Cys Ser Ser Asp
130                 135                 140
Glu Cys Asn Asp Asn Ile Ile Phe Ser Glu Glu Tyr Asn Thr Ser Asn
145                 150                 155                 160
Pro Asp
```

<210> SEQ ID NO 3103
<211> LENGTH: 101
<212> TYPE: PRT
<213> ORGANISM: Homo sapiens

<400> SEQUENCE: 3103

```
Gln Leu Cys Lys Phe Cys Asp Val Arg Phe Ser Thr Cys Asp Asn Gln
 1               5                  10                  15
Lys Ser Cys Met Ser Asn Cys Ser Ile Thr Ser Ile Cys Glu Lys Pro
            20                  25                  30
Gln Glu Val Cys Val Ala Val Trp Arg Lys Asn Asp Glu Asn Ile Thr
        35                  40                  45
Leu Glu Thr Val Cys His Asp Pro Lys Leu Pro Tyr His Asp Phe Ile
 50                  55                  60
Leu Glu Asp Ala Ala Ser Pro Lys Cys Ile Met Lys Glu Lys Lys Lys
 65                  70                  75                  80
Pro Gly Glu Thr Phe Phe Met Cys Ser Cys Ser Ser Asp Glu Cys Asn
                 85                  90                  95
Asp Asn Ile Ile Phe
            100
```

<210> SEQ ID NO 3104
<211> LENGTH: 93
<212> TYPE: PRT
<213> ORGANISM: Homo sapiens

<400> SEQUENCE: 3104

```
Leu Gln Cys Phe Cys His Leu Cys Thr Lys Asp Asn Phe Thr Cys Val
 1               5                  10                  15
Thr Asp Gly Leu Cys Phe Val Ser Val Thr Glu Thr Thr Asp Lys Val
            20                  25                  30
Ile His Asn Ser Met Cys Ile Ala Glu Ile Asp Leu Ile Pro Arg Asp
        35                  40                  45
Arg Pro Phe Val Cys Ala Pro Ser Ser Lys Thr Gly Ser Val Thr Thr
 50                  55                  60
Thr Tyr Cys Cys Asn Gln Asp His Cys Asn Lys Ile Glu Leu Pro Thr
 65                  70                  75                  80
Thr Val Lys Ser Ser Pro Gly Leu Gly Pro Val Glu Leu
                 85                  90
```

<210> SEQ ID NO 3105
<211> LENGTH: 79
<212> TYPE: PRT
<213> ORGANISM: Homo sapiens

<400> SEQUENCE: 3105

Ala Leu Gln Cys Phe Cys His Leu Cys Thr Lys Asp Asn Phe Thr Cys
1               5                   10                  15

Val Thr Asp Gly Leu Cys Phe Val Ser Val Thr Glu Thr Thr Asp Lys
            20                  25                  30

Val Ile His Asn Ser Met Cys Ile Ala Glu Ile Asp Leu Ile Pro Arg
        35                  40                  45

Asp Arg Pro Phe Val Cys Ala Pro Ser Ser Lys Thr Gly Ser Val Thr
    50                  55                  60

Thr Thr Tyr Cys Cys Asn Gln Asp His Cys Asn Lys Ile Glu Leu
65                  70                  75

<210> SEQ ID NO 3106
<211> LENGTH: 851
<212> TYPE: PRT
<213> ORGANISM: Homo sapiens

<400> SEQUENCE: 3106

Met Thr Ser His Tyr Val Ile Ala Ile Phe Ala Leu Met Ser Ser Cys
1               5                   10                  15

Leu Ala Thr Ala Gly Pro Glu Pro Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
        115                 120                 125

Val Ser Glu Gly Ser Val Val Gln Phe Ser Ser Ala Asn Phe Ser Leu
    130                 135                 140

Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
        195                 200                 205

Leu Ala Glu Tyr Leu Gln Pro Lys Ala Ala Glu Gly Cys Val Met Ser
    210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile

```
                260                 265                 270
Leu Lys Cys Lys Lys Ser Val Asn Trp Val Ile Lys Ser Phe Asp Val
            275                 280                 285
Lys Gly Ser Leu Lys Ile Ile Ala Pro Asn Ser Ile Gly Phe Gly Lys
        290                 295                 300
Glu Ser Glu Arg Ser Met Thr Met Thr Lys Ser Ile Arg Asp Asp Ile
305                 310                 315                 320
Pro Ser Thr Gln Gly Asn Leu Val Lys Trp Ala Leu Asp Asn Gly Tyr
                325                 330                 335
Ser Pro Ile Thr Ser Tyr Thr Met Ala Pro Val Ala Asn Arg Phe His
                340                 345                 350
Leu Arg Leu Glu Asn Asn Ala Glu Glu Met Gly Asp Glu Val His
            355                 360                 365
Thr Ile Pro Pro Glu Leu Arg Ile Leu Leu Asp Pro Gly Ala Leu Pro
        370                 375                 380
Ala Leu Gln Asn Pro Pro Ile Arg Gly Gly Glu Gly Gln Asn Gly Gly
385                 390                 395                 400
Leu Pro Phe Pro Phe Pro Asp Ile Ser Arg Arg Val Trp Asn Glu Glu
                405                 410                 415
Gly Glu Asp Gly Leu Pro Arg Pro Lys Asp Pro Val Ile Pro Ser Ile
                420                 425                 430
Gln Leu Phe Pro Gly Leu Arg Glu Pro Glu Val Gln Gly Ser Val
            435                 440                 445
Asp Ile Ala Leu Ser Val Lys Cys Asp Asn Glu Lys Met Ile Val Ala
        450                 455                 460
Val Glu Lys Asp Ser Phe Gln Ala Ser Gly Tyr Ser Gly Met Asp Val
465                 470                 475                 480
Thr Leu Leu Asp Pro Thr Cys Lys Ala Lys Met Asn Gly Thr His Phe
                485                 490                 495
Val Leu Glu Ser Pro Leu Asn Gly Cys Gly Thr Arg Pro Arg Trp Ser
                500                 505                 510
Ala Leu Asp Gly Val Val Tyr Tyr Asn Ser Ile Val Ile Gln Val Pro
                515                 520                 525
Ala Leu Gly Asp Ser Ser Gly Trp Pro Asp Gly Tyr Glu Asp Leu Glu
            530                 535                 540
Ser Gly Asp Asn Gly Phe Pro Gly Asp Met Asp Glu Gly Asp Ala Ser
545                 550                 555                 560
Leu Phe Thr Arg Pro Glu Ile Val Val Phe Asn Cys Ser Leu Gln Gln
                565                 570                 575
Val Arg Asn Pro Ser Ser Phe Gln Glu Gln Pro His Gly Asn Ile Thr
            580                 585                 590
Phe Asn Met Glu Leu Tyr Asn Thr Asp Leu Phe Leu Val Pro Ser Gln
            595                 600                 605
Gly Val Phe Ser Val Pro Glu Asn Gly His Val Tyr Val Glu Val Ser
        610                 615                 620
Val Thr Lys Ala Glu Gln Glu Leu Gly Phe Ala Ile Gln Thr Cys Phe
625                 630                 635                 640
Ile Ser Pro Tyr Ser Asn Pro Asp Arg Met Ser His Tyr Thr Ile Ile
                645                 650                 655
Glu Asn Ile Cys Pro Lys Asp Glu Ser Val Lys Phe Tyr Ser Pro Lys
            660                 665                 670
Arg Val His Phe Pro Ile Pro Gln Ala Asp Met Asp Lys Lys Arg Phe
            675                 680                 685
```

```
Ser Phe Val Phe Lys Pro Val Phe Asn Thr Ser Leu Leu Phe Leu Gln
    690             695                 700

Cys Glu Leu Thr Leu Cys Thr Lys Met Glu Lys His Pro Gln Lys Leu
705             710                 715                 720

Pro Lys Cys Val Pro Pro Asp Glu Ala Cys Thr Ser Leu Asp Ala Ser
                725                 730                 735

Ile Ile Trp Ala Met Met Gln Asn Lys Lys Thr Phe Thr Lys Pro Leu
            740                 745                 750

Ala Val Ile His His Glu Ala Glu Ser Lys Glu Lys Gly Pro Ser Met
        755                 760                 765

Lys Glu Pro Asn Pro Ile Ser Pro Pro Ile Phe His Gly Leu Asp Thr
770                 775                 780

Leu Thr Val Met Gly Ile Ala Phe Ala Ala Phe Val Ile Gly Ala Leu
785                 790                 795                 800

Leu Thr Gly Ala Leu Trp Tyr Ile Tyr Ser His Thr Gly Glu Thr Ala
            805                 810                 815

Gly Arg Gln Gln Val Pro Thr Ser Pro Pro Ala Ser Glu Asn Ser Ser
            820                 825                 830

Ala Ala His Ser Ile Gly Ser Thr Gln Ser Thr Pro Cys Ser Ser Ser
            835                 840                 845

Ser Thr Ala
    850

<210> SEQ ID NO 3107
<211> LENGTH: 850
<212> TYPE: PRT
<213> ORGANISM: Homo sapiens

<400> SEQUENCE: 3107

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
            35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65              70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
        115                 120                 125

Val Ser Glu Gly Ser Val Val Gln Phe Ser Ser Ala Asn Phe Ser Leu
    130                 135                 140

Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
```

-continued

```
                195                 200                 205
Leu Ala Glu Tyr Leu Gln Pro Lys Ala Ala Glu Gly Cys Val Met Ser
210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
        275                 280                 285

Lys Gly Ser Leu Lys Ile Ile Ala Pro Asn Ser Ile Gly Phe Gly Lys
    290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
            340                 345                 350

Leu Arg Leu Glu Asn Asn Glu Glu Met Gly Asp Glu Val His Thr
        355                 360                 365

Ile Pro Pro Glu Leu Arg Ile Leu Leu Asp Pro Gly Ala Leu Pro Ala
    370                 375                 380

Leu Gln Asn Pro Pro Ile Arg Gly Gly Glu Gly Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Glu Val Gln Gly Ser Val Asp
        435                 440                 445

Ile Ala Leu Ser Val Lys Cys Asp Asn Glu Lys Met Ile Val Ala Val
    450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val
                485                 490                 495

Leu Glu Ser Pro Leu Asn Gly Cys Gly Thr Arg Pro Arg Trp Ser Ala
            500                 505                 510

Leu Asp Gly Val Val Tyr Tyr Asn Ser Ile Val Ile Gln Val Pro Ala
        515                 520                 525

Leu Gly Asp Ser Ser Gly Trp Pro Asp Gly Tyr Glu Asp Leu Glu Ser
    530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
            580                 585                 590

Asn Met Glu Leu Tyr Asn Thr Asp Leu Phe Leu Val Pro Ser Gln Gly
        595                 600                 605

Val Phe Ser Val Pro Glu Asn Gly His Val Tyr Val Glu Val Ser Val
    610                 615                 620
```

```
Thr Lys Ala Glu Gln Glu Leu Gly Phe Ala Ile Gln Thr Cys Phe Ile
625                 630                 635                 640

Ser Pro Tyr Ser Asn Pro Asp Arg Met Ser His Tyr Thr Ile Ile Glu
            645                 650                 655

Asn Ile Cys Pro Lys Asp Glu Ser Val Lys Phe Tyr Ser Pro Lys Arg
        660                 665                 670

Val His Phe Pro Ile Pro Gln Ala Asp Met Asp Lys Lys Arg Phe Ser
    675                 680                 685

Phe Val Phe Lys Pro Val Phe Asn Thr Ser Leu Leu Phe Leu Gln Cys
690                 695                 700

Glu Leu Thr Leu Cys Thr Lys Met Glu Lys His Pro Gln Lys Leu Pro
705                 710                 715                 720

Lys Cys Val Pro Pro Asp Glu Ala Cys Thr Ser Leu Asp Ala Ser Ile
                725                 730                 735

Ile Trp Ala Met Met Gln Asn Lys Lys Thr Phe Thr Lys Pro Leu Ala
            740                 745                 750

Val Ile His His Glu Ala Glu Ser Lys Glu Lys Gly Pro Ser Met Lys
        755                 760                 765

Glu Pro Asn Pro Ile Ser Pro Ile Phe His Gly Leu Asp Thr Leu
770                 775                 780

Thr Val Met Gly Ile Ala Phe Ala Ala Phe Val Ile Gly Ala Leu Leu
785                 790                 795                 800

Thr Gly Ala Leu Trp Tyr Ile Tyr Ser His Thr Gly Glu Thr Ala Gly
                805                 810                 815

Arg Gln Gln Val Pro Thr Ser Pro Ala Ser Glu Asn Ser Ser Ala
                820                 825                 830

Ala His Ser Ile Gly Ser Thr Gln Ser Thr Pro Cys Ser Ser Ser Ser
            835                 840                 845

Thr Ala
    850

<210> SEQ ID NO 3108
<211> LENGTH: 767
<212> TYPE: PRT
<213> ORGANISM: Homo sapiens

<400> SEQUENCE: 3108

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
            20                  25                  30

Ala Ser Arg Gly Thr Thr Gly Leu Pro Gln Glu Val His Val Leu Asn
        35                  40                  45

Leu Arg Thr Ala Gly Gln Gly Pro Gly Gln Leu Gln Arg Glu Val Thr
    50                  55                  60

Leu His Leu Asn Pro Ile Ser Val His Ile His His Lys Ser Val
65                  70                  75                  80

Val Phe Leu Leu Asn Ser Pro His Pro Leu Val Trp His Leu Lys Thr
                85                  90                  95

Glu Arg Leu Ala Thr Gly Val Ser Arg Leu Phe Leu Val Ser Glu Gly
            100                 105                 110

Ser Val Val Gln Phe Ser Ser Ala Asn Phe Ser Leu Thr Ala Glu Thr
        115                 120                 125

Glu Glu Arg Asn Phe Pro His Gly Asn Glu His Leu Leu Asn Trp Ala
```

|     |     |     |     |     |     |     |     |     |     |     |     |     |     |     |
| --- | --- | --- | --- | --- | --- | --- | --- | --- | --- | --- | --- | --- | --- | --- |
|     |     |     | 130 |     |     |     | 135 |     |     |     | 140 |     |     |     |
| Arg | Lys | Glu | Tyr | Gly | Ala | Val | Thr | Ser | Phe | Thr | Glu | Leu | Lys | Ile | Ala |
| 145 |     |     |     |     | 150 |     |     |     |     | 155 |     |     |     |     | 160 |
| Arg | Asn | Ile | Tyr | Ile | Lys | Val | Gly | Glu | Asp | Gln | Val | Phe | Pro | Pro | Lys |
|     |     |     |     | 165 |     |     |     |     | 170 |     |     |     |     | 175 |     |
| Cys | Asn | Ile | Gly | Lys | Asn | Phe | Leu | Ser | Leu | Asn | Tyr | Leu | Ala | Glu | Tyr |
|     |     |     | 180 |     |     |     |     | 185 |     |     |     |     | 190 |     |     |
| Leu | Gln | Pro | Lys | Ala | Ala | Glu | Gly | Cys | Val | Met | Ser | Ser | Gln | Pro | Gln |
|     |     | 195 |     |     |     |     | 200 |     |     |     |     | 205 |     |     |     |
| Asn | Glu | Glu | Val | His | Ile | Ile | Glu | Leu | Ile | Thr | Pro | Asn | Ser | Asn | Pro |
| 210 |     |     |     |     | 215 |     |     |     |     |     |     | 220 |     |     |     |
| Tyr | Ser | Ala | Phe | Gln | Val | Asp | Ile | Thr | Ile | Asp | Ile | Arg | Pro | Ser | Gln |
| 225 |     |     |     |     | 230 |     |     |     |     | 235 |     |     |     |     | 240 |
| Glu | Asp | Leu | Glu | Val | Val | Lys | Asn | Leu | Ile | Leu | Ile | Leu | Lys | Cys | Lys |
|     |     |     |     | 245 |     |     |     |     | 250 |     |     |     |     | 255 |     |
| Lys | Ser | Val | Asn | Trp | Val | Ile | Lys | Ser | Phe | Asp | Val | Lys | Gly | Ser | Leu |
|     |     |     | 260 |     |     |     |     | 265 |     |     |     |     | 270 |     |     |
| Lys | Ile | Ile | Ala | Pro | Asn | Ser | Ile | Gly | Phe | Gly | Lys | Glu | Ser | Glu | Arg |
|     |     | 275 |     |     |     |     | 280 |     |     |     |     | 285 |     |     |     |
| Ser | Met | Thr | Met | Thr | Lys | Ser | Ile | Arg | Asp | Asp | Ile | Pro | Ser | Thr | Gln |
|     | 290 |     |     |     |     | 295 |     |     |     |     | 300 |     |     |     |     |
| Gly | Asn | Leu | Val | Lys | Trp | Ala | Leu | Asp | Asn | Gly | Tyr | Ser | Pro | Ile | Thr |
| 305 |     |     |     |     | 310 |     |     |     |     | 315 |     |     |     |     | 320 |
| Ser | Tyr | Thr | Met | Ala | Pro | Val | Ala | Asn | Arg | Phe | His | Leu | Arg | Leu | Glu |
|     |     |     |     | 325 |     |     |     |     | 330 |     |     |     |     | 335 |     |
| Asn | Asn | Ala | Glu | Glu | Met | Gly | Asp | Glu | Val | His | Thr | Ile | Pro | Pro |
|     |     |     | 340 |     |     |     |     | 345 |     |     |     |     | 350 |     |     |
| Glu | Leu | Arg | Ile | Leu | Leu | Asp | Pro | Gly | Ala | Leu | Pro | Ala | Leu | Gln | Asn |
|     |     | 355 |     |     |     |     | 360 |     |     |     |     | 365 |     |     |     |
| Pro | Pro | Ile | Arg | Gly | Gly | Glu | Gly | Gln | Asn | Gly | Gly | Leu | Pro | Phe | Pro |
|     | 370 |     |     |     |     | 375 |     |     |     |     | 380 |     |     |     |     |
| Phe | Pro | Asp | Ile | Ser | Arg | Arg | Val | Trp | Asn | Glu | Glu | Gly | Glu | Asp | Gly |
| 385 |     |     |     |     | 390 |     |     |     |     | 395 |     |     |     |     | 400 |
| Leu | Pro | Arg | Pro | Lys | Asp | Pro | Val | Ile | Pro | Ser | Ile | Gln | Leu | Phe | Pro |
|     |     |     |     | 405 |     |     |     |     | 410 |     |     |     |     | 415 |     |
| Gly | Leu | Arg | Glu | Pro | Glu | Glu | Val | Gln | Gly | Ser | Val | Asp | Ile | Ala | Leu |
|     |     |     | 420 |     |     |     |     | 425 |     |     |     |     | 430 |     |     |
| Ser | Val | Lys | Cys | Asp | Asn | Glu | Lys | Met | Ile | Val | Ala | Val | Glu | Lys | Asp |
|     |     | 435 |     |     |     |     | 440 |     |     |     |     | 445 |     |     |     |
| Ser | Phe | Gln | Ala | Ser | Gly | Tyr | Ser | Gly | Met | Asp | Val | Thr | Leu | Leu | Asp |
|     | 450 |     |     |     |     | 455 |     |     |     |     | 460 |     |     |     |     |
| Pro | Thr | Cys | Lys | Ala | Lys | Met | Asn | Gly | Thr | His | Phe | Val | Leu | Glu | Ser |
| 465 |     |     |     |     | 470 |     |     |     |     | 475 |     |     |     |     | 480 |
| Pro | Leu | Asn | Gly | Cys | Gly | Thr | Arg | Pro | Arg | Trp | Ser | Ala | Leu | Asp | Gly |
|     |     |     |     | 485 |     |     |     |     | 490 |     |     |     |     | 495 |     |
| Val | Val | Tyr | Tyr | Asn | Ser | Ile | Val | Ile | Gln | Val | Pro | Ala | Leu | Gly | Asp |
|     |     |     | 500 |     |     |     |     | 505 |     |     |     |     | 510 |     |     |
| Ser | Ser | Gly | Trp | Pro | Asp | Gly | Tyr | Glu | Asp | Leu | Glu | Ser | Gly | Asp | Asn |
|     |     | 515 |     |     |     |     | 520 |     |     |     |     | 525 |     |     |     |
| Gly | Phe | Pro | Gly | Asp | Met | Asp | Glu | Gly | Asp | Ala | Ser | Leu | Phe | Thr | Arg |
|     | 530 |     |     |     |     | 535 |     |     |     |     | 540 |     |     |     |     |
| Pro | Glu | Ile | Val | Val | Phe | Asn | Cys | Ser | Leu | Gln | Gln | Val | Arg | Asn | Pro |
| 545 |     |     |     |     | 550 |     |     |     |     | 555 |     |     |     |     | 560 |

```
Ser Ser Phe Gln Glu Gln Pro His Gly Asn Ile Thr Phe Asn Met Glu
                565                 570                 575

Leu Tyr Asn Thr Asp Leu Phe Leu Val Pro Ser Gln Gly Val Phe Ser
            580                 585                 590

Val Pro Glu Asn Gly His Val Tyr Val Glu Val Ser Val Thr Lys Ala
        595                 600                 605

Glu Gln Glu Leu Gly Phe Ala Ile Gln Thr Cys Phe Ile Ser Pro Tyr
    610                 615                 620

Ser Asn Pro Asp Arg Met Ser His Tyr Thr Ile Ile Glu Asn Ile Cys
625                 630                 635                 640

Pro Lys Asp Glu Ser Val Lys Phe Tyr Ser Pro Lys Arg Val His Phe
                645                 650                 655

Pro Ile Pro Gln Ala Asp Met Asp Lys Lys Arg Phe Ser Phe Val Phe
            660                 665                 670

Lys Pro Val Phe Asn Thr Ser Leu Leu Phe Leu Gln Cys Glu Leu Thr
        675                 680                 685

Leu Cys Thr Lys Met Glu Lys His Pro Gln Lys Leu Pro Lys Cys Val
    690                 695                 700

Pro Pro Asp Glu Ala Cys Thr Ser Leu Asp Ala Ser Ile Ile Trp Ala
705                 710                 715                 720

Met Met Gln Asn Lys Lys Thr Phe Thr Lys Pro Leu Ala Val Ile His
                725                 730                 735

His Glu Ala Glu Ser Lys Glu Lys Gly Pro Ser Met Lys Glu Pro Asn
            740                 745                 750

Pro Ile Ser Pro Pro Ile Phe His Gly Leu Asp Thr Leu Thr Val
        755                 760                 765
```

<210> SEQ ID NO 3109

<400> SEQUENCE: 3109

000

<210> SEQ ID NO 3110

<400> SEQUENCE: 3110

000

<210> SEQ ID NO 3111

<400> SEQUENCE: 3111

000

<210> SEQ ID NO 3112

<400> SEQUENCE: 3112

000

<210> SEQ ID NO 3113

<400> SEQUENCE: 3113

000

<210> SEQ ID NO 3114

<400> SEQUENCE: 3114

000

<210> SEQ ID NO 3115

<400> SEQUENCE: 3115

000

<210> SEQ ID NO 3116

<400> SEQUENCE: 3116

000

<210> SEQ ID NO 3117
<211> LENGTH: 361
<212> TYPE: PRT
<213> ORGANISM: Homo sapiens

<400> SEQUENCE: 3117

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285
```

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 3118
<211> LENGTH: 394
<212> TYPE: PRT
<213> ORGANISM: Homo sapiens

<400> SEQUENCE: 3118

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Glu Val Pro Pro Glu Val Ile
            35                  40                  45

Ser Ile Tyr Asn Ser Thr Arg Asp Leu Leu Gln Glu Lys Ala Ser Arg
50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Pro Phe Phe Pro Ser Glu Asn
                85                  90                  95

Ala Ile Pro Pro Thr Phe Tyr Arg Pro Tyr Phe Arg Ile Val Arg Phe
            100                 105                 110

Asp Val Ser Ala Met Glu Lys Asn Ala Ser Asn Leu Val Lys Ala Glu
            115                 120                 125

Phe Arg Val Phe Arg Leu Gln Asn Pro Lys Ala Arg Val Pro Glu Gln
130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
            195                 200                 205

Cys Thr Phe Val Pro Ser Asn Asn Tyr Ile Ile Pro Asn Lys Ser Glu
    210                 215                 220

Glu Leu Glu Ala Arg Phe Ala Gly Ile Asp Gly Thr Ser Thr Tyr Thr
225                 230                 235                 240

Ser Gly Asp Gln Lys Thr Ile Lys Ser Thr Arg Lys Lys Asn Ser Gly
                245                 250                 255

Lys Thr Pro His Leu Leu Leu Met Leu Leu Pro Ser Tyr Arg Leu Glu
            260                 265                 270

Ser Gln Gln Thr Asn Arg Arg Lys Lys Arg Ala Leu Asp Ala Ala Tyr
            275                 280                 285

Cys Phe Arg Asn Val Gln Asp Asn Cys Cys Leu Arg Pro Leu Tyr Ile
    290                 295                 300

```
Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
            325                 330                 335

Asp Thr Gln His Ser Arg Val Leu Ser Leu Tyr Asn Thr Ile Asn Pro
        340                 345                 350

Glu Ala Ser Ala Ser Pro Cys Cys Val Ser Gln Asp Leu Glu Pro Leu
    355                 360                 365

Thr Ile Leu Tyr Tyr Ile Gly Lys Thr Pro Lys Ile Glu Gln Leu Ser
370                 375                 380

Asn Met Ile Val Lys Ser Cys Lys Cys Ser
385                 390

<210> SEQ ID NO 3119
<211> LENGTH: 389
<212> TYPE: PRT
<213> ORGANISM: Homo sapiens

<400> SEQUENCE: 3119

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Thr Val Met Thr His Val Pro Tyr Gln Val Leu Ala
        35                  40                  45

Leu Tyr Asn Ser Thr Arg Glu Leu Leu Glu Glu Met His Gly Glu Arg
    50                  55                  60

Glu Glu Gly Cys Thr Gln Glu Asn Thr Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Arg Thr Asn Leu Phe Arg Ala Glu Phe
        115                 120                 125

Arg Val Leu Arg Val Pro Asn Pro Ser Ser Lys Arg Asn Glu Gln Arg
    130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
    195                 200                 205

Phe Gln Pro Asn Gly Asp Ile Leu Glu Asn Ile His Glu Val Met Glu
210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Asn Pro Gly Gln Gly Gly
            260                 265                 270

Gln Arg Lys Lys Arg Ala Leu Asp Thr Asn Tyr Cys Phe Arg Asn Leu
```

```
             275                 280                 285
Glu Glu Asn Cys Cys Val Arg Pro Leu Tyr Ile Asp Phe Arg Gln Asp
    290                 295                 300

Leu Gly Trp Lys Trp Val His Glu Pro Lys Gly Tyr Ala Asn Phe
305                 310                 315                 320

Cys Ser Gly Pro Cys Pro Tyr Leu Arg Ser Ala Asp Thr Thr His Ser
                    325                 330                 335

Thr Val Leu Gly Leu Tyr Asn Thr Leu Asn Pro Glu Ala Ser Ala Ser
                340                 345                 350

Pro Cys Cys Val Pro Gln Asp Leu Glu Pro Leu Thr Ile Leu Tyr Tyr
            355                 360                 365

Val Gly Arg Thr Pro Lys Val Glu Gln Leu Ser Asn Met Val Val Lys
        370                 375                 380

Ser Cys Lys Cys Ser
385

<210> SEQ ID NO 3120
<211> LENGTH: 470
<212> TYPE: PRT
<213> ORGANISM: Homo sapiens

<400> SEQUENCE: 3120

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
                20                  25                  30

Ile His Asn Ser Met Cys Ile Ala Glu Ile Asp Leu Ile Pro Arg Asp
            35                  40                  45

Arg Pro Phe Val Cys Ala Pro Ser Ser Lys Thr Gly Ser Val Thr Thr
        50                  55                  60

Thr Tyr Cys Cys Asn Gln Asp His Cys Asn Lys Ile Glu Leu Pro Thr
65                  70                  75                  80

Thr Val Lys Ser Ser Pro Gly Leu Gly Pro Val Glu Leu Ala Ala Val
                85                  90                  95

Ile Ala Gly Pro Val Cys Phe Val Cys Ile Ser Leu Met Leu Met Val
            100                 105                 110

Tyr Ile Cys His Asn Arg Thr Val Ile His His Arg Val Pro Asn Glu
        115                 120                 125

Glu Asp Pro Ser Leu Asp Arg Pro Phe Ile Ser Glu Gly Thr Thr Leu
    130                 135                 140

Lys Asp Leu Ile Tyr Asp Met Thr Thr Ser Gly Ser Gly Ser Gly Leu
145                 150                 155                 160

Pro Leu Leu Val Gln Arg Thr Ile Ala Arg Thr Ile Val Leu Gln Glu
                165                 170                 175

Ser Ile Gly Lys Gly Arg Phe Gly Glu Val Trp Arg Gly Lys Trp Arg
            180                 185                 190

Gly Glu Glu Val Ala Val Lys Ile Phe Ser Ser Arg Glu Glu Arg Ser
        195                 200                 205

Trp Phe Arg Glu Ala Glu Ile Tyr Gln Thr Val Met Leu Arg His Glu
    210                 215                 220

Asn Ile Leu Gly Phe Ile Ala Ala Asp Asn Lys Asp Asn Gly Thr Trp
225                 230                 235                 240

Thr Gln Leu Trp Leu Val Ser Asp Tyr His Glu His Gly Ser Leu Phe
                245                 250                 255
```

Asp Tyr Leu Asn Arg Tyr Thr Val Thr Val Glu Gly Met Ile Lys Leu
            260                 265                 270

Ala Leu Ser Thr Ala Ser Gly Leu Ala His Leu His Met Glu Ile Val
        275                 280                 285

Gly Thr Gln Gly Lys Pro Ala Ile Ala His Arg Asp Leu Lys Ser Lys
    290                 295                 300

Asn Ile Leu Val Lys Lys Asn Gly Thr Cys Cys Ile Ala Asp Leu Gly
305                 310                 315                 320

Leu Ala Val Arg His Asp Ser Ala Thr Asp Thr Ile Asp Ile Ala Pro
                325                 330                 335

Asn His Arg Val Gly Thr Lys Arg Tyr Met Ala Pro Glu Val Leu Asp
            340                 345                 350

Asp Ser Ile Asn Met Lys His Phe Glu Ser Phe Lys Arg Ala Asp Ile
        355                 360                 365

Tyr Ala Met Gly Leu Val Phe Trp Glu Ile Ala Arg Arg Cys Ser Ile
    370                 375                 380

Gly Gly Ile His Glu Asp Tyr Gln Leu Pro Tyr Tyr Asp Leu Val Pro
385                 390                 395                 400

Ser Asp Pro Ser Val Glu Glu Met Arg Lys Val Val Cys Glu Gln Lys
                405                 410                 415

Leu Arg Pro Asn Ile Pro Asn Arg Trp Gln Ser Cys Glu Ala Leu Arg
            420                 425                 430

Val Met Ala Lys Ile Met Arg Glu Cys Trp Tyr Ala Asn Gly Ala Ala
        435                 440                 445

Arg Leu Thr Ala Leu Arg Ile Lys Lys Thr Leu Ser Gln Leu Ser Gln
    450                 455                 460

Gln Glu Gly Ile Lys Met
465                 470

<210> SEQ ID NO 3121
<211> LENGTH: 474
<212> TYPE: PRT
<213> ORGANISM: Homo sapiens

<400> SEQUENCE: 3121

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
        35                  40                  45

Arg Pro Phe Val Cys Ala Pro Ser Ser Lys Thr Gly Ser Val Thr Thr
    50                  55                  60

Thr Tyr Cys Cys Asn Gln Asp His Cys Asn Lys Ile Glu Leu Pro Thr
65                  70                  75                  80

Thr Gly Pro Phe Ser Val Lys Ser Ser Pro Gly Leu Gly Pro Val Glu
                85                  90                  95

Leu Ala Ala Val Ile Ala Gly Pro Val Cys Phe Val Cys Ile Ser Leu
            100                 105                 110

Met Leu Met Val Tyr Ile Cys His Asn Arg Thr Val Ile His His Arg
        115                 120                 125

Val Pro Asn Glu Glu Asp Pro Ser Leu Asp Arg Pro Phe Ile Ser Glu
    130                 135                 140

Gly Thr Thr Leu Lys Asp Leu Ile Tyr Asp Met Thr Thr Ser Gly Ser
145                 150                 155                 160

```
Gly Ser Gly Leu Pro Leu Leu Val Gln Arg Thr Ile Ala Arg Thr Ile
                165                 170                 175
Val Leu Gln Glu Ser Ile Gly Lys Gly Arg Phe Gly Glu Val Trp Arg
            180                 185                 190
Gly Lys Trp Arg Gly Glu Glu Val Ala Val Lys Ile Phe Ser Ser Arg
        195                 200                 205
Glu Glu Arg Ser Trp Phe Arg Glu Ala Glu Ile Tyr Gln Thr Val Met
    210                 215                 220
Leu Arg His Glu Asn Ile Leu Gly Phe Ile Ala Ala Asp Asn Lys Asp
225                 230                 235                 240
Asn Gly Thr Trp Thr Gln Leu Trp Leu Val Ser Asp Tyr His Glu His
                245                 250                 255
Gly Ser Leu Phe Asp Tyr Leu Asn Arg Tyr Thr Val Thr Val Glu Gly
            260                 265                 270
Met Ile Lys Leu Ala Leu Ser Thr Ala Ser Gly Leu Ala His Leu His
        275                 280                 285
Met Glu Ile Val Gly Thr Gln Gly Lys Pro Ala Ile Ala His Arg Asp
    290                 295                 300
Leu Lys Ser Lys Asn Ile Leu Val Lys Lys Asn Gly Thr Cys Cys Ile
305                 310                 315                 320
Ala Asp Leu Gly Leu Ala Val Arg His Asp Ser Ala Thr Asp Thr Ile
                325                 330                 335
Asp Ile Ala Pro Asn His Arg Val Gly Thr Lys Arg Tyr Met Ala Pro
            340                 345                 350
Glu Val Leu Asp Asp Ser Ile Asn Met Lys His Phe Glu Ser Phe Lys
        355                 360                 365
Arg Ala Asp Ile Tyr Ala Met Gly Leu Val Phe Trp Glu Ile Ala Arg
    370                 375                 380
Arg Cys Ser Ile Gly Gly Ile His Glu Asp Tyr Gln Leu Pro Tyr Tyr
385                 390                 395                 400
Asp Leu Val Pro Ser Asp Pro Ser Val Glu Glu Met Arg Lys Val Val
                405                 410                 415
Cys Glu Gln Lys Leu Arg Pro Asn Ile Pro Asn Arg Trp Gln Ser Cys
            420                 425                 430
Glu Ala Leu Arg Val Met Ala Lys Ile Met Arg Glu Cys Trp Tyr Ala
        435                 440                 445
Asn Gly Ala Ala Arg Leu Thr Ala Leu Arg Ile Lys Lys Thr Leu Ser
    450                 455                 460
Gln Leu Ser Gln Gln Glu Gly Ile Lys Met
465                 470

<210> SEQ ID NO 3122
<211> LENGTH: 393
<212> TYPE: PRT
<213> ORGANISM: Homo sapiens

<400> SEQUENCE: 3122

Leu Gln Cys Phe Cys His Leu Cys Thr Lys Asp Asn Phe Thr Cys Val
1               5                   10                  15
Thr Asp Gly Leu Cys Phe Val Ser Val Thr Glu Thr Thr Asp Lys Val
            20                  25                  30
Ile His Asn Ser Met Cys Ile Ala Glu Ile Asp Leu Ile Pro Arg Asp
        35                  40                  45
Arg Pro Phe Val Cys Ala Pro Ser Ser Lys Thr Gly Ser Val Thr Thr
```

```
                  50                  55                  60
Thr Tyr Cys Cys Asn Gln Asp His Cys Asn Lys Ile Glu Leu Pro Thr
 65                  70                  75                  80

Thr Gly Leu Pro Leu Leu Val Gln Arg Thr Ile Ala Arg Thr Ile Val
                 85                  90                  95

Leu Gln Glu Ser Ile Gly Lys Gly Arg Phe Gly Glu Val Trp Arg Gly
            100                 105                 110

Lys Trp Arg Gly Glu Glu Val Ala Val Lys Ile Phe Ser Ser Arg Glu
        115                 120                 125

Glu Arg Ser Trp Phe Arg Glu Ala Glu Ile Tyr Gln Thr Val Met Leu
    130                 135                 140

Arg His Glu Asn Ile Leu Gly Phe Ile Ala Ala Asp Asn Lys Asp Asn
145                 150                 155                 160

Gly Thr Trp Thr Gln Leu Trp Leu Val Ser Asp Tyr His Glu His Gly
                165                 170                 175

Ser Leu Phe Asp Tyr Leu Asn Arg Tyr Thr Val Thr Val Glu Gly Met
            180                 185                 190

Ile Lys Leu Ala Leu Ser Thr Ala Ser Gly Leu Ala His Leu His Met
        195                 200                 205

Glu Ile Val Gly Thr Gln Gly Lys Pro Ala Ile Ala His Arg Asp Leu
    210                 215                 220

Lys Ser Lys Asn Ile Leu Val Lys Lys Asn Gly Thr Cys Cys Ile Ala
225                 230                 235                 240

Asp Leu Gly Leu Ala Val Arg His Asp Ser Ala Thr Asp Thr Ile Asp
                245                 250                 255

Ile Ala Pro Asn His Arg Val Gly Thr Lys Arg Tyr Met Ala Pro Glu
            260                 265                 270

Val Leu Asp Asp Ser Ile Asn Met Lys His Phe Glu Ser Phe Lys Arg
        275                 280                 285

Ala Asp Ile Tyr Ala Met Gly Leu Val Phe Trp Glu Ile Ala Arg Arg
    290                 295                 300

Cys Ser Ile Gly Gly Ile His Glu Asp Tyr Gln Leu Pro Tyr Tyr Asp
305                 310                 315                 320

Leu Val Pro Ser Asp Pro Ser Val Glu Glu Met Arg Lys Val Val Cys
                325                 330                 335

Glu Gln Lys Leu Arg Pro Asn Ile Pro Asn Arg Trp Gln Ser Cys Glu
            340                 345                 350

Ala Leu Arg Val Met Ala Lys Ile Met Arg Glu Cys Trp Tyr Ala Asn
        355                 360                 365

Gly Ala Ala Arg Leu Thr Ala Leu Arg Ile Lys Thr Leu Ser Gln
    370                 375                 380

Leu Ser Gln Gln Glu Gly Ile Lys Met
385                 390
```

<210> SEQ ID NO 3123
<211> LENGTH: 545
<212> TYPE: PRT
<213> ORGANISM: Homo sapiens

<400> SEQUENCE: 3123

```
Thr Ile Pro Pro His Val Gln Lys Ser Val Asn Asn Asp Met Ile Val
 1               5                  10                  15

Thr Asp Asn Asn Gly Ala Val Lys Phe Pro Gln Leu Cys Lys Phe Cys
                20                  25                  30
```

```
Asp Val Arg Phe Ser Thr Cys Asp Asn Gln Lys Ser Cys Met Ser Asn
    35                  40                  45

Cys Ser Ile Thr Ser Ile Cys Glu Lys Pro Gln Glu Val Cys Val Ala
 50                  55                  60

Val Trp Arg Lys Asn Asp Glu Asn Ile Thr Leu Glu Thr Val Cys His
 65              70                  75                      80

Asp Pro Lys Leu Pro Tyr His Asp Phe Ile Leu Glu Asp Ala Ala Ser
                 85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Leu Leu Val Ile Phe Gln
    130                 135                 140

Val Thr Gly Ile Ser Leu Leu Pro Pro Leu Gly Val Ala Ile Ser Val
145                 150                 155                 160

Ile Ile Ile Phe Tyr Cys Tyr Arg Val Asn Arg Gln Gln Lys Leu Ser
                165                 170                 175

Ser Thr Trp Glu Thr Gly Lys Thr Arg Lys Leu Met Glu Phe Ser Glu
            180                 185                 190

His Cys Ala Ile Ile Leu Glu Asp Asp Arg Ser Asp Ile Ser Ser Thr
    195                 200                 205

Cys Ala Asn Asn Ile Asn His Asn Thr Glu Leu Leu Pro Ile Glu Leu
    210                 215                 220

Asp Thr Leu Val Gly Lys Gly Arg Phe Ala Glu Val Tyr Lys Ala Lys
225                 230                 235                 240

Leu Lys Gln Asn Thr Ser Glu Gln Phe Glu Thr Val Ala Val Lys Ile
                245                 250                 255

Phe Pro Tyr Glu Glu Tyr Ala Ser Trp Lys Thr Glu Lys Asp Ile Phe
            260                 265                 270

Ser Asp Ile Asn Leu Lys His Glu Asn Ile Leu Gln Phe Leu Thr Ala
    275                 280                 285

Glu Glu Arg Lys Thr Glu Leu Gly Lys Gln Tyr Trp Leu Ile Thr Ala
    290                 295                 300

Phe His Ala Lys Gly Asn Leu Gln Glu Tyr Leu Thr Arg His Val Ile
305                 310                 315                 320

Ser Trp Glu Asp Leu Arg Lys Leu Gly Ser Ser Leu Ala Arg Gly Ile
                325                 330                 335

Ala His Leu His Ser Asp His Thr Pro Cys Gly Arg Pro Lys Met Pro
            340                 345                 350

Ile Val His Arg Asp Leu Lys Ser Ser Asn Ile Leu Val Lys Asn Asp
            355                 360                 365

Leu Thr Cys Cys Leu Cys Asp Phe Gly Leu Ser Leu Arg Leu Asp Pro
    370                 375                 380

Thr Leu Ser Val Asp Asp Leu Ala Asn Ser Gly Gln Val Gly Thr Ala
385                 390                 395                 400

Arg Tyr Met Ala Pro Glu Val Leu Glu Ser Arg Met Asn Leu Glu Asn
                405                 410                 415

Val Glu Ser Phe Lys Gln Thr Asp Val Tyr Ser Met Ala Leu Val Leu
            420                 425                 430

Trp Glu Met Thr Ser Arg Cys Asn Ala Val Gly Glu Val Lys Asp Tyr
            435                 440                 445

Glu Pro Pro Phe Gly Ser Lys Val Arg Glu His Pro Cys Val Glu Ser
```

```
            450                 455                 460
Met Lys Asp Asn Val Leu Arg Asp Arg Gly Arg Pro Glu Ile Pro Ser
465                 470                 475                 480

Phe Trp Leu Asn His Gln Gly Ile Gln Met Val Cys Glu Thr Leu Thr
                485                 490                 495

Glu Cys Trp Asp His Asp Pro Glu Ala Arg Leu Thr Ala Gln Cys Val
            500                 505                 510

Ala Glu Arg Phe Ser Glu Leu Glu His Leu Asp Arg Leu Ser Gly Arg
        515                 520                 525

Ser Cys Ser Glu Glu Lys Ile Pro Glu Asp Gly Ser Leu Asn Thr Thr
    530                 535                 540

Lys
545

<210> SEQ ID NO 3124
<211> LENGTH: 570
<212> TYPE: PRT
<213> ORGANISM: Homo sapiens

<400> SEQUENCE: 3124

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Leu Leu Leu Val Ile Phe Gln Val Thr Gly Ile Ser Leu Leu
                165                 170                 175

Pro Pro Leu Gly Val Ala Ile Ser Val Ile Ile Ile Phe Tyr Cys Tyr
            180                 185                 190

Arg Val Asn Arg Gln Gln Lys Leu Ser Ser Thr Trp Glu Thr Gly Lys
        195                 200                 205

Thr Arg Lys Leu Met Glu Phe Ser Glu His Cys Ala Ile Ile Leu Glu
    210                 215                 220

Asp Asp Arg Ser Asp Ile Ser Ser Thr Cys Ala Asn Asn Ile Asn His
225                 230                 235                 240

Asn Thr Glu Leu Leu Pro Ile Glu Leu Asp Thr Leu Val Gly Lys Gly
                245                 250                 255

Arg Phe Ala Glu Val Tyr Lys Ala Lys Leu Lys Gln Asn Thr Ser Glu
            260                 265                 270
```

```
Gln Phe Glu Thr Val Ala Val Lys Ile Phe Pro Tyr Glu Tyr Ala
            275                 280                 285

Ser Trp Lys Thr Glu Lys Asp Ile Phe Ser Asp Ile Asn Leu Lys His
290                 295                 300

Glu Asn Ile Leu Gln Phe Leu Thr Ala Glu Arg Lys Thr Glu Leu
305                 310                 315                 320

Gly Lys Gln Tyr Trp Leu Ile Thr Ala Phe His Ala Lys Gly Asn Leu
            325                 330                 335

Gln Glu Tyr Leu Thr Arg His Val Ile Ser Trp Glu Asp Leu Arg Lys
                340                 345                 350

Leu Gly Ser Ser Leu Ala Arg Gly Ile Ala His Leu His Ser Asp His
            355                 360                 365

Thr Pro Cys Gly Arg Pro Lys Met Pro Ile Val His Arg Asp Leu Lys
370                 375                 380

Ser Ser Asn Ile Leu Val Lys Asn Asp Leu Thr Cys Cys Leu Cys Asp
385                 390                 395                 400

Phe Gly Leu Ser Leu Arg Leu Asp Pro Thr Leu Ser Val Asp Asp Leu
            405                 410                 415

Ala Asn Ser Gly Gln Val Gly Thr Ala Arg Tyr Met Ala Pro Glu Val
            420                 425                 430

Leu Glu Ser Arg Met Asn Leu Glu Asn Val Glu Ser Phe Lys Gln Thr
            435                 440                 445

Asp Val Tyr Ser Met Ala Leu Val Leu Trp Glu Met Thr Ser Arg Cys
            450                 455                 460

Asn Ala Val Gly Glu Val Lys Asp Tyr Glu Pro Pro Phe Gly Ser Lys
465                 470                 475                 480

Val Arg Glu His Pro Cys Val Glu Ser Met Lys Asp Asn Val Leu Arg
            485                 490                 495

Asp Arg Gly Arg Pro Glu Ile Pro Ser Phe Trp Leu Asn His Gln Gly
            500                 505                 510

Ile Gln Met Val Cys Glu Thr Leu Thr Glu Cys Trp Asp His Asp Pro
            515                 520                 525

Glu Ala Arg Leu Thr Ala Gln Cys Val Ala Glu Arg Phe Ser Glu Leu
530                 535                 540

Glu His Leu Asp Arg Leu Ser Gly Arg Ser Cys Ser Glu Glu Lys Ile
545                 550                 555                 560

Pro Glu Asp Gly Ser Leu Asn Thr Thr Lys
            565                 570

<210> SEQ ID NO 3125
<211> LENGTH: 831
<212> TYPE: PRT
<213> ORGANISM: Homo sapiens

<400> SEQUENCE: 3125

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
            20                  25                  30

Ala Ser Arg Gly Thr Thr Gly Leu Pro Gln Glu Val His Val Leu Asn
        35                  40                  45

Leu Arg Thr Ala Gly Gln Gly Pro Gly Gln Leu Gln Arg Glu Val Thr
    50                  55                  60

Leu His Leu Asn Pro Ile Ser Ser Val His Ile His His Lys Ser Val
65                  70                  75                  80
```

```
Val Phe Leu Leu Asn Ser Pro His Pro Leu Trp His Leu Lys Thr
                85               90              95

Glu Arg Leu Ala Thr Gly Val Ser Arg Leu Phe Leu Val Ser Glu Gly
            100             105             110

Ser Val Val Gln Phe Ser Ser Ala Asn Phe Ser Leu Thr Ala Glu Thr
            115             120             125

Glu Glu Arg Asn Phe Pro His Gly Asn Glu His Leu Leu Asn Trp Ala
    130             135             140

Arg Lys Glu Tyr Gly Ala Val Thr Ser Phe Thr Glu Leu Lys Ile Ala
145             150             155             160

Arg Asn Ile Tyr Ile Lys Val Gly Glu Asp Gln Val Phe Pro Pro Lys
                165             170             175

Cys Asn Ile Gly Lys Asn Phe Leu Ser Leu Asn Tyr Leu Ala Glu Tyr
                180             185             190

Leu Gln Pro Lys Ala Ala Glu Gly Cys Val Met Ser Ser Gln Pro Gln
            195             200             205

Asn Glu Glu Val His Ile Ile Glu Leu Ile Thr Pro Asn Ser Asn Pro
    210             215             220

Tyr Ser Ala Phe Gln Val Asp Ile Thr Ile Asp Ile Arg Pro Ser Gln
225             230             235             240

Glu Asp Leu Glu Val Val Lys Asn Leu Ile Leu Ile Leu Lys Cys Lys
            245             250             255

Lys Ser Val Asn Trp Val Ile Lys Ser Phe Asp Val Lys Gly Ser Leu
            260             265             270

Lys Ile Ile Ala Pro Asn Ser Ile Gly Phe Gly Lys Glu Ser Glu Arg
            275             280             285

Ser Met Thr Met Thr Lys Ser Ile Arg Asp Asp Ile Pro Ser Thr Gln
    290             295             300

Gly Asn Leu Val Lys Trp Ala Leu Asp Asn Gly Tyr Ser Pro Ile Thr
305             310             315             320

Ser Tyr Thr Met Ala Pro Val Ala Asn Arg Phe His Leu Arg Leu Glu
                325             330             335

Asn Asn Ala Glu Glu Met Gly Asp Glu Glu Val His Thr Ile Pro Pro
            340             345             350

Glu Leu Arg Ile Leu Leu Asp Pro Gly Ala Leu Pro Ala Leu Gln Asn
    355             360             365

Pro Pro Ile Arg Gly Gly Gly Gln Asn Gly Gly Leu Pro Phe Pro
370             375             380

Phe Pro Asp Ile Ser Arg Arg Val Trp Asn Glu Gly Glu Asp Gly
385             390             395             400

Leu Pro Arg Pro Lys Asp Pro Val Ile Pro Ser Ile Gln Leu Phe Pro
            405             410             415

Gly Leu Arg Glu Pro Glu Glu Val Gln Gly Ser Val Asp Ile Ala Leu
            420             425             430

Ser Val Lys Cys Asp Asn Glu Lys Met Ile Val Ala Val Glu Lys Asp
            435             440             445

Ser Phe Gln Ala Ser Gly Tyr Ser Gly Met Asp Val Thr Leu Leu Asp
    450             455             460

Pro Thr Cys Lys Ala Lys Met Asn Gly Thr His Phe Val Leu Glu Ser
465             470             475             480

Pro Leu Asn Gly Cys Gly Thr Arg Pro Arg Trp Ser Ala Leu Asp Gly
            485             490             495
```

Val Val Tyr Tyr Asn Ser Ile Val Ile Gln Val Pro Ala Leu Gly Asp
                500                 505                 510

Ser Ser Gly Trp Pro Asp Gly Tyr Glu Asp Leu Glu Ser Gly Asp Asn
            515                 520                 525

Gly Phe Pro Gly Asp Met Asp Glu Gly Asp Ala Ser Leu Phe Thr Arg
        530                 535                 540

Pro Glu Ile Val Val Phe Asn Cys Ser Leu Gln Gln Val Arg Asn Pro
545                 550                 555                 560

Ser Ser Phe Gln Glu Gln Pro His Gly Asn Ile Thr Phe Asn Met Glu
                565                 570                 575

Leu Tyr Asn Thr Asp Leu Phe Leu Val Pro Ser Gln Gly Val Phe Ser
            580                 585                 590

Val Pro Glu Asn Gly His Val Tyr Val Glu Val Ser Val Thr Lys Ala
        595                 600                 605

Glu Gln Glu Leu Gly Phe Ala Ile Gln Thr Cys Phe Ile Ser Pro Tyr
610                 615                 620

Ser Asn Pro Asp Arg Met Ser His Tyr Thr Ile Ile Glu Asn Ile Cys
625                 630                 635                 640

Pro Lys Asp Glu Ser Val Lys Phe Tyr Ser Pro Lys Arg Val His Phe
                645                 650                 655

Pro Ile Pro Gln Ala Asp Met Asp Lys Lys Arg Phe Ser Phe Val Phe
            660                 665                 670

Lys Pro Val Phe Asn Thr Ser Leu Leu Phe Leu Gln Cys Glu Leu Thr
        675                 680                 685

Leu Cys Thr Lys Met Glu Lys His Pro Gln Lys Leu Pro Lys Cys Val
690                 695                 700

Pro Pro Asp Glu Ala Cys Thr Ser Leu Asp Ala Ser Ile Ile Trp Ala
705                 710                 715                 720

Met Met Gln Asn Lys Lys Thr Phe Thr Lys Pro Leu Ala Val Ile His
                725                 730                 735

His Glu Ala Glu Ser Lys Glu Lys Gly Pro Ser Met Lys Glu Pro Asn
            740                 745                 750

Pro Ile Ser Pro Pro Ile Phe His Gly Leu Asp Thr Leu Thr Val Met
        755                 760                 765

Gly Ile Ala Phe Ala Ala Phe Val Ile Gly Ala Leu Leu Thr Gly Ala
        770                 775                 780

Leu Trp Tyr Ile Tyr Ser His Thr Gly Glu Thr Ala Gly Arg Gln Gln
785                 790                 795                 800

Val Pro Thr Ser Pro Pro Ala Ser Glu Asn Ser Ser Ala Ala His Ser
                805                 810                 815

Ile Gly Ser Thr Gln Ser Thr Pro Cys Ser Ser Ser Thr Ala
            820                 825                 830

<210> SEQ ID NO 3126
<211> LENGTH: 830
<212> TYPE: PRT
<213> ORGANISM: Homo sapiens

<400> SEQUENCE: 3126

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
                20                  25                  30

Ala Ser Arg Gly Thr Thr Gly Leu Pro Gln Glu Val His Val Leu Asn
            35                  40                  45

```
Leu Arg Thr Ala Gly Gln Gly Pro Gly Gln Leu Gln Arg Glu Val Thr
 50                  55                  60

Leu His Leu Asn Pro Ile Ser Ser Val His Ile His Lys Ser Val
 65                  70                  75                  80

Val Phe Leu Leu Asn Ser Pro His Pro Leu Val Trp His Leu Lys Thr
                     85                  90                  95

Glu Arg Leu Ala Thr Gly Val Ser Arg Leu Phe Leu Val Ser Glu Gly
                100                 105                 110

Ser Val Val Gln Phe Ser Ser Ala Asn Phe Ser Leu Thr Ala Glu Thr
             115                 120                 125

Glu Glu Arg Asn Phe Pro His Gly Asn Glu His Leu Leu Asn Trp Ala
         130                 135                 140

Arg Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Lys
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Met Ser Ser Gln Pro Gln
        195                 200                 205

Asn Glu Glu Val His Ile Ile Glu Leu Ile Thr Pro Asn Ser Asn Pro
210                 215                 220

Tyr Ser Ala Phe Gln Val Asp Ile Thr Ile Asp Ile Arg Pro Ser Gln
225                 230                 235                 240

Glu Asp Leu Glu Val Val Lys Asn Leu Ile Leu Ile Leu Lys Cys Lys
                245                 250                 255

Lys Ser Val Asn Trp Val Ile Lys Ser Phe Asp Val Lys Gly Ser Leu
            260                 265                 270

Lys Ile Ile Ala Pro Asn Ser Ile Gly Phe Gly Lys Glu Ser Glu Arg
        275                 280                 285

Ser Met Thr Met Thr Lys Ser Ile Arg Asp Asp Ile Pro Ser Thr Gln
    290                 295                 300

Gly Asn Leu Val Lys Trp Ala Leu Asp Asn Gly Tyr Ser Pro Ile Thr
305                 310                 315                 320

Ser Tyr Thr Met Ala Pro Val Ala Asn Arg Phe His Leu Arg Leu Glu
                325                 330                 335

Asn Asn Glu Glu Met Gly Asp Glu Glu Val His Thr Ile Pro Pro Glu
            340                 345                 350

Leu Arg Ile Leu Leu Asp Pro Gly Ala Leu Pro Ala Leu Gln Asn Pro
        355                 360                 365

Pro Ile Arg Gly Gly Glu Gly Gln Asn Gly Leu Pro Phe Pro Phe
370                 375                 380

Pro Asp Ile Ser Arg Arg Val Trp Asn Glu Glu Gly Glu Asp Gly Leu
385                 390                 395                 400

Pro Arg Pro Lys Asp Pro Val Ile Pro Ser Ile Gln Leu Phe Pro Gly
                405                 410                 415

Leu Arg Glu Pro Glu Glu Val Gln Gly Ser Val Asp Ile Ala Leu Ser
            420                 425                 430

Val Lys Cys Asp Asn Glu Lys Met Ile Val Ala Val Glu Lys Asp Ser
        435                 440                 445

Phe Gln Ala Ser Gly Tyr Ser Gly Met Asp Val Thr Leu Leu Asp Pro
    450                 455                 460
```

-continued

Thr Cys Lys Ala Lys Met Asn Gly Thr His Phe Val Leu Glu Ser Pro
465                 470                 475                 480

Leu Asn Gly Cys Gly Thr Arg Pro Arg Trp Ser Ala Leu Asp Gly Val
            485                 490                 495

Val Tyr Tyr Asn Ser Ile Val Ile Gln Val Pro Ala Leu Gly Asp Ser
                500                 505                 510

Ser Gly Trp Pro Asp Gly Tyr Glu Asp Leu Glu Ser Gly Asp Asn Gly
        515                 520                 525

Phe Pro Gly Asp Met Asp Glu Gly Asp Ala Ser Leu Phe Thr Arg Pro
    530                 535                 540

Glu Ile Val Val Phe Asn Cys Ser Leu Gln Gln Val Arg Asn Pro Ser
545                 550                 555                 560

Ser Phe Gln Glu Gln Pro His Gly Asn Ile Thr Phe Asn Met Glu Leu
            565                 570                 575

Tyr Asn Thr Asp Leu Phe Leu Val Pro Ser Gln Gly Val Phe Ser Val
                580                 585                 590

Pro Glu Asn Gly His Val Tyr Val Glu Val Ser Val Thr Lys Ala Glu
        595                 600                 605

Gln Glu Leu Gly Phe Ala Ile Gln Thr Cys Phe Ile Ser Pro Tyr Ser
    610                 615                 620

Asn Pro Asp Arg Met Ser His Tyr Thr Ile Ile Glu Asn Ile Cys Pro
625                 630                 635                 640

Lys Asp Glu Ser Val Lys Phe Tyr Ser Pro Lys Arg Val His Phe Pro
            645                 650                 655

Ile Pro Gln Ala Asp Met Asp Lys Lys Arg Phe Ser Phe Val Phe Lys
                660                 665                 670

Pro Val Phe Asn Thr Ser Leu Leu Phe Leu Gln Cys Glu Leu Thr Leu
        675                 680                 685

Cys Thr Lys Met Glu Lys His Pro Gln Lys Leu Pro Lys Cys Val Pro
    690                 695                 700

Pro Asp Glu Ala Cys Thr Ser Leu Asp Ala Ser Ile Ile Trp Ala Met
705                 710                 715                 720

Met Gln Asn Lys Lys Thr Phe Thr Lys Pro Leu Ala Val Ile His His
            725                 730                 735

Glu Ala Glu Ser Lys Glu Lys Gly Pro Ser Met Lys Glu Pro Asn Pro
                740                 745                 750

Ile Ser Pro Pro Ile Phe His Gly Leu Asp Thr Leu Thr Val Met Gly
        755                 760                 765

Ile Ala Phe Ala Ala Phe Val Ile Gly Ala Leu Leu Thr Gly Ala Leu
    770                 775                 780

Trp Tyr Ile Tyr Ser His Thr Gly Glu Thr Ala Gly Arg Gln Gln Val
785                 790                 795                 800

Pro Thr Ser Pro Pro Ala Ser Glu Asn Ser Ser Ala Ala His Ser Ile
            805                 810                 815

Gly Ser Thr Gln Ser Thr Pro Cys Ser Ser Ser Thr Ala
                820                 825                 830

<210> SEQ ID NO 3127

<400> SEQUENCE: 3127

000

<210> SEQ ID NO 3128

<400> SEQUENCE: 3128

000

<210> SEQ ID NO 3129

<400> SEQUENCE: 3129

000

<210> SEQ ID NO 3130

<400> SEQUENCE: 3130

000

<210> SEQ ID NO 3131

<400> SEQUENCE: 3131

000

<210> SEQ ID NO 3132

<400> SEQUENCE: 3132

000

<210> SEQ ID NO 3133

<400> SEQUENCE: 3133

000

<210> SEQ ID NO 3134

<400> SEQUENCE: 3134

000

<210> SEQ ID NO 3135

<400> SEQUENCE: 3135

000

<210> SEQ ID NO 3136

<400> SEQUENCE: 3136

000

<210> SEQ ID NO 3137

<400> SEQUENCE: 3137

000

<210> SEQ ID NO 3138

<400> SEQUENCE: 3138

000

<210> SEQ ID NO 3139

<400> SEQUENCE: 3139

000

<210> SEQ ID NO 3140

<400> SEQUENCE: 3140

000

<210> SEQ ID NO 3141

<400> SEQUENCE: 3141

000

<210> SEQ ID NO 3142

<400> SEQUENCE: 3142

000

<210> SEQ ID NO 3143

<400> SEQUENCE: 3143

000

<210> SEQ ID NO 3144

<400> SEQUENCE: 3144

000

<210> SEQ ID NO 3145

<400> SEQUENCE: 3145

000

<210> SEQ ID NO 3146

<400> SEQUENCE: 3146

000

<210> SEQ ID NO 3147

<400> SEQUENCE: 3147

000

<210> SEQ ID NO 3148

<400> SEQUENCE: 3148

000

<210> SEQ ID NO 3149

<400> SEQUENCE: 3149

000

<210> SEQ ID NO 3150

<400> SEQUENCE: 3150

000

```
<210> SEQ ID NO 3151
<400> SEQUENCE: 3151
000

<210> SEQ ID NO 3152
<400> SEQUENCE: 3152
000

<210> SEQ ID NO 3153
<400> SEQUENCE: 3153
000

<210> SEQ ID NO 3154
<400> SEQUENCE: 3154
000

<210> SEQ ID NO 3155
<400> SEQUENCE: 3155
000

<210> SEQ ID NO 3156
<400> SEQUENCE: 3156
000

<210> SEQ ID NO 3157
<400> SEQUENCE: 3157
000

<210> SEQ ID NO 3158
<400> SEQUENCE: 3158
000

<210> SEQ ID NO 3159
<400> SEQUENCE: 3159
000

<210> SEQ ID NO 3160
<400> SEQUENCE: 3160
000

<210> SEQ ID NO 3161
<400> SEQUENCE: 3161
000

<210> SEQ ID NO 3162
```

<400> SEQUENCE: 3162

000

<210> SEQ ID NO 3163

<400> SEQUENCE: 3163

000

<210> SEQ ID NO 3164

<400> SEQUENCE: 3164

000

<210> SEQ ID NO 3165

<400> SEQUENCE: 3165

000

<210> SEQ ID NO 3166

<400> SEQUENCE: 3166

000

<210> SEQ ID NO 3167

<400> SEQUENCE: 3167

000

<210> SEQ ID NO 3168

<400> SEQUENCE: 3168

000

<210> SEQ ID NO 3169

<400> SEQUENCE: 3169

000

<210> SEQ ID NO 3170

<400> SEQUENCE: 3170

000

<210> SEQ ID NO 3171

<400> SEQUENCE: 3171

000

<210> SEQ ID NO 3172

<400> SEQUENCE: 3172

000

<210> SEQ ID NO 3173

<400> SEQUENCE: 3173

000

<210> SEQ ID NO 3174
<400> SEQUENCE: 3174
000

<210> SEQ ID NO 3175
<400> SEQUENCE: 3175
000

<210> SEQ ID NO 3176
<400> SEQUENCE: 3176
000

<210> SEQ ID NO 3177
<400> SEQUENCE: 3177
000

<210> SEQ ID NO 3178
<400> SEQUENCE: 3178
000

<210> SEQ ID NO 3179
<400> SEQUENCE: 3179
000

<210> SEQ ID NO 3180
<400> SEQUENCE: 3180
000

<210> SEQ ID NO 3181
<400> SEQUENCE: 3181
000

<210> SEQ ID NO 3182
<400> SEQUENCE: 3182
000

<210> SEQ ID NO 3183
<400> SEQUENCE: 3183
000

<210> SEQ ID NO 3184
<400> SEQUENCE: 3184
000

<210> SEQ ID NO 3185

<400> SEQUENCE: 3185

000

<210> SEQ ID NO 3186

<400> SEQUENCE: 3186

000

<210> SEQ ID NO 3187

<400> SEQUENCE: 3187

000

<210> SEQ ID NO 3188

<400> SEQUENCE: 3188

000

<210> SEQ ID NO 3189

<400> SEQUENCE: 3189

000

<210> SEQ ID NO 3190

<400> SEQUENCE: 3190

000

<210> SEQ ID NO 3191

<400> SEQUENCE: 3191

000

<210> SEQ ID NO 3192
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (330)..(330)
<223> OTHER INFORMATION: /replace=" "
<220> FEATURE:
<221> NAME/KEY: SITE
<222> LOCATION: (1)..(481)
<223> OTHER INFORMATION: /note="Variant residues given in the sequence have no preference with respect to those in the annotations for variant positions"

<400> SEQUENCE: 3192

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                 85                  90                  95
Arg Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
210                 215                 220
Gln Pro Arg Glu Pro Gln Val Cys Thr Leu Pro Pro Ser Arg Glu Glu
225                 230                 235                 240
Met Thr Lys Asn Gln Val Ser Leu Ser Cys Ala Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Val Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys Gly Gly Gly Gly Ser Gly
                325                 330                 335
Gly Gly Gly Ser Gly Gly Gly Ser Ile Pro Pro His Val Gln Lys
                340                 345                 350
Ser Val Asn Asn Asp Met Ile Val Thr Asp Asn Asn Gly Ala Val Lys
                355                 360                 365
Phe Pro Gln Leu Cys Lys Phe Cys Asp Val Arg Phe Ser Thr Cys Asp
                370                 375                 380
Asn Gln Lys Ser Cys Met Ser Asn Cys Ser Ile Thr Ser Ile Cys Glu
385                 390                 395                 400
Lys Pro Gln Glu Val Cys Val Ala Val Trp Arg Lys Asn Asp Glu Asn
                405                 410                 415
Ile Thr Leu Glu Thr Val Cys His Asp Pro Lys Leu Pro Tyr His Asp
                420                 425                 430
Phe Ile Leu Glu Asp Ala Ala Ser Pro Lys Cys Ile Met Lys Glu Lys
                435                 440                 445
Lys Lys Pro Gly Glu Thr Phe Phe Met Cys Ser Cys Ser Ser Asp Glu
                450                 455                 460
```

```
Cys Asn Asp Asn Ile Ile Phe Ser Glu Glu Tyr Asn Thr Ser Asn Pro
465                 470                 475                 480

Asp

<210> SEQ ID NO 3193
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (330)..(330)
<223> OTHER INFORMATION: /replace=" "
<220> FEATURE:
<221> NAME/KEY: SITE
<222> LOCATION: (1)..(481)
<223> OTHER INFORMATION: /note="Variant residues given in the sequence
      have no preference with respect to those in the annotations
      for variant positions"

<400> SEQUENCE: 3193

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Gly Gly Gly Ser Gly
            325                 330                 335

Gly Gly Gly Ser Gly Gly Gly Ser Ile Pro Pro His Val Gln Lys
            340                 345                 350

Ser Val Asn Asn Asp Met Ile Val Thr Asp Asn Asn Gly Ala Val Lys
            355                 360                 365

Phe Pro Gln Leu Cys Lys Phe Cys Asp Val Arg Phe Ser Thr Cys Asp
370                 375                 380

Asn Gln Lys Ser Cys Met Ser Asn Cys Ser Ile Thr Ser Ile Cys Glu
385                 390                 395                 400

Lys Pro Gln Glu Val Cys Val Ala Val Trp Arg Lys Asn Asp Glu Asn
            405                 410                 415

Ile Thr Leu Glu Thr Val Cys His Asp Pro Lys Leu Pro Tyr His Asp
            420                 425                 430

Phe Ile Leu Glu Asp Ala Ala Ser Pro Lys Cys Ile Met Lys Glu Lys
435                 440                 445

Lys Lys Pro Gly Glu Thr Phe Phe Met Cys Ser Cys Ser Ser Asp Glu
            450                 455                 460

Cys Asn Asp Asn Ile Ile Phe Ser Glu Glu Tyr Asn Thr Ser Asn Pro
465                 470                 475                 480

Asp

<210> SEQ ID NO 3194
<211> LENGTH: 378
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (227)..(227)
<223> OTHER INFORMATION: /replace=" "
<220> FEATURE:
<221> NAME/KEY: SITE
<222> LOCATION: (1)..(378)
<223> OTHER INFORMATION: /note="Variant residues given in the sequence
      have no preference with respect to those in the annotations
      for variant positions"

<400> SEQUENCE: 3194

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

85                  90                  95
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Glu Glu Met Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Gly Gly Ser Gly Gly Gly Gly Ser Gly Gly Gly
225                 230                 235                 240

Gly Ser Ile Pro Pro His Val Gln Lys Ser Val Asn Asn Asp Met Ile
            245                 250                 255

Val Thr Asp Asn Asn Gly Ala Val Lys Phe Pro Gln Leu Cys Lys Phe
        260                 265                 270

Cys Asp Val Arg Phe Ser Thr Cys Asp Asn Gln Lys Ser Cys Met Ser
    275                 280                 285

Asn Cys Ser Ile Thr Ser Ile Cys Glu Lys Pro Gln Glu Val Cys Val
290                 295                 300

Ala Val Trp Arg Lys Asn Asp Glu Asn Ile Thr Leu Glu Thr Val Cys
305                 310                 315                 320

His Asp Pro Lys Leu Pro Tyr His Asp Phe Ile Leu Glu Asp Ala Ala
                325                 330                 335

Ser Pro Lys Cys Ile Met Lys Glu Lys Lys Pro Gly Glu Thr Phe Phe
            340                 345                 350

Phe Met Cys Ser Cys Ser Ser Asp Glu Cys Asn Asp Asn Ile Ile Phe
        355                 360                 365

Ser Glu Glu Tyr Asn Thr Ser Asn Pro Asp
    370                 375

<210> SEQ ID NO 3195
<211> LENGTH: 378
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (227)..(227)
<223> OTHER INFORMATION: /replace=" "
<220> FEATURE:
<221> NAME/KEY: SITE
<222> LOCATION: (1)..(378)
<223> OTHER INFORMATION: /note="Variant residues given in the sequence
      have no preference with respect to those in the annotations
      for variant positions"

<400> SEQUENCE: 3195

Asp Lys Thr His Thr Cys Pro Pro Cys Pro Ala Pro Glu Leu Leu Gly

```
              1               5                  10                 15
            Gly Pro Ser Val Phe Leu Phe Pro Pro Lys Pro Lys Asp Thr Leu Met
                           20                 25                 30
            Ile Ser Arg Thr Pro Glu Val Thr Cys Val Val Val Asp Val Ser His
                           35                 40                 45
            Glu Asp Pro Glu Val Lys Phe Asn Trp Tyr Val Asp Gly Val Glu Val
             50                 55                 60
            His Asn Ala Lys Thr Lys Pro Arg Glu Glu Gln Tyr Asn Ser Thr Tyr
             65                 70                 75                 80
            Arg Val Val Ser Val Leu Thr Val Leu His Gln Asp Trp Leu Asn Gly
                           85                 90                 95
            Lys Glu Tyr Lys Cys Lys Val Ser Asn Lys Ala Leu Pro Ala Pro Ile
                          100                105                110
            Glu Lys Thr Ile Ser Lys Ala Lys Gly Gln Pro Arg Glu Pro Gln Val
                          115                120                125
            Tyr Thr Leu Pro Pro Cys Arg Glu Glu Met Thr Lys Asn Gln Val Ser
                          130                135                140
            Leu Trp Cys Leu Val Lys Gly Phe Tyr Pro Ser Asp Ile Ala Val Glu
            145                150                155                160
            Trp Glu Ser Asn Gly Gln Pro Glu Asn Asn Tyr Lys Thr Thr Pro Pro
                          165                170                175
            Val Leu Asp Ser Asp Gly Ser Phe Phe Leu Tyr Ser Lys Leu Thr Val
                          180                185                190
            Asp Lys Ser Arg Trp Gln Gln Gly Asn Val Phe Ser Cys Ser Val Met
                          195                200                205
            His Glu Ala Leu His Asn His Tyr Thr Gln Lys Ser Leu Ser Leu Ser
                          210                215                220
            Pro Gly Lys Gly Gly Gly Ser Gly Gly Gly Ser Gly Gly Gly Gly Gly
            225                230                235                240
            Gly Ser Ile Pro Pro His Val Gln Lys Ser Val Asn Asn Asp Met Ile
                          245                250                255
            Val Thr Asp Asn Asn Gly Ala Val Lys Phe Pro Gln Leu Cys Lys Phe
                          260                265                270
            Cys Asp Val Arg Phe Ser Thr Cys Asp Asn Gln Lys Ser Cys Met Ser
                          275                280                285
            Asn Cys Ser Ile Thr Ser Ile Cys Glu Lys Pro Gln Glu Val Cys Val
                          290                295                300
            Ala Val Trp Arg Lys Asn Asp Glu Asn Ile Thr Leu Glu Thr Val Cys
            305                310                315                320
            His Asp Pro Lys Leu Pro Tyr His Asp Phe Ile Leu Glu Asp Ala Ala
                          325                330                335
            Ser Pro Lys Cys Ile Met Lys Glu Lys Lys Pro Gly Glu Thr Phe
                          340                345                350
            Phe Met Cys Ser Cys Ser Ser Asp Glu Cys Asn Asp Asn Ile Ile Phe
                          355                360                365
            Ser Glu Glu Tyr Asn Thr Ser Asn Pro Asp
                          370                375
```

<210> SEQ ID NO 3196
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:

-continued

```
      Synthetic polypeptide"
<220> FEATURE:
<221> NAME/KEY: VARIANT
<222> LOCATION: (481)..(481)
<223> OTHER INFORMATION: /replace=" "
<220> FEATURE:
<221> NAME/KEY: SITE
<222> LOCATION: (1)..(481)
<223> OTHER INFORMATION: /note="Variant residues given in the sequence
      have no preference with respect to those in the annotations
      for variant positions"

<400> SEQUENCE: 3196

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Arg Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350
```

```
Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Cys Thr
        370                 375                 380

Leu Pro Pro Ser Arg Glu Glu Met Thr Lys Asn Gln Val Ser Leu Ser
385                 390                 395                 400

Cys Ala Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Val Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 3197
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (481)..(481)
<223> OTHER INFORMATION: /replace=" "
<220> FEATURE:
<221> NAME/KEY: SITE
<222> LOCATION: (1)..(481)
<223> OTHER INFORMATION: /note="Variant residues given in the sequence
      have no preference with respect to those in the annotations
      for variant positions"

<400> SEQUENCE: 3197

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ala Ser Thr Lys Gly Pro Ser Val Phe
145                 150                 155                 160
```

```
Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Arg Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Cys Arg Glu Glu Met Thr Lys Asn Gln Val Ser Leu Trp
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 3198
<211> LENGTH: 257
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3198

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30
```

```
Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
    130                 135                 140

Gly Ser Gly Gly Gly Ser Gly Gln Pro Lys Ala Asn Pro Thr Val
145                 150                 155                 160

Thr Leu Phe Pro Pro Ser Ser Glu Glu Leu Gln Ala Asn Lys Ala Thr
                165                 170                 175

Leu Val Cys Leu Ile Ser Asp Phe Tyr Pro Gly Ala Val Thr Val Ala
            180                 185                 190

Trp Lys Ala Asp Gly Ser Pro Val Lys Ala Gly Val Glu Thr Thr Lys
            195                 200                 205

Pro Ser Lys Gln Ser Asn Asn Lys Tyr Ala Ala Ser Ser Tyr Leu Ser
    210                 215                 220

Leu Thr Pro Glu Gln Trp Lys Ser His Arg Ser Tyr Ser Cys Gln Val
225                 230                 235                 240

Thr His Glu Gly Ser Thr Val Glu Lys Thr Val Ala Pro Thr Glu Cys
                245                 250                 255

Ser
```

<210> SEQ ID NO 3199
<211> LENGTH: 258
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3199

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
```

```
                115                 120                 125
Glu Tyr Asn Thr Ser Asn Pro Asp Gly Gly Gly Ser Gly Gly
    130                 135                 140
Gly Ser Gly Gly Gly Ser Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
                195                 200                 205
Glu Gln Asp Ser Lys Asp Ser Thr Tyr Ser Leu Ser Ser Thr Leu Thr
210                 215                 220
Leu Ser Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
                245                 250                 255
Glu Cys
```

<210> SEQ ID NO 3200

<400> SEQUENCE: 3200

000

<210> SEQ ID NO 3201

<400> SEQUENCE: 3201

000

<210> SEQ ID NO 3202

<400> SEQUENCE: 3202

000

<210> SEQ ID NO 3203

<400> SEQUENCE: 3203

000

<210> SEQ ID NO 3204

<400> SEQUENCE: 3204

000

<210> SEQ ID NO 3205

<400> SEQUENCE: 3205

000

<210> SEQ ID NO 3206

<400> SEQUENCE: 3206

000

<210> SEQ ID NO 3207

<400> SEQUENCE: 3207

000

<210> SEQ ID NO 3208

<400> SEQUENCE: 3208

000

<210> SEQ ID NO 3209

<400> SEQUENCE: 3209

000

<210> SEQ ID NO 3210

<400> SEQUENCE: 3210

000

<210> SEQ ID NO 3211

<400> SEQUENCE: 3211

000

<210> SEQ ID NO 3212

<400> SEQUENCE: 3212

000

<210> SEQ ID NO 3213

<400> SEQUENCE: 3213

000

<210> SEQ ID NO 3214

<400> SEQUENCE: 3214

000

<210> SEQ ID NO 3215

<400> SEQUENCE: 3215

000

<210> SEQ ID NO 3216

<400> SEQUENCE: 3216

000

<210> SEQ ID NO 3217

<400> SEQUENCE: 3217

000

<210> SEQ ID NO 3218

<400> SEQUENCE: 3218

000

<210> SEQ ID NO 3219

<400> SEQUENCE: 3219

000

<210> SEQ ID NO 3220

<400> SEQUENCE: 3220

000

<210> SEQ ID NO 3221

<400> SEQUENCE: 3221

000

<210> SEQ ID NO 3222

<400> SEQUENCE: 3222

000

<210> SEQ ID NO 3223

<400> SEQUENCE: 3223

000

<210> SEQ ID NO 3224

<400> SEQUENCE: 3224

000

<210> SEQ ID NO 3225

<400> SEQUENCE: 3225

000

<210> SEQ ID NO 3226

<400> SEQUENCE: 3226

000

<210> SEQ ID NO 3227

<400> SEQUENCE: 3227

000

<210> SEQ ID NO 3228

<400> SEQUENCE: 3228

000

<210> SEQ ID NO 3229

<400> SEQUENCE: 3229

000

-continued

<210> SEQ ID NO 3230

<400> SEQUENCE: 3230

000

<210> SEQ ID NO 3231

<400> SEQUENCE: 3231

000

<210> SEQ ID NO 3232

<400> SEQUENCE: 3232

000

<210> SEQ ID NO 3233

<400> SEQUENCE: 3233

000

<210> SEQ ID NO 3234

<400> SEQUENCE: 3234

000

<210> SEQ ID NO 3235

<400> SEQUENCE: 3235

000

<210> SEQ ID NO 3236

<400> SEQUENCE: 3236

000

<210> SEQ ID NO 3237

<400> SEQUENCE: 3237

000

<210> SEQ ID NO 3238

<400> SEQUENCE: 3238

000

<210> SEQ ID NO 3239

<400> SEQUENCE: 3239

000

<210> SEQ ID NO 3240

<400> SEQUENCE: 3240

000

-continued

<210> SEQ ID NO 3241

<400> SEQUENCE: 3241

000

<210> SEQ ID NO 3242

<400> SEQUENCE: 3242

000

<210> SEQ ID NO 3243

<400> SEQUENCE: 3243

000

<210> SEQ ID NO 3244

<400> SEQUENCE: 3244

000

<210> SEQ ID NO 3245

<400> SEQUENCE: 3245

000

<210> SEQ ID NO 3246

<400> SEQUENCE: 3246

000

<210> SEQ ID NO 3247

<400> SEQUENCE: 3247

000

<210> SEQ ID NO 3248

<400> SEQUENCE: 3248

000

<210> SEQ ID NO 3249

<400> SEQUENCE: 3249

000

<210> SEQ ID NO 3250

<400> SEQUENCE: 3250

000

<210> SEQ ID NO 3251

<400> SEQUENCE: 3251

000

<210> SEQ ID NO 3252

<400> SEQUENCE: 3252

000

<210> SEQ ID NO 3253

<400> SEQUENCE: 3253

000

<210> SEQ ID NO 3254

<400> SEQUENCE: 3254

000

<210> SEQ ID NO 3255

<400> SEQUENCE: 3255

000

<210> SEQ ID NO 3256

<400> SEQUENCE: 3256

000

<210> SEQ ID NO 3257

<400> SEQUENCE: 3257

000

<210> SEQ ID NO 3258

<400> SEQUENCE: 3258

000

<210> SEQ ID NO 3259

<400> SEQUENCE: 3259

000

<210> SEQ ID NO 3260

<400> SEQUENCE: 3260

000

<210> SEQ ID NO 3261

<400> SEQUENCE: 3261

000

<210> SEQ ID NO 3262

<400> SEQUENCE: 3262

000

<210> SEQ ID NO 3263

<400> SEQUENCE: 3263

000

<210> SEQ ID NO 3264

<400> SEQUENCE: 3264

000

<210> SEQ ID NO 3265

<400> SEQUENCE: 3265

000

<210> SEQ ID NO 3266

<400> SEQUENCE: 3266

000

<210> SEQ ID NO 3267

<400> SEQUENCE: 3267

000

<210> SEQ ID NO 3268

<400> SEQUENCE: 3268

000

<210> SEQ ID NO 3269

<400> SEQUENCE: 3269

000

<210> SEQ ID NO 3270

<400> SEQUENCE: 3270

000

<210> SEQ ID NO 3271

<400> SEQUENCE: 3271

000

<210> SEQ ID NO 3272

<400> SEQUENCE: 3272

000

<210> SEQ ID NO 3273

<400> SEQUENCE: 3273

000

<210> SEQ ID NO 3274

<400> SEQUENCE: 3274

000

-continued

<210> SEQ ID NO 3275
<400> SEQUENCE: 3275
000

<210> SEQ ID NO 3276
<400> SEQUENCE: 3276
000

<210> SEQ ID NO 3277
<400> SEQUENCE: 3277
000

<210> SEQ ID NO 3278
<400> SEQUENCE: 3278
000

<210> SEQ ID NO 3279
<400> SEQUENCE: 3279
000

<210> SEQ ID NO 3280
<400> SEQUENCE: 3280
000

<210> SEQ ID NO 3281
<400> SEQUENCE: 3281
000

<210> SEQ ID NO 3282
<400> SEQUENCE: 3282
000

<210> SEQ ID NO 3283
<400> SEQUENCE: 3283
000

<210> SEQ ID NO 3284
<400> SEQUENCE: 3284
000

<210> SEQ ID NO 3285
<400> SEQUENCE: 3285
000

<210> SEQ ID NO 3286

-continued

<210> SEQ ID NO 3286

<400> SEQUENCE: 3286

000

<210> SEQ ID NO 3287

<400> SEQUENCE: 3287

000

<210> SEQ ID NO 3288

<400> SEQUENCE: 3288

000

<210> SEQ ID NO 3289

<400> SEQUENCE: 3289

000

<210> SEQ ID NO 3290

<400> SEQUENCE: 3290

000

<210> SEQ ID NO 3291

<400> SEQUENCE: 3291

000

<210> SEQ ID NO 3292

<400> SEQUENCE: 3292

000

<210> SEQ ID NO 3293

<400> SEQUENCE: 3293

000

<210> SEQ ID NO 3294

<400> SEQUENCE: 3294

000

<210> SEQ ID NO 3295

<400> SEQUENCE: 3295

000

<210> SEQ ID NO 3296

<400> SEQUENCE: 3296

000

<210> SEQ ID NO 3297

<400> SEQUENCE: 3297

-continued

000

<210> SEQ ID NO 3298
<400> SEQUENCE: 3298
000

<210> SEQ ID NO 3299
<400> SEQUENCE: 3299
000

<210> SEQ ID NO 3300
<400> SEQUENCE: 3300
000

<210> SEQ ID NO 3301
<400> SEQUENCE: 3301
000

<210> SEQ ID NO 3302
<400> SEQUENCE: 3302
000

<210> SEQ ID NO 3303
<400> SEQUENCE: 3303
000

<210> SEQ ID NO 3304
<400> SEQUENCE: 3304
000

<210> SEQ ID NO 3305
<400> SEQUENCE: 3305
000

<210> SEQ ID NO 3306
<400> SEQUENCE: 3306
000

<210> SEQ ID NO 3307
<400> SEQUENCE: 3307
000

<210> SEQ ID NO 3308
<400> SEQUENCE: 3308
000

-continued

<210> SEQ ID NO 3309

<400> SEQUENCE: 3309

000

<210> SEQ ID NO 3310

<400> SEQUENCE: 3310

000

<210> SEQ ID NO 3311

<400> SEQUENCE: 3311

000

<210> SEQ ID NO 3312

<400> SEQUENCE: 3312

000

<210> SEQ ID NO 3313

<400> SEQUENCE: 3313

000

<210> SEQ ID NO 3314

<400> SEQUENCE: 3314

000

<210> SEQ ID NO 3315

<400> SEQUENCE: 3315

000

<210> SEQ ID NO 3316

<400> SEQUENCE: 3316

000

<210> SEQ ID NO 3317

<400> SEQUENCE: 3317

000

<210> SEQ ID NO 3318

<400> SEQUENCE: 3318

000

<210> SEQ ID NO 3319

<400> SEQUENCE: 3319

000

```
<210> SEQ ID NO 3320
<400> SEQUENCE: 3320
000

<210> SEQ ID NO 3321
<400> SEQUENCE: 3321
000

<210> SEQ ID NO 3322
<400> SEQUENCE: 3322
000

<210> SEQ ID NO 3323
<400> SEQUENCE: 3323
000

<210> SEQ ID NO 3324
<400> SEQUENCE: 3324
000

<210> SEQ ID NO 3325
<400> SEQUENCE: 3325
000

<210> SEQ ID NO 3326
<400> SEQUENCE: 3326
000

<210> SEQ ID NO 3327
<400> SEQUENCE: 3327
000

<210> SEQ ID NO 3328
<400> SEQUENCE: 3328
000

<210> SEQ ID NO 3329
<400> SEQUENCE: 3329
000

<210> SEQ ID NO 3330
<400> SEQUENCE: 3330
000

<210> SEQ ID NO 3331
```

<400> SEQUENCE: 3331

000

<210> SEQ ID NO 3332

<400> SEQUENCE: 3332

000

<210> SEQ ID NO 3333

<400> SEQUENCE: 3333

000

<210> SEQ ID NO 3334

<400> SEQUENCE: 3334

000

<210> SEQ ID NO 3335

<400> SEQUENCE: 3335

000

<210> SEQ ID NO 3336

<400> SEQUENCE: 3336

000

<210> SEQ ID NO 3337

<400> SEQUENCE: 3337

000

<210> SEQ ID NO 3338

<400> SEQUENCE: 3338

000

<210> SEQ ID NO 3339

<400> SEQUENCE: 3339

000

<210> SEQ ID NO 3340

<400> SEQUENCE: 3340

000

<210> SEQ ID NO 3341

<400> SEQUENCE: 3341

000

<210> SEQ ID NO 3342

<400> SEQUENCE: 3342

000

<210> SEQ ID NO 3343
<400> SEQUENCE: 3343
000

<210> SEQ ID NO 3344
<400> SEQUENCE: 3344
000

<210> SEQ ID NO 3345
<400> SEQUENCE: 3345
000

<210> SEQ ID NO 3346
<400> SEQUENCE: 3346
000

<210> SEQ ID NO 3347
<400> SEQUENCE: 3347
000

<210> SEQ ID NO 3348
<400> SEQUENCE: 3348
000

<210> SEQ ID NO 3349
<400> SEQUENCE: 3349
000

<210> SEQ ID NO 3350
<400> SEQUENCE: 3350
000

<210> SEQ ID NO 3351
<400> SEQUENCE: 3351
000

<210> SEQ ID NO 3352
<400> SEQUENCE: 3352
000

<210> SEQ ID NO 3353
<400> SEQUENCE: 3353
000

<210> SEQ ID NO 3354

<400> SEQUENCE: 3354

000

<210> SEQ ID NO 3355

<400> SEQUENCE: 3355

000

<210> SEQ ID NO 3356

<400> SEQUENCE: 3356

000

<210> SEQ ID NO 3357

<400> SEQUENCE: 3357

000

<210> SEQ ID NO 3358

<400> SEQUENCE: 3358

000

<210> SEQ ID NO 3359

<400> SEQUENCE: 3359

000

<210> SEQ ID NO 3360

<400> SEQUENCE: 3360

000

<210> SEQ ID NO 3361

<400> SEQUENCE: 3361

000

<210> SEQ ID NO 3362

<400> SEQUENCE: 3362

000

<210> SEQ ID NO 3363

<400> SEQUENCE: 3363

000

<210> SEQ ID NO 3364

<400> SEQUENCE: 3364

000

<210> SEQ ID NO 3365

<400> SEQUENCE: 3365

000

<210> SEQ ID NO 3366

<400> SEQUENCE: 3366

000

<210> SEQ ID NO 3367

<400> SEQUENCE: 3367

000

<210> SEQ ID NO 3368

<400> SEQUENCE: 3368

000

<210> SEQ ID NO 3369

<400> SEQUENCE: 3369

000

<210> SEQ ID NO 3370

<400> SEQUENCE: 3370

000

<210> SEQ ID NO 3371

<400> SEQUENCE: 3371

000

<210> SEQ ID NO 3372

<400> SEQUENCE: 3372

000

<210> SEQ ID NO 3373

<400> SEQUENCE: 3373

000

<210> SEQ ID NO 3374

<400> SEQUENCE: 3374

000

<210> SEQ ID NO 3375

<400> SEQUENCE: 3375

000

<210> SEQ ID NO 3376

<400> SEQUENCE: 3376

000

<210> SEQ ID NO 3377

<400> SEQUENCE: 3377

000

<210> SEQ ID NO 3378

<400> SEQUENCE: 3378

000

<210> SEQ ID NO 3379

<400> SEQUENCE: 3379

000

<210> SEQ ID NO 3380

<400> SEQUENCE: 3380

000

<210> SEQ ID NO 3381

<400> SEQUENCE: 3381

000

<210> SEQ ID NO 3382

<400> SEQUENCE: 3382

000

<210> SEQ ID NO 3383

<400> SEQUENCE: 3383

000

<210> SEQ ID NO 3384

<400> SEQUENCE: 3384

000

<210> SEQ ID NO 3385

<400> SEQUENCE: 3385

000

<210> SEQ ID NO 3386

<400> SEQUENCE: 3386

000

<210> SEQ ID NO 3387

<400> SEQUENCE: 3387

000

<210> SEQ ID NO 3388

<400> SEQUENCE: 3388

000

<210> SEQ ID NO 3389

<400> SEQUENCE: 3389

000

<210> SEQ ID NO 3390

<400> SEQUENCE: 3390

000

<210> SEQ ID NO 3391

<400> SEQUENCE: 3391

000

<210> SEQ ID NO 3392

<400> SEQUENCE: 3392

000

<210> SEQ ID NO 3393

<400> SEQUENCE: 3393

000

<210> SEQ ID NO 3394

<400> SEQUENCE: 3394

000

<210> SEQ ID NO 3395

<400> SEQUENCE: 3395

000

<210> SEQ ID NO 3396

<400> SEQUENCE: 3396

000

<210> SEQ ID NO 3397

<400> SEQUENCE: 3397

000

<210> SEQ ID NO 3398

<400> SEQUENCE: 3398

000

<210> SEQ ID NO 3399

<400> SEQUENCE: 3399

000

<210> SEQ ID NO 3400

<400> SEQUENCE: 3400

000

<210> SEQ ID NO 3401

<400> SEQUENCE: 3401

000

<210> SEQ ID NO 3402

<400> SEQUENCE: 3402

000

<210> SEQ ID NO 3403

<400> SEQUENCE: 3403

000

<210> SEQ ID NO 3404

<400> SEQUENCE: 3404

000

<210> SEQ ID NO 3405

<400> SEQUENCE: 3405

000

<210> SEQ ID NO 3406

<400> SEQUENCE: 3406

000

<210> SEQ ID NO 3407

<400> SEQUENCE: 3407

000

<210> SEQ ID NO 3408

<400> SEQUENCE: 3408

000

<210> SEQ ID NO 3409

<400> SEQUENCE: 3409

000

<210> SEQ ID NO 3410

<400> SEQUENCE: 3410

000

<210> SEQ ID NO 3411

<400> SEQUENCE: 3411

000

<210> SEQ ID NO 3412

<400> SEQUENCE: 3412

000

<210> SEQ ID NO 3413

<400> SEQUENCE: 3413

000

<210> SEQ ID NO 3414

<400> SEQUENCE: 3414

000

<210> SEQ ID NO 3415

<400> SEQUENCE: 3415

000

<210> SEQ ID NO 3416

<400> SEQUENCE: 3416

000

<210> SEQ ID NO 3417

<400> SEQUENCE: 3417

000

<210> SEQ ID NO 3418

<400> SEQUENCE: 3418

000

<210> SEQ ID NO 3419

<400> SEQUENCE: 3419

000

<210> SEQ ID NO 3420

<400> SEQUENCE: 3420

000

<210> SEQ ID NO 3421

<400> SEQUENCE: 3421

000

<210> SEQ ID NO 3422

<400> SEQUENCE: 3422

000

<210> SEQ ID NO 3423

<400> SEQUENCE: 3423

000

<210> SEQ ID NO 3424

<400> SEQUENCE: 3424

000

<210> SEQ ID NO 3425

<400> SEQUENCE: 3425

000

<210> SEQ ID NO 3426

<400> SEQUENCE: 3426

000

<210> SEQ ID NO 3427

<400> SEQUENCE: 3427

000

<210> SEQ ID NO 3428

<400> SEQUENCE: 3428

000

<210> SEQ ID NO 3429

<400> SEQUENCE: 3429

000

<210> SEQ ID NO 3430

<400> SEQUENCE: 3430

000

<210> SEQ ID NO 3431

<400> SEQUENCE: 3431

000

<210> SEQ ID NO 3432

<400> SEQUENCE: 3432

000

<210> SEQ ID NO 3433

<400> SEQUENCE: 3433

000

<210> SEQ ID NO 3434

<400> SEQUENCE: 3434

000

<210> SEQ ID NO 3435

<400> SEQUENCE: 3435

000

<210> SEQ ID NO 3436

<400> SEQUENCE: 3436

000

<210> SEQ ID NO 3437

<400> SEQUENCE: 3437

000

<210> SEQ ID NO 3438

<400> SEQUENCE: 3438

000

<210> SEQ ID NO 3439

<400> SEQUENCE: 3439

000

<210> SEQ ID NO 3440

<400> SEQUENCE: 3440

000

<210> SEQ ID NO 3441

<400> SEQUENCE: 3441

000

<210> SEQ ID NO 3442

<400> SEQUENCE: 3442

000

<210> SEQ ID NO 3443

<400> SEQUENCE: 3443

000

<210> SEQ ID NO 3444

<400> SEQUENCE: 3444

000

<210> SEQ ID NO 3445

<400> SEQUENCE: 3445

000

<210> SEQ ID NO 3446

<400> SEQUENCE: 3446

000

<210> SEQ ID NO 3447

<400> SEQUENCE: 3447

000

<210> SEQ ID NO 3448

<400> SEQUENCE: 3448

000

<210> SEQ ID NO 3449

<400> SEQUENCE: 3449

000

<210> SEQ ID NO 3450

<400> SEQUENCE: 3450

000

<210> SEQ ID NO 3451

<400> SEQUENCE: 3451

000

<210> SEQ ID NO 3452

<400> SEQUENCE: 3452

000

<210> SEQ ID NO 3453

<400> SEQUENCE: 3453

000

<210> SEQ ID NO 3454

<400> SEQUENCE: 3454

000

<210> SEQ ID NO 3455

<400> SEQUENCE: 3455

000

<210> SEQ ID NO 3456

<400> SEQUENCE: 3456

000

<210> SEQ ID NO 3457

<400> SEQUENCE: 3457

000

<210> SEQ ID NO 3458

<400> SEQUENCE: 3458

000

<210> SEQ ID NO 3459

<400> SEQUENCE: 3459

000

<210> SEQ ID NO 3460

<400> SEQUENCE: 3460

000

<210> SEQ ID NO 3461

<400> SEQUENCE: 3461

000

<210> SEQ ID NO 3462

<400> SEQUENCE: 3462

000

<210> SEQ ID NO 3463

<400> SEQUENCE: 3463

000

<210> SEQ ID NO 3464

<400> SEQUENCE: 3464

000

<210> SEQ ID NO 3465

<400> SEQUENCE: 3465

000

<210> SEQ ID NO 3466

<400> SEQUENCE: 3466

000

<210> SEQ ID NO 3467

<400> SEQUENCE: 3467

000

<210> SEQ ID NO 3468

<400> SEQUENCE: 3468

000

<210> SEQ ID NO 3469

<400> SEQUENCE: 3469

000

<210> SEQ ID NO 3470

<400> SEQUENCE: 3470

000

<210> SEQ ID NO 3471

<400> SEQUENCE: 3471

000

<210> SEQ ID NO 3472

<400> SEQUENCE: 3472

000

<210> SEQ ID NO 3473

<400> SEQUENCE: 3473

000

<210> SEQ ID NO 3474

<400> SEQUENCE: 3474

000

<210> SEQ ID NO 3475

<400> SEQUENCE: 3475

000

<210> SEQ ID NO 3476

<400> SEQUENCE: 3476

000

<210> SEQ ID NO 3477

<400> SEQUENCE: 3477

000

```
<210> SEQ ID NO 3478
<400> SEQUENCE: 3478
000

<210> SEQ ID NO 3479
<400> SEQUENCE: 3479
000

<210> SEQ ID NO 3480
<400> SEQUENCE: 3480
000

<210> SEQ ID NO 3481
<400> SEQUENCE: 3481
000

<210> SEQ ID NO 3482
<400> SEQUENCE: 3482
000

<210> SEQ ID NO 3483
<400> SEQUENCE: 3483
000

<210> SEQ ID NO 3484
<400> SEQUENCE: 3484
000

<210> SEQ ID NO 3485
<400> SEQUENCE: 3485
000

<210> SEQ ID NO 3486
<400> SEQUENCE: 3486
000

<210> SEQ ID NO 3487
<400> SEQUENCE: 3487
000

<210> SEQ ID NO 3488
<400> SEQUENCE: 3488
000

<210> SEQ ID NO 3489
```

<400> SEQUENCE: 3489

000

<210> SEQ ID NO 3490

<400> SEQUENCE: 3490

000

<210> SEQ ID NO 3491

<400> SEQUENCE: 3491

000

<210> SEQ ID NO 3492

<400> SEQUENCE: 3492

000

<210> SEQ ID NO 3493

<400> SEQUENCE: 3493

000

<210> SEQ ID NO 3494

<400> SEQUENCE: 3494

000

<210> SEQ ID NO 3495

<400> SEQUENCE: 3495

000

<210> SEQ ID NO 3496

<400> SEQUENCE: 3496

000

<210> SEQ ID NO 3497

<400> SEQUENCE: 3497

000

<210> SEQ ID NO 3498

<400> SEQUENCE: 3498

000

<210> SEQ ID NO 3499

<400> SEQUENCE: 3499

000

<210> SEQ ID NO 3500

<400> SEQUENCE: 3500

000

<210> SEQ ID NO 3501

<400> SEQUENCE: 3501

000

<210> SEQ ID NO 3502

<400> SEQUENCE: 3502

000

<210> SEQ ID NO 3503

<400> SEQUENCE: 3503

000

<210> SEQ ID NO 3504

<400> SEQUENCE: 3504

000

<210> SEQ ID NO 3505

<400> SEQUENCE: 3505

000

<210> SEQ ID NO 3506

<400> SEQUENCE: 3506

000

<210> SEQ ID NO 3507

<400> SEQUENCE: 3507

000

<210> SEQ ID NO 3508

<400> SEQUENCE: 3508

000

<210> SEQ ID NO 3509

<400> SEQUENCE: 3509

000

<210> SEQ ID NO 3510

<400> SEQUENCE: 3510

000

<210> SEQ ID NO 3511

<400> SEQUENCE: 3511

000

<210> SEQ ID NO 3512

<400> SEQUENCE: 3512

000

<210> SEQ ID NO 3513

<400> SEQUENCE: 3513

000

<210> SEQ ID NO 3514

<400> SEQUENCE: 3514

000

<210> SEQ ID NO 3515

<400> SEQUENCE: 3515

000

<210> SEQ ID NO 3516

<400> SEQUENCE: 3516

000

<210> SEQ ID NO 3517

<400> SEQUENCE: 3517

000

<210> SEQ ID NO 3518

<400> SEQUENCE: 3518

000

<210> SEQ ID NO 3519

<400> SEQUENCE: 3519

000

<210> SEQ ID NO 3520

<400> SEQUENCE: 3520

000

<210> SEQ ID NO 3521

<400> SEQUENCE: 3521

000

<210> SEQ ID NO 3522

<400> SEQUENCE: 3522

000

<210> SEQ ID NO 3523

<400> SEQUENCE: 3523

000

<210> SEQ ID NO 3524

<400> SEQUENCE: 3524

000

<210> SEQ ID NO 3525

<400> SEQUENCE: 3525

000

<210> SEQ ID NO 3526

<400> SEQUENCE: 3526

000

<210> SEQ ID NO 3527

<400> SEQUENCE: 3527

000

<210> SEQ ID NO 3528

<400> SEQUENCE: 3528

000

<210> SEQ ID NO 3529

<400> SEQUENCE: 3529

000

<210> SEQ ID NO 3530

<400> SEQUENCE: 3530

000

<210> SEQ ID NO 3531

<400> SEQUENCE: 3531

000

<210> SEQ ID NO 3532

<400> SEQUENCE: 3532

000

<210> SEQ ID NO 3533

<400> SEQUENCE: 3533

000

<210> SEQ ID NO 3534

<400> SEQUENCE: 3534

000

<210> SEQ ID NO 3535

<400> SEQUENCE: 3535

000

<210> SEQ ID NO 3536

<400> SEQUENCE: 3536

000

<210> SEQ ID NO 3537

<400> SEQUENCE: 3537

000

<210> SEQ ID NO 3538

<400> SEQUENCE: 3538

000

<210> SEQ ID NO 3539

<400> SEQUENCE: 3539

000

<210> SEQ ID NO 3540

<400> SEQUENCE: 3540

000

<210> SEQ ID NO 3541

<400> SEQUENCE: 3541

000

<210> SEQ ID NO 3542

<400> SEQUENCE: 3542

000

<210> SEQ ID NO 3543

<400> SEQUENCE: 3543

000

<210> SEQ ID NO 3544

<400> SEQUENCE: 3544

000

<210> SEQ ID NO 3545

<400> SEQUENCE: 3545

000

```
<210> SEQ ID NO 3546
<400> SEQUENCE: 3546
000

<210> SEQ ID NO 3547
<400> SEQUENCE: 3547
000

<210> SEQ ID NO 3548
<400> SEQUENCE: 3548
000

<210> SEQ ID NO 3549
<400> SEQUENCE: 3549
000

<210> SEQ ID NO 3550
<400> SEQUENCE: 3550
000

<210> SEQ ID NO 3551
<400> SEQUENCE: 3551
000

<210> SEQ ID NO 3552
<400> SEQUENCE: 3552
000

<210> SEQ ID NO 3553
<400> SEQUENCE: 3553
000

<210> SEQ ID NO 3554
<400> SEQUENCE: 3554
000

<210> SEQ ID NO 3555
<400> SEQUENCE: 3555
000

<210> SEQ ID NO 3556
<400> SEQUENCE: 3556
000
```

<210> SEQ ID NO 3557

<400> SEQUENCE: 3557

000

<210> SEQ ID NO 3558

<400> SEQUENCE: 3558

000

<210> SEQ ID NO 3559

<400> SEQUENCE: 3559

000

<210> SEQ ID NO 3560

<400> SEQUENCE: 3560

000

<210> SEQ ID NO 3561

<400> SEQUENCE: 3561

000

<210> SEQ ID NO 3562

<400> SEQUENCE: 3562

000

<210> SEQ ID NO 3563

<400> SEQUENCE: 3563

000

<210> SEQ ID NO 3564

<400> SEQUENCE: 3564

000

<210> SEQ ID NO 3565

<400> SEQUENCE: 3565

000

<210> SEQ ID NO 3566

<400> SEQUENCE: 3566

000

<210> SEQ ID NO 3567

<400> SEQUENCE: 3567

000

<210> SEQ ID NO 3568

<400> SEQUENCE: 3568

000

<210> SEQ ID NO 3569

<400> SEQUENCE: 3569

000

<210> SEQ ID NO 3570

<400> SEQUENCE: 3570

000

<210> SEQ ID NO 3571

<400> SEQUENCE: 3571

000

<210> SEQ ID NO 3572

<400> SEQUENCE: 3572

000

<210> SEQ ID NO 3573

<400> SEQUENCE: 3573

000

<210> SEQ ID NO 3574

<400> SEQUENCE: 3574

000

<210> SEQ ID NO 3575

<400> SEQUENCE: 3575

000

<210> SEQ ID NO 3576

<400> SEQUENCE: 3576

000

<210> SEQ ID NO 3577

<400> SEQUENCE: 3577

000

<210> SEQ ID NO 3578

<400> SEQUENCE: 3578

000

<210> SEQ ID NO 3579

<400> SEQUENCE: 3579

000

<210> SEQ ID NO 3580

<400> SEQUENCE: 3580

000

<210> SEQ ID NO 3581

<400> SEQUENCE: 3581

000

<210> SEQ ID NO 3582

<400> SEQUENCE: 3582

000

<210> SEQ ID NO 3583

<400> SEQUENCE: 3583

000

<210> SEQ ID NO 3584

<400> SEQUENCE: 3584

000

<210> SEQ ID NO 3585

<400> SEQUENCE: 3585

000

<210> SEQ ID NO 3586

<400> SEQUENCE: 3586

000

<210> SEQ ID NO 3587

<400> SEQUENCE: 3587

000

<210> SEQ ID NO 3588

<400> SEQUENCE: 3588

000

<210> SEQ ID NO 3589

<400> SEQUENCE: 3589

000

<210> SEQ ID NO 3590

<400> SEQUENCE: 3590

000

<210> SEQ ID NO 3591

<400> SEQUENCE: 3591

000

<210> SEQ ID NO 3592

<400> SEQUENCE: 3592

000

<210> SEQ ID NO 3593

<400> SEQUENCE: 3593

000

<210> SEQ ID NO 3594

<400> SEQUENCE: 3594

000

<210> SEQ ID NO 3595

<400> SEQUENCE: 3595

000

<210> SEQ ID NO 3596

<400> SEQUENCE: 3596

000

<210> SEQ ID NO 3597

<400> SEQUENCE: 3597

000

<210> SEQ ID NO 3598

<400> SEQUENCE: 3598

000

<210> SEQ ID NO 3599

<400> SEQUENCE: 3599

000

<210> SEQ ID NO 3600

<400> SEQUENCE: 3600

000

<210> SEQ ID NO 3601

<400> SEQUENCE: 3601

000

<210> SEQ ID NO 3602

<400> SEQUENCE: 3602

000

<210> SEQ ID NO 3603

<400> SEQUENCE: 3603

000

<210> SEQ ID NO 3604

<400> SEQUENCE: 3604

000

<210> SEQ ID NO 3605

<400> SEQUENCE: 3605

000

<210> SEQ ID NO 3606

<400> SEQUENCE: 3606

000

<210> SEQ ID NO 3607

<400> SEQUENCE: 3607

000

<210> SEQ ID NO 3608

<400> SEQUENCE: 3608

000

<210> SEQ ID NO 3609

<400> SEQUENCE: 3609

000

<210> SEQ ID NO 3610

<400> SEQUENCE: 3610

000

<210> SEQ ID NO 3611

<400> SEQUENCE: 3611

000

<210> SEQ ID NO 3612

<400> SEQUENCE: 3612

000

<210> SEQ ID NO 3613

<400> SEQUENCE: 3613

000

<210> SEQ ID NO 3614
<400> SEQUENCE: 3614
000

<210> SEQ ID NO 3615
<400> SEQUENCE: 3615
000

<210> SEQ ID NO 3616
<400> SEQUENCE: 3616
000

<210> SEQ ID NO 3617
<400> SEQUENCE: 3617
000

<210> SEQ ID NO 3618
<400> SEQUENCE: 3618
000

<210> SEQ ID NO 3619
<400> SEQUENCE: 3619
000

<210> SEQ ID NO 3620
<400> SEQUENCE: 3620
000

<210> SEQ ID NO 3621
<400> SEQUENCE: 3621
000

<210> SEQ ID NO 3622
<400> SEQUENCE: 3622
000

<210> SEQ ID NO 3623
<400> SEQUENCE: 3623
000

<210> SEQ ID NO 3624
<400> SEQUENCE: 3624
000

<210> SEQ ID NO 3625

<400> SEQUENCE: 3625

000

<210> SEQ ID NO 3626

<400> SEQUENCE: 3626

000

<210> SEQ ID NO 3627

<400> SEQUENCE: 3627

000

<210> SEQ ID NO 3628

<400> SEQUENCE: 3628

000

<210> SEQ ID NO 3629

<400> SEQUENCE: 3629

000

<210> SEQ ID NO 3630

<400> SEQUENCE: 3630

000

<210> SEQ ID NO 3631

<400> SEQUENCE: 3631

000

<210> SEQ ID NO 3632

<400> SEQUENCE: 3632

000

<210> SEQ ID NO 3633

<400> SEQUENCE: 3633

000

<210> SEQ ID NO 3634

<400> SEQUENCE: 3634

000

<210> SEQ ID NO 3635

<400> SEQUENCE: 3635

000

<210> SEQ ID NO 3636

<400> SEQUENCE: 3636

000

<210> SEQ ID NO 3637

<400> SEQUENCE: 3637

000

<210> SEQ ID NO 3638

<400> SEQUENCE: 3638

000

<210> SEQ ID NO 3639

<400> SEQUENCE: 3639

000

<210> SEQ ID NO 3640

<400> SEQUENCE: 3640

000

<210> SEQ ID NO 3641

<400> SEQUENCE: 3641

000

<210> SEQ ID NO 3642

<400> SEQUENCE: 3642

000

<210> SEQ ID NO 3643

<400> SEQUENCE: 3643

000

<210> SEQ ID NO 3644

<400> SEQUENCE: 3644

000

<210> SEQ ID NO 3645

<400> SEQUENCE: 3645

000

<210> SEQ ID NO 3646

<400> SEQUENCE: 3646

000

<210> SEQ ID NO 3647

<400> SEQUENCE: 3647

000

<210> SEQ ID NO 3648

<400> SEQUENCE: 3648

000

<210> SEQ ID NO 3649

<400> SEQUENCE: 3649

000

<210> SEQ ID NO 3650

<400> SEQUENCE: 3650

000

<210> SEQ ID NO 3651

<400> SEQUENCE: 3651

000

<210> SEQ ID NO 3652

<400> SEQUENCE: 3652

000

<210> SEQ ID NO 3653

<400> SEQUENCE: 3653

000

<210> SEQ ID NO 3654

<400> SEQUENCE: 3654

000

<210> SEQ ID NO 3655

<400> SEQUENCE: 3655

000

<210> SEQ ID NO 3656

<400> SEQUENCE: 3656

000

<210> SEQ ID NO 3657

<400> SEQUENCE: 3657

000

<210> SEQ ID NO 3658

<400> SEQUENCE: 3658

000

<210> SEQ ID NO 3659

<400> SEQUENCE: 3659

000

<210> SEQ ID NO 3660

<400> SEQUENCE: 3660

000

<210> SEQ ID NO 3661

<400> SEQUENCE: 3661

000

<210> SEQ ID NO 3662

<400> SEQUENCE: 3662

000

<210> SEQ ID NO 3663

<400> SEQUENCE: 3663

000

<210> SEQ ID NO 3664

<400> SEQUENCE: 3664

000

<210> SEQ ID NO 3665

<400> SEQUENCE: 3665

000

<210> SEQ ID NO 3666

<400> SEQUENCE: 3666

000

<210> SEQ ID NO 3667

<400> SEQUENCE: 3667

000

<210> SEQ ID NO 3668

<400> SEQUENCE: 3668

000

<210> SEQ ID NO 3669

<400> SEQUENCE: 3669

000

<210> SEQ ID NO 3670

<400> SEQUENCE: 3670

000

<210> SEQ ID NO 3671

<400> SEQUENCE: 3671

000

<210> SEQ ID NO 3672

<400> SEQUENCE: 3672

000

<210> SEQ ID NO 3673

<400> SEQUENCE: 3673

000

<210> SEQ ID NO 3674

<400> SEQUENCE: 3674

000

<210> SEQ ID NO 3675

<400> SEQUENCE: 3675

000

<210> SEQ ID NO 3676

<400> SEQUENCE: 3676

000

<210> SEQ ID NO 3677

<400> SEQUENCE: 3677

000

<210> SEQ ID NO 3678

<400> SEQUENCE: 3678

000

<210> SEQ ID NO 3679

<400> SEQUENCE: 3679

000

<210> SEQ ID NO 3680

<400> SEQUENCE: 3680

000

<210> SEQ ID NO 3681

```
<400> SEQUENCE: 3681
000

<210> SEQ ID NO 3682
<400> SEQUENCE: 3682
000

<210> SEQ ID NO 3683
<400> SEQUENCE: 3683
000

<210> SEQ ID NO 3684
<400> SEQUENCE: 3684
000

<210> SEQ ID NO 3685
<400> SEQUENCE: 3685
000

<210> SEQ ID NO 3686
<400> SEQUENCE: 3686
000

<210> SEQ ID NO 3687
<400> SEQUENCE: 3687
000

<210> SEQ ID NO 3688
<400> SEQUENCE: 3688
000

<210> SEQ ID NO 3689
<400> SEQUENCE: 3689
000

<210> SEQ ID NO 3690
<400> SEQUENCE: 3690
000

<210> SEQ ID NO 3691
<400> SEQUENCE: 3691
000

<210> SEQ ID NO 3692
<400> SEQUENCE: 3692
```

000

<210> SEQ ID NO 3693

<400> SEQUENCE: 3693

000

<210> SEQ ID NO 3694

<400> SEQUENCE: 3694

000

<210> SEQ ID NO 3695

<400> SEQUENCE: 3695

000

<210> SEQ ID NO 3696

<400> SEQUENCE: 3696

000

<210> SEQ ID NO 3697

<400> SEQUENCE: 3697

000

<210> SEQ ID NO 3698

<400> SEQUENCE: 3698

000

<210> SEQ ID NO 3699

<400> SEQUENCE: 3699

000

<210> SEQ ID NO 3700

<400> SEQUENCE: 3700

000

<210> SEQ ID NO 3701

<400> SEQUENCE: 3701

000

<210> SEQ ID NO 3702

<400> SEQUENCE: 3702

000

<210> SEQ ID NO 3703

<400> SEQUENCE: 3703

000

<210> SEQ ID NO 3704

<400> SEQUENCE: 3704

000

<210> SEQ ID NO 3705

<400> SEQUENCE: 3705

000

<210> SEQ ID NO 3706

<400> SEQUENCE: 3706

000

<210> SEQ ID NO 3707

<400> SEQUENCE: 3707

000

<210> SEQ ID NO 3708

<400> SEQUENCE: 3708

000

<210> SEQ ID NO 3709

<400> SEQUENCE: 3709

000

<210> SEQ ID NO 3710

<400> SEQUENCE: 3710

000

<210> SEQ ID NO 3711

<400> SEQUENCE: 3711

000

<210> SEQ ID NO 3712

<400> SEQUENCE: 3712

000

<210> SEQ ID NO 3713

<400> SEQUENCE: 3713

000

<210> SEQ ID NO 3714

<400> SEQUENCE: 3714

000

<210> SEQ ID NO 3715

<400> SEQUENCE: 3715

000

<210> SEQ ID NO 3716

<400> SEQUENCE: 3716

000

<210> SEQ ID NO 3717

<400> SEQUENCE: 3717

000

<210> SEQ ID NO 3718

<400> SEQUENCE: 3718

000

<210> SEQ ID NO 3719

<400> SEQUENCE: 3719

000

<210> SEQ ID NO 3720

<400> SEQUENCE: 3720

000

<210> SEQ ID NO 3721

<400> SEQUENCE: 3721

000

<210> SEQ ID NO 3722

<400> SEQUENCE: 3722

000

<210> SEQ ID NO 3723

<400> SEQUENCE: 3723

000

<210> SEQ ID NO 3724

<400> SEQUENCE: 3724

000

<210> SEQ ID NO 3725

<400> SEQUENCE: 3725

000

<210> SEQ ID NO 3726

```
<400> SEQUENCE: 3726

000

<210> SEQ ID NO 3727

<400> SEQUENCE: 3727

000

<210> SEQ ID NO 3728

<400> SEQUENCE: 3728

000

<210> SEQ ID NO 3729

<400> SEQUENCE: 3729

000

<210> SEQ ID NO 3730

<400> SEQUENCE: 3730

000

<210> SEQ ID NO 3731

<400> SEQUENCE: 3731

000

<210> SEQ ID NO 3732

<400> SEQUENCE: 3732

000

<210> SEQ ID NO 3733

<400> SEQUENCE: 3733

000

<210> SEQ ID NO 3734

<400> SEQUENCE: 3734

000

<210> SEQ ID NO 3735

<400> SEQUENCE: 3735

000

<210> SEQ ID NO 3736

<400> SEQUENCE: 3736

000

<210> SEQ ID NO 3737

<400> SEQUENCE: 3737
```

000

<210> SEQ ID NO 3738

<400> SEQUENCE: 3738

000

<210> SEQ ID NO 3739

<400> SEQUENCE: 3739

000

<210> SEQ ID NO 3740

<400> SEQUENCE: 3740

000

<210> SEQ ID NO 3741

<400> SEQUENCE: 3741

000

<210> SEQ ID NO 3742

<400> SEQUENCE: 3742

000

<210> SEQ ID NO 3743

<400> SEQUENCE: 3743

000

<210> SEQ ID NO 3744

<400> SEQUENCE: 3744

000

<210> SEQ ID NO 3745

<400> SEQUENCE: 3745

000

<210> SEQ ID NO 3746

<400> SEQUENCE: 3746

000

<210> SEQ ID NO 3747

<400> SEQUENCE: 3747

000

<210> SEQ ID NO 3748

<400> SEQUENCE: 3748

000

<210> SEQ ID NO 3749

<400> SEQUENCE: 3749

000

<210> SEQ ID NO 3750

<400> SEQUENCE: 3750

000

<210> SEQ ID NO 3751

<400> SEQUENCE: 3751

000

<210> SEQ ID NO 3752

<400> SEQUENCE: 3752

000

<210> SEQ ID NO 3753

<400> SEQUENCE: 3753

000

<210> SEQ ID NO 3754

<400> SEQUENCE: 3754

000

<210> SEQ ID NO 3755

<400> SEQUENCE: 3755

000

<210> SEQ ID NO 3756

<400> SEQUENCE: 3756

000

<210> SEQ ID NO 3757

<400> SEQUENCE: 3757

000

<210> SEQ ID NO 3758

<400> SEQUENCE: 3758

000

<210> SEQ ID NO 3759

<400> SEQUENCE: 3759

000

<210> SEQ ID NO 3760

<400> SEQUENCE: 3760

000

<210> SEQ ID NO 3761

<400> SEQUENCE: 3761

000

<210> SEQ ID NO 3762

<400> SEQUENCE: 3762

000

<210> SEQ ID NO 3763

<400> SEQUENCE: 3763

000

<210> SEQ ID NO 3764

<400> SEQUENCE: 3764

000

<210> SEQ ID NO 3765

<400> SEQUENCE: 3765

000

<210> SEQ ID NO 3766

<400> SEQUENCE: 3766

000

<210> SEQ ID NO 3767

<400> SEQUENCE: 3767

000

<210> SEQ ID NO 3768

<400> SEQUENCE: 3768

000

<210> SEQ ID NO 3769

<400> SEQUENCE: 3769

000

<210> SEQ ID NO 3770

<400> SEQUENCE: 3770

000

<210> SEQ ID NO 3771

<400> SEQUENCE: 3771

000

<210> SEQ ID NO 3772

<400> SEQUENCE: 3772

000

<210> SEQ ID NO 3773

<400> SEQUENCE: 3773

000

<210> SEQ ID NO 3774

<400> SEQUENCE: 3774

000

<210> SEQ ID NO 3775

<400> SEQUENCE: 3775

000

<210> SEQ ID NO 3776

<400> SEQUENCE: 3776

000

<210> SEQ ID NO 3777

<400> SEQUENCE: 3777

000

<210> SEQ ID NO 3778

<400> SEQUENCE: 3778

000

<210> SEQ ID NO 3779

<400> SEQUENCE: 3779

000

<210> SEQ ID NO 3780

<400> SEQUENCE: 3780

000

<210> SEQ ID NO 3781

<400> SEQUENCE: 3781

000

<210> SEQ ID NO 3782

<400> SEQUENCE: 3782

000

<210> SEQ ID NO 3783

<400> SEQUENCE: 3783

000

<210> SEQ ID NO 3784

<400> SEQUENCE: 3784

000

<210> SEQ ID NO 3785

<400> SEQUENCE: 3785

000

<210> SEQ ID NO 3786

<400> SEQUENCE: 3786

000

<210> SEQ ID NO 3787

<400> SEQUENCE: 3787

000

<210> SEQ ID NO 3788

<400> SEQUENCE: 3788

000

<210> SEQ ID NO 3789

<400> SEQUENCE: 3789

000

<210> SEQ ID NO 3790

<400> SEQUENCE: 3790

000

<210> SEQ ID NO 3791

<400> SEQUENCE: 3791

000

<210> SEQ ID NO 3792

<400> SEQUENCE: 3792

000

<210> SEQ ID NO 3793

<400> SEQUENCE: 3793

000

<210> SEQ ID NO 3794

<400> SEQUENCE: 3794

000

<210> SEQ ID NO 3795

<400> SEQUENCE: 3795

000

<210> SEQ ID NO 3796

<400> SEQUENCE: 3796

000

<210> SEQ ID NO 3797

<400> SEQUENCE: 3797

000

<210> SEQ ID NO 3798

<400> SEQUENCE: 3798

000

<210> SEQ ID NO 3799

<400> SEQUENCE: 3799

000

<210> SEQ ID NO 3800

<400> SEQUENCE: 3800

000

<210> SEQ ID NO 3801

<400> SEQUENCE: 3801

000

<210> SEQ ID NO 3802

<400> SEQUENCE: 3802

000

<210> SEQ ID NO 3803

<400> SEQUENCE: 3803

000

<210> SEQ ID NO 3804

<400> SEQUENCE: 3804

000

<210> SEQ ID NO 3805

-continued

<400> SEQUENCE: 3805

000

<210> SEQ ID NO 3806

<400> SEQUENCE: 3806

000

<210> SEQ ID NO 3807

<400> SEQUENCE: 3807

000

<210> SEQ ID NO 3808

<400> SEQUENCE: 3808

000

<210> SEQ ID NO 3809

<400> SEQUENCE: 3809

000

<210> SEQ ID NO 3810

<400> SEQUENCE: 3810

000

<210> SEQ ID NO 3811

<400> SEQUENCE: 3811

000

<210> SEQ ID NO 3812

<400> SEQUENCE: 3812

000

<210> SEQ ID NO 3813

<400> SEQUENCE: 3813

000

<210> SEQ ID NO 3814

<400> SEQUENCE: 3814

000

<210> SEQ ID NO 3815

<400> SEQUENCE: 3815

000

<210> SEQ ID NO 3816

<400> SEQUENCE: 3816

000

<210> SEQ ID NO 3817

<400> SEQUENCE: 3817

000

<210> SEQ ID NO 3818

<400> SEQUENCE: 3818

000

<210> SEQ ID NO 3819

<400> SEQUENCE: 3819

000

<210> SEQ ID NO 3820

<400> SEQUENCE: 3820

000

<210> SEQ ID NO 3821

<400> SEQUENCE: 3821

000

<210> SEQ ID NO 3822

<400> SEQUENCE: 3822

000

<210> SEQ ID NO 3823

<400> SEQUENCE: 3823

000

<210> SEQ ID NO 3824

<400> SEQUENCE: 3824

000

<210> SEQ ID NO 3825

<400> SEQUENCE: 3825

000

<210> SEQ ID NO 3826

<400> SEQUENCE: 3826

000

<210> SEQ ID NO 3827

<400> SEQUENCE: 3827

000

<210> SEQ ID NO 3828

<400> SEQUENCE: 3828

000

<210> SEQ ID NO 3829

<400> SEQUENCE: 3829

000

<210> SEQ ID NO 3830

<400> SEQUENCE: 3830

000

<210> SEQ ID NO 3831

<400> SEQUENCE: 3831

000

<210> SEQ ID NO 3832

<400> SEQUENCE: 3832

000

<210> SEQ ID NO 3833

<400> SEQUENCE: 3833

000

<210> SEQ ID NO 3834

<400> SEQUENCE: 3834

000

<210> SEQ ID NO 3835

<400> SEQUENCE: 3835

000

<210> SEQ ID NO 3836

<400> SEQUENCE: 3836

000

<210> SEQ ID NO 3837

<400> SEQUENCE: 3837

000

<210> SEQ ID NO 3838

<400> SEQUENCE: 3838

000

<210> SEQ ID NO 3839

```
<400> SEQUENCE: 3839

000

<210> SEQ ID NO 3840

<400> SEQUENCE: 3840

000

<210> SEQ ID NO 3841

<400> SEQUENCE: 3841

000

<210> SEQ ID NO 3842

<400> SEQUENCE: 3842

000

<210> SEQ ID NO 3843

<400> SEQUENCE: 3843

000

<210> SEQ ID NO 3844

<400> SEQUENCE: 3844

000

<210> SEQ ID NO 3845

<400> SEQUENCE: 3845

000

<210> SEQ ID NO 3846

<400> SEQUENCE: 3846

000

<210> SEQ ID NO 3847

<400> SEQUENCE: 3847

000

<210> SEQ ID NO 3848

<400> SEQUENCE: 3848

000

<210> SEQ ID NO 3849

<400> SEQUENCE: 3849

000

<210> SEQ ID NO 3850

<400> SEQUENCE: 3850
```

000

<210> SEQ ID NO 3851

<400> SEQUENCE: 3851

000

<210> SEQ ID NO 3852

<400> SEQUENCE: 3852

000

<210> SEQ ID NO 3853

<400> SEQUENCE: 3853

000

<210> SEQ ID NO 3854

<400> SEQUENCE: 3854

000

<210> SEQ ID NO 3855

<400> SEQUENCE: 3855

000

<210> SEQ ID NO 3856

<400> SEQUENCE: 3856

000

<210> SEQ ID NO 3857

<400> SEQUENCE: 3857

000

<210> SEQ ID NO 3858

<400> SEQUENCE: 3858

000

<210> SEQ ID NO 3859

<400> SEQUENCE: 3859

000

<210> SEQ ID NO 3860

<400> SEQUENCE: 3860

000

<210> SEQ ID NO 3861

<400> SEQUENCE: 3861

000

<210> SEQ ID NO 3862

<400> SEQUENCE: 3862

000

<210> SEQ ID NO 3863

<400> SEQUENCE: 3863

000

<210> SEQ ID NO 3864

<400> SEQUENCE: 3864

000

<210> SEQ ID NO 3865

<400> SEQUENCE: 3865

000

<210> SEQ ID NO 3866

<400> SEQUENCE: 3866

000

<210> SEQ ID NO 3867

<400> SEQUENCE: 3867

000

<210> SEQ ID NO 3868

<400> SEQUENCE: 3868

000

<210> SEQ ID NO 3869

<400> SEQUENCE: 3869

000

<210> SEQ ID NO 3870

<400> SEQUENCE: 3870

000

<210> SEQ ID NO 3871

<400> SEQUENCE: 3871

000

<210> SEQ ID NO 3872

<400> SEQUENCE: 3872

000

<210> SEQ ID NO 3873

<400> SEQUENCE: 3873

000

<210> SEQ ID NO 3874

<400> SEQUENCE: 3874

000

<210> SEQ ID NO 3875

<400> SEQUENCE: 3875

000

<210> SEQ ID NO 3876

<400> SEQUENCE: 3876

000

<210> SEQ ID NO 3877

<400> SEQUENCE: 3877

000

<210> SEQ ID NO 3878

<400> SEQUENCE: 3878

000

<210> SEQ ID NO 3879

<400> SEQUENCE: 3879

000

<210> SEQ ID NO 3880

<400> SEQUENCE: 3880

000

<210> SEQ ID NO 3881

<400> SEQUENCE: 3881

000

<210> SEQ ID NO 3882

<400> SEQUENCE: 3882

000

<210> SEQ ID NO 3883

<400> SEQUENCE: 3883

000

<210> SEQ ID NO 3884

<400> SEQUENCE: 3884

000

<210> SEQ ID NO 3885

<400> SEQUENCE: 3885

000

<210> SEQ ID NO 3886

<400> SEQUENCE: 3886

000

<210> SEQ ID NO 3887

<400> SEQUENCE: 3887

000

<210> SEQ ID NO 3888

<400> SEQUENCE: 3888

000

<210> SEQ ID NO 3889

<400> SEQUENCE: 3889

000

<210> SEQ ID NO 3890

<400> SEQUENCE: 3890

000

<210> SEQ ID NO 3891

<400> SEQUENCE: 3891

000

<210> SEQ ID NO 3892

<400> SEQUENCE: 3892

000

<210> SEQ ID NO 3893

<400> SEQUENCE: 3893

000

<210> SEQ ID NO 3894

<400> SEQUENCE: 3894

000

<210> SEQ ID NO 3895

<400> SEQUENCE: 3895

000

<210> SEQ ID NO 3896
<400> SEQUENCE: 3896
000

<210> SEQ ID NO 3897
<400> SEQUENCE: 3897
000

<210> SEQ ID NO 3898
<400> SEQUENCE: 3898
000

<210> SEQ ID NO 3899
<400> SEQUENCE: 3899
000

<210> SEQ ID NO 3900
<400> SEQUENCE: 3900
000

<210> SEQ ID NO 3901
<400> SEQUENCE: 3901
000

<210> SEQ ID NO 3902
<400> SEQUENCE: 3902
000

<210> SEQ ID NO 3903
<400> SEQUENCE: 3903
000

<210> SEQ ID NO 3904
<400> SEQUENCE: 3904
000

<210> SEQ ID NO 3905
<400> SEQUENCE: 3905
000

<210> SEQ ID NO 3906
<400> SEQUENCE: 3906
000

```
<210> SEQ ID NO 3907
<400> SEQUENCE: 3907
000

<210> SEQ ID NO 3908
<400> SEQUENCE: 3908
000

<210> SEQ ID NO 3909
<400> SEQUENCE: 3909
000

<210> SEQ ID NO 3910
<400> SEQUENCE: 3910
000

<210> SEQ ID NO 3911
<400> SEQUENCE: 3911
000

<210> SEQ ID NO 3912
<400> SEQUENCE: 3912
000

<210> SEQ ID NO 3913
<400> SEQUENCE: 3913
000

<210> SEQ ID NO 3914
<400> SEQUENCE: 3914
000

<210> SEQ ID NO 3915
<400> SEQUENCE: 3915
000

<210> SEQ ID NO 3916
<400> SEQUENCE: 3916
000

<210> SEQ ID NO 3917
<400> SEQUENCE: 3917
000

<210> SEQ ID NO 3918
```

-continued

<400> SEQUENCE: 3918

000

<210> SEQ ID NO 3919

<400> SEQUENCE: 3919

000

<210> SEQ ID NO 3920

<400> SEQUENCE: 3920

000

<210> SEQ ID NO 3921

<400> SEQUENCE: 3921

000

<210> SEQ ID NO 3922

<400> SEQUENCE: 3922

000

<210> SEQ ID NO 3923

<400> SEQUENCE: 3923

000

<210> SEQ ID NO 3924

<400> SEQUENCE: 3924

000

<210> SEQ ID NO 3925

<400> SEQUENCE: 3925

000

<210> SEQ ID NO 3926

<400> SEQUENCE: 3926

000

<210> SEQ ID NO 3927

<400> SEQUENCE: 3927

000

<210> SEQ ID NO 3928

<400> SEQUENCE: 3928

000

<210> SEQ ID NO 3929

<400> SEQUENCE: 3929

000

<210> SEQ ID NO 3930
<400> SEQUENCE: 3930
000

<210> SEQ ID NO 3931
<400> SEQUENCE: 3931
000

<210> SEQ ID NO 3932
<400> SEQUENCE: 3932
000

<210> SEQ ID NO 3933
<400> SEQUENCE: 3933
000

<210> SEQ ID NO 3934
<400> SEQUENCE: 3934
000

<210> SEQ ID NO 3935
<400> SEQUENCE: 3935
000

<210> SEQ ID NO 3936
<400> SEQUENCE: 3936
000

<210> SEQ ID NO 3937
<400> SEQUENCE: 3937
000

<210> SEQ ID NO 3938
<400> SEQUENCE: 3938
000

<210> SEQ ID NO 3939
<400> SEQUENCE: 3939
000

<210> SEQ ID NO 3940
<400> SEQUENCE: 3940
000

<210> SEQ ID NO 3941

<400> SEQUENCE: 3941

000

<210> SEQ ID NO 3942

<400> SEQUENCE: 3942

000

<210> SEQ ID NO 3943

<400> SEQUENCE: 3943

000

<210> SEQ ID NO 3944

<400> SEQUENCE: 3944

000

<210> SEQ ID NO 3945

<400> SEQUENCE: 3945

000

<210> SEQ ID NO 3946

<400> SEQUENCE: 3946

000

<210> SEQ ID NO 3947

<400> SEQUENCE: 3947

000

<210> SEQ ID NO 3948

<400> SEQUENCE: 3948

000

<210> SEQ ID NO 3949

<400> SEQUENCE: 3949

000

<210> SEQ ID NO 3950

<400> SEQUENCE: 3950

000

<210> SEQ ID NO 3951

<400> SEQUENCE: 3951

000

<210> SEQ ID NO 3952

<400> SEQUENCE: 3952

000

<210> SEQ ID NO 3953

<400> SEQUENCE: 3953

000

<210> SEQ ID NO 3954

<400> SEQUENCE: 3954

000

<210> SEQ ID NO 3955

<400> SEQUENCE: 3955

000

<210> SEQ ID NO 3956

<400> SEQUENCE: 3956

000

<210> SEQ ID NO 3957

<400> SEQUENCE: 3957

000

<210> SEQ ID NO 3958

<400> SEQUENCE: 3958

000

<210> SEQ ID NO 3959

<400> SEQUENCE: 3959

000

<210> SEQ ID NO 3960

<400> SEQUENCE: 3960

000

<210> SEQ ID NO 3961

<400> SEQUENCE: 3961

000

<210> SEQ ID NO 3962

<400> SEQUENCE: 3962

000

<210> SEQ ID NO 3963

<400> SEQUENCE: 3963

000

<210> SEQ ID NO 3964

<400> SEQUENCE: 3964

000

<210> SEQ ID NO 3965

<400> SEQUENCE: 3965

000

<210> SEQ ID NO 3966

<400> SEQUENCE: 3966

000

<210> SEQ ID NO 3967

<400> SEQUENCE: 3967

000

<210> SEQ ID NO 3968

<400> SEQUENCE: 3968

000

<210> SEQ ID NO 3969

<400> SEQUENCE: 3969

000

<210> SEQ ID NO 3970

<400> SEQUENCE: 3970

000

<210> SEQ ID NO 3971

<400> SEQUENCE: 3971

000

<210> SEQ ID NO 3972

<400> SEQUENCE: 3972

000

<210> SEQ ID NO 3973

<400> SEQUENCE: 3973

000

<210> SEQ ID NO 3974

<400> SEQUENCE: 3974

000

<210> SEQ ID NO 3975

<400> SEQUENCE: 3975

000

<210> SEQ ID NO 3976

<400> SEQUENCE: 3976

000

<210> SEQ ID NO 3977

<400> SEQUENCE: 3977

000

<210> SEQ ID NO 3978

<400> SEQUENCE: 3978

000

<210> SEQ ID NO 3979

<400> SEQUENCE: 3979

000

<210> SEQ ID NO 3980

<400> SEQUENCE: 3980

000

<210> SEQ ID NO 3981

<400> SEQUENCE: 3981

000

<210> SEQ ID NO 3982

<400> SEQUENCE: 3982

000

<210> SEQ ID NO 3983

<400> SEQUENCE: 3983

000

<210> SEQ ID NO 3984

<400> SEQUENCE: 3984

000

<210> SEQ ID NO 3985

<400> SEQUENCE: 3985

000

<210> SEQ ID NO 3986

<400> SEQUENCE: 3986

000

<210> SEQ ID NO 3987

<400> SEQUENCE: 3987

000

<210> SEQ ID NO 3988

<400> SEQUENCE: 3988

000

<210> SEQ ID NO 3989

<400> SEQUENCE: 3989

000

<210> SEQ ID NO 3990

<400> SEQUENCE: 3990

000

<210> SEQ ID NO 3991

<400> SEQUENCE: 3991

000

<210> SEQ ID NO 3992

<400> SEQUENCE: 3992

000

<210> SEQ ID NO 3993

<400> SEQUENCE: 3993

000

<210> SEQ ID NO 3994

<400> SEQUENCE: 3994

000

<210> SEQ ID NO 3995

<400> SEQUENCE: 3995

000

<210> SEQ ID NO 3996

<400> SEQUENCE: 3996

000

<210> SEQ ID NO 3997

-continued

```
<400> SEQUENCE: 3997
000

<210> SEQ ID NO 3998
<400> SEQUENCE: 3998
000

<210> SEQ ID NO 3999
<400> SEQUENCE: 3999
000

<210> SEQ ID NO 4000
<400> SEQUENCE: 4000
000

<210> SEQ ID NO 4001
<400> SEQUENCE: 4001
000

<210> SEQ ID NO 4002
<400> SEQUENCE: 4002
000

<210> SEQ ID NO 4003
<400> SEQUENCE: 4003
000

<210> SEQ ID NO 4004
<400> SEQUENCE: 4004
000

<210> SEQ ID NO 4005
<400> SEQUENCE: 4005
000

<210> SEQ ID NO 4006
<400> SEQUENCE: 4006
000

<210> SEQ ID NO 4007
<400> SEQUENCE: 4007
000

<210> SEQ ID NO 4008
<400> SEQUENCE: 4008
```

-continued

<210> SEQ ID NO 4009

<400> SEQUENCE: 4009

000

<210> SEQ ID NO 4010

<400> SEQUENCE: 4010

000

<210> SEQ ID NO 4011

<400> SEQUENCE: 4011

000

<210> SEQ ID NO 4012

<400> SEQUENCE: 4012

000

<210> SEQ ID NO 4013

<400> SEQUENCE: 4013

000

<210> SEQ ID NO 4014

<400> SEQUENCE: 4014

000

<210> SEQ ID NO 4015

<400> SEQUENCE: 4015

000

<210> SEQ ID NO 4016

<400> SEQUENCE: 4016

000

<210> SEQ ID NO 4017

<400> SEQUENCE: 4017

000

<210> SEQ ID NO 4018

<400> SEQUENCE: 4018

000

<210> SEQ ID NO 4019

<400> SEQUENCE: 4019

000

<210> SEQ ID NO 4020

<400> SEQUENCE: 4020

000

<210> SEQ ID NO 4021

<400> SEQUENCE: 4021

000

<210> SEQ ID NO 4022

<400> SEQUENCE: 4022

000

<210> SEQ ID NO 4023

<400> SEQUENCE: 4023

000

<210> SEQ ID NO 4024

<400> SEQUENCE: 4024

000

<210> SEQ ID NO 4025

<400> SEQUENCE: 4025

000

<210> SEQ ID NO 4026

<400> SEQUENCE: 4026

000

<210> SEQ ID NO 4027

<400> SEQUENCE: 4027

000

<210> SEQ ID NO 4028

<400> SEQUENCE: 4028

000

<210> SEQ ID NO 4029

<400> SEQUENCE: 4029

000

<210> SEQ ID NO 4030

<400> SEQUENCE: 4030

000

<210> SEQ ID NO 4031

<400> SEQUENCE: 4031

000

<210> SEQ ID NO 4032

<400> SEQUENCE: 4032

000

<210> SEQ ID NO 4033

<400> SEQUENCE: 4033

000

<210> SEQ ID NO 4034

<400> SEQUENCE: 4034

000

<210> SEQ ID NO 4035

<400> SEQUENCE: 4035

000

<210> SEQ ID NO 4036

<400> SEQUENCE: 4036

000

<210> SEQ ID NO 4037

<400> SEQUENCE: 4037

000

<210> SEQ ID NO 4038

<400> SEQUENCE: 4038

000

<210> SEQ ID NO 4039

<400> SEQUENCE: 4039

000

<210> SEQ ID NO 4040

<400> SEQUENCE: 4040

000

<210> SEQ ID NO 4041

<400> SEQUENCE: 4041

000

<210> SEQ ID NO 4042

```
<400> SEQUENCE: 4042
000

<210> SEQ ID NO 4043
<400> SEQUENCE: 4043
000

<210> SEQ ID NO 4044
<400> SEQUENCE: 4044
000

<210> SEQ ID NO 4045
<400> SEQUENCE: 4045
000

<210> SEQ ID NO 4046
<400> SEQUENCE: 4046
000

<210> SEQ ID NO 4047
<400> SEQUENCE: 4047
000

<210> SEQ ID NO 4048
<400> SEQUENCE: 4048
000

<210> SEQ ID NO 4049
<400> SEQUENCE: 4049
000

<210> SEQ ID NO 4050
<400> SEQUENCE: 4050
000

<210> SEQ ID NO 4051
<400> SEQUENCE: 4051
000

<210> SEQ ID NO 4052
<400> SEQUENCE: 4052
000

<210> SEQ ID NO 4053
<400> SEQUENCE: 4053
```

000

<210> SEQ ID NO 4054

<400> SEQUENCE: 4054

000

<210> SEQ ID NO 4055

<400> SEQUENCE: 4055

000

<210> SEQ ID NO 4056

<400> SEQUENCE: 4056

000

<210> SEQ ID NO 4057

<400> SEQUENCE: 4057

000

<210> SEQ ID NO 4058

<400> SEQUENCE: 4058

000

<210> SEQ ID NO 4059

<400> SEQUENCE: 4059

000

<210> SEQ ID NO 4060

<400> SEQUENCE: 4060

000

<210> SEQ ID NO 4061

<400> SEQUENCE: 4061

000

<210> SEQ ID NO 4062

<400> SEQUENCE: 4062

000

<210> SEQ ID NO 4063

<400> SEQUENCE: 4063

000

<210> SEQ ID NO 4064

<400> SEQUENCE: 4064

000

<210> SEQ ID NO 4065

<400> SEQUENCE: 4065

000

<210> SEQ ID NO 4066

<400> SEQUENCE: 4066

000

<210> SEQ ID NO 4067

<400> SEQUENCE: 4067

000

<210> SEQ ID NO 4068

<400> SEQUENCE: 4068

000

<210> SEQ ID NO 4069

<400> SEQUENCE: 4069

000

<210> SEQ ID NO 4070

<400> SEQUENCE: 4070

000

<210> SEQ ID NO 4071

<400> SEQUENCE: 4071

000

<210> SEQ ID NO 4072

<400> SEQUENCE: 4072

000

<210> SEQ ID NO 4073

<400> SEQUENCE: 4073

000

<210> SEQ ID NO 4074

<400> SEQUENCE: 4074

000

<210> SEQ ID NO 4075

<400> SEQUENCE: 4075

000

<210> SEQ ID NO 4076

<400> SEQUENCE: 4076

000

<210> SEQ ID NO 4077

<400> SEQUENCE: 4077

000

<210> SEQ ID NO 4078

<400> SEQUENCE: 4078

000

<210> SEQ ID NO 4079

<400> SEQUENCE: 4079

000

<210> SEQ ID NO 4080

<400> SEQUENCE: 4080

000

<210> SEQ ID NO 4081

<400> SEQUENCE: 4081

000

<210> SEQ ID NO 4082

<400> SEQUENCE: 4082

000

<210> SEQ ID NO 4083

<400> SEQUENCE: 4083

000

<210> SEQ ID NO 4084

<400> SEQUENCE: 4084

000

<210> SEQ ID NO 4085

<400> SEQUENCE: 4085

000

<210> SEQ ID NO 4086

<400> SEQUENCE: 4086

000

<210> SEQ ID NO 4087

<400> SEQUENCE: 4087

000

<210> SEQ ID NO 4088

<400> SEQUENCE: 4088

000

<210> SEQ ID NO 4089

<400> SEQUENCE: 4089

000

<210> SEQ ID NO 4090

<400> SEQUENCE: 4090

000

<210> SEQ ID NO 4091

<400> SEQUENCE: 4091

000

<210> SEQ ID NO 4092

<400> SEQUENCE: 4092

000

<210> SEQ ID NO 4093

<400> SEQUENCE: 4093

000

<210> SEQ ID NO 4094

<400> SEQUENCE: 4094

000

<210> SEQ ID NO 4095

<400> SEQUENCE: 4095

000

<210> SEQ ID NO 4096

<400> SEQUENCE: 4096

000

<210> SEQ ID NO 4097

<400> SEQUENCE: 4097

000

<210> SEQ ID NO 4098

<400> SEQUENCE: 4098

000

<210> SEQ ID NO 4099

<400> SEQUENCE: 4099

000

<210> SEQ ID NO 4100

<400> SEQUENCE: 4100

000

<210> SEQ ID NO 4101

<400> SEQUENCE: 4101

000

<210> SEQ ID NO 4102

<400> SEQUENCE: 4102

000

<210> SEQ ID NO 4103

<400> SEQUENCE: 4103

000

<210> SEQ ID NO 4104

<400> SEQUENCE: 4104

000

<210> SEQ ID NO 4105

<400> SEQUENCE: 4105

000

<210> SEQ ID NO 4106

<400> SEQUENCE: 4106

000

<210> SEQ ID NO 4107

<400> SEQUENCE: 4107

000

<210> SEQ ID NO 4108

<400> SEQUENCE: 4108

000

<210> SEQ ID NO 4109

<400> SEQUENCE: 4109

000

```
<210> SEQ ID NO 4110
<400> SEQUENCE: 4110
000

<210> SEQ ID NO 4111
<400> SEQUENCE: 4111
000

<210> SEQ ID NO 4112
<400> SEQUENCE: 4112
000

<210> SEQ ID NO 4113
<400> SEQUENCE: 4113
000

<210> SEQ ID NO 4114
<400> SEQUENCE: 4114
000

<210> SEQ ID NO 4115
<400> SEQUENCE: 4115
000

<210> SEQ ID NO 4116
<400> SEQUENCE: 4116
000

<210> SEQ ID NO 4117
<400> SEQUENCE: 4117
000

<210> SEQ ID NO 4118
<400> SEQUENCE: 4118
000

<210> SEQ ID NO 4119
<400> SEQUENCE: 4119
000

<210> SEQ ID NO 4120
<400> SEQUENCE: 4120
000

<210> SEQ ID NO 4121
```

<400> SEQUENCE: 4121

000

<210> SEQ ID NO 4122

<400> SEQUENCE: 4122

000

<210> SEQ ID NO 4123

<400> SEQUENCE: 4123

000

<210> SEQ ID NO 4124

<400> SEQUENCE: 4124

000

<210> SEQ ID NO 4125

<400> SEQUENCE: 4125

000

<210> SEQ ID NO 4126

<400> SEQUENCE: 4126

000

<210> SEQ ID NO 4127

<400> SEQUENCE: 4127

000

<210> SEQ ID NO 4128

<400> SEQUENCE: 4128

000

<210> SEQ ID NO 4129

<400> SEQUENCE: 4129

000

<210> SEQ ID NO 4130

<400> SEQUENCE: 4130

000

<210> SEQ ID NO 4131

<400> SEQUENCE: 4131

000

<210> SEQ ID NO 4132

<400> SEQUENCE: 4132

000

<210> SEQ ID NO 4133
<400> SEQUENCE: 4133
000

<210> SEQ ID NO 4134
<400> SEQUENCE: 4134
000

<210> SEQ ID NO 4135
<400> SEQUENCE: 4135
000

<210> SEQ ID NO 4136
<400> SEQUENCE: 4136
000

<210> SEQ ID NO 4137
<400> SEQUENCE: 4137
000

<210> SEQ ID NO 4138
<400> SEQUENCE: 4138
000

<210> SEQ ID NO 4139
<400> SEQUENCE: 4139
000

<210> SEQ ID NO 4140
<400> SEQUENCE: 4140
000

<210> SEQ ID NO 4141
<400> SEQUENCE: 4141
000

<210> SEQ ID NO 4142
<400> SEQUENCE: 4142
000

<210> SEQ ID NO 4143
<400> SEQUENCE: 4143
000

<210> SEQ ID NO 4144

<400> SEQUENCE: 4144

000

<210> SEQ ID NO 4145

<400> SEQUENCE: 4145

000

<210> SEQ ID NO 4146

<400> SEQUENCE: 4146

000

<210> SEQ ID NO 4147

<400> SEQUENCE: 4147

000

<210> SEQ ID NO 4148

<400> SEQUENCE: 4148

000

<210> SEQ ID NO 4149

<400> SEQUENCE: 4149

000

<210> SEQ ID NO 4150

<400> SEQUENCE: 4150

000

<210> SEQ ID NO 4151

<400> SEQUENCE: 4151

000

<210> SEQ ID NO 4152

<400> SEQUENCE: 4152

000

<210> SEQ ID NO 4153

<400> SEQUENCE: 4153

000

<210> SEQ ID NO 4154

<400> SEQUENCE: 4154

000

<210> SEQ ID NO 4155

<400> SEQUENCE: 4155

000

<210> SEQ ID NO 4156

<400> SEQUENCE: 4156

000

<210> SEQ ID NO 4157

<400> SEQUENCE: 4157

000

<210> SEQ ID NO 4158

<400> SEQUENCE: 4158

000

<210> SEQ ID NO 4159

<400> SEQUENCE: 4159

000

<210> SEQ ID NO 4160

<400> SEQUENCE: 4160

000

<210> SEQ ID NO 4161

<400> SEQUENCE: 4161

000

<210> SEQ ID NO 4162

<400> SEQUENCE: 4162

000

<210> SEQ ID NO 4163

<400> SEQUENCE: 4163

000

<210> SEQ ID NO 4164

<400> SEQUENCE: 4164

000

<210> SEQ ID NO 4165

<400> SEQUENCE: 4165

000

<210> SEQ ID NO 4166

<400> SEQUENCE: 4166

000

<210> SEQ ID NO 4167

<400> SEQUENCE: 4167

000

<210> SEQ ID NO 4168

<400> SEQUENCE: 4168

000

<210> SEQ ID NO 4169

<400> SEQUENCE: 4169

000

<210> SEQ ID NO 4170

<400> SEQUENCE: 4170

000

<210> SEQ ID NO 4171

<400> SEQUENCE: 4171

000

<210> SEQ ID NO 4172

<400> SEQUENCE: 4172

000

<210> SEQ ID NO 4173

<400> SEQUENCE: 4173

000

<210> SEQ ID NO 4174

<400> SEQUENCE: 4174

000

<210> SEQ ID NO 4175

<400> SEQUENCE: 4175

000

<210> SEQ ID NO 4176

<400> SEQUENCE: 4176

000

<210> SEQ ID NO 4177

<400> SEQUENCE: 4177

000

<210> SEQ ID NO 4178

<400> SEQUENCE: 4178

000

<210> SEQ ID NO 4179

<400> SEQUENCE: 4179

000

<210> SEQ ID NO 4180

<400> SEQUENCE: 4180

000

<210> SEQ ID NO 4181

<400> SEQUENCE: 4181

000

<210> SEQ ID NO 4182

<400> SEQUENCE: 4182

000

<210> SEQ ID NO 4183

<400> SEQUENCE: 4183

000

<210> SEQ ID NO 4184

<400> SEQUENCE: 4184

000

<210> SEQ ID NO 4185

<400> SEQUENCE: 4185

000

<210> SEQ ID NO 4186

<400> SEQUENCE: 4186

000

<210> SEQ ID NO 4187

<400> SEQUENCE: 4187

000

<210> SEQ ID NO 4188

<400> SEQUENCE: 4188

000

```
<210> SEQ ID NO 4189
<400> SEQUENCE: 4189
000

<210> SEQ ID NO 4190
<400> SEQUENCE: 4190
000

<210> SEQ ID NO 4191
<400> SEQUENCE: 4191
000

<210> SEQ ID NO 4192
<400> SEQUENCE: 4192
000

<210> SEQ ID NO 4193
<400> SEQUENCE: 4193
000

<210> SEQ ID NO 4194
<400> SEQUENCE: 4194
000

<210> SEQ ID NO 4195
<400> SEQUENCE: 4195
000

<210> SEQ ID NO 4196
<400> SEQUENCE: 4196
000

<210> SEQ ID NO 4197
<400> SEQUENCE: 4197
000

<210> SEQ ID NO 4198
<400> SEQUENCE: 4198
000

<210> SEQ ID NO 4199
<400> SEQUENCE: 4199
000

<210> SEQ ID NO 4200
```

<400> SEQUENCE: 4200

000

<210> SEQ ID NO 4201

<400> SEQUENCE: 4201

000

<210> SEQ ID NO 4202

<400> SEQUENCE: 4202

000

<210> SEQ ID NO 4203

<400> SEQUENCE: 4203

000

<210> SEQ ID NO 4204

<400> SEQUENCE: 4204

000

<210> SEQ ID NO 4205

<400> SEQUENCE: 4205

000

<210> SEQ ID NO 4206

<400> SEQUENCE: 4206

000

<210> SEQ ID NO 4207

<400> SEQUENCE: 4207

000

<210> SEQ ID NO 4208

<400> SEQUENCE: 4208

000

<210> SEQ ID NO 4209

<400> SEQUENCE: 4209

000

<210> SEQ ID NO 4210

<400> SEQUENCE: 4210

000

<210> SEQ ID NO 4211

<400> SEQUENCE: 4211

000

<210> SEQ ID NO 4212

<400> SEQUENCE: 4212

000

<210> SEQ ID NO 4213

<400> SEQUENCE: 4213

000

<210> SEQ ID NO 4214

<400> SEQUENCE: 4214

000

<210> SEQ ID NO 4215

<400> SEQUENCE: 4215

000

<210> SEQ ID NO 4216

<400> SEQUENCE: 4216

000

<210> SEQ ID NO 4217

<400> SEQUENCE: 4217

000

<210> SEQ ID NO 4218

<400> SEQUENCE: 4218

000

<210> SEQ ID NO 4219

<400> SEQUENCE: 4219

000

<210> SEQ ID NO 4220

<400> SEQUENCE: 4220

000

<210> SEQ ID NO 4221

<400> SEQUENCE: 4221

000

<210> SEQ ID NO 4222

<400> SEQUENCE: 4222

000

<210> SEQ ID NO 4223

<400> SEQUENCE: 4223

000

<210> SEQ ID NO 4224

<400> SEQUENCE: 4224

000

<210> SEQ ID NO 4225

<400> SEQUENCE: 4225

000

<210> SEQ ID NO 4226

<400> SEQUENCE: 4226

000

<210> SEQ ID NO 4227

<400> SEQUENCE: 4227

000

<210> SEQ ID NO 4228

<400> SEQUENCE: 4228

000

<210> SEQ ID NO 4229

<400> SEQUENCE: 4229

000

<210> SEQ ID NO 4230

<400> SEQUENCE: 4230

000

<210> SEQ ID NO 4231

<400> SEQUENCE: 4231

000

<210> SEQ ID NO 4232

<400> SEQUENCE: 4232

000

<210> SEQ ID NO 4233

<400> SEQUENCE: 4233

000

<210> SEQ ID NO 4234

<400> SEQUENCE: 4234

000

<210> SEQ ID NO 4235

<400> SEQUENCE: 4235

000

<210> SEQ ID NO 4236

<400> SEQUENCE: 4236

000

<210> SEQ ID NO 4237

<400> SEQUENCE: 4237

000

<210> SEQ ID NO 4238

<400> SEQUENCE: 4238

000

<210> SEQ ID NO 4239

<400> SEQUENCE: 4239

000

<210> SEQ ID NO 4240

<400> SEQUENCE: 4240

000

<210> SEQ ID NO 4241

<400> SEQUENCE: 4241

000

<210> SEQ ID NO 4242

<400> SEQUENCE: 4242

000

<210> SEQ ID NO 4243

<400> SEQUENCE: 4243

000

<210> SEQ ID NO 4244

<400> SEQUENCE: 4244

000

<210> SEQ ID NO 4245

<400> SEQUENCE: 4245

000

<210> SEQ ID NO 4246

<400> SEQUENCE: 4246

000

<210> SEQ ID NO 4247

<400> SEQUENCE: 4247

000

<210> SEQ ID NO 4248

<400> SEQUENCE: 4248

000

<210> SEQ ID NO 4249

<400> SEQUENCE: 4249

000

<210> SEQ ID NO 4250

<400> SEQUENCE: 4250

000

<210> SEQ ID NO 4251

<400> SEQUENCE: 4251

000

<210> SEQ ID NO 4252

<400> SEQUENCE: 4252

000

<210> SEQ ID NO 4253

<400> SEQUENCE: 4253

000

<210> SEQ ID NO 4254

<400> SEQUENCE: 4254

000

<210> SEQ ID NO 4255

<400> SEQUENCE: 4255

000

<210> SEQ ID NO 4256

<400> SEQUENCE: 4256

000

<210> SEQ ID NO 4257

<400> SEQUENCE: 4257

000

<210> SEQ ID NO 4258

<400> SEQUENCE: 4258

000

<210> SEQ ID NO 4259

<400> SEQUENCE: 4259

000

<210> SEQ ID NO 4260

<400> SEQUENCE: 4260

000

<210> SEQ ID NO 4261

<400> SEQUENCE: 4261

000

<210> SEQ ID NO 4262

<400> SEQUENCE: 4262

000

<210> SEQ ID NO 4263

<400> SEQUENCE: 4263

000

<210> SEQ ID NO 4264

<400> SEQUENCE: 4264

000

<210> SEQ ID NO 4265

<400> SEQUENCE: 4265

000

<210> SEQ ID NO 4266

<400> SEQUENCE: 4266

000

<210> SEQ ID NO 4267

<400> SEQUENCE: 4267

000

<210> SEQ ID NO 4268

<400> SEQUENCE: 4268

000

<210> SEQ ID NO 4269

<400> SEQUENCE: 4269

000

<210> SEQ ID NO 4270

<400> SEQUENCE: 4270

000

<210> SEQ ID NO 4271

<400> SEQUENCE: 4271

000

<210> SEQ ID NO 4272

<400> SEQUENCE: 4272

000

<210> SEQ ID NO 4273

<400> SEQUENCE: 4273

000

<210> SEQ ID NO 4274

<400> SEQUENCE: 4274

000

<210> SEQ ID NO 4275

<400> SEQUENCE: 4275

000

<210> SEQ ID NO 4276

<400> SEQUENCE: 4276

000

<210> SEQ ID NO 4277

<400> SEQUENCE: 4277

000

<210> SEQ ID NO 4278

<400> SEQUENCE: 4278

000

<210> SEQ ID NO 4279

```
<400> SEQUENCE: 4279

000

<210> SEQ ID NO 4280

<400> SEQUENCE: 4280

000

<210> SEQ ID NO 4281

<400> SEQUENCE: 4281

000

<210> SEQ ID NO 4282

<400> SEQUENCE: 4282

000

<210> SEQ ID NO 4283

<400> SEQUENCE: 4283

000

<210> SEQ ID NO 4284

<400> SEQUENCE: 4284

000

<210> SEQ ID NO 4285

<400> SEQUENCE: 4285

000

<210> SEQ ID NO 4286

<400> SEQUENCE: 4286

000

<210> SEQ ID NO 4287

<400> SEQUENCE: 4287

000

<210> SEQ ID NO 4288

<400> SEQUENCE: 4288

000

<210> SEQ ID NO 4289

<400> SEQUENCE: 4289

000

<210> SEQ ID NO 4290

<400> SEQUENCE: 4290
```

000

<210> SEQ ID NO 4291

<400> SEQUENCE: 4291

000

<210> SEQ ID NO 4292

<400> SEQUENCE: 4292

000

<210> SEQ ID NO 4293

<400> SEQUENCE: 4293

000

<210> SEQ ID NO 4294

<400> SEQUENCE: 4294

000

<210> SEQ ID NO 4295

<400> SEQUENCE: 4295

000

<210> SEQ ID NO 4296

<400> SEQUENCE: 4296

000

<210> SEQ ID NO 4297

<400> SEQUENCE: 4297

000

<210> SEQ ID NO 4298

<400> SEQUENCE: 4298

000

<210> SEQ ID NO 4299

<400> SEQUENCE: 4299

000

<210> SEQ ID NO 4300

<400> SEQUENCE: 4300

000

<210> SEQ ID NO 4301

<400> SEQUENCE: 4301

000

<210> SEQ ID NO 4302

<400> SEQUENCE: 4302

000

<210> SEQ ID NO 4303

<400> SEQUENCE: 4303

000

<210> SEQ ID NO 4304

<400> SEQUENCE: 4304

000

<210> SEQ ID NO 4305

<400> SEQUENCE: 4305

000

<210> SEQ ID NO 4306

<400> SEQUENCE: 4306

000

<210> SEQ ID NO 4307

<400> SEQUENCE: 4307

000

<210> SEQ ID NO 4308

<400> SEQUENCE: 4308

000

<210> SEQ ID NO 4309

<400> SEQUENCE: 4309

000

<210> SEQ ID NO 4310

<400> SEQUENCE: 4310

000

<210> SEQ ID NO 4311

<400> SEQUENCE: 4311

000

<210> SEQ ID NO 4312

<400> SEQUENCE: 4312

000

<210> SEQ ID NO 4313

-continued

<400> SEQUENCE: 4313

000

<210> SEQ ID NO 4314

<400> SEQUENCE: 4314

000

<210> SEQ ID NO 4315

<400> SEQUENCE: 4315

000

<210> SEQ ID NO 4316

<400> SEQUENCE: 4316

000

<210> SEQ ID NO 4317

<400> SEQUENCE: 4317

000

<210> SEQ ID NO 4318

<400> SEQUENCE: 4318

000

<210> SEQ ID NO 4319

<400> SEQUENCE: 4319

000

<210> SEQ ID NO 4320

<400> SEQUENCE: 4320

000

<210> SEQ ID NO 4321

<400> SEQUENCE: 4321

000

<210> SEQ ID NO 4322

<400> SEQUENCE: 4322

000

<210> SEQ ID NO 4323

<400> SEQUENCE: 4323

000

<210> SEQ ID NO 4324

<400> SEQUENCE: 4324

000

<210> SEQ ID NO 4325

<400> SEQUENCE: 4325

000

<210> SEQ ID NO 4326

<400> SEQUENCE: 4326

000

<210> SEQ ID NO 4327

<400> SEQUENCE: 4327

000

<210> SEQ ID NO 4328

<400> SEQUENCE: 4328

000

<210> SEQ ID NO 4329

<400> SEQUENCE: 4329

000

<210> SEQ ID NO 4330

<400> SEQUENCE: 4330

000

<210> SEQ ID NO 4331

<400> SEQUENCE: 4331

000

<210> SEQ ID NO 4332

<400> SEQUENCE: 4332

000

<210> SEQ ID NO 4333

<400> SEQUENCE: 4333

000

<210> SEQ ID NO 4334

<400> SEQUENCE: 4334

000

<210> SEQ ID NO 4335

<400> SEQUENCE: 4335

000

```
<210> SEQ ID NO 4336
<400> SEQUENCE: 4336
000

<210> SEQ ID NO 4337
<400> SEQUENCE: 4337
000

<210> SEQ ID NO 4338
<400> SEQUENCE: 4338
000

<210> SEQ ID NO 4339
<400> SEQUENCE: 4339
000

<210> SEQ ID NO 4340
<400> SEQUENCE: 4340
000

<210> SEQ ID NO 4341
<400> SEQUENCE: 4341
000

<210> SEQ ID NO 4342
<400> SEQUENCE: 4342
000

<210> SEQ ID NO 4343
<400> SEQUENCE: 4343
000

<210> SEQ ID NO 4344
<400> SEQUENCE: 4344
000

<210> SEQ ID NO 4345
<400> SEQUENCE: 4345
000

<210> SEQ ID NO 4346
<400> SEQUENCE: 4346
000
```

```
<210> SEQ ID NO 4347
<400> SEQUENCE: 4347
000

<210> SEQ ID NO 4348
<400> SEQUENCE: 4348
000

<210> SEQ ID NO 4349
<400> SEQUENCE: 4349
000

<210> SEQ ID NO 4350
<400> SEQUENCE: 4350
000

<210> SEQ ID NO 4351
<400> SEQUENCE: 4351
000

<210> SEQ ID NO 4352
<400> SEQUENCE: 4352
000

<210> SEQ ID NO 4353
<400> SEQUENCE: 4353
000

<210> SEQ ID NO 4354
<400> SEQUENCE: 4354
000

<210> SEQ ID NO 4355
<400> SEQUENCE: 4355
000

<210> SEQ ID NO 4356
<400> SEQUENCE: 4356
000

<210> SEQ ID NO 4357
<400> SEQUENCE: 4357
000

<210> SEQ ID NO 4358
```

<400> SEQUENCE: 4358

000

<210> SEQ ID NO 4359

<400> SEQUENCE: 4359

000

<210> SEQ ID NO 4360

<400> SEQUENCE: 4360

000

<210> SEQ ID NO 4361

<400> SEQUENCE: 4361

000

<210> SEQ ID NO 4362

<400> SEQUENCE: 4362

000

<210> SEQ ID NO 4363

<400> SEQUENCE: 4363

000

<210> SEQ ID NO 4364

<400> SEQUENCE: 4364

000

<210> SEQ ID NO 4365

<400> SEQUENCE: 4365

000

<210> SEQ ID NO 4366

<400> SEQUENCE: 4366

000

<210> SEQ ID NO 4367

<400> SEQUENCE: 4367

000

<210> SEQ ID NO 4368

<400> SEQUENCE: 4368

000

<210> SEQ ID NO 4369

<400> SEQUENCE: 4369

000

<210> SEQ ID NO 4370
<400> SEQUENCE: 4370
000

<210> SEQ ID NO 4371
<400> SEQUENCE: 4371
000

<210> SEQ ID NO 4372
<400> SEQUENCE: 4372
000

<210> SEQ ID NO 4373
<400> SEQUENCE: 4373
000

<210> SEQ ID NO 4374
<400> SEQUENCE: 4374
000

<210> SEQ ID NO 4375
<400> SEQUENCE: 4375
000

<210> SEQ ID NO 4376
<400> SEQUENCE: 4376
000

<210> SEQ ID NO 4377
<400> SEQUENCE: 4377
000

<210> SEQ ID NO 4378
<400> SEQUENCE: 4378
000

<210> SEQ ID NO 4379
<400> SEQUENCE: 4379
000

<210> SEQ ID NO 4380
<400> SEQUENCE: 4380
000

<210> SEQ ID NO 4381

<400> SEQUENCE: 4381

000

<210> SEQ ID NO 4382

<400> SEQUENCE: 4382

000

<210> SEQ ID NO 4383

<400> SEQUENCE: 4383

000

<210> SEQ ID NO 4384

<400> SEQUENCE: 4384

000

<210> SEQ ID NO 4385

<400> SEQUENCE: 4385

000

<210> SEQ ID NO 4386

<400> SEQUENCE: 4386

000

<210> SEQ ID NO 4387

<400> SEQUENCE: 4387

000

<210> SEQ ID NO 4388

<400> SEQUENCE: 4388

000

<210> SEQ ID NO 4389

<400> SEQUENCE: 4389

000

<210> SEQ ID NO 4390

<400> SEQUENCE: 4390

000

<210> SEQ ID NO 4391

<400> SEQUENCE: 4391

000

<210> SEQ ID NO 4392

<400> SEQUENCE: 4392

000

<210> SEQ ID NO 4393

<400> SEQUENCE: 4393

000

<210> SEQ ID NO 4394

<400> SEQUENCE: 4394

000

<210> SEQ ID NO 4395

<400> SEQUENCE: 4395

000

<210> SEQ ID NO 4396

<400> SEQUENCE: 4396

000

<210> SEQ ID NO 4397

<400> SEQUENCE: 4397

000

<210> SEQ ID NO 4398

<400> SEQUENCE: 4398

000

<210> SEQ ID NO 4399

<400> SEQUENCE: 4399

000

<210> SEQ ID NO 4400

<400> SEQUENCE: 4400

000

<210> SEQ ID NO 4401

<400> SEQUENCE: 4401

000

<210> SEQ ID NO 4402

<400> SEQUENCE: 4402

000

<210> SEQ ID NO 4403

<400> SEQUENCE: 4403

000

<210> SEQ ID NO 4404
<400> SEQUENCE: 4404
000

<210> SEQ ID NO 4405
<400> SEQUENCE: 4405
000

<210> SEQ ID NO 4406
<400> SEQUENCE: 4406
000

<210> SEQ ID NO 4407
<400> SEQUENCE: 4407
000

<210> SEQ ID NO 4408
<400> SEQUENCE: 4408
000

<210> SEQ ID NO 4409
<400> SEQUENCE: 4409
000

<210> SEQ ID NO 4410
<400> SEQUENCE: 4410
000

<210> SEQ ID NO 4411
<400> SEQUENCE: 4411
000

<210> SEQ ID NO 4412
<400> SEQUENCE: 4412
000

<210> SEQ ID NO 4413
<400> SEQUENCE: 4413
000

<210> SEQ ID NO 4414
<400> SEQUENCE: 4414
000

-continued

<210> SEQ ID NO 4415

<400> SEQUENCE: 4415

000

<210> SEQ ID NO 4416

<400> SEQUENCE: 4416

000

<210> SEQ ID NO 4417

<400> SEQUENCE: 4417

000

<210> SEQ ID NO 4418

<400> SEQUENCE: 4418

000

<210> SEQ ID NO 4419

<400> SEQUENCE: 4419

000

<210> SEQ ID NO 4420

<400> SEQUENCE: 4420

000

<210> SEQ ID NO 4421

<400> SEQUENCE: 4421

000

<210> SEQ ID NO 4422

<400> SEQUENCE: 4422

000

<210> SEQ ID NO 4423

<400> SEQUENCE: 4423

000

<210> SEQ ID NO 4424

<400> SEQUENCE: 4424

000

<210> SEQ ID NO 4425

<400> SEQUENCE: 4425

000

-continued

<210> SEQ ID NO 4426

<400> SEQUENCE: 4426

000

<210> SEQ ID NO 4427

<400> SEQUENCE: 4427

000

<210> SEQ ID NO 4428

<400> SEQUENCE: 4428

000

<210> SEQ ID NO 4429

<400> SEQUENCE: 4429

000

<210> SEQ ID NO 4430

<400> SEQUENCE: 4430

000

<210> SEQ ID NO 4431

<400> SEQUENCE: 4431

000

<210> SEQ ID NO 4432

<400> SEQUENCE: 4432

000

<210> SEQ ID NO 4433

<400> SEQUENCE: 4433

000

<210> SEQ ID NO 4434

<400> SEQUENCE: 4434

000

<210> SEQ ID NO 4435

<400> SEQUENCE: 4435

000

<210> SEQ ID NO 4436

<400> SEQUENCE: 4436

000

<210> SEQ ID NO 4437

```
<400> SEQUENCE: 4437

000

<210> SEQ ID NO 4438

<400> SEQUENCE: 4438

000

<210> SEQ ID NO 4439

<400> SEQUENCE: 4439

000

<210> SEQ ID NO 4440

<400> SEQUENCE: 4440

000

<210> SEQ ID NO 4441

<400> SEQUENCE: 4441

000

<210> SEQ ID NO 4442

<400> SEQUENCE: 4442

000

<210> SEQ ID NO 4443

<400> SEQUENCE: 4443

000

<210> SEQ ID NO 4444

<400> SEQUENCE: 4444

000

<210> SEQ ID NO 4445

<400> SEQUENCE: 4445

000

<210> SEQ ID NO 4446

<400> SEQUENCE: 4446

000

<210> SEQ ID NO 4447

<400> SEQUENCE: 4447

000

<210> SEQ ID NO 4448

<400> SEQUENCE: 4448
```

-continued

000

<210> SEQ ID NO 4449

<400> SEQUENCE: 4449

000

<210> SEQ ID NO 4450

<400> SEQUENCE: 4450

000

<210> SEQ ID NO 4451

<400> SEQUENCE: 4451

000

<210> SEQ ID NO 4452

<400> SEQUENCE: 4452

000

<210> SEQ ID NO 4453

<400> SEQUENCE: 4453

000

<210> SEQ ID NO 4454

<400> SEQUENCE: 4454

000

<210> SEQ ID NO 4455

<400> SEQUENCE: 4455

000

<210> SEQ ID NO 4456

<400> SEQUENCE: 4456

000

<210> SEQ ID NO 4457

<400> SEQUENCE: 4457

000

<210> SEQ ID NO 4458

<400> SEQUENCE: 4458

000

<210> SEQ ID NO 4459

<400> SEQUENCE: 4459

000

<210> SEQ ID NO 4460

<400> SEQUENCE: 4460

000

<210> SEQ ID NO 4461

<400> SEQUENCE: 4461

000

<210> SEQ ID NO 4462

<400> SEQUENCE: 4462

000

<210> SEQ ID NO 4463

<400> SEQUENCE: 4463

000

<210> SEQ ID NO 4464

<400> SEQUENCE: 4464

000

<210> SEQ ID NO 4465

<400> SEQUENCE: 4465

000

<210> SEQ ID NO 4466

<400> SEQUENCE: 4466

000

<210> SEQ ID NO 4467

<400> SEQUENCE: 4467

000

<210> SEQ ID NO 4468

<400> SEQUENCE: 4468

000

<210> SEQ ID NO 4469

<400> SEQUENCE: 4469

000

<210> SEQ ID NO 4470

<400> SEQUENCE: 4470

000

<210> SEQ ID NO 4471

```
<400> SEQUENCE: 4471
000

<210> SEQ ID NO 4472
<400> SEQUENCE: 4472
000

<210> SEQ ID NO 4473
<400> SEQUENCE: 4473
000

<210> SEQ ID NO 4474
<400> SEQUENCE: 4474
000

<210> SEQ ID NO 4475
<400> SEQUENCE: 4475
000

<210> SEQ ID NO 4476
<400> SEQUENCE: 4476
000

<210> SEQ ID NO 4477
<400> SEQUENCE: 4477
000

<210> SEQ ID NO 4478
<400> SEQUENCE: 4478
000

<210> SEQ ID NO 4479
<400> SEQUENCE: 4479
000

<210> SEQ ID NO 4480
<400> SEQUENCE: 4480
000

<210> SEQ ID NO 4481
<400> SEQUENCE: 4481
000

<210> SEQ ID NO 4482
<400> SEQUENCE: 4482
```

000

<210> SEQ ID NO 4483

<400> SEQUENCE: 4483

000

<210> SEQ ID NO 4484

<400> SEQUENCE: 4484

000

<210> SEQ ID NO 4485

<400> SEQUENCE: 4485

000

<210> SEQ ID NO 4486

<400> SEQUENCE: 4486

000

<210> SEQ ID NO 4487

<400> SEQUENCE: 4487

000

<210> SEQ ID NO 4488

<400> SEQUENCE: 4488

000

<210> SEQ ID NO 4489

<400> SEQUENCE: 4489

000

<210> SEQ ID NO 4490

<400> SEQUENCE: 4490

000

<210> SEQ ID NO 4491

<400> SEQUENCE: 4491

000

<210> SEQ ID NO 4492

<400> SEQUENCE: 4492

000

<210> SEQ ID NO 4493

<400> SEQUENCE: 4493

000

<210> SEQ ID NO 4494

<400> SEQUENCE: 4494

000

<210> SEQ ID NO 4495

<400> SEQUENCE: 4495

000

<210> SEQ ID NO 4496

<400> SEQUENCE: 4496

000

<210> SEQ ID NO 4497

<400> SEQUENCE: 4497

000

<210> SEQ ID NO 4498

<400> SEQUENCE: 4498

000

<210> SEQ ID NO 4499

<400> SEQUENCE: 4499

000

<210> SEQ ID NO 4500

<400> SEQUENCE: 4500

000

<210> SEQ ID NO 4501

<400> SEQUENCE: 4501

000

<210> SEQ ID NO 4502

<400> SEQUENCE: 4502

000

<210> SEQ ID NO 4503

<400> SEQUENCE: 4503

000

<210> SEQ ID NO 4504

<400> SEQUENCE: 4504

000

-continued

<210> SEQ ID NO 4505

<400> SEQUENCE: 4505

000

<210> SEQ ID NO 4506

<400> SEQUENCE: 4506

000

<210> SEQ ID NO 4507

<400> SEQUENCE: 4507

000

<210> SEQ ID NO 4508

<400> SEQUENCE: 4508

000

<210> SEQ ID NO 4509

<400> SEQUENCE: 4509

000

<210> SEQ ID NO 4510

<400> SEQUENCE: 4510

000

<210> SEQ ID NO 4511

<400> SEQUENCE: 4511

000

<210> SEQ ID NO 4512

<400> SEQUENCE: 4512

000

<210> SEQ ID NO 4513

<400> SEQUENCE: 4513

000

<210> SEQ ID NO 4514

<400> SEQUENCE: 4514

000

<210> SEQ ID NO 4515

<400> SEQUENCE: 4515

000

<210> SEQ ID NO 4516

```
<400> SEQUENCE: 4516
000

<210> SEQ ID NO 4517
<400> SEQUENCE: 4517
000

<210> SEQ ID NO 4518
<400> SEQUENCE: 4518
000

<210> SEQ ID NO 4519
<400> SEQUENCE: 4519
000

<210> SEQ ID NO 4520
<400> SEQUENCE: 4520
000

<210> SEQ ID NO 4521
<400> SEQUENCE: 4521
000

<210> SEQ ID NO 4522
<400> SEQUENCE: 4522
000

<210> SEQ ID NO 4523
<400> SEQUENCE: 4523
000

<210> SEQ ID NO 4524
<400> SEQUENCE: 4524
000

<210> SEQ ID NO 4525
<400> SEQUENCE: 4525
000

<210> SEQ ID NO 4526
<400> SEQUENCE: 4526
000

<210> SEQ ID NO 4527
<400> SEQUENCE: 4527
```

000

<210> SEQ ID NO 4528

<400> SEQUENCE: 4528

000

<210> SEQ ID NO 4529

<400> SEQUENCE: 4529

000

<210> SEQ ID NO 4530

<400> SEQUENCE: 4530

000

<210> SEQ ID NO 4531

<400> SEQUENCE: 4531

000

<210> SEQ ID NO 4532

<400> SEQUENCE: 4532

000

<210> SEQ ID NO 4533

<400> SEQUENCE: 4533

000

<210> SEQ ID NO 4534

<400> SEQUENCE: 4534

000

<210> SEQ ID NO 4535

<400> SEQUENCE: 4535

000

<210> SEQ ID NO 4536

<400> SEQUENCE: 4536

000

<210> SEQ ID NO 4537

<400> SEQUENCE: 4537

000

<210> SEQ ID NO 4538

<400> SEQUENCE: 4538

000

-continued

<210> SEQ ID NO 4539

<400> SEQUENCE: 4539

000

<210> SEQ ID NO 4540

<400> SEQUENCE: 4540

000

<210> SEQ ID NO 4541

<400> SEQUENCE: 4541

000

<210> SEQ ID NO 4542

<400> SEQUENCE: 4542

000

<210> SEQ ID NO 4543

<400> SEQUENCE: 4543

000

<210> SEQ ID NO 4544

<400> SEQUENCE: 4544

000

<210> SEQ ID NO 4545

<400> SEQUENCE: 4545

000

<210> SEQ ID NO 4546

<400> SEQUENCE: 4546

000

<210> SEQ ID NO 4547

<400> SEQUENCE: 4547

000

<210> SEQ ID NO 4548

<400> SEQUENCE: 4548

000

<210> SEQ ID NO 4549

<400> SEQUENCE: 4549

000

<210> SEQ ID NO 4550

<400> SEQUENCE: 4550

000

<210> SEQ ID NO 4551

<400> SEQUENCE: 4551

000

<210> SEQ ID NO 4552

<400> SEQUENCE: 4552

000

<210> SEQ ID NO 4553

<400> SEQUENCE: 4553

000

<210> SEQ ID NO 4554

<400> SEQUENCE: 4554

000

<210> SEQ ID NO 4555

<400> SEQUENCE: 4555

000

<210> SEQ ID NO 4556

<400> SEQUENCE: 4556

000

<210> SEQ ID NO 4557

<400> SEQUENCE: 4557

000

<210> SEQ ID NO 4558

<400> SEQUENCE: 4558

000

<210> SEQ ID NO 4559

<400> SEQUENCE: 4559

000

<210> SEQ ID NO 4560

<400> SEQUENCE: 4560

000

<210> SEQ ID NO 4561

<400> SEQUENCE: 4561

000

<210> SEQ ID NO 4562

<400> SEQUENCE: 4562

000

<210> SEQ ID NO 4563

<400> SEQUENCE: 4563

000

<210> SEQ ID NO 4564

<400> SEQUENCE: 4564

000

<210> SEQ ID NO 4565

<400> SEQUENCE: 4565

000

<210> SEQ ID NO 4566

<400> SEQUENCE: 4566

000

<210> SEQ ID NO 4567

<400> SEQUENCE: 4567

000

<210> SEQ ID NO 4568

<400> SEQUENCE: 4568

000

<210> SEQ ID NO 4569

<400> SEQUENCE: 4569

000

<210> SEQ ID NO 4570

<400> SEQUENCE: 4570

000

<210> SEQ ID NO 4571

<400> SEQUENCE: 4571

000

<210> SEQ ID NO 4572

<400> SEQUENCE: 4572

000

<210> SEQ ID NO 4573

<400> SEQUENCE: 4573

000

<210> SEQ ID NO 4574

<400> SEQUENCE: 4574

000

<210> SEQ ID NO 4575

<400> SEQUENCE: 4575

000

<210> SEQ ID NO 4576

<400> SEQUENCE: 4576

000

<210> SEQ ID NO 4577

<400> SEQUENCE: 4577

000

<210> SEQ ID NO 4578

<400> SEQUENCE: 4578

000

<210> SEQ ID NO 4579

<400> SEQUENCE: 4579

000

<210> SEQ ID NO 4580

<400> SEQUENCE: 4580

000

<210> SEQ ID NO 4581

<400> SEQUENCE: 4581

000

<210> SEQ ID NO 4582

<400> SEQUENCE: 4582

000

<210> SEQ ID NO 4583

<400> SEQUENCE: 4583

000

<210> SEQ ID NO 4584

<400> SEQUENCE: 4584

000

<210> SEQ ID NO 4585

<400> SEQUENCE: 4585

000

<210> SEQ ID NO 4586

<400> SEQUENCE: 4586

000

<210> SEQ ID NO 4587

<400> SEQUENCE: 4587

000

<210> SEQ ID NO 4588

<400> SEQUENCE: 4588

000

<210> SEQ ID NO 4589

<400> SEQUENCE: 4589

000

<210> SEQ ID NO 4590

<400> SEQUENCE: 4590

000

<210> SEQ ID NO 4591

<400> SEQUENCE: 4591

000

<210> SEQ ID NO 4592

<400> SEQUENCE: 4592

000

<210> SEQ ID NO 4593

<400> SEQUENCE: 4593

000

<210> SEQ ID NO 4594

<400> SEQUENCE: 4594

000

<210> SEQ ID NO 4595

<400> SEQUENCE: 4595

000

<210> SEQ ID NO 4596

<400> SEQUENCE: 4596

000

<210> SEQ ID NO 4597

<400> SEQUENCE: 4597

000

<210> SEQ ID NO 4598

<400> SEQUENCE: 4598

000

<210> SEQ ID NO 4599

<400> SEQUENCE: 4599

000

<210> SEQ ID NO 4600

<400> SEQUENCE: 4600

000

<210> SEQ ID NO 4601

<400> SEQUENCE: 4601

000

<210> SEQ ID NO 4602

<400> SEQUENCE: 4602

000

<210> SEQ ID NO 4603

<400> SEQUENCE: 4603

000

<210> SEQ ID NO 4604

<400> SEQUENCE: 4604

000

<210> SEQ ID NO 4605

<400> SEQUENCE: 4605

000

<210> SEQ ID NO 4606

<400> SEQUENCE: 4606

000

<210> SEQ ID NO 4607

<400> SEQUENCE: 4607

000

<210> SEQ ID NO 4608

<400> SEQUENCE: 4608

000

<210> SEQ ID NO 4609

<400> SEQUENCE: 4609

000

<210> SEQ ID NO 4610

<400> SEQUENCE: 4610

000

<210> SEQ ID NO 4611

<400> SEQUENCE: 4611

000

<210> SEQ ID NO 4612

<400> SEQUENCE: 4612

000

<210> SEQ ID NO 4613

<400> SEQUENCE: 4613

000

<210> SEQ ID NO 4614

<400> SEQUENCE: 4614

000

<210> SEQ ID NO 4615

<400> SEQUENCE: 4615

000

<210> SEQ ID NO 4616

<400> SEQUENCE: 4616

000

<210> SEQ ID NO 4617

<400> SEQUENCE: 4617

000

-continued

<210> SEQ ID NO 4618

<400> SEQUENCE: 4618

000

<210> SEQ ID NO 4619

<400> SEQUENCE: 4619

000

<210> SEQ ID NO 4620

<400> SEQUENCE: 4620

000

<210> SEQ ID NO 4621

<400> SEQUENCE: 4621

000

<210> SEQ ID NO 4622

<400> SEQUENCE: 4622

000

<210> SEQ ID NO 4623

<400> SEQUENCE: 4623

000

<210> SEQ ID NO 4624

<400> SEQUENCE: 4624

000

<210> SEQ ID NO 4625

<400> SEQUENCE: 4625

000

<210> SEQ ID NO 4626

<400> SEQUENCE: 4626

000

<210> SEQ ID NO 4627

<400> SEQUENCE: 4627

000

<210> SEQ ID NO 4628

<400> SEQUENCE: 4628

000

<210> SEQ ID NO 4629

-continued

<400> SEQUENCE: 4629

000

<210> SEQ ID NO 4630

<400> SEQUENCE: 4630

000

<210> SEQ ID NO 4631

<400> SEQUENCE: 4631

000

<210> SEQ ID NO 4632

<400> SEQUENCE: 4632

000

<210> SEQ ID NO 4633

<400> SEQUENCE: 4633

000

<210> SEQ ID NO 4634

<400> SEQUENCE: 4634

000

<210> SEQ ID NO 4635

<400> SEQUENCE: 4635

000

<210> SEQ ID NO 4636

<400> SEQUENCE: 4636

000

<210> SEQ ID NO 4637

<400> SEQUENCE: 4637

000

<210> SEQ ID NO 4638

<400> SEQUENCE: 4638

000

<210> SEQ ID NO 4639

<400> SEQUENCE: 4639

000

<210> SEQ ID NO 4640

<400> SEQUENCE: 4640

000

<210> SEQ ID NO 4641

<400> SEQUENCE: 4641

000

<210> SEQ ID NO 4642

<400> SEQUENCE: 4642

000

<210> SEQ ID NO 4643

<400> SEQUENCE: 4643

000

<210> SEQ ID NO 4644

<400> SEQUENCE: 4644

000

<210> SEQ ID NO 4645

<400> SEQUENCE: 4645

000

<210> SEQ ID NO 4646

<400> SEQUENCE: 4646

000

<210> SEQ ID NO 4647

<400> SEQUENCE: 4647

000

<210> SEQ ID NO 4648

<400> SEQUENCE: 4648

000

<210> SEQ ID NO 4649

<400> SEQUENCE: 4649

000

<210> SEQ ID NO 4650

<400> SEQUENCE: 4650

000

<210> SEQ ID NO 4651

<400> SEQUENCE: 4651

000

<210> SEQ ID NO 4652

<400> SEQUENCE: 4652

000

<210> SEQ ID NO 4653

<400> SEQUENCE: 4653

000

<210> SEQ ID NO 4654

<400> SEQUENCE: 4654

000

<210> SEQ ID NO 4655

<400> SEQUENCE: 4655

000

<210> SEQ ID NO 4656

<400> SEQUENCE: 4656

000

<210> SEQ ID NO 4657

<400> SEQUENCE: 4657

000

<210> SEQ ID NO 4658

<400> SEQUENCE: 4658

000

<210> SEQ ID NO 4659

<400> SEQUENCE: 4659

000

<210> SEQ ID NO 4660

<400> SEQUENCE: 4660

000

<210> SEQ ID NO 4661

<400> SEQUENCE: 4661

000

<210> SEQ ID NO 4662

<400> SEQUENCE: 4662

000

<210> SEQ ID NO 4663

<400> SEQUENCE: 4663

000

<210> SEQ ID NO 4664

<400> SEQUENCE: 4664

000

<210> SEQ ID NO 4665

<400> SEQUENCE: 4665

000

<210> SEQ ID NO 4666

<400> SEQUENCE: 4666

000

<210> SEQ ID NO 4667

<400> SEQUENCE: 4667

000

<210> SEQ ID NO 4668

<400> SEQUENCE: 4668

000

<210> SEQ ID NO 4669

<400> SEQUENCE: 4669

000

<210> SEQ ID NO 4670

<400> SEQUENCE: 4670

000

<210> SEQ ID NO 4671

<400> SEQUENCE: 4671

000

<210> SEQ ID NO 4672

<400> SEQUENCE: 4672

000

<210> SEQ ID NO 4673

<400> SEQUENCE: 4673

000

<210> SEQ ID NO 4674

-continued

<400> SEQUENCE: 4674

000

<210> SEQ ID NO 4675

<400> SEQUENCE: 4675

000

<210> SEQ ID NO 4676

<400> SEQUENCE: 4676

000

<210> SEQ ID NO 4677

<400> SEQUENCE: 4677

000

<210> SEQ ID NO 4678

<400> SEQUENCE: 4678

000

<210> SEQ ID NO 4679

<400> SEQUENCE: 4679

000

<210> SEQ ID NO 4680

<400> SEQUENCE: 4680

000

<210> SEQ ID NO 4681

<400> SEQUENCE: 4681

000

<210> SEQ ID NO 4682

<400> SEQUENCE: 4682

000

<210> SEQ ID NO 4683

<400> SEQUENCE: 4683

000

<210> SEQ ID NO 4684

<400> SEQUENCE: 4684

000

<210> SEQ ID NO 4685

<400> SEQUENCE: 4685

000

<210> SEQ ID NO 4686

<400> SEQUENCE: 4686

000

<210> SEQ ID NO 4687

<400> SEQUENCE: 4687

000

<210> SEQ ID NO 4688

<400> SEQUENCE: 4688

000

<210> SEQ ID NO 4689

<400> SEQUENCE: 4689

000

<210> SEQ ID NO 4690

<400> SEQUENCE: 4690

000

<210> SEQ ID NO 4691

<400> SEQUENCE: 4691

000

<210> SEQ ID NO 4692

<400> SEQUENCE: 4692

000

<210> SEQ ID NO 4693

<400> SEQUENCE: 4693

000

<210> SEQ ID NO 4694

<400> SEQUENCE: 4694

000

<210> SEQ ID NO 4695

<400> SEQUENCE: 4695

000

<210> SEQ ID NO 4696

<400> SEQUENCE: 4696

000

<210> SEQ ID NO 4697

<400> SEQUENCE: 4697

000

<210> SEQ ID NO 4698

<400> SEQUENCE: 4698

000

<210> SEQ ID NO 4699

<400> SEQUENCE: 4699

000

<210> SEQ ID NO 4700

<400> SEQUENCE: 4700

000

<210> SEQ ID NO 4701

<400> SEQUENCE: 4701

000

<210> SEQ ID NO 4702

<400> SEQUENCE: 4702

000

<210> SEQ ID NO 4703

<400> SEQUENCE: 4703

000

<210> SEQ ID NO 4704

<400> SEQUENCE: 4704

000

<210> SEQ ID NO 4705

<400> SEQUENCE: 4705

000

<210> SEQ ID NO 4706

<400> SEQUENCE: 4706

000

<210> SEQ ID NO 4707

<400> SEQUENCE: 4707

000

<210> SEQ ID NO 4708

<400> SEQUENCE: 4708

000

<210> SEQ ID NO 4709

<400> SEQUENCE: 4709

000

<210> SEQ ID NO 4710

<400> SEQUENCE: 4710

000

<210> SEQ ID NO 4711

<400> SEQUENCE: 4711

000

<210> SEQ ID NO 4712

<400> SEQUENCE: 4712

000

<210> SEQ ID NO 4713

<400> SEQUENCE: 4713

000

<210> SEQ ID NO 4714

<400> SEQUENCE: 4714

000

<210> SEQ ID NO 4715

<400> SEQUENCE: 4715

000

<210> SEQ ID NO 4716

<400> SEQUENCE: 4716

000

<210> SEQ ID NO 4717

<400> SEQUENCE: 4717

000

<210> SEQ ID NO 4718

<400> SEQUENCE: 4718

000

<210> SEQ ID NO 4719

<400> SEQUENCE: 4719

000

<210> SEQ ID NO 4720

<400> SEQUENCE: 4720

000

<210> SEQ ID NO 4721

<400> SEQUENCE: 4721

000

<210> SEQ ID NO 4722

<400> SEQUENCE: 4722

000

<210> SEQ ID NO 4723

<400> SEQUENCE: 4723

000

<210> SEQ ID NO 4724

<400> SEQUENCE: 4724

000

<210> SEQ ID NO 4725

<400> SEQUENCE: 4725

000

<210> SEQ ID NO 4726

<400> SEQUENCE: 4726

000

<210> SEQ ID NO 4727

<400> SEQUENCE: 4727

000

<210> SEQ ID NO 4728

<400> SEQUENCE: 4728

000

<210> SEQ ID NO 4729

<400> SEQUENCE: 4729

000

<210> SEQ ID NO 4730

<400> SEQUENCE: 4730

000

-continued

<210> SEQ ID NO 4731

<400> SEQUENCE: 4731

000

<210> SEQ ID NO 4732

<400> SEQUENCE: 4732

000

<210> SEQ ID NO 4733

<400> SEQUENCE: 4733

000

<210> SEQ ID NO 4734

<400> SEQUENCE: 4734

000

<210> SEQ ID NO 4735

<400> SEQUENCE: 4735

000

<210> SEQ ID NO 4736

<400> SEQUENCE: 4736

000

<210> SEQ ID NO 4737

<400> SEQUENCE: 4737

000

<210> SEQ ID NO 4738

<400> SEQUENCE: 4738

000

<210> SEQ ID NO 4739

<400> SEQUENCE: 4739

000

<210> SEQ ID NO 4740

<400> SEQUENCE: 4740

000

<210> SEQ ID NO 4741

<400> SEQUENCE: 4741

000

<210> SEQ ID NO 4742
<400> SEQUENCE: 4742
000

<210> SEQ ID NO 4743
<400> SEQUENCE: 4743
000

<210> SEQ ID NO 4744
<400> SEQUENCE: 4744
000

<210> SEQ ID NO 4745
<400> SEQUENCE: 4745
000

<210> SEQ ID NO 4746
<400> SEQUENCE: 4746
000

<210> SEQ ID NO 4747
<400> SEQUENCE: 4747
000

<210> SEQ ID NO 4748
<400> SEQUENCE: 4748
000

<210> SEQ ID NO 4749
<400> SEQUENCE: 4749
000

<210> SEQ ID NO 4750
<400> SEQUENCE: 4750
000

<210> SEQ ID NO 4751
<400> SEQUENCE: 4751
000

<210> SEQ ID NO 4752
<400> SEQUENCE: 4752
000

<210> SEQ ID NO 4753

<400> SEQUENCE: 4753

000

<210> SEQ ID NO 4754

<400> SEQUENCE: 4754

000

<210> SEQ ID NO 4755

<400> SEQUENCE: 4755

000

<210> SEQ ID NO 4756

<400> SEQUENCE: 4756

000

<210> SEQ ID NO 4757

<400> SEQUENCE: 4757

000

<210> SEQ ID NO 4758

<400> SEQUENCE: 4758

000

<210> SEQ ID NO 4759

<400> SEQUENCE: 4759

000

<210> SEQ ID NO 4760

<400> SEQUENCE: 4760

000

<210> SEQ ID NO 4761

<400> SEQUENCE: 4761

000

<210> SEQ ID NO 4762

<400> SEQUENCE: 4762

000

<210> SEQ ID NO 4763

<400> SEQUENCE: 4763

000

<210> SEQ ID NO 4764

<400> SEQUENCE: 4764

000

<210> SEQ ID NO 4765

<400> SEQUENCE: 4765

000

<210> SEQ ID NO 4766

<400> SEQUENCE: 4766

000

<210> SEQ ID NO 4767

<400> SEQUENCE: 4767

000

<210> SEQ ID NO 4768

<400> SEQUENCE: 4768

000

<210> SEQ ID NO 4769

<400> SEQUENCE: 4769

000

<210> SEQ ID NO 4770

<400> SEQUENCE: 4770

000

<210> SEQ ID NO 4771

<400> SEQUENCE: 4771

000

<210> SEQ ID NO 4772

<400> SEQUENCE: 4772

000

<210> SEQ ID NO 4773

<400> SEQUENCE: 4773

000

<210> SEQ ID NO 4774

<400> SEQUENCE: 4774

000

<210> SEQ ID NO 4775

<400> SEQUENCE: 4775

000

<210> SEQ ID NO 4776

<400> SEQUENCE: 4776

000

<210> SEQ ID NO 4777

<400> SEQUENCE: 4777

000

<210> SEQ ID NO 4778

<400> SEQUENCE: 4778

000

<210> SEQ ID NO 4779

<400> SEQUENCE: 4779

000

<210> SEQ ID NO 4780

<400> SEQUENCE: 4780

000

<210> SEQ ID NO 4781

<400> SEQUENCE: 4781

000

<210> SEQ ID NO 4782

<400> SEQUENCE: 4782

000

<210> SEQ ID NO 4783

<400> SEQUENCE: 4783

000

<210> SEQ ID NO 4784

<400> SEQUENCE: 4784

000

<210> SEQ ID NO 4785

<400> SEQUENCE: 4785

000

<210> SEQ ID NO 4786

<400> SEQUENCE: 4786

000

<210> SEQ ID NO 4787

<400> SEQUENCE: 4787

000

<210> SEQ ID NO 4788

<400> SEQUENCE: 4788

000

<210> SEQ ID NO 4789

<400> SEQUENCE: 4789

000

<210> SEQ ID NO 4790

<400> SEQUENCE: 4790

000

<210> SEQ ID NO 4791

<400> SEQUENCE: 4791

000

<210> SEQ ID NO 4792

<400> SEQUENCE: 4792

000

<210> SEQ ID NO 4793

<400> SEQUENCE: 4793

000

<210> SEQ ID NO 4794

<400> SEQUENCE: 4794

000

<210> SEQ ID NO 4795

<400> SEQUENCE: 4795

000

<210> SEQ ID NO 4796

<400> SEQUENCE: 4796

000

<210> SEQ ID NO 4797

<400> SEQUENCE: 4797

000

<210> SEQ ID NO 4798

<400> SEQUENCE: 4798

000

<210> SEQ ID NO 4799

<400> SEQUENCE: 4799

000

<210> SEQ ID NO 4800

<400> SEQUENCE: 4800

000

<210> SEQ ID NO 4801

<400> SEQUENCE: 4801

000

<210> SEQ ID NO 4802

<400> SEQUENCE: 4802

000

<210> SEQ ID NO 4803

<400> SEQUENCE: 4803

000

<210> SEQ ID NO 4804

<400> SEQUENCE: 4804

000

<210> SEQ ID NO 4805

<400> SEQUENCE: 4805

000

<210> SEQ ID NO 4806

<400> SEQUENCE: 4806

000

<210> SEQ ID NO 4807

<400> SEQUENCE: 4807

000

<210> SEQ ID NO 4808

<400> SEQUENCE: 4808

000

<210> SEQ ID NO 4809

<400> SEQUENCE: 4809

000

<210> SEQ ID NO 4810

<400> SEQUENCE: 4810

000

<210> SEQ ID NO 4811

<400> SEQUENCE: 4811

000

<210> SEQ ID NO 4812

<400> SEQUENCE: 4812

000

<210> SEQ ID NO 4813

<400> SEQUENCE: 4813

000

<210> SEQ ID NO 4814

<400> SEQUENCE: 4814

000

<210> SEQ ID NO 4815

<400> SEQUENCE: 4815

000

<210> SEQ ID NO 4816

<400> SEQUENCE: 4816

000

<210> SEQ ID NO 4817

<400> SEQUENCE: 4817

000

<210> SEQ ID NO 4818

<400> SEQUENCE: 4818

000

<210> SEQ ID NO 4819

<400> SEQUENCE: 4819

000

<210> SEQ ID NO 4820

<400> SEQUENCE: 4820

000

<210> SEQ ID NO 4821

<400> SEQUENCE: 4821

000

<210> SEQ ID NO 4822

<400> SEQUENCE: 4822

000

<210> SEQ ID NO 4823

<400> SEQUENCE: 4823

000

<210> SEQ ID NO 4824

<400> SEQUENCE: 4824

000

<210> SEQ ID NO 4825

<400> SEQUENCE: 4825

000

<210> SEQ ID NO 4826

<400> SEQUENCE: 4826

000

<210> SEQ ID NO 4827

<400> SEQUENCE: 4827

000

<210> SEQ ID NO 4828

<400> SEQUENCE: 4828

000

<210> SEQ ID NO 4829

<400> SEQUENCE: 4829

000

<210> SEQ ID NO 4830

<400> SEQUENCE: 4830

000

<210> SEQ ID NO 4831

<400> SEQUENCE: 4831

000

<210> SEQ ID NO 4832

-continued

<400> SEQUENCE: 4832

000

<210> SEQ ID NO 4833

<400> SEQUENCE: 4833

000

<210> SEQ ID NO 4834

<400> SEQUENCE: 4834

000

<210> SEQ ID NO 4835

<400> SEQUENCE: 4835

000

<210> SEQ ID NO 4836

<400> SEQUENCE: 4836

000

<210> SEQ ID NO 4837

<400> SEQUENCE: 4837

000

<210> SEQ ID NO 4838

<400> SEQUENCE: 4838

000

<210> SEQ ID NO 4839

<400> SEQUENCE: 4839

000

<210> SEQ ID NO 4840

<400> SEQUENCE: 4840

000

<210> SEQ ID NO 4841

<400> SEQUENCE: 4841

000

<210> SEQ ID NO 4842

<400> SEQUENCE: 4842

000

<210> SEQ ID NO 4843

<400> SEQUENCE: 4843

000

<210> SEQ ID NO 4844

<400> SEQUENCE: 4844

000

<210> SEQ ID NO 4845

<400> SEQUENCE: 4845

000

<210> SEQ ID NO 4846

<400> SEQUENCE: 4846

000

<210> SEQ ID NO 4847

<400> SEQUENCE: 4847

000

<210> SEQ ID NO 4848

<400> SEQUENCE: 4848

000

<210> SEQ ID NO 4849

<400> SEQUENCE: 4849

000

<210> SEQ ID NO 4850

<400> SEQUENCE: 4850

000

<210> SEQ ID NO 4851

<400> SEQUENCE: 4851

000

<210> SEQ ID NO 4852

<400> SEQUENCE: 4852

000

<210> SEQ ID NO 4853

<400> SEQUENCE: 4853

000

<210> SEQ ID NO 4854

<400> SEQUENCE: 4854

000

-continued

<210> SEQ ID NO 4855

<400> SEQUENCE: 4855

000

<210> SEQ ID NO 4856

<400> SEQUENCE: 4856

000

<210> SEQ ID NO 4857

<400> SEQUENCE: 4857

000

<210> SEQ ID NO 4858

<400> SEQUENCE: 4858

000

<210> SEQ ID NO 4859

<400> SEQUENCE: 4859

000

<210> SEQ ID NO 4860

<400> SEQUENCE: 4860

000

<210> SEQ ID NO 4861

<400> SEQUENCE: 4861

000

<210> SEQ ID NO 4862

<400> SEQUENCE: 4862

000

<210> SEQ ID NO 4863

<400> SEQUENCE: 4863

000

<210> SEQ ID NO 4864

<400> SEQUENCE: 4864

000

<210> SEQ ID NO 4865

<400> SEQUENCE: 4865

000

<210> SEQ ID NO 4866

<400> SEQUENCE: 4866

000

<210> SEQ ID NO 4867

<400> SEQUENCE: 4867

000

<210> SEQ ID NO 4868

<400> SEQUENCE: 4868

000

<210> SEQ ID NO 4869

<400> SEQUENCE: 4869

000

<210> SEQ ID NO 4870

<400> SEQUENCE: 4870

000

<210> SEQ ID NO 4871

<400> SEQUENCE: 4871

000

<210> SEQ ID NO 4872

<400> SEQUENCE: 4872

000

<210> SEQ ID NO 4873

<400> SEQUENCE: 4873

000

<210> SEQ ID NO 4874

<400> SEQUENCE: 4874

000

<210> SEQ ID NO 4875

<400> SEQUENCE: 4875

000

<210> SEQ ID NO 4876

<400> SEQUENCE: 4876

000

<210> SEQ ID NO 4877

<400> SEQUENCE: 4877

000

<210> SEQ ID NO 4878

<400> SEQUENCE: 4878

000

<210> SEQ ID NO 4879

<400> SEQUENCE: 4879

000

<210> SEQ ID NO 4880

<400> SEQUENCE: 4880

000

<210> SEQ ID NO 4881

<400> SEQUENCE: 4881

000

<210> SEQ ID NO 4882

<400> SEQUENCE: 4882

000

<210> SEQ ID NO 4883

<400> SEQUENCE: 4883

000

<210> SEQ ID NO 4884

<400> SEQUENCE: 4884

000

<210> SEQ ID NO 4885

<400> SEQUENCE: 4885

000

<210> SEQ ID NO 4886

<400> SEQUENCE: 4886

000

<210> SEQ ID NO 4887

<400> SEQUENCE: 4887

000

<210> SEQ ID NO 4888

<400> SEQUENCE: 4888

000

<210> SEQ ID NO 4889

<400> SEQUENCE: 4889

000

<210> SEQ ID NO 4890

<400> SEQUENCE: 4890

000

<210> SEQ ID NO 4891

<400> SEQUENCE: 4891

000

<210> SEQ ID NO 4892

<400> SEQUENCE: 4892

000

<210> SEQ ID NO 4893

<400> SEQUENCE: 4893

000

<210> SEQ ID NO 4894

<400> SEQUENCE: 4894

000

<210> SEQ ID NO 4895

<400> SEQUENCE: 4895

000

<210> SEQ ID NO 4896

<400> SEQUENCE: 4896

000

<210> SEQ ID NO 4897

<400> SEQUENCE: 4897

000

<210> SEQ ID NO 4898

<400> SEQUENCE: 4898

000

<210> SEQ ID NO 4899

<400> SEQUENCE: 4899

000

<210> SEQ ID NO 4900

<400> SEQUENCE: 4900

000

<210> SEQ ID NO 4901

<400> SEQUENCE: 4901

000

<210> SEQ ID NO 4902

<400> SEQUENCE: 4902

000

<210> SEQ ID NO 4903

<400> SEQUENCE: 4903

000

<210> SEQ ID NO 4904

<400> SEQUENCE: 4904

000

<210> SEQ ID NO 4905

<400> SEQUENCE: 4905

000

<210> SEQ ID NO 4906

<400> SEQUENCE: 4906

000

<210> SEQ ID NO 4907

<400> SEQUENCE: 4907

000

<210> SEQ ID NO 4908

<400> SEQUENCE: 4908

000

<210> SEQ ID NO 4909

<400> SEQUENCE: 4909

000

<210> SEQ ID NO 4910

<400> SEQUENCE: 4910

000

<210> SEQ ID NO 4911

<400> SEQUENCE: 4911

000

<210> SEQ ID NO 4912

<400> SEQUENCE: 4912

000

<210> SEQ ID NO 4913

<400> SEQUENCE: 4913

000

<210> SEQ ID NO 4914

<400> SEQUENCE: 4914

000

<210> SEQ ID NO 4915

<400> SEQUENCE: 4915

000

<210> SEQ ID NO 4916

<400> SEQUENCE: 4916

000

<210> SEQ ID NO 4917

<400> SEQUENCE: 4917

000

<210> SEQ ID NO 4918

<400> SEQUENCE: 4918

000

<210> SEQ ID NO 4919

<400> SEQUENCE: 4919

000

<210> SEQ ID NO 4920

<400> SEQUENCE: 4920

000

<210> SEQ ID NO 4921

<400> SEQUENCE: 4921

000

<210> SEQ ID NO 4922

<400> SEQUENCE: 4922

000

<210> SEQ ID NO 4923

<400> SEQUENCE: 4923

000

<210> SEQ ID NO 4924

<400> SEQUENCE: 4924

000

<210> SEQ ID NO 4925

<400> SEQUENCE: 4925

000

<210> SEQ ID NO 4926

<400> SEQUENCE: 4926

000

<210> SEQ ID NO 4927

<400> SEQUENCE: 4927

000

<210> SEQ ID NO 4928

<400> SEQUENCE: 4928

000

<210> SEQ ID NO 4929

<400> SEQUENCE: 4929

000

<210> SEQ ID NO 4930

<400> SEQUENCE: 4930

000

<210> SEQ ID NO 4931

<400> SEQUENCE: 4931

000

<210> SEQ ID NO 4932

<400> SEQUENCE: 4932

000

<210> SEQ ID NO 4933

<400> SEQUENCE: 4933

000

<210> SEQ ID NO 4934

<400> SEQUENCE: 4934

000

<210> SEQ ID NO 4935

<400> SEQUENCE: 4935

000

<210> SEQ ID NO 4936

<400> SEQUENCE: 4936

000

<210> SEQ ID NO 4937

<400> SEQUENCE: 4937

000

<210> SEQ ID NO 4938

<400> SEQUENCE: 4938

000

<210> SEQ ID NO 4939

<400> SEQUENCE: 4939

000

<210> SEQ ID NO 4940

<400> SEQUENCE: 4940

000

<210> SEQ ID NO 4941

<400> SEQUENCE: 4941

000

<210> SEQ ID NO 4942

<400> SEQUENCE: 4942

000

<210> SEQ ID NO 4943

<400> SEQUENCE: 4943

000

<210> SEQ ID NO 4944

<400> SEQUENCE: 4944

000

<210> SEQ ID NO 4945

-continued

<400> SEQUENCE: 4945

000

<210> SEQ ID NO 4946

<400> SEQUENCE: 4946

000

<210> SEQ ID NO 4947

<400> SEQUENCE: 4947

000

<210> SEQ ID NO 4948

<400> SEQUENCE: 4948

000

<210> SEQ ID NO 4949

<400> SEQUENCE: 4949

000

<210> SEQ ID NO 4950

<400> SEQUENCE: 4950

000

<210> SEQ ID NO 4951

<400> SEQUENCE: 4951

000

<210> SEQ ID NO 4952

<400> SEQUENCE: 4952

000

<210> SEQ ID NO 4953

<400> SEQUENCE: 4953

000

<210> SEQ ID NO 4954

<400> SEQUENCE: 4954

000

<210> SEQ ID NO 4955

<400> SEQUENCE: 4955

000

<210> SEQ ID NO 4956

<400> SEQUENCE: 4956

000

<210> SEQ ID NO 4957

<400> SEQUENCE: 4957

000

<210> SEQ ID NO 4958

<400> SEQUENCE: 4958

000

<210> SEQ ID NO 4959

<400> SEQUENCE: 4959

000

<210> SEQ ID NO 4960

<400> SEQUENCE: 4960

000

<210> SEQ ID NO 4961

<400> SEQUENCE: 4961

000

<210> SEQ ID NO 4962

<400> SEQUENCE: 4962

000

<210> SEQ ID NO 4963

<400> SEQUENCE: 4963

000

<210> SEQ ID NO 4964

<400> SEQUENCE: 4964

000

<210> SEQ ID NO 4965

<400> SEQUENCE: 4965

000

<210> SEQ ID NO 4966

<400> SEQUENCE: 4966

000

<210> SEQ ID NO 4967

<400> SEQUENCE: 4967

000

<210> SEQ ID NO 4968

<400> SEQUENCE: 4968

000

<210> SEQ ID NO 4969

<400> SEQUENCE: 4969

000

<210> SEQ ID NO 4970

<400> SEQUENCE: 4970

000

<210> SEQ ID NO 4971

<400> SEQUENCE: 4971

000

<210> SEQ ID NO 4972

<400> SEQUENCE: 4972

000

<210> SEQ ID NO 4973

<400> SEQUENCE: 4973

000

<210> SEQ ID NO 4974

<400> SEQUENCE: 4974

000

<210> SEQ ID NO 4975

<400> SEQUENCE: 4975

000

<210> SEQ ID NO 4976

<400> SEQUENCE: 4976

000

<210> SEQ ID NO 4977

<400> SEQUENCE: 4977

000

<210> SEQ ID NO 4978

<400> SEQUENCE: 4978

000

```
<210> SEQ ID NO 4979
<400> SEQUENCE: 4979
000

<210> SEQ ID NO 4980
<400> SEQUENCE: 4980
000

<210> SEQ ID NO 4981
<400> SEQUENCE: 4981
000

<210> SEQ ID NO 4982
<400> SEQUENCE: 4982
000

<210> SEQ ID NO 4983
<400> SEQUENCE: 4983
000

<210> SEQ ID NO 4984
<400> SEQUENCE: 4984
000

<210> SEQ ID NO 4985
<400> SEQUENCE: 4985
000

<210> SEQ ID NO 4986
<400> SEQUENCE: 4986
000

<210> SEQ ID NO 4987
<400> SEQUENCE: 4987
000

<210> SEQ ID NO 4988
<400> SEQUENCE: 4988
000

<210> SEQ ID NO 4989
<400> SEQUENCE: 4989
000

<210> SEQ ID NO 4990
```

-continued

<400> SEQUENCE: 4990

000

<210> SEQ ID NO 4991

<400> SEQUENCE: 4991

000

<210> SEQ ID NO 4992

<400> SEQUENCE: 4992

000

<210> SEQ ID NO 4993

<400> SEQUENCE: 4993

000

<210> SEQ ID NO 4994

<400> SEQUENCE: 4994

000

<210> SEQ ID NO 4995

<400> SEQUENCE: 4995

000

<210> SEQ ID NO 4996

<400> SEQUENCE: 4996

000

<210> SEQ ID NO 4997

<400> SEQUENCE: 4997

000

<210> SEQ ID NO 4998

<400> SEQUENCE: 4998

000

<210> SEQ ID NO 4999

<400> SEQUENCE: 4999

000

<210> SEQ ID NO 5000

<400> SEQUENCE: 5000

000

<210> SEQ ID NO 5001

<400> SEQUENCE: 5001

000

<210> SEQ ID NO 5002

<400> SEQUENCE: 5002

000

<210> SEQ ID NO 5003

<400> SEQUENCE: 5003

000

<210> SEQ ID NO 5004

<400> SEQUENCE: 5004

000

<210> SEQ ID NO 5005

<400> SEQUENCE: 5005

000

<210> SEQ ID NO 5006

<400> SEQUENCE: 5006

000

<210> SEQ ID NO 5007

<400> SEQUENCE: 5007

000

<210> SEQ ID NO 5008

<400> SEQUENCE: 5008

000

<210> SEQ ID NO 5009

<400> SEQUENCE: 5009

000

<210> SEQ ID NO 5010

<400> SEQUENCE: 5010

000

<210> SEQ ID NO 5011

<400> SEQUENCE: 5011

000

<210> SEQ ID NO 5012

<400> SEQUENCE: 5012

000

<210> SEQ ID NO 5013

<400> SEQUENCE: 5013

000

<210> SEQ ID NO 5014

<400> SEQUENCE: 5014

000

<210> SEQ ID NO 5015

<400> SEQUENCE: 5015

000

<210> SEQ ID NO 5016

<400> SEQUENCE: 5016

000

<210> SEQ ID NO 5017

<400> SEQUENCE: 5017

000

<210> SEQ ID NO 5018

<400> SEQUENCE: 5018

000

<210> SEQ ID NO 5019

<400> SEQUENCE: 5019

000

<210> SEQ ID NO 5020

<400> SEQUENCE: 5020

000

<210> SEQ ID NO 5021

<400> SEQUENCE: 5021

000

<210> SEQ ID NO 5022

<400> SEQUENCE: 5022

000

<210> SEQ ID NO 5023

<400> SEQUENCE: 5023

000

<210> SEQ ID NO 5024

<210> SEQ ID NO 5024

<400> SEQUENCE: 5024

000

<210> SEQ ID NO 5025

<400> SEQUENCE: 5025

000

<210> SEQ ID NO 5026

<400> SEQUENCE: 5026

000

<210> SEQ ID NO 5027

<400> SEQUENCE: 5027

000

<210> SEQ ID NO 5028

<400> SEQUENCE: 5028

000

<210> SEQ ID NO 5029

<400> SEQUENCE: 5029

000

<210> SEQ ID NO 5030

<400> SEQUENCE: 5030

000

<210> SEQ ID NO 5031

<400> SEQUENCE: 5031

000

<210> SEQ ID NO 5032

<400> SEQUENCE: 5032

000

<210> SEQ ID NO 5033

<400> SEQUENCE: 5033

000

<210> SEQ ID NO 5034

<400> SEQUENCE: 5034

000

<210> SEQ ID NO 5035

<400> SEQUENCE: 5035

000

<210> SEQ ID NO 5036

<400> SEQUENCE: 5036

000

<210> SEQ ID NO 5037

<400> SEQUENCE: 5037

000

<210> SEQ ID NO 5038

<400> SEQUENCE: 5038

000

<210> SEQ ID NO 5039

<400> SEQUENCE: 5039

000

<210> SEQ ID NO 5040

<400> SEQUENCE: 5040

000

<210> SEQ ID NO 5041

<400> SEQUENCE: 5041

000

<210> SEQ ID NO 5042

<400> SEQUENCE: 5042

000

<210> SEQ ID NO 5043

<400> SEQUENCE: 5043

000

<210> SEQ ID NO 5044

<400> SEQUENCE: 5044

000

<210> SEQ ID NO 5045

<400> SEQUENCE: 5045

000

<210> SEQ ID NO 5046

<400> SEQUENCE: 5046

000

<210> SEQ ID NO 5047

<400> SEQUENCE: 5047

000

<210> SEQ ID NO 5048

<400> SEQUENCE: 5048

000

<210> SEQ ID NO 5049

<400> SEQUENCE: 5049

000

<210> SEQ ID NO 5050

<400> SEQUENCE: 5050

000

<210> SEQ ID NO 5051

<400> SEQUENCE: 5051

000

<210> SEQ ID NO 5052

<400> SEQUENCE: 5052

000

<210> SEQ ID NO 5053

<400> SEQUENCE: 5053

000

<210> SEQ ID NO 5054

<400> SEQUENCE: 5054

000

<210> SEQ ID NO 5055

<400> SEQUENCE: 5055

000

<210> SEQ ID NO 5056

<400> SEQUENCE: 5056

000

<210> SEQ ID NO 5057

<400> SEQUENCE: 5057

000

-continued

<210> SEQ ID NO 5058

<400> SEQUENCE: 5058

000

<210> SEQ ID NO 5059

<400> SEQUENCE: 5059

000

<210> SEQ ID NO 5060

<400> SEQUENCE: 5060

000

<210> SEQ ID NO 5061

<400> SEQUENCE: 5061

000

<210> SEQ ID NO 5062

<400> SEQUENCE: 5062

000

<210> SEQ ID NO 5063

<400> SEQUENCE: 5063

000

<210> SEQ ID NO 5064

<400> SEQUENCE: 5064

000

<210> SEQ ID NO 5065

<400> SEQUENCE: 5065

000

<210> SEQ ID NO 5066

<400> SEQUENCE: 5066

000

<210> SEQ ID NO 5067

<400> SEQUENCE: 5067

000

<210> SEQ ID NO 5068

<400> SEQUENCE: 5068

000

<210> SEQ ID NO 5069

<400> SEQUENCE: 5069

000

<210> SEQ ID NO 5070

<400> SEQUENCE: 5070

000

<210> SEQ ID NO 5071

<400> SEQUENCE: 5071

000

<210> SEQ ID NO 5072

<400> SEQUENCE: 5072

000

<210> SEQ ID NO 5073

<400> SEQUENCE: 5073

000

<210> SEQ ID NO 5074

<400> SEQUENCE: 5074

000

<210> SEQ ID NO 5075

<400> SEQUENCE: 5075

000

<210> SEQ ID NO 5076

<400> SEQUENCE: 5076

000

<210> SEQ ID NO 5077

<400> SEQUENCE: 5077

000

<210> SEQ ID NO 5078

<400> SEQUENCE: 5078

000

<210> SEQ ID NO 5079

<400> SEQUENCE: 5079

000

<210> SEQ ID NO 5080

<400> SEQUENCE: 5080

000

<210> SEQ ID NO 5081

<400> SEQUENCE: 5081

000

<210> SEQ ID NO 5082

<400> SEQUENCE: 5082

000

<210> SEQ ID NO 5083

<400> SEQUENCE: 5083

000

<210> SEQ ID NO 5084

<400> SEQUENCE: 5084

000

<210> SEQ ID NO 5085

<400> SEQUENCE: 5085

000

<210> SEQ ID NO 5086

<400> SEQUENCE: 5086

000

<210> SEQ ID NO 5087

<400> SEQUENCE: 5087

000

<210> SEQ ID NO 5088

<400> SEQUENCE: 5088

000

<210> SEQ ID NO 5089

<400> SEQUENCE: 5089

000

<210> SEQ ID NO 5090

<400> SEQUENCE: 5090

000

<210> SEQ ID NO 5091

<400> SEQUENCE: 5091

000

<210> SEQ ID NO 5092

<400> SEQUENCE: 5092

000

<210> SEQ ID NO 5093

<400> SEQUENCE: 5093

000

<210> SEQ ID NO 5094

<400> SEQUENCE: 5094

000

<210> SEQ ID NO 5095

<400> SEQUENCE: 5095

000

<210> SEQ ID NO 5096

<400> SEQUENCE: 5096

000

<210> SEQ ID NO 5097

<400> SEQUENCE: 5097

000

<210> SEQ ID NO 5098

<400> SEQUENCE: 5098

000

<210> SEQ ID NO 5099

<400> SEQUENCE: 5099

000

<210> SEQ ID NO 5100

<400> SEQUENCE: 5100

000

<210> SEQ ID NO 5101

<400> SEQUENCE: 5101

000

<210> SEQ ID NO 5102

<400> SEQUENCE: 5102

000

<210> SEQ ID NO 5103

```
<400> SEQUENCE: 5103
000

<210> SEQ ID NO 5104
<400> SEQUENCE: 5104
000

<210> SEQ ID NO 5105
<400> SEQUENCE: 5105
000

<210> SEQ ID NO 5106
<400> SEQUENCE: 5106
000

<210> SEQ ID NO 5107
<400> SEQUENCE: 5107
000

<210> SEQ ID NO 5108
<400> SEQUENCE: 5108
000

<210> SEQ ID NO 5109
<400> SEQUENCE: 5109
000

<210> SEQ ID NO 5110
<400> SEQUENCE: 5110
000

<210> SEQ ID NO 5111
<400> SEQUENCE: 5111
000

<210> SEQ ID NO 5112
<400> SEQUENCE: 5112
000

<210> SEQ ID NO 5113
<400> SEQUENCE: 5113
000

<210> SEQ ID NO 5114
<400> SEQUENCE: 5114
```

000

<210> SEQ ID NO 5115

<400> SEQUENCE: 5115

000

<210> SEQ ID NO 5116

<400> SEQUENCE: 5116

000

<210> SEQ ID NO 5117

<400> SEQUENCE: 5117

000

<210> SEQ ID NO 5118

<400> SEQUENCE: 5118

000

<210> SEQ ID NO 5119

<400> SEQUENCE: 5119

000

<210> SEQ ID NO 5120

<400> SEQUENCE: 5120

000

<210> SEQ ID NO 5121

<400> SEQUENCE: 5121

000

<210> SEQ ID NO 5122

<400> SEQUENCE: 5122

000

<210> SEQ ID NO 5123

<400> SEQUENCE: 5123

000

<210> SEQ ID NO 5124

<400> SEQUENCE: 5124

000

<210> SEQ ID NO 5125

<400> SEQUENCE: 5125

000

<210> SEQ ID NO 5126

<400> SEQUENCE: 5126

000

<210> SEQ ID NO 5127

<400> SEQUENCE: 5127

000

<210> SEQ ID NO 5128

<400> SEQUENCE: 5128

000

<210> SEQ ID NO 5129

<400> SEQUENCE: 5129

000

<210> SEQ ID NO 5130

<400> SEQUENCE: 5130

000

<210> SEQ ID NO 5131

<400> SEQUENCE: 5131

000

<210> SEQ ID NO 5132

<400> SEQUENCE: 5132

000

<210> SEQ ID NO 5133

<400> SEQUENCE: 5133

000

<210> SEQ ID NO 5134

<400> SEQUENCE: 5134

000

<210> SEQ ID NO 5135

<400> SEQUENCE: 5135

000

<210> SEQ ID NO 5136

<400> SEQUENCE: 5136

000

<210> SEQ ID NO 5137

<400> SEQUENCE: 5137

000

<210> SEQ ID NO 5138

<400> SEQUENCE: 5138

000

<210> SEQ ID NO 5139

<400> SEQUENCE: 5139

000

<210> SEQ ID NO 5140

<400> SEQUENCE: 5140

000

<210> SEQ ID NO 5141

<400> SEQUENCE: 5141

000

<210> SEQ ID NO 5142

<400> SEQUENCE: 5142

000

<210> SEQ ID NO 5143

<400> SEQUENCE: 5143

000

<210> SEQ ID NO 5144

<400> SEQUENCE: 5144

000

<210> SEQ ID NO 5145

<400> SEQUENCE: 5145

000

<210> SEQ ID NO 5146

<400> SEQUENCE: 5146

000

<210> SEQ ID NO 5147

<400> SEQUENCE: 5147

000

<210> SEQ ID NO 5148

<400> SEQUENCE: 5148

000

<210> SEQ ID NO 5149

<400> SEQUENCE: 5149

000

<210> SEQ ID NO 5150

<400> SEQUENCE: 5150

000

<210> SEQ ID NO 5151

<400> SEQUENCE: 5151

000

<210> SEQ ID NO 5152

<400> SEQUENCE: 5152

000

<210> SEQ ID NO 5153

<400> SEQUENCE: 5153

000

<210> SEQ ID NO 5154

<400> SEQUENCE: 5154

000

<210> SEQ ID NO 5155

<400> SEQUENCE: 5155

000

<210> SEQ ID NO 5156

<400> SEQUENCE: 5156

000

<210> SEQ ID NO 5157

<400> SEQUENCE: 5157

000

<210> SEQ ID NO 5158

<400> SEQUENCE: 5158

000

<210> SEQ ID NO 5159

<400> SEQUENCE: 5159

000

<210> SEQ ID NO 5160

<400> SEQUENCE: 5160

000

<210> SEQ ID NO 5161

<400> SEQUENCE: 5161

000

<210> SEQ ID NO 5162

<400> SEQUENCE: 5162

000

<210> SEQ ID NO 5163

<400> SEQUENCE: 5163

000

<210> SEQ ID NO 5164

<400> SEQUENCE: 5164

000

<210> SEQ ID NO 5165

<400> SEQUENCE: 5165

000

<210> SEQ ID NO 5166

<400> SEQUENCE: 5166

000

<210> SEQ ID NO 5167

<400> SEQUENCE: 5167

000

<210> SEQ ID NO 5168

<400> SEQUENCE: 5168

000

<210> SEQ ID NO 5169

<400> SEQUENCE: 5169

000

<210> SEQ ID NO 5170

<400> SEQUENCE: 5170

000

-continued

<210> SEQ ID NO 5171

<400> SEQUENCE: 5171

000

<210> SEQ ID NO 5172

<400> SEQUENCE: 5172

000

<210> SEQ ID NO 5173

<400> SEQUENCE: 5173

000

<210> SEQ ID NO 5174

<400> SEQUENCE: 5174

000

<210> SEQ ID NO 5175

<400> SEQUENCE: 5175

000

<210> SEQ ID NO 5176

<400> SEQUENCE: 5176

000

<210> SEQ ID NO 5177

<400> SEQUENCE: 5177

000

<210> SEQ ID NO 5178

<400> SEQUENCE: 5178

000

<210> SEQ ID NO 5179

<400> SEQUENCE: 5179

000

<210> SEQ ID NO 5180

<400> SEQUENCE: 5180

000

<210> SEQ ID NO 5181

<400> SEQUENCE: 5181

000

<210> SEQ ID NO 5182

<400> SEQUENCE: 5182

000

<210> SEQ ID NO 5183

<400> SEQUENCE: 5183

000

<210> SEQ ID NO 5184

<400> SEQUENCE: 5184

000

<210> SEQ ID NO 5185

<400> SEQUENCE: 5185

000

<210> SEQ ID NO 5186

<400> SEQUENCE: 5186

000

<210> SEQ ID NO 5187

<400> SEQUENCE: 5187

000

<210> SEQ ID NO 5188

<400> SEQUENCE: 5188

000

<210> SEQ ID NO 5189

<400> SEQUENCE: 5189

000

<210> SEQ ID NO 5190

<400> SEQUENCE: 5190

000

<210> SEQ ID NO 5191

<400> SEQUENCE: 5191

000

<210> SEQ ID NO 5192

<400> SEQUENCE: 5192

000

<210> SEQ ID NO 5193

<400> SEQUENCE: 5193

000

<210> SEQ ID NO 5194

<400> SEQUENCE: 5194

000

<210> SEQ ID NO 5195

<400> SEQUENCE: 5195

000

<210> SEQ ID NO 5196

<400> SEQUENCE: 5196

000

<210> SEQ ID NO 5197

<400> SEQUENCE: 5197

000

<210> SEQ ID NO 5198

<400> SEQUENCE: 5198

000

<210> SEQ ID NO 5199

<400> SEQUENCE: 5199

000

<210> SEQ ID NO 5200

<400> SEQUENCE: 5200

000

<210> SEQ ID NO 5201

<400> SEQUENCE: 5201

000

<210> SEQ ID NO 5202

<400> SEQUENCE: 5202

000

<210> SEQ ID NO 5203

<400> SEQUENCE: 5203

000

<210> SEQ ID NO 5204

<400> SEQUENCE: 5204

000

<210> SEQ ID NO 5205

<400> SEQUENCE: 5205

000

<210> SEQ ID NO 5206

<400> SEQUENCE: 5206

000

<210> SEQ ID NO 5207

<400> SEQUENCE: 5207

000

<210> SEQ ID NO 5208

<400> SEQUENCE: 5208

000

<210> SEQ ID NO 5209

<400> SEQUENCE: 5209

000

<210> SEQ ID NO 5210

<400> SEQUENCE: 5210

000

<210> SEQ ID NO 5211

<400> SEQUENCE: 5211

000

<210> SEQ ID NO 5212

<400> SEQUENCE: 5212

000

<210> SEQ ID NO 5213

<400> SEQUENCE: 5213

000

<210> SEQ ID NO 5214

<400> SEQUENCE: 5214

000

<210> SEQ ID NO 5215

<400> SEQUENCE: 5215

000

```
<210> SEQ ID NO 5216

<400> SEQUENCE: 5216

000

<210> SEQ ID NO 5217

<400> SEQUENCE: 5217

000

<210> SEQ ID NO 5218

<400> SEQUENCE: 5218

000

<210> SEQ ID NO 5219

<400> SEQUENCE: 5219

000

<210> SEQ ID NO 5220

<400> SEQUENCE: 5220

000

<210> SEQ ID NO 5221

<400> SEQUENCE: 5221

000

<210> SEQ ID NO 5222

<400> SEQUENCE: 5222

000

<210> SEQ ID NO 5223

<400> SEQUENCE: 5223

000

<210> SEQ ID NO 5224

<400> SEQUENCE: 5224

000

<210> SEQ ID NO 5225

<400> SEQUENCE: 5225

000

<210> SEQ ID NO 5226

<400> SEQUENCE: 5226

000

<210> SEQ ID NO 5227
```

<400> SEQUENCE: 5227

000

<210> SEQ ID NO 5228

<400> SEQUENCE: 5228

000

<210> SEQ ID NO 5229

<400> SEQUENCE: 5229

000

<210> SEQ ID NO 5230

<400> SEQUENCE: 5230

000

<210> SEQ ID NO 5231

<400> SEQUENCE: 5231

000

<210> SEQ ID NO 5232

<400> SEQUENCE: 5232

000

<210> SEQ ID NO 5233

<400> SEQUENCE: 5233

000

<210> SEQ ID NO 5234

<400> SEQUENCE: 5234

000

<210> SEQ ID NO 5235

<400> SEQUENCE: 5235

000

<210> SEQ ID NO 5236

<400> SEQUENCE: 5236

000

<210> SEQ ID NO 5237

<400> SEQUENCE: 5237

000

<210> SEQ ID NO 5238

<400> SEQUENCE: 5238

000

<210> SEQ ID NO 5239

<400> SEQUENCE: 5239

000

<210> SEQ ID NO 5240

<400> SEQUENCE: 5240

000

<210> SEQ ID NO 5241

<400> SEQUENCE: 5241

000

<210> SEQ ID NO 5242

<400> SEQUENCE: 5242

000

<210> SEQ ID NO 5243

<400> SEQUENCE: 5243

000

<210> SEQ ID NO 5244

<400> SEQUENCE: 5244

000

<210> SEQ ID NO 5245

<400> SEQUENCE: 5245

000

<210> SEQ ID NO 5246

<400> SEQUENCE: 5246

000

<210> SEQ ID NO 5247

<400> SEQUENCE: 5247

000

<210> SEQ ID NO 5248

<400> SEQUENCE: 5248

000

<210> SEQ ID NO 5249

<400> SEQUENCE: 5249

000

<210> SEQ ID NO 5250

<400> SEQUENCE: 5250

000

<210> SEQ ID NO 5251

<400> SEQUENCE: 5251

000

<210> SEQ ID NO 5252

<400> SEQUENCE: 5252

000

<210> SEQ ID NO 5253

<400> SEQUENCE: 5253

000

<210> SEQ ID NO 5254

<400> SEQUENCE: 5254

000

<210> SEQ ID NO 5255

<400> SEQUENCE: 5255

000

<210> SEQ ID NO 5256

<400> SEQUENCE: 5256

000

<210> SEQ ID NO 5257

<400> SEQUENCE: 5257

000

<210> SEQ ID NO 5258

<400> SEQUENCE: 5258

000

<210> SEQ ID NO 5259

<400> SEQUENCE: 5259

000

<210> SEQ ID NO 5260

<400> SEQUENCE: 5260

000

<210> SEQ ID NO 5261

<400> SEQUENCE: 5261

000

<210> SEQ ID NO 5262

<400> SEQUENCE: 5262

000

<210> SEQ ID NO 5263

<400> SEQUENCE: 5263

000

<210> SEQ ID NO 5264

<400> SEQUENCE: 5264

000

<210> SEQ ID NO 5265

<400> SEQUENCE: 5265

000

<210> SEQ ID NO 5266

<400> SEQUENCE: 5266

000

<210> SEQ ID NO 5267

<400> SEQUENCE: 5267

000

<210> SEQ ID NO 5268

<400> SEQUENCE: 5268

000

<210> SEQ ID NO 5269

<400> SEQUENCE: 5269

000

<210> SEQ ID NO 5270

<400> SEQUENCE: 5270

000

<210> SEQ ID NO 5271

<400> SEQUENCE: 5271

000

<210> SEQ ID NO 5272

<400> SEQUENCE: 5272

000

<210> SEQ ID NO 5273

<400> SEQUENCE: 5273

000

<210> SEQ ID NO 5274

<400> SEQUENCE: 5274

000

<210> SEQ ID NO 5275

<400> SEQUENCE: 5275

000

<210> SEQ ID NO 5276

<400> SEQUENCE: 5276

000

<210> SEQ ID NO 5277

<400> SEQUENCE: 5277

000

<210> SEQ ID NO 5278

<400> SEQUENCE: 5278

000

<210> SEQ ID NO 5279

<400> SEQUENCE: 5279

000

<210> SEQ ID NO 5280

<400> SEQUENCE: 5280

000

<210> SEQ ID NO 5281

<400> SEQUENCE: 5281

000

<210> SEQ ID NO 5282

<400> SEQUENCE: 5282

000

<210> SEQ ID NO 5283

<400> SEQUENCE: 5283

000

```
<210> SEQ ID NO 5284
<400> SEQUENCE: 5284
000

<210> SEQ ID NO 5285
<400> SEQUENCE: 5285
000

<210> SEQ ID NO 5286
<400> SEQUENCE: 5286
000

<210> SEQ ID NO 5287
<400> SEQUENCE: 5287
000

<210> SEQ ID NO 5288
<400> SEQUENCE: 5288
000

<210> SEQ ID NO 5289
<400> SEQUENCE: 5289
000

<210> SEQ ID NO 5290
<400> SEQUENCE: 5290
000

<210> SEQ ID NO 5291
<400> SEQUENCE: 5291
000

<210> SEQ ID NO 5292
<400> SEQUENCE: 5292
000

<210> SEQ ID NO 5293
<400> SEQUENCE: 5293
000

<210> SEQ ID NO 5294
<400> SEQUENCE: 5294
000
```

<210> SEQ ID NO 5295

<400> SEQUENCE: 5295

000

<210> SEQ ID NO 5296

<400> SEQUENCE: 5296

000

<210> SEQ ID NO 5297

<400> SEQUENCE: 5297

000

<210> SEQ ID NO 5298

<400> SEQUENCE: 5298

000

<210> SEQ ID NO 5299

<400> SEQUENCE: 5299

000

<210> SEQ ID NO 5300

<400> SEQUENCE: 5300

000

<210> SEQ ID NO 5301

<400> SEQUENCE: 5301

000

<210> SEQ ID NO 5302

<400> SEQUENCE: 5302

000

<210> SEQ ID NO 5303

<400> SEQUENCE: 5303

000

<210> SEQ ID NO 5304

<400> SEQUENCE: 5304

000

<210> SEQ ID NO 5305

<400> SEQUENCE: 5305

000

<210> SEQ ID NO 5306

```
<400> SEQUENCE: 5306

000

<210> SEQ ID NO 5307

<400> SEQUENCE: 5307

000

<210> SEQ ID NO 5308

<400> SEQUENCE: 5308

000

<210> SEQ ID NO 5309

<400> SEQUENCE: 5309

000

<210> SEQ ID NO 5310

<400> SEQUENCE: 5310

000

<210> SEQ ID NO 5311

<400> SEQUENCE: 5311

000

<210> SEQ ID NO 5312

<400> SEQUENCE: 5312

000

<210> SEQ ID NO 5313

<400> SEQUENCE: 5313

000

<210> SEQ ID NO 5314

<400> SEQUENCE: 5314

000

<210> SEQ ID NO 5315

<400> SEQUENCE: 5315

000

<210> SEQ ID NO 5316

<400> SEQUENCE: 5316

000

<210> SEQ ID NO 5317

<400> SEQUENCE: 5317
```

000

<210> SEQ ID NO 5318

<400> SEQUENCE: 5318

000

<210> SEQ ID NO 5319

<400> SEQUENCE: 5319

000

<210> SEQ ID NO 5320

<400> SEQUENCE: 5320

000

<210> SEQ ID NO 5321

<400> SEQUENCE: 5321

000

<210> SEQ ID NO 5322

<400> SEQUENCE: 5322

000

<210> SEQ ID NO 5323

<400> SEQUENCE: 5323

000

<210> SEQ ID NO 5324

<400> SEQUENCE: 5324

000

<210> SEQ ID NO 5325

<400> SEQUENCE: 5325

000

<210> SEQ ID NO 5326

<400> SEQUENCE: 5326

000

<210> SEQ ID NO 5327

<400> SEQUENCE: 5327

000

<210> SEQ ID NO 5328

<400> SEQUENCE: 5328

000

<210> SEQ ID NO 5329

<400> SEQUENCE: 5329

000

<210> SEQ ID NO 5330

<400> SEQUENCE: 5330

000

<210> SEQ ID NO 5331

<400> SEQUENCE: 5331

000

<210> SEQ ID NO 5332

<400> SEQUENCE: 5332

000

<210> SEQ ID NO 5333

<400> SEQUENCE: 5333

000

<210> SEQ ID NO 5334

<400> SEQUENCE: 5334

000

<210> SEQ ID NO 5335

<400> SEQUENCE: 5335

000

<210> SEQ ID NO 5336

<400> SEQUENCE: 5336

000

<210> SEQ ID NO 5337

<400> SEQUENCE: 5337

000

<210> SEQ ID NO 5338

<400> SEQUENCE: 5338

000

<210> SEQ ID NO 5339

<400> SEQUENCE: 5339

000

<210> SEQ ID NO 5340

```
<400> SEQUENCE: 5340

000

<210> SEQ ID NO 5341

<400> SEQUENCE: 5341

000

<210> SEQ ID NO 5342

<400> SEQUENCE: 5342

000

<210> SEQ ID NO 5343

<400> SEQUENCE: 5343

000

<210> SEQ ID NO 5344

<400> SEQUENCE: 5344

000

<210> SEQ ID NO 5345

<400> SEQUENCE: 5345

000

<210> SEQ ID NO 5346

<400> SEQUENCE: 5346

000

<210> SEQ ID NO 5347

<400> SEQUENCE: 5347

000

<210> SEQ ID NO 5348

<400> SEQUENCE: 5348

000

<210> SEQ ID NO 5349

<400> SEQUENCE: 5349

000

<210> SEQ ID NO 5350

<400> SEQUENCE: 5350

000

<210> SEQ ID NO 5351

<400> SEQUENCE: 5351
```

000

<210> SEQ ID NO 5352

<400> SEQUENCE: 5352

000

<210> SEQ ID NO 5353

<400> SEQUENCE: 5353

000

<210> SEQ ID NO 5354

<400> SEQUENCE: 5354

000

<210> SEQ ID NO 5355

<400> SEQUENCE: 5355

000

<210> SEQ ID NO 5356

<400> SEQUENCE: 5356

000

<210> SEQ ID NO 5357

<400> SEQUENCE: 5357

000

<210> SEQ ID NO 5358

<400> SEQUENCE: 5358

000

<210> SEQ ID NO 5359

<400> SEQUENCE: 5359

000

<210> SEQ ID NO 5360

<400> SEQUENCE: 5360

000

<210> SEQ ID NO 5361

<400> SEQUENCE: 5361

000

<210> SEQ ID NO 5362

<400> SEQUENCE: 5362

000

<210> SEQ ID NO 5363

<400> SEQUENCE: 5363

000

<210> SEQ ID NO 5364

<400> SEQUENCE: 5364

000

<210> SEQ ID NO 5365

<400> SEQUENCE: 5365

000

<210> SEQ ID NO 5366

<400> SEQUENCE: 5366

000

<210> SEQ ID NO 5367

<400> SEQUENCE: 5367

000

<210> SEQ ID NO 5368

<400> SEQUENCE: 5368

000

<210> SEQ ID NO 5369

<400> SEQUENCE: 5369

000

<210> SEQ ID NO 5370

<400> SEQUENCE: 5370

000

<210> SEQ ID NO 5371

<400> SEQUENCE: 5371

000

<210> SEQ ID NO 5372

<400> SEQUENCE: 5372

000

<210> SEQ ID NO 5373

<400> SEQUENCE: 5373

000

<210> SEQ ID NO 5374

<400> SEQUENCE: 5374

000

<210> SEQ ID NO 5375

<400> SEQUENCE: 5375

000

<210> SEQ ID NO 5376

<400> SEQUENCE: 5376

000

<210> SEQ ID NO 5377

<400> SEQUENCE: 5377

000

<210> SEQ ID NO 5378

<400> SEQUENCE: 5378

000

<210> SEQ ID NO 5379

<400> SEQUENCE: 5379

000

<210> SEQ ID NO 5380

<400> SEQUENCE: 5380

000

<210> SEQ ID NO 5381

<400> SEQUENCE: 5381

000

<210> SEQ ID NO 5382

<400> SEQUENCE: 5382

000

<210> SEQ ID NO 5383

<400> SEQUENCE: 5383

000

<210> SEQ ID NO 5384

<400> SEQUENCE: 5384

000

<210> SEQ ID NO 5385

-continued

<400> SEQUENCE: 5385

000

<210> SEQ ID NO 5386

<400> SEQUENCE: 5386

000

<210> SEQ ID NO 5387

<400> SEQUENCE: 5387

000

<210> SEQ ID NO 5388

<400> SEQUENCE: 5388

000

<210> SEQ ID NO 5389

<400> SEQUENCE: 5389

000

<210> SEQ ID NO 5390

<400> SEQUENCE: 5390

000

<210> SEQ ID NO 5391

<400> SEQUENCE: 5391

000

<210> SEQ ID NO 5392

<400> SEQUENCE: 5392

000

<210> SEQ ID NO 5393

<400> SEQUENCE: 5393

000

<210> SEQ ID NO 5394

<400> SEQUENCE: 5394

000

<210> SEQ ID NO 5395

<400> SEQUENCE: 5395

000

<210> SEQ ID NO 5396

<400> SEQUENCE: 5396

000

<210> SEQ ID NO 5397

<400> SEQUENCE: 5397

000

<210> SEQ ID NO 5398

<400> SEQUENCE: 5398

000

<210> SEQ ID NO 5399

<400> SEQUENCE: 5399

000

<210> SEQ ID NO 5400

<400> SEQUENCE: 5400

000

<210> SEQ ID NO 5401

<400> SEQUENCE: 5401

000

<210> SEQ ID NO 5402

<400> SEQUENCE: 5402

000

<210> SEQ ID NO 5403

<400> SEQUENCE: 5403

000

<210> SEQ ID NO 5404

<400> SEQUENCE: 5404

000

<210> SEQ ID NO 5405

<400> SEQUENCE: 5405

000

<210> SEQ ID NO 5406

<400> SEQUENCE: 5406

000

<210> SEQ ID NO 5407

<400> SEQUENCE: 5407

000

<210> SEQ ID NO 5408

<400> SEQUENCE: 5408

000

<210> SEQ ID NO 5409

<400> SEQUENCE: 5409

000

<210> SEQ ID NO 5410

<400> SEQUENCE: 5410

000

<210> SEQ ID NO 5411

<400> SEQUENCE: 5411

000

<210> SEQ ID NO 5412

<400> SEQUENCE: 5412

000

<210> SEQ ID NO 5413

<400> SEQUENCE: 5413

000

<210> SEQ ID NO 5414

<400> SEQUENCE: 5414

000

<210> SEQ ID NO 5415

<400> SEQUENCE: 5415

000

<210> SEQ ID NO 5416

<400> SEQUENCE: 5416

000

<210> SEQ ID NO 5417

<400> SEQUENCE: 5417

000

<210> SEQ ID NO 5418

<400> SEQUENCE: 5418

000

<210> SEQ ID NO 5419

<400> SEQUENCE: 5419

000

<210> SEQ ID NO 5420

<400> SEQUENCE: 5420

000

<210> SEQ ID NO 5421

<400> SEQUENCE: 5421

000

<210> SEQ ID NO 5422

<400> SEQUENCE: 5422

000

<210> SEQ ID NO 5423

<400> SEQUENCE: 5423

000

<210> SEQ ID NO 5424

<400> SEQUENCE: 5424

000

<210> SEQ ID NO 5425

<400> SEQUENCE: 5425

000

<210> SEQ ID NO 5426

<400> SEQUENCE: 5426

000

<210> SEQ ID NO 5427

<400> SEQUENCE: 5427

000

<210> SEQ ID NO 5428

<400> SEQUENCE: 5428

000

<210> SEQ ID NO 5429

<400> SEQUENCE: 5429

000

<210> SEQ ID NO 5430

<400> SEQUENCE: 5430

000

<210> SEQ ID NO 5431

<400> SEQUENCE: 5431

000

<210> SEQ ID NO 5432

<400> SEQUENCE: 5432

000

<210> SEQ ID NO 5433

<400> SEQUENCE: 5433

000

<210> SEQ ID NO 5434

<400> SEQUENCE: 5434

000

<210> SEQ ID NO 5435

<400> SEQUENCE: 5435

000

<210> SEQ ID NO 5436

<400> SEQUENCE: 5436

000

<210> SEQ ID NO 5437

<400> SEQUENCE: 5437

000

<210> SEQ ID NO 5438

<400> SEQUENCE: 5438

000

<210> SEQ ID NO 5439

<400> SEQUENCE: 5439

000

<210> SEQ ID NO 5440

<400> SEQUENCE: 5440

000

<210> SEQ ID NO 5441

<400> SEQUENCE: 5441

000

<210> SEQ ID NO 5442

<400> SEQUENCE: 5442

000

<210> SEQ ID NO 5443

<400> SEQUENCE: 5443

000

<210> SEQ ID NO 5444

<400> SEQUENCE: 5444

000

<210> SEQ ID NO 5445

<400> SEQUENCE: 5445

000

<210> SEQ ID NO 5446

<400> SEQUENCE: 5446

000

<210> SEQ ID NO 5447

<400> SEQUENCE: 5447

000

<210> SEQ ID NO 5448

<400> SEQUENCE: 5448

000

<210> SEQ ID NO 5449

<400> SEQUENCE: 5449

000

<210> SEQ ID NO 5450

<400> SEQUENCE: 5450

000

<210> SEQ ID NO 5451

<400> SEQUENCE: 5451

000

<210> SEQ ID NO 5452

<400> SEQUENCE: 5452

000

```
<210> SEQ ID NO 5453
<400> SEQUENCE: 5453
000

<210> SEQ ID NO 5454
<400> SEQUENCE: 5454
000

<210> SEQ ID NO 5455
<400> SEQUENCE: 5455
000

<210> SEQ ID NO 5456
<400> SEQUENCE: 5456
000

<210> SEQ ID NO 5457
<400> SEQUENCE: 5457
000

<210> SEQ ID NO 5458
<400> SEQUENCE: 5458
000

<210> SEQ ID NO 5459
<400> SEQUENCE: 5459
000

<210> SEQ ID NO 5460
<400> SEQUENCE: 5460
000

<210> SEQ ID NO 5461
<400> SEQUENCE: 5461
000

<210> SEQ ID NO 5462
<400> SEQUENCE: 5462
000

<210> SEQ ID NO 5463
<400> SEQUENCE: 5463
000

<210> SEQ ID NO 5464
```

-continued

<400> SEQUENCE: 5464

000

<210> SEQ ID NO 5465

<400> SEQUENCE: 5465

000

<210> SEQ ID NO 5466

<400> SEQUENCE: 5466

000

<210> SEQ ID NO 5467

<400> SEQUENCE: 5467

000

<210> SEQ ID NO 5468

<400> SEQUENCE: 5468

000

<210> SEQ ID NO 5469

<400> SEQUENCE: 5469

000

<210> SEQ ID NO 5470

<400> SEQUENCE: 5470

000

<210> SEQ ID NO 5471

<400> SEQUENCE: 5471

000

<210> SEQ ID NO 5472

<400> SEQUENCE: 5472

000

<210> SEQ ID NO 5473

<400> SEQUENCE: 5473

000

<210> SEQ ID NO 5474

<400> SEQUENCE: 5474

000

<210> SEQ ID NO 5475

<400> SEQUENCE: 5475

000

<210> SEQ ID NO 5476

<400> SEQUENCE: 5476

000

<210> SEQ ID NO 5477

<400> SEQUENCE: 5477

000

<210> SEQ ID NO 5478

<400> SEQUENCE: 5478

000

<210> SEQ ID NO 5479

<400> SEQUENCE: 5479

000

<210> SEQ ID NO 5480

<400> SEQUENCE: 5480

000

<210> SEQ ID NO 5481

<400> SEQUENCE: 5481

000

<210> SEQ ID NO 5482

<400> SEQUENCE: 5482

000

<210> SEQ ID NO 5483

<400> SEQUENCE: 5483

000

<210> SEQ ID NO 5484

<400> SEQUENCE: 5484

000

<210> SEQ ID NO 5485

<400> SEQUENCE: 5485

000

<210> SEQ ID NO 5486

<400> SEQUENCE: 5486

000

<210> SEQ ID NO 5487

<400> SEQUENCE: 5487

000

<210> SEQ ID NO 5488

<400> SEQUENCE: 5488

000

<210> SEQ ID NO 5489

<400> SEQUENCE: 5489

000

<210> SEQ ID NO 5490

<400> SEQUENCE: 5490

000

<210> SEQ ID NO 5491

<400> SEQUENCE: 5491

000

<210> SEQ ID NO 5492

<400> SEQUENCE: 5492

000

<210> SEQ ID NO 5493

<400> SEQUENCE: 5493

000

<210> SEQ ID NO 5494

<400> SEQUENCE: 5494

000

<210> SEQ ID NO 5495

<400> SEQUENCE: 5495

000

<210> SEQ ID NO 5496

<400> SEQUENCE: 5496

000

<210> SEQ ID NO 5497

<400> SEQUENCE: 5497

000

<210> SEQ ID NO 5498

<400> SEQUENCE: 5498

000

<210> SEQ ID NO 5499

<400> SEQUENCE: 5499

000

<210> SEQ ID NO 5500

<400> SEQUENCE: 5500

000

<210> SEQ ID NO 5501

<400> SEQUENCE: 5501

000

<210> SEQ ID NO 5502

<400> SEQUENCE: 5502

000

<210> SEQ ID NO 5503

<400> SEQUENCE: 5503

000

<210> SEQ ID NO 5504

<400> SEQUENCE: 5504

000

<210> SEQ ID NO 5505

<400> SEQUENCE: 5505

000

<210> SEQ ID NO 5506

<400> SEQUENCE: 5506

000

<210> SEQ ID NO 5507

<400> SEQUENCE: 5507

000

<210> SEQ ID NO 5508

<400> SEQUENCE: 5508

000

<210> SEQ ID NO 5509

<400> SEQUENCE: 5509

000

<210> SEQ ID NO 5510

<400> SEQUENCE: 5510

000

<210> SEQ ID NO 5511

<400> SEQUENCE: 5511

000

<210> SEQ ID NO 5512

<400> SEQUENCE: 5512

000

<210> SEQ ID NO 5513

<400> SEQUENCE: 5513

000

<210> SEQ ID NO 5514

<400> SEQUENCE: 5514

000

<210> SEQ ID NO 5515

<400> SEQUENCE: 5515

000

<210> SEQ ID NO 5516

<400> SEQUENCE: 5516

000

<210> SEQ ID NO 5517

<400> SEQUENCE: 5517

000

<210> SEQ ID NO 5518

<400> SEQUENCE: 5518

000

<210> SEQ ID NO 5519

<400> SEQUENCE: 5519

000

<210> SEQ ID NO 5520

<400> SEQUENCE: 5520

000

<210> SEQ ID NO 5521

<400> SEQUENCE: 5521

000

<210> SEQ ID NO 5522

<400> SEQUENCE: 5522

000

<210> SEQ ID NO 5523

<400> SEQUENCE: 5523

000

<210> SEQ ID NO 5524

<400> SEQUENCE: 5524

000

<210> SEQ ID NO 5525

<400> SEQUENCE: 5525

000

<210> SEQ ID NO 5526

<400> SEQUENCE: 5526

000

<210> SEQ ID NO 5527

<400> SEQUENCE: 5527

000

<210> SEQ ID NO 5528

<400> SEQUENCE: 5528

000

<210> SEQ ID NO 5529

<400> SEQUENCE: 5529

000

<210> SEQ ID NO 5530

<400> SEQUENCE: 5530

000

<210> SEQ ID NO 5531

<400> SEQUENCE: 5531

000

<210> SEQ ID NO 5532

<400> SEQUENCE: 5532

000

<210> SEQ ID NO 5533

<400> SEQUENCE: 5533

000

<210> SEQ ID NO 5534

<400> SEQUENCE: 5534

000

<210> SEQ ID NO 5535

<400> SEQUENCE: 5535

000

<210> SEQ ID NO 5536

<400> SEQUENCE: 5536

000

<210> SEQ ID NO 5537

<400> SEQUENCE: 5537

000

<210> SEQ ID NO 5538

<400> SEQUENCE: 5538

000

<210> SEQ ID NO 5539

<400> SEQUENCE: 5539

000

<210> SEQ ID NO 5540

<400> SEQUENCE: 5540

000

<210> SEQ ID NO 5541

<400> SEQUENCE: 5541

000

<210> SEQ ID NO 5542

<400> SEQUENCE: 5542

000

<210> SEQ ID NO 5543

<400> SEQUENCE: 5543

000

<210> SEQ ID NO 5544

<400> SEQUENCE: 5544

000

<210> SEQ ID NO 5545

<400> SEQUENCE: 5545

000

<210> SEQ ID NO 5546

<400> SEQUENCE: 5546

000

<210> SEQ ID NO 5547

<400> SEQUENCE: 5547

000

<210> SEQ ID NO 5548

<400> SEQUENCE: 5548

000

<210> SEQ ID NO 5549

<400> SEQUENCE: 5549

000

<210> SEQ ID NO 5550

<400> SEQUENCE: 5550

000

<210> SEQ ID NO 5551

<400> SEQUENCE: 5551

000

<210> SEQ ID NO 5552

<400> SEQUENCE: 5552

000

<210> SEQ ID NO 5553

<400> SEQUENCE: 5553

000

<210> SEQ ID NO 5554

<400> SEQUENCE: 5554

-continued

000

<210> SEQ ID NO 5555
<400> SEQUENCE: 5555
000

<210> SEQ ID NO 5556
<400> SEQUENCE: 5556
000

<210> SEQ ID NO 5557
<400> SEQUENCE: 5557
000

<210> SEQ ID NO 5558
<400> SEQUENCE: 5558
000

<210> SEQ ID NO 5559
<400> SEQUENCE: 5559
000

<210> SEQ ID NO 5560
<400> SEQUENCE: 5560
000

<210> SEQ ID NO 5561
<400> SEQUENCE: 5561
000

<210> SEQ ID NO 5562
<400> SEQUENCE: 5562
000

<210> SEQ ID NO 5563
<400> SEQUENCE: 5563
000

<210> SEQ ID NO 5564
<400> SEQUENCE: 5564
000

<210> SEQ ID NO 5565
<400> SEQUENCE: 5565
000

<210> SEQ ID NO 5566

<400> SEQUENCE: 5566

000

<210> SEQ ID NO 5567

<400> SEQUENCE: 5567

000

<210> SEQ ID NO 5568

<400> SEQUENCE: 5568

000

<210> SEQ ID NO 5569

<400> SEQUENCE: 5569

000

<210> SEQ ID NO 5570

<400> SEQUENCE: 5570

000

<210> SEQ ID NO 5571

<400> SEQUENCE: 5571

000

<210> SEQ ID NO 5572

<400> SEQUENCE: 5572

000

<210> SEQ ID NO 5573

<400> SEQUENCE: 5573

000

<210> SEQ ID NO 5574

<400> SEQUENCE: 5574

000

<210> SEQ ID NO 5575

<400> SEQUENCE: 5575

000

<210> SEQ ID NO 5576

<400> SEQUENCE: 5576

000

<210> SEQ ID NO 5577

<210> SEQ ID NO 5577

000

<210> SEQ ID NO 5578
<400> SEQUENCE: 5578

000

<210> SEQ ID NO 5579
<400> SEQUENCE: 5579

000

<210> SEQ ID NO 5580
<400> SEQUENCE: 5580

000

<210> SEQ ID NO 5581
<400> SEQUENCE: 5581

000

<210> SEQ ID NO 5582
<400> SEQUENCE: 5582

000

<210> SEQ ID NO 5583
<400> SEQUENCE: 5583

000

<210> SEQ ID NO 5584
<400> SEQUENCE: 5584

000

<210> SEQ ID NO 5585
<400> SEQUENCE: 5585

000

<210> SEQ ID NO 5586
<400> SEQUENCE: 5586

000

<210> SEQ ID NO 5587
<400> SEQUENCE: 5587

000

<210> SEQ ID NO 5588
<400> SEQUENCE: 5588

000

<210> SEQ ID NO 5589

<400> SEQUENCE: 5589

000

<210> SEQ ID NO 5590

<400> SEQUENCE: 5590

000

<210> SEQ ID NO 5591

<400> SEQUENCE: 5591

000

<210> SEQ ID NO 5592

<400> SEQUENCE: 5592

000

<210> SEQ ID NO 5593

<400> SEQUENCE: 5593

000

<210> SEQ ID NO 5594

<400> SEQUENCE: 5594

000

<210> SEQ ID NO 5595

<400> SEQUENCE: 5595

000

<210> SEQ ID NO 5596

<400> SEQUENCE: 5596

000

<210> SEQ ID NO 5597

<400> SEQUENCE: 5597

000

<210> SEQ ID NO 5598

<400> SEQUENCE: 5598

000

<210> SEQ ID NO 5599

<400> SEQUENCE: 5599

000

<210> SEQ ID NO 5600

<400> SEQUENCE: 5600

000

<210> SEQ ID NO 5601

<400> SEQUENCE: 5601

000

<210> SEQ ID NO 5602

<400> SEQUENCE: 5602

000

<210> SEQ ID NO 5603

<400> SEQUENCE: 5603

000

<210> SEQ ID NO 5604

<400> SEQUENCE: 5604

000

<210> SEQ ID NO 5605

<400> SEQUENCE: 5605

000

<210> SEQ ID NO 5606

<400> SEQUENCE: 5606

000

<210> SEQ ID NO 5607

<400> SEQUENCE: 5607

000

<210> SEQ ID NO 5608

<400> SEQUENCE: 5608

000

<210> SEQ ID NO 5609

<400> SEQUENCE: 5609

000

<210> SEQ ID NO 5610

<400> SEQUENCE: 5610

000

<210> SEQ ID NO 5611

<400> SEQUENCE: 5611

000

<210> SEQ ID NO 5612

<400> SEQUENCE: 5612

000

<210> SEQ ID NO 5613

<400> SEQUENCE: 5613

000

<210> SEQ ID NO 5614

<400> SEQUENCE: 5614

000

<210> SEQ ID NO 5615

<400> SEQUENCE: 5615

000

<210> SEQ ID NO 5616

<400> SEQUENCE: 5616

000

<210> SEQ ID NO 5617

<400> SEQUENCE: 5617

000

<210> SEQ ID NO 5618

<400> SEQUENCE: 5618

000

<210> SEQ ID NO 5619

<400> SEQUENCE: 5619

000

<210> SEQ ID NO 5620

<400> SEQUENCE: 5620

000

<210> SEQ ID NO 5621

<400> SEQUENCE: 5621

000

<210> SEQ ID NO 5622

<400> SEQUENCE: 5622

000

<210> SEQ ID NO 5623

<400> SEQUENCE: 5623

000

<210> SEQ ID NO 5624

<400> SEQUENCE: 5624

000

<210> SEQ ID NO 5625

<400> SEQUENCE: 5625

000

<210> SEQ ID NO 5626

<400> SEQUENCE: 5626

000

<210> SEQ ID NO 5627

<400> SEQUENCE: 5627

000

<210> SEQ ID NO 5628

<400> SEQUENCE: 5628

000

<210> SEQ ID NO 5629

<400> SEQUENCE: 5629

000

<210> SEQ ID NO 5630

<400> SEQUENCE: 5630

000

<210> SEQ ID NO 5631

<400> SEQUENCE: 5631

000

<210> SEQ ID NO 5632

<400> SEQUENCE: 5632

000

<210> SEQ ID NO 5633

<400> SEQUENCE: 5633

000

<210> SEQ ID NO 5634
<400> SEQUENCE: 5634
000

<210> SEQ ID NO 5635
<400> SEQUENCE: 5635
000

<210> SEQ ID NO 5636
<400> SEQUENCE: 5636
000

<210> SEQ ID NO 5637
<400> SEQUENCE: 5637
000

<210> SEQ ID NO 5638
<400> SEQUENCE: 5638
000

<210> SEQ ID NO 5639
<400> SEQUENCE: 5639
000

<210> SEQ ID NO 5640
<400> SEQUENCE: 5640
000

<210> SEQ ID NO 5641
<400> SEQUENCE: 5641
000

<210> SEQ ID NO 5642
<400> SEQUENCE: 5642
000

<210> SEQ ID NO 5643
<400> SEQUENCE: 5643
000

<210> SEQ ID NO 5644
<400> SEQUENCE: 5644
000

-continued

<210> SEQ ID NO 5645

<400> SEQUENCE: 5645

000

<210> SEQ ID NO 5646

<400> SEQUENCE: 5646

000

<210> SEQ ID NO 5647

<400> SEQUENCE: 5647

000

<210> SEQ ID NO 5648

<400> SEQUENCE: 5648

000

<210> SEQ ID NO 5649

<400> SEQUENCE: 5649

000

<210> SEQ ID NO 5650

<400> SEQUENCE: 5650

000

<210> SEQ ID NO 5651

<400> SEQUENCE: 5651

000

<210> SEQ ID NO 5652

<400> SEQUENCE: 5652

000

<210> SEQ ID NO 5653

<400> SEQUENCE: 5653

000

<210> SEQ ID NO 5654

<400> SEQUENCE: 5654

000

<210> SEQ ID NO 5655

<400> SEQUENCE: 5655

000

<210> SEQ ID NO 5656

<400> SEQUENCE: 5656

000

<210> SEQ ID NO 5657

<400> SEQUENCE: 5657

000

<210> SEQ ID NO 5658

<400> SEQUENCE: 5658

000

<210> SEQ ID NO 5659

<400> SEQUENCE: 5659

000

<210> SEQ ID NO 5660

<400> SEQUENCE: 5660

000

<210> SEQ ID NO 5661

<400> SEQUENCE: 5661

000

<210> SEQ ID NO 5662

<400> SEQUENCE: 5662

000

<210> SEQ ID NO 5663

<400> SEQUENCE: 5663

000

<210> SEQ ID NO 5664

<400> SEQUENCE: 5664

000

<210> SEQ ID NO 5665

<400> SEQUENCE: 5665

000

<210> SEQ ID NO 5666

<400> SEQUENCE: 5666

000

<210> SEQ ID NO 5667

<400> SEQUENCE: 5667

000

<210> SEQ ID NO 5668

<400> SEQUENCE: 5668

000

<210> SEQ ID NO 5669

<400> SEQUENCE: 5669

000

<210> SEQ ID NO 5670

<400> SEQUENCE: 5670

000

<210> SEQ ID NO 5671

<400> SEQUENCE: 5671

000

<210> SEQ ID NO 5672

<400> SEQUENCE: 5672

000

<210> SEQ ID NO 5673

<400> SEQUENCE: 5673

000

<210> SEQ ID NO 5674

<400> SEQUENCE: 5674

000

<210> SEQ ID NO 5675

<400> SEQUENCE: 5675

000

<210> SEQ ID NO 5676

<400> SEQUENCE: 5676

000

<210> SEQ ID NO 5677

<400> SEQUENCE: 5677

000

<210> SEQ ID NO 5678

<400> SEQUENCE: 5678

000

<210> SEQ ID NO 5679

<400> SEQUENCE: 5679

000

<210> SEQ ID NO 5680

<400> SEQUENCE: 5680

000

<210> SEQ ID NO 5681

<400> SEQUENCE: 5681

000

<210> SEQ ID NO 5682

<400> SEQUENCE: 5682

000

<210> SEQ ID NO 5683

<400> SEQUENCE: 5683

000

<210> SEQ ID NO 5684

<400> SEQUENCE: 5684

000

<210> SEQ ID NO 5685

<400> SEQUENCE: 5685

000

<210> SEQ ID NO 5686

<400> SEQUENCE: 5686

000

<210> SEQ ID NO 5687

<400> SEQUENCE: 5687

000

<210> SEQ ID NO 5688

<400> SEQUENCE: 5688

000

<210> SEQ ID NO 5689

<400> SEQUENCE: 5689

000

```
<210> SEQ ID NO 5690
<400> SEQUENCE: 5690
000

<210> SEQ ID NO 5691
<400> SEQUENCE: 5691
000

<210> SEQ ID NO 5692
<400> SEQUENCE: 5692
000

<210> SEQ ID NO 5693
<400> SEQUENCE: 5693
000

<210> SEQ ID NO 5694
<400> SEQUENCE: 5694
000

<210> SEQ ID NO 5695
<400> SEQUENCE: 5695
000

<210> SEQ ID NO 5696
<400> SEQUENCE: 5696
000

<210> SEQ ID NO 5697
<400> SEQUENCE: 5697
000

<210> SEQ ID NO 5698
<400> SEQUENCE: 5698
000

<210> SEQ ID NO 5699
<400> SEQUENCE: 5699
000

<210> SEQ ID NO 5700
<400> SEQUENCE: 5700
000

<210> SEQ ID NO 5701
```

```
<400> SEQUENCE: 5701
000

<210> SEQ ID NO 5702
<400> SEQUENCE: 5702
000

<210> SEQ ID NO 5703
<400> SEQUENCE: 5703
000

<210> SEQ ID NO 5704
<400> SEQUENCE: 5704
000

<210> SEQ ID NO 5705
<400> SEQUENCE: 5705
000

<210> SEQ ID NO 5706
<400> SEQUENCE: 5706
000

<210> SEQ ID NO 5707
<400> SEQUENCE: 5707
000

<210> SEQ ID NO 5708
<400> SEQUENCE: 5708
000

<210> SEQ ID NO 5709
<400> SEQUENCE: 5709
000

<210> SEQ ID NO 5710
<400> SEQUENCE: 5710
000

<210> SEQ ID NO 5711
<400> SEQUENCE: 5711
000

<210> SEQ ID NO 5712
<400> SEQUENCE: 5712
```

000

<210> SEQ ID NO 5713

<400> SEQUENCE: 5713

000

<210> SEQ ID NO 5714

<400> SEQUENCE: 5714

000

<210> SEQ ID NO 5715

<400> SEQUENCE: 5715

000

<210> SEQ ID NO 5716

<400> SEQUENCE: 5716

000

<210> SEQ ID NO 5717

<400> SEQUENCE: 5717

000

<210> SEQ ID NO 5718

<400> SEQUENCE: 5718

000

<210> SEQ ID NO 5719

<400> SEQUENCE: 5719

000

<210> SEQ ID NO 5720

<400> SEQUENCE: 5720

000

<210> SEQ ID NO 5721

<400> SEQUENCE: 5721

000

<210> SEQ ID NO 5722

<400> SEQUENCE: 5722

000

<210> SEQ ID NO 5723

<400> SEQUENCE: 5723

000

-continued

<210> SEQ ID NO 5724

<400> SEQUENCE: 5724

000

<210> SEQ ID NO 5725

<400> SEQUENCE: 5725

000

<210> SEQ ID NO 5726

<400> SEQUENCE: 5726

000

<210> SEQ ID NO 5727

<400> SEQUENCE: 5727

000

<210> SEQ ID NO 5728

<400> SEQUENCE: 5728

000

<210> SEQ ID NO 5729

<400> SEQUENCE: 5729

000

<210> SEQ ID NO 5730

<400> SEQUENCE: 5730

000

<210> SEQ ID NO 5731

<400> SEQUENCE: 5731

000

<210> SEQ ID NO 5732

<400> SEQUENCE: 5732

000

<210> SEQ ID NO 5733

<400> SEQUENCE: 5733

000

<210> SEQ ID NO 5734

<400> SEQUENCE: 5734

000

<210> SEQ ID NO 5735

<400> SEQUENCE: 5735

000

<210> SEQ ID NO 5736

<400> SEQUENCE: 5736

000

<210> SEQ ID NO 5737

<400> SEQUENCE: 5737

000

<210> SEQ ID NO 5738

<400> SEQUENCE: 5738

000

<210> SEQ ID NO 5739

<400> SEQUENCE: 5739

000

<210> SEQ ID NO 5740

<400> SEQUENCE: 5740

000

<210> SEQ ID NO 5741

<400> SEQUENCE: 5741

000

<210> SEQ ID NO 5742

<400> SEQUENCE: 5742

000

<210> SEQ ID NO 5743

<400> SEQUENCE: 5743

000

<210> SEQ ID NO 5744

<400> SEQUENCE: 5744

000

<210> SEQ ID NO 5745

<400> SEQUENCE: 5745

000

<210> SEQ ID NO 5746

<400> SEQUENCE: 5746

000

<210> SEQ ID NO 5747

<400> SEQUENCE: 5747

000

<210> SEQ ID NO 5748

<400> SEQUENCE: 5748

000

<210> SEQ ID NO 5749

<400> SEQUENCE: 5749

000

<210> SEQ ID NO 5750

<400> SEQUENCE: 5750

000

<210> SEQ ID NO 5751

<400> SEQUENCE: 5751

000

<210> SEQ ID NO 5752

<400> SEQUENCE: 5752

000

<210> SEQ ID NO 5753

<400> SEQUENCE: 5753

000

<210> SEQ ID NO 5754

<400> SEQUENCE: 5754

000

<210> SEQ ID NO 5755

<400> SEQUENCE: 5755

000

<210> SEQ ID NO 5756

<400> SEQUENCE: 5756

000

<210> SEQ ID NO 5757

<400> SEQUENCE: 5757

000

<210> SEQ ID NO 5758

<400> SEQUENCE: 5758

000

<210> SEQ ID NO 5759

<400> SEQUENCE: 5759

000

<210> SEQ ID NO 5760

<400> SEQUENCE: 5760

000

<210> SEQ ID NO 5761

<400> SEQUENCE: 5761

000

<210> SEQ ID NO 5762

<400> SEQUENCE: 5762

000

<210> SEQ ID NO 5763

<400> SEQUENCE: 5763

000

<210> SEQ ID NO 5764

<400> SEQUENCE: 5764

000

<210> SEQ ID NO 5765

<400> SEQUENCE: 5765

000

<210> SEQ ID NO 5766

<400> SEQUENCE: 5766

000

<210> SEQ ID NO 5767

<400> SEQUENCE: 5767

000

<210> SEQ ID NO 5768

<400> SEQUENCE: 5768

000

-continued

<210> SEQ ID NO 5769

<400> SEQUENCE: 5769

000

<210> SEQ ID NO 5770

<400> SEQUENCE: 5770

000

<210> SEQ ID NO 5771

<400> SEQUENCE: 5771

000

<210> SEQ ID NO 5772

<400> SEQUENCE: 5772

000

<210> SEQ ID NO 5773

<400> SEQUENCE: 5773

000

<210> SEQ ID NO 5774

<400> SEQUENCE: 5774

000

<210> SEQ ID NO 5775

<400> SEQUENCE: 5775

000

<210> SEQ ID NO 5776

<400> SEQUENCE: 5776

000

<210> SEQ ID NO 5777

<400> SEQUENCE: 5777

000

<210> SEQ ID NO 5778

<400> SEQUENCE: 5778

000

<210> SEQ ID NO 5779

<400> SEQUENCE: 5779

000

<210> SEQ ID NO 5780

```
<400> SEQUENCE: 5780

000

<210> SEQ ID NO 5781

<400> SEQUENCE: 5781

000

<210> SEQ ID NO 5782

<400> SEQUENCE: 5782

000

<210> SEQ ID NO 5783

<400> SEQUENCE: 5783

000

<210> SEQ ID NO 5784

<400> SEQUENCE: 5784

000

<210> SEQ ID NO 5785

<400> SEQUENCE: 5785

000

<210> SEQ ID NO 5786

<400> SEQUENCE: 5786

000

<210> SEQ ID NO 5787

<400> SEQUENCE: 5787

000

<210> SEQ ID NO 5788

<400> SEQUENCE: 5788

000

<210> SEQ ID NO 5789

<400> SEQUENCE: 5789

000

<210> SEQ ID NO 5790

<400> SEQUENCE: 5790

000

<210> SEQ ID NO 5791

<400> SEQUENCE: 5791
```

000

<210> SEQ ID NO 5792

<400> SEQUENCE: 5792

000

<210> SEQ ID NO 5793

<400> SEQUENCE: 5793

000

<210> SEQ ID NO 5794

<400> SEQUENCE: 5794

000

<210> SEQ ID NO 5795

<400> SEQUENCE: 5795

000

<210> SEQ ID NO 5796

<400> SEQUENCE: 5796

000

<210> SEQ ID NO 5797

<400> SEQUENCE: 5797

000

<210> SEQ ID NO 5798

<400> SEQUENCE: 5798

000

<210> SEQ ID NO 5799

<400> SEQUENCE: 5799

000

<210> SEQ ID NO 5800

<400> SEQUENCE: 5800

000

<210> SEQ ID NO 5801

<400> SEQUENCE: 5801

000

<210> SEQ ID NO 5802

<400> SEQUENCE: 5802

000

-continued

<210> SEQ ID NO 5803

<400> SEQUENCE: 5803

000

<210> SEQ ID NO 5804

<400> SEQUENCE: 5804

000

<210> SEQ ID NO 5805

<400> SEQUENCE: 5805

000

<210> SEQ ID NO 5806

<400> SEQUENCE: 5806

000

<210> SEQ ID NO 5807

<400> SEQUENCE: 5807

000

<210> SEQ ID NO 5808

<400> SEQUENCE: 5808

000

<210> SEQ ID NO 5809

<400> SEQUENCE: 5809

000

<210> SEQ ID NO 5810

<400> SEQUENCE: 5810

000

<210> SEQ ID NO 5811

<400> SEQUENCE: 5811

000

<210> SEQ ID NO 5812

<400> SEQUENCE: 5812

000

<210> SEQ ID NO 5813

<400> SEQUENCE: 5813

000

<210> SEQ ID NO 5814

<400> SEQUENCE: 5814

000

<210> SEQ ID NO 5815

<400> SEQUENCE: 5815

000

<210> SEQ ID NO 5816

<400> SEQUENCE: 5816

000

<210> SEQ ID NO 5817

<400> SEQUENCE: 5817

000

<210> SEQ ID NO 5818

<400> SEQUENCE: 5818

000

<210> SEQ ID NO 5819

<400> SEQUENCE: 5819

000

<210> SEQ ID NO 5820

<400> SEQUENCE: 5820

000

<210> SEQ ID NO 5821

<400> SEQUENCE: 5821

000

<210> SEQ ID NO 5822

<400> SEQUENCE: 5822

000

<210> SEQ ID NO 5823

<400> SEQUENCE: 5823

000

<210> SEQ ID NO 5824

<400> SEQUENCE: 5824

000

<210> SEQ ID NO 5825

<400> SEQUENCE: 5825

000

<210> SEQ ID NO 5826

<400> SEQUENCE: 5826

000

<210> SEQ ID NO 5827

<400> SEQUENCE: 5827

000

<210> SEQ ID NO 5828

<400> SEQUENCE: 5828

000

<210> SEQ ID NO 5829

<400> SEQUENCE: 5829

000

<210> SEQ ID NO 5830

<400> SEQUENCE: 5830

000

<210> SEQ ID NO 5831

<400> SEQUENCE: 5831

000

<210> SEQ ID NO 5832

<400> SEQUENCE: 5832

000

<210> SEQ ID NO 5833

<400> SEQUENCE: 5833

000

<210> SEQ ID NO 5834

<400> SEQUENCE: 5834

000

<210> SEQ ID NO 5835

<400> SEQUENCE: 5835

000

<210> SEQ ID NO 5836

<400> SEQUENCE: 5836

000

<210> SEQ ID NO 5837

<400> SEQUENCE: 5837

000

<210> SEQ ID NO 5838

<400> SEQUENCE: 5838

000

<210> SEQ ID NO 5839

<400> SEQUENCE: 5839

000

<210> SEQ ID NO 5840

<400> SEQUENCE: 5840

000

<210> SEQ ID NO 5841

<400> SEQUENCE: 5841

000

<210> SEQ ID NO 5842

<400> SEQUENCE: 5842

000

<210> SEQ ID NO 5843

<400> SEQUENCE: 5843

000

<210> SEQ ID NO 5844

<400> SEQUENCE: 5844

000

<210> SEQ ID NO 5845

<400> SEQUENCE: 5845

000

<210> SEQ ID NO 5846

<400> SEQUENCE: 5846

000

<210> SEQ ID NO 5847

<400> SEQUENCE: 5847

000

-continued

<210> SEQ ID NO 5848

<400> SEQUENCE: 5848

000

<210> SEQ ID NO 5849

<400> SEQUENCE: 5849

000

<210> SEQ ID NO 5850

<400> SEQUENCE: 5850

000

<210> SEQ ID NO 5851

<400> SEQUENCE: 5851

000

<210> SEQ ID NO 5852

<400> SEQUENCE: 5852

000

<210> SEQ ID NO 5853

<400> SEQUENCE: 5853

000

<210> SEQ ID NO 5854

<400> SEQUENCE: 5854

000

<210> SEQ ID NO 5855

<400> SEQUENCE: 5855

000

<210> SEQ ID NO 5856

<400> SEQUENCE: 5856

000

<210> SEQ ID NO 5857

<400> SEQUENCE: 5857

000

<210> SEQ ID NO 5858

<400> SEQUENCE: 5858

000

<210> SEQ ID NO 5859

```
<400> SEQUENCE: 5859

000

<210> SEQ ID NO 5860

<400> SEQUENCE: 5860

000

<210> SEQ ID NO 5861

<400> SEQUENCE: 5861

000

<210> SEQ ID NO 5862

<400> SEQUENCE: 5862

000

<210> SEQ ID NO 5863

<400> SEQUENCE: 5863

000

<210> SEQ ID NO 5864

<400> SEQUENCE: 5864

000

<210> SEQ ID NO 5865

<400> SEQUENCE: 5865

000

<210> SEQ ID NO 5866

<400> SEQUENCE: 5866

000

<210> SEQ ID NO 5867

<400> SEQUENCE: 5867

000

<210> SEQ ID NO 5868

<400> SEQUENCE: 5868

000

<210> SEQ ID NO 5869

<400> SEQUENCE: 5869

000

<210> SEQ ID NO 5870

<400> SEQUENCE: 5870
```

000

<210> SEQ ID NO 5871

<400> SEQUENCE: 5871

000

<210> SEQ ID NO 5872

<400> SEQUENCE: 5872

000

<210> SEQ ID NO 5873

<400> SEQUENCE: 5873

000

<210> SEQ ID NO 5874

<400> SEQUENCE: 5874

000

<210> SEQ ID NO 5875

<400> SEQUENCE: 5875

000

<210> SEQ ID NO 5876

<400> SEQUENCE: 5876

000

<210> SEQ ID NO 5877

<400> SEQUENCE: 5877

000

<210> SEQ ID NO 5878

<400> SEQUENCE: 5878

000

<210> SEQ ID NO 5879

<400> SEQUENCE: 5879

000

<210> SEQ ID NO 5880

<400> SEQUENCE: 5880

000

<210> SEQ ID NO 5881

<400> SEQUENCE: 5881

000

```
<210> SEQ ID NO 5882
<400> SEQUENCE: 5882
000

<210> SEQ ID NO 5883
<400> SEQUENCE: 5883
000

<210> SEQ ID NO 5884
<400> SEQUENCE: 5884
000

<210> SEQ ID NO 5885
<400> SEQUENCE: 5885
000

<210> SEQ ID NO 5886
<400> SEQUENCE: 5886
000

<210> SEQ ID NO 5887
<400> SEQUENCE: 5887
000

<210> SEQ ID NO 5888
<400> SEQUENCE: 5888
000

<210> SEQ ID NO 5889
<400> SEQUENCE: 5889
000

<210> SEQ ID NO 5890
<400> SEQUENCE: 5890
000

<210> SEQ ID NO 5891
<400> SEQUENCE: 5891
000

<210> SEQ ID NO 5892
<400> SEQUENCE: 5892
000

<210> SEQ ID NO 5893
```

```
<400> SEQUENCE: 5893
000

<210> SEQ ID NO 5894
<400> SEQUENCE: 5894
000

<210> SEQ ID NO 5895
<400> SEQUENCE: 5895
000

<210> SEQ ID NO 5896
<400> SEQUENCE: 5896
000

<210> SEQ ID NO 5897
<400> SEQUENCE: 5897
000

<210> SEQ ID NO 5898
<400> SEQUENCE: 5898
000

<210> SEQ ID NO 5899
<400> SEQUENCE: 5899
000

<210> SEQ ID NO 5900
<400> SEQUENCE: 5900
000

<210> SEQ ID NO 5901
<400> SEQUENCE: 5901
000

<210> SEQ ID NO 5902
<400> SEQUENCE: 5902
000

<210> SEQ ID NO 5903
<400> SEQUENCE: 5903
000

<210> SEQ ID NO 5904
<400> SEQUENCE: 5904
```

000

<210> SEQ ID NO 5905

<400> SEQUENCE: 5905

000

<210> SEQ ID NO 5906

<400> SEQUENCE: 5906

000

<210> SEQ ID NO 5907

<400> SEQUENCE: 5907

000

<210> SEQ ID NO 5908

<400> SEQUENCE: 5908

000

<210> SEQ ID NO 5909

<400> SEQUENCE: 5909

000

<210> SEQ ID NO 5910

<400> SEQUENCE: 5910

000

<210> SEQ ID NO 5911

<400> SEQUENCE: 5911

000

<210> SEQ ID NO 5912

<400> SEQUENCE: 5912

000

<210> SEQ ID NO 5913

<400> SEQUENCE: 5913

000

<210> SEQ ID NO 5914

<400> SEQUENCE: 5914

000

<210> SEQ ID NO 5915

<400> SEQUENCE: 5915

000

<210> SEQ ID NO 5916

<400> SEQUENCE: 5916

000

<210> SEQ ID NO 5917

<400> SEQUENCE: 5917

000

<210> SEQ ID NO 5918

<400> SEQUENCE: 5918

000

<210> SEQ ID NO 5919

<400> SEQUENCE: 5919

000

<210> SEQ ID NO 5920

<400> SEQUENCE: 5920

000

<210> SEQ ID NO 5921

<400> SEQUENCE: 5921

000

<210> SEQ ID NO 5922

<400> SEQUENCE: 5922

000

<210> SEQ ID NO 5923

<400> SEQUENCE: 5923

000

<210> SEQ ID NO 5924

<400> SEQUENCE: 5924

000

<210> SEQ ID NO 5925

<400> SEQUENCE: 5925

000

<210> SEQ ID NO 5926

<400> SEQUENCE: 5926

000

-continued

<210> SEQ ID NO 5927

<400> SEQUENCE: 5927

000

<210> SEQ ID NO 5928

<400> SEQUENCE: 5928

000

<210> SEQ ID NO 5929

<400> SEQUENCE: 5929

000

<210> SEQ ID NO 5930

<400> SEQUENCE: 5930

000

<210> SEQ ID NO 5931

<400> SEQUENCE: 5931

000

<210> SEQ ID NO 5932

<400> SEQUENCE: 5932

000

<210> SEQ ID NO 5933

<400> SEQUENCE: 5933

000

<210> SEQ ID NO 5934

<400> SEQUENCE: 5934

000

<210> SEQ ID NO 5935

<400> SEQUENCE: 5935

000

<210> SEQ ID NO 5936

<400> SEQUENCE: 5936

000

<210> SEQ ID NO 5937

<400> SEQUENCE: 5937

000

<210> SEQ ID NO 5938

<400> SEQUENCE: 5938

000

<210> SEQ ID NO 5939

<400> SEQUENCE: 5939

000

<210> SEQ ID NO 5940

<400> SEQUENCE: 5940

000

<210> SEQ ID NO 5941

<400> SEQUENCE: 5941

000

<210> SEQ ID NO 5942

<400> SEQUENCE: 5942

000

<210> SEQ ID NO 5943

<400> SEQUENCE: 5943

000

<210> SEQ ID NO 5944

<400> SEQUENCE: 5944

000

<210> SEQ ID NO 5945

<400> SEQUENCE: 5945

000

<210> SEQ ID NO 5946

<400> SEQUENCE: 5946

000

<210> SEQ ID NO 5947

<400> SEQUENCE: 5947

000

<210> SEQ ID NO 5948

<400> SEQUENCE: 5948

000

<210> SEQ ID NO 5949

<400> SEQUENCE: 5949

000

<210> SEQ ID NO 5950
<400> SEQUENCE: 5950
000

<210> SEQ ID NO 5951
<400> SEQUENCE: 5951
000

<210> SEQ ID NO 5952
<400> SEQUENCE: 5952
000

<210> SEQ ID NO 5953
<400> SEQUENCE: 5953
000

<210> SEQ ID NO 5954
<400> SEQUENCE: 5954
000

<210> SEQ ID NO 5955
<400> SEQUENCE: 5955
000

<210> SEQ ID NO 5956
<400> SEQUENCE: 5956
000

<210> SEQ ID NO 5957
<400> SEQUENCE: 5957
000

<210> SEQ ID NO 5958
<400> SEQUENCE: 5958
000

<210> SEQ ID NO 5959
<400> SEQUENCE: 5959
000

<210> SEQ ID NO 5960
<400> SEQUENCE: 5960
000

<210> SEQ ID NO 5961

<400> SEQUENCE: 5961

000

<210> SEQ ID NO 5962

<400> SEQUENCE: 5962

000

<210> SEQ ID NO 5963

<400> SEQUENCE: 5963

000

<210> SEQ ID NO 5964

<400> SEQUENCE: 5964

000

<210> SEQ ID NO 5965

<400> SEQUENCE: 5965

000

<210> SEQ ID NO 5966

<400> SEQUENCE: 5966

000

<210> SEQ ID NO 5967

<400> SEQUENCE: 5967

000

<210> SEQ ID NO 5968

<400> SEQUENCE: 5968

000

<210> SEQ ID NO 5969

<400> SEQUENCE: 5969

000

<210> SEQ ID NO 5970

<400> SEQUENCE: 5970

000

<210> SEQ ID NO 5971

<400> SEQUENCE: 5971

000

<210> SEQ ID NO 5972

<210> SEQ ID NO 5972

<400> SEQUENCE: 5972

000

<210> SEQ ID NO 5973

<400> SEQUENCE: 5973

000

<210> SEQ ID NO 5974

<400> SEQUENCE: 5974

000

<210> SEQ ID NO 5975

<400> SEQUENCE: 5975

000

<210> SEQ ID NO 5976

<400> SEQUENCE: 5976

000

<210> SEQ ID NO 5977

<400> SEQUENCE: 5977

000

<210> SEQ ID NO 5978

<400> SEQUENCE: 5978

000

<210> SEQ ID NO 5979

<400> SEQUENCE: 5979

000

<210> SEQ ID NO 5980

<400> SEQUENCE: 5980

000

<210> SEQ ID NO 5981

<400> SEQUENCE: 5981

000

<210> SEQ ID NO 5982

<400> SEQUENCE: 5982

000

<210> SEQ ID NO 5983

<400> SEQUENCE: 5983

000

<210> SEQ ID NO 5984

<400> SEQUENCE: 5984

000

<210> SEQ ID NO 5985

<400> SEQUENCE: 5985

000

<210> SEQ ID NO 5986

<400> SEQUENCE: 5986

000

<210> SEQ ID NO 5987

<400> SEQUENCE: 5987

000

<210> SEQ ID NO 5988

<400> SEQUENCE: 5988

000

<210> SEQ ID NO 5989

<400> SEQUENCE: 5989

000

<210> SEQ ID NO 5990

<400> SEQUENCE: 5990

000

<210> SEQ ID NO 5991

<400> SEQUENCE: 5991

000

<210> SEQ ID NO 5992

<400> SEQUENCE: 5992

000

<210> SEQ ID NO 5993

<400> SEQUENCE: 5993

000

<210> SEQ ID NO 5994

<400> SEQUENCE: 5994

000

<210> SEQ ID NO 5995

<400> SEQUENCE: 5995

000

<210> SEQ ID NO 5996

<400> SEQUENCE: 5996

000

<210> SEQ ID NO 5997

<400> SEQUENCE: 5997

000

<210> SEQ ID NO 5998

<400> SEQUENCE: 5998

000

<210> SEQ ID NO 5999

<400> SEQUENCE: 5999

000

<210> SEQ ID NO 6000
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6000

Thr Gly Gly Tyr His Trp Asn
1               5

<210> SEQ ID NO 6001
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6001

Tyr Ile Tyr Ser Ser Gly Ser Thr Tyr Asn Pro Ser Leu Lys Ser
1               5                   10                  15

<210> SEQ ID NO 6002
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6002

Gly Asn Trp His Tyr Phe Asp Phe

<210> SEQ ID NO 6003
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6003

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn
            20                  25                  30

<210> SEQ ID NO 6004
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6004

Trp Ile Arg Gln Phe Pro Gly Lys Lys Leu Glu Trp Met Gly
1               5                   10

<210> SEQ ID NO 6005
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6005

Arg Ile Ser Ile Thr Arg Asp Thr Ser Lys Asn Gln Phe Phe Leu Gln
1               5                   10                  15

Leu Asn Ser Val Thr Thr Glu Asp Thr Ala Thr Tyr Tyr Cys Ala Arg
            20                  25                  30

<210> SEQ ID NO 6006
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6006

Trp Gly Gln Gly Thr Met Val Thr Val Ser Ser
1               5                   10

<210> SEQ ID NO 6007
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6007

```
Thr Gly Gly Tyr His Trp Asn
1               5

<210> SEQ ID NO 6008
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6008

Tyr Ile Tyr Ser Ser Gly Thr Thr Arg Tyr Asn Pro Ser Leu Lys Ser
1               5                   10                  15

<210> SEQ ID NO 6009
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6009

Gly Asn Trp His Tyr Phe Asp Tyr
1               5

<210> SEQ ID NO 6010
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6010

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn
            20                  25                  30

<210> SEQ ID NO 6011
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6011

Trp Ile Arg Gln Phe Pro Gly Lys Lys Leu Glu Trp Met Gly
1               5                   10

<210> SEQ ID NO 6012
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6012
```

-continued

Arg Ile Ser Ile Thr Arg Asp Thr Ser Lys Asn Gln Phe Phe Leu Gln
1               5                   10                  15

Leu Asn Ser Val Thr Pro Glu Asp Thr Ala Thr Tyr Tyr Cys Thr Arg
            20                  25                  30

<210> SEQ ID NO 6013
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6013

Trp Gly Gln Gly Thr Leu Val Ala Val Ser Ser
1               5                   10

<210> SEQ ID NO 6014
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6014

Gln Ile Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Asn
            20                  25                  30

<210> SEQ ID NO 6015
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6015

Trp Ile Arg Gln Pro Ala Gly Lys Gly Leu Glu Trp Ile Gly
1               5                   10

<210> SEQ ID NO 6016
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6016

Arg Val Thr Met Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 6017
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 6017

Trp Gly Gln Gly Thr Met Val Thr Val Ser Ser
1               5                   10

<210> SEQ ID NO 6018
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 6018

Gln Ile Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Asn
            20                  25                  30

<210> SEQ ID NO 6019
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 6019

Trp Ile Arg Gln His Pro Gly Lys Gly Leu Glu Trp Ile Gly
1               5                   10

<210> SEQ ID NO 6020
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 6020

Leu Val Thr Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 6021
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 6021

Trp Gly Gln Gly Thr Met Val Thr Val Ser Ser
1               5                   10

<210> SEQ ID NO 6022
<211> LENGTH: 30
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 6022

Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Asn
            20                  25                  30

<210> SEQ ID NO 6023
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6023

Trp Val Arg Gln Ala Pro Gly Lys Gly Leu Glu Trp Val Gly
1               5                   10

<210> SEQ ID NO 6024
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6024

Arg Phe Thr Ile Ser Arg Asp Thr Ser Lys Asn Thr Phe Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 6025
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6025

Trp Gly Gln Gly Thr Met Val Thr Val Ser Ser
1               5                   10

<210> SEQ ID NO 6026
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6026

Gln Ile Gln Leu Val Gln Ser Gly Ala Glu Val Lys Lys Pro Gly Ser
1               5                   10                  15

Ser Val Lys Val Ser Cys Lys Val Ser Gly Phe Ser Ile Asn
            20                  25                  30
```

<210> SEQ ID NO 6027
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6027

Trp Val Arg Gln Ala Pro Gly Gln Gly Leu Glu Trp Met Gly
1               5                   10

<210> SEQ ID NO 6028
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6028

Arg Val Thr Ile Thr Arg Asp Thr Ser Thr Asn Thr Phe Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 6029
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6029

Trp Gly Gln Gly Thr Met Val Thr Val Ser Ser
1               5                   10

<210> SEQ ID NO 6030
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6030

Glu Ile Gln Leu Val Glu Ser Gly Gly Gly Leu Val Gln Pro Gly Gly
1               5                   10                  15

Ser Leu Arg Leu Ser Cys Ala Val Ser Gly Phe Ser Ile Asn
                20                  25                  30

<210> SEQ ID NO 6031

<400> SEQUENCE: 6031

000

<210> SEQ ID NO 6032
<211> LENGTH: 14
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 6032

Trp Val Arg Gln Ala Pro Gly Lys Gly Leu Glu Trp Val Gly
1               5                   10

<210> SEQ ID NO 6033
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6033

Arg Phe Thr Ile Ser Arg Asp Thr Ala Lys Asn Ser Phe Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 6034
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6034

Trp Gly Gln Gly Thr Met Val Thr Val Ser Ser
1               5                   10

<210> SEQ ID NO 6035
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6035

Gln Ile Gln Leu Val Gln Ser Gly Ala Glu Val Lys Lys Pro Gly Ala
1               5                   10                  15

Ser Val Lys Val Ser Cys Lys Val Ser Gly Phe Ser Ile Asn
                20                  25                  30

<210> SEQ ID NO 6036
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6036

Trp Val Arg Gln Ala Pro Gly Gln Gly Leu Glu Trp Met Gly
1               5                   10

<210> SEQ ID NO 6037
<211> LENGTH: 32
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6037

Arg Val Thr Met Thr Arg Asp Thr Ser Thr Asn Thr Phe Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 6038
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6038

Trp Gly Gln Gly Thr Met Val Thr Val Ser Ser
1               5                   10

<210> SEQ ID NO 6039
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6039

Gln Ile Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Asn
            20                  25                  30

<210> SEQ ID NO 6040
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6040

Trp Ile Arg Gln His Pro Gly Lys Gly Leu Glu Trp Ile Gly
1               5                   10

<210> SEQ ID NO 6041
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6041

Leu Val Thr Ile Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 6042
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6042

Trp Gly Gln Gly Thr Leu Val Thr Val Ser Ser
1               5                   10

<210> SEQ ID NO 6043
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6043

Gln Ile Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Asn
            20                  25                  30

<210> SEQ ID NO 6044
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6044

Trp Ile Arg Gln Pro Ala Gly Lys Gly Leu Glu Trp Ile Gly
1               5                   10

<210> SEQ ID NO 6045
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6045

Arg Val Thr Met Ser Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 6046
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6046

```
Trp Gly Gln Gly Thr Leu Val Thr Val Ser Ser
1               5                   10
```

<210> SEQ ID NO 6047
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6047

```
Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Asn
            20                  25                  30
```

<210> SEQ ID NO 6048
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6048

```
Trp Val Arg Gln Ala Pro Gly Lys Gly Leu Glu Trp Val Gly
1               5                   10
```

<210> SEQ ID NO 6049
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6049

```
Arg Phe Thr Ile Ser Arg Asp Thr Ser Lys Asn Thr Phe Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 6050
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6050

```
Trp Gly Gln Gly Thr Leu Val Thr Val Ser Ser
1               5                   10
```

<210> SEQ ID NO 6051
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

```
<400> SEQUENCE: 6051

Gln Ile Gln Leu Val Glu Ser Gly Gly Gly Leu Val Lys Pro Gly Gly
1               5                   10                  15

Ser Leu Arg Leu Ser Cys Ala Val Ser Gly Phe Ser Ile Asn
            20                  25                  30

<210> SEQ ID NO 6052
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6052

Trp Ile Arg Gln Ala Pro Gly Lys Gly Leu Glu Trp Val Gly
1               5                   10

<210> SEQ ID NO 6053
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6053

Arg Phe Thr Ile Ser Arg Asp Thr Ala Lys Asn Ser Phe Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 6054
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6054

Trp Gly Gln Gly Thr Leu Val Thr Val Ser Ser
1               5                   10

<210> SEQ ID NO 6055
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6055

Gln Ile Gln Leu Val Gln Ser Gly Ala Glu Val Lys Lys Pro Gly Ala
1               5                   10                  15

Ser Val Lys Val Ser Cys Lys Val Ser Gly Phe Ser Ile Asn
            20                  25                  30

<210> SEQ ID NO 6056
<211> LENGTH: 14
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 6056

Trp Val Arg Gln Ala Pro Gly Gln Gly Leu Glu Trp Met Gly
1               5                   10

<210> SEQ ID NO 6057
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6057

Arg Val Thr Met Thr Arg Asp Thr Ser Thr Asn Thr Phe Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 6058
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6058

Trp Gly Gln Gly Thr Leu Val Thr Val Ser Ser
1               5                   10

<210> SEQ ID NO 6059
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6059

Glu Ile Gln Leu Val Gln Ser Gly Ala Glu Val Lys Lys Pro Gly Ala
1               5                   10                  15

Thr Val Lys Ile Ser Cys Lys Val Ser Gly Phe Ser Ile Asn
            20                  25                  30

<210> SEQ ID NO 6060
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6060

Trp Val Gln Gln Ala Pro Gly Lys Gly Leu Glu Trp Met Gly
1               5                   10

<210> SEQ ID NO 6061
<211> LENGTH: 32
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6061

Arg Val Thr Ile Thr Arg Asp Thr Ser Thr Asn Thr Phe Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 6062
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6062

Trp Gly Gln Gly Thr Leu Val Thr Val Ser Ser
1               5                   10

<210> SEQ ID NO 6063
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6063

Ser Gly Glu Arg Leu Ser Asp Lys Tyr Val His
1               5                   10

<210> SEQ ID NO 6064
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6064

Glu Asn Asp Lys Arg Pro Ser
1               5

<210> SEQ ID NO 6065
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6065

Gln Ala Gly Tyr Glu Ala Asp Tyr Tyr Cys
1               5                   10

<210> SEQ ID NO 6066
<211> LENGTH: 22
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6066

Ser Tyr Thr Leu Thr Gln Pro Pro Leu Leu Ser Val Ala Leu Gly His
1               5                   10                  15

Lys Ala Thr Ile Thr Cys
            20

<210> SEQ ID NO 6067
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6067

Trp Tyr Gln Gln Lys Pro Gly Arg Ala Pro Val Met Val Ile Tyr
1               5                   10                  15

<210> SEQ ID NO 6068
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6068

Gly Ile Pro Asp Gln Phe Ser Gly Ser Asn Ser Gly Asn Ile Ala Thr
1               5                   10                  15

Leu Thr Ile Ser Lys Ala
            20

<210> SEQ ID NO 6069
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6069

Phe Gly Ser Gly Thr Gln Leu Thr Val Leu
1               5                   10

<210> SEQ ID NO 6070
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6070

Ser Gly Glu Asn Leu Ser Asp Lys Tyr Val His
1               5                   10

<210> SEQ ID NO 6071
```

```
-continued

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6071

Glu Asn Glu Lys Arg Pro Ser
1               5

<210> SEQ ID NO 6072
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6072

His Tyr Trp Glu Ser Ile Asn Ser Val Val
1               5                   10

<210> SEQ ID NO 6073
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6073

Ser Tyr Thr Leu Thr Gln Pro Pro Ser Leu Ser Val Ala Pro Gly Gln
1               5                   10                  15

Lys Ala Thr Ile Ile Cys
            20

<210> SEQ ID NO 6074
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6074

Trp Tyr Gln Gln Lys Pro Gly Arg Ala Pro Val Met Val Ile Tyr
1               5                   10                  15

<210> SEQ ID NO 6075
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6075

Gly Ile Pro Asp Gln Phe Ser Gly Ser Asn Ser Gly Asn Ile Ala Thr
1               5                   10                  15

Leu Thr Ile Ser Lys Ala Gln Pro Gly Ser Glu Ala Asp Tyr Tyr Cys
            20                  25                  30
```

<210> SEQ ID NO 6076
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6076

Phe Gly Ser Gly Thr His Leu Thr Val Leu
1               5                   10

<210> SEQ ID NO 6077
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6077

Gln Ser Val Thr Thr Gln Pro Pro Ser Val Ser Gly Ala Pro Gly Gln
1               5                   10                  15

Arg Val Thr Ile Ser Cys
            20

<210> SEQ ID NO 6078
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6078

Trp Tyr Gln Gln Leu Pro Gly Thr Ala Pro Lys Met Leu Ile Tyr
1               5                   10                  15

<210> SEQ ID NO 6079
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6079

Gly Val Pro Asp Arg Phe Ser Gly Ser Asn Ser Gly Asn Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 6080
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6080

Phe Gly Gly Gly Thr Gln Leu Thr Val Leu

<210> SEQ ID NO 6081
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6081

Gln Ser Val Thr Thr Gln Pro Pro Ser Ala Ser Gly Thr Pro Gly Gln
1               5                   10                  15

Arg Val Thr Ile Ser Cys
            20

<210> SEQ ID NO 6082
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6082

Trp Tyr Gln Gln Leu Pro Gly Thr Ala Pro Lys Met Leu Ile Tyr
1               5                   10                  15

<210> SEQ ID NO 6083
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6083

Gly Val Pro Asp Arg Phe Ser Gly Ser Asn Ser Gly Asn Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 6084
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6084

Phe Gly Gly Gly Thr Gln Leu Thr Val Leu
1               5                   10

<210> SEQ ID NO 6085
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6085

```
Gln Ser Val Thr Thr Gln Pro Pro Ser Ala Ser Gly Thr Pro Gln
1               5                   10                  15

Arg Val Thr Ile Ser Cys
                20
```

<210> SEQ ID NO 6086
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6086

```
Trp Tyr Gln Gln Leu Pro Gly Thr Ala Pro Lys Met Leu Ile Tyr
1               5                   10                  15
```

<210> SEQ ID NO 6087
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6087

```
Gly Val Pro Asp Arg Phe Ser Gly Ser Asn Ser Gly Asn Ser Ala Ser
1               5                   10                  15

Leu Ala Ile Ser Gly Leu Arg Ser Glu Asp Glu Ala Asp Tyr Tyr Cys
                20                  25                  30
```

<210> SEQ ID NO 6088
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6088

```
Phe Gly Gly Gly Thr Gln Leu Thr Val Leu
1               5                   10
```

<210> SEQ ID NO 6089
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6089

```
Ser Ser Glu Thr Thr Gln Pro His Ser Val Ser Val Ala Thr Ala Gln
1               5                   10                  15

Met Ala Arg Ile Thr Cys
                20
```

<210> SEQ ID NO 6090
<211> LENGTH: 15
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 6090

Trp Tyr Gln Gln Lys Pro Gly Gln Asp Pro Val Met Val Ile Tyr
1               5                   10                  15

<210> SEQ ID NO 6091
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6091

Gly Ile Pro Glu Arg Phe Ser Gly Ser Asn Pro Gly Asn Thr Ala Thr
1               5                   10                  15

Leu Thr Ile Ser Arg Ile Glu Ala Gly Asp Glu Ala Asp Tyr Tyr Cys
            20                  25                  30

<210> SEQ ID NO 6092
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6092

Phe Gly Gly Gly Thr Gln Leu Thr Val Leu
1               5                   10

<210> SEQ ID NO 6093
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6093

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 6094
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6094

Trp Tyr Gln Gln Lys Pro Gly Lys Ala Pro Lys Met Leu Ile Tyr
1               5                   10                  15

<210> SEQ ID NO 6095
<211> LENGTH: 32
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6095

Gly Val Pro Ser Arg Phe Ser Gly Ser Asn Ser Gly Asn Glu Ala Thr
1               5                   10                  15
Leu Thr Ile Ser Ser Leu Gln Pro Asp Asp Phe Ala Thr Tyr Tyr Cys
            20                  25                  30

<210> SEQ ID NO 6096
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6096

Phe Gly Gln Gly Thr Lys Val Glu Ile Lys
1               5                   10

<210> SEQ ID NO 6097
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6097

Gln Tyr Val Leu Thr Gln Pro Pro Ser Ala Ser Gly Thr Pro Gly Gln
1               5                   10                  15
Arg Val Thr Ile Ser Cys
            20

<210> SEQ ID NO 6098
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6098

Trp Tyr Gln Gln Leu Pro Gly Thr Ala Pro Lys Met Leu Ile Tyr
1               5                   10                  15

<210> SEQ ID NO 6099
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6099

Gly Val Pro Asp Arg Phe Ser Gly Ser Asn Ser Gly Asn Ser Ala Ser
1               5                   10                  15
Leu Ala Ile Ser Gly Leu Gln Ser Glu Asp Glu Ala Asp Tyr Tyr Cys
            20                  25                  30
```

<210> SEQ ID NO 6100
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 6100

Phe Gly Glu Gly Thr Glu Leu Thr Val Leu
1               5                   10

<210> SEQ ID NO 6101
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 6101

Gln Tyr Val Leu Thr Gln Pro Pro Ser Ala Ser Gly Thr Pro Gly Gln
1               5                   10                  15

Arg Val Thr Ile Ser Cys
            20

<210> SEQ ID NO 6102
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 6102

Trp Tyr Gln Gln Leu Pro Gly Thr Ala Pro Lys Met Leu Ile Tyr
1               5                   10                  15

<210> SEQ ID NO 6103
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6103

Gly Val Pro Asp Arg Phe Ser Gly Ser Asn Ser Gly Asn Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 6104
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 6104

Phe Gly Glu Gly Thr Glu Leu Thr Val Leu
1               5                   10

<210> SEQ ID NO 6105
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6105

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 6106
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6106

Trp Tyr Gln Gln Lys Pro Gly Gln Ser Pro Val Met Val Ile Tyr
1               5                   10                  15

<210> SEQ ID NO 6107
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6107

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 6108
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6108

Phe Gly Glu Gly Thr Glu Leu Thr Val Leu
1               5                   10

<210> SEQ ID NO 6109
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 6109

Asp Tyr Val Leu Thr Gln Ser Pro Leu Ser Leu Pro Val Thr Pro Gly
1               5                   10                  15

Glu Pro Ala Ser Ile Ser Cys
            20

<210> SEQ ID NO 6110
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6110

Trp Tyr Leu Gln Lys Pro Gly Gln Ser Pro Gln Met Leu Ile Tyr
1               5                   10                  15

<210> SEQ ID NO 6111
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6111

Gly Val Pro Asp Arg Phe Ser Gly Ser Asn Ser Gly Asn Asp Ala Thr
1               5                   10                  15

Leu Lys Ile Ser Arg Val Glu Ala Glu Asp Val Gly Val Tyr Tyr Cys
            20                  25                  30

<210> SEQ ID NO 6112
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6112

Phe Gly Gln Gly Thr Lys Val Glu Ile Lys
1               5                   10

<210> SEQ ID NO 6113
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6113

Ala Tyr Gln Leu Thr Gln Ser Pro Ser Ser Leu Ser Ala Ser Val Gly
1               5                   10                  15

Asp Arg Val Thr Ile Thr Cys
            20

<210> SEQ ID NO 6114
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 6114

Trp Tyr Gln Gln Lys Pro Gly Lys Ala Pro Lys Met Leu Ile Tyr
1               5                  10                  15

<210> SEQ ID NO 6115
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6115

Gly Val Pro Ser Arg Phe Ser Gly Ser Asn Ser Gly Asn Asp Ala Thr
1               5                   10                  15

Leu Thr Ile Ser Ser Leu Gln Pro Glu Asp Phe Ala Thr Tyr Tyr Cys
            20                  25                  30

<210> SEQ ID NO 6116
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6116

Phe Gly Gln Gly Thr Lys Val Glu Ile Lys
1               5                  10

<210> SEQ ID NO 6117
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6117

Glu Tyr Val Leu Thr Gln Ser Pro Ala Thr Leu Ser Val Ser Pro Gly
1               5                   10                  15

Glu Arg Ala Thr Leu Ser Cys
            20

<210> SEQ ID NO 6118
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6118

Trp Tyr Gln Gln Lys Pro Gly Gln Ala Pro Arg Met Leu Ile Tyr
1               5                  10                  15

<210> SEQ ID NO 6119
<211> LENGTH: 32
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6119

Gly Ile Pro Ala Arg Phe Ser Gly Ser Asn Ser Gly Asn Glu Ala Thr
1               5                   10                  15

Leu Thr Ile Ser Ser Leu Gln Ser Glu Asp Phe Ala Val Tyr Tyr Cys
            20                  25                  30

<210> SEQ ID NO 6120
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6120

Phe Gly Gln Gly Thr Lys Val Glu Ile Lys
1               5                   10

<210> SEQ ID NO 6121
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6121

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn Thr Gly
            20                  25                  30

Gly Tyr His Trp Asn Trp Ile Arg Gln Phe Pro Gly Lys Lys Leu Glu
        35                  40                  45

Trp Met Gly Tyr Ile Tyr Ser Ser Gly Ser Thr Ser Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Gly Asn Trp His Tyr Phe Asp Phe Trp Gly Gln Gly Thr
            100                 105                 110

Met Val Thr Val Ser Ser
        115

<210> SEQ ID NO 6122
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6122

Gln Ile Gln Leu Gln Glu Ser Gly Pro Gly Leu Val Lys Pro Ser Gln
```

```
                1               5                   10                  15
            Ser Leu Ser Leu Thr Cys Ser Val Thr Gly Phe Ser Ile Asn Thr Gly
                        20                  25                  30

Gly Tyr His Trp Asn Trp Ile Arg Gln Phe Pro Gly Lys Lys Leu Glu
                        35                  40                  45

Trp Met Gly Tyr Ile Tyr Ser Ser Gly Thr Thr Arg Tyr Asn Pro Ser
                50                  55                  60

Leu Lys Ser Arg Ile Ser Ile Thr Arg Asp Thr Ser Lys Asn Gln Phe
            65                  70                  75                  80

Phe Leu Gln Leu Asn Ser Val Thr Pro Glu Asp Thr Ala Thr Tyr Tyr
                        85                  90                  95

Cys Thr Arg Gly Asn Trp His Tyr Phe Asp Tyr Trp Gly Gln Gly Thr
                        100                 105                 110

Leu Val Ala Val Ser Ser
                    115
```

<210> SEQ ID NO 6123
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6123

```
            Gln Ile Gln Leu Gln Glu Ser Gly Pro Gly Leu Val Lys Pro Ser Glu
            1               5                   10                  15

Thr Leu Ser Leu Thr Cys Thr Val Ser Gly Phe Ser Ile Asn Thr Gly
                        20                  25                  30

Gly Tyr His Trp Asn Trp Ile Arg Gln Pro Ala Gly Lys Gly Leu Glu
                        35                  40                  45

Trp Ile Gly Tyr Ile Tyr Ser Ser Gly Ser Thr Ser Tyr Asn Pro Ser
                50                  55                  60

Leu Lys Ser Arg Val Thr Met Ser Arg Asp Thr Ser Lys Asn Gln Phe
            65                  70                  75                  80

Ser Leu Lys Leu Ser Ser Val Thr Ala Ala Asp Thr Ala Val Tyr Tyr
                        85                  90                  95

Cys Ala Arg Gly Asn Trp His Tyr Phe Asp Phe Trp Gly Gln Gly Thr
                        100                 105                 110

Met Val Thr Val Ser Ser
                    115
```

<210> SEQ ID NO 6124
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6124

```
            Gln Ile Gln Leu Gln Glu Ser Gly Pro Gly Leu Val Lys Pro Ser Gln
            1               5                   10                  15

Thr Leu Ser Leu Thr Cys Thr Val Ser Gly Phe Ser Ile Asn Thr Gly
                        20                  25                  30

Gly Tyr His Trp Asn Trp Ile Arg Gln His Pro Gly Lys Gly Leu Glu
                        35                  40                  45
```

```
Trp Ile Gly Tyr Ile Tyr Ser Ser Gly Ser Thr Ser Tyr Asn Pro Ser
    50                  55                  60

Leu Lys Ser Leu Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asn Trp His Tyr Phe Asp Phe Trp Gly Gln Gly Thr
                100                 105                 110

Met Val Thr Val Ser Ser
            115
```

<210> SEQ ID NO 6125
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6125

```
Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Asn Thr Gly
                20                  25                  30

Gly Tyr His Trp Asn Trp Val Arg Gln Ala Pro Gly Lys Gly Leu Glu
            35                  40                  45

Trp Val Gly Tyr Ile Tyr Ser Ser Gly Ser Thr Ser Tyr Asn Pro Ser
    50                  55                  60

Leu Lys Ser Arg Phe Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Asn Trp His Tyr Phe Asp Phe Trp Gly Gln Gly Thr
                100                 105                 110

Met Val Thr Val Ser Ser
            115
```

<210> SEQ ID NO 6126
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6126

```
Gln Ile Gln Leu Val Gln Ser Gly Ala Glu Val Lys Lys Pro Gly Ser
1               5                   10                  15

Ser Val Lys Val Ser Cys Lys Val Ser Gly Phe Ser Ile Asn Thr Gly
                20                  25                  30

Gly Tyr His Trp Asn Trp Val Arg Gln Ala Pro Gly Gln Gly Leu Glu
            35                  40                  45

Trp Met Gly Tyr Ile Tyr Ser Ser Gly Ser Thr Ser Tyr Asn Pro Ser
    50                  55                  60

Leu Lys Ser Arg Val Thr Ile Thr Arg Asp Thr Ser Asn Thr Phe
65                  70                  75                  80
```

-continued

Tyr Met Glu Leu Ser Ser Leu Arg Ser Glu Asp Thr Ala Val Tyr Tyr
                85                  90                  95

Cys Ala Arg Gly Asn Trp His Tyr Phe Asp Phe Trp Gly Gln Gly Thr
            100                 105                 110

Met Val Thr Val Ser Ser
        115

<210> SEQ ID NO 6127
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6127

Glu Ile Gln Leu Val Glu Ser Gly Gly Gly Leu Val Gln Pro Gly Gly
1               5                   10                  15

Ser Leu Arg Leu Ser Cys Ala Val Ser Gly Phe Ser Ile Asn Thr Gly
            20                  25                  30

Gly Tyr His Trp Asn Trp Val Arg Gln Ala Pro Gly Lys Gly Leu Glu
        35                  40                  45

Trp Val Gly Tyr Ile Tyr Ser Ser Gly Ser Thr Ser Tyr Asn Pro Ser
    50                  55                  60

Leu Lys Ser Arg Phe Thr Ile Ser Arg Asp Thr Ala Lys Asn Ser Phe
65                  70                  75                  80

Tyr Leu Gln Met Asn Ser Leu Arg Ala Glu Asp Thr Ala Val Tyr Tyr
                85                  90                  95

Cys Ala Arg Gly Asn Trp His Tyr Phe Asp Phe Trp Gly Gln Gly Thr
            100                 105                 110

Met Val Thr Val Ser Ser
        115

<210> SEQ ID NO 6128
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6128

Gln Ile Gln Leu Val Gln Ser Gly Ala Glu Val Lys Lys Pro Gly Ala
1               5                   10                  15

Ser Val Lys Val Ser Cys Lys Val Ser Gly Phe Ser Ile Asn Thr Gly
            20                  25                  30

Gly Tyr His Trp Asn Trp Val Arg Gln Ala Pro Gly Gln Gly Leu Glu
        35                  40                  45

Trp Met Gly Tyr Ile Tyr Ser Ser Gly Ser Thr Ser Tyr Asn Pro Ser
    50                  55                  60

Leu Lys Ser Arg Val Thr Met Thr Arg Asp Thr Ser Thr Asn Thr Phe
65                  70                  75                  80

Tyr Met Glu Leu Ser Ser Leu Arg Ser Glu Asp Thr Ala Val Tyr Tyr
                85                  90                  95

Cys Ala Arg Gly Asn Trp His Tyr Phe Asp Phe Trp Gly Gln Gly Thr
            100                 105                 110

Met Val Thr Val Ser Ser

115

<210> SEQ ID NO 6129
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6129

Gln Ile Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Asn Thr Gly
            20                  25                  30

Gly Tyr His Trp Asn Trp Ile Arg Gln His Pro Gly Lys Gly Leu Glu
        35                  40                  45

Trp Ile Gly Tyr Ile Tyr Ser Ser Gly Thr Thr Arg Tyr Asn Pro Ser
    50                  55                  60

Leu Lys Ser Leu Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asn Trp His Tyr Phe Asp Tyr Trp Gly Gln Gly Thr
            100                 105                 110

Leu Val Thr Val Ser Ser
        115

<210> SEQ ID NO 6130
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6130

Gln Ile Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Asn Thr Gly
            20                  25                  30

Gly Tyr His Trp Asn Trp Ile Arg Gln Pro Ala Gly Lys Gly Leu Glu
        35                  40                  45

Trp Ile Gly Tyr Ile Tyr Ser Ser Gly Thr Thr Arg Tyr Asn Pro Ser
    50                  55                  60

Leu Lys Ser Arg Val Thr Met Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asn Trp His Tyr Phe Asp Tyr Trp Gly Gln Gly Thr
            100                 105                 110

Leu Val Thr Val Ser Ser
        115

<210> SEQ ID NO 6131
<211> LENGTH: 118
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 6131

Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Asn Thr Gly
            20                  25                  30

Gly Tyr His Trp Asn Trp Val Arg Gln Ala Pro Gly Lys Gly Leu Glu
        35                  40                  45

Trp Val Gly Tyr Ile Tyr Ser Ser Gly Thr Thr Arg Tyr Asn Pro Ser
    50                  55                  60

Leu Lys Ser Arg Phe Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Asn Trp His Tyr Phe Asp Tyr Trp Gly Gln Gly Thr
            100                 105                 110

Leu Val Thr Val Ser Ser
        115

<210> SEQ ID NO 6132
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6132

Gln Ile Gln Leu Val Glu Ser Gly Gly Gly Leu Val Lys Pro Gly Gly
1               5                   10                  15

Ser Leu Arg Leu Ser Cys Ala Val Ser Gly Phe Ser Ile Asn Thr Gly
            20                  25                  30

Gly Tyr His Trp Asn Trp Ile Arg Gln Ala Pro Gly Lys Gly Leu Glu
        35                  40                  45

Trp Val Gly Tyr Ile Tyr Ser Ser Gly Thr Thr Arg Tyr Asn Pro Ser
    50                  55                  60

Leu Lys Ser Arg Phe Thr Ile Ser Arg Asp Thr Ala Lys Asn Ser Phe
65                  70                  75                  80

Tyr Leu Gln Met Asn Ser Leu Arg Ala Glu Asp Thr Ala Val Tyr Tyr
                85                  90                  95

Cys Ala Arg Gly Asn Trp His Tyr Phe Asp Tyr Trp Gly Gln Gly Thr
            100                 105                 110

Leu Val Thr Val Ser Ser
        115

<210> SEQ ID NO 6133
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6133
```

-continued

```
Gln Ile Gln Leu Val Gln Ser Gly Ala Glu Val Lys Lys Pro Gly Ala
1               5                   10                  15

Ser Val Lys Val Ser Cys Lys Val Ser Gly Phe Ser Ile Asn Thr Gly
            20                  25                  30

Gly Tyr His Trp Asn Trp Val Arg Gln Ala Pro Gly Gln Gly Leu Glu
        35                  40                  45

Trp Met Gly Tyr Ile Tyr Ser Ser Gly Thr Thr Arg Tyr Asn Pro Ser
50                  55                  60

Leu Lys Ser Arg Val Thr Met Thr Arg Asp Thr Ser Thr Asn Thr Phe
65                  70                  75                  80

Tyr Met Glu Leu Ser Ser Leu Arg Ser Glu Asp Thr Ala Val Tyr Tyr
                85                  90                  95

Cys Ala Arg Gly Asn Trp His Tyr Phe Asp Tyr Trp Gly Gln Gly Thr
            100                 105                 110

Leu Val Thr Val Ser Ser
        115
```

<210> SEQ ID NO 6134
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6134

```
Glu Ile Gln Leu Val Gln Ser Gly Ala Glu Val Lys Lys Pro Gly Ala
1               5                   10                  15

Thr Val Lys Ile Ser Cys Lys Val Ser Gly Phe Ser Ile Asn Thr Gly
            20                  25                  30

Gly Tyr His Trp Asn Trp Val Gln Gln Ala Pro Gly Lys Gly Leu Glu
        35                  40                  45

Trp Met Gly Tyr Ile Tyr Ser Ser Gly Thr Thr Arg Tyr Asn Pro Ser
50                  55                  60

Leu Lys Ser Arg Val Thr Ile Thr Arg Asp Thr Ser Thr Asn Thr Phe
65                  70                  75                  80

Tyr Met Glu Leu Ser Ser Leu Arg Ser Glu Asp Thr Ala Val Tyr Tyr
                85                  90                  95

Cys Ala Arg Gly Asn Trp His Tyr Phe Asp Tyr Trp Gly Gln Gly Thr
            100                 105                 110

Leu Val Thr Val Ser Ser
        115
```

<210> SEQ ID NO 6135
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6135

```
Ser Tyr Thr Leu Thr Gln Pro Pro Leu Leu Ser Val Ala Leu Gly His
1               5                   10                  15

Lys Ala Thr Ile Thr Cys Ser Gly Glu Arg Leu Ser Asp Lys Tyr Val
            20                  25                  30

His Trp Tyr Gln Gln Lys Pro Gly Arg Ala Pro Val Met Val Ile Tyr
```

```
                35                  40                  45
Glu Asn Asp Lys Arg Pro Ser Gly Ile Pro Asp Gln Phe Ser Gly Ser
         50                  55                  60
Asn Ser Gly Asn Ile Ala Thr Leu Thr Ile Ser Lys Ala Gln Ala Gly
 65                  70                  75                  80
Tyr Glu Ala Asp Tyr Tyr Cys Phe Gly Ser Gly Thr Gln Leu Thr Val
                 85                  90                  95
Leu
```

<210> SEQ ID NO 6136
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6136

```
Ser Tyr Thr Leu Thr Gln Pro Pro Ser Leu Ser Val Ala Pro Gly Gln
 1               5                  10                  15
Lys Ala Thr Ile Ile Cys Ser Gly Glu Asn Leu Ser Asp Lys Tyr Val
                20                  25                  30
His Trp Tyr Gln Gln Lys Pro Gly Arg Ala Pro Val Met Val Ile Tyr
                35                  40                  45
Glu Asn Glu Lys Arg Pro Ser Gly Ile Pro Asp Gln Phe Ser Gly Ser
         50                  55                  60
Asn Ser Gly Asn Ile Ala Thr Leu Thr Ile Ser Lys Ala Gln Pro Gly
 65                  70                  75                  80
Ser Glu Ala Asp Tyr Tyr Cys His Tyr Trp Glu Ser Ile Asn Ser Val
                 85                  90                  95
Val Phe Gly Ser Gly Thr His Leu Thr Val Leu
                100                 105
```

<210> SEQ ID NO 6137
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6137

```
Gln Ser Val Thr Thr Gln Pro Pro Ser Val Ser Gly Ala Pro Gly Gln
 1               5                  10                  15
Arg Val Thr Ile Ser Cys Ser Gly Glu Arg Leu Ser Asp Lys Tyr Val
                20                  25                  30
His Trp Tyr Gln Gln Leu Pro Gly Thr Ala Pro Lys Met Leu Ile Tyr
                35                  40                  45
Glu Asn Asp Lys Arg Pro Ser Gly Val Pro Asp Arg Phe Ser Gly Ser
         50                  55                  60
Asn Ser Gly Asn Ser Ala Ser Leu Ala Ile Thr Gly Leu Gln Ala Glu
 65                  70                  75                  80
Asp Glu Ala Asp Tyr Tyr Cys Gln Ser Trp Asp Ser Thr Asn Ser Ala
                 85                  90                  95
Val Phe Gly Gly Gly Thr Gln Leu Thr Val Leu
                100                 105
```

<210> SEQ ID NO 6138
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6138

Gln Ser Val Thr Thr Gln Pro Pro Ser Ala Ser Gly Thr Pro Gly Gln
1               5                   10                  15

Arg Val Thr Ile Ser Cys Ser Gly Glu Arg Leu Ser Asp Lys Tyr Val
            20                  25                  30

His Trp Tyr Gln Gln Leu Pro Gly Thr Ala Pro Lys Met Leu Ile Tyr
        35                  40                  45

Glu Asn Asp Lys Arg Pro Ser Gly Val Pro Asp Arg Phe Ser Gly Ser
    50                  55                  60

Asn Ser Gly Asn Ser Ala Ser Leu Ala Ile Ser Gly Leu Gln Ser Glu
65                  70                  75                  80

Asp Glu Ala Asp Tyr Tyr Cys Gln Ser Trp Asp Ser Thr Asn Ser Ala
                85                  90                  95

Val Phe Gly Gly Gly Thr Gln Leu Thr Val Leu
            100                 105

<210> SEQ ID NO 6139
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6139

Gln Ser Val Thr Thr Gln Pro Pro Ser Ala Ser Gly Thr Pro Gly Gln
1               5                   10                  15

Arg Val Thr Ile Ser Cys Ser Gly Glu Arg Leu Ser Asp Lys Tyr Val
            20                  25                  30

His Trp Tyr Gln Gln Leu Pro Gly Thr Ala Pro Lys Met Leu Ile Tyr
        35                  40                  45

Glu Asn Asp Lys Arg Pro Ser Gly Val Pro Asp Arg Phe Ser Gly Ser
    50                  55                  60

Asn Ser Gly Asn Ser Ala Ser Leu Ala Ile Ser Gly Leu Arg Ser Glu
65                  70                  75                  80

Asp Glu Ala Asp Tyr Tyr Cys Gln Ser Trp Asp Ser Thr Asn Ser Ala
                85                  90                  95

Val Phe Gly Gly Gly Thr Gln Leu Thr Val Leu
            100                 105

<210> SEQ ID NO 6140
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6140

Ser Ser Glu Thr Thr Gln Pro His Ser Val Ser Val Ala Thr Ala Gln

-continued

```
                1               5               10              15
            Met Ala Arg Ile Thr Cys Ser Gly Glu Arg Leu Ser Asp Lys Tyr Val
                            20              25              30

His Trp Tyr Gln Gln Lys Pro Gly Gln Asp Pro Val Met Val Ile Tyr
                            35              40              45

Glu Asn Asp Lys Arg Pro Ser Gly Ile Pro Glu Arg Phe Ser Gly Ser
                            50              55              60

Asn Pro Gly Asn Thr Ala Thr Leu Thr Ile Ser Arg Ile Glu Ala Gly
            65              70              75              80

Asp Glu Ala Asp Tyr Tyr Cys Gln Ser Trp Asp Ser Thr Asn Ser Ala
                            85              90              95

Val Phe Gly Gly Gly Thr Gln Leu Thr Val Leu
                            100             105
```

<210> SEQ ID NO 6141
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6141

```
            Asp Ile Gln Met Thr Gln Ser Pro Ser Thr Leu Ser Ala Ser Val Gly
            1               5               10              15

Asp Arg Val Thr Ile Thr Cys Ser Gly Glu Arg Leu Ser Asp Lys Tyr
                            20              25              30

Val His Trp Tyr Gln Gln Lys Pro Gly Lys Ala Pro Lys Met Leu Ile
                            35              40              45

Tyr Glu Asn Asp Lys Arg Pro Ser Gly Val Pro Ser Arg Phe Ser Gly
                            50              55              60

Ser Asn Ser Gly Asn Glu Ala Thr Leu Thr Ile Ser Ser Leu Gln Pro
            65              70              75              80

Asp Asp Phe Ala Thr Tyr Tyr Cys Gln Ser Trp Asp Ser Thr Asn Ser
                            85              90              95

Ala Val Phe Gly Gln Gly Thr Lys Val Glu Ile Lys
                            100             105
```

<210> SEQ ID NO 6142
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6142

```
            Gln Tyr Val Leu Thr Gln Pro Pro Ser Ala Ser Gly Thr Pro Gly Gln
            1               5               10              15

Arg Val Thr Ile Ser Cys Ser Gly Glu Asn Leu Ser Asp Lys Tyr Val
                            20              25              30

His Trp Tyr Gln Gln Leu Pro Gly Thr Ala Pro Lys Met Leu Ile Tyr
                            35              40              45

Glu Asn Glu Lys Arg Pro Ser Gly Val Pro Asp Arg Phe Ser Gly Ser
                            50              55              60

Asn Ser Gly Asn Ser Ala Ser Leu Ala Ile Ser Gly Leu Gln Ser Glu
            65              70              75              80
```

-continued

Asp Glu Ala Asp Tyr Tyr Cys His Tyr Trp Glu Ser Ile Asn Ser Val
                85                  90                  95

Val Phe Gly Glu Gly Thr Glu Leu Thr Val Leu
            100                 105

<210> SEQ ID NO 6143
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6143

Gln Tyr Val Leu Thr Gln Pro Pro Ser Ala Ser Gly Thr Pro Gly Gln
1               5                   10                  15

Arg Val Thr Ile Ser Cys Ser Gly Glu Asn Leu Ser Asp Lys Tyr Val
            20                  25                  30

His Trp Tyr Gln Gln Leu Pro Gly Thr Ala Pro Lys Met Leu Ile Tyr
        35                  40                  45

Glu Asn Glu Lys Arg Pro Ser Gly Val Pro Asp Arg Phe Ser Gly Ser
    50                  55                  60

Asn Ser Gly Asn Ser Ala Ser Leu Ala Ile Ser Gly Leu Arg Ser Glu
65                  70                  75                  80

Asp Glu Ala Asp Tyr Tyr Cys His Tyr Trp Glu Ser Ile Asn Ser Val
                85                  90                  95

Val Phe Gly Glu Gly Thr Glu Leu Thr Val Leu
            100                 105

<210> SEQ ID NO 6144
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6144

Ser Tyr Glu Leu Thr Gln Pro Pro Ser Val Ser Val Ser Pro Gly Gln
1               5                   10                  15

Thr Ala Ser Ile Thr Cys Ser Gly Glu Asn Leu Ser Asp Lys Tyr Val
            20                  25                  30

His Trp Tyr Gln Gln Lys Pro Gly Gln Ser Pro Val Met Val Ile Tyr
        35                  40                  45

Glu Asn Glu Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Tyr Trp Glu Ser Ile Asn Ser Val
                85                  90                  95

Val Phe Gly Glu Gly Thr Glu Leu Thr Val Leu
            100                 105

<210> SEQ ID NO 6145
<211> LENGTH: 108
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 6145

Asp Tyr Val Leu Thr Gln Ser Pro Leu Ser Leu Pro Val Thr Pro Gly
1               5                   10                  15

Glu Pro Ala Ser Ile Ser Cys Ser Gly Glu Asn Leu Ser Asp Lys Tyr
            20                  25                  30

Val His Trp Tyr Leu Gln Lys Pro Gly Gln Ser Pro Gln Met Leu Ile
        35                  40                  45

Tyr Glu Asn Glu Lys Arg Pro Ser Gly Val Pro Asp Arg Phe Ser Gly
    50                  55                  60

Ser Asn Ser Gly Asn Asp Ala Thr Leu Lys Ile Ser Arg Val Glu Ala
65                  70                  75                  80

Glu Asp Val Gly Val Tyr Tyr Cys His Tyr Trp Glu Ser Ile Asn Ser
                85                  90                  95

Val Val Phe Gly Gln Gly Thr Lys Val Glu Ile Lys
            100                 105

<210> SEQ ID NO 6146
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6146

Ala Tyr Gln Leu Thr Gln Ser Pro Ser Ser Leu Ser Ala Ser Val Gly
1               5                   10                  15

Asp Arg Val Thr Ile Thr Cys Ser Gly Glu Asn Leu Ser Asp Lys Tyr
            20                  25                  30

Val His Trp Tyr Gln Gln Lys Pro Gly Lys Ala Pro Lys Met Leu Ile
        35                  40                  45

Tyr Glu Asn Glu Lys Arg Pro Ser Gly Val Pro Ser Arg Phe Ser Gly
    50                  55                  60

Ser Asn Ser Gly Asn Asp Ala Thr Leu Thr Ile Ser Ser Leu Gln Pro
65                  70                  75                  80

Glu Asp Phe Ala Thr Tyr Tyr Cys His Tyr Trp Glu Ser Ile Asn Ser
                85                  90                  95

Val Val Phe Gly Gln Gly Thr Lys Val Glu Ile Lys
            100                 105

<210> SEQ ID NO 6147
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6147

Glu Tyr Val Leu Thr Gln Ser Pro Ala Thr Leu Ser Val Ser Pro Gly
1               5                   10                  15

Glu Arg Ala Thr Leu Ser Cys Ser Gly Glu Asn Leu Ser Asp Lys Tyr
            20                  25                  30

Val His Trp Tyr Gln Gln Lys Pro Gly Gln Ala Pro Arg Met Leu Ile

```
            35                  40                  45
Tyr Glu Asn Glu Lys Arg Pro Ser Gly Ile Pro Ala Arg Phe Ser Gly
 50                  55                  60

Ser Asn Ser Gly Asn Glu Ala Thr Leu Thr Ile Ser Ser Leu Gln Ser
65                  70                  75                  80

Glu Asp Phe Ala Val Tyr Tyr Cys His Tyr Trp Glu Ser Ile Asn Ser
                85                  90                  95

Val Val Phe Gly Gln Gly Thr Lys Val Glu Ile Lys
            100                 105

<210> SEQ ID NO 6148
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6148

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn Thr Gly
            20                  25                  30

Gly Tyr His Trp Asn Trp Ile Arg Gln Phe Pro Gly Lys Lys Leu Glu
        35                  40                  45

Trp Met Gly Tyr Ile Tyr Ser Ser Gly Ser Thr Ser Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Gly Asn Trp His Tyr Phe Asp Phe Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 6149
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6149

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn Thr Gly
            20                  25                  30

Gly Tyr His Trp Asn Trp Ile Arg Gln Phe Pro Gly Lys Lys Leu Glu
        35                  40                  45

Trp Met Gly Tyr Ile Tyr Ser Ser Gly Ser Thr Ser Tyr Asn Pro Ser
50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Gly Asn Trp His Tyr Phe Asp Phe Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 6150
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6150

Ser Tyr Thr Leu Thr Gln Pro Pro Leu Leu Ser Val Ala Leu Gly His
1               5                   10                  15

Lys Ala Thr Ile Thr Cys Ser Gly Glu Arg Leu Ser Asp Lys Tyr Val
            20                  25                  30

His Trp Tyr Gln Gln Lys Pro Gly Arg Ala Pro Val Met Val Ile Tyr
        35                  40                  45

Glu Asn Asp Lys Arg Pro Ser Gly Ile Pro Asp Gln Phe Ser Gly Ser
    50                  55                  60

Asn Ser Gly Asn Ile Ala Thr Leu Thr Ile Ser Lys Ala Gln Ala Gly
65                  70                  75                  80

Tyr Glu Ala Asp Tyr Tyr Cys Gln Ser Trp Asp Ser Thr Asn Ser Ala
                85                  90                  95

Val Phe Gly Ser Gly Thr Gln Leu Thr Val Leu Gly Gln Pro Lys Ala

```
            100                 105                 110
Asn Pro Thr Val Thr Leu Phe Pro Pro Ser Ser Glu Glu Leu Gln Ala
        115                 120                 125
Asn Lys Ala Thr Leu Val Cys Leu Ile Ser Asp Phe Tyr Pro Gly Ala
    130                 135                 140
Val Thr Val Ala Trp Lys Ala Asp Gly Ser Pro Val Lys Ala Gly Val
145                 150                 155                 160
Glu Thr Thr Lys Pro Ser Lys Gln Ser Asn Asn Lys Tyr Ala Ala Ser
                165                 170                 175
Ser Tyr Leu Ser Leu Thr Pro Glu Gln Trp Lys Ser His Arg Ser Tyr
            180                 185                 190
Ser Cys Gln Val Thr His Glu Gly Ser Thr Val Glu Lys Thr Val Ala
        195                 200                 205
Pro Thr Glu Cys Ser
    210

<210> SEQ ID NO 6151
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6151

Gln Ile Gln Leu Gln Glu Ser Gly Pro Gly Leu Val Lys Pro Ser Gln
1               5                   10                  15
Ser Leu Ser Leu Thr Cys Ser Val Thr Gly Phe Ser Ile Asn Thr Gly
            20                  25                  30
Gly Tyr His Trp Asn Trp Ile Arg Gln Phe Pro Gly Lys Lys Leu Glu
        35                  40                  45
Trp Met Gly Tyr Ile Tyr Ser Ser Gly Thr Thr Arg Tyr Asn Pro Ser
    50                  55                  60
Leu Lys Ser Arg Ile Ser Ile Thr Arg Asp Thr Ser Lys Asn Gln Phe
65                  70                  75                  80
Phe Leu Gln Leu Asn Ser Val Thr Pro Glu Asp Thr Ala Thr Tyr Tyr
                85                  90                  95
Cys Thr Arg Gly Asn Trp His Tyr Phe Asp Tyr Trp Gly Gln Gly Thr
            100                 105                 110
Leu Val Ala Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 6152
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6152

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn Thr Gly
            20                  25                  30

Gly Tyr His Trp Asn Trp Ile Arg Gln Phe Pro Gly Lys Lys Leu Glu
        35                  40                  45

Trp Met Gly Tyr Ile Tyr Ser Ser Gly Thr Thr Arg Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Pro Glu Asp Thr Ala Thr Tyr Tyr
                85                  90                  95

Cys Thr Arg Gly Asn Trp His Tyr Phe Asp Tyr Trp Gly Gln Gly Thr
            100                 105                 110

Leu Val Ala Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 6153
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6153

Ser Tyr Thr Leu Thr Gln Pro Pro Ser Leu Ser Val Ala Pro Gly Gln
1               5                   10                  15

Lys Ala Thr Ile Ile Cys Ser Gly Glu Asn Leu Ser Asp Lys Tyr Val
                20                  25                  30

His Trp Tyr Gln Gln Lys Pro Gly Arg Ala Pro Val Met Val Ile Tyr
            35                  40                  45

Glu Asn Glu Lys Arg Pro Ser Gly Ile Pro Asp Gln Phe Ser Gly Ser
```

```
                50             55              60
Asn Ser Gly Asn Ile Ala Thr Leu Thr Ile Ser Lys Ala Gln Pro Gly
 65                  70              75                  80

Ser Glu Ala Asp Tyr Tyr Cys His Tyr Trp Glu Ser Ile Asn Ser Val
                     85              90              95

Val Phe Gly Ser Gly Thr His Leu Thr Val Leu Gly Gln Pro Lys Ala
            100             105             110

Asn Pro Thr Val Thr Leu Phe Pro Pro Ser Ser Glu Glu Leu Gln Ala
        115             120             125

Asn Lys Ala Thr Leu Val Cys Leu Ile Ser Asp Phe Tyr Pro Gly Ala
    130             135             140

Val Thr Val Ala Trp Lys Ala Asp Gly Ser Pro Val Lys Ala Gly Val
145             150             155             160

Glu Thr Thr Lys Pro Ser Lys Gln Ser Asn Asn Lys Tyr Ala Ala Ser
                165             170             175

Ser Tyr Leu Ser Leu Thr Pro Glu Gln Trp Lys Ser His Arg Ser Tyr
            180             185             190

Ser Cys Gln Val Thr His Glu Gly Ser Thr Val Glu Lys Thr Val Ala
        195             200             205

Pro Thr Glu Cys Ser
    210
```

```
<210> SEQ ID NO 6154
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (2)..(26)
<223> OTHER INFORMATION: /note="This region may encompass 2-5 'Glu Ala
      Ala Ala Lys' repeating units"

<400> SEQUENCE: 6154

Ala Glu Ala Ala Ala Lys Glu Ala Ala Lys Glu Ala Ala Lys
 1               5                  10                  15

Glu Ala Ala Ala Lys Glu Ala Ala Ala Lys Ala
            20                  25

<210> SEQ ID NO 6155

<400> SEQUENCE: 6155

000

<210> SEQ ID NO 6156

<400> SEQUENCE: 6156

000

<210> SEQ ID NO 6157

<400> SEQUENCE: 6157

000

<210> SEQ ID NO 6158
```

-continued

<400> SEQUENCE: 6158

000

<210> SEQ ID NO 6159

<400> SEQUENCE: 6159

000

<210> SEQ ID NO 6160

<400> SEQUENCE: 6160

000

<210> SEQ ID NO 6161

<400> SEQUENCE: 6161

000

<210> SEQ ID NO 6162

<400> SEQUENCE: 6162

000

<210> SEQ ID NO 6163

<400> SEQUENCE: 6163

000

<210> SEQ ID NO 6164

<400> SEQUENCE: 6164

000

<210> SEQ ID NO 6165

<400> SEQUENCE: 6165

000

<210> SEQ ID NO 6166

<400> SEQUENCE: 6166

000

<210> SEQ ID NO 6167

<400> SEQUENCE: 6167

000

<210> SEQ ID NO 6168

<400> SEQUENCE: 6168

000

<210> SEQ ID NO 6169

<400> SEQUENCE: 6169

000

<210> SEQ ID NO 6170

<400> SEQUENCE: 6170

000

<210> SEQ ID NO 6171

<400> SEQUENCE: 6171

000

<210> SEQ ID NO 6172

<400> SEQUENCE: 6172

000

<210> SEQ ID NO 6173

<400> SEQUENCE: 6173

000

<210> SEQ ID NO 6174

<400> SEQUENCE: 6174

000

<210> SEQ ID NO 6175

<400> SEQUENCE: 6175

000

<210> SEQ ID NO 6176

<400> SEQUENCE: 6176

000

<210> SEQ ID NO 6177

<400> SEQUENCE: 6177

000

<210> SEQ ID NO 6178

<400> SEQUENCE: 6178

000

<210> SEQ ID NO 6179

<400> SEQUENCE: 6179

000

<210> SEQ ID NO 6180

<400> SEQUENCE: 6180

000

-continued

<210> SEQ ID NO 6181

<400> SEQUENCE: 6181

000

<210> SEQ ID NO 6182

<400> SEQUENCE: 6182

000

<210> SEQ ID NO 6183

<400> SEQUENCE: 6183

000

<210> SEQ ID NO 6184

<400> SEQUENCE: 6184

000

<210> SEQ ID NO 6185

<400> SEQUENCE: 6185

000

<210> SEQ ID NO 6186

<400> SEQUENCE: 6186

000

<210> SEQ ID NO 6187

<400> SEQUENCE: 6187

000

<210> SEQ ID NO 6188

<400> SEQUENCE: 6188

000

<210> SEQ ID NO 6189

<400> SEQUENCE: 6189

000

<210> SEQ ID NO 6190

<400> SEQUENCE: 6190

000

<210> SEQ ID NO 6191

<400> SEQUENCE: 6191

000

<210> SEQ ID NO 6192

```
<400> SEQUENCE: 6192
000

<210> SEQ ID NO 6193
<400> SEQUENCE: 6193
000

<210> SEQ ID NO 6194
<400> SEQUENCE: 6194
000

<210> SEQ ID NO 6195
<400> SEQUENCE: 6195
000

<210> SEQ ID NO 6196
<400> SEQUENCE: 6196
000

<210> SEQ ID NO 6197
<400> SEQUENCE: 6197
000

<210> SEQ ID NO 6198
<400> SEQUENCE: 6198
000

<210> SEQ ID NO 6199
<400> SEQUENCE: 6199
000

<210> SEQ ID NO 6200
<400> SEQUENCE: 6200
000

<210> SEQ ID NO 6201
<400> SEQUENCE: 6201
000

<210> SEQ ID NO 6202
<400> SEQUENCE: 6202
000

<210> SEQ ID NO 6203
<400> SEQUENCE: 6203
```

000

<210> SEQ ID NO 6204
<400> SEQUENCE: 6204
000

<210> SEQ ID NO 6205
<400> SEQUENCE: 6205
000

<210> SEQ ID NO 6206
<400> SEQUENCE: 6206
000

<210> SEQ ID NO 6207
<400> SEQUENCE: 6207
000

<210> SEQ ID NO 6208
<400> SEQUENCE: 6208
000

<210> SEQ ID NO 6209
<400> SEQUENCE: 6209
000

<210> SEQ ID NO 6210
<400> SEQUENCE: 6210
000

<210> SEQ ID NO 6211
<400> SEQUENCE: 6211
000

<210> SEQ ID NO 6212
<400> SEQUENCE: 6212
000

<210> SEQ ID NO 6213
<400> SEQUENCE: 6213
000

<210> SEQ ID NO 6214
<400> SEQUENCE: 6214
000

<210> SEQ ID NO 6215

<400> SEQUENCE: 6215

000

<210> SEQ ID NO 6216

<400> SEQUENCE: 6216

000

<210> SEQ ID NO 6217

<400> SEQUENCE: 6217

000

<210> SEQ ID NO 6218

<400> SEQUENCE: 6218

000

<210> SEQ ID NO 6219

<400> SEQUENCE: 6219

000

<210> SEQ ID NO 6220

<400> SEQUENCE: 6220

000

<210> SEQ ID NO 6221

<400> SEQUENCE: 6221

000

<210> SEQ ID NO 6222

<400> SEQUENCE: 6222

000

<210> SEQ ID NO 6223

<400> SEQUENCE: 6223

000

<210> SEQ ID NO 6224

<400> SEQUENCE: 6224

000

<210> SEQ ID NO 6225

<400> SEQUENCE: 6225

000

-continued

<210> SEQ ID NO 6226

<400> SEQUENCE: 6226

000

<210> SEQ ID NO 6227

<400> SEQUENCE: 6227

000

<210> SEQ ID NO 6228

<400> SEQUENCE: 6228

000

<210> SEQ ID NO 6229

<400> SEQUENCE: 6229

000

<210> SEQ ID NO 6230

<400> SEQUENCE: 6230

000

<210> SEQ ID NO 6231

<400> SEQUENCE: 6231

000

<210> SEQ ID NO 6232

<400> SEQUENCE: 6232

000

<210> SEQ ID NO 6233

<400> SEQUENCE: 6233

000

<210> SEQ ID NO 6234

<400> SEQUENCE: 6234

000

<210> SEQ ID NO 6235

<400> SEQUENCE: 6235

000

<210> SEQ ID NO 6236

<400> SEQUENCE: 6236

000

<210> SEQ ID NO 6237

<400> SEQUENCE: 6237

000

<210> SEQ ID NO 6238

<400> SEQUENCE: 6238

000

<210> SEQ ID NO 6239

<400> SEQUENCE: 6239

000

<210> SEQ ID NO 6240

<400> SEQUENCE: 6240

000

<210> SEQ ID NO 6241

<400> SEQUENCE: 6241

000

<210> SEQ ID NO 6242

<400> SEQUENCE: 6242

000

<210> SEQ ID NO 6243

<400> SEQUENCE: 6243

000

<210> SEQ ID NO 6244

<400> SEQUENCE: 6244

000

<210> SEQ ID NO 6245

<400> SEQUENCE: 6245

000

<210> SEQ ID NO 6246

<400> SEQUENCE: 6246

000

<210> SEQ ID NO 6247

<400> SEQUENCE: 6247

000

<210> SEQ ID NO 6248

<400> SEQUENCE: 6248

000

<210> SEQ ID NO 6249

<400> SEQUENCE: 6249

000

<210> SEQ ID NO 6250

<400> SEQUENCE: 6250

000

<210> SEQ ID NO 6251

<400> SEQUENCE: 6251

000

<210> SEQ ID NO 6252

<400> SEQUENCE: 6252

000

<210> SEQ ID NO 6253

<400> SEQUENCE: 6253

000

<210> SEQ ID NO 6254

<400> SEQUENCE: 6254

000

<210> SEQ ID NO 6255

<400> SEQUENCE: 6255

000

<210> SEQ ID NO 6256

<400> SEQUENCE: 6256

000

<210> SEQ ID NO 6257

<400> SEQUENCE: 6257

000

<210> SEQ ID NO 6258

<400> SEQUENCE: 6258

000

<210> SEQ ID NO 6259

<400> SEQUENCE: 6259

000

<210> SEQ ID NO 6260

<400> SEQUENCE: 6260

000

<210> SEQ ID NO 6261

<400> SEQUENCE: 6261

000

<210> SEQ ID NO 6262

<400> SEQUENCE: 6262

000

<210> SEQ ID NO 6263

<400> SEQUENCE: 6263

000

<210> SEQ ID NO 6264

<400> SEQUENCE: 6264

000

<210> SEQ ID NO 6265

<400> SEQUENCE: 6265

000

<210> SEQ ID NO 6266

<400> SEQUENCE: 6266

000

<210> SEQ ID NO 6267

<400> SEQUENCE: 6267

000

<210> SEQ ID NO 6268

<400> SEQUENCE: 6268

000

<210> SEQ ID NO 6269

<400> SEQUENCE: 6269

000

<210> SEQ ID NO 6270

<400> SEQUENCE: 6270

000

<210> SEQ ID NO 6271

-continued

<400> SEQUENCE: 6271

000

<210> SEQ ID NO 6272

<400> SEQUENCE: 6272

000

<210> SEQ ID NO 6273

<400> SEQUENCE: 6273

000

<210> SEQ ID NO 6274

<400> SEQUENCE: 6274

000

<210> SEQ ID NO 6275

<400> SEQUENCE: 6275

000

<210> SEQ ID NO 6276

<400> SEQUENCE: 6276

000

<210> SEQ ID NO 6277

<400> SEQUENCE: 6277

000

<210> SEQ ID NO 6278

<400> SEQUENCE: 6278

000

<210> SEQ ID NO 6279

<400> SEQUENCE: 6279

000

<210> SEQ ID NO 6280

<400> SEQUENCE: 6280

000

<210> SEQ ID NO 6281

<400> SEQUENCE: 6281

000

<210> SEQ ID NO 6282

<400> SEQUENCE: 6282

000

<210> SEQ ID NO 6283

<400> SEQUENCE: 6283

000

<210> SEQ ID NO 6284

<400> SEQUENCE: 6284

000

<210> SEQ ID NO 6285

<400> SEQUENCE: 6285

000

<210> SEQ ID NO 6286

<400> SEQUENCE: 6286

000

<210> SEQ ID NO 6287

<400> SEQUENCE: 6287

000

<210> SEQ ID NO 6288

<400> SEQUENCE: 6288

000

<210> SEQ ID NO 6289

<400> SEQUENCE: 6289

000

<210> SEQ ID NO 6290

<400> SEQUENCE: 6290

000

<210> SEQ ID NO 6291

<400> SEQUENCE: 6291

000

<210> SEQ ID NO 6292

<400> SEQUENCE: 6292

000

<210> SEQ ID NO 6293

<400> SEQUENCE: 6293

000

-continued

<210> SEQ ID NO 6294

<400> SEQUENCE: 6294

000

<210> SEQ ID NO 6295

<400> SEQUENCE: 6295

000

<210> SEQ ID NO 6296

<400> SEQUENCE: 6296

000

<210> SEQ ID NO 6297

<400> SEQUENCE: 6297

000

<210> SEQ ID NO 6298

<400> SEQUENCE: 6298

000

<210> SEQ ID NO 6299

<400> SEQUENCE: 6299

000

<210> SEQ ID NO 6300

<400> SEQUENCE: 6300

000

<210> SEQ ID NO 6301

<400> SEQUENCE: 6301

000

<210> SEQ ID NO 6302

<400> SEQUENCE: 6302

000

<210> SEQ ID NO 6303

<400> SEQUENCE: 6303

000

<210> SEQ ID NO 6304

<400> SEQUENCE: 6304

000

<210> SEQ ID NO 6305

<400> SEQUENCE: 6305

000

<210> SEQ ID NO 6306

<400> SEQUENCE: 6306

000

<210> SEQ ID NO 6307

<400> SEQUENCE: 6307

000

<210> SEQ ID NO 6308

<400> SEQUENCE: 6308

000

<210> SEQ ID NO 6309

<400> SEQUENCE: 6309

000

<210> SEQ ID NO 6310

<400> SEQUENCE: 6310

000

<210> SEQ ID NO 6311

<400> SEQUENCE: 6311

000

<210> SEQ ID NO 6312

<400> SEQUENCE: 6312

000

<210> SEQ ID NO 6313

<400> SEQUENCE: 6313

000

<210> SEQ ID NO 6314

<400> SEQUENCE: 6314

000

<210> SEQ ID NO 6315

<400> SEQUENCE: 6315

000

<210> SEQ ID NO 6316

<400> SEQUENCE: 6316

000

<210> SEQ ID NO 6317

<400> SEQUENCE: 6317

000

<210> SEQ ID NO 6318

<400> SEQUENCE: 6318

000

<210> SEQ ID NO 6319

<400> SEQUENCE: 6319

000

<210> SEQ ID NO 6320

<400> SEQUENCE: 6320

000

<210> SEQ ID NO 6321

<400> SEQUENCE: 6321

000

<210> SEQ ID NO 6322

<400> SEQUENCE: 6322

000

<210> SEQ ID NO 6323

<400> SEQUENCE: 6323

000

<210> SEQ ID NO 6324

<400> SEQUENCE: 6324

000

<210> SEQ ID NO 6325

<400> SEQUENCE: 6325

000

<210> SEQ ID NO 6326

<400> SEQUENCE: 6326

000

<210> SEQ ID NO 6327

<400> SEQUENCE: 6327

000

<210> SEQ ID NO 6328

<400> SEQUENCE: 6328

000

<210> SEQ ID NO 6329

<400> SEQUENCE: 6329

000

<210> SEQ ID NO 6330

<400> SEQUENCE: 6330

000

<210> SEQ ID NO 6331

<400> SEQUENCE: 6331

000

<210> SEQ ID NO 6332

<400> SEQUENCE: 6332

000

<210> SEQ ID NO 6333

<400> SEQUENCE: 6333

000

<210> SEQ ID NO 6334

<400> SEQUENCE: 6334

000

<210> SEQ ID NO 6335

<400> SEQUENCE: 6335

000

<210> SEQ ID NO 6336

<400> SEQUENCE: 6336

000

<210> SEQ ID NO 6337

<400> SEQUENCE: 6337

000

<210> SEQ ID NO 6338

<400> SEQUENCE: 6338

000

<210> SEQ ID NO 6339

<400> SEQUENCE: 6339

000

<210> SEQ ID NO 6340

<400> SEQUENCE: 6340

000

<210> SEQ ID NO 6341

<400> SEQUENCE: 6341

000

<210> SEQ ID NO 6342

<400> SEQUENCE: 6342

000

<210> SEQ ID NO 6343

<400> SEQUENCE: 6343

000

<210> SEQ ID NO 6344

<400> SEQUENCE: 6344

000

<210> SEQ ID NO 6345

<400> SEQUENCE: 6345

000

<210> SEQ ID NO 6346

<400> SEQUENCE: 6346

000

<210> SEQ ID NO 6347

<400> SEQUENCE: 6347

000

<210> SEQ ID NO 6348

<400> SEQUENCE: 6348

000

<210> SEQ ID NO 6349

<400> SEQUENCE: 6349

000

<210> SEQ ID NO 6350

-continued

<400> SEQUENCE: 6350

000

<210> SEQ ID NO 6351

<400> SEQUENCE: 6351

000

<210> SEQ ID NO 6352

<400> SEQUENCE: 6352

000

<210> SEQ ID NO 6353

<400> SEQUENCE: 6353

000

<210> SEQ ID NO 6354

<400> SEQUENCE: 6354

000

<210> SEQ ID NO 6355

<400> SEQUENCE: 6355

000

<210> SEQ ID NO 6356

<400> SEQUENCE: 6356

000

<210> SEQ ID NO 6357

<400> SEQUENCE: 6357

000

<210> SEQ ID NO 6358

<400> SEQUENCE: 6358

000

<210> SEQ ID NO 6359

<400> SEQUENCE: 6359

000

<210> SEQ ID NO 6360

<400> SEQUENCE: 6360

000

<210> SEQ ID NO 6361

<400> SEQUENCE: 6361

000

<210> SEQ ID NO 6362

<400> SEQUENCE: 6362

000

<210> SEQ ID NO 6363

<400> SEQUENCE: 6363

000

<210> SEQ ID NO 6364

<400> SEQUENCE: 6364

000

<210> SEQ ID NO 6365

<400> SEQUENCE: 6365

000

<210> SEQ ID NO 6366

<400> SEQUENCE: 6366

000

<210> SEQ ID NO 6367

<400> SEQUENCE: 6367

000

<210> SEQ ID NO 6368

<400> SEQUENCE: 6368

000

<210> SEQ ID NO 6369

<400> SEQUENCE: 6369

000

<210> SEQ ID NO 6370

<400> SEQUENCE: 6370

000

<210> SEQ ID NO 6371

<400> SEQUENCE: 6371

000

<210> SEQ ID NO 6372

<400> SEQUENCE: 6372

000

<210> SEQ ID NO 6373

<400> SEQUENCE: 6373

000

<210> SEQ ID NO 6374

<400> SEQUENCE: 6374

000

<210> SEQ ID NO 6375

<400> SEQUENCE: 6375

000

<210> SEQ ID NO 6376

<400> SEQUENCE: 6376

000

<210> SEQ ID NO 6377

<400> SEQUENCE: 6377

000

<210> SEQ ID NO 6378

<400> SEQUENCE: 6378

000

<210> SEQ ID NO 6379

<400> SEQUENCE: 6379

000

<210> SEQ ID NO 6380

<400> SEQUENCE: 6380

000

<210> SEQ ID NO 6381

<400> SEQUENCE: 6381

000

<210> SEQ ID NO 6382

<400> SEQUENCE: 6382

000

<210> SEQ ID NO 6383

<400> SEQUENCE: 6383

000

```
<210> SEQ ID NO 6384
<400> SEQUENCE: 6384
000

<210> SEQ ID NO 6385
<400> SEQUENCE: 6385
000

<210> SEQ ID NO 6386
<400> SEQUENCE: 6386
000

<210> SEQ ID NO 6387
<400> SEQUENCE: 6387
000

<210> SEQ ID NO 6388
<400> SEQUENCE: 6388
000

<210> SEQ ID NO 6389
<400> SEQUENCE: 6389
000

<210> SEQ ID NO 6390
<400> SEQUENCE: 6390
000

<210> SEQ ID NO 6391
<400> SEQUENCE: 6391
000

<210> SEQ ID NO 6392
<400> SEQUENCE: 6392
000

<210> SEQ ID NO 6393
<400> SEQUENCE: 6393
000

<210> SEQ ID NO 6394
<400> SEQUENCE: 6394
000

<210> SEQ ID NO 6395
```

-continued

<400> SEQUENCE: 6395

000

<210> SEQ ID NO 6396

<400> SEQUENCE: 6396

000

<210> SEQ ID NO 6397

<400> SEQUENCE: 6397

000

<210> SEQ ID NO 6398

<400> SEQUENCE: 6398

000

<210> SEQ ID NO 6399

<400> SEQUENCE: 6399

000

<210> SEQ ID NO 6400

<400> SEQUENCE: 6400

000

<210> SEQ ID NO 6401

<400> SEQUENCE: 6401

000

<210> SEQ ID NO 6402

<400> SEQUENCE: 6402

000

<210> SEQ ID NO 6403

<400> SEQUENCE: 6403

000

<210> SEQ ID NO 6404

<400> SEQUENCE: 6404

000

<210> SEQ ID NO 6405

<400> SEQUENCE: 6405

000

<210> SEQ ID NO 6406

<400> SEQUENCE: 6406

000

<210> SEQ ID NO 6407

<400> SEQUENCE: 6407

000

<210> SEQ ID NO 6408

<400> SEQUENCE: 6408

000

<210> SEQ ID NO 6409

<400> SEQUENCE: 6409

000

<210> SEQ ID NO 6410

<400> SEQUENCE: 6410

000

<210> SEQ ID NO 6411

<400> SEQUENCE: 6411

000

<210> SEQ ID NO 6412

<400> SEQUENCE: 6412

000

<210> SEQ ID NO 6413

<400> SEQUENCE: 6413

000

<210> SEQ ID NO 6414

<400> SEQUENCE: 6414

000

<210> SEQ ID NO 6415

<400> SEQUENCE: 6415

000

<210> SEQ ID NO 6416

<400> SEQUENCE: 6416

000

<210> SEQ ID NO 6417

<400> SEQUENCE: 6417

000

<210> SEQ ID NO 6418

<400> SEQUENCE: 6418

000

<210> SEQ ID NO 6419

<400> SEQUENCE: 6419

000

<210> SEQ ID NO 6420

<400> SEQUENCE: 6420

000

<210> SEQ ID NO 6421

<400> SEQUENCE: 6421

000

<210> SEQ ID NO 6422

<400> SEQUENCE: 6422

000

<210> SEQ ID NO 6423

<400> SEQUENCE: 6423

000

<210> SEQ ID NO 6424

<400> SEQUENCE: 6424

000

<210> SEQ ID NO 6425

<400> SEQUENCE: 6425

000

<210> SEQ ID NO 6426

<400> SEQUENCE: 6426

000

<210> SEQ ID NO 6427

<400> SEQUENCE: 6427

000

<210> SEQ ID NO 6428

<400> SEQUENCE: 6428

000

<210> SEQ ID NO 6429

```
<400> SEQUENCE: 6429

000

<210> SEQ ID NO 6430

<400> SEQUENCE: 6430

000

<210> SEQ ID NO 6431

<400> SEQUENCE: 6431

000

<210> SEQ ID NO 6432

<400> SEQUENCE: 6432

000

<210> SEQ ID NO 6433

<400> SEQUENCE: 6433

000

<210> SEQ ID NO 6434

<400> SEQUENCE: 6434

000

<210> SEQ ID NO 6435

<400> SEQUENCE: 6435

000

<210> SEQ ID NO 6436

<400> SEQUENCE: 6436

000

<210> SEQ ID NO 6437

<400> SEQUENCE: 6437

000

<210> SEQ ID NO 6438

<400> SEQUENCE: 6438

000

<210> SEQ ID NO 6439

<400> SEQUENCE: 6439

000

<210> SEQ ID NO 6440

<400> SEQUENCE: 6440
```

000

<210> SEQ ID NO 6441

<400> SEQUENCE: 6441

000

<210> SEQ ID NO 6442

<400> SEQUENCE: 6442

000

<210> SEQ ID NO 6443

<400> SEQUENCE: 6443

000

<210> SEQ ID NO 6444

<400> SEQUENCE: 6444

000

<210> SEQ ID NO 6445

<400> SEQUENCE: 6445

000

<210> SEQ ID NO 6446

<400> SEQUENCE: 6446

000

<210> SEQ ID NO 6447

<400> SEQUENCE: 6447

000

<210> SEQ ID NO 6448

<400> SEQUENCE: 6448

000

<210> SEQ ID NO 6449

<400> SEQUENCE: 6449

000

<210> SEQ ID NO 6450

<400> SEQUENCE: 6450

000

<210> SEQ ID NO 6451

<400> SEQUENCE: 6451

000

<210> SEQ ID NO 6452

<400> SEQUENCE: 6452

000

<210> SEQ ID NO 6453

<400> SEQUENCE: 6453

000

<210> SEQ ID NO 6454

<400> SEQUENCE: 6454

000

<210> SEQ ID NO 6455

<400> SEQUENCE: 6455

000

<210> SEQ ID NO 6456

<400> SEQUENCE: 6456

000

<210> SEQ ID NO 6457

<400> SEQUENCE: 6457

000

<210> SEQ ID NO 6458

<400> SEQUENCE: 6458

000

<210> SEQ ID NO 6459

<400> SEQUENCE: 6459

000

<210> SEQ ID NO 6460

<400> SEQUENCE: 6460

000

<210> SEQ ID NO 6461

<400> SEQUENCE: 6461

000

<210> SEQ ID NO 6462

<400> SEQUENCE: 6462

000

-continued

```
<210> SEQ ID NO 6463
<400> SEQUENCE: 6463
000

<210> SEQ ID NO 6464
<400> SEQUENCE: 6464
000

<210> SEQ ID NO 6465
<400> SEQUENCE: 6465
000

<210> SEQ ID NO 6466
<400> SEQUENCE: 6466
000

<210> SEQ ID NO 6467
<400> SEQUENCE: 6467
000

<210> SEQ ID NO 6468
<400> SEQUENCE: 6468
000

<210> SEQ ID NO 6469
<400> SEQUENCE: 6469
000

<210> SEQ ID NO 6470
<400> SEQUENCE: 6470
000

<210> SEQ ID NO 6471
<400> SEQUENCE: 6471
000

<210> SEQ ID NO 6472
<400> SEQUENCE: 6472
000

<210> SEQ ID NO 6473
<400> SEQUENCE: 6473
000

<210> SEQ ID NO 6474
```

-continued

<400> SEQUENCE: 6474

000

<210> SEQ ID NO 6475

<400> SEQUENCE: 6475

000

<210> SEQ ID NO 6476

<400> SEQUENCE: 6476

000

<210> SEQ ID NO 6477

<400> SEQUENCE: 6477

000

<210> SEQ ID NO 6478

<400> SEQUENCE: 6478

000

<210> SEQ ID NO 6479

<400> SEQUENCE: 6479

000

<210> SEQ ID NO 6480

<400> SEQUENCE: 6480

000

<210> SEQ ID NO 6481

<400> SEQUENCE: 6481

000

<210> SEQ ID NO 6482

<400> SEQUENCE: 6482

000

<210> SEQ ID NO 6483

<400> SEQUENCE: 6483

000

<210> SEQ ID NO 6484

<400> SEQUENCE: 6484

000

<210> SEQ ID NO 6485

<400> SEQUENCE: 6485

-continued

000

<210> SEQ ID NO 6486

<400> SEQUENCE: 6486

000

<210> SEQ ID NO 6487

<400> SEQUENCE: 6487

000

<210> SEQ ID NO 6488

<400> SEQUENCE: 6488

000

<210> SEQ ID NO 6489

<400> SEQUENCE: 6489

000

<210> SEQ ID NO 6490

<400> SEQUENCE: 6490

000

<210> SEQ ID NO 6491

<400> SEQUENCE: 6491

000

<210> SEQ ID NO 6492

<400> SEQUENCE: 6492

000

<210> SEQ ID NO 6493

<400> SEQUENCE: 6493

000

<210> SEQ ID NO 6494

<400> SEQUENCE: 6494

000

<210> SEQ ID NO 6495

<400> SEQUENCE: 6495

000

<210> SEQ ID NO 6496

<400> SEQUENCE: 6496

000

<210> SEQ ID NO 6497

<400> SEQUENCE: 6497

000

<210> SEQ ID NO 6498

<400> SEQUENCE: 6498

000

<210> SEQ ID NO 6499

<400> SEQUENCE: 6499

000

<210> SEQ ID NO 6500

<400> SEQUENCE: 6500

000

<210> SEQ ID NO 6501

<400> SEQUENCE: 6501

000

<210> SEQ ID NO 6502

<400> SEQUENCE: 6502

000

<210> SEQ ID NO 6503

<400> SEQUENCE: 6503

000

<210> SEQ ID NO 6504

<400> SEQUENCE: 6504

000

<210> SEQ ID NO 6505

<400> SEQUENCE: 6505

000

<210> SEQ ID NO 6506

<400> SEQUENCE: 6506

000

<210> SEQ ID NO 6507

<400> SEQUENCE: 6507

000

<210> SEQ ID NO 6508

```
<400> SEQUENCE: 6508
000

<210> SEQ ID NO 6509
<400> SEQUENCE: 6509
000

<210> SEQ ID NO 6510
<400> SEQUENCE: 6510
000

<210> SEQ ID NO 6511
<400> SEQUENCE: 6511
000

<210> SEQ ID NO 6512
<400> SEQUENCE: 6512
000

<210> SEQ ID NO 6513
<400> SEQUENCE: 6513
000

<210> SEQ ID NO 6514
<400> SEQUENCE: 6514
000

<210> SEQ ID NO 6515
<400> SEQUENCE: 6515
000

<210> SEQ ID NO 6516
<400> SEQUENCE: 6516
000

<210> SEQ ID NO 6517
<400> SEQUENCE: 6517
000

<210> SEQ ID NO 6518
<400> SEQUENCE: 6518
000

<210> SEQ ID NO 6519
<400> SEQUENCE: 6519
```

000

<210> SEQ ID NO 6520

<400> SEQUENCE: 6520

000

<210> SEQ ID NO 6521

<400> SEQUENCE: 6521

000

<210> SEQ ID NO 6522

<400> SEQUENCE: 6522

000

<210> SEQ ID NO 6523

<400> SEQUENCE: 6523

000

<210> SEQ ID NO 6524

<400> SEQUENCE: 6524

000

<210> SEQ ID NO 6525

<400> SEQUENCE: 6525

000

<210> SEQ ID NO 6526

<400> SEQUENCE: 6526

000

<210> SEQ ID NO 6527

<400> SEQUENCE: 6527

000

<210> SEQ ID NO 6528

<400> SEQUENCE: 6528

000

<210> SEQ ID NO 6529

<400> SEQUENCE: 6529

000

<210> SEQ ID NO 6530

<400> SEQUENCE: 6530

000

<210> SEQ ID NO 6531

<400> SEQUENCE: 6531

000

<210> SEQ ID NO 6532

<400> SEQUENCE: 6532

000

<210> SEQ ID NO 6533

<400> SEQUENCE: 6533

000

<210> SEQ ID NO 6534

<400> SEQUENCE: 6534

000

<210> SEQ ID NO 6535

<400> SEQUENCE: 6535

000

<210> SEQ ID NO 6536

<400> SEQUENCE: 6536

000

<210> SEQ ID NO 6537

<400> SEQUENCE: 6537

000

<210> SEQ ID NO 6538

<400> SEQUENCE: 6538

000

<210> SEQ ID NO 6539

<400> SEQUENCE: 6539

000

<210> SEQ ID NO 6540

<400> SEQUENCE: 6540

000

<210> SEQ ID NO 6541

<400> SEQUENCE: 6541

000

<210> SEQ ID NO 6542

<400> SEQUENCE: 6542

000

<210> SEQ ID NO 6543

<400> SEQUENCE: 6543

000

<210> SEQ ID NO 6544

<400> SEQUENCE: 6544

000

<210> SEQ ID NO 6545

<400> SEQUENCE: 6545

000

<210> SEQ ID NO 6546

<400> SEQUENCE: 6546

000

<210> SEQ ID NO 6547

<400> SEQUENCE: 6547

000

<210> SEQ ID NO 6548

<400> SEQUENCE: 6548

000

<210> SEQ ID NO 6549

<400> SEQUENCE: 6549

000

<210> SEQ ID NO 6550

<400> SEQUENCE: 6550

000

<210> SEQ ID NO 6551

<400> SEQUENCE: 6551

000

<210> SEQ ID NO 6552

<400> SEQUENCE: 6552

000

<210> SEQ ID NO 6553

-continued

<400> SEQUENCE: 6553

000

<210> SEQ ID NO 6554

<400> SEQUENCE: 6554

000

<210> SEQ ID NO 6555

<400> SEQUENCE: 6555

000

<210> SEQ ID NO 6556

<400> SEQUENCE: 6556

000

<210> SEQ ID NO 6557

<400> SEQUENCE: 6557

000

<210> SEQ ID NO 6558

<400> SEQUENCE: 6558

000

<210> SEQ ID NO 6559

<400> SEQUENCE: 6559

000

<210> SEQ ID NO 6560

<400> SEQUENCE: 6560

000

<210> SEQ ID NO 6561

<400> SEQUENCE: 6561

000

<210> SEQ ID NO 6562

<400> SEQUENCE: 6562

000

<210> SEQ ID NO 6563

<400> SEQUENCE: 6563

000

<210> SEQ ID NO 6564

<400> SEQUENCE: 6564

000

<210> SEQ ID NO 6565

<400> SEQUENCE: 6565

000

<210> SEQ ID NO 6566

<400> SEQUENCE: 6566

000

<210> SEQ ID NO 6567

<400> SEQUENCE: 6567

000

<210> SEQ ID NO 6568

<400> SEQUENCE: 6568

000

<210> SEQ ID NO 6569

<400> SEQUENCE: 6569

000

<210> SEQ ID NO 6570

<400> SEQUENCE: 6570

000

<210> SEQ ID NO 6571

<400> SEQUENCE: 6571

000

<210> SEQ ID NO 6572

<400> SEQUENCE: 6572

000

<210> SEQ ID NO 6573

<400> SEQUENCE: 6573

000

<210> SEQ ID NO 6574

<400> SEQUENCE: 6574

000

<210> SEQ ID NO 6575

<400> SEQUENCE: 6575

000

<210> SEQ ID NO 6576

<400> SEQUENCE: 6576

000

<210> SEQ ID NO 6577

<400> SEQUENCE: 6577

000

<210> SEQ ID NO 6578

<400> SEQUENCE: 6578

000

<210> SEQ ID NO 6579

<400> SEQUENCE: 6579

000

<210> SEQ ID NO 6580

<400> SEQUENCE: 6580

000

<210> SEQ ID NO 6581

<400> SEQUENCE: 6581

000

<210> SEQ ID NO 6582

<400> SEQUENCE: 6582

000

<210> SEQ ID NO 6583

<400> SEQUENCE: 6583

000

<210> SEQ ID NO 6584

<400> SEQUENCE: 6584

000

<210> SEQ ID NO 6585

<400> SEQUENCE: 6585

000

<210> SEQ ID NO 6586

<400> SEQUENCE: 6586

000

<210> SEQ ID NO 6587

```
<400> SEQUENCE: 6587
000

<210> SEQ ID NO 6588
<400> SEQUENCE: 6588
000

<210> SEQ ID NO 6589
<400> SEQUENCE: 6589
000

<210> SEQ ID NO 6590
<400> SEQUENCE: 6590
000

<210> SEQ ID NO 6591
<400> SEQUENCE: 6591
000

<210> SEQ ID NO 6592
<400> SEQUENCE: 6592
000

<210> SEQ ID NO 6593
<400> SEQUENCE: 6593
000

<210> SEQ ID NO 6594
<400> SEQUENCE: 6594
000

<210> SEQ ID NO 6595
<400> SEQUENCE: 6595
000

<210> SEQ ID NO 6596
<400> SEQUENCE: 6596
000

<210> SEQ ID NO 6597
<400> SEQUENCE: 6597
000

<210> SEQ ID NO 6598
<400> SEQUENCE: 6598
```

000

<210> SEQ ID NO 6599

<400> SEQUENCE: 6599

000

<210> SEQ ID NO 6600

<400> SEQUENCE: 6600

000

<210> SEQ ID NO 6601

<400> SEQUENCE: 6601

000

<210> SEQ ID NO 6602

<400> SEQUENCE: 6602

000

<210> SEQ ID NO 6603

<400> SEQUENCE: 6603

000

<210> SEQ ID NO 6604

<400> SEQUENCE: 6604

000

<210> SEQ ID NO 6605

<400> SEQUENCE: 6605

000

<210> SEQ ID NO 6606

<400> SEQUENCE: 6606

000

<210> SEQ ID NO 6607

<400> SEQUENCE: 6607

000

<210> SEQ ID NO 6608

<400> SEQUENCE: 6608

000

<210> SEQ ID NO 6609

<400> SEQUENCE: 6609

000

<210> SEQ ID NO 6610

<400> SEQUENCE: 6610

000

<210> SEQ ID NO 6611

<400> SEQUENCE: 6611

000

<210> SEQ ID NO 6612

<400> SEQUENCE: 6612

000

<210> SEQ ID NO 6613

<400> SEQUENCE: 6613

000

<210> SEQ ID NO 6614

<400> SEQUENCE: 6614

000

<210> SEQ ID NO 6615

<400> SEQUENCE: 6615

000

<210> SEQ ID NO 6616

<400> SEQUENCE: 6616

000

<210> SEQ ID NO 6617

<400> SEQUENCE: 6617

000

<210> SEQ ID NO 6618

<400> SEQUENCE: 6618

000

<210> SEQ ID NO 6619

<400> SEQUENCE: 6619

000

<210> SEQ ID NO 6620

<400> SEQUENCE: 6620

000

<210> SEQ ID NO 6621

<400> SEQUENCE: 6621

000

<210> SEQ ID NO 6622

<400> SEQUENCE: 6622

000

<210> SEQ ID NO 6623

<400> SEQUENCE: 6623

000

<210> SEQ ID NO 6624

<400> SEQUENCE: 6624

000

<210> SEQ ID NO 6625

<400> SEQUENCE: 6625

000

<210> SEQ ID NO 6626

<400> SEQUENCE: 6626

000

<210> SEQ ID NO 6627

<400> SEQUENCE: 6627

000

<210> SEQ ID NO 6628

<400> SEQUENCE: 6628

000

<210> SEQ ID NO 6629

<400> SEQUENCE: 6629

000

<210> SEQ ID NO 6630

<400> SEQUENCE: 6630

000

<210> SEQ ID NO 6631

<400> SEQUENCE: 6631

000

<210> SEQ ID NO 6632

<400> SEQUENCE: 6632

000

<210> SEQ ID NO 6633

<400> SEQUENCE: 6633

000

<210> SEQ ID NO 6634

<400> SEQUENCE: 6634

000

<210> SEQ ID NO 6635

<400> SEQUENCE: 6635

000

<210> SEQ ID NO 6636

<400> SEQUENCE: 6636

000

<210> SEQ ID NO 6637

<400> SEQUENCE: 6637

000

<210> SEQ ID NO 6638

<400> SEQUENCE: 6638

000

<210> SEQ ID NO 6639

<400> SEQUENCE: 6639

000

<210> SEQ ID NO 6640

<400> SEQUENCE: 6640

000

<210> SEQ ID NO 6641

<400> SEQUENCE: 6641

000

<210> SEQ ID NO 6642

<400> SEQUENCE: 6642

000

<210> SEQ ID NO 6643

<400> SEQUENCE: 6643

000

<210> SEQ ID NO 6644

<400> SEQUENCE: 6644

000

<210> SEQ ID NO 6645

<400> SEQUENCE: 6645

000

<210> SEQ ID NO 6646

<400> SEQUENCE: 6646

000

<210> SEQ ID NO 6647

<400> SEQUENCE: 6647

000

<210> SEQ ID NO 6648

<400> SEQUENCE: 6648

000

<210> SEQ ID NO 6649

<400> SEQUENCE: 6649

000

<210> SEQ ID NO 6650

<400> SEQUENCE: 6650

000

<210> SEQ ID NO 6651

<400> SEQUENCE: 6651

000

<210> SEQ ID NO 6652

<400> SEQUENCE: 6652

000

<210> SEQ ID NO 6653

<400> SEQUENCE: 6653

000

<210> SEQ ID NO 6654

<400> SEQUENCE: 6654

000

<210> SEQ ID NO 6655

<400> SEQUENCE: 6655

000

<210> SEQ ID NO 6656

<400> SEQUENCE: 6656

000

<210> SEQ ID NO 6657

<400> SEQUENCE: 6657

000

<210> SEQ ID NO 6658

<400> SEQUENCE: 6658

000

<210> SEQ ID NO 6659

<400> SEQUENCE: 6659

000

<210> SEQ ID NO 6660

<400> SEQUENCE: 6660

000

<210> SEQ ID NO 6661

<400> SEQUENCE: 6661

000

<210> SEQ ID NO 6662

<400> SEQUENCE: 6662

000

<210> SEQ ID NO 6663

<400> SEQUENCE: 6663

000

<210> SEQ ID NO 6664

<400> SEQUENCE: 6664

000

<210> SEQ ID NO 6665

<400> SEQUENCE: 6665

000

<210> SEQ ID NO 6666

```
<400> SEQUENCE: 6666
000

<210> SEQ ID NO 6667
<400> SEQUENCE: 6667
000

<210> SEQ ID NO 6668
<400> SEQUENCE: 6668
000

<210> SEQ ID NO 6669
<400> SEQUENCE: 6669
000

<210> SEQ ID NO 6670
<400> SEQUENCE: 6670
000

<210> SEQ ID NO 6671
<400> SEQUENCE: 6671
000

<210> SEQ ID NO 6672
<400> SEQUENCE: 6672
000

<210> SEQ ID NO 6673
<400> SEQUENCE: 6673
000

<210> SEQ ID NO 6674
<400> SEQUENCE: 6674
000

<210> SEQ ID NO 6675
<400> SEQUENCE: 6675
000

<210> SEQ ID NO 6676
<400> SEQUENCE: 6676
000

<210> SEQ ID NO 6677
<400> SEQUENCE: 6677
```

000

<210> SEQ ID NO 6678

<400> SEQUENCE: 6678

000

<210> SEQ ID NO 6679

<400> SEQUENCE: 6679

000

<210> SEQ ID NO 6680

<400> SEQUENCE: 6680

000

<210> SEQ ID NO 6681

<400> SEQUENCE: 6681

000

<210> SEQ ID NO 6682

<400> SEQUENCE: 6682

000

<210> SEQ ID NO 6683

<400> SEQUENCE: 6683

000

<210> SEQ ID NO 6684

<400> SEQUENCE: 6684

000

<210> SEQ ID NO 6685

<400> SEQUENCE: 6685

000

<210> SEQ ID NO 6686

<400> SEQUENCE: 6686

000

<210> SEQ ID NO 6687

<400> SEQUENCE: 6687

000

<210> SEQ ID NO 6688

<400> SEQUENCE: 6688

000

<210> SEQ ID NO 6689

<400> SEQUENCE: 6689

000

<210> SEQ ID NO 6690

<400> SEQUENCE: 6690

000

<210> SEQ ID NO 6691

<400> SEQUENCE: 6691

000

<210> SEQ ID NO 6692

<400> SEQUENCE: 6692

000

<210> SEQ ID NO 6693

<400> SEQUENCE: 6693

000

<210> SEQ ID NO 6694

<400> SEQUENCE: 6694

000

<210> SEQ ID NO 6695

<400> SEQUENCE: 6695

000

<210> SEQ ID NO 6696

<400> SEQUENCE: 6696

000

<210> SEQ ID NO 6697

<400> SEQUENCE: 6697

000

<210> SEQ ID NO 6698

<400> SEQUENCE: 6698

000

<210> SEQ ID NO 6699

<400> SEQUENCE: 6699

000

<210> SEQ ID NO 6700

<400> SEQUENCE: 6700

000

<210> SEQ ID NO 6701

<400> SEQUENCE: 6701

000

<210> SEQ ID NO 6702

<400> SEQUENCE: 6702

000

<210> SEQ ID NO 6703

<400> SEQUENCE: 6703

000

<210> SEQ ID NO 6704

<400> SEQUENCE: 6704

000

<210> SEQ ID NO 6705

<400> SEQUENCE: 6705

000

<210> SEQ ID NO 6706

<400> SEQUENCE: 6706

000

<210> SEQ ID NO 6707

<400> SEQUENCE: 6707

000

<210> SEQ ID NO 6708

<400> SEQUENCE: 6708

000

<210> SEQ ID NO 6709

<400> SEQUENCE: 6709

000

<210> SEQ ID NO 6710

<400> SEQUENCE: 6710

000

<210> SEQ ID NO 6711

<400> SEQUENCE: 6711

000

<210> SEQ ID NO 6712

<400> SEQUENCE: 6712

000

<210> SEQ ID NO 6713

<400> SEQUENCE: 6713

000

<210> SEQ ID NO 6714

<400> SEQUENCE: 6714

000

<210> SEQ ID NO 6715

<400> SEQUENCE: 6715

000

<210> SEQ ID NO 6716

<400> SEQUENCE: 6716

000

<210> SEQ ID NO 6717

<400> SEQUENCE: 6717

000

<210> SEQ ID NO 6718

<400> SEQUENCE: 6718

000

<210> SEQ ID NO 6719

<400> SEQUENCE: 6719

000

<210> SEQ ID NO 6720

<400> SEQUENCE: 6720

000

<210> SEQ ID NO 6721

<400> SEQUENCE: 6721

000

<210> SEQ ID NO 6722

<400> SEQUENCE: 6722

000

<210> SEQ ID NO 6723

<400> SEQUENCE: 6723

000

<210> SEQ ID NO 6724

<400> SEQUENCE: 6724

000

<210> SEQ ID NO 6725

<400> SEQUENCE: 6725

000

<210> SEQ ID NO 6726

<400> SEQUENCE: 6726

000

<210> SEQ ID NO 6727

<400> SEQUENCE: 6727

000

<210> SEQ ID NO 6728

<400> SEQUENCE: 6728

000

<210> SEQ ID NO 6729

<400> SEQUENCE: 6729

000

<210> SEQ ID NO 6730

<400> SEQUENCE: 6730

000

<210> SEQ ID NO 6731

<400> SEQUENCE: 6731

000

<210> SEQ ID NO 6732

<400> SEQUENCE: 6732

000

<210> SEQ ID NO 6733

<400> SEQUENCE: 6733

000

<210> SEQ ID NO 6734

<400> SEQUENCE: 6734

000

<210> SEQ ID NO 6735

<400> SEQUENCE: 6735

000

<210> SEQ ID NO 6736

<400> SEQUENCE: 6736

000

<210> SEQ ID NO 6737

<400> SEQUENCE: 6737

000

<210> SEQ ID NO 6738

<400> SEQUENCE: 6738

000

<210> SEQ ID NO 6739

<400> SEQUENCE: 6739

000

<210> SEQ ID NO 6740

<400> SEQUENCE: 6740

000

<210> SEQ ID NO 6741

<400> SEQUENCE: 6741

000

<210> SEQ ID NO 6742

<400> SEQUENCE: 6742

000

<210> SEQ ID NO 6743

<400> SEQUENCE: 6743

000

<210> SEQ ID NO 6744

<400> SEQUENCE: 6744

000

<210> SEQ ID NO 6745

```
<400> SEQUENCE: 6745
000

<210> SEQ ID NO 6746
<400> SEQUENCE: 6746
000

<210> SEQ ID NO 6747
<400> SEQUENCE: 6747
000

<210> SEQ ID NO 6748
<400> SEQUENCE: 6748
000

<210> SEQ ID NO 6749
<400> SEQUENCE: 6749
000

<210> SEQ ID NO 6750
<400> SEQUENCE: 6750
000

<210> SEQ ID NO 6751
<400> SEQUENCE: 6751
000

<210> SEQ ID NO 6752
<400> SEQUENCE: 6752
000

<210> SEQ ID NO 6753
<400> SEQUENCE: 6753
000

<210> SEQ ID NO 6754
<400> SEQUENCE: 6754
000

<210> SEQ ID NO 6755
<400> SEQUENCE: 6755
000

<210> SEQ ID NO 6756
<400> SEQUENCE: 6756
```

000

<210> SEQ ID NO 6757

<400> SEQUENCE: 6757

000

<210> SEQ ID NO 6758

<400> SEQUENCE: 6758

000

<210> SEQ ID NO 6759

<400> SEQUENCE: 6759

000

<210> SEQ ID NO 6760

<400> SEQUENCE: 6760

000

<210> SEQ ID NO 6761

<400> SEQUENCE: 6761

000

<210> SEQ ID NO 6762

<400> SEQUENCE: 6762

000

<210> SEQ ID NO 6763

<400> SEQUENCE: 6763

000

<210> SEQ ID NO 6764

<400> SEQUENCE: 6764

000

<210> SEQ ID NO 6765

<400> SEQUENCE: 6765

000

<210> SEQ ID NO 6766

<400> SEQUENCE: 6766

000

<210> SEQ ID NO 6767

<400> SEQUENCE: 6767

000

<210> SEQ ID NO 6768

<400> SEQUENCE: 6768

000

<210> SEQ ID NO 6769

<400> SEQUENCE: 6769

000

<210> SEQ ID NO 6770

<400> SEQUENCE: 6770

000

<210> SEQ ID NO 6771

<400> SEQUENCE: 6771

000

<210> SEQ ID NO 6772

<400> SEQUENCE: 6772

000

<210> SEQ ID NO 6773

<400> SEQUENCE: 6773

000

<210> SEQ ID NO 6774

<400> SEQUENCE: 6774

000

<210> SEQ ID NO 6775

<400> SEQUENCE: 6775

000

<210> SEQ ID NO 6776

<400> SEQUENCE: 6776

000

<210> SEQ ID NO 6777

<400> SEQUENCE: 6777

000

<210> SEQ ID NO 6778

<400> SEQUENCE: 6778

000

<210> SEQ ID NO 6779

<400> SEQUENCE: 6779

000

<210> SEQ ID NO 6780

<400> SEQUENCE: 6780

000

<210> SEQ ID NO 6781

<400> SEQUENCE: 6781

000

<210> SEQ ID NO 6782

<400> SEQUENCE: 6782

000

<210> SEQ ID NO 6783

<400> SEQUENCE: 6783

000

<210> SEQ ID NO 6784

<400> SEQUENCE: 6784

000

<210> SEQ ID NO 6785

<400> SEQUENCE: 6785

000

<210> SEQ ID NO 6786

<400> SEQUENCE: 6786

000

<210> SEQ ID NO 6787

<400> SEQUENCE: 6787

000

<210> SEQ ID NO 6788

<400> SEQUENCE: 6788

000

<210> SEQ ID NO 6789

<400> SEQUENCE: 6789

000

<210> SEQ ID NO 6790

-continued

<400> SEQUENCE: 6790

000

<210> SEQ ID NO 6791

<400> SEQUENCE: 6791

000

<210> SEQ ID NO 6792

<400> SEQUENCE: 6792

000

<210> SEQ ID NO 6793

<400> SEQUENCE: 6793

000

<210> SEQ ID NO 6794

<400> SEQUENCE: 6794

000

<210> SEQ ID NO 6795

<400> SEQUENCE: 6795

000

<210> SEQ ID NO 6796

<400> SEQUENCE: 6796

000

<210> SEQ ID NO 6797

<400> SEQUENCE: 6797

000

<210> SEQ ID NO 6798

<400> SEQUENCE: 6798

000

<210> SEQ ID NO 6799

<400> SEQUENCE: 6799

000

<210> SEQ ID NO 6800

<400> SEQUENCE: 6800

000

<210> SEQ ID NO 6801

<400> SEQUENCE: 6801

000

<210> SEQ ID NO 6802

<400> SEQUENCE: 6802

000

<210> SEQ ID NO 6803

<400> SEQUENCE: 6803

000

<210> SEQ ID NO 6804

<400> SEQUENCE: 6804

000

<210> SEQ ID NO 6805

<400> SEQUENCE: 6805

000

<210> SEQ ID NO 6806

<400> SEQUENCE: 6806

000

<210> SEQ ID NO 6807

<400> SEQUENCE: 6807

000

<210> SEQ ID NO 6808

<400> SEQUENCE: 6808

000

<210> SEQ ID NO 6809

<400> SEQUENCE: 6809

000

<210> SEQ ID NO 6810

<400> SEQUENCE: 6810

000

<210> SEQ ID NO 6811

<400> SEQUENCE: 6811

000

<210> SEQ ID NO 6812

<400> SEQUENCE: 6812

000

<210> SEQ ID NO 6813

<400> SEQUENCE: 6813

000

<210> SEQ ID NO 6814

<400> SEQUENCE: 6814

000

<210> SEQ ID NO 6815

<400> SEQUENCE: 6815

000

<210> SEQ ID NO 6816

<400> SEQUENCE: 6816

000

<210> SEQ ID NO 6817

<400> SEQUENCE: 6817

000

<210> SEQ ID NO 6818

<400> SEQUENCE: 6818

000

<210> SEQ ID NO 6819

<400> SEQUENCE: 6819

000

<210> SEQ ID NO 6820

<400> SEQUENCE: 6820

000

<210> SEQ ID NO 6821

<400> SEQUENCE: 6821

000

<210> SEQ ID NO 6822

<400> SEQUENCE: 6822

000

<210> SEQ ID NO 6823

<400> SEQUENCE: 6823

000

<210> SEQ ID NO 6824

<400> SEQUENCE: 6824

000

<210> SEQ ID NO 6825

<400> SEQUENCE: 6825

000

<210> SEQ ID NO 6826

<400> SEQUENCE: 6826

000

<210> SEQ ID NO 6827

<400> SEQUENCE: 6827

000

<210> SEQ ID NO 6828

<400> SEQUENCE: 6828

000

<210> SEQ ID NO 6829

<400> SEQUENCE: 6829

000

<210> SEQ ID NO 6830

<400> SEQUENCE: 6830

000

<210> SEQ ID NO 6831

<400> SEQUENCE: 6831

000

<210> SEQ ID NO 6832

<400> SEQUENCE: 6832

000

<210> SEQ ID NO 6833

<400> SEQUENCE: 6833

000

<210> SEQ ID NO 6834

<400> SEQUENCE: 6834

000

<210> SEQ ID NO 6835

<400> SEQUENCE: 6835

000

<210> SEQ ID NO 6836

<400> SEQUENCE: 6836

000

<210> SEQ ID NO 6837

<400> SEQUENCE: 6837

000

<210> SEQ ID NO 6838

<400> SEQUENCE: 6838

000

<210> SEQ ID NO 6839

<400> SEQUENCE: 6839

000

<210> SEQ ID NO 6840

<400> SEQUENCE: 6840

000

<210> SEQ ID NO 6841

<400> SEQUENCE: 6841

000

<210> SEQ ID NO 6842

<400> SEQUENCE: 6842

000

<210> SEQ ID NO 6843

<400> SEQUENCE: 6843

000

<210> SEQ ID NO 6844

<400> SEQUENCE: 6844

000

<210> SEQ ID NO 6845

<400> SEQUENCE: 6845

000

<210> SEQ ID NO 6846

<400> SEQUENCE: 6846

000

<210> SEQ ID NO 6847

<400> SEQUENCE: 6847

000

<210> SEQ ID NO 6848

<400> SEQUENCE: 6848

000

<210> SEQ ID NO 6849

<400> SEQUENCE: 6849

000

<210> SEQ ID NO 6850

<400> SEQUENCE: 6850

000

<210> SEQ ID NO 6851

<400> SEQUENCE: 6851

000

<210> SEQ ID NO 6852

<400> SEQUENCE: 6852

000

<210> SEQ ID NO 6853

<400> SEQUENCE: 6853

000

<210> SEQ ID NO 6854

<400> SEQUENCE: 6854

000

<210> SEQ ID NO 6855

<400> SEQUENCE: 6855

000

<210> SEQ ID NO 6856

<400> SEQUENCE: 6856

000

<210> SEQ ID NO 6857

<400> SEQUENCE: 6857

000

```
<210> SEQ ID NO 6858
<400> SEQUENCE: 6858
000

<210> SEQ ID NO 6859
<400> SEQUENCE: 6859
000

<210> SEQ ID NO 6860
<400> SEQUENCE: 6860
000

<210> SEQ ID NO 6861
<400> SEQUENCE: 6861
000

<210> SEQ ID NO 6862
<400> SEQUENCE: 6862
000

<210> SEQ ID NO 6863
<400> SEQUENCE: 6863
000

<210> SEQ ID NO 6864
<400> SEQUENCE: 6864
000

<210> SEQ ID NO 6865
<400> SEQUENCE: 6865
000

<210> SEQ ID NO 6866
<400> SEQUENCE: 6866
000

<210> SEQ ID NO 6867
<400> SEQUENCE: 6867
000

<210> SEQ ID NO 6868
<400> SEQUENCE: 6868
000

<210> SEQ ID NO 6869
```

```
<400> SEQUENCE: 6869

000

<210> SEQ ID NO 6870

<400> SEQUENCE: 6870

000

<210> SEQ ID NO 6871

<400> SEQUENCE: 6871

000

<210> SEQ ID NO 6872

<400> SEQUENCE: 6872

000

<210> SEQ ID NO 6873

<400> SEQUENCE: 6873

000

<210> SEQ ID NO 6874

<400> SEQUENCE: 6874

000

<210> SEQ ID NO 6875

<400> SEQUENCE: 6875

000

<210> SEQ ID NO 6876

<400> SEQUENCE: 6876

000

<210> SEQ ID NO 6877

<400> SEQUENCE: 6877

000

<210> SEQ ID NO 6878

<400> SEQUENCE: 6878

000

<210> SEQ ID NO 6879

<400> SEQUENCE: 6879

000

<210> SEQ ID NO 6880

<400> SEQUENCE: 6880
```

000

<210> SEQ ID NO 6881

<400> SEQUENCE: 6881

000

<210> SEQ ID NO 6882

<400> SEQUENCE: 6882

000

<210> SEQ ID NO 6883

<400> SEQUENCE: 6883

000

<210> SEQ ID NO 6884

<400> SEQUENCE: 6884

000

<210> SEQ ID NO 6885

<400> SEQUENCE: 6885

000

<210> SEQ ID NO 6886

<400> SEQUENCE: 6886

000

<210> SEQ ID NO 6887

<400> SEQUENCE: 6887

000

<210> SEQ ID NO 6888

<400> SEQUENCE: 6888

000

<210> SEQ ID NO 6889

<400> SEQUENCE: 6889

000

<210> SEQ ID NO 6890

<400> SEQUENCE: 6890

000

<210> SEQ ID NO 6891

<400> SEQUENCE: 6891

000

<210> SEQ ID NO 6892

<400> SEQUENCE: 6892

000

<210> SEQ ID NO 6893

<400> SEQUENCE: 6893

000

<210> SEQ ID NO 6894

<400> SEQUENCE: 6894

000

<210> SEQ ID NO 6895

<400> SEQUENCE: 6895

000

<210> SEQ ID NO 6896

<400> SEQUENCE: 6896

000

<210> SEQ ID NO 6897

<400> SEQUENCE: 6897

000

<210> SEQ ID NO 6898

<400> SEQUENCE: 6898

000

<210> SEQ ID NO 6899

<400> SEQUENCE: 6899

000

<210> SEQ ID NO 6900

<400> SEQUENCE: 6900

000

<210> SEQ ID NO 6901

<400> SEQUENCE: 6901

000

<210> SEQ ID NO 6902

<400> SEQUENCE: 6902

000

<210> SEQ ID NO 6903

<400> SEQUENCE: 6903

000

<210> SEQ ID NO 6904

<400> SEQUENCE: 6904

000

<210> SEQ ID NO 6905

<400> SEQUENCE: 6905

000

<210> SEQ ID NO 6906

<400> SEQUENCE: 6906

000

<210> SEQ ID NO 6907

<400> SEQUENCE: 6907

000

<210> SEQ ID NO 6908

<400> SEQUENCE: 6908

000

<210> SEQ ID NO 6909

<400> SEQUENCE: 6909

000

<210> SEQ ID NO 6910

<400> SEQUENCE: 6910

000

<210> SEQ ID NO 6911

<400> SEQUENCE: 6911

000

<210> SEQ ID NO 6912

<400> SEQUENCE: 6912

000

<210> SEQ ID NO 6913

<400> SEQUENCE: 6913

000

<210> SEQ ID NO 6914

<400> SEQUENCE: 6914

-continued

000

<210> SEQ ID NO 6915

<400> SEQUENCE: 6915

000

<210> SEQ ID NO 6916

<400> SEQUENCE: 6916

000

<210> SEQ ID NO 6917

<400> SEQUENCE: 6917

000

<210> SEQ ID NO 6918

<400> SEQUENCE: 6918

000

<210> SEQ ID NO 6919

<400> SEQUENCE: 6919

000

<210> SEQ ID NO 6920

<400> SEQUENCE: 6920

000

<210> SEQ ID NO 6921

<400> SEQUENCE: 6921

000

<210> SEQ ID NO 6922

<400> SEQUENCE: 6922

000

<210> SEQ ID NO 6923

<400> SEQUENCE: 6923

000

<210> SEQ ID NO 6924

<400> SEQUENCE: 6924

000

<210> SEQ ID NO 6925

<400> SEQUENCE: 6925

000

<210> SEQ ID NO 6926

<400> SEQUENCE: 6926

000

<210> SEQ ID NO 6927

<400> SEQUENCE: 6927

000

<210> SEQ ID NO 6928

<400> SEQUENCE: 6928

000

<210> SEQ ID NO 6929

<400> SEQUENCE: 6929

000

<210> SEQ ID NO 6930

<400> SEQUENCE: 6930

000

<210> SEQ ID NO 6931

<400> SEQUENCE: 6931

000

<210> SEQ ID NO 6932

<400> SEQUENCE: 6932

000

<210> SEQ ID NO 6933

<400> SEQUENCE: 6933

000

<210> SEQ ID NO 6934

<400> SEQUENCE: 6934

000

<210> SEQ ID NO 6935

<400> SEQUENCE: 6935

000

<210> SEQ ID NO 6936

<400> SEQUENCE: 6936

000

<210> SEQ ID NO 6937

<400> SEQUENCE: 6937

000

<210> SEQ ID NO 6938

<400> SEQUENCE: 6938

000

<210> SEQ ID NO 6939

<400> SEQUENCE: 6939

000

<210> SEQ ID NO 6940

<400> SEQUENCE: 6940

000

<210> SEQ ID NO 6941

<400> SEQUENCE: 6941

000

<210> SEQ ID NO 6942

<400> SEQUENCE: 6942

000

<210> SEQ ID NO 6943

<400> SEQUENCE: 6943

000

<210> SEQ ID NO 6944

<400> SEQUENCE: 6944

000

<210> SEQ ID NO 6945

<400> SEQUENCE: 6945

000

<210> SEQ ID NO 6946

<400> SEQUENCE: 6946

000

<210> SEQ ID NO 6947

<400> SEQUENCE: 6947

000

<210> SEQ ID NO 6948

<400> SEQUENCE: 6948

000

<210> SEQ ID NO 6949

<400> SEQUENCE: 6949

000

<210> SEQ ID NO 6950

<400> SEQUENCE: 6950

000

<210> SEQ ID NO 6951

<400> SEQUENCE: 6951

000

<210> SEQ ID NO 6952

<400> SEQUENCE: 6952

000

<210> SEQ ID NO 6953

<400> SEQUENCE: 6953

000

<210> SEQ ID NO 6954

<400> SEQUENCE: 6954

000

<210> SEQ ID NO 6955

<400> SEQUENCE: 6955

000

<210> SEQ ID NO 6956

<400> SEQUENCE: 6956

000

<210> SEQ ID NO 6957

<400> SEQUENCE: 6957

000

<210> SEQ ID NO 6958

<400> SEQUENCE: 6958

000

<210> SEQ ID NO 6959

<400> SEQUENCE: 6959

000

<210> SEQ ID NO 6960

<400> SEQUENCE: 6960

000

<210> SEQ ID NO 6961

<400> SEQUENCE: 6961

000

<210> SEQ ID NO 6962

<400> SEQUENCE: 6962

000

<210> SEQ ID NO 6963

<400> SEQUENCE: 6963

000

<210> SEQ ID NO 6964

<400> SEQUENCE: 6964

000

<210> SEQ ID NO 6965

<400> SEQUENCE: 6965

000

<210> SEQ ID NO 6966

<400> SEQUENCE: 6966

000

<210> SEQ ID NO 6967

<400> SEQUENCE: 6967

000

<210> SEQ ID NO 6968

<400> SEQUENCE: 6968

000

<210> SEQ ID NO 6969

<400> SEQUENCE: 6969

000

<210> SEQ ID NO 6970

<400> SEQUENCE: 6970

000

<210> SEQ ID NO 6971

<400> SEQUENCE: 6971

000

<210> SEQ ID NO 6972

<400> SEQUENCE: 6972

000

<210> SEQ ID NO 6973

<400> SEQUENCE: 6973

000

<210> SEQ ID NO 6974

<400> SEQUENCE: 6974

000

<210> SEQ ID NO 6975

<400> SEQUENCE: 6975

000

<210> SEQ ID NO 6976

<400> SEQUENCE: 6976

000

<210> SEQ ID NO 6977

<400> SEQUENCE: 6977

000

<210> SEQ ID NO 6978

<400> SEQUENCE: 6978

000

<210> SEQ ID NO 6979

<400> SEQUENCE: 6979

000

<210> SEQ ID NO 6980

<400> SEQUENCE: 6980

000

<210> SEQ ID NO 6981

<400> SEQUENCE: 6981

000

<210> SEQ ID NO 6982

<400> SEQUENCE: 6982

000

<210> SEQ ID NO 6983

<400> SEQUENCE: 6983

000

<210> SEQ ID NO 6984

<400> SEQUENCE: 6984

000

<210> SEQ ID NO 6985

<400> SEQUENCE: 6985

000

<210> SEQ ID NO 6986

<400> SEQUENCE: 6986

000

<210> SEQ ID NO 6987

<400> SEQUENCE: 6987

000

<210> SEQ ID NO 6988

<400> SEQUENCE: 6988

000

<210> SEQ ID NO 6989

<400> SEQUENCE: 6989

000

<210> SEQ ID NO 6990

<400> SEQUENCE: 6990

000

<210> SEQ ID NO 6991

<400> SEQUENCE: 6991

000

<210> SEQ ID NO 6992

<400> SEQUENCE: 6992

000

<210> SEQ ID NO 6993

<400> SEQUENCE: 6993

000

<210> SEQ ID NO 6994

<400> SEQUENCE: 6994

000

<210> SEQ ID NO 6995

<400> SEQUENCE: 6995

000

<210> SEQ ID NO 6996

<400> SEQUENCE: 6996

000

<210> SEQ ID NO 6997

<400> SEQUENCE: 6997

000

<210> SEQ ID NO 6998

<400> SEQUENCE: 6998

000

<210> SEQ ID NO 6999

<400> SEQUENCE: 6999

000

<210> SEQ ID NO 7000

<400> SEQUENCE: 7000

000

<210> SEQ ID NO 7001

<400> SEQUENCE: 7001

000

<210> SEQ ID NO 7002

<400> SEQUENCE: 7002

000

<210> SEQ ID NO 7003

<400> SEQUENCE: 7003

000

<210> SEQ ID NO 7004

<400> SEQUENCE: 7004

000

<210> SEQ ID NO 7005

<400> SEQUENCE: 7005

000

<210> SEQ ID NO 7006

<400> SEQUENCE: 7006

000

<210> SEQ ID NO 7007

<400> SEQUENCE: 7007

000

<210> SEQ ID NO 7008

<400> SEQUENCE: 7008

000

<210> SEQ ID NO 7009

<400> SEQUENCE: 7009

000

<210> SEQ ID NO 7010

<400> SEQUENCE: 7010

000

<210> SEQ ID NO 7011

<400> SEQUENCE: 7011

000

<210> SEQ ID NO 7012

<400> SEQUENCE: 7012

000

<210> SEQ ID NO 7013

<400> SEQUENCE: 7013

000

<210> SEQ ID NO 7014

<400> SEQUENCE: 7014

000

<210> SEQ ID NO 7015

<400> SEQUENCE: 7015

000

-continued

<210> SEQ ID NO 7016

<400> SEQUENCE: 7016

000

<210> SEQ ID NO 7017

<400> SEQUENCE: 7017

000

<210> SEQ ID NO 7018

<400> SEQUENCE: 7018

000

<210> SEQ ID NO 7019

<400> SEQUENCE: 7019

000

<210> SEQ ID NO 7020

<400> SEQUENCE: 7020

000

<210> SEQ ID NO 7021

<400> SEQUENCE: 7021

000

<210> SEQ ID NO 7022

<400> SEQUENCE: 7022

000

<210> SEQ ID NO 7023

<400> SEQUENCE: 7023

000

<210> SEQ ID NO 7024

<400> SEQUENCE: 7024

000

<210> SEQ ID NO 7025

<400> SEQUENCE: 7025

000

<210> SEQ ID NO 7026

<400> SEQUENCE: 7026

000

<210> SEQ ID NO 7027

<400> SEQUENCE: 7027

000

<210> SEQ ID NO 7028

<400> SEQUENCE: 7028

000

<210> SEQ ID NO 7029

<400> SEQUENCE: 7029

000

<210> SEQ ID NO 7030

<400> SEQUENCE: 7030

000

<210> SEQ ID NO 7031

<400> SEQUENCE: 7031

000

<210> SEQ ID NO 7032

<400> SEQUENCE: 7032

000

<210> SEQ ID NO 7033

<400> SEQUENCE: 7033

000

<210> SEQ ID NO 7034

<400> SEQUENCE: 7034

000

<210> SEQ ID NO 7035

<400> SEQUENCE: 7035

000

<210> SEQ ID NO 7036

<400> SEQUENCE: 7036

000

<210> SEQ ID NO 7037

<400> SEQUENCE: 7037

000

<210> SEQ ID NO 7038

<400> SEQUENCE: 7038

000

<210> SEQ ID NO 7039

<400> SEQUENCE: 7039

000

<210> SEQ ID NO 7040

<400> SEQUENCE: 7040

000

<210> SEQ ID NO 7041

<400> SEQUENCE: 7041

000

<210> SEQ ID NO 7042

<400> SEQUENCE: 7042

000

<210> SEQ ID NO 7043

<400> SEQUENCE: 7043

000

<210> SEQ ID NO 7044

<400> SEQUENCE: 7044

000

<210> SEQ ID NO 7045

<400> SEQUENCE: 7045

000

<210> SEQ ID NO 7046

<400> SEQUENCE: 7046

000

<210> SEQ ID NO 7047

<400> SEQUENCE: 7047

000

<210> SEQ ID NO 7048

<400> SEQUENCE: 7048

000

<210> SEQ ID NO 7049

<400> SEQUENCE: 7049

000

<210> SEQ ID NO 7050

<400> SEQUENCE: 7050

000

<210> SEQ ID NO 7051

<400> SEQUENCE: 7051

000

<210> SEQ ID NO 7052

<400> SEQUENCE: 7052

000

<210> SEQ ID NO 7053

<400> SEQUENCE: 7053

000

<210> SEQ ID NO 7054

<400> SEQUENCE: 7054

000

<210> SEQ ID NO 7055

<400> SEQUENCE: 7055

000

<210> SEQ ID NO 7056

<400> SEQUENCE: 7056

000

<210> SEQ ID NO 7057

<400> SEQUENCE: 7057

000

<210> SEQ ID NO 7058

<400> SEQUENCE: 7058

000

<210> SEQ ID NO 7059

<400> SEQUENCE: 7059

000

<210> SEQ ID NO 7060

<400> SEQUENCE: 7060

000

<210> SEQ ID NO 7061

<400> SEQUENCE: 7061

000

<210> SEQ ID NO 7062

<400> SEQUENCE: 7062

000

<210> SEQ ID NO 7063

<400> SEQUENCE: 7063

000

<210> SEQ ID NO 7064

<400> SEQUENCE: 7064

000

<210> SEQ ID NO 7065

<400> SEQUENCE: 7065

000

<210> SEQ ID NO 7066

<400> SEQUENCE: 7066

000

<210> SEQ ID NO 7067

<400> SEQUENCE: 7067

000

<210> SEQ ID NO 7068

<400> SEQUENCE: 7068

000

<210> SEQ ID NO 7069

<400> SEQUENCE: 7069

000

<210> SEQ ID NO 7070

<400> SEQUENCE: 7070

000

<210> SEQ ID NO 7071

<400> SEQUENCE: 7071

000

<210> SEQ ID NO 7072

<400> SEQUENCE: 7072

000

<210> SEQ ID NO 7073

<400> SEQUENCE: 7073

000

<210> SEQ ID NO 7074

<400> SEQUENCE: 7074

000

<210> SEQ ID NO 7075

<400> SEQUENCE: 7075

000

<210> SEQ ID NO 7076

<400> SEQUENCE: 7076

000

<210> SEQ ID NO 7077

<400> SEQUENCE: 7077

000

<210> SEQ ID NO 7078

<400> SEQUENCE: 7078

000

<210> SEQ ID NO 7079

<400> SEQUENCE: 7079

000

<210> SEQ ID NO 7080

<400> SEQUENCE: 7080

000

<210> SEQ ID NO 7081

<400> SEQUENCE: 7081

000

<210> SEQ ID NO 7082

<400> SEQUENCE: 7082

000

<210> SEQ ID NO 7083

<400> SEQUENCE: 7083

000

<210> SEQ ID NO 7084

<400> SEQUENCE: 7084

000

<210> SEQ ID NO 7085

<400> SEQUENCE: 7085

000

<210> SEQ ID NO 7086

<400> SEQUENCE: 7086

000

<210> SEQ ID NO 7087

<400> SEQUENCE: 7087

000

<210> SEQ ID NO 7088

<400> SEQUENCE: 7088

000

<210> SEQ ID NO 7089

<400> SEQUENCE: 7089

000

<210> SEQ ID NO 7090

<400> SEQUENCE: 7090

000

<210> SEQ ID NO 7091

<400> SEQUENCE: 7091

000

<210> SEQ ID NO 7092

<400> SEQUENCE: 7092

000

<210> SEQ ID NO 7093

<400> SEQUENCE: 7093

000

<210> SEQ ID NO 7094

<400> SEQUENCE: 7094

000

-continued

<210> SEQ ID NO 7095

<400> SEQUENCE: 7095

000

<210> SEQ ID NO 7096

<400> SEQUENCE: 7096

000

<210> SEQ ID NO 7097

<400> SEQUENCE: 7097

000

<210> SEQ ID NO 7098

<400> SEQUENCE: 7098

000

<210> SEQ ID NO 7099

<400> SEQUENCE: 7099

000

<210> SEQ ID NO 7100

<400> SEQUENCE: 7100

000

<210> SEQ ID NO 7101

<400> SEQUENCE: 7101

000

<210> SEQ ID NO 7102

<400> SEQUENCE: 7102

000

<210> SEQ ID NO 7103

<400> SEQUENCE: 7103

000

<210> SEQ ID NO 7104

<400> SEQUENCE: 7104

000

<210> SEQ ID NO 7105

<400> SEQUENCE: 7105

000

<210> SEQ ID NO 7106

```
<400> SEQUENCE: 7106
000

<210> SEQ ID NO 7107
<400> SEQUENCE: 7107
000

<210> SEQ ID NO 7108
<400> SEQUENCE: 7108
000

<210> SEQ ID NO 7109
<400> SEQUENCE: 7109
000

<210> SEQ ID NO 7110
<400> SEQUENCE: 7110
000

<210> SEQ ID NO 7111
<400> SEQUENCE: 7111
000

<210> SEQ ID NO 7112
<400> SEQUENCE: 7112
000

<210> SEQ ID NO 7113
<400> SEQUENCE: 7113
000

<210> SEQ ID NO 7114
<400> SEQUENCE: 7114
000

<210> SEQ ID NO 7115
<400> SEQUENCE: 7115
000

<210> SEQ ID NO 7116
<400> SEQUENCE: 7116
000

<210> SEQ ID NO 7117
<400> SEQUENCE: 7117
```

000

<210> SEQ ID NO 7118

<400> SEQUENCE: 7118

000

<210> SEQ ID NO 7119

<400> SEQUENCE: 7119

000

<210> SEQ ID NO 7120

<400> SEQUENCE: 7120

000

<210> SEQ ID NO 7121

<400> SEQUENCE: 7121

000

<210> SEQ ID NO 7122

<400> SEQUENCE: 7122

000

<210> SEQ ID NO 7123

<400> SEQUENCE: 7123

000

<210> SEQ ID NO 7124

<400> SEQUENCE: 7124

000

<210> SEQ ID NO 7125

<400> SEQUENCE: 7125

000

<210> SEQ ID NO 7126

<400> SEQUENCE: 7126

000

<210> SEQ ID NO 7127

<400> SEQUENCE: 7127

000

<210> SEQ ID NO 7128

<400> SEQUENCE: 7128

000

<210> SEQ ID NO 7129

<400> SEQUENCE: 7129

000

<210> SEQ ID NO 7130

<400> SEQUENCE: 7130

000

<210> SEQ ID NO 7131

<400> SEQUENCE: 7131

000

<210> SEQ ID NO 7132

<400> SEQUENCE: 7132

000

<210> SEQ ID NO 7133

<400> SEQUENCE: 7133

000

<210> SEQ ID NO 7134

<400> SEQUENCE: 7134

000

<210> SEQ ID NO 7135

<400> SEQUENCE: 7135

000

<210> SEQ ID NO 7136

<400> SEQUENCE: 7136

000

<210> SEQ ID NO 7137

<400> SEQUENCE: 7137

000

<210> SEQ ID NO 7138

<400> SEQUENCE: 7138

000

<210> SEQ ID NO 7139

<400> SEQUENCE: 7139

000

<210> SEQ ID NO 7140

<400> SEQUENCE: 7140

000

<210> SEQ ID NO 7141

<400> SEQUENCE: 7141

000

<210> SEQ ID NO 7142

<400> SEQUENCE: 7142

000

<210> SEQ ID NO 7143

<400> SEQUENCE: 7143

000

<210> SEQ ID NO 7144

<400> SEQUENCE: 7144

000

<210> SEQ ID NO 7145

<400> SEQUENCE: 7145

000

<210> SEQ ID NO 7146

<400> SEQUENCE: 7146

000

<210> SEQ ID NO 7147

<400> SEQUENCE: 7147

000

<210> SEQ ID NO 7148

<400> SEQUENCE: 7148

000

<210> SEQ ID NO 7149

<400> SEQUENCE: 7149

000

<210> SEQ ID NO 7150

<400> SEQUENCE: 7150

000

<210> SEQ ID NO 7151

<400> SEQUENCE: 7151

000

<210> SEQ ID NO 7152

<400> SEQUENCE: 7152

000

<210> SEQ ID NO 7153

<400> SEQUENCE: 7153

000

<210> SEQ ID NO 7154

<400> SEQUENCE: 7154

000

<210> SEQ ID NO 7155

<400> SEQUENCE: 7155

000

<210> SEQ ID NO 7156

<400> SEQUENCE: 7156

000

<210> SEQ ID NO 7157

<400> SEQUENCE: 7157

000

<210> SEQ ID NO 7158

<400> SEQUENCE: 7158

000

<210> SEQ ID NO 7159

<400> SEQUENCE: 7159

000

<210> SEQ ID NO 7160

<400> SEQUENCE: 7160

000

<210> SEQ ID NO 7161

<400> SEQUENCE: 7161

000

<210> SEQ ID NO 7162

<400> SEQUENCE: 7162

000

-continued

<210> SEQ ID NO 7163

<400> SEQUENCE: 7163

000

<210> SEQ ID NO 7164

<400> SEQUENCE: 7164

000

<210> SEQ ID NO 7165

<400> SEQUENCE: 7165

000

<210> SEQ ID NO 7166

<400> SEQUENCE: 7166

000

<210> SEQ ID NO 7167

<400> SEQUENCE: 7167

000

<210> SEQ ID NO 7168

<400> SEQUENCE: 7168

000

<210> SEQ ID NO 7169

<400> SEQUENCE: 7169

000

<210> SEQ ID NO 7170

<400> SEQUENCE: 7170

000

<210> SEQ ID NO 7171

<400> SEQUENCE: 7171

000

<210> SEQ ID NO 7172

<400> SEQUENCE: 7172

000

<210> SEQ ID NO 7173

<400> SEQUENCE: 7173

000

<210> SEQ ID NO 7174

<400> SEQUENCE: 7174

000

<210> SEQ ID NO 7175

<400> SEQUENCE: 7175

000

<210> SEQ ID NO 7176

<400> SEQUENCE: 7176

000

<210> SEQ ID NO 7177

<400> SEQUENCE: 7177

000

<210> SEQ ID NO 7178

<400> SEQUENCE: 7178

000

<210> SEQ ID NO 7179

<400> SEQUENCE: 7179

000

<210> SEQ ID NO 7180

<400> SEQUENCE: 7180

000

<210> SEQ ID NO 7181

<400> SEQUENCE: 7181

000

<210> SEQ ID NO 7182

<400> SEQUENCE: 7182

000

<210> SEQ ID NO 7183

<400> SEQUENCE: 7183

000

<210> SEQ ID NO 7184

<400> SEQUENCE: 7184

000

<210> SEQ ID NO 7185

<400> SEQUENCE: 7185

000

<210> SEQ ID NO 7186

<400> SEQUENCE: 7186

000

<210> SEQ ID NO 7187

<400> SEQUENCE: 7187

000

<210> SEQ ID NO 7188

<400> SEQUENCE: 7188

000

<210> SEQ ID NO 7189

<400> SEQUENCE: 7189

000

<210> SEQ ID NO 7190

<400> SEQUENCE: 7190

000

<210> SEQ ID NO 7191

<400> SEQUENCE: 7191

000

<210> SEQ ID NO 7192

<400> SEQUENCE: 7192

000

<210> SEQ ID NO 7193

<400> SEQUENCE: 7193

000

<210> SEQ ID NO 7194

<400> SEQUENCE: 7194

000

<210> SEQ ID NO 7195

<400> SEQUENCE: 7195

000

<210> SEQ ID NO 7196

<400> SEQUENCE: 7196

000

<210> SEQ ID NO 7197

<400> SEQUENCE: 7197

000

<210> SEQ ID NO 7198

<400> SEQUENCE: 7198

000

<210> SEQ ID NO 7199

<400> SEQUENCE: 7199

000

<210> SEQ ID NO 7200

<400> SEQUENCE: 7200

000

<210> SEQ ID NO 7201

<400> SEQUENCE: 7201

000

<210> SEQ ID NO 7202

<400> SEQUENCE: 7202

000

<210> SEQ ID NO 7203

<400> SEQUENCE: 7203

000

<210> SEQ ID NO 7204

<400> SEQUENCE: 7204

000

<210> SEQ ID NO 7205

<400> SEQUENCE: 7205

000

<210> SEQ ID NO 7206

<400> SEQUENCE: 7206

000

<210> SEQ ID NO 7207

<400> SEQUENCE: 7207

000

<210> SEQ ID NO 7208

<400> SEQUENCE: 7208

000

<210> SEQ ID NO 7209

<400> SEQUENCE: 7209

000

<210> SEQ ID NO 7210

<400> SEQUENCE: 7210

000

<210> SEQ ID NO 7211

<400> SEQUENCE: 7211

000

<210> SEQ ID NO 7212

<400> SEQUENCE: 7212

000

<210> SEQ ID NO 7213

<400> SEQUENCE: 7213

000

<210> SEQ ID NO 7214

<400> SEQUENCE: 7214

000

<210> SEQ ID NO 7215

<400> SEQUENCE: 7215

000

<210> SEQ ID NO 7216

<400> SEQUENCE: 7216

000

<210> SEQ ID NO 7217

<400> SEQUENCE: 7217

000

<210> SEQ ID NO 7218

<400> SEQUENCE: 7218

000

<210> SEQ ID NO 7219

<400> SEQUENCE: 7219

000

<210> SEQ ID NO 7220

<400> SEQUENCE: 7220

000

<210> SEQ ID NO 7221

<400> SEQUENCE: 7221

000

<210> SEQ ID NO 7222

<400> SEQUENCE: 7222

000

<210> SEQ ID NO 7223

<400> SEQUENCE: 7223

000

<210> SEQ ID NO 7224

<400> SEQUENCE: 7224

000

<210> SEQ ID NO 7225

<400> SEQUENCE: 7225

000

<210> SEQ ID NO 7226

<400> SEQUENCE: 7226

000

<210> SEQ ID NO 7227

<400> SEQUENCE: 7227

000

<210> SEQ ID NO 7228

<400> SEQUENCE: 7228

000

<210> SEQ ID NO 7229

<400> SEQUENCE: 7229

000

<210> SEQ ID NO 7230

<400> SEQUENCE: 7230

000

<210> SEQ ID NO 7231

<400> SEQUENCE: 7231

000

<210> SEQ ID NO 7232

<400> SEQUENCE: 7232

000

<210> SEQ ID NO 7233

<400> SEQUENCE: 7233

000

<210> SEQ ID NO 7234

<400> SEQUENCE: 7234

000

<210> SEQ ID NO 7235

<400> SEQUENCE: 7235

000

<210> SEQ ID NO 7236

<400> SEQUENCE: 7236

000

<210> SEQ ID NO 7237

<400> SEQUENCE: 7237

000

<210> SEQ ID NO 7238

<400> SEQUENCE: 7238

000

<210> SEQ ID NO 7239

<400> SEQUENCE: 7239

000

<210> SEQ ID NO 7240

<400> SEQUENCE: 7240

000

<210> SEQ ID NO 7241

<400> SEQUENCE: 7241

000

<210> SEQ ID NO 7242

<400> SEQUENCE: 7242

000

<210> SEQ ID NO 7243

<400> SEQUENCE: 7243

000

<210> SEQ ID NO 7244

<400> SEQUENCE: 7244

000

<210> SEQ ID NO 7245

<400> SEQUENCE: 7245

000

<210> SEQ ID NO 7246

<400> SEQUENCE: 7246

000

<210> SEQ ID NO 7247

<400> SEQUENCE: 7247

000

<210> SEQ ID NO 7248

<400> SEQUENCE: 7248

000

<210> SEQ ID NO 7249

<400> SEQUENCE: 7249

000

<210> SEQ ID NO 7250

<400> SEQUENCE: 7250

000

<210> SEQ ID NO 7251

<400> SEQUENCE: 7251

000

<210> SEQ ID NO 7252

<400> SEQUENCE: 7252

000

<210> SEQ ID NO 7253

<400> SEQUENCE: 7253

000

<210> SEQ ID NO 7254

<400> SEQUENCE: 7254

000

<210> SEQ ID NO 7255

<400> SEQUENCE: 7255

000

<210> SEQ ID NO 7256

<400> SEQUENCE: 7256

000

<210> SEQ ID NO 7257

<400> SEQUENCE: 7257

000

<210> SEQ ID NO 7258

<400> SEQUENCE: 7258

000

<210> SEQ ID NO 7259

<400> SEQUENCE: 7259

000

<210> SEQ ID NO 7260

<400> SEQUENCE: 7260

000

<210> SEQ ID NO 7261

<400> SEQUENCE: 7261

000

<210> SEQ ID NO 7262

<400> SEQUENCE: 7262

000

<210> SEQ ID NO 7263

<400> SEQUENCE: 7263

000

<210> SEQ ID NO 7264

```
<400> SEQUENCE: 7264
000

<210> SEQ ID NO 7265
<400> SEQUENCE: 7265
000

<210> SEQ ID NO 7266
<400> SEQUENCE: 7266
000

<210> SEQ ID NO 7267
<400> SEQUENCE: 7267
000

<210> SEQ ID NO 7268
<400> SEQUENCE: 7268
000

<210> SEQ ID NO 7269
<400> SEQUENCE: 7269
000

<210> SEQ ID NO 7270
<400> SEQUENCE: 7270
000

<210> SEQ ID NO 7271
<400> SEQUENCE: 7271
000

<210> SEQ ID NO 7272
<400> SEQUENCE: 7272
000

<210> SEQ ID NO 7273
<400> SEQUENCE: 7273
000

<210> SEQ ID NO 7274
<400> SEQUENCE: 7274
000

<210> SEQ ID NO 7275
<400> SEQUENCE: 7275
```

000

<210> SEQ ID NO 7276

<400> SEQUENCE: 7276

000

<210> SEQ ID NO 7277

<400> SEQUENCE: 7277

000

<210> SEQ ID NO 7278

<400> SEQUENCE: 7278

000

<210> SEQ ID NO 7279

<400> SEQUENCE: 7279

000

<210> SEQ ID NO 7280

<400> SEQUENCE: 7280

000

<210> SEQ ID NO 7281

<400> SEQUENCE: 7281

000

<210> SEQ ID NO 7282

<400> SEQUENCE: 7282

000

<210> SEQ ID NO 7283

<400> SEQUENCE: 7283

000

<210> SEQ ID NO 7284

<400> SEQUENCE: 7284

000

<210> SEQ ID NO 7285

<400> SEQUENCE: 7285

000

<210> SEQ ID NO 7286

<400> SEQUENCE: 7286

000

<210> SEQ ID NO 7287

<400> SEQUENCE: 7287

000

<210> SEQ ID NO 7288

<400> SEQUENCE: 7288

000

<210> SEQ ID NO 7289

<400> SEQUENCE: 7289

000

<210> SEQ ID NO 7290

<400> SEQUENCE: 7290

000

<210> SEQ ID NO 7291

<400> SEQUENCE: 7291

000

<210> SEQ ID NO 7292
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7292

Gly Ile Pro Asp Gln Phe Ser Gly Ser Asn Ser Gly Asn Ile Ala Thr
1               5                   10                  15

Leu Thr Ile Ser Lys Ala Gln Ala Gly Tyr Glu Ala Asp Tyr Tyr Cys
            20                  25                  30

<210> SEQ ID NO 7293
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7293

Gln Ser Trp Asp Ser Thr Asn Ser Ala Val
1               5                   10

<210> SEQ ID NO 7294
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7294

Ser Tyr Thr Leu Thr Gln Pro Pro Leu Leu Ser Val Ala Leu Gly His
1               5                   10                  15

Lys Ala Thr Ile Thr Cys Ser Gly Glu Arg Leu Ser Asp Lys Tyr Val
                20                  25                  30

His Trp Tyr Gln Gln Lys Pro Gly Arg Ala Pro Val Met Val Ile Tyr
            35                  40                  45

Glu Asn Asp Lys Arg Pro Ser Gly Ile Pro Asp Gln Phe Ser Gly Ser
        50                  55                  60

Asn Ser Gly Asn Ile Ala Thr Leu Thr Ile Ser Lys Ala Gln Ala Gly
65                  70                  75                  80

Tyr Glu Ala Asp Tyr Tyr Cys Gln Ser Trp Asp Ser Thr Asn Ser Ala
                85                  90                  95

Val Phe Gly Ser Gly Thr Gln Leu Thr Val Leu
            100                 105

<210> SEQ ID NO 7295
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7295

Gln Ile Gln Leu Gln Glu Ser Gly Pro Gly Leu Val Lys Pro Ser Gln
1               5                   10                  15

Ser Leu Ser Leu Ser Cys Ser Val Thr Gly Phe Ser Ile Asn Thr Gly
                20                  25                  30

Gly Tyr His Trp Asn Trp Ile Arg Gln Phe Pro Gly Lys Lys Val Glu
            35                  40                  45

Trp Met Gly Tyr Ile Tyr Ser Ser Gly Thr Thr Lys Tyr Asn Pro Ser
        50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Gly Asp Trp His Tyr Phe Asp Tyr Trp Gly Gln Gly Thr
                100                 105                 110

Met Val Ala Val Ser Ser
        115

<210> SEQ ID NO 7296
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7296

Ser Tyr Thr Leu Thr Gln Pro Pro Leu Val Ser Val Ala Leu Gly Gln
1               5                   10                  15

Lys Ala Thr Ile Ile Cys Ser Gly Glu Asn Leu Ser Asp Lys Tyr Val
                20                  25                  30

His Trp Tyr Gln Gln Lys Pro Gly Arg Ala Pro Val Met Val Ile Tyr
            35                  40                  45

Glu Asn Asp Lys Arg Pro Ser Gly Ile Pro Asp Gln Phe Ser Gly Ser
        50                  55                  60

Asn Ser Gly Asn Ile Ala Thr Leu Thr Ile Ser Lys Ala Gln Ala Gly
65                  70                  75                  80

Tyr Glu Ala Asp Tyr Tyr Cys His Cys Trp Asp Ser Thr Asn Ser Ala
                85                  90                  95

Val Phe Gly Ser Gly Thr His Leu Thr Val Leu
            100                 105

<210> SEQ ID NO 7297
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7297

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn Thr Gly
            20                  25                  30

Gly Tyr His Trp Asn Trp Ile Arg Gln Phe Pro Gly Lys Lys Leu Glu
        35                  40                  45

Trp Met Gly Tyr Ile Tyr Ser Ser Gly Ser Thr Arg Tyr Asn Pro Ser
    50                  55                  60

Leu Lys Ser Arg Phe Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Thr Arg Gly Asn Trp His Tyr Phe Asp Tyr Trp Gly Gln Gly Thr
            100                 105                 110

Leu Val Ala Val Ser Ser
        115

<210> SEQ ID NO 7298
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7298

Gln Ile Gln Leu Gln Glu Ser Gly Pro Gly Leu Val Lys Pro Ser Gln
1               5                   10                  15

Ser Leu Ser Leu Ser Cys Ser Val Thr Gly Phe Ser Ile Thr Thr Thr
            20                  25                  30

Gly Tyr His Trp Asn Trp Ile Arg Gln Phe Pro Gly Lys Lys Leu Glu
        35                  40                  45

Trp Met Gly Tyr Ile Tyr Ser Ser Gly Ser Thr Ser Tyr Asn Pro Ser
    50                  55                  60

Leu Lys Ser Arg Phe Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Gly Asp Trp His Tyr Phe Asp Tyr Trp Gly Pro Gly Thr

Met Val Thr Val Ser Ser
        115

<210> SEQ ID NO 7299
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7299

Ser Phe Thr Leu Thr Gln Pro Pro Leu Val Ser Val Ala Val Gly Gln
1               5                   10                  15

Val Ala Thr Ile Thr Cys Ser Gly Glu Lys Leu Ser Asp Lys Tyr Val
            20                  25                  30

His Trp Tyr Gln Gln Lys Pro Gly Arg Ala Pro Val Met Val Ile Tyr
        35                  40                  45

Glu Asn Asp Arg Arg Pro Ser Gly Ile Pro Asp Gln Phe Ser Gly Ser
    50                  55                  60

Asn Ser Gly Asn Ile Ala Ser Leu Thr Ile Ser Lys Ala Gln Ala Gly
65                  70                  75                  80

Asp Glu Ala Asp Tyr Phe Cys Gln Phe Trp Asp Ser Thr Asn Ser Ala
                85                  90                  95

Val Phe Gly Gly Gly Thr Gln Leu Thr Val Leu
            100                 105

<210> SEQ ID NO 7300
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7300

Gln Ile Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Thr
            20                  25                  30

Gly Tyr His Trp Asn Trp Ile Arg Gln His Pro Gly Lys Gly Leu Glu
        35                  40                  45

Trp Ile Gly Tyr Ile Tyr Ser Ser Gly Ser Thr Ser Tyr Asn Pro Ser
    50                  55                  60

Leu Lys Ser Leu Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asp Trp His Tyr Phe Asp Tyr Trp Gly Gln Gly Thr
            100                 105                 110

Met Val Thr Val Ser Ser
        115

<210> SEQ ID NO 7301
<211> LENGTH: 118
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 7301
```

Gln Ile Gln Leu Val Glu Ser Gly Gly Gly Leu Val Lys Pro Gly Gly
1               5                   10                  15

Ser Leu Arg Leu Ser Cys Ala Val Ser Gly Phe Ser Ile Thr Thr Thr
            20                  25                  30

Gly Tyr His Trp Asn Trp Ile Arg Gln Ala Pro Gly Lys Gly Leu Glu
        35                  40                  45

Trp Val Gly Tyr Ile Tyr Ser Ser Gly Ser Thr Ser Tyr Asn Pro Ser
    50                  55                  60

Leu Lys Ser Arg Phe Thr Ile Ser Arg Asp Thr Ala Lys Asn Ser Phe
65                  70                  75                  80

Tyr Leu Gln Met Asn Ser Leu Arg Ala Glu Asp Thr Ala Val Tyr Tyr
                85                  90                  95

Cys Ala Arg Gly Asp Trp His Tyr Phe Asp Tyr Trp Gly Gln Gly Thr
            100                 105                 110

Met Val Thr Val Ser Ser
        115

```
<210> SEQ ID NO 7302
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7302
```

Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Thr Thr Thr
            20                  25                  30

Gly Tyr His Trp Asn Trp Val Arg Gln Ala Pro Gly Lys Gly Leu Glu
        35                  40                  45

Trp Val Gly Tyr Ile Tyr Ser Ser Gly Ser Thr Ser Tyr Asn Pro Ser
    50                  55                  60

Leu Lys Ser Arg Phe Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Asp Trp His Tyr Phe Asp Tyr Trp Gly Gln Gly Thr
            100                 105                 110

Met Val Thr Val Ser Ser
        115

```
<210> SEQ ID NO 7303
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7303
```

-continued

Glu Ile Gln Leu Val Glu Ser Gly Gly Leu Val Gln Pro Gly Gly
1               5                   10                  15

Ser Leu Arg Leu Ser Cys Ala Val Ser Gly Phe Ser Ile Thr Thr Thr
            20                  25                  30

Gly Tyr His Trp Asn Trp Val Arg Gln Ala Pro Gly Lys Gly Leu Glu
            35                  40                  45

Trp Val Gly Tyr Ile Tyr Ser Ser Gly Ser Thr Ser Tyr Asn Pro Ser
    50                  55                  60

Leu Lys Ser Arg Phe Thr Ile Ser Arg Asp Thr Ala Lys Asn Ser Phe
65                  70                  75                  80

Tyr Leu Gln Met Asn Ser Leu Arg Ala Glu Asp Thr Ala Val Tyr Tyr
                85                  90                  95

Cys Ala Arg Gly Asp Trp His Tyr Phe Asp Tyr Trp Gly Gln Gly Thr
            100                 105                 110

Met Val Thr Val Ser Ser
            115

<210> SEQ ID NO 7304
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7304

Gln Ile Gln Leu Val Gln Ser Gly Ala Glu Val Lys Lys Pro Gly Ala
1               5                   10                  15

Ser Val Lys Val Ser Cys Lys Val Ser Gly Phe Ser Ile Thr Thr Thr
            20                  25                  30

Gly Tyr His Trp Asn Trp Val Arg Gln Ala Pro Gly Gln Gly Leu Glu
            35                  40                  45

Trp Met Gly Tyr Ile Tyr Ser Ser Gly Ser Thr Ser Tyr Asn Pro Ser
    50                  55                  60

Leu Lys Ser Arg Val Thr Met Thr Arg Asp Thr Ser Thr Asn Thr Phe
65                  70                  75                  80

Tyr Met Glu Leu Ser Ser Leu Arg Ser Glu Asp Thr Ala Val Tyr Tyr
                85                  90                  95

Cys Ala Arg Gly Asp Trp His Tyr Phe Asp Tyr Trp Gly Gln Gly Thr
            100                 105                 110

Met Val Thr Val Ser Ser
            115

<210> SEQ ID NO 7305
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7305

Ser Ser Glu Thr Thr Gln Pro Pro Ser Val Ser Val Ser Pro Gly Gln
1               5                   10                  15

Thr Ala Ser Ile Thr Cys Ser Gly Glu Lys Leu Ser Asp Lys Tyr Val
            20                  25                  30

His Trp Tyr Gln Gln Lys Pro Gly Gln Ser Pro Val Met Val Ile Tyr

```
                    35                  40                  45

Glu Asn Asp Arg Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Phe Trp Asp Ser Thr Asn Ser Ala
                85                  90                  95

Val Phe Gly Gly Gly Thr Gln Leu Thr Val Leu
            100                 105

<210> SEQ ID NO 7306
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7306

Ser Ser Glu Thr Thr Gln Pro His Ser Val Ser Val Ala Thr Ala Gln
1                5                  10                  15

Met Ala Arg Ile Thr Cys Ser Gly Glu Lys Leu Ser Asp Lys Tyr Val
                20                  25                  30

His Trp Tyr Gln Gln Lys Pro Gly Gln Asp Pro Val Met Val Ile Tyr
                35                  40                  45

Glu Asn Asp Arg Arg Pro Ser Gly Ile Pro Glu Arg Phe Ser Gly Ser
 50                  55                  60

Asn Pro Gly Asn Thr Ala Thr Leu Thr Ile Ser Arg Ile Glu Ala Gly
65                  70                  75                  80

Asp Glu Ala Asp Tyr Phe Cys Gln Phe Trp Asp Ser Thr Asn Ser Ala
                85                  90                  95

Val Phe Gly Gly Gly Thr Gln Leu Thr Val Leu
            100                 105

<210> SEQ ID NO 7307
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7307

Gln Ser Val Thr Thr Gln Pro Pro Ser Ala Ser Gly Thr Pro Gly Gln
1                5                  10                  15

Arg Val Thr Ile Ser Cys Ser Gly Glu Lys Leu Ser Asp Lys Tyr Val
                20                  25                  30

His Trp Tyr Gln Gln Leu Pro Gly Thr Ala Pro Lys Met Leu Ile Tyr
                35                  40                  45

Glu Asn Asp Arg Arg Pro Ser Gly Val Pro Asp Arg Phe Ser Gly Ser
 50                  55                  60

Asn Ser Gly Asn Ser Ala Ser Leu Ala Ile Ser Gly Leu Arg Ser Glu
65                  70                  75                  80

Asp Glu Ala Asp Tyr Phe Cys Gln Phe Trp Asp Ser Thr Asn Ser Ala
                85                  90                  95

Val Phe Gly Gly Gly Thr Gln Leu Thr Val Leu
            100                 105
```

<210> SEQ ID NO 7308
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7308

```
Gln Ser Val Thr Thr Gln Pro Pro Ser Val Ser Gly Ala Pro Gly Gln
1               5                   10                  15

Arg Val Thr Ile Ser Cys Ser Gly Glu Lys Leu Ser Asp Lys Tyr Val
            20                  25                  30

His Trp Tyr Gln Gln Leu Pro Gly Thr Ala Pro Lys Met Leu Ile Tyr
        35                  40                  45

Glu Asn Asp Arg Arg Pro Ser Gly Val Pro Asp Arg Phe Ser Gly Ser
    50                  55                  60

Asn Ser Gly Asn Ser Ala Ser Leu Ala Ile Thr Gly Leu Gln Ala Glu
65                  70                  75                  80

Asp Glu Ala Asp Tyr Phe Cys Gln Phe Trp Asp Ser Thr Asn Ser Ala
                85                  90                  95

Val Phe Gly Gly Gly Thr Gln Leu Thr Val Leu
            100                 105
```

<210> SEQ ID NO 7309
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7309

```
Asp Ser Val Thr Thr Gln Ser Pro Leu Ser Leu Pro Val Thr Leu Gly
1               5                   10                  15

Gln Pro Ala Ser Ile Ser Cys Ser Gly Glu Lys Leu Ser Asp Lys Tyr
            20                  25                  30

Val His Trp Tyr Gln Gln Arg Pro Gly Gln Ser Pro Arg Met Leu Ile
        35                  40                  45

Tyr Glu Asn Asp Arg Arg Pro Ser Gly Val Pro Asp Arg Phe Ser Gly
    50                  55                  60

Ser Asn Ser Gly Asn Asp Ala Thr Leu Lys Ile Ser Arg Val Glu Ala
65                  70                  75                  80

Glu Asp Val Gly Val Tyr Phe Cys Gln Phe Trp Asp Ser Thr Asn Ser
                85                  90                  95

Ala Val Phe Gly Gly Gly Thr Lys Val Glu Ile Lys
            100                 105
```

<210> SEQ ID NO 7310
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7310

-continued

Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Thr Thr Thr
            20                  25                  30

Gly Tyr His Trp Asn Trp Val Arg Gln Ala Pro Gly Lys Gly Leu Glu
        35                  40                  45

Trp Val Gly Tyr Ile Tyr Ser Ser Gly Ser Thr Ser Tyr Asn Pro Ser
50                  55                  60

Leu Lys Ser Arg Phe Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Asp Trp His Tyr Phe Asp Tyr Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Gly Gly Ser Ser Glu Thr Thr Gln
        130                 135                 140

Pro Pro Ser Val Ser Val Ser Pro Gly Gln Thr Ala Ser Ile Thr Cys
145                 150                 155                 160

Ser Gly Glu Lys Leu Ser Asp Lys Tyr Val His Trp Tyr Gln Gln Lys
            165                 170                 175

Pro Gly Gln Ser Pro Val Met Val Ile Tyr Glu Asn Asp Arg Arg Pro
            180                 185                 190

Ser Gly Ile Pro Glu Arg Phe Ser Gly Ser Asn Ser Gly Asn Thr Ala
        195                 200                 205

Thr Leu Thr Ile Ser Gly Thr Gln Ala Met Asp Glu Ala Asp Tyr Phe
210                 215                 220

Cys Gln Phe Trp Asp Ser Thr Asn Ser Ala Val Phe Gly Gly Gly Thr
225                 230                 235                 240

Gln Leu Thr Val Leu
            245

<210> SEQ ID NO 7311
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7311

Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Thr Thr Thr
            20                  25                  30

Gly Tyr His Trp Asn Trp Val Arg Gln Ala Pro Gly Lys Gly Leu Glu
        35                  40                  45

Trp Val Gly Tyr Ile Tyr Ser Ser Gly Ser Thr Ser Tyr Asn Pro Ser
50                  55                  60

Leu Lys Ser Arg Phe Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Asp Trp His Tyr Phe Asp Tyr Trp Gly Gln Gly Thr

```
                100             105              110
Met Val Thr Val Ser Gly Gly Gly Gly Gly Gly Gly Ser
                115             120              125
Gly Gly Gly Gly Ser Gly Gly Gly Ser Asp Ser Val Thr Thr Gln
                130             135             140
Ser Pro Leu Ser Leu Pro Val Thr Leu Gly Gln Pro Ala Ser Ile Ser
145             150             155              160
Cys Ser Gly Glu Lys Leu Ser Asp Lys Tyr Val His Trp Tyr Gln Gln
                165             170              175
Arg Pro Gly Gln Ser Pro Arg Met Leu Ile Tyr Glu Asn Asp Arg Arg
                180             185              190
Pro Ser Gly Val Pro Asp Arg Phe Ser Gly Ser Asn Ser Gly Asn Asp
                195             200             205
Ala Thr Leu Lys Ile Ser Arg Val Glu Ala Glu Asp Val Gly Val Tyr
                210             215             220
Phe Cys Gln Phe Trp Asp Ser Thr Asn Ser Ala Val Phe Gly Gly Gly
225             230             235              240
Thr Lys Val Glu Ile Lys
                245
```

<210> SEQ ID NO 7312
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7312

```
Gln Ile Gln Leu Gln Glu Ser Gly Pro Gly Leu Val Lys Pro Ser Gln
1               5                   10                  15
Ser Leu Ser Leu Ser Cys Ser Val Thr Gly Phe Ser Ile Asn Thr Gly
                20                  25                  30
```

<210> SEQ ID NO 7313
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7313

```
Gly Tyr His Trp Asn
1               5
```

<210> SEQ ID NO 7314
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7314

```
Trp Ile Arg Gln Phe Pro Gly Lys Lys Val Glu Trp Met Gly
1               5                   10
```

<210> SEQ ID NO 7315

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7315

Gly Asp Trp His Tyr Phe Asp Tyr
1               5

<210> SEQ ID NO 7316
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7316

Trp Gly Gln Gly Thr Met Val Ala Val Ser Ser
1               5                   10

<210> SEQ ID NO 7317
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7317

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Asn Thr Gly
                20                  25                  30

<210> SEQ ID NO 7318
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7318

Tyr Ile Tyr Ser Ser Gly Ser Thr Arg Tyr Asn Pro Ser Leu Lys Ser
1               5                   10                  15

<210> SEQ ID NO 7319
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7319

Arg Phe Ser Ile Thr Arg Asp Thr Ser Lys Asn Gln Phe Phe Leu Gln
1               5                   10                  15

Leu Asn Ser Val Thr Thr Glu Asp Thr Ala Thr Tyr Tyr Cys Thr Arg
                20                  25                  30
```

<210> SEQ ID NO 7320
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7320

Ser Tyr Thr Leu Thr Gln Pro Pro Leu Val Ser Val Ala Leu Gly Gln
1               5                   10                  15

Lys Ala Thr Ile Ile Cys
            20

<210> SEQ ID NO 7321
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7321

His Cys Trp Asp Ser Thr Asn Ser Ala Val
1               5                   10

<210> SEQ ID NO 7322
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7322

Gln Ile Gln Leu Gln Glu Ser Gly Pro Gly Leu Val Lys Pro Ser Gln
1               5                   10                  15

Ser Leu Ser Leu Ser Cys Ser Val Thr Gly Phe Ser Ile Thr Thr Thr
            20                  25                  30

<210> SEQ ID NO 7323
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7323

Arg Phe Ser Ile Thr Arg Asp Thr Ser Lys Asn Gln Phe Phe Leu Gln
1               5                   10                  15

Leu Asn Ser Val Thr Thr Glu Asp Thr Ala Thr Tyr Tyr Cys Ala Arg
            20                  25                  30

<210> SEQ ID NO 7324
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 7324

Trp Gly Pro Gly Thr Met Val Thr Val Ser Ser
1               5                   10

<210> SEQ ID NO 7325
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7325

Ser Phe Thr Leu Thr Gln Pro Pro Leu Val Ser Val Ala Val Gly Gln
1               5                   10                  15

Val Ala Thr Ile Thr Cys
            20

<210> SEQ ID NO 7326
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7326

Ser Gly Glu Lys Leu Ser Asp Lys Tyr Val His
1               5                   10

<210> SEQ ID NO 7327
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7327

Glu Asn Asp Arg Arg Pro Ser
1               5

<210> SEQ ID NO 7328
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7328

Gly Ile Pro Asp Gln Phe Ser Gly Ser Asn Ser Gly Asn Ile Ala Ser
1               5                   10                  15

Leu Thr Ile Ser Lys Ala Gln Ala Gly Asp Glu Ala Asp Tyr Phe Cys
            20                  25                  30

<210> SEQ ID NO 7329
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 7329

Gln Phe Trp Asp Ser Thr Asn Ser Ala Val
1               5                   10

<210> SEQ ID NO 7330
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7330

Gln Ile Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Thr
            20                  25                  30

<210> SEQ ID NO 7331
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7331

Gln Ile Gln Leu Val Glu Ser Gly Gly Gly Leu Val Lys Pro Gly Gly
1               5                   10                  15

Ser Leu Arg Leu Ser Cys Ala Val Ser Gly Phe Ser Ile Thr Thr Thr
            20                  25                  30

<210> SEQ ID NO 7332
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7332

Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Thr Thr Thr
            20                  25                  30

<210> SEQ ID NO 7333
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7333

Glu Ile Gln Leu Val Glu Ser Gly Gly Gly Leu Val Gln Pro Gly Gly
1               5                   10                  15

Ser Leu Arg Leu Ser Cys Ala Val Ser Gly Phe Ser Ile Thr Thr Thr
            20                  25                  30

<210> SEQ ID NO 7334
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7334

Gln Ile Gln Leu Val Gln Ser Gly Ala Glu Val Lys Lys Pro Gly Ala
1               5                   10                  15

Ser Val Lys Val Ser Cys Lys Val Ser Gly Phe Ser Ile Thr Thr Thr
            20                  25                  30

<210> SEQ ID NO 7335
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7335

Ser Ser Glu Thr Thr Gln Pro Pro Ser Val Ser Val Ser Pro Gly Gln
1               5                   10                  15

Thr Ala Ser Ile Thr Cys
            20

<210> SEQ ID NO 7336
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7336

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Phe Cys
            20                  25                  30

<210> SEQ ID NO 7337
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7337

Gly Ile Pro Glu Arg Phe Ser Gly Ser Asn Pro Gly Asn Thr Ala Thr
1               5                   10                  15

Leu Thr Ile Ser Arg Ile Glu Ala Gly Asp Glu Ala Asp Tyr Phe Cys
            20                  25                  30

<210> SEQ ID NO 7338
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7338

Gly Val Pro Asp Arg Phe Ser Gly Ser Asn Ser Gly Asn Ser Ala Ser
1               5                   10                  15

Leu Ala Ile Ser Gly Leu Arg Ser Glu Asp Glu Ala Asp Tyr Phe Cys
            20                  25                  30

<210> SEQ ID NO 7339
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7339

Gly Val Pro Asp Arg Phe Ser Gly Ser Asn Ser Gly Asn Ser Ala Ser
1               5                   10                  15

Leu Ala Ile Thr Gly Leu Gln Ala Glu Asp Glu Ala Asp Tyr Phe Cys
            20                  25                  30

<210> SEQ ID NO 7340
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7340

Asp Ser Val Thr Thr Gln Ser Pro Leu Ser Leu Pro Val Thr Leu Gly
1               5                   10                  15

Gln Pro Ala Ser Ile Ser Cys
            20

<210> SEQ ID NO 7341
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7341

Trp Tyr Gln Gln Arg Pro Gly Gln Ser Pro Arg Met Leu Ile Tyr
1               5                   10                  15

<210> SEQ ID NO 7342
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7342

Gly Val Pro Asp Arg Phe Ser Gly Ser Asn Ser Gly Asn Asp Ala Thr
1               5                   10                  15

Leu Lys Ile Ser Arg Val Glu Ala Glu Asp Val Gly Val Tyr Phe Cys
            20                  25                  30

<210> SEQ ID NO 7343

<400> SEQUENCE: 7343

000

<210> SEQ ID NO 7344

<400> SEQUENCE: 7344

000

<210> SEQ ID NO 7345

<400> SEQUENCE: 7345

000

<210> SEQ ID NO 7346

<400> SEQUENCE: 7346

000

<210> SEQ ID NO 7347

<400> SEQUENCE: 7347

000

<210> SEQ ID NO 7348

<400> SEQUENCE: 7348

000

<210> SEQ ID NO 7349

<400> SEQUENCE: 7349

000

<210> SEQ ID NO 7350

<400> SEQUENCE: 7350

000

<210> SEQ ID NO 7351

<400> SEQUENCE: 7351

000

<210> SEQ ID NO 7352

<400> SEQUENCE: 7352

000

<210> SEQ ID NO 7353

<400> SEQUENCE: 7353

000

-continued

<210> SEQ ID NO 7354

<400> SEQUENCE: 7354

000

<210> SEQ ID NO 7355

<400> SEQUENCE: 7355

000

<210> SEQ ID NO 7356

<400> SEQUENCE: 7356

000

<210> SEQ ID NO 7357

<400> SEQUENCE: 7357

000

<210> SEQ ID NO 7358

<400> SEQUENCE: 7358

000

<210> SEQ ID NO 7359

<400> SEQUENCE: 7359

000

<210> SEQ ID NO 7360

<400> SEQUENCE: 7360

000

<210> SEQ ID NO 7361

<400> SEQUENCE: 7361

000

<210> SEQ ID NO 7362

<400> SEQUENCE: 7362

000

<210> SEQ ID NO 7363

<400> SEQUENCE: 7363

000

<210> SEQ ID NO 7364

<400> SEQUENCE: 7364

000

<210> SEQ ID NO 7365

```
<400> SEQUENCE: 7365

000

<210> SEQ ID NO 7366

<400> SEQUENCE: 7366

000

<210> SEQ ID NO 7367

<400> SEQUENCE: 7367

000

<210> SEQ ID NO 7368

<400> SEQUENCE: 7368

000

<210> SEQ ID NO 7369

<400> SEQUENCE: 7369

000

<210> SEQ ID NO 7370

<400> SEQUENCE: 7370

000

<210> SEQ ID NO 7371
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7371

Gln Ile Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Asn Thr Gly
            20                  25                  30

<210> SEQ ID NO 7372
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7372

Gln Ile Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Asn Thr Gly
            20                  25                  30

<210> SEQ ID NO 7373
<211> LENGTH: 32
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7373

Glu Ile Gln Leu Leu Glu Ser Gly Gly Gly Leu Val Gln Pro Gly Gly
1               5                   10                  15

Ser Leu Arg Leu Ser Cys Ala Val Ser Gly Phe Ser Ile Asn Thr Gly
            20                  25                  30

<210> SEQ ID NO 7374
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7374

Gln Ile Gln Leu Val Gln Ser Gly Ala Glu Val Lys Lys Pro Gly Ser
1               5                   10                  15

Ser Val Lys Val Ser Cys Lys Val Ser Gly Phe Ser Ile Asn Thr Gly
            20                  25                  30

<210> SEQ ID NO 7375
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7375

Glu Ile Gln Leu Val Glu Ser Gly Gly Gly Leu Val Gln Pro Gly Gly
1               5                   10                  15

Ser Leu Arg Leu Ser Cys Ala Val Ser Gly Phe Ser Ile Asn Thr Gly
            20                  25                  30

<210> SEQ ID NO 7376
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7376

Gln Ile Gln Leu Val Gln Ser Gly Ala Glu Val Lys Lys Pro Gly Ala
1               5                   10                  15

Ser Val Lys Val Ser Cys Lys Val Ser Gly Phe Ser Ile Asn Thr Gly
            20                  25                  30

<210> SEQ ID NO 7377
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7377
```

Gln Ile Gln Leu Val Glu Ser Gly Gly Gly Leu Val Lys Pro Gly Gly
1               5                   10                  15

Ser Leu Arg Leu Ser Cys Ala Val Ser Gly Phe Ser Ile Asn Thr Gly
            20                  25                  30

<210> SEQ ID NO 7378
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7378

Glu Ile Gln Leu Val Gln Ser Gly Ala Glu Val Lys Lys Pro Gly Ala
1               5                   10                  15

Thr Val Lys Ile Ser Cys Lys Val Ser Gly Phe Ser Ile Asn Thr Gly
            20                  25                  30

<210> SEQ ID NO 7379

<400> SEQUENCE: 7379

000

<210> SEQ ID NO 7380

<400> SEQUENCE: 7380

000

<210> SEQ ID NO 7381

<400> SEQUENCE: 7381

000

<210> SEQ ID NO 7382

<400> SEQUENCE: 7382

000

<210> SEQ ID NO 7383

<400> SEQUENCE: 7383

000

<210> SEQ ID NO 7384

<400> SEQUENCE: 7384

000

<210> SEQ ID NO 7385
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7385

-continued

```
Tyr Ile Tyr Ser Ser Gly Thr Thr Lys Tyr Asn Pro Ser Leu Lys Ser
1               5                   10                  15
```

ANTIBODY MOLECULES THAT BIND TO NKP30 AND USES THEREOF

RELATED APPLICATIONS

This application is a continuation of International Application No. PCT/US2020/019329, filed on Feb. 21, 2020, which claims the benefit of U.S. Provisional Application 62/808,582 filed Feb. 21, 2019, the entire contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Feb. 20, 2020, is named 53676-735.301_SL.txt and is 517,567 bytes in size.

BACKGROUND

Natural Killer (NK) cells recognize and destroy tumors and virus-infected cells in an antibody-independent manner. The regulation of NK cells is mediated by activating and inhibiting receptors on the NK cell surface. One family of activating receptors is the natural cytotoxicity receptors (NCRs) which include NKp30, NKp44 and NKp46.

Given the importance of immune checkpoint pathways in regulating an immune response, the need exists for developing novel agents that modulate the activity of immunoinhibitory proteins, such as PD-1, thus leading to activation of the immune system. Such agents can be used, e.g., for cancer immunotherapy and treatment of other conditions, such as chronic infection.

SUMMARY OF THE INVENTION

Disclosed herein are antibody molecules (e.g., humanized antibody molecules) that bind to NKp30 with high affinity and specificity. Nucleic acid molecules encoding the antibody molecules, expression vectors, host cells and methods for making the antibody molecules are also provided. Multi- or bispecific or multifunctional antibody molecules and pharmaceutical compositions comprising the antibody molecules are also provided. The anti-NKp30antibody molecules disclosed herein can be used (alone or in combination with other agents or therapeutic modalities) to treat, prevent and/or diagnose disorders, such as cancerous disorders (e.g., solid and soft-tissue tumors), as well as autoimmune and infectious diseases. Thus, compositions and methods for detecting NKp30, as well as methods for treating various disorders including cancer, autoimmune and/or infectious diseases, using the anti-NKp30 antibody molecules are disclosed herein.

Accordingly, in one aspect, the invention features an antibody molecule (e.g., an isolated or recombinant antibody molecule), comprising one or more sequences according to the following enumerated embodiments. Additional features of any of the disclosed antibody molecules, multifunctional molecules, nucleic acids, vectors, host cells, or methods include one or more of the following enumerated embodiments.

Those skilled in the art will recognize, or be able to ascertain using no more than routine experimentation, many equivalents to the specific embodiments of the invention described herein. Such equivalents are intended to be encompassed by the following enumerated embodiments.

ENUMERATED EMBODIMENTS

1. An isolated antibody molecule that binds to NKp30, comprising:
   (i) a heavy chain variable region (VH) comprising a heavy chain complementarity determining region 1 (VHCDR1) amino acid sequence of SEQ ID NO: 7313 (or a sequence with no more than 1, 2, 3, or 4 mutations, e.g., substitutions, additions, or deletions), a VHCDR2 amino acid sequence of SEQ ID NO: 6001 (or a sequence with no more than 1, 2, 3, or 4 mutations, e.g., substitutions, additions, or deletions, and/or a VHCDR3 amino acid sequence of SEQ ID NO: 7315 (or a sequence with no more than 1, 2, 3, or 4 mutations, e.g., substitutions, additions, or deletions; and/or
   (ii) a light chain variable region (VL) comprising a light chain complementarity determining region 1 (VLCDR1) amino acid sequence of SEQ ID NO: 7326 (or a sequence with no more than 1, 2, 3, or 4 mutations, e.g., substitutions, additions, or deletions), a VLCDR2 amino acid sequence of SEQ ID NO: 7327 (or a sequence with no more than 1, 2, 3, or 4 mutations, e.g., substitutions, additions, or deletions), and/or a VLCDR3 amino acid sequence of SEQ ID NO: 7329 (or a sequence with no more than 1, 2, 3, or 4 mutations, e.g., substitutions, additions, or deletions).

2. The antibody molecule of embodiment 1, wherein the antigen binding domain comprises:
   (i) a VH comprising the amino acid sequence of any of SEQ ID NOs: 7298 or 7300-7304 (or an amino acid sequence having at least about 75%, 80%, 85%, 90%, 95%, or 99% sequence identity to any of SEQ ID NOs: 7298 or 7300-7304), and/or
   (ii) a VL comprising the amino acid sequence of any of SEQ ID NOs: 7299 or 7305-7309 (or an amino acid sequence having at least about 93%, 95%, or 99% sequence identity to any of SEQ ID NOs: 7299 or 7305-7309).

3. The antibody molecule of embodiment 2, wherein the antigen binding domain comprises:
   (i) a VH comprising the amino acid sequence of SEQ ID NO: 7302 (or an amino acid sequence having at least about 75%, 80%, 85%, 90%, 95%, or 99% sequence identity to 7302), and a VL comprising the amino acid sequence of SEQ ID NO: 7305 (or an amino acid sequence having at least about 75%, 80%, 85%, 90%, 95%, or 99% sequence identity to 7305); or
   (ii) a VH comprising the amino acid sequence of SEQ ID NO: 7302 (or an amino acid sequence having at least about 75%, 80%, 85%, 90%, 95%, or 99% sequence identity to 7302), and a VL comprising the amino acid sequence of SEQ ID NO: 7309 (or an amino acid sequence having at least about 75%, 80%, 85%, 90%, 95%, or 99% sequence identity to 7309).

4. The antibody molecule of any of embodiments 1-3, wherein the antigen binding domain comprises:
   (i) an amino acid sequence of SEQ ID NO: 7310 (or an amino acid sequence having at least about 75%, 80%, 85%, 90%, 95%, or 99% sequence identity to 7310); or
   (ii) an amino acid sequence of SEQ ID NO: 7311 (or an amino acid sequence having at least about 75%, 80%, 85%, 90%, 95%, or 99% sequence identity to 7311).

5. An isolated antibody molecule that binds to NKp30, comprising:

(i) a heavy chain variable region (VH) comprising a heavy chain complementarity determining region 1 (VHCDR1) amino acid sequence of SEQ ID NO: 6000 (or a sequence with no more than 1, 2, 3, or 4 mutations, e.g., substitutions, additions, or deletions), a VHCDR2 amino acid sequence of SEQ ID NO: 6001 (or a sequence with no more than 1, 2, 3, or 4 mutations, e.g., substitutions, additions, or deletions), and/or a VHCDR3 amino acid sequence of SEQ ID NO: 6002 (or a sequence with no more than 1, 2, 3, or 4 mutations, e.g., substitutions, additions, or deletions), and (ii) a light chain variable region (VL) comprising a light chain complementarity determining region 1 (VLCDR1) amino acid sequence of SEQ ID NO: 6063 (or a sequence with no more than 1, 2, 3, or 4 mutations, e.g., substitutions, additions, or deletions), a VLCDR2 amino acid sequence of SEQ ID NO: 6064 (or a sequence with no more than 1, 2, 3, or 4 mutations, e.g., substitutions, additions, or deletions), and/or a VLCDR3 amino acid sequence of SEQ ID NO: 7293 (or a sequence with no more than 1, 2, 3, or 4 mutations, e.g., substitutions, additions, or deletions).

6. The antibody molecule of embodiment 5, wherein the antigen binding domain comprises:
   (i) a heavy chain variable region (VH) comprising a heavy chain complementarity determining region 1 (VHCDR1) amino acid sequence of SEQ ID NO: 6000, a VHCDR2 amino acid sequence of SEQ ID NO: 6001, and/or a VHCDR3 amino acid sequence of SEQ ID NO: 6002, and
   (ii) a light chain variable region (VL) comprising a light chain complementarity determining region 1 (VLCDR1) amino acid sequence of SEQ ID NO: 6063, a VLCDR2 amino acid sequence of SEQ ID NO: 6064, and/or a VLCDR3 amino acid sequence of SEQ ID NO: 7293.

7. The antibody molecule of embodiment 5 or 6, wherein the antigen binding domain comprises:
   (1) a heavy chain variable region (VH) comprising a heavy chain framework region 1 (VHFWR1) amino acid sequence of SEQ ID NO: 6003 (or a sequence with no more than 1, 2, 3, 4, 5, or 6 mutations, e.g., substitutions, additions, or deletions, therefrom), a VHFWR2 amino acid sequence of SEQ ID NO: 6004 (or a sequence with no more than 1, 2, 3, 4, 5, or 6 mutations, e.g., substitutions, additions, or deletions, therefrom), a VHFWR3 amino acid sequence of SEQ ID NO: 6005 (or a sequence with no more than 1, 2, 3, 4, 5, or 6 mutations, e.g., substitutions, additions, or deletions, therefrom), or a VHFWR4 amino acid sequence of SEQ ID NO: 6006 (or a sequence with no more than 1, 2, 3, 4, 5, or 6 mutations, e.g., substitutions, additions, or deletions, therefrom), and/or
   (2) a light chain variable region (VL) comprising a light chain framework region 1 (VLFWR1) amino acid sequence of SEQ ID NO: 6066 (or a sequence with no more than 1, 2, 3, 4, 5, or 6 mutations, e.g., substitutions, additions, or deletions, therefrom), a VLFWR2 amino acid sequence of SEQ ID NO: 6067 (or a sequence with no more than 1, 2, 3, 4, 5, or 6 mutations, e.g., substitutions, additions, or deletions, therefrom), a VLFWR3 amino acid sequence of SEQ ID NO: 7292 (or a sequence with no more than 1, 2, 3, 4, 5, or 6 mutations, e.g., substitutions, additions, or deletions, therefrom), or a VLFWR4 amino acid sequence of SEQ ID NO: 6069 (or a sequence with no more than 1, 2, 3, 4, 5, or 6 mutations, e.g., substitutions, additions, or deletions, therefrom).

8. The antibody molecule of embodiment 7, wherein the antigen binding domain comprises:
   (1) a heavy chain variable region (VH) comprising a heavy chain framework region 1 (VHFWR1) amino acid sequence of SEQ ID NO: 6003, a VHFWR2 amino acid sequence of SEQ ID NO: 6004, a VHFWR3 amino acid sequence of SEQ ID NO: 6005, or a VHFWR4 amino acid sequence of SEQ ID NO: 6006, and
   (3) a light chain variable region (VL) comprising a light chain framework region 1 (VLFWR1) amino acid sequence of SEQ ID NO: 6066, a VLFWR2 amino acid sequence of SEQ ID NO: 6067, a VLFWR3 amino acid sequence of SEQ ID NO: 7292, or a VLFWR4 amino acid sequence of SEQ ID NO: 6069.

9. The antibody molecule of any one of embodiments 5-8, wherein the antigen binding domain comprises:
   (i) a VH comprising the amino acid sequence of SEQ ID NO: 6121 (or an amino acid sequence having at least about 75%, 80%, 85%, 90%, 95%, or 99% sequence identity to SEQ ID NO: 6121), and/or
   (ii) a VL comprising the amino acid sequence of SEQ ID NO: 7294 (or an amino acid sequence having at least about 93%, 95%, or 99% sequence identity to SEQ ID NO: 7294).

10. The antibody molecule of any one of embodiments 5-9, wherein the antigen binding domain comprises a heavy chain comprising the amino acid sequence of SEQ ID NOs: 6148 or 6149 (or an amino acid sequence having at least about 75%, 80%, 85%, 90%, 95%, or 99% sequence identity to SEQ ID NOs: 6148 or 6149).

11. The antibody molecule of either of embodiments 5-10, wherein the antigen binding domain comprises a light chain comprising the amino acid sequence of SEQ ID NO: 6150 (or an amino acid sequence having at least about 75%, 80%, 85%, 90%, 95%, or 99% sequence identity to SEQ ID NO: 6150).

12. The antibody molecule of either of embodiments 5-11, wherein the antigen binding domain comprises a heavy chain comprising the amino acid sequence of SEQ ID NOs: 6148 or 6149 (or an amino acid sequence having at least about 75%, 80%, 85%, 90%, 95%, or 99% sequence identity to SEQ ID NOs: 6148 or 6149), and a light chain comprising the amino acid sequence of SEQ ID NO: 6150 (or an amino acid sequence having at least about 75%, 80%, 85%, 90%, 95%, or 99% sequence identity to SEQ ID NO: 6150).

13. The antibody molecule of any of embodiments 5-12, wherein the antigen binding domain comprises a heavy chain variable region (VH) comprising a heavy chain framework region 1 (VHFWR1) amino acid sequence of SEQ ID NO: 6014 (or a sequence with no more than 1, 2, 3, 4, 5, or 6 mutations, e.g., substitutions, additions, or deletions, therefrom), a VHFWR2 amino acid sequence of SEQ ID NO: 6015 (or a sequence with no more than 1, 2, 3, 4, 5, or 6 mutations, e.g., substitutions, additions, or deletions, therefrom), a VHFWR3 amino acid sequence of SEQ ID NO: 6016 (or a sequence with no more than 1, 2, 3, 4, 5, or 6 mutations, e.g., substitutions, additions, or deletions, therefrom), or a VHFWR4 amino acid sequence of SEQ ID NO: 6017 (or a sequence with no more than 1, 2, 3, 4, 5, or 6 mutations, e.g., substitutions, additions, or deletions, therefrom).

14. The antibody molecule of embodiment 13, wherein the antigen binding domain comprises a heavy chain variable region (VH) comprising a heavy chain framework region 1 (VHFWR1) amino acid sequence of SEQ ID NO: 6014, a VHFWR2 amino acid sequence of SEQ ID NO: 6015, a VHFWR3 amino acid sequence of SEQ ID NO: 6016, or a VHFWR4 amino acid sequence of SEQ ID NO: 6017.

15. The antibody molecule of embodiment 14, wherein the antigen binding domain comprises a VH comprising the amino acid sequence of SEQ ID NO: 6123 (or an amino acid sequence having at least about 75%, 80%, 85%, 90%, 95%, or 99% sequence identity to SEQ ID NO: 6123).

16. The antibody molecule of any of embodiments 5-15, wherein the antigen binding domain comprises a heavy chain variable region (VH) comprising a heavy chain framework region 1 (VHFWR1) amino acid sequence of SEQ ID NO: 6018 (or a sequence with no more than 1, 2, 3, 4, 5, or 6 mutations, e.g., substitutions, additions, or deletions, therefrom), a VHFWR2 amino acid sequence of SEQ ID NO: 6019 (or a sequence with no more than 1, 2, 3, 4, 5, or 6 mutations, e.g., substitutions, additions, or deletions, therefrom), a VHFWR3 amino acid sequence of SEQ ID NO: 6020 (or a sequence with no more than 1, 2, 3, 4, 5, or 6 mutations, e.g., substitutions, additions, or deletions, therefrom), or a VHFWR4 amino acid sequence of SEQ ID NO: 6021 (or a sequence with no more than 1, 2, 3, 4, 5, or 6 mutations, e.g., substitutions, additions, or deletions, therefrom).

17. The antibody molecule of embodiment 16, wherein the antigen binding domain comprises a heavy chain variable region (VH) comprising a heavy chain framework region 1 (VHFWR1) amino acid sequence of SEQ ID NO: 6018, a VHFWR2 amino acid sequence of SEQ ID NO: 6019, a VHFWR3 amino acid sequence of SEQ ID NO: 6020, or a VHFWR4 amino acid sequence of SEQ ID NO: 6021.

18. The antibody molecule of embodiment 17, wherein the antigen binding domain comprises a VH comprising the amino acid sequence of SEQ ID NO: 6124 (or an amino acid sequence having at least about 75%, 80%, 85%, 90%, 95%, or 99% sequence identity to SEQ ID NO: 6124).

19. The antibody molecule of any of embodiments 5-18, wherein the antigen binding domain comprises a heavy chain variable region (VH) comprising a heavy chain framework region 1 (VHFWR1) amino acid sequence of SEQ ID NO: 6022 (or a sequence with no more than 1, 2, 3, 4, 5, or 6 mutations, e.g., substitutions, additions, or deletions, therefrom), a VHFWR2 amino acid sequence of SEQ ID NO: 6023 (or a sequence with no more than 1, 2, 3, 4, 5, or 6 mutations, e.g., substitutions, additions, or deletions, therefrom), a VHFWR3 amino acid sequence of SEQ ID NO: 6024 (or a sequence with no more than 1, 2, 3, 4, 5, or 6 mutations, e.g., substitutions, additions, or deletions, therefrom), or a VHFWR4 amino acid sequence of SEQ ID NO: 6025 (or a sequence with no more than 1, 2, 3, 4, 5, or 6 mutations, e.g., substitutions, additions, or deletions, therefrom).

20. The antibody molecule of embodiment 19, wherein the antigen binding domain comprises a heavy chain variable region (VH) comprising a heavy chain framework region 1 (VHFWR1) amino acid sequence of SEQ ID NO: 6022, a VHFWR2 amino acid sequence of SEQ ID NO: 6023, a VHFWR3 amino acid sequence of SEQ ID NO: 6024, or a VHFWR4 amino acid sequence of SEQ ID NO: 6025.

21. The antibody molecule of embodiment 20, wherein the antigen binding domain comprises a VH comprising the amino acid sequence of SEQ ID NO: 6125 (or an amino acid sequence having at least about 75%, 80%, 85%, 90%, 95%, or 99% sequence identity to SEQ ID NO: 6125).

22. The antibody molecule of any of embodiments 5-21, wherein the antigen binding domain comprises a heavy chain variable region (VH) comprising a heavy chain framework region 1 (VHFWR1) amino acid sequence of SEQ ID NO: 6026 (or a sequence with no more than 1, 2, 3, 4, 5, or 6 mutations, e.g., substitutions, additions, or deletions, therefrom), a VHFWR2 amino acid sequence of SEQ ID NO: 6027 (or a sequence with no more than 1, 2, 3, 4, 5, or 6 mutations, e.g., substitutions, additions, or deletions, therefrom), a VHFWR3 amino acid sequence of SEQ ID NO: 6028 (or a sequence with no more than 1, 2, 3, 4, 5, or 6 mutations, e.g., substitutions, additions, or deletions, therefrom), or a VHFWR4 amino acid sequence of SEQ ID NO: 6029 (or a sequence with no more than 1, 2, 3, 4, 5, or 6 mutations, e.g., substitutions, additions, or deletions, therefrom).

23. The antibody molecule of embodiment 22, wherein the antigen binding domain comprises a heavy chain variable region (VH) comprising a heavy chain framework region 1 (VHFWR1) amino acid sequence of SEQ ID NO: 6026, a VHFWR2 amino acid sequence of SEQ ID NO: 6027, a VHFWR3 amino acid sequence of SEQ ID NO: 6028, or a VHFWR4 amino acid sequence of SEQ ID NO: 6029.

24. The antibody molecule of embodiment 23, wherein the antigen binding domain comprises a VH comprising the amino acid sequence of SEQ ID NO: 6126 (or an amino acid sequence having at least about 75%, 80%, 85%, 90%, 95%, or 99% sequence identity to SEQ ID NO: 6126).

25. The antibody molecule of any of embodiments 5-24, wherein the antigen binding domain comprises a heavy chain variable region (VH) comprising a heavy chain framework region 1 (VHFWR1) amino acid sequence of SEQ ID NO: 6030 (or a sequence with no more than 1, 2, 3, 4, 5, or 6 mutations, e.g., substitutions, additions, or deletions, therefrom), a VHFWR2 amino acid sequence of SEQ ID NO: 6032 (or a sequence with no more than 1, 2, 3, 4, 5, or 6 mutations, e.g., substitutions, additions, or deletions, therefrom), a VHFWR3 amino acid sequence of SEQ ID NO: 6033 (or a sequence with no more than 1, 2, 3, 4, 5, or 6 mutations, e.g., substitutions, additions, or deletions, therefrom), or a VHFWR4 amino acid sequence of SEQ ID NO: 6034 (or a sequence with no more than 1, 2, 3, 4, 5, or 6 mutations, e.g., substitutions, additions, or deletions, therefrom).

26. The antibody molecule of embodiment 25, wherein the antigen binding domain comprises a heavy chain variable region (VH) comprising a heavy chain framework region 1 (VHFWR1) amino acid sequence of SEQ ID NO: 6030, a VHFWR2 amino acid sequence of SEQ ID NO: 6032, a VHFWR3 amino acid sequence of SEQ ID NO: 6033, or a VHFWR4 amino acid sequence of SEQ ID NO: 6034.

27. The antibody molecule of embodiment 26, wherein the antigen binding domain comprises a VH comprising the amino acid sequence of SEQ ID NO: 6127 (or an amino acid sequence having at least about 75%, 80%, 85%, 90%, 95%, or 99% sequence identity to SEQ ID NO: 6127).

28. The antibody molecule of any of embodiments 5-27, wherein the antigen binding domain comprises a heavy chain variable region (VH) comprising a heavy chain framework region 1 (VHFWR1) amino acid sequence of SEQ ID NO: 6035 (or a sequence with no more than 1, 2, 3, 4, 5, or 6 mutations, e.g., substitutions, additions, or deletions, therefrom), a VHFWR2 amino acid sequence of SEQ ID NO: 6036 (or a sequence with no more than 1, 2, 3, 4, 5, or 6 mutations, e.g., substitutions, additions, or deletions, therefrom), a VHFWR3 amino acid sequence of SEQ ID NO: 6037 (or a sequence with no more than 1, 2, 3, 4, 5, or 6 mutations, e.g., substitutions, additions, or deletions, therefrom), or a VHFWR4 amino acid sequence of SEQ ID NO: 6038 (or a sequence with no more than 1, 2, 3, 4, 5, or 6 mutations, e.g., substitutions, additions, or deletions, therefrom).

29. The antibody molecule of embodiment 28, wherein the antigen binding domain comprises a heavy chain variable region (VH) comprising a heavy chain framework region 1 (VHFWR1) amino acid sequence of SEQ ID NO: 6035, a VHFWR2 amino acid sequence of SEQ ID NO: 6036, a VHFWR3 amino acid sequence of SEQ ID NO: 6037, or a VHFWR4 amino acid sequence of SEQ ID NO: 6038.

30. The antibody molecule of embodiment 29, wherein the antigen binding domain comprises a VH comprising the amino acid sequence of SEQ ID NO: 6128 (or an amino acid sequence having at least about 75%, 80%, 85%, 90%, 95%, or 99% sequence identity to SEQ ID NO: 6128).

31. The antibody molecule of any of embodiments 5, 6, or 13-30, wherein the antigen binding domain comprises a light chain variable region (VL) comprising a light chain framework region 1 (VLFWR1) amino acid sequence of SEQ ID NO: 6077 (or a sequence with no more than 1, 2, 3, 4, 5, or 6 mutations, e.g., substitutions, additions, or deletions, therefrom), a VLFWR2 amino acid sequence of SEQ ID NO: 6078 (or a sequence with no more than 1, 2, 3, 4, 5, or 6 mutations, e.g., substitutions, additions, or deletions, therefrom), a VLFWR3 amino acid sequence of SEQ ID NO: 6079 (or a sequence with no more than 1, 2, 3, 4, 5, or 6 mutations, e.g., substitutions, additions, or deletions, therefrom), or a VLFWR4 amino acid sequence of SEQ ID NO: 6080 (or a sequence with no more than 1, 2, 3, 4, 5, or 6 mutations, e.g., substitutions, additions, or deletions, therefrom).

32. The antibody molecule of embodiment 31, wherein the antigen binding domain comprises a light chain variable region (VL) comprising a light chain framework region 1 (VLFWR1) amino acid sequence of SEQ ID NO: 6077, a VLFWR2 amino acid sequence of SEQ ID NO: 6078, a VLFWR3 amino acid sequence of SEQ ID NO: 6079, or a VLFWR4 amino acid sequence of SEQ ID NO: 6080.

33. The antibody molecule of embodiment 32, wherein the antigen binding domain comprises a VL comprising the amino acid sequence of SEQ ID NO: 6137 (or an amino acid sequence having at least about 93%, 95%, or 99% sequence identity to SEQ ID NO: 6137).

34. The antibody molecule of any of embodiments 5, 6, or 13-30, wherein the antigen binding domain comprises a light chain variable region (VL) comprising a light chain framework region 1 (VLFWR1) amino acid sequence of SEQ ID NO: 6081 (or a sequence with no more than 1, 2, 3, 4, 5, or 6 mutations, e.g., substitutions, additions, or deletions, therefrom), a VLFWR2 amino acid sequence of SEQ ID NO: 6082 (or a sequence with no more than 1, 2, 3, 4, 5, or 6 mutations, e.g., substitutions, additions, or deletions, therefrom), a VLFWR3 amino acid sequence of SEQ ID NO: 6083 (or a sequence with no more than 1, 2, 3, 4, 5, or 6 mutations, e.g., substitutions, additions, or deletions, therefrom), or a VLFWR4 amino acid sequence of SEQ ID NO: 6084 (or a sequence with no more than 1, 2, 3, 4, 5, or 6 mutations, e.g., substitutions, additions, or deletions, therefrom).

35. The antibody molecule of embodiment 34, wherein the antigen binding domain comprises a light chain variable region (VL) comprising a light chain framework region 1 (VLFWR1) amino acid sequence of SEQ ID NO: 6081, a VLFWR2 amino acid sequence of SEQ ID NO: 6082, a VLFWR3 amino acid sequence of SEQ ID NO: 6083, or a VLFWR4 amino acid sequence of SEQ ID NO: 6084.

36. The antibody molecule of embodiment 35, wherein the antigen binding domain comprises a VL comprising the amino acid sequence of SEQ ID NO: 6138 (or an amino acid sequence having at least about 93%, 95%, or 99% sequence identity to SEQ ID NO: 6138).

37. The antibody molecule of any of embodiments 5, 6, or 13-30, wherein the antigen binding domain comprises a light chain variable region (VL) comprising a light chain framework region 1 (VLFWR1) amino acid sequence of SEQ ID NO: 6085 (or a sequence with no more than 1, 2, 3, 4, 5, or 6 mutations, e.g., substitutions, additions, or deletions, therefrom), a VLFWR2 amino acid sequence of SEQ ID NO: 6086 (or a sequence with no more than 1, 2, 3, 4, 5, or 6 mutations, e.g., substitutions, additions, or deletions, therefrom), a VLFWR3 amino acid sequence of SEQ ID NO: 6087 (or a sequence with no more than 1, 2, 3, 4, 5, or 6 mutations, e.g., substitutions, additions, or deletions, therefrom), or a VLFWR4 amino acid sequence of SEQ ID NO: 6088 (or a sequence with no more than 1, 2, 3, 4, 5, or 6 mutations, e.g., substitutions, additions, or deletions, therefrom).

38. The antibody molecule of embodiment 37, wherein the antigen binding domain comprises a light chain variable region (VL) comprising a light chain framework region 1 (VLFWR1) amino acid sequence of SEQ ID NO: 6085, a VLFWR2 amino acid sequence of SEQ ID NO: 6086, a VLFWR3 amino acid sequence of SEQ ID NO: 6087, or a VLFWR4 amino acid sequence of SEQ ID NO: 6088.

39. The antibody molecule of embodiment 38, wherein the antigen binding domain comprises a VL comprising the amino acid sequence of SEQ ID NO: 6139 (or an amino acid sequence having at least about 93%, 95%, or 99% sequence identity to SEQ ID NO: 6139).

40. The antibody molecule of any of embodiments 5, 6, or 13-30, wherein the antigen binding domain comprises a light chain variable region (VL) comprising a light chain framework region 1 (VLFWR1) amino acid sequence of SEQ ID NO: 6089 (or a sequence with no more than 1, 2, 3, 4, 5, or 6 mutations, e.g., substitutions, additions, or deletions, therefrom), a VLFWR2 amino acid sequence of SEQ ID NO: 6090 (or a sequence with no more than 1, 2, 3, 4, 5, or 6 mutations, e.g., substitutions, additions, or deletions, therefrom), a VLFWR3 amino acid sequence of SEQ ID NO: 6091 (or a sequence with no more than 1, 2, 3, 4, 5, or 6 mutations, e.g., substitutions, additions, or deletions, therefrom), or a VLFWR4 amino acid sequence of SEQ ID NO: 6092 (or a sequence with no more than 1, 2, 3, 4, 5, or 6 mutations, e.g., substitutions, additions, or deletions, therefrom).

41. The antibody molecule of embodiment 40, wherein the antigen binding domain comprises a light chain variable region (VL) comprising a light chain framework region 1 (VLFWR1) amino acid sequence of SEQ ID NO: 6089, a VLFWR2 amino acid sequence of SEQ ID NO: 6090, a VLFWR3 amino acid sequence of SEQ ID NO: 6091, or a VLFWR4 amino acid sequence of SEQ ID NO: 6092.

42. The antibody molecule of embodiment 41, wherein the antigen binding domain comprises a VL comprising the amino acid sequence of SEQ ID NO: 6140 (or an amino acid sequence having at least about 93%, 95%, or 99% sequence identity to SEQ ID NO: 6140).

43. The antibody molecule of any of embodiments 5, 6, or 13-30, wherein the antigen binding domain comprises a light chain variable region (VL) comprising a light chain framework region 1 (VLFWR1) amino acid sequence of SEQ ID NO: 6093 (or a sequence with no more than 1, 2, 3, 4, 5, or 6 mutations, e.g., substitutions, additions, or deletions, therefrom), a VLFWR2 amino acid sequence of SEQ ID NO: 6094 (or a sequence with no more than 1, 2, 3, 4, 5, or 6 mutations, e.g., substitutions, additions, or deletions, therefrom), a VLFWR3 amino acid sequence of SEQ ID NO: 6095 (or a sequence with no more than 1, 2, 3, 4, 5, or 6 mutations, e.g., substitutions, additions, or deletions, therefrom), or a VLFWR4 amino acid sequence of SEQ ID NO: 6096 (or a sequence with no more than 1, 2, 3, 4, 5, or 6 mutations, e.g., substitutions, additions, or deletions, therefrom).

44. The antibody molecule of embodiment 43, wherein the antigen binding domain comprises a light chain variable region (VL) comprising a light chain framework region 1 (VLFWR1) amino acid sequence of SEQ ID NO: 6093, a VLFWR2 amino acid sequence of SEQ ID NO: 6094, a VLFWR3 amino acid sequence of SEQ ID NO: 6095, or a VLFWR4 amino acid sequence of SEQ ID NO: 6096.

45. The antibody molecule of embodiment 44, wherein the antigen binding domain comprises a VL comprising the amino acid sequence of SEQ ID NO: 6141 (or an amino acid sequence having at least about 93%, 95%, or 99% sequence identity to SEQ ID NO: 6141).

46. An isolated antibody molecule that binds to NKp30, comprising:
(i) a heavy chain variable region (VH) comprising a heavy chain complementarity determining region 1 (VHCDR1) amino acid sequence of SEQ ID NO: 6007 (or a sequence with no more than 1, 2, 3, or 4 mutations, e.g., substitutions, additions, or deletions), a VHCDR2 amino acid sequence of SEQ ID NO: 6008 (or a sequence with no more than 1, 2, 3, or 4 mutations, e.g., substitutions, additions, or deletions), and/or a VHCDR3 amino acid sequence of SEQ ID NO: 6009 (or a sequence with no more than 1, 2, 3, or 4 mutations, e.g., substitutions, additions, or deletions), and
(ii) a light chain variable region (VL) comprising a light chain complementarity determining region 1 (VLCDR1) amino acid sequence of SEQ ID NO: 6070 (or a sequence with no more than 1, 2, 3, or 4 mutations, e.g., substitutions, additions, or deletions), a VLCDR2 amino acid sequence of SEQ ID NO: 6071 (or a sequence with no more than 1, 2, 3, or 4 mutations, e.g., substitutions, additions, or deletions), and/or a VLCDR3 amino acid sequence of SEQ ID NO: 6072 (or a sequence with no more than 1, 2, 3, or 4 mutations, e.g., substitutions, additions, or deletions).

47. The antibody molecule of embodiment 46, wherein the antigen binding domain comprises:
(i) a heavy chain variable region (VH) comprising a heavy chain complementarity determining region 1 (VHCDR1) amino acid sequence of SEQ ID NO: 6007, a VHCDR2 amino acid sequence of SEQ ID NO: 6008, and/or a VHCDR3 amino acid sequence of SEQ ID NO: 6009, and
(ii) a light chain variable region (VL) comprising a light chain complementarity determining region 1 (VLCDR1) amino acid sequence of SEQ ID NO: 6070, a VLCDR2 amino acid sequence of SEQ ID NO: 6071, and/or a VLCDR3 amino acid sequence of SEQ ID NO: 6072.

48. The antibody molecule of embodiments 46 or 47, wherein the antigen binding domain comprises:
(1) a heavy chain variable region (VH) comprising a heavy chain framework region 1 (VHFWR1) amino acid sequence of SEQ ID NO: 6010 (or a sequence with no more than 1, 2, 3, 4, 5, or 6 mutations, e.g., substitutions, additions, or deletions, therefrom), a VHFWR2 amino acid sequence of SEQ ID NO: 6011 (or a sequence with no more than 1, 2, 3, 4, 5, or 6 mutations, e.g., substitutions, additions, or deletions, therefrom), a VHFWR3 amino acid sequence of SEQ ID NO: 6012 (or a sequence with no more than 1, 2, 3, 4, 5, or 6 mutations, e.g., substitutions, additions, or deletions, therefrom), or a VHFWR4 amino acid sequence of SEQ ID NO: 6013 (or a sequence with no more than 1, 2, 3, 4, 5, or 6 mutations, e.g., substitutions, additions, or deletions, therefrom), and/or
(2) a light chain variable region (VL) comprising a light chain framework region 1 (VLFWR1) amino acid sequence of SEQ ID NO: 6073 (or a sequence with no more than 1, 2, 3, 4, 5, or 6 mutations, e.g., substitutions, additions, or deletions, therefrom), a VLFWR2 amino acid sequence of SEQ ID NO: 6074 (or a sequence with no more than 1, 2, 3, 4, 5, or 6 mutations, e.g., substitutions, additions, or deletions, therefrom), a VLFWR3 amino acid sequence of SEQ ID NO: 6075 (or a sequence with no more than 1, 2, 3, 4, 5, or 6 mutations, e.g., substitutions, additions, or deletions, therefrom), or a VLFWR4 amino acid sequence of SEQ ID NO: 6076 (or a sequence with no more than 1, 2, 3, 4, 5, or 6 mutations, e.g., substitutions, additions, or deletions, therefrom).

49. The antibody molecule of embodiment 48, wherein the antigen binding domain comprises:
(1) a heavy chain variable region (VH) comprising a heavy chain framework region 1 (VHFWR1) amino acid sequence of SEQ ID NO: 6010, a VHFWR2 amino acid sequence of SEQ ID NO: 6011, a VHFWR3 amino acid sequence of SEQ ID NO: 6012, or a VHFWR4 amino acid sequence of SEQ ID NO: 6013, and
(3) a light chain variable region (VL) comprising a light chain framework region 1 (VLFWR1) amino acid sequence of SEQ ID NO: 6073, a VLFWR2 amino acid sequence of SEQ ID NO: 6074, a VLFWR3 amino acid sequence of SEQ ID NO: 6075, or a VLFWR4 amino acid sequence of SEQ ID NO: 6076.

50. The antibody molecule of any one of embodiments 46-49, wherein the antigen binding domain comprises:
(i) a VH comprising the amino acid sequence of SEQ ID NO: 6122 (or an amino acid sequence having at least about 75%, 80%, 85%, 90%, 95%, or 99% sequence identity to SEQ ID NO: 6122), and/or
(ii) a VL comprising the amino acid sequence of SEQ ID NO: 6136 (or an amino acid sequence having at least about 93%, 95%, or 99% sequence identity to SEQ ID NO: 6136).

51. The antibody molecule of any of embodiments 46-50, wherein the antigen binding domain comprises a heavy chain comprising the amino acid sequence of SEQ ID NOs: 6151 or 6152 (or an amino acid sequence having at least about 75%, 80%, 85%, 90%, 95%, or 99% sequence identity to SEQ ID NOs: 6151 or 6152).

52. The antibody molecule of any of embodiments 46-51, wherein the antigen binding domain comprises a light chain comprising the amino acid sequence of SEQ ID NO: 6153 (or an amino acid sequence having at least about 75%, 80%, 85%, 90%, 95%, or 99% sequence identity to SEQ ID NO: 6153).

53. The antibody molecule of any of embodiments 46-51, wherein the antigen binding domain comprises a heavy chain comprising the amino acid sequence of SEQ ID NOs: 6151 or 6152 (or an amino acid sequence having at least about 75%, 80%, 85%, 90%, 95%, or 99% sequence identity to SEQ ID NOs: 6151 or 6152), and a light chain comprising the amino acid sequence of SEQ ID NO: 6153 (or an amino acid sequence having at least about 75%, 80%, 85%, 90%, 95%, or 99% sequence identity to SEQ ID NO: 6153).

54. The antibody molecule of embodiments 46 or 47, wherein the antigen binding domain comprises a heavy chain variable region (VH) comprising a heavy chain framework region 1 (VHFWR1) amino acid sequence of SEQ ID NO: 6039 (or a sequence with no more than 1, 2, 3, 4, 5, or 6 mutations, e.g., substitutions, additions, or deletions, therefrom), a VHFWR2 amino acid sequence of SEQ ID NO: 6040 (or a sequence with no more than 1, 2, 3, 4, 5, or 6 mutations, e.g., substitutions, additions, or deletions, therefrom), a VHFWR3 amino acid sequence of SEQ ID NO: 6041 (or a sequence with no more than 1, 2, 3, 4, 5, or 6 mutations, e.g., substitutions, additions, or deletions, therefrom), or a VHFWR4 amino acid sequence of SEQ ID NO: 6042 (or a sequence with no more than 1, 2, 3, 4, 5, or 6 mutations, e.g., substitutions, additions, or deletions, therefrom).

55. The antibody molecule of embodiment 54, wherein the antigen binding domain comprises a heavy chain variable region (VH) comprising a heavy chain framework region 1 (VHFWR1) amino acid sequence of SEQ ID NO: 6039, a VHFWR2 amino acid sequence of SEQ ID NO: 6040, a VHFWR3 amino acid sequence of SEQ ID NO: 6041, or a VHFWR4 amino acid sequence of SEQ ID NO: 6042.

56. The antibody molecule of embodiment 55, wherein the antigen binding domain comprises a VH comprising the amino acid sequence of SEQ ID NO: 6129 (or an amino acid sequence having at least about 75%, 80%, 85%, 90%, 95%, or 99% sequence identity to SEQ ID NO: 6129).

57. The antibody molecule of embodiments 46 or 47, wherein the antigen binding domain comprises a heavy chain variable region (VH) comprising a heavy chain framework region 1 (VHFWR1) amino acid sequence of SEQ ID NO: 6043 (or a sequence with no more than 1, 2, 3, 4, 5, or 6 mutations, e.g., substitutions, additions, or deletions, therefrom), a VHFWR2 amino acid sequence of SEQ ID NO: 6044 (or a sequence with no more than 1, 2, 3, 4, 5, or 6 mutations, e.g., substitutions, additions, or deletions, therefrom), a VHFWR3 amino acid sequence of SEQ ID NO: 6045 (or a sequence with no more than 1, 2, 3, 4, 5, or 6 mutations, e.g., substitutions, additions, or deletions, therefrom), or a VHFWR4 amino acid sequence of SEQ ID NO: 6046 (or a sequence with no more than 1, 2, 3, 4, 5, or 6 mutations, e.g., substitutions, additions, or deletions, therefrom).

58. The antibody molecule of embodiment 57, wherein the antigen binding domain comprises a heavy chain variable region (VH) comprising a heavy chain framework region 1 (VHFWR1) amino acid sequence of SEQ ID NO: 6043, a VHFWR2 amino acid sequence of SEQ ID NO: 6044, a VHFWR3 amino acid sequence of SEQ ID NO: 6045, or a VHFWR4 amino acid sequence of SEQ ID NO: 6046.

59. The antibody molecule of embodiment 58, wherein the antigen binding domain comprises a VH comprising the amino acid sequence of SEQ ID NO: 6130 (or an amino acid sequence having at least about 75%, 80%, 85%, 90%, 95%, or 99% sequence identity to SEQ ID NO: 6130).

60. The antibody molecule of any of embodiments 46 or 47, wherein the antigen binding domain comprises a heavy chain variable region (VH) comprising a heavy chain framework region 1 (VHFWR1) amino acid sequence of SEQ ID NO: 6047 (or a sequence with no more than 1, 2, 3, 4, 5, or 6 mutations, e.g., substitutions, additions, or deletions, therefrom), a VHFWR2 amino acid sequence of SEQ ID NO: 6048 (or a sequence with no more than 1, 2, 3, 4, 5, or 6 mutations, e.g., substitutions, additions, or deletions, therefrom), a VHFWR3 amino acid sequence of SEQ ID NO: 6049 (or a sequence with no more than 1, 2, 3, 4, 5, or 6 mutations, e.g., substitutions, additions, or deletions, therefrom), or a VHFWR4 amino acid sequence of SEQ ID NO: 6050 (or a sequence with no more than 1, 2, 3, 4, 5, or 6 mutations, e.g., substitutions, additions, or deletions, therefrom).

61. The antibody molecule of embodiment 60, wherein the antigen binding domain comprises a heavy chain variable region (VH) comprising a heavy chain framework region 1 (VHFWR1) amino acid sequence of SEQ ID NO: 6047, a VHFWR2 amino acid sequence of SEQ ID NO: 6048, a VHFWR3 amino acid sequence of SEQ ID NO: 6049, or a VHFWR4 amino acid sequence of SEQ ID NO: 6050.

62. The antibody molecule of embodiment 61, wherein the antigen binding domain comprises a VH comprising the amino acid sequence of SEQ ID NO: 6131 (or an amino acid sequence having at least about 75%, 80%, 85%, 90%, 95%, or 99% sequence identity to SEQ ID NO: 6131).

63. The antibody molecule of any of embodiments 46 or 47, wherein the antigen binding domain comprises a heavy chain variable region (VH) comprising a heavy chain framework region 1 (VHFWR1) amino acid sequence of SEQ ID NO: 6051 (or a sequence with no more than 1, 2, 3, 4, 5, or 6 mutations, e.g., substitutions, additions, or deletions, therefrom), a VHFWR2 amino acid sequence of SEQ ID NO: 6052 (or a sequence with no more than 1, 2, 3, 4, 5, or 6 mutations, e.g., substitutions, additions, or deletions, therefrom), a VHFWR3 amino acid sequence of SEQ ID NO: 6053 (or a sequence with no more than 1, 2, 3, 4, 5, or 6 mutations, e.g., substitutions, additions, or deletions, therefrom), or a VHFWR4 amino acid sequence of SEQ ID NO: 6054 (or a sequence with no more than 1, 2, 3, 4, 5, or 6 mutations, e.g., substitutions, additions, or deletions, therefrom).

64. The antibody molecule of embodiment 63, wherein the antigen binding domain comprises a heavy chain variable region (VH) comprising a heavy chain framework region 1 (VHFWR1) amino acid sequence of SEQ ID NO: 6051, a VHFWR2 amino acid sequence of SEQ ID NO: 6052, a VHFWR3 amino acid sequence of SEQ ID NO: 6053, or a VHFWR4 amino acid sequence of SEQ ID NO: 6054.

65. The antibody molecule of embodiment 64, wherein the antigen binding domain comprises a VH comprising the amino acid sequence of SEQ ID NO: 6132 (or an amino acid sequence having at least about 75%, 80%, 85%, 90%, 95%, or 99% sequence identity to SEQ ID NO: 6132).

66. The antibody molecule of any of embodiments 46 or 47, wherein the antigen binding domain comprises a heavy chain variable region (VH) comprising a heavy chain framework region 1 (VHFWR1) amino acid sequence of SEQ ID NO: 6055 (or a sequence with no more than 1, 2, 3, 4, 5, or 6 mutations, e.g., substitutions, additions, or deletions, therefrom), a VHFWR2 amino acid sequence of SEQ ID NO: 6056 (or a sequence with no more than 1, 2, 3, 4, 5, or 6 mutations, e.g., substitutions, additions, or deletions, therefrom), a VHFWR3 amino acid sequence of SEQ ID NO: 6057 (or a sequence with no more than 1, 2, 3, 4, 5, or 6 mutations, e.g., substitutions, additions, or deletions, therefrom), or a VHFWR4 amino acid sequence of SEQ ID NO: 6058 (or a sequence with no more than 1, 2, 3, 4, 5, or 6 mutations, e.g., substitutions, additions, or deletions, therefrom).

67. The antibody molecule of embodiment 66, wherein the antigen binding domain comprises a heavy chain variable region (VH) comprising a heavy chain framework region 1 (VHFWR1) amino acid sequence of SEQ ID NO: 6055, a VHFWR2 amino acid sequence of SEQ ID NO: 6056, a VHFWR3 amino acid sequence of SEQ ID NO: 6057, or a VHFWR4 amino acid sequence of SEQ ID NO: 6058.

68. The antibody molecule of embodiment 67, wherein the antigen binding domain comprises a VH comprising the amino acid sequence of SEQ ID NO: 6133 (or an amino acid sequence having at least about 75%, 80%, 85%, 90%, 95%, or 99% sequence identity to SEQ ID NO: 6133).

69. The antibody molecule of any of embodiments 46 or 47, wherein the antigen binding domain comprises a heavy chain variable region (VH) comprising a heavy chain framework region 1 (VHFWR1) amino acid sequence of SEQ ID NO: 6059 (or a sequence with no more than 1, 2, 3, 4, 5, or 6 mutations, e.g., substitutions, additions, or deletions, therefrom), a VHFWR2 amino acid sequence of SEQ ID NO: 6060 (or a sequence with no more than 1, 2, 3, 4, 5, or 6 mutations, e.g., substitutions, additions, or deletions, therefrom), a VHFWR3 amino acid sequence of SEQ ID NO: 6061 (or a sequence with no more than 1, 2, 3, 4, 5, or 6 mutations, e.g., substitutions, additions, or deletions, therefrom), or a VHFWR4 amino acid sequence of SEQ ID NO: 6062 (or a sequence with no more than 1, 2, 3, 4, 5, or 6 mutations, e.g., substitutions, additions, or deletions, therefrom).

70. The antibody molecule of embodiment 69, wherein the antigen binding domain comprises a heavy chain variable region (VH) comprising a heavy chain framework region 1 (VHFWR1) amino acid sequence of SEQ ID NO: 6059, a VHFWR2 amino acid sequence of SEQ ID NO: 6060, a VHFWR3 amino acid sequence of SEQ ID NO: 6061, or a VHFWR4 amino acid sequence of SEQ ID NO: 6062.

71. The antibody molecule of embodiment 70, wherein the antigen binding domain comprises a VH comprising the amino acid sequence of SEQ ID NO: 6134 (or an amino acid sequence having at least about 75%, 80%, 85%, 90%, 95%, or 99% sequence identity to SEQ ID NO: 6134).

72. The antibody molecule of any of embodiments 46, 47, or 54-71, wherein the antigen binding domain comprises a light chain variable region (VL) comprising a light chain framework region 1 (VLFWR1) amino acid sequence of SEQ ID NO: 6097 (or a sequence with no more than 1, 2, 3, 4, 5, or 6 mutations, e.g., substitutions, additions, or deletions, therefrom), a VLFWR2 amino acid sequence of SEQ ID NO: 6098 (or a sequence with no more than 1, 2, 3, 4, 5, or 6 mutations, e.g., substitutions, additions, or deletions, therefrom), a VLFWR3 amino acid sequence of SEQ ID NO: 6099 (or a sequence with no more than 1, 2, 3, 4, 5, or 6 mutations, e.g., substitutions, additions, or deletions, therefrom), or a VLFWR4 amino acid sequence of SEQ ID NO: 6100 (or a sequence with no more than 1, 2, 3, 4, 5, or 6 mutations, e.g., substitutions, additions, or deletions, therefrom).

73. The antibody molecule of embodiment 72, wherein the antigen binding domain comprises a light chain variable region (VL) comprising a light chain framework region 1 (VLFWR1) amino acid sequence of SEQ ID NO: 6097, a VLFWR2 amino acid sequence of SEQ ID NO: 6098, a VLFWR3 amino acid sequence of SEQ ID NO: 6099, or a VLFWR4 amino acid sequence of SEQ ID NO: 6100.

74. The antibody molecule of embodiment 73, wherein the antigen binding domain comprises a VL comprising the amino acid sequence of SEQ ID NO: 6142 (or an amino acid sequence having at least about 93%, 95%, or 99% sequence identity to SEQ ID NO: 6142).

75. The antibody molecule of any of embodiments 46, 47, or 54-74, wherein the antigen binding domain comprises a light chain variable region (VL) comprising a light chain framework region 1 (VLFWR1) amino acid sequence of SEQ ID NO: 6101 (or a sequence with no more than 1, 2, 3, 4, 5, or 6 mutations, e.g., substitutions, additions, or deletions, therefrom), a VLFWR2 amino acid sequence of SEQ ID NO: 6102 (or a sequence with no more than 1, 2, 3, 4, 5, or 6 mutations, e.g., substitutions, additions, or deletions, therefrom), a VLFWR3 amino acid sequence of SEQ ID NO: 6103 (or a sequence with no more than 1, 2, 3, 4, 5, or 6 mutations, e.g., substitutions, additions, or deletions, therefrom), or a VLFWR4 amino acid sequence of SEQ ID NO: 6104 (or a sequence with no more than 1, 2, 3, 4, 5, or 6 mutations, e.g., substitutions, additions, or deletions, therefrom).

76. The antibody molecule of embodiment 75, wherein the antigen binding domain comprises a light chain variable region (VL) comprising a light chain framework region 1 (VLFWR1) amino acid sequence of SEQ ID NO: 6101, a VLFWR2 amino acid sequence of SEQ ID NO: 6102, a VLFWR3 amino acid sequence of SEQ ID NO: 6103, or a VLFWR4 amino acid sequence of SEQ ID NO: 6104.

77. The antibody molecule of embodiment 76, wherein the antigen binding domain comprises a VL comprising the amino acid sequence of SEQ ID NO: 6143 (or an amino acid sequence having at least about 93%, 95%, or 99% sequence identity to SEQ ID NO: 6143).

78. The antibody molecule of any of embodiments 46, 47, or 54-77, wherein the antigen binding domain comprises a light chain variable region (VL) comprising a light chain framework region 1 (VLFWR1) amino acid sequence of SEQ ID NO: 6105 (or a sequence with no more than 1, 2, 3, 4, 5, or 6 mutations, e.g., substitutions, additions, or deletions, therefrom), a VLFWR2 amino acid sequence of SEQ ID NO: 6106 (or a sequence with no more than 1, 2, 3, 4, 5, or 6 mutations, e.g., substitutions, additions, or deletions, therefrom), a VLFWR3 amino acid sequence of SEQ ID NO: 6107 (or a sequence with no more than 1, 2, 3, 4, 5, or 6 mutations, e.g., substitutions, additions, or deletions, therefrom), or a VLFWR4 amino acid sequence of SEQ ID NO: 6108 (or a sequence with no more than 1, 2, 3, 4, 5, or 6 mutations, e.g., substitutions, additions, or deletions, therefrom).

79. The antibody molecule of embodiment 78, wherein the antigen binding domain comprises a light chain variable region (VL) comprising a light chain framework region 1 (VLFWR1) amino acid sequence of SEQ ID NO: 6105, a VLFWR2 amino acid sequence of SEQ ID NO: 6106, a VLFWR3 amino acid sequence of SEQ ID NO: 6107, or a VLFWR4 amino acid sequence of SEQ ID NO: 6108.

80. The antibody molecule of embodiment 79, wherein the antigen binding domain comprises a VL comprising the amino acid sequence of SEQ ID NO: 6144 (or an amino acid sequence having at least about 93%, 95%, or 99% sequence identity to SEQ ID NO: 6144).

81. The antibody molecule of any of embodiments 46, 47, or 54-80, wherein the antigen binding domain comprises a light chain variable region (VL) comprising a light chain framework region 1 (VLFWR1) amino acid sequence of SEQ ID NO: 6109 (or a sequence with no more than 1, 2, 3, 4, 5, or 6 mutations, e.g., substitutions, additions, or deletions, therefrom), a VLFWR2 amino acid sequence of SEQ ID NO: 6110 (or a sequence with no more than 1, 2, 3, 4, 5, or 6 mutations, e.g., substitutions, additions, or deletions, therefrom), a VLFWR3 amino acid sequence of SEQ ID NO: 6111 (or a sequence with no more than 1, 2, 3, 4, 5, or 6 mutations, e.g., substitutions, additions, or deletions, therefrom), or a VLFWR4 amino acid sequence of SEQ ID NO: 6112 (or a sequence with no more than 1, 2, 3, 4, 5, or 6 mutations, e.g., substitutions, additions, or deletions, therefrom).

82. The antibody molecule of embodiment 81, wherein the antigen binding domain comprises a light chain variable region (VL) comprising a light chain framework region 1 (VLFWR1) amino acid sequence of SEQ ID NO: 6109, a VLFWR2 amino acid sequence of SEQ ID NO: 6110, a VLFWR3 amino acid sequence of SEQ ID NO: 6111, or a VLFWR4 amino acid sequence of SEQ ID NO: 6112.

83. The antibody molecule of embodiment 78, wherein the antigen binding domain comprises a VL comprising the amino acid sequence of SEQ ID NO: 6145 (or an amino acid sequence having at least about 93%, 95%, or 99% sequence identity to SEQ ID NO: 6145).

84. The antibody molecule of any of embodiments 46, 47, or 54-83, wherein the antigen binding domain comprises a light chain variable region (VL) comprising a light chain framework region 1 (VLFWR1) amino acid sequence of SEQ ID NO: 6113 (or a sequence with no more than 1, 2, 3, 4, 5, or 6 mutations, e.g., substitutions, additions, or deletions, therefrom), a VLFWR2 amino acid sequence of SEQ ID NO: 6114 (or a sequence with no more than 1, 2, 3, 4, 5, or 6 mutations, e.g., substitutions, additions, or deletions, therefrom), a VLFWR3 amino acid sequence of SEQ ID NO: 6115 (or a sequence with no more than 1, 2, 3, 4, 5, or 6 mutations, e.g., substitutions, additions, or deletions, therefrom), or a VLFWR4 amino acid sequence of SEQ ID NO: 6116 (or a sequence with no more than 1, 2, 3, 4, 5, or 6 mutations, e.g., substitutions, additions, or deletions, therefrom).

85. The antibody molecule of embodiment 84, wherein the antigen binding domain comprises a light chain variable region (VL) comprising a light chain framework region 1 (VLFWR1) amino acid sequence of SEQ ID NO: 6113, a VLFWR2 amino acid sequence of SEQ ID NO: 6114, a VLFWR3 amino acid sequence of SEQ ID NO: 6115, or a VLFWR4 amino acid sequence of SEQ ID NO: 6116.

86. The antibody molecule of embodiment 85, wherein the antigen binding domain comprises a VL comprising the amino acid sequence of SEQ ID NO: 6146 (or an amino acid sequence having at least about 93%, 95%, or 99% sequence identity to SEQ ID NO: 6146).

87. The antibody molecule of any of embodiments 46, 47, or 54-86, wherein the antigen binding domain comprises a light chain variable region (VL) comprising a light chain framework region 1 (VLFWR1) amino acid sequence of SEQ ID NO: 6117 (or a sequence with no more than 1, 2, 3, 4, 5, or 6 mutations, e.g., substitutions, additions, or deletions, therefrom), a VLFWR2 amino acid sequence of SEQ ID NO: 6118 (or a sequence with no more than 1, 2, 3, 4, 5, or 6 mutations, e.g., substitutions, additions, or deletions, therefrom), a VLFWR3 amino acid sequence of SEQ ID NO: 6119 (or a sequence with no more than 1, 2, 3, 4, 5, or 6 mutations, e.g., substitutions, additions, or deletions, therefrom), or a VLFWR4 amino acid sequence of SEQ ID NO: 6120 (or a sequence with no more than 1, 2, 3, 4, 5, or 6 mutations, e.g., substitutions, additions, or deletions, therefrom).

88. The antibody molecule of embodiment 87, wherein the antigen binding domain comprises a light chain variable region (VL) comprising a light chain framework region 1 (VLFWR1) amino acid sequence of SEQ ID NO: 6117, a VLFWR2 amino acid sequence of SEQ ID NO: 6118, a VLFWR3 amino acid sequence of SEQ ID NO: 6119, or a VLFWR4 amino acid sequence of SEQ ID NO: 6120.

89. The antibody molecule of embodiment 88, wherein the antigen binding domain comprises a VL comprising the amino acid sequence of SEQ ID NO: 6147 (or an amino acid sequence having at least about 93%, 95%, or 99% sequence identity to SEQ ID NO: 6147).

90. The antibody molecule of any one of the preceding embodiments, wherein the antigen binding domain comprises:
(i) a VH comprising the amino acid sequence of SEQ ID NO: 6122 (or an amino acid sequence having at least about 75%, 80%, 85%, 90%, 95%, or 99% sequence identity to SEQ ID NO: 6122), and/or
(ii) a VL comprising the amino acid sequence of SEQ ID NO: 6136 (or an amino acid sequence having at least about 93%, 95%, or 99% sequence identity to SEQ ID NO: 6136).

91. A multispecific molecule comprising the antibody molecule of any of embodiments 1-90.

92. The multispecific molecule of embodiment 91, further comprising one, two, three, four or more of:
 a. a tumor targeting moiety, e.g., as described herein;
 b. a cytokine molecule, e.g., as described herein;
 c. a T cell engager, e.g., as described herein; or
 d. a stromal modifying moiety, e.g., as described herein.

93. The multispecific molecule of embodiment 91, further comprising a binding specificity that binds to an autoreactive T cell, e.g., an antigen present on the surface of an autoreactive T cell that is associated with the inflammatory or autoimmune disorder.

94. The multispecific molecule of embodiment 91, further comprising a binding specificity that binds to an infected cell, e.g., a viral or bacterial infected cell.

95. The antibody molecule, or the multispecific molecule of any of the preceding embodiments, which is a monospecific antibody molecule, a bispecific antibody molecule, or a trispecific antibody molecule.

96. The antibody molecule, or the multispecific molecule of any of the preceding embodiments, which is a monovalent antibody molecule, a bivalent antibody molecule, or a trivalent antibody molecule.

97. The antibody molecule, or the multispecific molecule of any of the preceding embodiments, which is a full antibody (e.g., an antibody that includes at least one, and preferably two, complete heavy chains, and at least one, and preferably two, complete light chains), or an antigen-binding fragment (e.g., a Fab, F(ab')$_2$, Fv, a single chain Fv, a single domain antibody, a diabody (dAb), a bivalent antibody, or bispecific antibody or fragment thereof, a single domain variant thereof, or a camelid antibody).

98. The antibody molecule, or the multispecific molecule of any of the preceding embodiments, which comprises a heavy chain constant region chosen from IgG1, IgG2, IgG3, or IgG4, or a fragment thereof.

99. The antibody molecule, or the multispecific molecule of any of the preceding embodiments, which comprises a light chain constant region chosen from the light chain constant regions of kappa or lambda, or a fragment thereof.

100. The antibody molecule, or the multispecific molecule of any of the preceding embodiments, wherein the immunoglobulin chain constant region (e.g., Fc region) is altered, e.g., mutated, to increase or decrease one or more of: Fc receptor binding, antibody glycosylation, the number of cysteine residues, effector cell function, or complement function.

101. The antibody molecule, or the multispecific molecule of any of the preceding embodiments, wherein an interface of a first and second immunoglobulin chain constant regions (e.g., Fc region) is altered, e.g., mutated, to increase or decrease dimerization, e.g., relative to a non-engineered interface.

102. The antibody molecule or the multispecific molecule of embodiment 101, wherein the dimerization of the immunoglobulin chain constant region (e.g., Fc region) is enhanced by providing an Fc interface of a first and a second Fc region with one or more of: a paired cavity-protuberance ("knob-in-a hole"), an electrostatic interaction, or a strand-exchange, such that a greater ratio of heteromultimer:homomultimer forms, e.g., relative to a non-engineered interface.

103. The antibody molecule or the multispecific molecule of embodiment 101 or 102, wherein the immunoglobulin chain constant region (e.g., Fc region) comprises an amino acid substitution at a position chosen from one or more of 347, 349, 350, 351, 366, 368, 370, 392, 394, 395, 397, 398, 399, 405, 407, or 409, e.g., of the Fc region of human IgG1.

104. The antibody molecule or the multispecific molecule of embodiment 103, wherein the immunoglobulin chain constant region (e.g., Fc region) comprises an amino acid substitution chosen from: T366S, L368A, or Y407V (e.g., corresponding to a cavity or hole), or T366W (e.g., corresponding to a protuberance or knob), or a combination thereof.

105. The antibody molecule or the multispecific molecule of any of embodiments 1-104, further comprising a linker, e.g., a linker between one or more of: the targeting moiety and the cytokine molecule or the stromal modifying moiety, the targeting moiety and the immune cell engager, the cytokine molecule or the stromal modifying moiety and the immune cell engager, the cytokine molecule or the stromal modifying moiety and the immunoglobulin chain constant region (e.g., the Fc region), the targeting moiety and the immunoglobulin chain constant region, or the immune cell engager and the immunoglobulin chain constant region.

106. The antibody molecule or the multispecific molecule of embodiment 105, wherein the linker is selected from: a cleavable linker, a non-cleavable linker, a peptide linker, a flexible linker, a rigid linker, a helical linker, or a non-helical linker.

107. The antibody molecule or the multispecific molecule of embodiment 106, wherein the linker is a peptide linker.

108. The antibody molecule or the multispecific molecule of embodiment 107, wherein the peptide linker comprises Gly and Ser.

109. An isolated nucleic acid molecule, which comprises the nucleotide sequence encoding any of the antibody molecules or multispecific or multifunctional molecules described herein, or a nucleotide sequence substantially homologous thereto (e.g., at least 95% to 99.9% identical thereto).

110. An isolated nucleic acid encoding the antibody molecule or the multispecific molecule of any of embodiments 1-108.

111. A vector, e.g., an expression vector, comprising one or more of the nucleic acid molecules of any of embodiments 109 or 110.

112. A host cell comprising the nucleic acid molecule or the vector of embodiment 111.

113. A method of making, e.g., producing, the antibody molecule or the multispecific or multifunctional molecule polypeptide of any of embodiments 1-108, comprising culturing the host cell of embodiment 112, under suitable conditions, e.g., conditions suitable for gene expression and/or homo- or heterodimerization.

114. A pharmaceutical composition comprising the antibody molecule or the multispecific or multifunctional molecule polypeptide of any of embodiments 1-108 and a pharmaceutically acceptable carrier, excipient, or stabilizer.

115. A method of treating a cancer, comprising administering to a subject in need thereof the antibody molecule or the multispecific or multifunctional molecule polypeptide of any of the preceding embodiments, wherein the multispecific antibody is administered in an amount effective to treat the cancer.

116. The antibody molecule or the multispecific or multifunctional molecule polypeptide of any of the preceding embodiments for use in treating cancer.

117. The method of embodiment 115 or the use of embodiment 116, wherein the cancer is a solid tumor cancer, or a metastatic lesion.

118. The method of embodiment 117 or the use of embodiment 117, wherein the solid tumor cancer is one or more of pancreatic (e.g., pancreatic adenocarcinoma), breast, colorectal, lung (e.g., small or non-small cell lung cancer), skin, ovarian, or liver cancer.

119. The method of embodiment 115 or the use of embodiment 116, wherein the cancer is a hematological cancer.

120. The method of any of embodiments 115 or 116-119 or the use of any of embodiments 116-119, further comprising administering a second therapeutic treatment.

121. The method of embodiment 120 or the use of embodiment 120, wherein the second therapeutic treatment comprises a therapeutic agent (e.g., a chemotherapeutic agent, a biologic agent, hormonal therapy), radiation, or surgery.

122. The method of embodiment 121 or the use of embodiment 121, wherein the therapeutic agent is selected from: a chemotherapeutic agent, or a biologic agent.

123. A method of treating an autoimmune or an inflammatory disorder, comprising administering to a subject in need thereof the antibody molecule or the multispecific or multifunctional molecule polypeptide of any of the preceding embodiments, wherein the multispecific antibody is administered in an amount effective to treat the autoimmune or the inflammatory disorder.

124. The antibody molecule or the multispecific or multifunctional molecule polypeptide of any of the preceding embodiments for use in treating an autoimmune or an inflammatory disorder.

125. A method of treating an infectious disorder, comprising administering to a subject in need thereof the antibody molecule or the multispecific or multifunctional molecule polypeptide of any of the preceding embodiments, wherein the multispecific antibody is administered in an amount effective to treat the infectious disorder.

126. The antibody molecule or the multispecific or multifunctional molecule polypeptide of any of the preceding embodiments for use in treating an infectious disorder.

DETAILED DESCRIPTION OF THE INVENTION

Definitions

Figure 1:
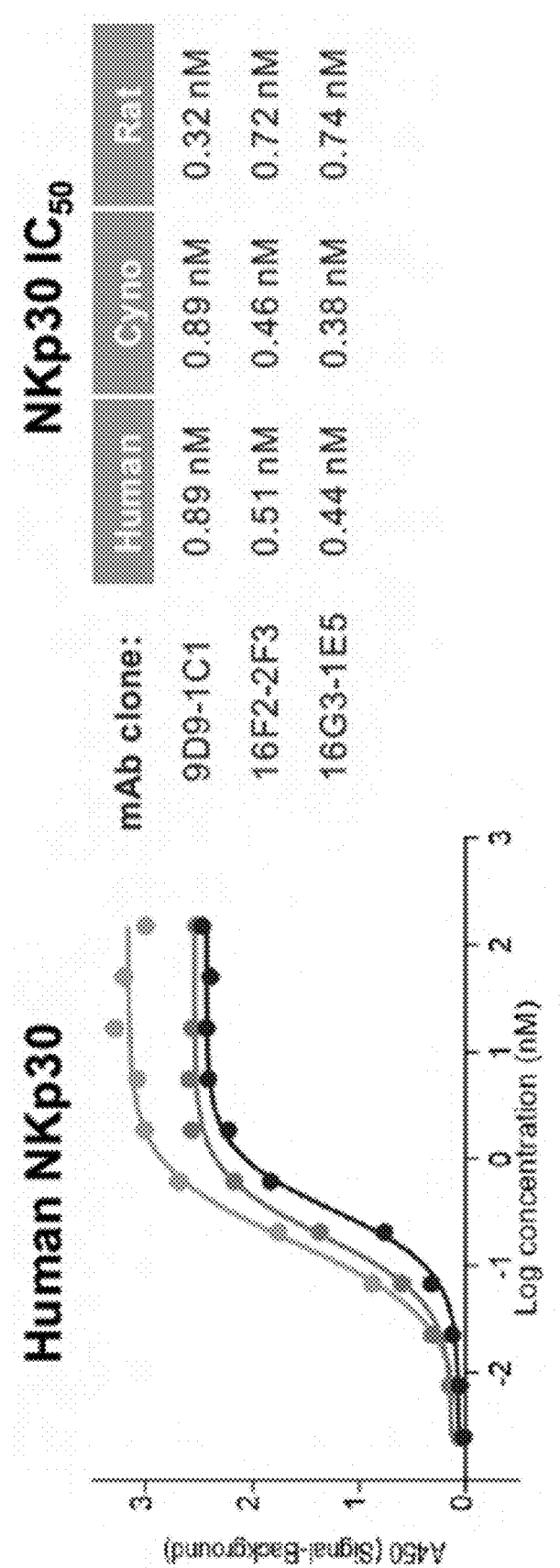
FIG. 1 is a graph showing binding of NKp30 antibodies to NK92 cells. Data was calculated as the percent-AF747 positive population.

Certain terms are defined below.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

As used herein, the term "molecule" as used in, e.g., antibody molecule, cytokine molecule, receptor molecule, includes full-length, naturally-occurring molecules, as well as variants, e.g., functional variants (e.g., truncations, fragments, mutated (e.g., substantially similar sequences) or derivatized form thereof), so long as at least one function and/or activity of the unmodified (e.g., naturally-occurring) molecule remains.

"Antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full-length antibody, or a full-length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs).

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a molecule that can provoke an immune response, e.g., involving activation of certain immune cells and/or antibody generation. Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full-length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site," or "binding portion" of an antibody molecule refers to the part of an antibody molecule, e.g., an immunoglobulin (Ig) molecule, that participates in antigen binding. In embodiments, the antigen binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions," (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4.

"Cancer" as used herein can encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. Innate leukocytes include phagocytes (e.g., macrophages, neutrophils, and dendritic cells), mast cells, eosinophils, basophils, and natural killer cells. Innate leukocytes identify and eliminate pathogens, either by attacking larger pathogens through contact or by engulfing and then killing microorganisms, and are mediators in the activation of an adaptive immune response. The cells of the adaptive immune system are special types of leukocytes, called lymphocytes. B cells and T cells are important types of lymphocytes and are derived from hematopoietic stem cells in the bone marrow. B cells are involved in the humoral immune response, whereas T cells are involved in cell-mediated immune response. The term "immune cell" includes immune effector cells.

"Immune effector cell," as that term is used herein, refers to a cell that is involved in an immune response, e.g., in the promotion of an immune effector response. Examples of immune effector cells include, but are not limited to, T cells, e.g., alpha/beta T cells and gamma/delta T cells, B cells, natural killer (NK) cells, natural killer T (NK T) cells, and mast cells.

The term "effector function" or "effector response" refers to a specialized function of a cell. Effector function of a T cell, for example, may be cytolytic activity or helper activity including the secretion of cytokines.

The compositions and methods of the present invention encompass polypeptides and nucleic acids having the sequences specified, or sequences substantially identical or similar thereto, e.g., sequences at least 80%, 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 80%, 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 80%, 85%, 90%, 91%, 92%, 93%, 94%, 95%, 96%, 97%, 98% or 99% identity to a reference sequence, e.g., a sequence provided herein.

The term "variant" refers to a polypeptide that has a substantially identical amino acid sequence to a reference amino acid sequence, or is encoded by a substantially identical nucleotide sequence. In some embodiments, the variant is a functional variant.

The term "functional variant" refers to a polypeptide that has a substantially identical amino acid sequence to a reference amino acid sequence, or is encoded by a substantially identical nucleotide sequence, and is capable of having one or more activities of the reference amino acid sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and) XBLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See ncbi.nlm.nih.gov.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Natural Killer Cell Engagers

Natural Killer (NK) cells recognize and destroy tumors and virus-infected cells in an antibody-independent manner. The regulation of NK cells is mediated by activating and inhibiting receptors on the NK cell surface. One family of activating receptors is the natural cytotoxicity receptors (NCRs) which include NKp30, NKp44 and NKp46. The NCRs initiate tumor targeting by recognition of heparan sulfate on cancer cells. NKG2D is a receptor that provides both stimulatory and costimulatory innate immune responses on activated killer (NK) cells, leading to cytotoxic activity. DNAM1 is a receptor involved in intercellular adhesion, lymphocyte signaling, cytotoxicity and lymphokine secretion mediated by cytotoxic T-lymphocyte (CTL) and NK cell. DAP10 (also known as HCST) is a transmembrane adapter protein which associates with KLRK1 to form an activation receptor KLRK1-HCST in lymphoid and myeloid cells; this receptor plays a major role in triggering cytotoxicity against target cells expressing cell surface ligands such as MHC class I chain-related MICA and MICB, and U (optionally L1)6-binding proteins (ULBPs); it KLRK1-HCST receptor plays a role in immune surveillance against tumors and is required for cytolysis of tumors cells; indeed, melanoma cells that do not express KLRK1 ligands escape from immune surveillance mediated by NK cells. CD16 is a receptor for the Fc region of IgG, which binds complexed or aggregated IgG and also monomeric IgG and thereby mediates antibody-dependent cellular cytotoxicity (ADCC) and other antibody-dependent responses, such as phagocytosis.

The present disclosure provides, inter alia, antibody molecules, e.g., multispecific (e.g., bi-, tri-, quad-specific) or multifunctional molecules, that are engineered to contain one or more NK cell engagers that mediate binding to and/or activation of an NK cell. Accordingly, in some embodiments, the NK cell engager is selected from an antigen binding domain or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80, CD244 (also known as SLAMF4 or 2B4), SLAMF6, SLAMF7, KIR2DS2, KIR2DS4, KIR3DS1, KIR2DS3, KIR2DS5, KIR2DS1, CD94, NKG2C, NKG2E, or CD160.

In some embodiments, the NK cell engager is an antigen binding domain that binds to NKp30 (e.g., NKp30 present, e.g., expressed or displayed, on the surface of an NK cell) and comprises any CDR amino acid sequence, framework region (FWR) amino acid sequence, or variable region amino acid sequence disclosed in Tables 7-10. In some embodiments, the NK cell engager is an antigen binding domain that binds to NKp30 (e.g., NKp30 present, e.g., expressed or displayed, on the surface of an NK cell) and comprises any CDR amino acid sequence, framework region (FWR) amino acid sequence, or variable region amino acid sequence disclosed in U.S. Pat. Nos. 6,979,546, 9,447,185, PCT Application No. WO2015121383A1, PCT Application No. WO2016110468A1, PCT Application No. WO2004056392A1, or U.S. Application Publication No. US20070231322A1, the sequences of which are hereby incorporated by reference. In some embodiments, binding of the NK cell engager, e.g., antigen binding domain that binds to NKp30, to the NK cell activates the NK cell. An antigen binding domain that binds to NKp30 (e.g., NKp30 present, e.g., expressed or displayed, on the surface of an NK cell) may be said to target NKp30, the NK cell, or both.

In some embodiments, the antigen binding domain that binds to NKp30 comprises one or more CDRs (e.g., VHCDR1, VHCDR2, VHCDR3, VLCDR1, VLCDR2, and/or VLCDR3) disclosed in Table 7, Table 18, or Table 8, or a sequence having at least 85%, 90%, 95%, or 99% identity thereto. In some embodiments, the antigen binding domain that binds to NKp30 comprises one or more framework regions (e.g., VHFWR1, VHFWR2, VHFWR3, VHFWR4, VLFWR1, VLFWR2, VLFWR3, and/or VLFWR4) disclosed in Table 7, Table 18, or Table 8, or a sequence having at least 85%, 90%, 95%, or 99% identity thereto. In some embodiments, the antigen binding domain that binds to NKp30 comprises a VH and/or a VL disclosed in Table 9, or a sequence having at least 85%, 90%, 95%, or 99% identity thereto. In some embodiments, any of the VH domains disclosed in Table 9 may be paired with any of the VL domains disclosed in Table 9 to form the antigen binding domain that binds to NKp30. In some embodiments, the antigen binding domain that binds to NKp30 comprises an amino acid sequence disclosed in Table 10, or a sequence having at least 85%, 90%, 95%, or 99% identity thereto.

In some embodiments, the antigen binding domain that binds to NKp30 comprises a VH comprising a heavy chain complementarity determining region 1 (VHCDR1), a VHCDR2, and a VHCDR3, and a VL comprising a light chain complementarity determining region 1 (VLCDR1), a VLCDR2, and a VLCDR3.

In some embodiments, the VHCDR1, VHCDR2, and VHCDR3 comprise the amino acid sequences of SEQ ID NOs: 7313, 6001, and 7315, respectively (or a sequence having at least 85%, 90%, 95%, or 99% identity thereto). In some embodiments, the VHCDR1, VHCDR2, and VHCDR3 comprise the amino acid sequences of SEQ ID NOs: 7313, 6001, and 6002, respectively (or a sequence having at least 85%, 90%, 95%, or 99% identity thereto). In some embodiments, the VHCDR1, VHCDR2, and VHCDR3 comprise the amino acid sequences of SEQ ID NOs: 7313, 6008, and 6009, respectively (or a sequence having at least 85%, 90%, 95%, or 99% identity thereto). In some embodiments, the VHCDR1, VHCDR2, and VHCDR3 comprise the amino acid sequences of SEQ ID NOs: 7313, 7385, and 7315, respectively (or a sequence having at least 85%, 90%, 95%, or 99% identity thereto). In some embodiments, the VHCDR1, VHCDR2, and VHCDR3 comprise the amino acid sequences of SEQ ID NOs: 7313, 7318, and 6009, respectively (or a sequence having at least 85%, 90%, 95%, or 99% identity thereto).

In some embodiments, the VLCDR1, VLCDR2, and VLCDR3 comprise the amino acid sequences of SEQ ID NOs: 7326, 7327, and 7329, respectively (or a sequence having at least 85%, 90%, 95%, or 99% identity thereto). In some embodiments, the VLCDR1, VLCDR2, and VLCDR3 comprise the amino acid sequences of SEQ ID NOs: 6063, 6064, and 7293, respectively (or a sequence having at least 85%, 90%, 95%, or 99% identity thereto). In some embodiments, the VLCDR1, VLCDR2, and VLCDR3 comprise the amino acid sequences of SEQ ID NOs: 6070, 6071, and 6072, respectively (or a sequence having at least 85%, 90%, 95%, or 99% identity thereto). In some embodiments, the VLCDR1, VLCDR2, and VLCDR3 comprise the amino acid sequences of SEQ ID NOs: 6070, 6064, and 7321, respectively (or a sequence having at least 85%, 90%, 95%, or 99% identity thereto).

In some embodiments, the VHCDR1, VHCDR2, VHCDR3, VLCDR1, VLCDR2, and VLCDR3 comprise the amino acid sequences of SEQ ID NOs: 7313, 6001, 7315, 7326, 7327, and 7329, respectively (or a sequence having at least 85%, 90%, 95%, or 99% identity thereto). In some embodiments, the VHCDR1, VHCDR2, VHCDR3, VLCDR1, VLCDR2, and VLCDR3 comprise the amino acid sequences of SEQ ID NOs: 7313, 6001, 6002, 6063, 6064, and 7293, respectively (or a sequence having at least 85%, 90%, 95%, or 99% identity thereto). In some embodiments, the VHCDR1, VHCDR2, VHCDR3, VLCDR1, VLCDR2, and VLCDR3 comprise the amino acid sequences of SEQ ID NOs: 7313, 6008, 6009, 6070, 6071, and 6072, respectively (or a sequence having at least 85%, 90%, 95%, or 99% identity thereto). In some embodiments, the VHCDR1, VHCDR2, VHCDR3, VLCDR1, VLCDR2, and VLCDR3 comprise the amino acid sequences of SEQ ID NOs: 7313, 7385, 7315, 6070, 6064, and 7321, respectively (or a sequence having at least 85%, 90%, 95%, or 99% identity thereto). In some embodiments, the VHCDR1, VHCDR2, VHCDR3, VLCDR1, VLCDR2, and VLCDR3 comprise the amino acid sequences of SEQ ID NOs: 7313, 7318, 6009, 6070, 6064, and 7321, respectively (or a sequence having at least 85%, 90%, 95%, or 99% identity thereto).

In some embodiments, the VH comprises an amino acid sequence selected from the group consisting of SEQ ID NOs: 7298 or 7300-7304 (or a sequence having at least 85%, 90%, 95%, or 99% identity thereto) and/or the VL comprises an amino acid sequence selected from the group consisting of SEQ ID NOs: 7299 or 7305-7309 (or a sequence having at least 85%, 90%, 95%, or 99% identity thereto). In some embodiments, the VH and VL comprise the amino acid sequences of SEQ ID NOs: 7302 and 7305, respectively (or a sequence having at least 85%, 90%, 95%, or 99% identity thereto). In some embodiments, the VH and VL comprise the amino acid sequences of SEQ ID NOs: 7302 and 7309, respectively (or a sequence having at least 85%, 90%, 95%, or 99% identity thereto).

In some embodiments, the VH comprises an amino acid sequence selected from the group consisting of SEQ ID NOs: 6121 or 6123-6128 (or a sequence having at least 85%, 90%, 95%, or 99% identity thereto) and/or the VL comprises an amino acid sequence selected from the group consisting of SEQ ID NOs: 7294 or 6137-6141 (or a sequence having at least 85%, 90%, 95%, or 99% identity thereto). In some embodiments, the VH comprises an amino acid sequence selected from the group consisting of SEQ ID NOs: 6122 or 6129-6134 (or a sequence having at least 85%, 90%, 95%, or 99% identity thereto) and/or the VL comprises an amino acid sequence selected from the group consisting of SEQ ID NOs: 6136 or 6142-6147 (or a sequence having at least 85%, 90%, 95%, or 99% identity thereto). In some embodiments, the VH and VL comprise the amino acid sequences of SEQ ID NOs: 7295 and 7296, respectively (or a sequence having at least 85%, 90%, 95%, or 99% identity thereto). In some embodiments, the VH and VL comprise the amino acid sequences of SEQ ID NOs: 7297 and 7296, respectively (or a sequence having at least 85%, 90%, 95%, or 99% identity thereto). In some embodiments, the VH and VL comprise the amino acid sequences of SEQ ID NOs: 6122 and 6136, respectively (or a sequence having at least 85%, 90%, 95%, or 99% identity thereto).

In some embodiments, the antigen binding domain that binds to NKp30 comprises the amino acid sequence of SEQ ID NO: 7310 (or a sequence having at least 85%, 90%, 95%, or 99% identity thereto). In some embodiments, the antigen binding domain that binds to NKp30 comprises the amino acid sequence of SEQ ID NO: 7311 (or a sequence having at least 85%, 90%, 95%, or 99% identity thereto). In some embodiments, the antigen binding domain that binds to NKp30 comprises the amino acid sequence of SEQ ID NO: 6187, 6188, 6189 or 6190 (or a sequence having at least 85%, 90%, 95%, or 99% identity thereto).

In some embodiments, the antigen binding domain that targets NKp30 comprises a VH comprising a heavy chain complementarity determining region 1 (VHCDR1) amino acid sequence of SEQ ID NO: 6000 (or a sequence with no more than 1, 2, 3, or 4 mutations, e.g., substitutions, additions, or deletions), a VHCDR2 amino acid sequence of SEQ ID NO: 6001 (or a sequence with no more than 1, 2, 3, or 4 mutations, e.g., substitutions, additions, or deletions), and/or a VHCDR3 amino acid sequence of SEQ ID NO: 6002 (or a sequence with no more than 1, 2, 3, or 4 mutations, e.g., substitutions, additions, or deletions). In some embodiments, the NKp30 antigen binding domain comprises a VH comprising a VHCDR1 amino acid sequence of SEQ ID NO: 6000, a VHCDR2 amino acid sequence of SEQ ID NO: 6001, and/or a VHCDR3 amino acid sequence of SEQ ID NO: 6002.

In some embodiments, the antigen binding domain that targets NKp30 comprises a VL comprising a light chain complementarity determining region 1 (VLCDR1) amino acid sequence of SEQ ID NO: 6063 (or a sequence with no more than 1, 2, 3, or 4 mutations, e.g., substitutions, additions, or deletions), a VLCDR2 amino acid sequence of SEQ ID NO: 6064 (or a sequence with no more than 1, 2, 3, or 4 mutations, e.g., substitutions, additions, or deletions), and/or a VLCDR3 amino acid sequence of SEQ ID NO: 7293 (or a sequence with no more than 1, 2, 3, or 4 mutations, e.g., substitutions, additions, or deletions). In some embodiments, the antigen binding domain that targets NKp30 comprises a VL comprising a VLCDR1 amino acid sequence of SEQ ID NO: 6063, a VLCDR2 amino acid sequence of SEQ ID NO: 6064, and a VLCDR3 amino acid sequence of SEQ ID NO: 7293.

In some embodiments, the antigen binding domain that targets NKp30 comprises a VH comprising a heavy chain complementarity determining region 1 (VHCDR1) amino acid sequence of SEQ ID NO: 6000 (or a sequence with no more than 1, 2, 3, or 4 mutations, e.g., substitutions, additions, or deletions), a VHCDR2 amino acid sequence of SEQ ID NO: 6001 (or a sequence with no more than 1, 2, 3, or 4 mutations, e.g., substitutions, additions, or deletions), and/or a VHCDR3 amino acid sequence of SEQ ID NO: 6002 (or a sequence with no more than 1, 2, 3, or 4 mutations, e.g., substitutions, additions, or deletions), and a VL comprising a light chain complementarity determining region 1 (VLCDR1) amino acid sequence of SEQ ID NO: 6063 (or a sequence with no more than 1, 2, 3, or 4 mutations, e.g., substitutions, additions, or deletions), a VLCDR2 amino acid sequence of SEQ ID NO: 6064 (or a sequence with no more than 1, 2, 3, or 4 mutations, e.g., substitutions, additions, or deletions), and/or a VLCDR3 amino acid sequence of SEQ ID NO: 7293 (or a sequence with no more than 1, 2, 3, or 4 mutations, e.g., substitutions, additions, or deletions). In some embodiments, the NKp30 antigen binding domain comprises a VH comprising a VHCDR1 amino acid sequence of SEQ ID NO: 6000, a VHCDR2 amino acid sequence of SEQ ID NO: 6001, and/or a VHCDR3 amino acid sequence of SEQ ID NO: 6002, and a VL comprising a VLCDR1 amino acid sequence of SEQ ID NO: 6063, a VLCDR2 amino acid sequence of SEQ ID NO: 6064, and a VLCDR3 amino acid sequence of SEQ ID NO: 7293.

In some embodiments, the antigen binding domain that targets NKp30 comprises a VH comprising a heavy chain complementarity determining region 1 (VHCDR1) amino acid sequence of SEQ ID NO: 6007 (or a sequence with no more than 1, 2, 3, or 4 mutations, e.g., substitutions, additions, or deletions), a VHCDR2 amino acid sequence of SEQ ID NO: 6008 (or a sequence with no more than 1, 2, 3, or 4 mutations, e.g., substitutions, additions, or deletions), and/or a VHCDR3 amino acid sequence of SEQ ID NO: 6009 (or a sequence with no more than 1, 2, 3, or 4 mutations, e.g., substitutions, additions, or deletions). In some embodiments, the NKp30 antigen binding domain comprises a VH comprising a VHCDR1 amino acid sequence of SEQ ID NO: 6007, a VHCDR2 amino acid sequence of SEQ ID NO: 6008, and/or a VHCDR3 amino acid sequence of SEQ ID NO: 6009.

In some embodiments, the antigen binding domain that targets NKp30 comprises a VL comprising a light chain complementarity determining region 1 (VLCDR1) amino acid sequence of SEQ ID NO: 6070 (or a sequence with no more than 1, 2, 3, or 4 mutations, e.g., substitutions, additions, or deletions), a VLCDR2 amino acid sequence of SEQ ID NO: 6071 (or a sequence with no more than 1, 2, 3, or 4 mutations, e.g., substitutions, additions, or deletions), and/or a VLCDR3 amino acid sequence of SEQ ID NO: 6072 (or a sequence with no more than 1, 2, 3, or 4 mutations, e.g., substitutions, additions, or deletions). In some embodiments, the antigen binding domain that targets NKp30 comprises a VL comprising a VLCDR1 amino acid sequence of SEQ ID NO: 6070, a VLCDR2 amino acid sequence of SEQ ID NO: 6071, and a VLCDR3 amino acid sequence of SEQ ID NO: 6072.

In some embodiments, the antigen binding domain that targets NKp30 comprises a VH comprising a heavy chain complementarity determining region 1 (VHCDR1) amino acid sequence of SEQ ID NO: 6007 (or a sequence with no more than 1, 2, 3, or 4 mutations, e.g., substitutions, additions, or deletions), a VHCDR2 amino acid sequence of SEQ ID NO: 6008 (or a sequence with no more than 1, 2, 3, or 4 mutations, e.g., substitutions, additions, or deletions), and/or a VHCDR3 amino acid sequence of SEQ ID NO: 6009 (or a sequence with no more than 1, 2, 3, or 4 mutations, e.g., substitutions, additions, or deletions), and a VL comprising a light chain complementarity determining region 1 (VLCDR1) amino acid sequence of SEQ ID NO: 6070 (or a sequence with no more than 1, 2, 3, or 4 mutations, e.g., substitutions, additions, or deletions), a VLCDR2 amino acid sequence of SEQ ID NO: 6071 (or a sequence with no more than 1, 2, 3, or 4 mutations, e.g., substitutions, additions, or deletions), and/or a VLCDR3 amino acid sequence of SEQ ID NO: 6072 (or a sequence with no more than 1, 2, 3, or 4 mutations, e.g., substitutions, additions, or deletions). In some embodiments, the NKp30 antigen binding domain comprises a VH comprising a VHCDR1 amino acid sequence of SEQ ID NO: 6007, a VHCDR2 amino acid sequence of SEQ ID NO: 6008, and/or a VHCDR3 amino acid sequence of SEQ ID NO: 6009, and a VL comprising a VLCDR1 amino acid sequence of SEQ ID NO: 6070, a VLCDR2 amino acid sequence of SEQ ID NO: 6071, and a VLCDR3 amino acid sequence of SEQ ID NO: 6072.

In some embodiments, the antigen binding domain that targets NKp30 comprises a VH comprising a heavy chain framework region 1 (VHFWR1) amino acid sequence of SEQ ID NO: 6003, a VHFWR2 amino acid sequence of SEQ ID NO: 6004, a VHFWR3 amino acid sequence of SEQ ID NO: 6005, and/or a VHFWR4 amino acid sequence of SEQ ID NO: 6006.

In some embodiments, the antigen binding domain that targets NKp30 comprises a VL comprising a light chain framework region 1 (VLFWR1) amino acid sequence of SEQ ID NO: 6066, a VLFWR2 amino acid sequence of SEQ ID NO: 6067, a VLFWR3 amino acid sequence of SEQ ID NO: 7292, and/or a VLFWR4 amino acid sequence of SEQ ID NO: 6069.

In some embodiments, the antigen binding domain that targets NKp30 comprises a VH comprising a heavy chain framework region 1 (VHFWR1) amino acid sequence of SEQ ID NO: 6003, a VHFWR2 amino acid sequence of SEQ ID NO: 6004, a VHFWR3 amino acid sequence of SEQ ID NO: 6005, and/or a VHFWR4 amino acid sequence of SEQ ID NO: 6006, and a VL comprising a light chain framework region 1 (VLFWR1) amino acid sequence of SEQ ID NO: 6066, a VLFWR2 amino acid sequence of SEQ ID NO: 6067, a VLFWR3 amino acid sequence of SEQ ID NO: 7292, and/or a VLFWR4 amino acid sequence of SEQ ID NO: 6069.

In some embodiments, the antigen binding domain that targets NKp30 comprises a VH comprising a VHFWR1 amino acid sequence of SEQ ID NO: 6003 (or a sequence with no more than 1, 2, 3, 4, 5, or 6 mutations, e.g., substitutions, additions, or deletions, therefrom), a VHFWR2 amino acid sequence of SEQ ID NO: 6004 (or a sequence with no more than 1, 2, 3, 4, 5, or 6 mutations, e.g., substitutions, additions, or deletions, therefrom), a VHFWR3 amino acid sequence of SEQ ID NO: 6005 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6006.

In some embodiments, the antigen binding domain that targets NKp30 comprises a VL comprising a VLFWR1 amino acid sequence of SEQ ID NO: 6066 (or a sequence with no more than 1, 2, or 3 mutations, e.g., substitutions, additions, or deletions), a VLFWR2 amino acid sequence of SEQ ID NO: 6067 (or a sequence with no more than 1 mutation, e.g., substitution, addition, or deletion), a VLFWR3 amino acid sequence of SEQ ID NO: 7292 (or a sequence with no more than 1 mutation, e.g., substitution, addition, or deletion), and/or a VLFWR4 amino acid sequence of SEQ ID NO: 6069.

In some embodiments, the antigen binding domain that targets NKp30 comprises a VH comprising a VHFWR1 amino acid sequence of SEQ ID NO: 6003 (or a sequence with no more than 1, 2, 3, 4, 5, or 6 mutations, e.g., substitutions, additions, or deletions, therefrom), a VHFWR2 amino acid sequence of SEQ ID NO: 6004 (or a sequence with no more than 1, 2, 3, 4, 5, or 6 mutations, e.g., substitutions, additions, or deletions, therefrom), a VHFWR3 amino acid sequence of SEQ ID NO: 6005 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6006, and a VL comprising a VLFWR1 amino acid sequence of SEQ ID NO: 6066 (or a sequence with no more than 1, 2, or 3 mutations, e.g., substitutions, additions, or deletions), a VLFWR2 amino acid sequence of SEQ ID NO: 6067 (or a sequence with no more than 1 mutation, e.g., substitution, addition, or deletion), a VLFWR3 amino acid sequence of SEQ ID NO: 7292 (or a sequence with no more than 1 mutation, e.g., substitution, addition, or deletion), and/or a VLFWR4 amino acid sequence of SEQ ID NO: 6069.

In some embodiments, the antigen binding domain that targets NKp30 comprises a VH comprising a heavy chain framework region 1 (VHFWR1) amino acid sequence of SEQ ID NO: 6010, a VHFWR2 amino acid sequence of SEQ ID NO: 6011, a VHFWR3 amino acid sequence of SEQ ID NO: 6012, and/or a VHFWR4 amino acid sequence of SEQ ID NO: 6013.

In some embodiments, the antigen binding domain that targets NKp30 comprises a VL comprising a light chain framework region 1 (VLFWR1) amino acid sequence of SEQ ID NO: 6073, a VLFWR2 amino acid sequence of SEQ ID NO: 6074, a VLFWR3 amino acid sequence of SEQ ID NO: 6075, and/or a VLFWR4 amino acid sequence of SEQ ID NO: 6076.

In some embodiments, the antigen binding domain that targets NKp30 comprises a VH comprising a heavy chain framework region 1 (VHFWR1) amino acid sequence of SEQ ID NO: 6010, a VHFWR2 amino acid sequence of SEQ ID NO: 6011, a VHFWR3 amino acid sequence of SEQ ID NO: 6012, and/or a VHFWR4 amino acid sequence of SEQ ID NO: 6013, and a VL comprising a light chain framework region 1 (VLFWR1) amino acid sequence of SEQ ID NO: 6073, a VLFWR2 amino acid sequence of SEQ ID NO: 6074, a VLFWR3 amino acid sequence of SEQ ID NO: 6075, and/or a VLFWR4 amino acid sequence of SEQ ID NO: 6076.

In some embodiments, the antigen binding domain that targets NKp30 comprises a VH comprising a VHFWR1 amino acid sequence of SEQ ID NO: 6010 (or a sequence with no more than 1, 2, 3, 4, 5, or 6 mutations, e.g., substitutions, additions, or deletions, therefrom), a VHFWR2 amino acid sequence of SEQ ID NO: 6011 (or a sequence with no more than 1, 2, 3, 4, 5, or 6 mutations, e.g., substitutions, additions, or deletions, therefrom), a VHFWR3 amino acid sequence of SEQ ID NO: 6012 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6013.

In some embodiments, the antigen binding domain that targets NKp30 comprises a VL comprising a VLFWR1 amino acid sequence of SEQ ID NO: 6073 (or a sequence with no more than 1, 2, or 3 mutations, e.g., substitutions, additions, or deletions), a VLFWR2 amino acid sequence of SEQ ID NO: 6074 (or a sequence with no more than 1 mutation, e.g., substitution, addition, or deletion), a VLFWR3 amino acid sequence of SEQ ID NO: 6075 (or a sequence with no more than 1 mutation, e.g., substitution, addition, or deletion), and/or a VLFWR4 amino acid sequence of SEQ ID NO: 6076.

In some embodiments, the antigen binding domain that targets NKp30 comprises a VH comprising a VHFWR1 amino acid sequence of SEQ ID NO: 6010 (or a sequence with no more than 1, 2, 3, 4, 5, or 6 mutations, e.g., substitutions, additions, or deletions, therefrom), a VHFWR2 amino acid sequence of SEQ ID NO: 6011 (or a sequence with no more than 1, 2, 3, 4, 5, or 6 mutations, e.g., substitutions, additions, or deletions, therefrom), a VHFWR3 amino acid sequence of SEQ ID NO: 6012 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6013, and a VL comprising a VLFWR1 amino acid sequence of SEQ ID NO: 6073 (or a sequence with no more than 1, 2, or 3 mutations, e.g., substitutions, additions, or deletions), a VLFWR2 amino acid sequence of SEQ ID NO: 6074 (or a sequence with no more than 1 mutation, e.g., substitution, addition, or deletion), a VLFWR3 amino acid sequence of SEQ ID NO: 6075 (or a sequence with no more than 1 mutation, e.g., substitution, addition, or deletion), and/or a VLFWR4 amino acid sequence of SEQ ID NO: 6076.

In some embodiments, the antigen binding domain that targets NKp30 comprises a VH comprising a heavy chain framework region 1 (VHFWR1) amino acid sequence of SEQ ID NO: 6014, a VHFWR2 amino acid sequence of SEQ ID NO: 6015, a VHFWR3 amino acid sequence of SEQ ID NO: 6016, and/or a VHFWR4 amino acid sequence of SEQ ID NO: 6017.

In some embodiments, the antigen binding domain that targets NKp30 comprises a VH comprising a VHFWR1 amino acid sequence of SEQ ID NO: 6014 (or a sequence with no more than 1, 2, 3, 4, 5, or 6 mutations, e.g., substitutions, additions, or deletions, therefrom), a VHFWR2 amino acid sequence of SEQ ID NO: 6015 (or a sequence with no more than 1, 2, 3, 4, 5, or 6 mutations, e.g., substitutions, additions, or deletions, therefrom), a VHFWR3 amino acid sequence of SEQ ID NO: 6016 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6017.

In some embodiments, the antigen binding domain that targets NKp30 comprises a VL comprising a light chain framework region 1 (VLFWR1) amino acid sequence of SEQ ID NO: 6077, a VLFWR2 amino acid sequence of SEQ ID NO: 6078, a VLFWR3 amino acid sequence of SEQ ID NO: 6079, and/or a VLFWR4 amino acid sequence of SEQ ID NO: 6080.

In some embodiments, the antigen binding domain that targets NKp30 comprises a VL comprising a VLFWR1 amino acid sequence of SEQ ID NO: 6077 (or a sequence with no more than 1, 2, or 3 mutations, e.g., substitutions, additions, or deletions), a VLFWR2 amino acid sequence of SEQ ID NO: 6078 (or a sequence with no more than 1 mutation, e.g., substitution, addition, or deletion), a VLFWR3 amino acid sequence of SEQ ID NO: 6079 (or a sequence with no more than 1 mutation, e.g., substitution, addition, or deletion), and/or a VLFWR4 amino acid sequence of SEQ ID NO: 6080.

In some embodiments, the antigen binding domain that targets NKp30 comprises a VH comprising a heavy chain framework region 1 (VHFWR1) amino acid sequence of SEQ ID NO: 6018, a VHFWR2 amino acid sequence of SEQ ID NO: 6019, a VHFWR3 amino acid sequence of SEQ ID NO: 6020, and/or a VHFWR4 amino acid sequence of SEQ ID NO: 6021.

In some embodiments, the antigen binding domain that targets NKp30 comprises a VH comprising a VHFWR1 amino acid sequence of SEQ ID NO: 6018 (or a sequence with no more than 1, 2, 3, 4, 5, or 6 mutations, e.g., substitutions, additions, or deletions, therefrom), a VHFWR2 amino acid sequence of SEQ ID NO: 6019 (or a sequence with no more than 1, 2, 3, 4, 5, or 6 mutations, e.g., substitutions, additions, or deletions, therefrom), a VHFWR3 amino acid sequence of SEQ ID NO: 6020 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6021.

In some embodiments, the antigen binding domain that targets NKp30 comprises a VL comprising a light chain framework region 1 (VLFWR1) amino acid sequence of SEQ ID NO: 6081, a VLFWR2 amino acid sequence of SEQ ID NO: 6082, a VLFWR3 amino acid sequence of SEQ ID NO: 6083, and/or a VLFWR4 amino acid sequence of SEQ ID NO: 6084.

In some embodiments, the antigen binding domain that targets NKp30 comprises a VL comprising a VLFWR1 amino acid sequence of SEQ ID NO: 6081 (or a sequence with no more than 1, 2, or 3 mutations, e.g., substitutions, additions, or deletions), a VLFWR2 amino acid sequence of SEQ ID NO: 6082 (or a sequence with no more than 1 mutation, e.g., substitution, addition, or deletion), a VLFWR3 amino acid sequence of SEQ ID NO: 6083 (or a sequence with no more than 1 mutation, e.g., substitution, addition, or deletion), and/or a VLFWR4 amino acid sequence of SEQ ID NO: 6084.

In some embodiments, the antigen binding domain that targets NKp30 comprises a VH comprising a heavy chain framework region 1 (VHFWR1) amino acid sequence of SEQ ID NO: 6022, a VHFWR2 amino acid sequence of SEQ ID NO: 6023, a VHFWR3 amino acid sequence of SEQ ID NO: 6024, and/or a VHFWR4 amino acid sequence of SEQ ID NO: 6025.

In some embodiments, the antigen binding domain that targets NKp30 comprises a VH comprising a VHFWR1 amino acid sequence of SEQ ID NO: 6022 (or a sequence with no more than 1, 2, 3, 4, 5, or 6 mutations, e.g., substitutions, additions, or deletions, therefrom), a VHFWR2 amino acid sequence of SEQ ID NO: 6023 (or a sequence with no more than 1, 2, 3, 4, 5, or 6 mutations, e.g., substitutions, additions, or deletions, therefrom), a VHFWR3 amino acid sequence of SEQ ID NO: 6024 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6025.

In some embodiments, the antigen binding domain that targets NKp30 comprises a VL comprising a light chain framework region 1 (VLFWR1) amino acid sequence of SEQ ID NO: 6085, a VLFWR2 amino acid sequence of SEQ ID NO: 6086, a VLFWR3 amino acid sequence of SEQ ID NO: 6087, and/or a VLFWR4 amino acid sequence of SEQ ID NO: 6088.

In some embodiments, the antigen binding domain that targets NKp30 comprises a VL comprising a VLFWR1 amino acid sequence of SEQ ID NO: 6085 (or a sequence with no more than 1, 2, or 3 mutations, e.g., substitutions, additions, or deletions), a VLFWR2 amino acid sequence of SEQ ID NO: 6086 (or a sequence with no more than 1 mutation, e.g., substitution, addition, or deletion), a VLFWR3 amino acid sequence of SEQ ID NO: 6087 (or a sequence with no more than 1 mutation, e.g., substitution, addition, or deletion), and/or a VLFWR4 amino acid sequence of SEQ ID NO: 6088.

In some embodiments, the antigen binding domain that targets NKp30 comprises a VH comprising a heavy chain framework region 1 (VHFWR1) amino acid sequence of SEQ ID NO: 6026, a VHFWR2 amino acid sequence of SEQ ID NO: 6027, a VHFWR3 amino acid sequence of SEQ ID NO: 6028, and/or a VHFWR4 amino acid sequence of SEQ ID NO: 6029.

In some embodiments, the antigen binding domain that targets NKp30 comprises a VH comprising a VHFWR1 amino acid sequence of SEQ ID NO: 6026 (or a sequence with no more than 1, 2, 3, 4, 5, or 6 mutations, e.g., substitutions, additions, or deletions, therefrom), a VHFWR2 amino acid sequence of SEQ ID NO: 6027 (or a sequence with no more than 1, 2, 3, 4, 5, or 6 mutations, e.g., substitutions, additions, or deletions, therefrom), a VHFWR3 amino acid sequence of SEQ ID NO: 6028 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6029.

In some embodiments, the antigen binding domain that targets NKp30 comprises a VL comprising a light chain framework region 1 (VLFWR1) amino acid sequence of SEQ ID NO: 6089, a VLFWR2 amino acid sequence of SEQ ID NO: 6090, a VLFWR3 amino acid sequence of SEQ ID NO: 6091, and/or a VLFWR4 amino acid sequence of SEQ ID NO: 6092.

In some embodiments, the antigen binding domain that targets NKp30 comprises a VL comprising a VLFWR1 amino acid sequence of SEQ ID NO: 6089 (or a sequence with no more than 1, 2, or 3 mutations, e.g., substitutions, additions, or deletions), a VLFWR2 amino acid sequence of SEQ ID NO: 6090 (or a sequence with no more than 1 mutation, e.g., substitution, addition, or deletion), a VLFWR3 amino acid sequence of SEQ ID NO: 6091 (or a sequence with no more than 1 mutation, e.g., substitution, addition, or deletion), and/or a VLFWR4 amino acid sequence of SEQ ID NO: 6092.

In some embodiments, the antigen binding domain that targets NKp30 comprises a VH comprising a heavy chain framework region 1 (VHFWR1) amino acid sequence of SEQ ID NO: 6030, a VHFWR2 amino acid sequence of SEQ ID NO: 6032, a VHFWR3 amino acid sequence of SEQ ID NO: 6033, and/or a VHFWR4 amino acid sequence of SEQ ID NO: 6034.

In some embodiments, the antigen binding domain that targets NKp30 comprises a VH comprising a VHFWR1 amino acid sequence of SEQ ID NO: 6030 (or a sequence with no more than 1, 2, 3, 4, 5, or 6 mutations, e.g., substitutions, additions, or deletions, therefrom), a VHFWR2 amino acid sequence of SEQ ID NO: 6032 (or a sequence with no more than 1, 2, 3, 4, 5, or 6 mutations, e.g., substitutions, additions, or deletions, therefrom), a VHFWR3 amino acid sequence of SEQ ID NO: 6033 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6034.

In some embodiments, the antigen binding domain that targets NKp30 comprises a VL comprising a light chain framework region 1 (VLFWR1) amino acid sequence of SEQ ID NO: 6093, a VLFWR2 amino acid sequence of SEQ ID NO: 6094, a VLFWR3 amino acid sequence of SEQ ID NO: 6095, and/or a VLFWR4 amino acid sequence of SEQ ID NO: 6096.

In some embodiments, the antigen binding domain that targets NKp30 comprises a VL comprising a VLFWR1 amino acid sequence of SEQ ID NO: 6093 (or a sequence with no more than 1, 2, or 3 mutations, e.g., substitutions, additions, or deletions), a VLFWR2 amino acid sequence of SEQ ID NO: 6094 (or a sequence with no more than 1 mutation, e.g., substitution, addition, or deletion), a VLFWR3 amino acid sequence of SEQ ID NO: 6095 (or a sequence with no more than 1 mutation, e.g., substitution, addition, or deletion), and/or a VLFWR4 amino acid sequence of SEQ ID NO: 6096.

In some embodiments, the antigen binding domain that targets NKp30 comprises a VH comprising a heavy chain framework region 1 (VHFWR1) amino acid sequence of SEQ ID NO: 6035, a VHFWR2 amino acid sequence of SEQ ID NO: 6036, a VHFWR3 amino acid sequence of SEQ ID NO: 6037, and/or a VHFWR4 amino acid sequence of SEQ ID NO: 6038.

In some embodiments, the antigen binding domain that targets NKp30 comprises a VH comprising a VHFWR1 amino acid sequence of SEQ ID NO: 6035 (or a sequence with no more than 1, 2, 3, 4, 5, or 6 mutations, e.g., substitutions, additions, or deletions, therefrom), a VHFWR2 amino acid sequence of SEQ ID NO: 6036 (or a sequence with no more than 1, 2, 3, 4, 5, or 6 mutations, e.g., substitutions, additions, or deletions, therefrom), a VHFWR3 amino acid sequence of SEQ ID NO: 6037 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6038.

In some embodiments, the antigen binding domain that targets NKp30 comprises a VH comprising a heavy chain framework region 1 (VHFWR1) amino acid sequence of SEQ ID NO: 6039, a VHFWR2 amino acid sequence of SEQ ID NO: 6040, a VHFWR3 amino acid sequence of SEQ ID NO: 6041, and/or a VHFWR4 amino acid sequence of SEQ ID NO: 6042.

In some embodiments, the antigen binding domain that targets NKp30 comprises a VH comprising a VHFWR1 amino acid sequence of SEQ ID NO: 6039 (or a sequence with no more than 1, 2, 3, 4, 5, or 6 mutations, e.g., substitutions, additions, or deletions, therefrom), a VHFWR2 amino acid sequence of SEQ ID NO: 6040 (or a sequence with no more than 1, 2, 3, 4, 5, or 6 mutations, e.g., substitutions, additions, or deletions, therefrom), a VHFWR3 amino acid sequence of SEQ ID NO: 6041 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6042.

In some embodiments, the antigen binding domain that targets NKp30 comprises a VL comprising a light chain framework region 1 (VLFWR1) amino acid sequence of SEQ ID NO: 6097, a VLFWR2 amino acid sequence of SEQ ID NO: 6098, a VLFWR3 amino acid sequence of SEQ ID NO: 6099, and/or a VLFWR4 amino acid sequence of SEQ ID NO: 6100.

In some embodiments, the antigen binding domain that targets NKp30 comprises a VL comprising a VLFWR1 amino acid sequence of SEQ ID NO: 6097 (or a sequence with no more than 1, 2, or 3 mutations, e.g., substitutions, additions, or deletions), a VLFWR2 amino acid sequence of SEQ ID NO: 6098 (or a sequence with no more than 1 mutation, e.g., substitution, addition, or deletion), a VLFWR3 amino acid sequence of SEQ ID NO: 6099 (or a sequence with no more than 1 mutation, e.g., substitution, addition, or deletion), and/or a VLFWR4 amino acid sequence of SEQ ID NO: 6100.

In some embodiments, the antigen binding domain that targets NKp30 comprises a VH comprising a heavy chain framework region 1 (VHFWR1) amino acid sequence of SEQ ID NO: 6043, a VHFWR2 amino acid sequence of SEQ ID NO: 6044, a VHFWR3 amino acid sequence of SEQ ID NO: 6045, and/or a VHFWR4 amino acid sequence of SEQ ID NO: 6046.

In some embodiments, the antigen binding domain that targets NKp30 comprises a VH comprising a VHFWR1 amino acid sequence of SEQ ID NO: 6043 (or a sequence with no more than 1, 2, 3, 4, 5, or 6 mutations, e.g., substitutions, additions, or deletions, therefrom), a VHFWR2 amino acid sequence of SEQ ID NO: 6044 (or a sequence with no more than 1, 2, 3, 4, 5, or 6 mutations, e.g., substitutions, additions, or deletions, therefrom), a VHFWR3 amino acid sequence of SEQ ID NO: 6045 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6046.

In some embodiments, the antigen binding domain that targets NKp30 comprises a VL comprising a light chain framework region 1 (VLFWR1) amino acid sequence of SEQ ID NO: 6101, a VLFWR2 amino acid sequence of SEQ ID NO: 6102, a VLFWR3 amino acid sequence of SEQ ID NO: 6103, and/or a VLFWR4 amino acid sequence of SEQ ID NO: 6104.

In some embodiments, the antigen binding domain that targets NKp30 comprises a VL comprising a VLFWR1 amino acid sequence of SEQ ID NO: 6101 (or a sequence with no more than 1, 2, or 3 mutations, e.g., substitutions, additions, or deletions), a VLFWR2 amino acid sequence of SEQ ID NO: 6102 (or a sequence with no more than 1 mutation, e.g., substitution, addition, or deletion), a VLFWR3 amino acid sequence of SEQ ID NO: 6103 (or a sequence with no more than 1 mutation, e.g., substitution, addition, or deletion), and/or a VLFWR4 amino acid sequence of SEQ ID NO: 6104.

In some embodiments, the antigen binding domain that targets NKp30 comprises a VH comprising a heavy chain framework region 1 (VHFWR1) amino acid sequence of SEQ ID NO: 6047, a VHFWR2 amino acid sequence of SEQ ID NO: 6048, a VHFWR3 amino acid sequence of SEQ ID NO: 6049, and/or a VHFWR4 amino acid sequence of SEQ ID NO: 6050.

In some embodiments, the antigen binding domain that targets NKp30 comprises a VH comprising a VHFWR1 amino acid sequence of SEQ ID NO: 6047 (or a sequence with no more than 1, 2, 3, 4, 5, or 6 mutations, e.g., substitutions, additions, or deletions, therefrom), a VHFWR2 amino acid sequence of SEQ ID NO: 6048 (or a sequence with no more than 1, 2, 3, 4, 5, or 6 mutations, e.g., substitutions, additions, or deletions, therefrom), a VHFWR3 amino acid sequence of SEQ ID NO: 6049 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6050.

In some embodiments, the antigen binding domain that targets NKp30 comprises a VL comprising a light chain framework region 1 (VLFWR1) amino acid sequence of SEQ ID NO: 6105, a VLFWR2 amino acid sequence of SEQ ID NO: 6106, a VLFWR3 amino acid sequence of SEQ ID NO: 6107, and/or a VLFWR4 amino acid sequence of SEQ ID NO: 6108.

In some embodiments, the antigen binding domain that targets NKp30 comprises a VL comprising a VLFWR1 amino acid sequence of SEQ ID NO: 6105 (or a sequence with no more than 1, 2, or 3 mutations, e.g., substitutions, additions, or deletions), a VLFWR2 amino acid sequence of SEQ ID NO: 6106 (or a sequence with no more than 1 mutation, e.g., substitution, addition, or deletion), a VLFWR3 amino acid sequence of SEQ ID NO: 6107 (or a sequence with no more than 1 mutation, e.g., substitution, addition, or deletion), and/or a VLFWR4 amino acid sequence of SEQ ID NO: 6108.

In some embodiments, the antigen binding domain that targets NKp30 comprises a VH comprising a heavy chain framework region 1 (VHFWR1) amino acid sequence of SEQ ID NO: 6051, a VHFWR2 amino acid sequence of SEQ ID NO: 6052, a VHFWR3 amino acid sequence of SEQ ID NO: 6053, and/or a VHFWR4 amino acid sequence of SEQ ID NO: 6054.

In some embodiments, the antigen binding domain that targets NKp30 comprises a VH comprising a VHFWR1 amino acid sequence of SEQ ID NO: 6051 (or a sequence with no more than 1, 2, 3, 4, 5, or 6 mutations, e.g., substitutions, additions, or deletions, therefrom), a VHFWR2 amino acid sequence of SEQ ID NO: 6052 (or a sequence with no more than 1, 2, 3, 4, 5, or 6 mutations, e.g., substitutions, additions, or deletions, therefrom), a VHFWR3 amino acid sequence of SEQ ID NO: 6053 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6054.

In some embodiments, the antigen binding domain that targets NKp30 comprises a VL comprising a light chain framework region 1 (VLFWR1) amino acid sequence of SEQ ID NO: 6109, a VLFWR2 amino acid sequence of SEQ ID NO: 6110, a VLFWR3 amino acid sequence of SEQ ID NO: 6111, and/or a VLFWR4 amino acid sequence of SEQ ID NO: 6112.

In some embodiments, the antigen binding domain that targets NKp30 comprises a VL comprising a VLFWR1 amino acid sequence of SEQ ID NO: 6109 (or a sequence with no more than 1, 2, or 3 mutations, e.g., substitutions, additions, or deletions), a VLFWR2 amino acid sequence of SEQ ID NO: 6110 (or a sequence with no more than 1 mutation, e.g., substitution, addition, or deletion), a VLFWR3 amino acid sequence of SEQ ID NO: 6111 (or a sequence with no more than 1 mutation, e.g., substitution, addition, or deletion), and/or a VLFWR4 amino acid sequence of SEQ ID NO: 6112.

In some embodiments, the antigen binding domain that targets NKp30 comprises a VH comprising a heavy chain framework region 1 (VHFWR1) amino acid sequence of SEQ ID NO: 6055, a VHFWR2 amino acid sequence of SEQ ID NO: 6056, a VHFWR3 amino acid sequence of SEQ ID NO: 6057, and/or a VHFWR4 amino acid sequence of SEQ ID NO: 6058.

In some embodiments, the antigen binding domain that targets NKp30 comprises a VH comprising a VHFWR1 amino acid sequence of SEQ ID NO: 6055 (or a sequence with no more than 1, 2, 3, 4, 5, or 6 mutations, e.g., substitutions, additions, or deletions, therefrom), a VHFWR2 amino acid sequence of SEQ ID NO: 6056 (or a sequence with no more than 1, 2, 3, 4, 5, or 6 mutations, e.g., substitutions, additions, or deletions, therefrom), a VHFWR3 amino acid sequence of SEQ ID NO: 6057 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6058.

In some embodiments, the antigen binding domain that targets NKp30 comprises a VL comprising a light chain framework region 1 (VLFWR1) amino acid sequence of SEQ ID NO: 6113, a VLFWR2 amino acid sequence of SEQ ID NO: 6114, a VLFWR3 amino acid sequence of SEQ ID NO: 6115, and/or a VLFWR4 amino acid sequence of SEQ ID NO: 6116.

In some embodiments, the antigen binding domain that targets NKp30 comprises a VL comprising a VLFWR1 amino acid sequence of SEQ ID NO: 6113 (or a sequence with no more than 1, 2, or 3 mutations, e.g., substitutions, additions, or deletions), a VLFWR2 amino acid sequence of SEQ ID NO: 6114 (or a sequence with no more than 1 mutation, e.g., substitution, addition, or deletion), a VLFWR3 amino acid sequence of SEQ ID NO: 6115 (or a sequence with no more than 1 mutation, e.g., substitution, addition, or deletion), and/or a VLFWR4 amino acid sequence of SEQ ID NO: 6116.

In some embodiments, the antigen binding domain that targets NKp30 comprises a VH comprising a heavy chain framework region 1 (VHFWR1) amino acid sequence of SEQ ID NO: 6059, a VHFWR2 amino acid sequence of SEQ ID NO: 6060, a VHFWR3 amino acid sequence of SEQ ID NO: 6061, and/or a VHFWR4 amino acid sequence of SEQ ID NO: 6062.

In some embodiments, the antigen binding domain that targets NKp30 comprises a VH comprising a VHFWR1 amino acid sequence of SEQ ID NO: 6059 (or a sequence with no more than 1, 2, 3, 4, 5, or 6 mutations, e.g., substitutions, additions, or deletions, therefrom), a VHFWR2 amino acid sequence of SEQ ID NO: 6060 (or a sequence with no more than 1, 2, 3, 4, 5, or 6 mutations, e.g., substitutions, additions, or deletions, therefrom), a VHFWR3 amino acid sequence of SEQ ID NO: 6061 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 6062.

In some embodiments, the antigen binding domain that targets NKp30 comprises a VL comprising a light chain framework region 1 (VLFWR1) amino acid sequence of SEQ ID NO: 6117, a VLFWR2 amino acid sequence of SEQ ID NO: 6118, a VLFWR3 amino acid sequence of SEQ ID NO: 6119, and/or a VLFWR4 amino acid sequence of SEQ ID NO: 6120.

In some embodiments, the antigen binding domain that targets NKp30 comprises a VL comprising a VLFWR1 amino acid sequence of SEQ ID NO: 6117 (or a sequence with no more than 1, 2, or 3 mutations, e.g., substitutions, additions, or deletions), a VLFWR2 amino acid sequence of SEQ ID NO: 6118 (or a sequence with no more than 1 mutation, e.g., substitution, addition, or deletion), a VLFWR3 amino acid sequence of SEQ ID NO: 6119 (or a sequence with no more than 1 mutation, e.g., substitution, addition, or deletion), and/or a VLFWR4 amino acid sequence of SEQ ID NO: 6120.

In some embodiments, the antigen binding domain that targets NKp30 comprises a VH comprising the amino acid sequence of SEQ ID NO: 6148 (or an amino acid sequence having at least about 77%, 80%, 85%, 90%, 95%, or 99% sequence identity to SEQ ID NO: 6148). In some embodiments, the antigen binding domain that targets NKp30 comprises a VH comprising the amino acid sequence of SEQ ID NO: 6149 (or an amino acid sequence having at least about 77%, 80%, 85%, 90%, 95%, or 99% sequence identity to SEQ ID NO: 6149). In some embodiments, the antigen binding domain that targets NKp30 comprises a VL comprising the amino acid sequence of SEQ ID NO: 6150 (or an amino acid sequence having at least about 93%, 95%, or 99% sequence identity to SEQ ID NO: 6150). In some embodiments, antigen binding domain that targets NKp30 comprises a VH comprising the amino acid sequence of SEQ ID NO: 6148. In some embodiments, antigen binding domain that targets NKp30 comprises a VH comprising the amino acid sequence of SEQ ID NO: 6149. In some embodiments, the antigen binding domain that targets NKp30 comprises a VL comprising the amino acid sequence of SEQ ID NO: 6150.

In some embodiments, the antigen binding domain that targets NKp30 comprises a VH comprising the amino acid sequence of SEQ ID NO: 6148, and a VL comprising the amino acid sequence of SEQ ID NO: 6150. In some embodiments, the antigen binding domain that targets NKp30 comprises a VH comprising the amino acid sequence of SEQ ID NO: 6149, and a VL comprising the amino acid sequence of SEQ ID NO: 6150.

In some embodiments, the antigen binding domain that targets NKp30 comprises a VH comprising the amino acid sequence of SEQ ID NO: 6151 (or an amino acid sequence having at least about 77%, 80%, 85%, 90%, 95%, or 99% sequence identity to SEQ ID NO: 6151). In some embodiments, the antigen binding domain that targets NKp30 comprises a VH comprising the amino acid sequence of SEQ ID NO: 6152 (or an amino acid sequence having at least about 77%, 80%, 85%, 90%, 95%, or 99% sequence identity to SEQ ID NO: 6152). In some embodiments, the antigen binding domain that targets NKp30 comprises a VL comprising the amino acid sequence of SEQ ID NO: 6153 (or an amino acid sequence having at least about 93%, 95%, or 99% sequence identity to SEQ ID NO: 6153). In some embodiments, antigen binding domain that targets NKp30 comprises a VH comprising the amino acid sequence of SEQ ID NO: 6151. In some embodiments, antigen binding domain that targets NKp30 comprises a VH comprising the amino acid sequence of SEQ ID NO: 6152. In some embodiments, the antigen binding domain that targets NKp30 comprises a VL comprising the amino acid sequence of SEQ ID NO: 6153.

In some embodiments, the antigen binding domain that targets NKp30 comprises a VH comprising the amino acid sequence of SEQ ID NO: 6151, and a VL comprising the amino acid sequence of SEQ ID NO: 6153. In some embodiments, the antigen binding domain that targets NKp30 comprises a VH comprising the amino acid sequence of SEQ ID NO: 6152, and a VL comprising the amino acid sequence of SEQ ID NO: 6153.

In some embodiments, the antigen binding domain that targets NKp30 comprises an scFv. In some embodiments, the scFv comprises an amino acid sequence selected from SEQ ID NOs: 6187-6190, or an amino acid sequence having at least about 93%, 95%, or 99% sequence identity thereto.

TABLE 7

Exemplary heavy chain CDRs and FWRs of NKp30-targeting antigen binding domains

| Ab ID | VHFWR1 | VHCDR1 | VHFWR2 | VHCDR2 | VHFWR3 | VHCDR3 | VHFWR4 |
|---|---|---|---|---|---|---|---|
| 9G1-HC | QIQLQESGPGLVKPSQSLSLTCSVTGFSIN (SEQ ID NO: 6003) | TGGYHWN (SEQ ID NO: 6000) | WIRQFPGKKLEWMG (SEQ ID NO: 6004) | YIYSSGSTSYNPSLKS (SEQ ID NO: 6001) | RISITRDTSKNQFFLQLNSVTTEDTATYYCAR (SEQ ID NO: 6005) | GNWHYFDF (SEQ ID NO: 6002) | WGQGTMVTVSS (SEQ ID NO: 6006) |
| 15H6-HC | QIQLQESGPGLVKPSQSLSLTCSVTGFSIN (SEQ ID NO: 6010) | TGGYHWN (SEQ ID NO: 6007) | WIRQFPGKKLEWMG (SEQ ID NO: 6011) | YIYSSGTTRYNPSLKS (SEQ ID NO: 6008) | RISITRDTSKNQFFLQLNSVTPEDTATYYCTR (SEQ ID NO: 6012) | GNWHYFDY (SEQ ID NO: 6009) | WGQGTLVAVSS (SEQ ID NO: 6013) |
| 9G1-HC_1 | QIQLQESGPGLVKPSETLSLTCTVSGFSIN (SEQ ID NO: 6014) | TGGYHWN (SEQ ID NO: 6000) | WIRQPAGKGLEWIG (SEQ ID NO: 6015) | YIYSSGSTSYNPSLKS (SEQ ID NO: 6001) | RVTMSRDTSKNQFSLKLSSVTAADTAVYYCAR (SEQ ID NO: 6016) | GNWHYFDF (SEQ ID NO: 6002) | WGQGTMVTVSS (SEQ ID NO: 6017) |
| 9G1-HC_2 | QIQLQESGPGLVKPSQTLSLTCTVSGFSIN (SEQ ID NO: 6018) | TGGYHWN (SEQ ID NO: 6000) | WIRQHPGKGLEWIG (SEQ ID NO: 6019) | YIYSSGSTSYNPSLKS (SEQ ID NO: 6001) | LVTISRDTSKNQFSLKLSSVTAADTAVYYCAR (SEQ ID NO: 6020) | GNWHYFDF (SEQ ID NO: 6002) | WGQGTMVTVSS (SEQ ID NO: 6021) |
| 9G1-HC_3 | EIQLLESGGGLVQPGGSLRLSCAVSGFSIN (SEQ ID NO: 6022) | TGGYHWN (SEQ ID NO: 6000) | WVRQAPGKGLEWVG (SEQ ID NO: 6023) | YIYSSGSTSYNPSLKS (SEQ ID NO: 6001) | RFTISRDTSKNTFYLQMNSLRAEDTAVYYCAR (SEQ ID NO: 6024) | GNWHYFDF (SEQ ID NO: 6002) | WGQGTMVTVSS (SEQ ID NO: 6025) |
| 9G1-HC_4 | QIQLVQSGAEVKKPGSSVKVSCKVSGFSIN (SEQ ID NO: 6026) | TGGYHWN (SEQ ID NO: 6000) | WVRQAPGQGLEWMG (SEQ ID NO: 6027) | YIYSSGSTSYNPSLKS (SEQ ID NO: 6001) | RVTITRDTSTNTFYMELSSLRSEDTAVYYCAR (SEQ ID NO: 6028) | GNWHYFDF (SEQ ID NO: 6002) | WGQGTMVTVSS (SEQ ID NO: 6029) |
| 9G1-HC_5 | EIQLVESGGGLVQPGGSLRLSCAVSGFSIN (SEQ ID NO: 6030) | TGGYHWN (SEQ ID NO: 6000) | WVRQAPGKGLEWVG (SEQ ID NO: 6032) | YIYSSGSTSYNPSLKS (SEQ ID NO: 6001) | RFTISRDTAKNSFYLQMNSLRAEDTAVYYCAR (SEQ ID NO: 6033) | GNWHYFDF (SEQ ID NO: 6002) | WGQGTMVTVSS (SEQ ID NO: 6034) |
| 9G1-HC_6 | QIQLVQSGAEVKKPGASVKVSCKVSGFSIN (SEQ ID NO: 6035) | TGGYHWN (SEQ ID NO: 6000) | WVRQAPGQGLEWMG (SEQ ID NO: 6036) | YIYSSGSTSYNPSLKS (SEQ ID NO: 6001) | RVTMTRDTSTNTFYMELSSLRSEDTAVYYCAR (SEQ ID NO: 6037) | GNWHYFDF (SEQ ID NO: 6002) | WGQGTMVTVSS (SEQ ID NO: 6038) |
| 15H6-HC_1 | QIQLQESGPGLVKPSQTLSLTCTVSGFSIN (SEQ ID NO: 6039) | TGGYHWN (SEQ ID NO: 6007) | WIRQHPGKGLEWIG (SEQ ID NO: 6040) | YIYSSGTTRYNPSLKS (SEQ ID NO: 6008) | LVTISRDTSKNQFSLKLSSVTAADTAVYYCAR (SEQ ID NO: 6041) | GNWHYFDY (SEQ ID NO: 6009) | WGQGTLVTVSS (SEQ ID NO: 6042) |
| 15H6-HC_2 | QIQLQESGPGLVKPSETLSLTCTVSGFSIN (SEQ ID NO: 6043) | TGGYHWN (SEQ ID NO: 6007) | WIRQPAGKGLEWIG (SEQ ID NO: 6044) | YIYSSGTTRYNPSLKS (SEQ ID NO: 6008) | RVTMSRDTSKNQFSLKLSSVTAADTAVYYCAR (SEQ ID NO: 6045) | GNWHYFDY (SEQ ID NO: 6009) | WGQGTLVTVSS (SEQ ID NO: 6046) |
| 15H6-HC_3 | EIQLLESGGGLVQPGGSLRLSCAVSGFSIN | TGGYHWN (SEQ ID NO: 6007) | WVRQAPGKGLEWVG (SEQ ID NO: | YIYSSGTTRYNPSLKS (SEQ ID NO: | RFTISRDTSKNTFYLQMNSLRAEDTAVYYCAR (SEQ ID | GNWHYFDY (SEQ ID NO: | WGQGTLVTVSS (SEQ ID NO: |

TABLE 7-continued

Exemplary heavy chain CDRs and FWRs of NKp30-targeting antigen binding domains

| Ab ID | VHFWR1 | VHCDR1 | VHFWR2 | VHCDR2 | VHFWR3 | VHCDR3 | VHFWR4 |
|---|---|---|---|---|---|---|---|
| | (SEQ ID NO: 6047) | | ID NO: 6048) | 6008) | (SEQ ID NO: 6049) | 6009) | 6050) |
| 15H6-HC_4 | QIQLVESGGGLVKPGGSLRLSCAVSGFSIN (SEQ ID NO: 6051) | TGGYHWN (SEQ ID NO: 6007) | WIRQAPGKGLEWVG (SEQ ID NO: 6052) | YIYSSGTTRYNPSLKS (SEQ ID NO: 6008) | RFTISRDTAKNSFYLQMNSLRAEDTAVYYCAR (SEQ ID NO: 6053) | GNWHYFDY (SEQ ID NO: 6009) | WGQGTLVTVSS (SEQ ID NO: 6054) |
| 15H6-HC_5 | QIQLVQSGAEVKKPGASVKVSCKVSGFSIN (SEQ ID NO: 6055) | TGGYHWN (SEQ ID NO: 6007) | WVRQAPGQGLEWMG (SEQ ID NO: 6056) | YIYSSGTTRYNPSLKS (SEQ ID NO: 6008) | RVTMTRDTSTNTFYMELSSLRSEDTAVYYCAR (SEQ ID NO: 6057) | GNWHYFDY (SEQ ID NO: 6009) | WGQGTLVTVSS (SEQ ID NO: 6058) |
| 15H6-HC_6 | EIQLVQSGAEVKKPGATVKISCKVSGFSIN (SEQ ID NO: 6059) | TGGYHWN (SEQ ID NO: 6007) | WVQQAPGKGLEWMG (SEQ ID NO: 6060) | YIYSSGTTRYNPSLKS (SEQ ID NO: 6008) | RVTITRDTSTNTFYMELSSLRSEDTAVYYCAR (SEQ ID NO: 6061) | GNWHYFDY (SEQ ID NO: 6009) | WGQGTLVTVSS (SEQ ID NO: 6062) |

TABLE 18

Exemplary heavy chain CDRs and FWRs of NKp30-targeting antigen binding domains (according to the Kabat numbering scheme)

| Ab ID | VHFWR1 | VHCDR1 | VHFWR2 | VHCDR2 | VHFWR3 | VHCDR3 | VHFWR4 |
|---|---|---|---|---|---|---|---|
| 9G1-HC | QIQLQESGPGLVKPSQSLSLTCSVTGFSINTG (SEQ ID NO: 7317) | GYHWN (SEQ ID NO: 7313) | WIRQFPGKKLEWMG (SEQ ID NO: 6004) | YIYSSGSTSYNPSLKS (SEQ ID NO: 6001) | RISITRDTSKNQFFLQLNSVTTEDTATYYCAR (SEQ ID NO: 6005) | GNWHYFDF (SEQ ID NO: 6002) | WGQGTMVTVSS (SEQ ID NO: 6006) |
| 15H6-HC | QIQLQESGPGLVKPSQSLSLTCSVTGFSINTG (SEQ ID NO: 7317) | GYHWN (SEQ ID NO: 7313) | WIRQFPGKKLEWMG (SEQ ID NO: 6011) | YIYSSGTTRYNPSLKS (SEQ ID NO: 6008) | RISITRDTSKNQFFLQLNSVTPEDTATYYCTR (SEQ ID NO: 6012) | GNWHYFDY (SEQ ID NO: 6009) | WGQGTLVAVSS (SEQ ID NO: 6013) |
| 9G1-HC_1 | QIQLQESGPGLVKPSETLSLTCTVSGFSINTG (SEQ ID NO: 7371) | GYHWN (SEQ ID NO: 7313) | WIRQPAGKGLEWIG (SEQ ID NO: 6015) | YIYSSGSTSYNPSLKS (SEQ ID NO: 6001) | RVTMSRDTSKNQFSLKLSSVTAADTAVYYCAR (SEQ ID NO: 6016) | GNWHYFDF (SEQ ID NO: 6002) | WGQGTMVTVSS (SEQ ID NO: 6017) |
| 9G1-HC_2 | QIQLQESGPGLVKPSQTLSLTCTVSGFSINTG (SEQ ID NO: 7372) | GYHWN (SEQ ID NO: 7313) | WIRQHPGKGLEWIG (SEQ ID NO: 6019) | YIYSSGSTSYNPSLKS (SEQ ID NO: 6001) | LVTISRDTSKNQFSLKLSSVTAADTAVYYCAR (SEQ ID NO: 6020) | GNWHYFDF (SEQ ID NO: 6002) | WGQGTMVTVSS (SEQ ID NO: 6021) |
| 9G1-HC_3 | EIQLLESGGGLVQPGGSLRLSCAVSGFS | GYHWN (SEQ ID NO: 7313) | WVRQAPGKGLEWVG | YIYSSGSTSYNPSLKS (SEQ ID NO: 6001) | RFTISRDTSKNTFYLQMNSLRAEDTAVYYCAR | GNWHYFDF (SEQ ID NO: 6002) | WGQGTMVTVSS (SEQ ID NO: |

TABLE 18-continued

Exemplary heavy chain CDRs and FWRs
of NKp30-targeting antigen binding domains
(according to the Kabat numbering scheme)

| Ab ID | VHFWR1 | VHCDR1 | VHFWR2 | VHCDR2 | VHFWR3 | VHCDR3 | VHFWR4 |
|---|---|---|---|---|---|---|---|
| | INTG (SEQ ID NO: 7373) | | | ID NO: 6023) | (SEQ ID NO: 6024) | 6002) | 6025) |
| 9G1-HC_4 | QIQLVQS GAEVKKP GSSVKVS CKVSGFS INTG (SEQ ID NO: 7374) | GYHWN (SEQ ID NO: 7313) | WVRQAP GQGLEW MG (SEQ ID NO: 6027) | YIYSSGS TSYNPSL KS (SEQ ID NO: 6001) | RVTITRDT STNTFYME LSSLRSED TAVYYCAR (SEQ ID NO: 6028) | GNWHY FDF (SEQ ID NO: 6002) | WGQGTM VTVSS (SEQ ID NO: 6029) |
| 9G1-HC_5 | EIQLVES GGGLVQP GGSLRLS CAVSGFS INTG (SEQ ID NO: 7375) | GYHWN (SEQ ID NO: 7313) | WVRQAP GKGLEW VG (SEQ ID NO: 6032) | YIYSSGS TSYNPSL KS (SEQ ID NO: 6001) | RFTISRDT AKNSFYLQ MNSLRAED TAVYYCAR (SEQ ID NO: 6033) | GNWHY FDF (SEQ ID NO: 6002) | WGQGTM VTVSS (SEQ ID NO: 6034) |
| 9G1-HC_6 | QIQLVQS GAEVKKP GASVKVS CKVSGFS INTG (SEQ ID NO: 7376) | GYHWN (SEQ ID NO: 7313) | WVRQAP GQGLEW MG (SEQ ID NO: 6036) | YIYSSGS TSYNPSL KS (SEQ ID NO: 6001) | RVTMTRDT STNTFYME LSSLRSED TAVYYCAR (SEQ ID NO: 6037) | GNWHY FDF (SEQ ID NO: 6002) | WGQGTM VTVSS (SEQ ID NO: 6038) |
| 15H6-HC_1 | QIQLQES GPGLVKP SQTLSLT CTVSGFS INTG (SEQ ID NO: 7372) | GYHWN (SEQ ID NO: 7313) | WIRQHP GKGLEW IG (SEQ ID NO: 6040) | YIYSSGT TRYNPSL KS (SEQ ID NO: 6008) | LVTISRDT SKNQFSLK LSSVTAAD TAVYYCAR (SEQ ID NO: 6041) | GNWHY FDY (SEQ ID NO: 6009) | WGQGTL VTVSS (SEQ ID NO: 6042) |
| 15H6-HC_2 | QIQLQES GPGLVKP SETLSLT CTVSGFS INTG (SEQ ID NO: 7371) | GYHWN (SEQ ID NO: 7313) | WIRQPA GKGLEW IG (SEQ ID NO: 6044) | YIYSSGT TRYNPSL KS (SEQ ID NO: 6008) | RVTMSRDT SKNQFSLK LSSVTAAD TAVYYCAR (SEQ ID NO: 6045) | GNWHY FDY (SEQ ID NO: 6009) | WGQGTL VTVSS (SEQ ID NO: 6046) |
| 15H6-HC_3 | EIQLLES GGGLVQP GGSLRLS CAVSGFS INTG (SEQ ID NO: 7373) | GYHWN (SEQ ID NO: 7313) | WVRQAP GKGLEW VG (SEQ ID NO: 6048) | YIYSSGT TRYNPSL KS (SEQ ID NO: 6008) | RFTISRDT SKNTFYLQ MNSLRAED TAVYYCAR (SEQ ID NO: 6049) | GNWHY FDY (SEQ ID NO: 6009) | WGQGTL VTVSS (SEQ ID NO: 6050) |
| 15H6-HC_4 | QIQLVES GGGLVKP GGSLRLS CAVSGFS INTG (SEQ ID NO: 7377) | GYHWN (SEQ ID NO: 7313) | WIRQAP GKGLEW VG (SEQ ID NO: 6052) | YIYSSGT TRYNPSL KS (SEQ ID NO: 6008) | RFTISRDT AKNSFYLQ MNSLRAED TAVYYCAR (SEQ ID NO: 6053) | GNWHY FDY (SEQ ID NO: 6009) | WGQGTL VTVSS (SEQ ID NO: 6054) |
| 15H6-HC_5 | QIQLVQS GAEVKKP GASVKVS CKVSGFS INTG (SEQ | GYHWN (SEQ ID NO: 7313) | WVRQAP GQGLEW MG (SEQ ID NO: 6056) | YIYSSGT TRYNPS LKS (SEQ ID NO: 6008) | RVTMTRDT STNTFYME LSSLRSED TAVYYCAR (SEQ ID NO: | GNWHY FDY (SEQ ID NO: 6009) | WGQGTL VTVSS (SEQ ID NO: 6058) |

TABLE 18-continued

Exemplary heavy chain CDRs and FWRs
of NKp30-targeting antigen binding domains
(according to the Kabat numbering scheme)

| Ab ID | VHFWR1 | VHCDR1 | VHFWR2 | VHCDR2 | VHFWR3 | VHCDR3 | VHFWR4 |
|---|---|---|---|---|---|---|---|
| | | | | | ID NO: 6057) | | |
| 15H6-HC_6 | EIQLVQS GAEVKKP GATVKIS CKVSGFS INTG (SEQ ID NO: 7378) | GYHWN (SEQ ID NO: 7313) | WVQQAP GKGLEW MG (SEQ ID NO: 7060) | YIYSSGT TRYNPSL KS (SEQ ID NO: 6008) | RVTITRDT STNTFYME LSSLRSED TAVYYCAR (SEQ ID NO: 6061) | GNWHY FDY (SEQ ID NO: 6009) | WGQGTL VTVSS (SEQ ID NO: 6062) |
| 9D9-HC | QIQLQES GPGLVKP SQSLSLS CSVTGFS INTG (SEQ ID NO: 7312) | GYHWN (SEQ ID NO: 7313) | WIRQFP GKKVEW MG (SEQ ID NO: 7314) | YIYSSGT TKYNPSL KS (SEQ ID NO: 7385) | RISITRDT SKNQFFLQ LNSVTTED TATYYCAR (SEQ ID NO: 6005) | GDWHY FDY (SEQ ID NO: 7315) | WGQGTM VAVSS (SEQ ID NO: 7316) |
| 3A12-HC | QIQLQES GPGLVKP SQSLSLT CSVTGFS INTG (SEQ ID NO: 7317) | GYHWN (SEQ ID NO: 7313) | WIRQFP GKKLEW MG (SEQ ID NO: 6004) | YIYSSGS TRYNPSL KS (SEQ ID NO: 7318) | RFSITRDT SKNQFFLQ LNSVTTED TATYYCTR (SEQ ID NO: 7319) | GNWHY FDY (SEQ ID NO: 6009) | WGQGTL VAVSS (SEQ ID NO: 6013) |
| 12D10-HC | QIQLQES GPGLVKP SQSLSLT CSVTGFS INTG (SEQ ID NO: 7317) | GYHWN (SEQ ID NO: 7313) | WIRQFP GKKLEW MG (SEQ ID NO: 6004) | YIYSSGT TRYNPSL KS (SEQ ID NO: 6008) | RISITRDT SKNQFFLQ LNSVTPED TATYYCTR (SEQ ID NO: 6012) | GNWHY FDY (SEQ ID NO: 6009) | WGQGTL VAVSS (SEQ ID NO: 6013) |
| 15E1-HC | QIQLQES GPGLVKP SQSLSLS CSVTGFS ITTT (SEQ ID NO: 7322) | GYHWN (SEQ ID NO: 7313) | WIRQFP GKKLEW MG (SEQ ID NO: 6004) | YIYSSGS TSYNPSL KS (SEQ ID NO: 6001) | RFSITRDT SKNQFFLQ LNSVTTED TATYYCAR (SEQ ID NO: 7323) | GDWHY FDY (SEQ ID NO: 7315) | WGPGTM VTVSS (SEQ ID NO: 7324) |
| 15E1_Humanized variant_VH1 | QIQLQES GPGLVKP SQTLSLT CTVSGFS ITTT (SEQ ID NO: 7330) | GYHWN (SEQ ID NO: 7313) | WIRQHP GKGLEW IG (SEQ ID NO: 6019) | YIYSSGS TSYNPSL KS (SEQ ID NO: 6001) | LVTISRDT SKNQFSLK LSSVTAAD TAVYYCAR (SEQ ID NO: 6020) | GDWHY FDY (SEQ ID NO: 7315) | WGQGTM VTVSS (SEQ ID NO: 6006) |
| 15E1_Humanized variant_VH2 | QIQLVES GGGLVKP GGSLRLS CAVSGFS ITTT (SEQ ID NO: 7331) | GYHWN (SEQ ID NO: 7313) | WIRQAP GKGLEW VG (SEQ ID NO: 6052) | YIYSSGS TSYNPSL KS (SEQ ID NO: 6001) | RFTISRDT AKNSFYLQ MNSLRAED TAVYYCAR (SEQ ID NO: 6033) | GDWHY FDY (SEQ ID NO: 7315) | WGQGTM VTVSS (SEQ ID NO: 6006) |
| 15E1_Humanized variant_VH3 | EIQLLES GGGLVQP GGSLRLS CAVSGFS ITTT (SEQ ID NO: 7332) | GYHWN (SEQ ID NO: 7313) | WVRQAP GKGLEW VG (SEQ ID NO: 6023) | YIYSSGS TSYNPSL KS (SEQ ID NO: 6001) | RFTISRDT SKNTFYLQ MNSLRAED TAVYYCAR (SEQ ID NO: 6024) | GDWHY FDY (SEQ ID NO: 7315) | WGQGTM VTVSS (SEQ ID NO: 6006) |

TABLE 18-continued

Exemplary heavy chain CDRs and FWRs
of NKp30-targeting antigen binding domains
(according to the Kabat numbering scheme)

| Ab ID | VHFWR1 | VHCDR1 | VHFWR2 | VHCDR2 | VHFWR3 | VHCDR3 | VHFWR4 |
|---|---|---|---|---|---|---|---|
| 15E1_Humanized variant_VH4 | EIQLVES GGGLVQP GGSLRLS CAVSGFS ITTT (SEQ ID NO: 7333) | GYHWN (SEQ ID NO: 7313) | WVRQAP GKGLEW VG (SEQ ID NO: 6023) | YIYSSGS TSYNPSL KS (SEQ ID NO: 6001) | RFTISRDT AKNSFYLQ MNSLRAED TAVYYCAR (SEQ ID NO: 6033) | GDWHY FDY (SEQ ID NO: 7315) | WGQGTM VTVSS (SEQ ID NO: 6006) |
| 15E1_Humanized variant_VH5 | QIQLVQS GAEVKKP GASVKVS CKVSGFS ITTT (SEQ ID NO: 7334) | GYHWN (SEQ ID NO: 7313) | WVRQAP GQGLEW MG (SEQ ID NO: 6027) | YIYSSGS TSYNPSL KS (SEQ ID NO: 6001) | RVTMTRDT STNTFYME LSSLRSED TAVYYCAR (SEQ ID NO: 6037) | GDWHY FDY (SEQ ID NO: 7315) | WGQGTM VTVSS (SEQ ID NO: 6006) |

TABLE 8

Exemplary light chain CDRs and FWRs of
NKp30-targeting antigen binding domains

| Ab ID | VLFWR1 | VLCDR1 | VLFWR2 | VLCDR2 | VLFWR3 | VLCDR3 | VLFWR4 |
|---|---|---|---|---|---|---|---|
| 9G1-LC | SYTLTQ PPLLSV ALGHKA TITC (SEQ ID NO: 6066) | SGERLS DKYVH (SEQ ID NO: 6063) | WYQQKP GRAPVM VIY (SEQ ID NO: 6067) | ENDKRP S (SEQ ID NO: 6064) | GIPDQFSG SNSGNIAT LTISKAQA GYEADYYC (SEQ ID NO: 7292) | QSWDST NSAV (SEQ ID NO: 7293) | FGSGTQ LTVL (SEQ ID NO: 6069) |
| 15H6-LC | SYTLTQ PPSLSV APGQKA TIIC (SEQ ID NO: 6073) | SGENLS DKYVH (SEQ ID NO: 6070) | WYQQKP GRAPVM VIY (SEQ ID NO: 6074) | ENEKRP S (SEQ ID NO: 6071) | GIPDQFSG SNSGNIAT LTISKAQP GSEADYYC (SEQ ID NO: 6075) | HYWESI NSVV (SEQ ID NO: 6072) | FGSGTH LTVL (SEQ ID NO: 6076) |
| 9G1-LC_1 | QSVTTQ PPSVSG APGQRV TISC (SEQ ID NO: 6077) | SGERLS DKYVH (SEQ ID NO: 6063) | WYQQLP GTAPKM LIY (SEQ ID NO: 6078) | ENDKRP S (SEQ ID NO: 6064) | GVPDRFSG SNSGNSAS LAITGLQA EDEADYYC (SEQ ID NO: 6079) | QSWDST NSAV (SEQ ID NO: 7293) | FGGGTQ LTVL (SEQ ID NO: 6080) |
| 9G1-LC_2 | QSVTTQ PPSASG TPGQRV TISC (SEQ ID NO: 6081) | SGERLS DKYVH (SEQ ID NO: 6063) | WYQQLP GTAPKM LIY (SEQ ID NO: 6082) | ENDKRP S (SEQ ID NO: 6064) | GVPDRFSG SNSGNSAS LAISGLQS EDEADYYC (SEQ ID NO: 6083) | QSWDST NSAV (SEQ ID NO: 7293) | FGGGTQ LTVL (SEQ ID NO: 6084) |
| 9G1-LC_3 | QSVTTQ PPSASG TPGQRV TISC (SEQ ID NO: 6085) | SGERLS DKYVH (SEQ ID NO: 6063) | WYQQLP GTAPKM LIY (SEQ ID NO: 6086) | ENDKRP S (SEQ ID NO: 6064) | GVPDRFSG SNSGNSAS LAISGLRS EDEADYYC (SEQ ID NO: 6087) | QSWDST NSAV (SEQ ID NO: 7293) | FGGGTQ LTVL (SEQ ID NO: 6088) |
| 9G1-LC_4 | SSETTQ PHSVSV ATAQMA RITC (SEQ ID NO: 6063) | SGERLS DKYVH (SEQ ID NO: 6063) | WYQQKP GQDPVM VIY (SEQ ID NO: | ENDKRP S (SEQ ID NO: 6064) | GIPERFSG SNPGNTAT LTISRIEA GDEADYYC (SEQ ID NO: 7293) | QSWDST NSAV (SEQ ID NO: 7293) | FGGGTQ LTVL (SEQ ID NO: 6092) |

TABLE 8-continued

Exemplary light chain CDRs and FWRs of
NKp30-targeting antigen binding domains

| Ab ID | VLFWR1 | VLCDR1 | VLFWR2 | VLCDR2 | VLFWR3 | VLCDR3 | VLFWR4 |
|---|---|---|---|---|---|---|---|
| | ID NO: 6089) | | 6090) | | NO: 6091) | | |
| 9G1-LC_5 | DIQMTQ SPSTLS ASVGDR VTITC (SEQ ID NO: 6093) | SGERLS DKYVH (SEQ ID NO: 6063) | WYQQKP GKAPKM LIY (SEQ ID NO: 6094) | ENDKRP S (SEQ ID NO: 6064) | GVPSRFSG SNSGNEAT LTISSLQP DDFATYYC (SEQ ID NO: 6095) | QSWDST NSAV (SEQ ID NO: 7293) | FGQGTK VEIK (SEQ ID NO: 6096) |
| 15H6-LC_1 | QYVLTQ PPSASG TPGQRV TISC (SEQ ID NO: 6097) | SGENLS DKYVH (SEQ ID NO: 6070) | WYQQLP GTAPKM LIY (SEQ ID NO: 6098) | ENEKRP S (SEQ ID NO: 6071) | GVPDRFSG SNSGNSAS LAISGLQS EDEADYYC (SEQ ID NO: 6099) | HYWESI NSVV (SEQ ID NO: 6072) | FGEGTE LTVL (SEQ ID NO: 6100) |
| 15H6-LC_2 | QYVLTQ PPSASG TPGQRV TISC (SEQ ID NO: 6101) | SGENLS DKYVH (SEQ ID NO: 6070) | WYQQLP GTAPKM LIY (SEQ ID NO: 6102) | ENEKRP S (SEQ ID NO: 6071) | GVPDRFSG SNSGNSAS LAISGLRS EDEADYYC (SEQ ID NO: 6103) | HYWESI NSVV (SEQ ID NO: 6072) | FGEGTE LTVL (SEQ ID NO: 6104) |
| 15H6-LC_3 | SYELTQ PPSVSV SPGQTA SITC (SEQ ID NO: 6105) | SGENLS DKYVH (SEQ ID NO: 6070) | WYQQKP GQSPVM VIY (SEQ ID NO: 6106) | ENEKRP S (SEQ ID NO: 6071) | GIPERFSG SNSGNTAT LTISGTQA MDEADYYC (SEQ ID NO: 6107) | HYWESI NSVV (SEQ ID NO: 6072) | FGEGTE LTVL (SEQ ID NO: 6108) |
| 15H6-LC_4 | DYVLTQ SPLSLP VTPGEP ASISC (SEQ ID NO: 6109) | SGENLS DKYVH (SEQ ID NO: 6070) | WYLQKP GQSPQM LIY (SEQ ID NO: 6110) | ENEKRP S (SEQ ID NO: 6071) | GVPDRFSG SNSGNDAT LKISRVEA EDVGVYYC (SEQ ID NO: 6111) | HYWESI NSVV (SEQ ID NO: 6072) | FGQGTK VEIK (SEQ ID NO: 6112) |
| 15H6-LC_5 | AYQLTQ SPSSLS ASVGDR VTITC (SEQ ID NO: 6113) | SGENLS DKYVH (SEQ ID NO: 6070) | WYQQKP GKAPKM LIY (SEQ ID NO: 6114) | ENEKRP S (SEQ ID NO: 6071) | GVPSRFSG SNSGNDAT LTISSLQP EDFATYYC (SEQ ID NO: 6115) | HYWESI NSVV (SEQ ID NO: 6072) | FGQGTK VEIK (SEQ ID NO: 6116) |
| 15H6-LC_6 | EYVLTQ SPATLS VSPGER ATLSC (SEQ ID NO: 6117) | SGENLS DKYVH (SEQ ID NO: 6070) | WYQQKP GQAPRM LIY (SEQ ID NO: 6118) | ENEKRP S (SEQ ID NO: 6071) | GIPARFSG SNSGNEAT LTISSLQS EDFAVYYC (SEQ ID NO: 6119) | HYWESI NSVV (SEQ ID NO: 6072) | FGQGTK VEIK (SEQ ID NO: 6120) |
| 9D9-LC | SYTLTQ PPLVSV ALGQKA TIIC (SEQ ID NO: 7320) | SGENLS DKYVH (SEQ ID NO: 6070) | WYQQKP GRAPVM VIY (SEQ ID NO: 6067) | ENDKRP S (SEQ ID NO: 6064) | GIPDQFSG SNSGNIAT LTISKAQA GYEADYYC (SEQ ID NO: 7292) | HCWDST NSAV (SEQ ID NO: 7321) | FGSGTH LTVL (SEQ ID NO: 6076) |
| 3A12-LC | SYTLTQ PPLVSV ALGQKA TIIC (SEQ ID NO: 7320) | SGENLS DKYVH (SEQ ID NO: 6070) | WYQQKP GRAPVM VIY (SEQ ID NO: 6067) | ENDKRP S (SEQ ID NO: 6064) | GIPDQFSG SNSGNIAT LTISKAQA GYEADYYC (SEQ ID NO: 7292) | HCWDST NSAV (SEQ ID NO: 7321) | FGSGTH LTVL (SEQ ID NO: 6076) |

TABLE 8-continued

Exemplary light chain CDRs and FWRs of
NKp30-targeting antigen binding domains

| Ab ID | VLFWR1 | VLCDR1 | VLFWR2 | VLCDR2 | VLFWR3 | VLCDR3 | VLFWR4 |
|---|---|---|---|---|---|---|---|
| 12D10-LC | SYTLTQ PPSLSV APGQKA TIIC (SEQ ID NO: 6073) | SGENLS DKYVH (SEQ ID NO: 6070) | WYQQKP GRAPVM VIY (SEQ ID NO: 6074) | ENEKRP S (SEQ ID NO: 6071) | GIPDQFSG SNSGNIAT LTISKAQP GSEADYYC (SEQ ID NO: 6075) | HYWESI NSVV (SEQ ID NO: 6072) | FGSGTH LTVL (SEQ ID NO: 6076) |
| 15E1-LC | SFTLTQ PPLVSV AVGQVA TITC (SEQ ID NO: 7325) | SGEKLS DKYVH (SEQ ID NO: 7326) | WYQQKP GRAPVM VIY (SEQ ID NO: 6067) | ENDRRP S (SEQ ID NO: 7327) | GIPDQFSG SNSGNIAS LTISKAQA GDEADYFC (SEQ ID NO: 7328) | QFWDST NSAV (SEQ ID NO: 7329) | FGGGTQ LTVL (SEQ ID NO: 6080) |
| 15E1_Humanized variant_VL1 | SSETTQ PPSVSV SPGQTA SITC (SEQ ID NO: 7335) | SGEKLS DKYVH (SEQ ID NO: 7326) | WYQQKP GQSPVM VIY (SEQ ID NO: 6106) | ENDRRP S (SEQ ID NO: 7327) | GIPERFSG SNSGNTAT LTISGTQA MDEADYFC (SEQ ID NO: 7336) | QFWDST NSAV (SEQ ID NO: 7329) | FGGGTQ LTVL (SEQ ID NO: 6080) |
| 15E1_Humanized variant_VL2 | SSETTQ PHSVSV ATAQMA RITC (SEQ ID NO: 6089) | SGEKLS DKYVH (SEQ ID NO: 7326) | WYQQKP GQDPVM VIY (SEQ ID NO: 6090) | ENDRRP S (SEQ ID NO: 7327) | GIPERFSG SNPGNTAT LTISRIEA GDEADYFC (SEQ ID NO: 7337) | QFWDST NSAV (SEQ ID NO: 7329) | FGGGTQ LTVL (SEQ ID NO: 6080) |
| 15E1_Humanized variant_VL3 | QSVTTQ PPSASG TPGQRV TISC (SEQ ID NO: 6081) | SGEKLS DKYVH (SEQ ID NO: 7326) | WYQQLP GTAPKM LIY (SEQ ID NO: 6078) | ENDRRP S (SEQ ID NO: 7327) | GVPDRFSG SNSGNSAS LAISGLRS EDEADYFC (SEQ ID NO: 7338) | QFWDST NSAV (SEQ ID NO: 7329) | FGGGTQ LTVL (SEQ ID NO: 6080) |
| 15E1_Humanized variant_VL4 | QSVTTQ PPSVSG APGQRV TISC (SEQ ID NO: 6077) | SGEKLS DKYVH (SEQ ID NO: 7326) | WYQQLP GTAPKM LIY (SEQ ID NO: 6078) | ENDRRP S (SEQ ID NO: 7327) | GVPDRFSG SNSGNSAS LAITGLQA EDEADYFC (SEQ ID NO: 7339) | QFWDST NSAV (SEQ ID NO: 7329) | FGGGTQ LTVL (SEQ ID NO: 6080) |
| 15E1_Humanized variant_VL5 | DSVTTQ SPLSLP VTLGQP ASISC (SEQ ID NO: 7340) | SGEKLS DKYVH (SEQ ID NO: 7326) | WYQQRP GQSPRM LIY (SEQ ID NO: 7341) | ENDRRP S (SEQ ID NO: 7327) | GVPDRFSG SNSGNDAT LKISRVEA EDVGVYFC (SEQ ID NO: 7342) | QFWDST NSAV (SEQ ID NO: 7329) | FGGGTK VEIK (SEQ ID NO: 233) |

TABLE 9

Exemplary variable regions of NKp30-targeting
antigen binding domains

| SEQ ID NO | Ab ID | Description | Sequence |
|---|---|---|---|
| SEQ ID NO: 6121 | 9G1-HC | 9G1 heavy chain variable region | QIQLQESGPGLVKPSQSLSLTCSVTGFSINTGGYHWN WIRQFPGKKLEWMGYIYSSGSTSYNPSLKSRISITRD TSKNQFFLQLNSVTTEDTATYYCARGNWHYFDFWGQG TMVTVSS |
| SEQ ID NO: | 15H6-HC | 15H6 heavy chain variable | QIQLQESGPGLVKPSQSLSLTCSVTGFSINTGGYHWN WIRQFPGKKLEWMGYIYSSGTTRYNPSLKSRISITRD |

TABLE 9-continued

Exemplary variable regions of NKp30-targeting antigen binding domains

| SEQ ID NO | Ab ID | Description | Sequence |
|---|---|---|---|
| 6122 | | region | TSKNQFFLQLNSVTPEDTATYYCTRGNWHYFDYWGQG TLVAVSS |
| SEQ ID NO: 6123 | 9G1-HC_1 | 9G1 heavy chain variable region humanized variant 1 | QIQLQESGPGLVKPSETLSLTCTVSGFSINTGGYHWN WIRQPAGKGLEWIGYIYSSGSTSYNPSLKSRVTMSRD TSKNQFSLKLSSVTAADTAVYYCARGNWHYFDFWGQG TMVTVSS |
| SEQ ID NO: 6124 | 9G1-HC_2 | 9G1 heavy chain variable region humanized variant 2 | QIQLQESGPGLVKPSQTLSLTCTVSGFSINTGGYHWN WIRQHPGKGLEWIGYIYSSGSTSYNPSLKSLVTISRD TSKNQFSLKLSSVTAADTAVYYCARGNWHYFDFWGQG TMVTVSS |
| SEQ ID NO: 6125 | 9G1-HC_3 | 9G1 heavy chain variable region humanized variant 3 | EIQLLESGGGLVQPGGSLRLSCAVSGFSINTGGYHWN WVRQAPGKGLEWVGYIYSSGSTSYNPSLKSRFTISRD TSKNTFYLQMNSLRAEDTAVYYCARGNWHYFDFWGQG TMVTVSS |
| SEQ ID NO: 6126 | 9G1-HC_4 | 9G1 heavy chain variable region humanized variant 4 | QIQLVQSGAEVKKPGSSVKVSCKVSGFSINTGGYHWN WVRQAPGQGLEWMGYIYSSGSTSYNPSLKSRVTITRD TSTNTFYMELSSLRSEDTAVYYCARGNWHYFDFWGQG TMVTVSS |
| SEQ ID NO: 6127 | 9G1-HC_5 | 9G1 heavy chain variable region humanized variant 5 | EIQLVESGGGLVQPGGSLRLSCAVSGFSINTGGYHWN WVRQAPGKGLEWVGYIYSSGSTSYNPSLKSRFTISRD TAKNSFYLQMNSLRAEDTAVYYCARGNWHYFDFWGQG TMVTVSS |
| SEQ ID NO: 6128 | 9G1-HC_6 | 9G1 heavy chain variable region humanized variant 6 | QIQLVQSGAEVKKPGASVKVSCKVSGFSINTGGYHWN WVRQAPGQGLEWMGYIYSSGSTSYNPSLKSRVTMTRD TSTNTFYMELSSLRSEDTAVYYCARGNWHYFDFWGQG TMVTVSS |
| SEQ ID NO: 6129 | 15H6-HC_1 | 15H6 heavy chain variable region humanized variant 1 | QIQLQESGPGLVKPSQTLSLTCTVSGFSINTGGYHWN WIRQHPGKGLEWIGYIYSSGTTRYNPSLKSLVTISRD TSKNQFSLKLSSVTAADTAVYYCARGNWHYFDYW GQGTLVTVSS |
| SEQ ID NO: 6130 | 15H6-HC_2 | 15H6 heavy chain variable region humanized variant 2 | QIQLQESGPGLVKPSETLSLTCTVSGFSINTGGYHWN WIRQPAGKGLEWIGYIYSSGTTRYNPSLKSRVTMSRD TSKNQFSLKLSSVTAADTAVYYCARGNWHYFDYWGQG TLVTVSS |
| SEQ ID NO: 6131 | 15H6-HC_3 | 15H6 heavy chain variable region humanized variant 3 | EIQLLESGGGLVQPGGSLRLSCAVSGFSINTGGYHWN WVRQAPGKGLEWVGYIYSSGTTRYNPSLKSRFTISRD TSKNTFYLQMNSLRAEDTAVYYCARGNWHYFDYWGQG TLVTVSS |
| SEQ ID NO: 6132 | 15H6-HC_4 | 15H6 heavy chain variable region humanized variant 4 | QIQLVESGGGLVKPGGSLRLSCAVSGFSINTGGYHWN WIRQAPGKGLEWVGYIYSSGTTRYNPSLKSRFTISRD TAKNSFYLQMNSLRAEDTAVYYCARGNWHYFDYWGQG TLVTVSS |
| SEQ ID NO: 6133 | 15H6-HC_5 | 15H6 heavy chain variable region humanized variant 5 | QIQLVQSGAEVKKPGASVKVSCKVSGFSINTGGYHWN WVRQAPGQGLEWMGYIYSSGTTRYNPSLKSRVTMTRD TSTNTFYMELSSLRSEDTAVYYCARGNWHYFDYWGQG TLVTVSS |
| SEQ ID NO: 6134 | 15H6-HC_6 | 15H6 heavy chain variable region humanized variant 6 | EIQLVQSGAEVKKPGATVKISCKVSGFSINTGGYHWN WVQQAPGKGLEWMGYIYSSGTTRYNPSLKSRVTITRD TSTNTFYMELSSLRSEDTAVYYCARGNWHYFDYWGQG TLVTVSS |

TABLE 9-continued

Exemplary variable regions of NKp30-targeting antigen binding domains

| SEQ ID NO | Ab ID | Description | Sequence |
|---|---|---|---|
| SEQ ID NO: 7294 | 9G1-LC | 9G1 light chain variable region | SYTLTQPPLLSVALGHKATITCSGERLSDKYVHWYQQ KPGRAPVMVIYENDKRPSGIPDQFSGSNSGNIATLTI SKAQAGYEADYYCQSWDSTNSAVFGSGTQLTVL |
| SEQ ID NO: 6136 | 15H6-LC | 15H6 light chain variable region | SYTLTQPPSLSVAPGQKATIICSGENLSDKYVHWYQQ KPGRAPVMVIYENEKRPSGIPDQFSGSNSGNIATLTI SKAQPGSEADYYCHYWESINSVVFGSGTHLTVL |
| SEQ ID NO: 6137 | 9G1-LC_1 | 9G1 light chain variable region humanized variant 1 | QSVTTQPPSVSGAPGQRVTISCSGERLSDKYVHWYQQ LPGTAPKMLIYENDKRPSGVPDRFSGSNSGNSASLAI TGLQAEDEADYYCQSWDSTNSAVFGGGTQLTVL |
| SEQ ID NO: 6138 | 9G1-LC_2 | 9G1 light chain variable region humanized variant 2 | QSVTTQPPSASGTPGQRVTISCSGERLSDKYVHWYQQ LPGTAPKMLIYENDKRPSGVPDRFSGSNSGNSASLAI SGLQSEDEADYYCQSWDSTNSAVFGGGTQLTVL |
| SEQ ID NO: 6139 | 9G1-LC_3 | 9G1 light chain variable region humanized variant 3 | QSVTTQPPSASGTPGQRVTISCSGERLSDKYVHWYQQ LPGTAPKMLIYENDKRPSGVPDRFSGSNSGNSASLAI SGLRSEDEADYYCQSWDSTNSAVFGGGTQLTVL |
| SEQ ID NO: 6140 | 9G1-LC_4 | 9G1 light chain variable region humanized variant 4 | SSETTQPHSVSVATAQMARITCSGERLSDKYVHWYQQ KPGQDPVMVIYENDKRPSGIPERFSGSNPGNTATLTI SRIEAGDEADYYCQSWDSTNSAVFGGGTQLTVL |
| SEQ ID NO: 6141 | 9G1-LC_5 | 9G1 light chain variable region humanized variant 5 | DIQMTQSPSTLSASVGDRVTITCSGERLSDKYVHWYQ QKPGKAPKMLIYENDKRPSGVPSRFSGSNSGNEATLT ISSLQPDDFATYYCQSWDSTNSAVFGQGTKVEIK |
| SEQ ID NO: 6142 | 15H6-LC_1 | 15H6 light chain variable region humanized variant 1 | QYVLTQPPSASGTPGQRVTISCSGENLSDKYVHWYQQ LPGTAPKMLIYENEKRPSGVPDRFSGSNSGNSASLAI SGLQSEDEADYYCHYWESINSVVFGEGTELTVL |
| SEQ ID NO: 6143 | 15H6-LC_2 | 15H6 light chain variable region humanized variant 2 | QYVLTQPPSASGTPGQRVTISCSGENLSDKYVHWYQQ LPGTAPKMLIYENEKRPSGVPDRFSGSNSGNSASLAI SGLRSEDEADYYCHYWESINSVVFGEGTELTVL |
| SEQ ID NO: 6144 | 15H6-LC_3 | 15H6 light chain variable region humanized variant 3 | SYELTQPPSVSVSPGQTASITCSGENLSDKYVHWYQQ KPGQSPVMVIYENEKRPSGIPERFSGSNSGNTATLTI SGTQAMDEADYYCHYWESINSVVFGEGTELTVL |
| SEQ ID NO: 6145 | 15H6-LC_4 | 15H6 light chain variable region humanized variant 4 | DYVLTQSPLSLPVTPGEPASISCSGENLSDKYVHWYL QKPGQSPQMLIYENEKRPSGVPDRFSGSNSGNDATLK ISRVEAEDVGVYYCHYWESINSVVFGQGTKVEIK |
| SEQ ID NO: 6146 | 15H6-LC_5 | 15H6 light chain variable region humanized variant 5 | AYQLTQSPSSLSASVGDRVTITCSGENLSDKYVHWYQ QKPGKAPKMLIYENEKRPSGVPSRFSGSNSGNDATLT ISSLQPEDFATYYCHYWESINSVVFGQGTKVEIK |
| SEQ ID NO: 6147 | 15H6-LC_6 | 15H6 light chain variable region humanized variant 6 | EYVLTQSPATLSVSPGERATLSCSGENLSDKYVHWYQ QKPGQAPRMLIYENEKRPSGIPARFSGSNSGNEATLT ISSLQSEDFAVYYCHYWESINSVVFGQGTKVEIK |

TABLE 9-continued

Exemplary variable regions of NKp30-targeting antigen binding domains

| SEQ ID NO | Ab ID | Description | Sequence |
|---|---|---|---|
| SEQ ID NO: 7295 | 9D9-HC | 9D9 heavy chain variable region | QIQLQESGPGLVKPSQSLSLSCSVTGFSINTGGYHWN WIRQFPGKKVEWMGYIYSSGTTKYNPSLKSRISITRD TSKNQFFLQLNSVTTEDTATYYCARGDWHYFDYWGQG TMVAVSS |
| SEQ ID NO: 7296 | 9D9-LC | 9D9 light chain variable region | SYTLTQPPLVSVALGQKATIICSGENLSDKYVHWYQQ KPGRAPVMVIYENDKRPSGIPDQFSGSNSGNIATLTI SKAQAGYEADYYCHCWDSTNSAVFGSGTHLTVL |
| SEQ ID NO: 7297 | 3A12-HC | 3A12 heavy chain variable region | QIQLQESGPGLVKPSQSLSLTCSVTGFSINTGGYHWN WIRQFPGKKLEWMGYIYSSGSTRYNPSLKSRFSITRD TSKNQFFLQLNSVTTEDTATYYCTRGNWHYFDYWGQG TLVAVSS |
| SEQ ID NO: 7296 | 3A12-LC | 3A12 light chain variable region | SYTLTQPPLVSVALGQKATIICSGENLSDKYVHWYQQ KPGRAPVMVIYENDKRPSGIPDQFSGSNSGNIATLTI SKAQAGYEADYYCHCWDSTNSAVFGSGTHLTVL |
| SEQ ID NO: 6122 | 12D10-HC | 12D10 heavy chain variable region | QIQLQESGPGLVKPSQSLSLTCSVTGFSINTGGYHWN WIRQFPGKKLEWMGYIYSSGTTRYNPSLKSRISITRD TSKNQFFLQLNSVTPEDTATYYCTRGNWHYFDYWGQG TLVAVSS |
| SEQ ID NO: 6136 | 12D10-LC | 12D10 light chain variable region | SYTLTQPPSLSVAPGQKATIICSGENLSDKYVHWYQQ KPGRAPVMVIYENEKRPSGIPDQFSGSNSGNIATLTI SKAQPGSEADYYCHYWESINSVVFGSGTHLTVL |
| SEQ ID NO: 7298 | 15E1-HC | 15E1 heavy chain variable region | QIQLQESGPGLVKPSQSLSLSCSVTGFSITTTGYHWN WIRQFPGKKLEWMGYIYSSGSTSYNPSLKSRFSITRD TSKNQFFLQLNSVTTEDTATYYCARGDWHYFDYWG PGTMVTVSS |
| SEQ ID NO: 7299 | 15E1-LC | 15E1 light chain variable region | SFTLTQPPLVSVAVGQVATITCSGEKLSDKYVHWYQQ KPGRAPVMVIYENDRRPSGIPDQFSGSNSGNIASLTI SKAQAGDEADYFCQFWDSTNSAVFGGGTQLTVL |
| SEQ ID NO: 7300 | 15E1_Humanized variant_VH1 | 15E1 heavy chain variable region humanized variant 1 | QIQLQESGPGLVKPSQTLSLTCTVSGFSITTTGYHWN WIRQHPGKGLEWIGYIYSSGSTSYNPSLKSLVTISRD TSKNQFSLKLSSVTAADTAVYYCARGDWHYFDYWGQG TMVTVSS |
| SEQ ID NO: 7301 | 15E1_Humanized variant_VH2 | 15E1 heavy chain variable region humanized variant 2 | QIQLVESGGGLVKPGGSLRLSCAVSGFSITTTGYHWN WIRQAPGKGLEWVGYIYSSGSTSYNPSLKSRFTISRD TAKNSFYLQMNSLRAEDTAVYYCARGDWHYFDYWGQG TMVTVSS |
| SEQ ID NO: 7302 | 15E1_Humanized variant_VH3 (BJM0407 VH and BJM0411VH) | 15E1 heavy chain variable region humanized variant 3 | EIQLLESGGGLVQPGGSLRLSCAVSGFSITTTGYHWN WVRQAPGKGLEWVGYIYSSGSTSYNPSLKSRFTISRD TSKNTFYLQMNSLRAEDTAVYYCARGDWHYFDYWGQG TMVTVSS |
| SEQ ID NO: 7303 | 15E1_Humanized variant_VH4 | 15E1 heavy chain variable region humanized variant 4 | EIQLVESGGGLVQPGGSLRLSCAVSGFSITTTGYHWN WVRQAPGKGLEWVGYIYSSGSTSYNPSLKSRFTISRD TAKNSFYLQMNSLRAEDTAVYYCARGDWHYFDYWGQG TMVTVSS |
| SEQ ID NO: 7304 | 15E1_Humanized variant_VH5 | 15E1 heavy chain variable region humanized variant 5 | QIQLVQSGAEVKKPGASVKVSCKVSGFSITTTGYHWN WVRQAPGQGLEWMGYIYSSGSTSYNPSLKSRVTMTRD TSTNTFYMELSSLRSEDTAVYYCARGDWHYFDYWGQG TMVTVSS |
| SEQ ID NO: 7305 | 15E1_Humanized variant_VL1 (BJM0407VL) | 15E1 light chain variable region humanized variant 1 | SSETTQPPSVSVSPGQTASITCSGEKLSDKYVHWYQQ KPGQSPVMVIYENDRRPSGIPERFSGSNSGNTATLTI SGTQAMDEADYFCQFWDSTNSAVFGGGTQLTVL |

TABLE 9-continued

Exemplary variable regions of NKp30-targeting antigen binding domains

| SEQ ID NO | Ab ID | Description | Sequence |
|---|---|---|---|
| SEQ ID NO: 7306 | 15E1_Humanized variant_VL2 | 15E1 light chain variable region humanized variant 2 | SSETTQPHSVSVATAQMARITCSGEKLSDKYVHWYQQ KPGQDPVMVIYENDRRPSGIPERFSGSNPGNTATLTI SRIEAGDEADYFCQFWDSTNSAVFGGGTQLTVL |
| SEQ ID NO: 7307 | 15E1_Humanized variant_VL3 | 15E1 light chain variable region humanized variant 3 | QSVTTQPPSASGTPGQRVTISCSGEKLSDKYVHWYQQ LPGTAPKMLIYENDRRPSGVPDRFSGSNSGNSASLAI SGLRSEDEADYFCQFWDSTNSAVFGGGTQLTVL |
| SEQ ID NO: 7308 | 15E1_Humanized variant_VL4 | 15E1 light chain variable region humanized variant 4 | QSVTTQPPSVSGAPGQRVTISCSGEKLSDKYVHWYQQ LPGTAPKMLIYENDRRPSGVPDRFSGSNSGNSASLAI TGLQAEDEADYFCQFWDSTNSAVFGGGTQLTVL |
| SEQ ID NO: 7309 | 15E1_Humanized variant_VL5 (BJM0411VL) | 15E1 light chain variable region humanized variant 5 | DSVTTQSPLSLPVTLGQPASISCSGEKLSDKYVHWYQ QRPGQSPRMLIYENDRRPSGVPDRFSGSNSGNDATLK ISRVEAEDVGVYFCQFWDSTNSAVFGGGTKVEIK |

TABLE 10

Exemplary NKp30-targeting antigen binding domains/antibody molecules

| SEQ ID NO | Ab ID | Description | Sequence |
|---|---|---|---|
| SEQ ID NO: 6148 | Ch(anti-NKp30 9G1) HC N297A | 9G1 heavy chain | QIQLQESGPGLVKPSQSLSLTCSVTGFSINTGGYHWNWIRQ FPGKKLEWMGYIYSSGSTSYNPSLKSRISITRDTSKNQFFL QLNSVTTEDTATYYCARGNWHYFDFWGQGTMVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPSVFLFPP KPKDTLMISRTPEVTCVVVDVSHEDPEVKFNWYVDGVEVHN AKTKPREEQYASTYRVVSVLTVLHQDWLNGKEYKCKVSNKA LPAPIEKTISKAKGQPREPQVCTLPPSREEMTKNQVSLSCA VKGFYPSDIAVEWESNGQPENNYKTTPPVLDSDGSFFLVSK LTVDKSRWQQGNVFSCSVMHEALHNHYTQKSLSLSPGK |
| SEQ ID NO: 6149 | Ch(anti-NKp30 9G1) HC | 9G1 heavy chain | QIQLQESGPGLVKPSQSLSLTCSVTGFSINTGGYHWNWIRQ FPGKKLEWMGYIYSSGSTSYNPSLKSRISITRDTSKNQFFL QLNSVTTEDTATYYCARGNWHYFDFWGQGTMVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPSVFLFPP KPKDTLMISRTPEVTCVVVDVSHEDPEVKFNWYVDGVEVHN AKTKPREEQYNSTYRVVSVLTVLHQDWLNGKEYKCKVSNKA LPAPIEKTISKAKGQPREPQVCTLPPSREEMTKNQVSLSCA VKGFYPSDIAVEWESNGQPENNYKTTPPVLDSDGSFFLVSK LTVDKSRWQQGNVFSCSVMHEALHNHYTQKSLSLSPGK |
| SEQ ID NO: 6150 | Ch(anti-NKp30 9G1) LC | 9G1 light chain | SYTLTQPPLLSVALGHKATITCSGERLSDKYVHWYQQKPGR APVMVIYENDKRPSGIPDQFSGSNSGNIATLTISKAQAGYE ADYYCQSWDSTNSAVFGSGTQLTVLGQPKANPTVTLFPPSS EELQANKATLVCLISDFYPGAVTVAWKADGSPVKAGVETTK PSKQSNNKYAASSYLSLTPEQWKSHRSYSCQVTHEGSTVEK TVAPTECS |
| SEQ ID NO: 6151 | Ch(anti-NKp30 15H6) HC N297A | 15H6 heavy chain | QIQLQESGPGLVKPSQSLSLTCSVTGFSINTGGYHWNWIRQ FPGKKLEWMGYIYSSGTTRYNPSLKSRISITRDTSKNQFFL QLNSVTPEDTATYYCTRGNWHYFDYWGQGTLVAVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPSVFLFPP KPKDTLMISRTPEVTCVVVDVSHEDPEVKFNWYVDGVEVHN |

TABLE 10-continued

Exemplary NKp30-targeting antigen binding
domains/antibody molecules

| SEQ ID NO | Ab ID | Description | Sequence |
|---|---|---|---|
| | | | AKTKPREEQYASTYRVVSVLTVLHQDWLNGKEYKCKVSNKA LPAPIEKTISKAKGQPREPQVCTLPPSREEMTKNQVSLSCA VKGFYPSDIAVEWESNGQPENNYKTTPPVLDSDGSFFLVSK LTVDKSRWQQGNVFSCSVMHEALHNHYTQKSLSLSPGK |
| SEQ ID NO: 6152 | Ch(anti-NKp30 15H6)HC (hole) | 15H6 heavy chain | QIQLQESGPGLVKPSQSLSLTCSVTGFSINTGGYHWNWIRQ FPGKKLEWMGYIYSSGTTRYNPSLKSRISITRDTSKNQFFL QLNSVTPEDTATYYCTRGNWHYFDYWGQGTLVAVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPELLGGPSVFLFPP KPKDTLMISRTPEVTCVVVDVSHEDPEVKFNWYVDGVEVHN AKTKPREEQYNSTYRVVSVLTVLHQDWLNGKEYKCKVSNKA LPAPIEKTISKAKGQPREPQVCTLPPSREEMTKNQVSLSCA VKGFYPSDIAVEWESNGQPENNYKTTPPVLDSDGSFFLVSK LTVDKSRWQQGNVFSCSVMHEALHNHYTQKSLSLSPGK |
| SEQ ID NO: 6153 | Ch(anti-NKp30 15H6)LC | 15H6 light chain | SYTLTQPPSLSVAPGQKATIICSGENLSDKYVHWYQQKPGR APVMVIYENEKRPSGIPDQFSGSNSGNIATLTISKAQPGSE ADYYCHYWESINSVVFGSGTHLTVLGQPKANPTVTLFPPSS EELQANKATLVCLISDFYPGAVTVAWKADGSPVKAGVETTK PSKQSNNKYAASSYLSLTPEQWKSHRSYSCQVTHEGSTVEK TVAPTECS |
| SEQ ID NO: 7310 | BJM0859 lambda scFv | | EIQLLESGGGLVQPGGSLRLSCAVSGFSITTTGYHWNWVRQ APGKGLEWVGYIYSSGSTSYNPSLKSRFTISRDTSKNTFYL QMNSLRAEDTAVYYCARGDWHYFDYWGQGTMVTVSSGGGGS GGGGSGGGGSGGGGSSETTQPPSVSVSPGQTASITCSGEK LSDKYVHWYQQKPGQSPVMVIYENDRRPSGIPERFSGSNSG NTATLTISGTQAMDEADYFCQFWDSTNSAVFGGGTQLTVL |
| SEQ ID NO: 7311 | BJM0860 kappa scFv | | EIQLLESGGGLVQPGGSLRLSCAVSGFSITTTGYHWNWVRQ APGKGLEWVGYIYSSGSTSYNPSLKSRFTISRDTSKNTFYL QMNSLRAEDTAVYYCARGDWHYFDYWGQGTMVTVSSGGGGS GGGGSGGGGSGGGGSDSVTTQSPLSLPVTLGQPASISCSGE KLSDKYVHWYQQRPGQSPRMLIYENDRRPSGVPDRFSGSNS GNDATLKISRVEAEDVGVYFCQFWDSTNSAVFGGGTKVEIK |

In some embodiments, the NK cell engager is an antigen binding domain that binds to NKp46 (e.g., NKp46 present, e.g., expressed or displayed, on the surface of an NK cell) and comprises any CDR amino acid sequence, framework region (FWR) amino acid sequence, or variable region amino acid sequence disclosed in Table 15. In some embodiments, binding of the NK cell engager, e.g., antigen binding domain that binds to NKp46, to the NK cell activates the NK cell. An antigen binding domain that binds to NKp46 (e.g., NKp46 present, e.g., expressed or displayed, on the surface of an NK cell) may be said to target NKp46, the NK cell, or both.

In some embodiments, the NK cell engager is an antigen binding domain that binds to NKG2D (e.g., NKG2D present, e.g., expressed or displayed, on the surface of an NK cell) and comprises any CDR amino acid sequence, framework region (FWR) amino acid sequence, or variable region amino acid sequence disclosed in Table 15. In some embodiments, binding of the NK cell engager, e.g., antigen binding domain that binds to NKG2D, to the NK cell activates the NK cell. An antigen binding domain that binds to NKG2D (e.g., NKG2D present, e.g., expressed or displayed, on the surface of an NK cell) may be said to target NKG2D, the NK cell, or both.

In some embodiments, the NK cell engager is an antigen binding domain that binds to CD16 (e.g., CD16 present, e.g., expressed or displayed, on the surface of an NK cell) and comprises any CDR amino acid sequence, framework region (FWR) amino acid sequence, or variable region amino acid sequence disclosed in Table 15. In some embodiments, binding of the NK cell engager, e.g., antigen binding domain that binds to CD16, to the NK cell activates the NK cell. An antigen binding domain that binds to CD16 (e.g., CD16 present, e.g., expressed or displayed, on the surface of an NK cell) may be said to target CD16, the NK cell, or both.

TABLE 15

Exemplary variable regions of NKp46, NKG2D, or CD16-targeting antigen binding domains

| SEQ ID NO | Ab ID | Description | Sequence |
|---|---|---|---|
| SEQ ID NO: 6175 | NKG2D_1scFv | scFv that binds NKG2D | QVHLQESGPGLVKPSETLSLTCTVSDDSISSYYWSWIRQ PPGKGLEWIGHISYSGSANYNPSLKSRVTISVDTSKNQF SLKLSSVTAADTAVYYCANWDDAFNIWGQGTMVTVSSGG |

TABLE 15-continued

Exemplary variable regions of NKp46, NKG2D, or CD16-targeting antigen binding domains

| SEQ ID NO | Ab ID | Description | Sequence |
|---|---|---|---|
| | | | GGSGGGGSGGGGSGGGGSEIVLTQSPGTLSLSPGERATL SCRASQSVSSSYLAWYQQKPGQAPRLLIYGASSRATGIP DRFSGSGSGTDFTLTISRLEPEDFAVYYCQQYGSSPWTF GQGTKVEIK |
| SEQ ID NO: 6176 | NKG2D_1VH | VH that binds NKG2D | QVHLQESGPGLVKPSETLSLTCTVSDDSISSYYWSWIRQ PPGKGLEWIGHISYSGSANYNPSLKSRVTISVDTSKNQF SLKLSSVTAADTAVYYCANWDDAFNIWGQGTMVTVSS |
| SEQ ID NO: 6177 | NKG2D_1VL | VL that binds NKG2D | EIVLTQSPGTLSLSPGERATLSCRASQSVSSSYLAWYQQ KPGQAPRLLIYGASSRATGIPDRFSGSGSGTDFTLTISR LEPEDFAVYYCQQYGSSPWTFGQGTKVEIK |
| SEQ ID NO: 6178 | NKG2D_2scFv | scFv that binds NKG2D | EVQLVQSGAEVKEPGESLKISCKNSGYSFTNYWVGWVRQ MPGKGLEWMGIIYPGDSDTRYSPSFQGQVTISADKSINT AYLQWSSLKASDTAMYYCGRLTMFRGIIIGYFDYWGQGT LVTVSSGGGGSGGGGSGGGGSGGGGSEIVLTQSPATLSL SPGERATLSCRASQSVSSYLAWYQQKPGQAPRLLIYDAS NRATGIPARFSGSGSGTDFTLTISSLEPEDFAVYYCQQR SNWPWTFGQGTKVEIK |
| SEQ ID NO: 6179 | NKG2D_2VH | VH that binds NKG2D | EVQLVQSGAEVKEPGESLKISCKNSGYSFTNYWVGWVRQ MPGKGLEWMGIIYPGDSDTRYSPSFQGQVTISADKSINT AYLQWSSLKASDTAMYYCGRLTMFRGIIIGYFDYWGQGT LVTVSS |
| SEQ ID NO: 6180 | NKG2D_2VL | VL that binds NKG2D | EIVLTQSPATLSLSPGERATLSCRASQSVSSYLAWYQQK PGQAPRLLIYDASNRATGIPARFSGSGSGTDFTLTISSL EPEDFAVYYCQQRSNWPWTFGQGTKVEIK |
| SEQ ID NO: 6181 | NKp46scFv | scFv that binds NKp46 | QVQLQQSGPELVKPGASVKMSCKASGYTFTDYVINWGKQ RSGQGLEWIGEIYPGSGTNYYNEKFKAKATLTADKSSNI AYMQLSSLTSEDSAVYFCARRGRYGLYAMDYWGQGTSVT VSSGGGGSGGGGSGGGGSGGGGSDIQMTQTTSSLSASLG DRVTISCRASQDISNYLNWYQQKPDGTVKLLIYYTSRLH SGVPSRFSGSGSGTDYSLTINNLEQEDIATYFCQQGNTR PWTFGGGTKLEIK |
| SEQ ID NO: 6182 | NKp46VH | VH that binds NKp46 | QVQLQQSGPELVKPGASVKMSCKASGYTFTDYVINWGKQ RSGQGLEWIGEIYPGSGTNYYNEKFKAKATLTADKSSNI AYMQLSSLTSEDSAVYFCARRGRYGLYAMDYWGQGTSVT VSS |
| SEQ ID NO: 6183 | NKp46VL | VL that binds NKp46 | DIQMTQTTSSLSASLGDRVTISCRASQDISNYLNWYQQK PDGTVKLLIYYTSRLHSGVPSRFSGSGSGTDYSLTINNL EQEDIATYFCQQGNTRPWTFGGGTKLEIK |
| SEQ ID NO: 6184 | CD16scFv | scFv that binds CD16 | EVQLVESGGGVVRPGGSLRLSCAASGFTFDDYGMSWVRQ APGKGLEWVSGINWNGGSTGYADSVKGRFTISRDNAKNS LYLQMNSLRAEDTAVYYCARGRSLLFDYWGQGTLVTVSR GGGGSGGGGSGGGGSSELTQDPAVSVALGQTVRITCQGD SLRSYYASWYQQKPGQAPVLVIYGKNNRPSGIPDRFSGS SSGNTASLTITGAQAEDEADYYCNSRDSSGNHVVFGGGT KLTVL |
| SEQ ID NO: 6185 | CD16VH | VH that binds CD16 | EVQLVESGGGVVRPGGSLRLSCAASGFTFDDYGMSWVRQ APGKGLEWVSGINWNGGSTGYADSVKGRFTISRDNAKNS LYLQMNSLRAEDTAVYYCARGRSLLFDYWGQGTLVTVSR |
| SEQ ID NO: 6186 | CD16VL | VL that binds CD16 | SSELTQDPAVSVALGQTVRITCQGDSLRSYYASWYQQKP GQAPVLVIYGKNNRPSGIPDRFSGSSSGNTASLTITGAQ AEDEADYYCNSRDSSGNHVVFGGGTKLTVL |

In one embodiment, the NK cell engager is a ligand of NKp30, e.g., is a B7-6, e.g., comprises the amino acid sequence of: DLKVEMMAGGTQITPLNDNVTIFCNI-FYSQPLNITSMGITWFWKSLTFDKEVKVFEFFGD HQEAFRPGAIVSPWRLKSGDASLRLPGIQLEEAGEY-RCEVVVTPLKAQGTVQLEVVASP ASRLLL-DQVGMKENEDKYMCESSGFYPEAINIT-WEKQTQKFPHPIEISEDVITGPTIKNM DGTFNVTSCLKLNSSQEDPGTVYQCVVRHASLHTPL RSNFTLTAARHSLSETEKTDNFS (SEQ ID NO: 7233), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7233.

In other embodiments, the NK cell engager is a ligand of NKp44 or NKp46, which is a viral HA. Viral hemagglutinins (HA) are glyco proteins which are on the surface of viruses. HA proteins allow viruses to bind to the membrane of cells via sialic acid sugar moieties which contributes to the fusion of viral membranes with the cell membranes (see e.g., Eur J Immunol. 2001 September; 31(9):2680-9 "Recognition of viral hemagglutinins by NKp44 but not by NKp30"; and Nature. 2001 Feb. 22; 409(6823):1055-60 "Recognition of haemaglutinins on virus-infected cells by NKp46 activates lysis by human NK cells" the contents of each of which are incorporated by reference herein).

In other embodiments, the NK cell engager is a ligand of NKG2D chosen from MICA, MICB, or ULBP1, e.g., wherein:
(i) MICA comprises the amino acid sequence: EPHSLRYNLTVLSWDGSVQSGFLTEVHLDGQPFLRCDRQKCRAKPQGWAEDVLGNKTWDRETRDLTGNGKDLRMTLAHIKDQKEGLHSLQEIRVCEIHEDNSTRSSQHFYYDGELFLSQNLETKEWTMPQSSRAQTLAMNVRNFLKEDAMKTKTHYHAMHADCLQELRRYLKSGVVLRRTVPPMVNVTRSEASEGNITVTCRASGFYPWNITLSWRQDGVSLSHDTQQWGDVLPDGNGTYQTWVATRICQGEEQRFTCYMEHSGNHSTHPVPSGKVLVLQSHW (SEQ ID NO: 7234), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7234;
(ii) MICB comprises the amino acid sequence: AEPHSLRYNLMVLSQDESVQSGFLAEGHLDGQPFLRYDRQKRRAKPQGWAEDVLGA KTWDTETEDLTENGQDLRRTLTHIKDQKGGLHSLQEIRVCEIHEDSSTRGSRHFYYDGELFLSQNLETQESTVPQSSRAQTLAMNVTNFWKEDAMKTKTHYRAMQADCLQKLQRYLKSGVAIRRTVPPMVNVTCSEVSEGNITVTCRASSFYPRNITLTWRQDGVSLSHNTQQWGDVLPDGNGTYQTWVATRIRQGEEQRFTCYMEHSGNHGTHPVPSGKVLVLQSQRTD (SEQ ID NO: 7235), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7235; or
(iii) ULBP1 comprises the amino acid sequence: GWVDTHCLCYDFIITPKSRPEPQWCEVQGLVDERPFLHYDCVNHKAKAFASLGKKVNVTKTWEEQTETLRDVVDFLKGQLLDIQVENLIPIEPLTLQARMSCEHEAHGHGRGSWQFLFNGQKFLLFDSNNRKWTALHPGAKKMTEKWEKNRDVTMFFQKISLGDCKMWLEEFLMYWEQMLDPTKPPSLAPG (SEQ ID NO: 7236), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7236.

In other embodiments, the NK cell engager is a ligand of DNAM1 chosen from NECTIN2 or NECL5, e.g., wherein:
(i) NECTIN2 comprises the amino acid sequence: QDVRVQVLPEVRGQLGGTVELPCHLLPPVPGLYISLVTWQRPDAPANHQNVAAFHPKMGPSFPSPKPGSERLSFVSAKQSTGQDTEAELQDATLALHGLTVEDEGNYTCEFATFPKGSVRGMTWLRVIAKPKNQAEAQKVTFSQDPTTVALCISKEGRPPARISWLSSLDWEAKETQ VSGTLAGTVTVTSRFTLVPSGRADGVTVTCKVEHESFEEPALIPVTLSVRYPPEVSISGYD DNWYLGRTDATLSCDVRSNPEPTGYDWSTTSGTFPTSAVAQGSQLVIHAVDSLFNTTFV CTVTNAVGMGRAEQVIFVRETPNTAGAGATGG (SEQ ID NO: 7237), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7237; or
(ii) NECL5 comprises the amino acid sequence: WPPPGTGDVVVQAPTQVPGFLGDSVTLPCYLQ VPNMEVTHVSQLTWARHGESGSMAV FHQTQGPSYSESKRLEFVAARLGAELRNASLRMFGLRVEDEGNYTCLFVTFPQGSRSVD IWLRVLAKPQNTAEVQKVQLTGEPVPMARCVSTGGRPPAQITWHSDLGGMPNTSQVPG FLSGTVTVTSLWILVPSSQVDGKNVTCKVEHESFEKPQLLTVNLTVYYPPEVSISGYDNN WYLGQNEATLTCDARSNPEPTGYNWSTTMGPLPPFAVAQGAQLLIRPVDKPINTTLICN VTNALGARQAELTVQVKEGPPSEHSGISRN (SEQ ID NO: 7238), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7238.

In yet other embodiments, the NK cell engager is a ligand of DAP10, which is an adapter for NKG2D (see e.g., Proc Natl Acad Sci USA. 2005 May 24; 102(21): 7641-7646; and Blood, 15 Sep. 2011 Volume 118, Number 11, the full contents of each of which is incorporated by reference herein).

In other embodiments, the NK cell engager is a ligand of CD16, which is a CD16a/b ligand, e.g., a CD16a/b ligand further comprising an antibody Fc region (see e.g., Front Immunol. 2013; 4: 76 discusses how antibodies use the Fc to trigger NK cells through CD16, the full contents of which are incorporated herein).

In other embodiments, the NK cell engager is a ligand of CRTAM, which is NECL2, e.g., wherein NECL2 comprises the amino acid sequence: QNLFTKDVTVIEGEVATISCQVNKSDDSVIQLLNPNRQTIYFRDFRPLKDSRFQLLNFSSS ELKVSLTNVSISDEGRYFCQLYTDPPQESYTTITVLVPPRNLMIDIQKDTAVEGEEIEVNC TAMASKPATTIRWFKGNTELKGKSEVEEWSDMYTVTSQLMLKVHKEDDGVPVICQVE HPAVTGNLQTQRYLEVQYKPQVHIQMTYPLQGLTREGDALELTCEAIGKPQPVMVTWV RVDDEMPQHAVLSGPNLFINNLNKTDNGTYRCEASNIVGKAHSDYMLYVYDPPTTIPPP TTTTTTTTTTTTTILTIITDSRAGEEGSIRAVDH (SEQ ID NO: 7239), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7239.

In other embodiments, the NK cell engager is a ligand of CD27, which is CD70, e.g., wherein CD70 comprises the amino acid sequence: QRFAQAQQQLPLESLGWDVAELQLNHTGPQQDPRLYWQGGPALGRSFLHGPELDKGQ LRIHRDGIYMVHIQVTLAICSSTTASRHHPTTLAVGICSPASRSISLLRLSFHQGCTIASQR LTPLARGDTLCTNLTGTLLPSRNTDETFFGVQWVRP (SEQ ID NO: 7240), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7240.

In other embodiments, the NK cell engager is a ligand of PSGL1, which is L-selectin (CD62L), e.g., wherein L-selectin comprises the amino acid sequence: WTYHYSEKPMNWQRARRFCRDNYTDLVAIQNKAEIEYLEKTLPFSRSYYWIGIRKIGGI WTWVGTNKSLTEEAENWGDGEPNNKKNKEDCVEIYIKRNKDAGKWNDDACHKLKAA LCYTASCQPWSCSGHGECVEIINNYTCNCDVGYYGPQCQFVIQCEPLEAPELGTMDCTH PLGNFSFSSQCAFSCSEGTNLTGIEETTCGPFGNWSSPEPTCQVIQCEPLSAPDLGIMNCSH PLASFSFTSACTFICSEGTELIGKKKTICESSGIWSNPSPICQKLDKSFSMIKEGDYN (SEQ ID NO: 7241), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7241.

In other embodiments, the NK cell engager is a ligand of CD96, which is NECL5, e.g., wherein NECL5 comprises the amino acid sequence: WPPPGTGDVVVQAPTQVPGFLGDSVTLPCYLQVPNMEVTHVSQLTWARHGESGSMAV FHQTQGPSYSESKRLEFVAARLGAELRNASLRMFGLRVEDEGNYTCLFVTFPQGSRSVD IWLRVLAKPQNTAEVQKVQLTGEPVPMARCVSTGGRPPAQITWHSDLGGMPNTSQVPG FLSGTVTVTSLWILVPSSQVDGKNVTCKVEHESFEKPQLLTVNLTVYYPPEVSISGYDNN WYLGQNEATLTCDARSNPEPTGYNWSTTMGPLPPFAVAQGAQLLIRPVDKPINTTLICN VTNALGARQAELTVQVKEGPPSEHSGISRN (SEQ ID NO: 7238), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7238.

In other embodiments, the NK cell engager is a ligand of CD100 (SEMA4D), which is CD72, e.g., wherein CD72 comprises the amino acid sequence: RYLQVSQQLQQTNRVLEVTNSSLRQQLRLKITQLGQSAEDLQGSRRELAQSQEALQVEQ RAHQAAEGQLQACQADRQKTKETLQSEEQQRRALEQKLSNMENRLKPFFTCGSADTCC PSGWIMHQKSCFYISLTSKNWQESQKQCETLSSKLATFSEIYPQSHSYYFLNSLLPNGGS GNSYWTGLSSNKDWKLTDDTQRTRTYAQSSKCNKVHKTWSWWTLESESCRSSLPYICE MTAFRFPD (SEQ ID NO: 7242), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7242.

In other embodiments, the NK cell engager is a ligand of NKp80, which is CLEC2B (AICL), e.g., wherein CLEC2B (AICL) comprises the amino acid sequence: KLTRDSQSLCPYDWIGFQNKCYYFSKEEGDWNSSKYNCSTQHADLTIIDNIEEMNFLRR YKCSSDHWIGLKMAKNRTGQWVDGATFTKSFGMRGSEGCAYLSDDGAATARCYTER KWICRKRIH (SEQ ID NO: 7243), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7243.

In other embodiments, the NK cell engager is a ligand of CD244, which is CD48, e.g., wherein CD48 comprises the amino acid sequence: QGHLVHMTVVSGSNVTLNISESLPENYKQLTWFYTFDQKIVEWDSRKSKYFESKFKGR VRLDPQSGALYISKVQKEDNSTYIMRVLKKTGNEQEWKIKLQVLDPVPKPVIKIEKIEDM DDNCYLKLSCVIPGESVNYTWYGDKRPFPKELQNSVLETTLMPHNYSRCYTCQVSNSVS SKNGTVCLSPPCTLARS (SEQ ID NO: 7244), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7244.

In some embodiments, the NK cell engager is a viral hemagglutinin (HA), HA is a glycoprotein found on the surface of influenza viruses. It is responsible for binding the virus to cells with sialic acid on the membranes, such as cells in the upper respiratory tract or erythrocytes. HA has at least 18 different antigens. These subtypes are named H1 through H18. NCRs can recognize viral proteins. NKp46 has been shown to be able to interact with the HA of influenza and the HA-NA of Paramyxovirus, including Sendai virus and Newcastle disease virus. Besides NKp46, NKp44 can also functionally interact with HA of different influenza subtypes.

Antibody Molecules

In an embodiment, the anti-NKp30 antibody molecule is a monospecific antibody molecule and binds a single epitope on NKp30. E.g., a monospecific antibody molecule having a plurality of immunoglobulin variable domain sequences, each of which binds the same epitope.

In another embodiment, the anti-NKp30 antibody molecule is a multispecific or multifunctional antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure*

*Analysis of Antibody Variable Domains.* In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273, 927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) *Hum Antibody Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibody molecules generated in a non-human organism, e.g., a rat or mouse, and then modified, e.g., in the variable framework or constant region, to decrease antigenicity in a human are within the invention.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239: 1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibody molecules in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFv) may be engineered (see, for example, Colcher, D. et al. (1999) *Ann NY Acad Sci* 880: 263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement.

In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Multispecific or Multifunctional Antibody Molecules

Exemplary structures of multispecific and multifunctional molecules defined herein are described throughout. Exemplary structures are further described in: Weidle U et al. (2013) The Intriguing Options of Multispecific Antibody Formats for Treatment of Cancer. *Cancer Genomics & Proteomics* 10: 1-18 (2013); and Spiess C et al. (2015) Alternative molecular formats and therapeutic applications for bispecific antibodies. *Molecular Immunology* 67: 95-106; the full contents of each of which is incorporated by reference herein).

In embodiments, multispecific antibody molecules can comprise more than one antigen-binding site, where different sites are specific for different antigens. In embodiments, multispecific antibody molecules can bind more than one (e.g., two or more) epitopes on the same antigen. In embodiments, multispecific antibody molecules comprise an antigen-binding site specific for a target cell (e.g., cancer cell) and a different antigen-binding site specific for an immune effector cell. In one embodiment, the multispecific antibody molecule is a bispecific antibody molecule. Bispecific antibody molecules can be classified into five different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates.

BsIgG is a format that is monovalent for each antigen. Exemplary BsIgG formats include but are not limited to crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, κλ-body, orthogonal Fab. See Spiess et al. Mol. Immunol. 67(2015):95-106. Exemplary BsIgGs include catumaxomab (Fresenius Biotech, Trion Pharma, Neopharm), which contains an anti-CD3 arm and an anti-EpCAM arm; and ertumaxomab (Neovii Biotech, Fresenius Biotech), which targets CD3 and HER2. In some embodiments, BsIgG comprises heavy chains that are engineered for heterodimerization. For example, heavy chains can be engineered for heterodimerization using a "knobs-into-holes" strategy, a SEED platform, a common heavy chain (e.g., in κλ-bodies), and use of heterodimeric Fc regions. See Spiess et al. Mol. Immunol. 67(2015):95-106. Strategies that have been used to avoid heavy chain pairing of homodimers in BsIgG include knobs-in-holes, duobody, azymetric, charge pair, HA-TF, SEEDbody, and differential protein A affinity. See Id. BsIgG can be produced by separate expression of the component antibodies in different host cells and subsequent purification/assembly into a BsIgG. BsIgG can also be produced by expression of the component antibodies in a single host cell. BsIgG can be purified using affinity chromatography, e.g., using protein A and sequential pH elution.

IgG appended with an additional antigen-binding moiety is another format of bispecific antibody molecules. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). See Id. Examples of appended IgG formats include dual variable domain IgG (DVD-Ig), IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. An example of an IgG-scFv is MM-141 (Merrimack Pharmaceuticals), which binds IGF-1R and HER3. Examples of DVD-Ig include ABT-981 (AbbVie), which binds IL-1α and IL-1β; and ABT-122 (AbbVie), which binds TNF and IL-17A.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Exemplary bispecific antibody fragments include but are not limited to nanobody, nanobody-HAS, BiTE, Diabody, DART, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody. See Id. For example, the BiTE format comprises tandem scFvs, where the component scFvs bind to CD3 on T cells and a surface antigen on cancer cells Bispecific fusion proteins include antibody fragments linked to other proteins, e.g., to add additional specificity and/or functionality. An example of a bispecific fusion protein is an immTAC, which comprises an anti-CD3 scFv linked to an affinity-matured T-cell receptor that recognizes HLA-presented peptides. In embodiments, the dock-and-lock (DNL) method can be used to generate bispecific antibody molecules with higher valency. Also, fusions to albumin binding proteins or human serum albumin can be extend the serum half-life of antibody fragments. See Id.

In embodiments, chemical conjugation, e.g., chemical conjugation of antibodies and/or antibody fragments, can be used to create BsAb molecules. See Id. An exemplary bispecific antibody conjugate includes the CovX-body format, in which a low molecular weight drug is conjugated site-specifically to a single reactive lysine in each Fab arm or an antibody or fragment thereof. In embodiments, the conjugation improves the serum half-life of the low molecular weight drug. An exemplary CovX-body is CVX-241 (NCT01004822), which comprises an antibody conjugated to two short peptides inhibiting either VEGF or Ang2. See Id.

The antibody molecules can be produced by recombinant expression, e.g., of at least one or more component, in a host system. Exemplary host systems include eukaryotic cells (e.g., mammalian cells, e.g., CHO cells, or insect cells, e.g., SF9 or S2 cells) and prokaryotic cells (e.g., *E. coli*). Bispecific antibody molecules can be produced by separate expression of the components in different host cells and subsequent purification/assembly. Alternatively, the antibody molecules can be produced by expression of the components in a single host cell. Purification of bispecific antibody molecules can be performed by various methods such as affinity chromatography, e.g., using protein A and sequential pH elution. In other embodiments, affinity tags can be used for purification, e.g., histidine-containing tag, myc tag, or streptavidin tag.

CDR-Grafted Scaffolds

In embodiments, the antibody molecule is a CDR-grafted scaffold domain. In embodiments, the scaffold domain is based on a fibronectin domain, e.g., fibronectin type III domain. The overall fold of the fibronectin type III (Fn3) domain is closely related to that of the smallest functional antibody fragment, the variable domain of the antibody heavy chain. There are three loops at the end of Fn3; the positions of BC, DE and FG loops approximately correspond to those of CDR1, 2 and 3 of the VH domain of an antibody. Fn3 does not have disulfide bonds; and therefore Fn3 is stable under reducing conditions, unlike antibodies and their fragments (see, e.g., WO 98/56915; WO 01/64942; WO 00/34784). An Fn3 domain can be modified (e.g., using CDRs or hypervariable loops described herein) or varied, e.g., to select domains that bind to an antigen/marker/cell described herein.

In embodiments, a scaffold domain, e.g., a folded domain, is based on an antibody, e.g., a "minibody" scaffold created by deleting three beta strands from a heavy chain variable domain of a monoclonal antibody (see, e.g., Tramontano et al., 1994, J Mol. Recognit. 7:9; and Martin et al., 1994, EMBO J. 13:5303-5309). The "minibody" can be used to present two hypervariable loops. In embodiments, the scaffold domain is a V-like domain (see, e.g., Coia et al. WO 99/45110) or a domain derived from tendamistatin, which is a 74 residue, six-strand beta sheet sandwich held together by two disulfide bonds (see, e.g., McConnell and Hoess, 1995, J Mol. Biol. 250:460). For example, the loops of tendamistatin can be modified (e.g., using CDRs or hypervariable loops) or varied, e.g., to select domains that bind to a marker/antigen/cell described herein. Another exemplary scaffold domain is a beta-sandwich structure derived from the extracellular domain of CTLA-4 (see, e.g., WO 00/60070).

Other exemplary scaffold domains include but are not limited to T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). See, e.g., US 20040009530 and U.S. Pat. No. 7,501,121, incorporated herein by reference.

In embodiments, a scaffold domain is evaluated and chosen, e.g., by one or more of the following criteria: (1) amino acid sequence, (2) sequences of several homologous domains, (3) 3-dimensional structure, and/or (4) stability data over a range of pH, temperature, salinity, organic solvent, oxidant concentration. In embodiments, the scaffold domain is a small, stable protein domain, e.g., a protein of less than 100, 70, 50, 40 or 30 amino acids. The domain may include one or more disulfide bonds or may chelate a metal, e.g., zinc.

Antibody-Based Fusions

A variety of formats can be generated which contain additional binding entities attached to the N or C terminus of antibodies. These fusions with single chain or disulfide stabilized Fvs or Fabs result in the generation of tetravalent molecules with bivalent binding specificity for each antigen. Combinations of scFvs and scFabs with IgGs enable the production of molecules which can recognize three or more different antigens.

Antibody-Fab Fusion

Antibody-Fab fusions are bispecific antibodies comprising a traditional antibody to a first target and a Fab to a second target fused to the C terminus of the antibody heavy chain. Commonly the antibody and the Fab will have a common light chain. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Antibody-scFv Fusion

Antibody-scFv Fusions are bispecific antibodies comprising a traditional antibody and a scFv of unique specificity fused to the C terminus of the antibody heavy chain. The scFv can be fused to the C terminus through the Heavy Chain of the scFv either directly or through a linker peptide. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Variable Domain Immunoglobulin DVD

A related format is the dual variable domain immunoglobulin (DVD), which are composed of VH and VL domains of a second specificity place upon the N termini of the V domains by shorter linker sequences.

Other exemplary multispecific antibody formats include, e.g., those described in the following US20160114057A1, US20130243775A1, US20140051833, US20130022601, US20150017187A1, US20120201746A1, US20150133638A1, US20130266568A1, US20160145340A1, WO2015127158A1, US20150203591A1, US20140322221A1, US20130303396A1, US20110293613, US20130017200A1, US20160102135A1, WO2015197598A2, WO2015197582A1, U.S. Pat. No. 9,359,437, US20150018529, WO2016115274A1, WO2016087416A1, US20080069820A1, U.S. Pat. Nos. 9,145,588B, 7,919,257, and US20150232560A1. Exemplary multispecific molecules utilizing a full antibody-Fab/scFab format include those described in the following, U.S. Pat. No. 9,382,323B2, US20140072581A1, US20140308285A1, US20130165638A1, US20130267686A1, US20140377269A1, U.S. Pat. No. 7,741,446B2, and WO1995009917A1. Exemplary multispecific molecules utilizing a domain exchange format include those described in the following, US20150315296A1, WO2016087650A1, US20160075785A1, WO2016016299A1, US20160130347A1, US20150166670, U.S. Pat. No. 8,703, 132B2, US20100316645, U.S. Pat. No. 8,227,577B2, US20130078249.

Fc-Containing Entities (Mini-Antibodies)

Fc-containing entities, also known as mini-antibodies, can be generated by fusing scFv to the C-termini of constant heavy region domain 3 (CH3-scFv) and/or to the hinge region (scFv-hinge-Fc) of an antibody with a different specificity. Trivalent entities can also be made which have disulfide stabilized variable domains (without peptide linker) fused to the C-terminus of CH3 domains of IgGs.

Fc-Containing Multispecific Molecules

In some embodiments, the multispecific molecules disclosed herein includes an immunoglobulin constant region (e.g., an Fc region). Exemplary Fc regions can be chosen from the heavy chain constant regions of IgG1, IgG2, IgG3 or IgG4; more particularly, the heavy chain constant region of human IgG1, IgG2, IgG3, or IgG4.

In some embodiments, the immunoglobulin chain constant region (e.g., the Fc region) is altered, e.g., mutated, to increase or decrease one or more of: Fc receptor binding, antibody glycosylation, the number of cysteine residues, effector cell function, or complement function.

In other embodiments, an interface of a first and second immunoglobulin chain constant regions (e.g., a first and a second Fc region) is altered, e.g., mutated, to increase or decrease dimerization, e.g., relative to a non-engineered interface, e.g., a naturally-occurring interface. For example, dimerization of the immunoglobulin chain constant region (e.g., the Fc region) can be enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface.

In some embodiments, the multispecific molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) can include a paired an amino acid substitution chosen from: T366S, L368A, or Y407V (e.g., corresponding to a cavity or hole), and T366W (e.g., corresponding to a protuberance or knob).

In other embodiments, the multifunctional molecule includes a half-life extender, e.g., a human serum albumin or an antibody molecule to human serum albumin.

Heterodimerized Antibody Molecules & Methods of Making

Various methods of producing multispecific antibodies have been disclosed to address the problem of incorrect heavy chain pairing. Exemplary methods are described below. Exemplary multispecific antibody formats and methods of making said multispecific antibodies are also disclosed in e.g., Speiss et al. Molecular Immunology 67 (2015) 95-106; and Klein et al mAbs 4:6, 653-663; November/December 2012; the entire contents of each of which are incorporated by reference herein.

Heterodimerized bispecific antibodies are based on the natural IgG structure, wherein the two binding arms recognize different antigens. IgG derived formats that enable defined monovalent (and simultaneous) antigen binding are generated by forced heavy chain heterodimerization, combined with technologies that minimize light chain mispairing (e.g., common light chain). Forced heavy chain heterodimerization can be obtained using, e.g., knob-in-hole OR strand exchange engineered domains (SEED).

Knob-in-Hole

Knob-in-Hole as described in U.S. Pat. Nos. 5,731,116, 7,476,724 and Ridgway, J. et al. (1996) *Prot. Engineering* 9(7): 617-621, broadly involves: (1) mutating the CH3 domain of one or both antibodies to promote heterodimerization; and (2) combining the mutated antibodies under conditions that promote heterodimerization. "Knobs" or "protuberances" are typically created by replacing a small amino acid in a parental antibody with a larger amino acid (e.g., T366Y or T366W); "Holes" or "cavities" are created by replacing a larger residue in a parental antibody with a smaller amino acid (e.g., Y407T, T366S, L368A and/or Y407V).

For bispecific antibodies including an Fc domain, introduction of specific mutations into the constant region of the heavy chains to promote the correct heterodimerization of the Fc portion can be utilized. Several such techniques are reviewed in Klein et al. (mAbs (2012) 4:6, 1-11), the contents of which are incorporated herein by reference in their entirety. These techniques include the "knobs-into-holes" (KiH) approach which involves the introduction of a bulky residue into one of the CH3 domains of one of the antibody heavy chains. This bulky residue fits into a complementary "hole" in the other CH3 domain of the paired heavy chain so as to promote correct pairing of heavy chains (see e.g., U.S. Pat. No. 7,642,228).

Exemplary KiH mutations include S354C, T366W in the "knob" heavy chain and Y349C, T366S, L368A, Y407V in the "hole" heavy chain. Other exemplary KiH mutations are provided in Table 1, with additional optional stabilizing Fc cysteine mutations.

TABLE 1

Exemplary Fc KiH mutations and optional Cysteine mutations

| Position | Knob Mutation | Hole Mutation |
|---|---|---|
| T366 | T366W | T366S |
| L368 | — | L368A |
| Y407 | — | Y407V |

TABLE 1-continued

Exemplary Fc KiH mutations and optional Cysteine mutations

Additional Cysteine Mutations to form a stabilizing disulfide bridge

| Position | Knob CH3 | Hole CH3 |
|---|---|---|
| S354 | S354C | — |
| Y349 | — | Y349C |

Other Fc mutations are provided by Igawa and Tsunoda who identified 3 negatively charged residues in the CH3 domain of one chain that pair with three positively charged residues in the CH3 domain of the other chain. These specific charged residue pairs are: E356-K439, E357-K370, D399-K409 and vice versa. By introducing at least two of the following three mutations in chain A: E356K, E357K and D399K, as well as K370E, K409D, K439E in chain B, alone or in combination with newly identified disulfide bridges, they were able to favor very efficient heterodimerization while suppressing homodimerization at the same time (Martens T et al. A novel one-armed antic-Met antibody inhibits glioblastoma growth in vivo. Clin Cancer Res 2006; 12:6144-52; PMID:17062691). Xencor defined 41 variant pairs based on combining structural calculations and sequence information that were subsequently screened for maximal heterodimerization, defining the combination of S364H, F405A (HA) on chain A and Y349T, T394F on chain B (TF) (Moore G L et al. A novel bispecific antibody format enables simultaneous bivalent and monovalent co-engagement of distinct target antigens. MAbs 2011; 3:546-57; PMID: 22123055).

Other exemplary Fc mutations to promote heterodimerization of multispecific antibodies include those described in the following references, the contents of each of which is incorporated by reference herein, WO2016071377A1, US20140079689A1, US20160194389A1, US20160257763, WO2016071376A2, WO2015107026A1, WO2015107025A1, WO2015107015A1, US20150353636A1, US20140199294A1, U.S. Pat. No. 7,750,128B2, US20160229915A1, US20150344570A1, U.S. Pat. No. 8,003,774A1, US20150337049A1, US20150175707A1, US20140242075A1, US20130195849A1, US20120149876A1, US20140200331A1, U.S. Pat. No. 9,309,311B2, U.S. Pat. No. 8,586,713, US20140037621A1, US20130178605A1, US20140363426A1, US20140051835A1 and US20110054151A1.

Stabilizing cysteine mutations have also been used in combination with KiH and other Fc heterodimerization promoting variants, see e.g., U.S. Pat. No. 7,183,076. Other exemplary cysteine modifications include, e.g., those disclosed in US20140348839A1, U.S. Pat. No. 7,855,275B2, and U.S. Pat. No. 9,000,130B2.

Strand Exchange Engineered Domains (SEED)

Heterodimeric Fc platform that support the design of bispecific and asymmetric fusion proteins by devising strand-exchange engineered domain (SEED) C(H)3 heterodimers are known. These derivatives of human IgG and IgA C(H)3 domains create complementary human SEED C(H)3 heterodimers that are composed of alternating segments of human IgA and IgG C(H)3 sequences. The resulting pair of SEED C(H)3 domains preferentially associates to form heterodimers when expressed in mammalian cells. SEEDbody (Sb) fusion proteins consist of [IgG1 hinge]-C(H)2-[SEED C(H)3], that may be genetically linked to one or more fusion partners (see e.g., Davis J H et al. SEED-bodies: fusion proteins based on strand exchange engineered domain (SEED) CH3 heterodimers in an Fc analogue platform for asymmetric binders or immunofusions and bispecific antibodies. Protein Eng Des Sel 2010; 23:195-202; PMID:20299542 and U.S. Pat. No. 8,871,912. The contents of each of which are incorporated by reference herein).

Duobody

"Duobody" technology to produce bispecific antibodies with correct heavy chain pairing are known. The DuoBody technology involves three basic steps to generate stable bispecific human IgG1 antibodies in a post-production exchange reaction. In a first step, two IgG1s, each containing single matched mutations in the third constant (CH3) domain, are produced separately using standard mammalian recombinant cell lines. Subsequently, these IgG1 antibodies are purified according to standard processes for recovery and purification. After production and purification (post-production), the two antibodies are recombined under tailored laboratory conditions resulting in a bispecific antibody product with a very high yield (typically >95%) (see e.g., Labrijn et al, PNAS 2013; 110(13):5145-5150 and Labrijn et al. Nature Protocols 2014; 9(10):2450-63, the contents of each of which are incorporated by reference herein).

Electrostatic Interactions

Methods of making multispecific antibodies using CH3 amino acid changes with charged amino acids such that homodimer formation is electrostatically unfavorable are disclosed. EP1870459 and WO 2009089004 describe other strategies for favoring heterodimer formation upon co-expression of different antibody domains in a host cell. In these methods, one or more residues that make up the heavy chain constant domain 3 (CH3), CH3-CH3 interfaces in both CH3 domains are replaced with a charged amino acid such that homodimer formation is electrostatically unfavorable and heterodimerization is electrostatically favorable. Additional methods of making multispecific molecules using electrostatic interactions are described in the following references, the contents of each of which is incorporated by reference herein, include US20100015133, U.S. Pat. No. 8,592,562B2, U.S. Pat. No. 9,200,060B2, US20140154254A1, and U.S. Pat. No. 9,358,286A1.

Common Light Chain

Light chain mispairing needs to be avoided to generate homogenous preparations of bispecific IgGs. One way to achieve this is through the use of the common light chain principle, i.e. combining two binders that share one light chain but still have separate specificities. An exemplary method of enhancing the formation of a desired bispecific antibody from a mixture of monomers is by providing a common variable light chain to interact with each of the heteromeric variable heavy chain regions of the bispecific antibody. Compositions and methods of producing bispecific antibodies with a common light chain as disclosed in, e.g., U.S. Pat. No. 7,183,076B2, US20110177073A1, EP2847231A1, WO2016079081A1, and EP3055329A1, the contents of each of which is incorporated by reference herein.

CrossMab

Another option to reduce light chain mispairing is the CrossMab technology which avoids non-specific L chain mispairing by exchanging CH1 and CL domains in the Fab of one half of the bispecific antibody. Such crossover variants retain binding specificity and affinity, but make the two arms so different that L chain mispairing is prevented. The CrossMab technology (as reviewed in Klein et al. Supra) involves domain swapping between heavy and light chains so as to promote the formation of the correct pairings. Briefly, to construct a bispecific IgG-like CrossMab antibody that could bind to two antigens by using two distinct light chain-heavy chain pairs, a two-step modification process is applied. First, a dimerization interface is engineered into the C-terminus of each heavy chain using a heterodimerization approach, e.g., Knob-into-hole (KiH) technology, to ensure that only a heterodimer of two distinct heavy chains from one antibody (e.g., Antibody A) and a second antibody (e.g., Antibody B) is efficiently formed. Next, the constant heavy 1 (CH1) and constant light (CL) domains of one antibody are exchanged (Antibody A), keeping the variable heavy (VH) and variable light (VL) domains consistent. The exchange of the CH1 and CL domains ensured that the modified antibody (Antibody A) light chain would only efficiently dimerize with the modified antibody (antibody A) heavy chain, while the unmodified antibody (Antibody B) light chain would only efficiently dimerize with the unmodified antibody (Antibody B) heavy chain; and thus only the desired bispecific CrossMab would be efficiently formed (see e.g., Cain, C. SciBX 4(28); doi:10.1038/scibx.2011.783, the contents of which are incorporated by reference herein).

Common Heavy Chain

An exemplary method of enhancing the formation of a desired bispecific antibody from a mixture of monomers is by providing a common variable heavy chain to interact with each of the heteromeric variable light chain regions of the bispecific antibody. Compositions and methods of producing bispecific antibodies with a common heavy chain are disclosed in, e.g., US20120184716, US20130317200, and US20160264685A1, the contents of each of which is incorporated by reference herein.

Amino Acid Modifications

Alternative compositions and methods of producing multispecific antibodies with correct light chain pairing include various amino acid modifications. For example, Zymeworks describes heterodimers with one or more amino acid modifications in the CH1 and/or CL domains, one or more amino acid modifications in the VH and/or VL domains, or a combination thereof, which are part of the interface between the light chain and heavy chain and create preferential pairing between each heavy chain and a desired light chain such that when the two heavy chains and two light chains of the heterodimer pair are co-expressed in a cell, the heavy chain of the first heterodimer preferentially pairs with one of the light chains rather than the other (see e.g., WO2015181805). Other exemplary methods are described in WO2016026943 (Argen-X), US20150211001, US20140072581A1, US20160039947A1, and US20150368352.

Lambda/Kappa Formats

Multispecific molecules (e.g., multispecific antibody molecules) that include the lambda light chain polypeptide and a kappa light chain polypeptides, can be used to allow for heterodimerization. Methods for generating bispecific antibody molecules comprising the lambda light chain polypeptide and a kappa light chain polypeptides are disclosed in PCT/US17/53053 filed on Sep. 22, 2017, incorporated herein by reference in its entirety.

In embodiments, the multispecific molecules includes a multispecific antibody molecule, e.g., an antibody molecule comprising two binding specificities, e.g., a bispecific antibody molecule. The multispecific antibody molecule includes:

a lambda light chain polypeptide 1 (LLCP1) specific for a first epitope;

a heavy chain polypeptide 1 (HCP1) specific for the first epitope;

a kappa light chain polypeptide 2 (KLCP2) specific for a second epitope; and a heavy chain polypeptide 2 (HCP2) specific for the second epitope.

"Lambda light chain polypeptide 1 (LLCP1)", as that term is used herein, refers to a polypeptide comprising sufficient light chain (LC) sequence, such that when combined with a cognate heavy chain variable region, can mediate specific binding to its epitope and complex with an HCP1. In an embodiment it comprises all or a fragment of a CH1 region. In an embodiment, an LLCP1 comprises LC-CDR1, LC-CDR2, LC-CDR3, FR1, FR2, FR3, FR4, and CH1, or sufficient sequence therefrom to mediate specific binding of its epitope and complex with an HCP1. LLCP1, together with its HCP1, provide specificity for a first epitope (while KLCP2, together with its HCP2, provide specificity for a second epitope). As described elsewhere herein, LLCP1 has a higher affinity for HCP1 than for HCP2.

"Kappa light chain polypeptide 2 (KLCP2)", as that term is used herein, refers to a polypeptide comprising sufficient light chain (LC) sequence, such that when combined with a cognate heavy chain variable region, can mediate specific binding to its epitope and complex with an HCP2. In an embodiments it comprises all or a fragment of a CH1 region. In an embodiment, a KLCP2 comprises LC-CDR1, LC-CDR2, LC-CDR3, FR1, FR2, FR3, FR4, and CH1, or sufficient sequence therefrom to mediate specific binding of its epitope and complex with an HCP2. KLCP2, together with its HCP2, provide specificity for a second epitope (while LLCP1, together with its HCP1, provide specificity for a first epitope).

"Heavy chain polypeptide 1 (HCP1)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an LLCP1, (ii) to complex preferentially, as described herein to LLCP1 as opposed to KLCP2; and (iii) to complex preferentially, as described herein, to an HCP2, as opposed to another molecule of HCP1. HCP1, together with its LLCP1, provide specificity for a first epitope (while KLCP2, together with its HCP2, provide specificity for a second epitope).

"Heavy chain polypeptide 2 (HCP2)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiments it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an KLCP2, (ii) to complex preferentially, as described herein to KLCP2 as opposed to LLCP1; and (iii) to complex preferentially, as described herein, to an HCP1, as opposed to another molecule of HCP2. HCP2, together with its KLCP2, provide specificity for a second epitope (while LLCP1, together with its HCP1, provide specificity for a first epitope).

In some embodiments of the multispecific antibody molecule disclosed herein:

LLCP1 has a higher affinity for HCP1 than for HCP2; and/or

KLCP2 has a higher affinity for HCP2 than for HCP1.

In embodiments, the affinity of LLCP1 for HCP1 is sufficiently greater than its affinity for HCP2, such that under preselected conditions, e.g., in aqueous buffer, e.g., at pH 7, in saline, e.g., at pH 7, or under physiological conditions, at least 75, 80, 90, 95, 98, 99, 99.5, or 99.9% of the multispecific antibody molecule molecules have a LLCP1 complexed, or interfaced with, a HCP1.

In some embodiments of the multispecific antibody molecule disclosed herein:

the HCP1 has a greater affinity for HCP2, than for a second molecule of HCP1; and/or the HCP2 has a greater affinity for HCP1, than for a second molecule of HCP2.

In embodiments, the affinity of HCP1 for HCP2 is sufficiently greater than its affinity for a second molecule of HCP1, such that under preselected conditions, e.g., in aqueous buffer, e.g., at pH 7, in saline, e.g., at pH 7, or under physiological conditions, at least 75%, 80, 90, 95, 98, 99 99.5 or 99.9% of the multispecific antibody molecule molecules have a HCP1 complexed, or interfaced with, a HCP2.

In another aspect, disclosed herein is a method for making, or producing, a multispecific antibody molecule. The method includes:

(i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both));

(ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));

(iii) providing a lambda chain polypeptide (e.g., a lambda light variable region (VLλ), a lambda light constant chain (VLλ), or both) that preferentially associates with the first heavy chain polypeptide (e.g., the first VH); and (iv) providing a kappa chain polypeptide (e.g., a lambda light variable region (VLκ), a lambda light constant chain (VLκ), or both) that preferentially associates with the second heavy chain polypeptide (e.g., the second VH), under conditions where (i)-(iv) associate.

In embodiments, the first and second heavy chain polypeptides form an Fc interface that enhances heterodimerization.

In embodiments, (i)-(iv) (e.g., nucleic acid encoding (i)-(iv)) are introduced in a single cell, e.g., a single mammalian cell, e.g., a CHO cell. In embodiments, (i)-(iv) are expressed in the cell.

In embodiments, (i)-(iv) (e.g., nucleic acid encoding (i)-(iv)) are introduced in different cells, e.g., different mammalian cells, e.g., two or more CHO cell. In embodiments, (i)-(iv) are expressed in the cells.

In one embodiment, the method further comprises purifying a cell-expressed antibody molecule, e.g., using a lambda-and/or-kappa-specific purification, e.g., affinity chromatography.

In embodiments, the method further comprises evaluating the cell-expressed multispecific antibody molecule. For example, the purified cell-expressed multispecific antibody molecule can be analyzed by techniques known in the art, include mass spectrometry. In one embodiment, the purified cell-expressed antibody molecule is cleaved, e.g., digested with papain to yield the Fab moieties and evaluated using mass spectrometry.

In embodiments, the method produces correctly paired kappa/lambda multispecific, e.g., bispecific, antibody molecules in a high yield, e.g., at least 75%, 80, 90, 95, 98, 99 99.5 or 99.9%.

In other embodiments, the multispecific, e.g., a bispecific, antibody molecule that includes:
  (i) a first heavy chain polypeptide (HCP1) (e.g., a heavy chain polypeptide comprising one, two, three or all of a first heavy chain variable region (first VH), a first CH1, a first heavy chain constant region (e.g., a first CH2, a first CH3, or both)), e.g., wherein the HCP1 binds to a first epitope;
  (ii) a second heavy chain polypeptide (HCP2) (e.g., a heavy chain polypeptide comprising one, two, three or all of a second heavy chain variable region (second VH), a second CH1, a second heavy chain constant region (e.g., a second CH2, a second CH3, or both)), e.g., wherein the HCP2 binds to a second epitope;
  (iii) a lambda light chain polypeptide (LLCP1) (e.g., a lambda light variable region (VL1), a lambda light constant chain (VL1), or both) that preferentially associates with the first heavy chain polypeptide (e.g., the first VH), e.g., wherein the LLCP1 binds to a first epitope; and (iv) a kappa light chain polypeptide (KLCP2) (e.g., a lambda light variable region (VLk), a lambda light constant chain (VLk), or both) that preferentially associates with the second heavy chain polypeptide (e.g., the second VH), e.g., wherein the KLCP2 binds to a second epitope.

In embodiments, the first and second heavy chain polypeptides form an Fc interface that enhances heterodimerization. In embodiments, the multispecific antibody molecule has a first binding specificity that includes a hybrid VL1-CL1 heterodimerized to a first heavy chain variable region connected to the Fc constant, CH2-CH3 domain (having a knob modification) and a second binding specificity that includes a hybrid VLk-CLk heterodimerized to a second heavy chain variable region connected to the Fc constant, CH2-CH3 domain (having a hole modification).

Linkers

The multispecific or multifunctional molecule disclosed herein can further include a linker, e.g., a linker between one or more of: the antigen binding domain and the cytokine molecule, the antigen binding domain and the immune cell engager, the antigen binding domain and the stromal modifying moiety, the cytokine molecule and the immune cell engager, the cytokine molecule and the stromal modifying moiety, the immune cell engager and the stromal modifying moiety, the antigen binding domain and the immunoglobulin chain constant region, the cytokine molecule and the immunoglobulin chain constant region, the immune cell engager and the immunoglobulin chain constant region, or the stromal modifying moiety and the immunoglobulin chain constant region. In embodiments, the linker is chosen from: a cleavable linker, a non-cleavable linker, a peptide linker, a flexible linker, a rigid linker, a helical linker, or a non-helical linker, or a combination thereof.

In one embodiment, the multispecific molecule can include one, two, three or four linkers, e.g., a peptide linker.

In one embodiment, the peptide linker includes Gly and Ser. In some embodiments, the peptide linker is selected from GGGGS (SEQ ID NO: 42); GGGGSGGGGS (SEQ ID NO: 43); GGGGSGGGGSGGGGS (SEQ ID NO: 44); and DVPSGPGGGGGSGGGGS (SEQ ID NO: 45). In some embodiments, the peptide linker is a A(EAAAK)nA (SEQ ID NO: 6154) family of linkers (e.g., as described in Protein Eng. (2001) 14 (8): 529-532). These are stiff helical linkers with n ranging from 2-5. In some embodiments, the peptide linker is selected from AEAAAKEAAAKAAA (SEQ ID NO: 75); AEAAAKEAAAKEAAAKAAA (SEQ ID NO: 76); AEAAAKEAAAKEAAAKEAAAKAAA (SEQ ID NO: 77); and AEAAAKEAAAKEAAAKEAAAKEAAAKAAA(SEQ ID NO: 78).

Targeting Moieties

In one embodiment, the anti-NKp30 antibody molecule further comprises a second antigen binding moiety, e.g., tumor targeting moiety, that binds to a cancer antigen, e.g., a tumor antigen or a stromal antigen. In some embodiments, the cancer antigen is, e.g., a mammalian, e.g., a human, cancer antigen. In other embodiments, the antibody molecule further comprises a second binding moiety that binds to an immune cell antigen, e.g., a mammalian, e.g., a human, immune cell antigen. In other embodiments, the antibody molecule further comprises a second binding moiety that binds to a viral antigen. For example, the antibody molecule binds specifically to an epitope, e.g., linear or conformational epitope, on the cancer antigen, the immune cell antigen.

In some embodiments, the multispecific (e.g., bi-, tri-, tetra-specific) molecule, includes, e.g., is engineered to contain, one or more tumor specific targeting moieties that direct the molecule to a tumor cell. In certain embodiments, the multispecific molecules disclosed herein include a tumor-targeting moiety. The tumor targeting moiety can be chosen from an antibody molecule (e.g., an antigen binding domain as described herein), a receptor or a receptor fragment, or a ligand or a ligand fragment, or a combination thereof. In some embodiments, the tumor targeting moiety associates with, e.g., binds to, a tumor cell (e.g., a molecule, e.g., antigen, present on the surface of the tumor cell). In certain embodiments, the tumor targeting moiety targets, e.g., directs the multispecific molecules disclosed herein to a cancer (e.g., a cancer or tumor cells). In some embodiments, the cancer is chosen from a hematological cancer, a solid cancer, a metastatic cancer, or a combination thereof.

In some embodiments, the multispecific molecule, e.g., the tumor-targeting moiety, binds to a solid tumor antigen or a stromal antigen. The solid tumor antigen or stromal antigen can be present on a solid tumor, or a metastatic lesion thereof. In some embodiments, the solid tumor is chosen from one or more of pancreatic (e.g., pancreatic adenocarcinoma), breast, colorectal, lung (e.g., small or non-small cell lung cancer), skin, ovarian, or liver cancer. In one embodiment, the solid tumor is a fibrotic or desmoplastic solid tumor. For example, the solid tumor antigen or stromal antigen can be present on a tumor, e.g., a tumor of a class typified by having one or more of: limited tumor perfusion, compressed blood vessels, or fibrotic tumor interstitium.

In certain embodiments, the solid tumor antigen is chosen from one or more of: PDL1, CD47, mesothelin, ganglioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep- CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, CD47, a actinin-4, TRP1/gp75, TRP2, gp100, Melan-A/MART1, gangliosides, WT1, EphA3, Epidermal growth factor receptor (EGFR), CD20, MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, EGFRvIII, gpA33, GD3, GM2, VEGFR, Intergrins (Integrin alphaVbeta3, Integrin alpha5Beta1), Carbohydrates (Le), IGF1R, EPHA3, TRAILR1, TRAILR2, or RANKL. In some embodiments, the solid tumor antigen is chosen from: PDL1, Mesothelin, CD47, GD2, PMSA, PSCA, CEA, Ron Kinase, or c-Met. Exemplary amino acid and nucleotide sequences for tumor targeting moieties are disclosed in WO 2017/165464, see e.g., pages 102-108, 172-290, incorporated herein by reference.

In some embodiments, the anti-NKp30 antibody molecule (e.g., the multispecific antibody molecule) further comprises a targeting moiety, e.g., a binding specificity, that binds to an autoreactive T cell, e.g., an antigen present on the surface of an autoreactive T cell that is associated with the inflammatory or autoimmune disorder.

In some embodiments, the anti-NKp30 antibody molecule (e.g., the multispecific antibody molecule) further comprises a targeting moiety, e.g., a binding specificity, that binds to an infected cell, e.g., a viral infected cell.

T Cell Engagers

In other embodiments, the anti-NKp30 antibody molecule (e.g., the multispecific antibody molecule) further comprises one or more T cell engager that mediate binding to and/or activation of a T cell. Accordingly, in some embodiments, the T cell engager is selected from an antigen binding domain or ligand that binds to (e.g., and in some embodiments activates) one or more of CD3, TCRα, TCRβ, TCRγ, TCRζ, ICOS, CD28, CD27, HVEM, LIGHT, CD40, 4-1BB, OX40, DR3, GITR, CD30, TIM1, SLAM, CD2, or CD226. In other embodiments, the T cell engager is selected from an antigen binding domain or ligand that binds to and does not activate one or more of CD3, TCRα, TCRβ, TCRγ, TCRζ, ICOS, CD28, CD27, HVEM, LIGHT, CD40, 4-1BB, OX40, DR3, GITR, CD30, TIM1, SLAM, CD2, or CD226.

Exemplary T cell engagers are disclosed in WO 2017/165464, incorporated herein by reference.

Cytokine Molecules

In other embodiments, the anti-NKp30 antibody molecule (e.g., the multispecific antibody molecule) further comprises one or more cytokine molecules, e.g., immunomodulatory (e.g., proinflammatory) cytokines and variants, e.g., functional variants, thereof. Accordingly, in some embodiments, the cytokine molecule is an interleukin or a variant, e.g., a functional variant thereof. In some embodiments the interleukin is a proinflammatory interleukin. In some embodiments the interleukin is chosen from interleukin-2 (IL-2), interleukin-12 (IL-12), interleukin-15 (IL-15), interleukin-18 (IL-18), interleukin-21 (IL-21), interleukin-7 (IL-7), or interferon gamma. In some embodiments, the cytokine molecule is a proinflammatory cytokine.

In certain embodiments, the cytokine is a single chain cytokine. In certain embodiments, the cytokine is a multichain cytokine (e.g., the cytokine comprises 2 or more (e.g., 2) polypeptide chains. An exemplary multichain cytokine is IL-12.

Examples of useful cytokines include, but are not limited to, GM-CSF, IL-1α, IL-1β, IL-2, IL-3, IL-4, IL-5, IL-6, IL-7, IL-8, IL-10, IL-12, IL-21, IFN-α, IFN-γ, MIP-1α, MIP-1β, TGF-β, TNF-α, and TNFβ. In one embodiment the cytokine of the multispecific or multifunctional polypeptide is a cytokine selected from the group of GM-CSF, IL-2, IL-7, IL-8, IL-10, IL-12, IL-15, IL-21, IFN-α, IFN-γ, MIP-1α, MIP-1β and TGF-β. In one embodiment the cytokine of the i the multispecific or multifunctional polypeptide is a cytokine selected from the group of IL-2, IL-7, IL-10, IL-12, IL-15, IFN-α, and IFN-γ. In certain embodiments the cytokine is mutated to remove N- and/or O-glycosylation sites. Elimination of glycosylation increases homogeneity of the product obtainable in recombinant production.

In one embodiment, the cytokine of the multispecific or multifunctional polypeptide is IL-2. In a specific embodiment, the IL-2 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity. In another particular embodiment the IL-2 cytokine is a mutant IL-2 cytokine having reduced binding affinity to the .alpha.-subunit of the IL-2 receptor. Together with the beta- and gamma-subunits (also known as CD122 and CD132, respectively), the .alpha.-subunit (also known as CD25) forms the heterotrimeric high-affinity IL-2 receptor, while the dimeric receptor consisting only of the β- and γ-subunits is termed the intermediate-affinity IL-2 receptor. As described in PCT patent application number PCT/EP2012/051991, which is incorporated herein by reference in its entirety, a mutant IL-2 polypeptide with reduced binding to the .alpha.-subunit of the IL-2 receptor has a reduced ability to induce IL-2 signaling in regulatory T cells, induces less activation-induced cell death (AICD) in T cells, and has a reduced toxicity profile in vivo, compared to a wild-type IL-2 polypeptide. The use of such an cytokine with reduced toxicity is particularly advantageous in a multispecific or multifunctional polypeptide according to the invention, having a long serum half-life due to the presence of an Fc domain. In one embodiment, the mutant IL-2 cytokine of the multispecific or multifunctional polypeptide according to the invention comprises at least one amino acid mutation that reduces or abolishes the affinity of the mutant IL-2 cytokine to the .alpha.-subunit of the IL-2 receptor (CD25) but preserves the affinity of the mutant IL-2 cytokine to the intermediate-affinity IL-2 receptor (consisting of the β and γ subunits of the IL-2 receptor), compared to the non-mutated IL-2 cytokine. In one embodiment the one or more amino acid mutations are amino acid substitutions. In a specific embodiment, the mutant IL-2 cytokine comprises one, two or three amino acid substitutions at one, two or three position(s) selected from the positions corresponding to residue 42, 45, and 72 of human IL-2. In a more specific embodiment, the mutant IL-2 cytokine comprises three amino acid substitutions at the positions corresponding to residue 42, 45 and 72 of human IL-2. In an even more specific embodiment, the mutant IL-2 cytokine is human IL-2 comprising the amino acid substitutions F42A, Y45A and L72G. In one embodiment the mutant IL-2 cytokine additionally comprises an amino acid mutation at a position corresponding to position 3 of human IL-2, which eliminates the 0-glycosylation site of IL-2. Particularly, said additional amino acid mutation is an amino acid substitution replacing a threonine residue by an alanine residue. A particular mutant IL-2 cytokine useful in the invention comprises four amino acid substitutions at positions corresponding to residues 3, 42, 45 and 72 of human IL-2. Specific amino acid substitutions are T3A, F42A, Y45A and L72G. As demonstrated in PCT patent application number PCT/EP2012/051991 and in the appended Examples, said quadruple mutant IL-2 polypeptide (IL-2 qm) exhibits no detectable binding to CD25, reduced ability to induce apoptosis in T cells, reduced ability to induce IL-2 signaling in T.sub.reg cells, and a reduced toxicity profile in vivo. However, it retains ability to activate IL-2 signaling in effector cells, to induce proliferation of effector cells, and to generate IFN-γ as a secondary cytokine by NK cells.

The IL-2 or mutant IL-2 cytokine according to any of the above embodiments may comprise additional mutations that provide further advantages such as increased expression or stability. For example, the cysteine at position 125 may be replaced with a neutral amino acid such as alanine, to avoid the formation of disulfide-bridged IL-2 dimers. Thus, in certain embodiments the IL-2 or mutant IL-2 cytokine of the multispecific or multifunctional polypeptide according to the invention comprises an additional amino acid mutation at a position corresponding to residue 125 of human IL-2. In one embodiment said additional amino acid mutation is the amino acid substitution C125A.

Exemplary cytokine molecules are disclosed in WO 2017/165464, see e.g., pages 108-118, 169-172, incorporated herein by reference.

TGF-β Inhibitor

In other embodiments, the anti-NKp30 antibody molecule (e.g., the multispecific antibody molecule) further comprises one or more modulators of TGF-β (e.g., a TGF-β inhibitor). In some embodiments, the TGF-β inhibitor binds to and inhibits TGF-β, e.g., reduces the activity of TGF-β. In some embodiments, the TGF-β inhibitor inhibits (e.g., reduces the activity of) TGF-β1. In some embodiments, the TGF-β inhibitor inhibits (e.g., reduces the activity of) TGF-β2. In some embodiments, the TGF-β inhibitor inhibits (e.g., reduces the activity of) TGF-β3. In some embodiments, the TGF-β inhibitor inhibits (e.g., reduces the activity of) TGF-β1 and TGF-β3. In some embodiments, the TGF-β inhibitor inhibits (e.g., reduces the activity of) TGF-β1, TGF-β2, and TGF-β3.

In some embodiments, the TGF-β inhibitor comprises a portion of a TGF-β receptor (e.g., an extracellular domain of a TGF-β receptor) that is capable of inhibiting (e.g., reducing the activity of) TGF-β, or functional fragment or variant thereof. In some embodiments, the TGF-β inhibitor comprises a TGFBR1 polypeptide (e.g., an extracellular domain of TGFBR1 or functional variant thereof). In some embodiments, the TGF-β inhibitor comprises a TGFBR2 polypeptide (e.g., an extracellular domain of TGFBR2 or functional variant thereof). In some embodiments, the TGF-β inhibitor comprises a TGFBR3 polypeptide (e.g., an extracellular domain of TGFBR3 or functional variant thereof). In some embodiments, the TGF-β inhibitor comprises a TGFBR1 polypeptide (e.g., an extracellular domain of TGFBR1 or functional variant thereof) and a TGFBR2 polypeptide (e.g., an extracellular domain of TGFBR2 or functional variant thereof). In some embodiments, the TGF-β inhibitor comprises a TGFBR1 polypeptide (e.g., an extracellular domain of TGFBR1 or functional variant thereof) and a TGFBR3 polypeptide (e.g., an extracellular domain of TGFBR3 or functional variant thereof). In some embodiments, the TGF-β inhibitor comprises a TGFBR2 polypeptide (e.g., an extracellular domain of TGFBR2 or functional variant thereof) and a TGFBR3 polypeptide (e.g., an extracellular domain of TGFBR3 or functional variant thereof).

Exemplary TGF-β receptor polypeptides that can be used as TGF-β inhibitors have been disclosed in U.S. Pat. Nos. 8,993,524, 9,676,863, 8,658,135, US20150056199, US20070184052, and WO2017037634, all of which are herein incorporated by reference in their entirety.

In some embodiments, the TGF-β inhibitor comprises an extracellular domain of TGFBR1 or a sequence substantially identical thereto (e.g., a sequence that is at least 80%, 85%, 90%, or 95% identical thereto). In some embodiments, the TGF-β inhibitor comprises an extracellular domain of SEQ ID NO: 3095, or a sequence substantially identical thereto (e.g., a sequence that is at least 80%, 85%, 90%, or 95% identical thereto). In some embodiments, the TGF-β inhibitor comprises an extracellular domain of SEQ ID NO: 3096, or a sequence substantially identical thereto (e.g., a sequence that is at least 80%, 85%, 90%, or 95% identical thereto). In some embodiments, the TGF-β inhibitor comprises an extracellular domain of SEQ ID NO: 3097, or a sequence substantially identical thereto (e.g., a sequence that is at least 80%, 85%, 90%, or 95% identical thereto). In some embodiments, the TGF-β inhibitor comprises the amino acid sequence of SEQ ID NO: 3104, or a sequence substantially identical thereto (e.g., a sequence that is at least 80%, 85%, 90%, or 95% identical thereto). In some embodiments, the TGF-β inhibitor comprises the amino acid sequence of SEQ ID NO: 3105, or a sequence substantially identical thereto (e.g., a sequence that is at least 80%, 85%, 90%, or 95% identical thereto).

In some embodiments, the TGF-β inhibitor comprises an extracellular domain of TGFBR2 or a sequence substantially identical thereto (e.g., a sequence that is at least 80%, 85%, 90%, or 95% identical thereto). In some embodiments, the TGF-β inhibitor comprises an extracellular domain of SEQ ID NO: 3098, or a sequence substantially identical thereto (e.g., a sequence that is at least 80%, 85%, 90%, or 95% identical thereto). In some embodiments, the TGF-β inhibitor comprises an extracellular domain of SEQ ID NO: 3099, or a sequence substantially identical thereto (e.g., a sequence that is at least 80%, 85%, 90%, or 95% identical thereto). In some embodiments, the TGF-β inhibitor comprises the amino acid sequence of SEQ ID NO: 3100, or a sequence substantially identical thereto (e.g., a sequence that is at least 80%, 85%, 90%, or 95% identical thereto). In some embodiments, the TGF-β inhibitor comprises the amino acid sequence of SEQ ID NO: 3101, or a sequence substantially identical thereto (e.g., a sequence that is at least 80%, 85%, 90%, or 95% identical thereto). In some embodiments, the TGF-β inhibitor comprises the amino acid sequence of SEQ ID NO: 3102, or a sequence substantially identical thereto (e.g., a sequence that is at least 80%, 85%, 90%, or 95% identical thereto). In some embodiments, the TGF-β inhibitor comprises the amino acid sequence of SEQ ID NO: 3103, or a sequence substantially identical thereto (e.g., a sequence that is at least 80%, 85%, 90%, or 95% identical thereto).

In some embodiments, the TGF-β inhibitor comprises an extracellular domain of TGFBR3 or a sequence substantially identical thereto (e.g., a sequence that is at least 80%, 85%, 90%, or 95% identical thereto). In some embodiments, the TGF-β inhibitor comprises an extracellular domain of SEQ ID NO: 3106, or a sequence substantially identical thereto (e.g., a sequence that is at least 80%, 85%, 90%, or 95% identical thereto). In some embodiments, the TGF-β inhibitor comprises an extracellular domain of SEQ ID NO: 3107, or a sequence substantially identical thereto (e.g., a sequence that is at least 80%, 85%, 90%, or 95% identical thereto). In some embodiments, the TGF-β inhibitor comprises the amino acid sequence of SEQ ID NO: 3108, or a sequence substantially identical thereto (e.g., a sequence that is at least 80%, 85%, 90%, or 95% identical thereto).

In some embodiments, the TGF-β inhibitor comprises no more than one TGF-β receptor extracellular domain. In some embodiments, the TGF-β inhibitor comprises two or more (e.g., two, three, four, five, or more) TGF-β receptor extracellular domains, linked together, e.g., via a linker.

TABLE 4

Exemplary amino acid sequences of TGF-β polypeptides or TGF-β receptor polypeptides

| SEQ ID NO | Description | Amino acid sequence |
|---|---|---|
| SEQ ID NO: 3092 | Immature human TGF-β 1 (P01137-1) | MPPSGLRLLLLLLPLLWLLVLTPGRPAAGLSTCKTIDMELVKRKRIE AIRGQILSKLRLASPPSQGEVPPGPLPEAVLALYNSTRDRVAGESAE PEPEPEADYYAKEVTRVLMVETHNEIYDKFKQSTHSIYMFFNTSELR EAVPEPVLLSRAELRLLRLKLKVEQHVELYQKYSNNSWRYLSNRLLA PSDSPEWLSFDVTGVVRQWLSRGGEIEGFRLSAHCSCDSRDNTLQVD INGFTTGRRGDLATIHGMNRPFLLLMATPLERAQHLQSSRHRRALDT NYCFSSTEKNCCVRQLYIDFRKDLGWKWIHEPKGYHANFCLGPCPYI WSLDTQYSKVLALYNQHNPGASAAPCCVPQALEPLPIVYYVGRKPKV EQLSNMIVRSCKCS |
| SEQ ID NO: 3117 | Human TGF-β 1 (P01137-1) | LSTCKTIDMELVKRKRIEAIRGQILSKLRLASPPSQGEVPPGPLPEA VLALYNSTRDRVAGESAEPEPEPEADYYAKEVTRVLMVETHNEIYDK FKQSTHSIYMFFNTSELREAVPEPVLLSRAELRLLRLKLKVEQHVEL YQKYSNNSWRYLSNRLLAPSDSPEWLSFDVTGVVRQWLSRGGEIEGF RLSAHCSCDSRDNTLQVDINGFTTGRRGDLATIHGMNRPFLLLMATP LERAQHLQSSRHRRALDTNYCFSSTEKNCCVRQLYIDFRKDLGWKWI HEPKGYHANFCLGPCPYIWSLDTQYSKVLALYNQHNPGASAAPCCVP QALEPLPIVYYVGRKPKVEQLSNMIVRSCKCS |
| SEQ ID NO: 3093 | Immature human TGF-β 2 (P61812-1) | MHYCVLSAFLILHLVTVALSLSTCSTLDMDQFMRKRIEAIRGQILSK LKLTSPPEDYPEPEEVPPEVISIYNSTRDLLQEKASRRAAACERERS DEEYYAKEVYKIDMPPFFPSENAIPPTFYRPYFRIVRFDVSAMEKNA SNLVKAEFRVFRLQNPKARVPEQRIELYQILKSKDLTSPTQRYIDSK VVKTRAEGEWLSFDVTDAVHEWLHHKDRNLGFKISLHCPCCTFVPSN NYIIPNKSEELEARFAGIDGTSTYTSGDQKTIKSTRKKNSGKTPHLL LMLLPSYRLESQQTNRRKKRALDAAYCFRNVQDNCCLRPLYIDFKRD LGWKWIHEPKGYNANFCAGACPYLWSSDTQHSRVLSLYNTINPEASA SPCCVSQDLEPLTILYYIGKTPKIEQLSNMIVKSCKCS |
| SEQ ID NO: 3118 | Human TGF-β 2 (P61812-1) | LSTCSTLDMDQFMRKRIEAIRGQILSKLKLTSPPEDYPEPEEVPPEV ISIYNSTRDLLQEKASRRAAACERERSDEEYYAKEVYKIDMPPFFPS ENAIPPTFYRPYFRIVRFDVSAMEKNASNLVKAEFRVFRLQNPKARV PEQRIELYQILKSKDLTSPTQRYIDSKVVKTRAEGEWLSFDVTDAVH EWLHHKDRNLGFKISLHCPCCTFVPSNNYIIPNKSEELEARFAGIDG TSTYTSGDQKTIKSTRKKNSGKTPHLLLMLLPSYRLESQQTNRRKKR ALDAAYCFRNVQDNCCLRPLYIDFKRDLGWKWIHEPKGYNANFCAGA CPYLWSSDTQHSRVLSLYNTINPEASASPCCVSQDLEPLTILYYIGK TPKIEQLSNMIVKSCKCS |
| SEQ ID NO: 3094 | Immature human TGF-β 3 (P10600-1) | MKMHLQRALVVLALLNFATVSLSLSTCTTLDFGHIKKKRVEAIRGQI LSKLRLTSPPEPTVMTHVPYQVLALYNSTRELLEEMHGEREEGCTQE NTESEYYAKEIHKFDMIQGLAEHNELAVCPKGITSKVFRFNVSSVEK NRTNLFRAEFRVLRVPNPSSKRNEQRIELFQILRPDEHIAKQRYIGG KNLPTRGTAEWLSFDVTDTVREWLLRRESNLGLEISIHCPCHTFQPN GDILENIHEVMEIKFKGVDNEDDHGRGDLGRLKKQKDHHNPHLILMM IPPHRLDNPGQGGQRKKRALDTNYCFRNLEENCCVRPLYIDFRQDLG WKWVHEPKGYYANFCSGPCPYLRSADTTHSTVLGLYNTLNPEASASP CCVPQDLEPLTILYYVGRTPKVEQLSNMVVKSCKCS |
| SEQ ID NO: 3119 | Human TGF-β 3 (P10600-1) | LSTCTTLDFGHIKKKRVEAIRGQILSKLRLTSPPEPTVMTHVPYQVL ALYNSTRELLEEMHGEREEGCTQENTESEYYAKEIHKFDMIQGLAEH NELAVCPKGITSKVFRFNVSSVEKNRTNLFRAEFRVLRVPNPSSKRN EQRIELFQILRPDEHIAKQRYIGGKNLPTRGTAEWLSFDVTDTVREW LLRRESNLGLEISIHCPCHTFQPNGDILENIHEVMEIKFKGVDNEDD HGRGDLGRLKKQKDFIHNPHLILMMIPPHRLDNPGQGGQRKKRALDT NYCFRNLEENCCVRPLYIDFRQDLGWKWVHEPKGYYANFCSGPCPYL RSADTTHSTVLGLYNTLNPEASASPCCVPQDLEPLTILYYVGRTPKV EQLSNMVVKSCKCS |
| SEQ ID NO: 3095 | Immature human TGFBR1 isoform 1 (P36897-1) | MEAAVAAPRPRLLLLVLAAAAAAAALLPGATALQCFCHLCTKDNFT CVTDGLCFVSVTETTDKVIHNSMCIAEIDLIPRDRPFVCAPSSKTGS VTTTYCCNQDHCNKIELPTTVKSSPGLGPVELAAVIAGPVCFVCISL MLMVYICHNRTVIFIHRVPNEEDPSLDRPFISEGTTLKDLIYDMTTS GSGSGLPLLVQRTIARTIVLQESIGKGRFGEVWRGKWRGEEVAVKIF SSREERSWFREAEIYQTVMLRHENILGFIAADNKDNGTWTQLWLVSD YHEHGSLFDYLNRYTVTVEGMIKLALSTASGLAHLHMEIVGTQGKPA IAHRDLKSKNILVKKNGTCCIADLGLAVRHDSATDTIDIAPNHRVGT |

TABLE 4-continued

Exemplary amino acid sequences of TGF-β polypeptides or TGF-β receptor polypeptides

| SEQ ID NO | Description | Amino acid sequence |
|---|---|---|
| | | KRYMAPEVLDDSINMKHFESFKRADIYAMGLVFWEIARRCSIGGIHE DYQLPYYDLVPSDPSVEEMRKVVCEQKLRPNIPNRWQSCEALRVMAK IMRECWYANGAARLTALRIKKTLSQLSQQEGIKM |
| SEQ ID NO: 3120 | Human TGFBR1 isoform 1 (P36897-1) | LQCFCHLCTKDNFTCVTDGLCFVSVTETTDKVIHNSMCIAEIDLIPR DRPFVCAPSSKTGSVTTTYCCNQDHCNKIELPTTVKSSPGLGPVELA AVIAGPVCFVCISLMLMVYICHNRTVIHHRVPNEEDPSLDRPFISEG TTLKDLIYDMTTSGSGSGLPLLVQRTIARTIVLQESIGKGRFGEVWR GKWRGEEVAVKIFSSREERSWFREAEIYQTVMLRHENILGFIAADNK DNGTWTQLWLVSDYHEHGSLFDYLNRYTVTVEGMIKLALSTASGLAH LHMEIVGTQGKPAIAHRDLKSKNILVKKNGTCCIADLGLAVRHDSAT DTIDIAPNHRVGTKRYMAPEVLDDSINMKHFESFKRADIYAMGLVFW EIARRCSIGGIHEDYQLPYYDLVPSDPSVEEMRKVVCEQKLRPNIPN RWQSCEALRVMAKIMRECWYANGAARLTALRIKKTLSQLSQQEGIKM |
| SEQ ID NO: 3096 | Immature human TGFBR1 isoform 2 (P36897-2) | MEAAVAAPRPRLLLLVLAAAAAAAAAALLPGATALQCFCHLCTKDNFT CVTDGLCFVSVTETTDKVIHNSMCIAEIDLIPRDRPFVCAPSSKTGS VTTTYCCNQDHCNKIELPTTGPFSVKSSPGLGPVELAAVIAGPVCFV CISLMLMVYICHNRTVIFIHRVPNEEDPSLDRPFISEGTTLKDLIYD MTTSGSGSGLPLLVQRTIARTIVLQESIGKGRFGEVWRGKWRGEEVA VKIFSSREERSWFREAEIYQTVMLRHENILGFIAADNKDNGTWTQLW LVSDYHEHGSLFDYLNRYTVTVEGMIKLALSTASGLAHLHMEIVGTQ GKPAIAHRDLKSKNILVKKNGTCCIADLGLAVRHDSATDTIDIAPNH RVGTKRYMAPEVLDDSINMKHFESFKRADIYAMGLVFWEIARRCSIG GIHEDYQLPYYDLVPSDPSVEEMRKVVCEQKLRPNIPNRWQSCEALR VMAKIMRECWYANGAARLTALRIKKTLSQLSQQEGIKM |
| SEQ ID NO: 3121 | Human TGFBR1 isoform 2 (P36897-2) | LQCFCHLCTKDNFTCVTDGLCFVSVTETTDKVIHNSMCIAEIDLIPR DRPFVCAPSSKTGSVTTTYCCNQDHCNKIELPTTGPFSVKSSPGLGP VELAAVIAGPVCFVCISLMLMVYICHNRTVIFIHRVPNEEDPSLDRP FISEGTTLKDLIYDMTTSGSGSGLPLLVQRTIARTIVLQESIGKGRF GEVWRGKWRGEEVAVKIFSSREERSWFREAEIYQTVMLRHENILGFI AADNKDNGTWTQLWLVSDYHEHGSLFDYLNRYTVTVEGMIKLALSTA SGLAHLHMEIVGTQGKPAIAHRDLKSKNILVKKNGTCCIADLGLAVR HDSATDTIDIAPNHRVGTKRYMAPEVLDDSINMKHFESFKRADIYAM GLVFWEIARRCSIGGIHEDYQLPYYDLVPSDPSVEEMRKVVCEQKLR PNIPNRWQSCEALRVMAKIMRECWYANGAARLTALRIKKTLSQLSQQ EGIKM |
| SEQ ID NO: 3097 | Immature human TGFBR1 isoform 3 (P36897-3) | MEAAVAAPRPRLLLLVLAAAAAAAAAALLPGATALQCFCHLCTKDNFT CVTDGLCFVSVTETTDKVIHNSMCIAEIDLIPRDRPFVCAPSSKTGS VTTTYCCNQDHCNKIELPTTGLPLLVQRTIARTIVLQESIGKGRFGE VWRGKWRGEEVAVKIFSSREERSWFREAEIYQTVMLRHENILGFIAA DNKDNGTWTQLWLVSDYHEHGSLFDYLNRYTVTVEGMIKLALSTASG LAHLHMEIVGTQGKPAIAHRDLKSKNILVKKNGTCCIADLGLAVRHD SATDTIDIAPNHRVGTKRYMAPEVLDDSINMKHFESFKRADIYAMGL VFWEIARRCSIGGIHEDYQLPYYDLVPSDPSVEEMRKVVCEQKLRPN IPNRWQSCEALRVMAKIMRECWYANGAARLTALRIKKTLSQLSQQEG IKM |
| SEQ ID NO: 3122 | Human TGFBR1 isoform 3 (P36897-3) | LQCFCHLCTKDNFTCVTDGLCFVSVTETTDKVIHNSMCIAEIDLIPR DRPFVCAPSSKTGSVTTTYCCNQDHCNKIELPTTGLPLLVQRTIART IVLQESIGKGRFGEVWRGKWRGEEVAVKIFSSREERSWFREAEIYQT VMLRHENILGFIAADNKDNGTWTQLWLVSDYHEHGSLFDYLNRYTVT VEGMIKLALSTASGLAHLHMEIVGTQGKPAIAHRDLKSKNILVKKNG TCCIADLGLAVRHDSATDTIDIAPNHRVGTKRYMAPEVLDDSINMKH FESFKRADIYAMGLVFWEIARRCSIGGIHEDYQLPYYDLVPSDPSVE EMRKVVCEQKLRPNIPNRWQSCEALRVMAKIMRECWYANGAARLTAL RIKKTLSQLSQQEGIKM |
| SEQ ID NO: 3104 | Human TGFBR1 fragment 1 | LQCFCHLCTKDNFTCVTDGLCFVSVTETTDKVIHNSMCIAEIDLIPR DRPFVCAPSSKTGSVTTTYCCNQDHCNKIELPTTVKSSPGLGPVEL |
| SEQ ID NO: 3105 | Human TGFBR1 fragment 2 | ALQCFCHLCTKDNFTCVTDGLCFVSVTETTDKVIHNSMCIAEIDLIP RDRPFVCAPSSKTGSVTTTYCCNQDHCNKIEL |
| SEQ ID NO: 3098 | Immature human TGFBR2 isoform B (short isoform) | MGRGLLRGLWPLHIVLWTRIASTIPPHVQKSVNNDMIVTDNNGAVKF PQLCKFCDVRFSTCDNQKSCMSNCSITSICEKPQEVCVAVWRKNDEN ITLETVCHDPKLPYHDFILEDAASPKCIMKEKKKPGETFFMCSCSSD ECNDNIIFSEEYNTSNPDLLLVIFQVTGISLLPPLGVAISVIIIFYC YRVNRQQKLSSTWETGKTRKLMEFSEHCAIILEDDRSDISSTCANNI NHNTELLPIELDTLVGKGRFAEVYKAKLKQNTSEQFETVAVKIFPYE |

TABLE 4-continued

Exemplary amino acid sequences of TGF-β polypeptides or TGF-β receptor polypeptides

| SEQ ID NO | Description | Amino acid sequence |
|---|---|---|
| | (P37173-1) | EYASWKTEKDIFSDINLKHENILQFLTAEERKTELGKQYWLITAFHA KGNLQEYLTRHVISWEDLRKLGSSLARGIAHLHSDHTPCGRPKMPIV HRDLKSSNILVKNDLTCCLCDFGLSLRLDPTLSVDDLANSGQVGTAR YMAPEVLESRMNLENVESFKQTDVYSMALVLWEMTSRCNAVGEVKDY EPPFGSKVREHPCVESMKDNVLRDRGRPEIPSFWLNHQGIQMVCETL TECWDHDPEARLTAQCVAERFSELEHLDRLSGRSCSEEKIPEDGSLN TTK |
| SEQ ID NO: 3123 | Human TGFBR2 isoform B (short isoform) (P37173-1) | TIPPHVQKSVNNDMIVTDNNGAVKFPQLCKFCDVRFSTCDNQKSCMS NCSITSICEKPQEVCVAVWRKNDENITLETVCHDPKLPYHDFILEDA ASPKCIMKEKKKPGETFFMCSCSSDECNDNIIFSEEYNTSNPDLLLV IFQVTGISLLPPLGVAISVIIIFYCYRVNRQQKLSSTWETGKTRKLM EFSEHCAIILEDDRSDISSTCANNINHNTELLPIELDTLVGKGRFAE VYKAKLKQNTSEQFETVAVKIFPYEEYASWKTEKDIFSDINLKHENI LQFLTAEERKTELGKQYWLITAFHAKGNLQEYLTRHVISWEDLRKLG SSLARGIAHLHSDHTPCGRPKMPIVHRDLKSSNILVKNDLTCCLCDF GLSLRLDPTLSVDDLANSGQVGTARYMAPEVLESRMNLENVESFKQT DVYSMALVLWEMTSRCNAVGEVKDYEPPFGSKVREHPCVESMKDNVL RDRGRPEIPSFWLNHQGIQMVCETLTECWDHDPEARLTAQCVAERFS ELEHLDRLSGRSCSEEKIPEDGSLNTTK |
| SEQ ID NO: 3099 | Immature human TGFBR2 isoform A (long isoform) (P37173-2) | MGRGLLRGLWPLHIVLWTRIASTIPPHVQKSDVEMEAQKDEIICPSC NRTAHPLRHINNDMIVTDNNGAVKFPQLCKFCDVRFSTCDNQKSCMS NCSITSICEKPQEVCVAVWRKNDENITLETVCHDPKLPYHDFILEDA ASPKCIMKEKKKPGETFFMCSCSSDECNDNIIFSEEYNTSNPDLLLV IFQVTGISLLPPLGVAISVIIIFYCYRVNRQQKLSSTWETGKTRKLM EFSEHCAIILEDDRSDISSTCANNINHNTELLPIELDTLVGKGRFAE VYKAKLKQNTSEQFETVAVKIFPYEEYASWKTEKDIFSDINLKHENI LQFLTAEERKTELGKQYWLITAFHAKGNLQEYLTRHVISWEDLRKLG SSLARGIAHLHSDHTPCGRPKMPIVHRDLKSSNILVKNDLTCCLCDF GLSLRLDPTLSVDDLANSGQVGTARYMAPEVLESRMNLENVESFKQT DVYSMALVLWEMTSRCNAVGEVKDYEPPFGSKVREHPCVESMKDNVL RDRGRPEIPSFWLNHQGIQMVCETLTECWDHDPEARLTAQCVAERFS ELEHLDRLSGRSCSEEKIPEDGSLNTTK |
| SEQ ID NO: 3124 | Human TGFBR2 isoform A (long isoform) (P37173-2) | TIPPHVQKSDVEMEAQKDEIICPSCNRTAHPLRHINNDMIVTDNNGA VKFPQLCKFCDVRFSTCDNQKSCMSNCSITSICEKPQEVCVAVWRKN DENITLETVCHDPKLPYHDFILEDAASPKCIMKEKKKPGETFFMCSC SSDECNDNIIFSEEYNTSNPDLLLVIFQVTGISLLPPLGVAISVIII FYCYRVNRQQKLSSTWETGKTRKLMEFSEHCAIILEDDRSDISSTCA NNINHNTELLPIELDTLVGKGRFAEVYKAKLKQNTSEQFETVAVKIF PYEEYASWKTEKDIFSDINLKHENILQFLTAEERKTELGKQYWLITA FHAKGNLQEYLTRHVISWEDLRKLGSSLARGIAHLHSDHTPCGRPKM PIVHRDLKSSNILVKNDLTCCLCDFGLSLRLDPTLSVDDLANSGQVG TARYMAPEVLESRMNLENVESFKQTDVYSMALVLWEMTSRCNAVGEV KDYEPPFGSKVREHPCVESMKDNVLRDRGRPEIPSFWLNHQGIQMVC ETLTECWDHDPEARLTAQCVAERFSELEHLDRLSGRSCSEEKIPEDG SLNTTK |
| SEQ ID NO: 3100 | Human TGFBR2 fragment 1 (ECD of human TGFBR2 isoform B) | TIPPHVQKSVNNDMIVTDNNGAVKFPQLCKFCDVRFSTCDNQKSCMS NCSITSICEKPQEVCVAVWRKNDENITLETVCHDPKLPYHDFILEDA ASPKCIMKEKKKPGETFFMCSCSSDECNDNIIFSEEYNTSNPD |
| SEQ ID NO: 3101 | Human TGFBR2 fragment 2 | IPPHVQKSVNNDMIVTDNNGAVKFPQLCKFCDVRFSTCDNQKSCMSN CSITSICEKPQEVCVAVWRKNDENITLETVCHDPKLPYHDFILEDAA SPKCIMKEKKKPGETFFMCSCSSDECNDNIIFSEEYNTSNPD |
| SEQ ID NO: 3102 | Human TGFBR2 fragment 3 (ECD of human TGFBR2 isoform A) | TIPPHVQKSDVEMEAQKDEIICPSCNRTAHPLRHINNDMIVTDNNGA VKFPQLCKFCDVRFSTCDNQKSCMSNCSITSICEKPQEVCVAVWRKN DENITLETVCHDPKLPYHDFILEDAASPKCIMKEKKKPGETFFMCSC SSDECNDNIIFSEEYNTSNPD |
| SEQ ID NO: 3103 | Human TGFBR2 fragment 4 | QLCKFCDVRFSTCDNQKSCMSNCSITSICEKPQEVCVAVWRKNDENI TLETVCHDPKLPYHDFILEDAASPKCIMKEKKKPGETFFMCSCSSDE CNDNIIF |

TABLE 4-continued

Exemplary amino acid sequences of TGF-β polypeptides or TGF-β receptor polypeptides

| SEQ ID NO | Description | Amino acid sequence |
|---|---|---|
| SEQ ID NO: 3106 | Immature human TGFBR3 isoform 1 (Q03167-1) | MTSHYVIAIFALMSSCLATAGPEPGALCELSPVSASHPVQALMESFT VLSGCASRGTTGLPQEVHVLNLRTAGQGPGQLQREVTLHLNPISSV HIHHKSVVFLLNSPHPLVWHLKTERLATGVSRLFLVSEGSVVQFSSA NFSLTAETEERNFPHGNEHLLNWARKEYGAVTSFTELKIARNIYIKV GEDQVFPPKCNIGKNFLSLNYLAEYLQPKAAEGCVMSSQPQNEEVHI IELITPNSNPYSAFQVDITIDIRPSQEDLEVVKNLILILKCKKSVNW VIKSFDVKGSLKIIAPNSIGFGKESERSMTMTKSIRDDIPSTQGNLV KWALDNGYSPITSYTMAPVANRFHLRLENNAEEMGDEEVHTIPPELR ILLDPGALPALQNPPIRGGEGQNGGLPFPFPPDISRRVWNEEGEDGLP RPKDPVIPSIQLFPGLREPEEVQGSVDIALSVKCDNEKMIVAVEKDS FQASGYSGMDVTLLDPTCKAKMNGTHFVLESPLNGCGTRPRWSALDG VVYYNSIVIQVPALGDSSGWPDGYEDLESGDNGFPGDMDEGDASLFT RPEIVVFNCSLQQVRNPSSFQEQPHGNITFNMELYNTDLFLVPSQGV FSVPENGHVYVEVSVTKAEQELGFAIQTCFISPYSNPDRMSHYTIIE NICPKDESVKFYSPKRVHFPIPQADMDKKRFSFVFKPVFNTSLLFLQ CELTLCTKMEKHPQKLPKCVPPDEACTSLDASIIWAMMQNKKTFTKP LAVIHHEAESKEKGPSMKEPNPISPPIFHGLDTLTVMGIAFAAFVIG ALLTGALWYIYSHTGETAGRQQVPTSPPASENSSAAHSIGSTQSTPC SSSSTA |
| SEQ ID NO: 3125 | Human TGFBR3 isoform 1 (Q03167-1) | GPEPGALCELSPVSASHPVQALMESFTVLSGCASRGTTGLPQEVHVL NLRTAGQGPGQLQREVTLHLNPISSVHIFIHKSVVFLLNSPHPLVWH LKTERLATGVSRLFLVSEGSVVQFSSANFSLTAETEERNFPHGNEHL LNWARKEYGAVTSFTELKIARNIYIKVGEDQVFPPKCNIGKNFLSLN YLAEYLQPKAAEGCVMSSQPQNEEVHIIELITPNSNPYSAFQVDITI DIRPSQEDLEVVKNLILILKCKKSVNWVIKSFDVKGSLKIIAPNSIG FGKESERSMTMTKSIRDDIPSTQGNLVKWALDNGYSPITSYTMAPVA NRFHLRLENNAEEMGDEEVHTIPPELRILLDPGALPALQNPPIRGGE GQNGGLPFPFPPDISRRVWNEEGEDGLPRPKDPVIPSIQLFPGLREPE EVQGSVDIALSVKCDNEKMIVAVEKDSFQASGYSGMDVTLLDPTCKA KMNGTHFVLESPLNGCGTRPRWSALDGVVYYNSIVIQVPALGDSSGW PDGYEDLESGDNGFPGDMDEGDASLFTRPEIVVFNCSLQQVRNPSSF QEQPHGNITFNMELYNTDLFLVPSQGVFSVPENGHVYVEVSVTKAEQ ELGFAIQTCFISPYSNPDRMSHYTIIENICPKDESVKFYSPKRVHFP IPQADMDKKRFSFVFKPVFNTSLLFLQCELTLCTKMEKHPQKLPKCV PPDEACTSLDASIIWAMMQNKKTFTKPLAVIHHEAESKEKGPSMKEP NPISPPIFHGLDTLTVMGIAFAAFVIGALLTGALWYIYSHTGETAGR QQVPTSPPASENSSAAHSIGSTQSTPCSSSSTA |
| SEQ ID NO: 3107 | Immature human TGFBR3 isoform 2 (Q03167-2) | MTSHYVIAIFALMSSCLATAGPEPGALCELSPVSASHPVQALMESFT VLSGCASRGTTGLPQEVHVLNLRTAGQGPGQLQREVTLHLNPISSVH IHHKSVVFLLNSPHPLVWHLKTERLATGVSRLFLVSEGSVVQFSSAN FSLTAETEERNFPHGNEHLLNWARKEYGAVTSFTELKIARNIYIKVG EDQVFPPKCNIGKNFLSLNYLAEYLQPKAAEGCVMSSQPQNEEVHII ELITPNSNPYSAFQVDITIDIRPSQEDLEVVKNLILILKCKKSVNWV IKSFDVKGSLKIIAPNSIGFGKESERSMTMTKSIRDDIPSTQGNLVK WALDNGYSPITSYTMAPVANRFHLRLENNEEMGDEEVHTIPPELRIL LDPGALPALQNPPIRGGEGQNGGLPFPFPPDISRRVWNEEGEDGLPRP KDPVIPSIQLFPGLREPEEVQGSVDIALSVKCDNEKMIVAVEKDSFQ ASGYSGMDVTLLDPTCKAKMNGTHFVLESPLNGCGTRPRWSALDGVV YYNSIVIQVPALGDSSGWPDGYEDLESGDNGFPGDMDEGDASLFTRP EIVVFNCSLQQVRNPSSFQEQPHGNITFNMELYNTDLFLVPSQGVFS VPENGHVYVEVSVTKAEQELGFAIQTCFISPYSNPDRMSHYTIIENI CPKDESVKFYSPKRVHFPIPQADMDKKRFSFVFKPVFNTSLLFLQCE LTLCTKMEKHPQKLPKCVPPDEACTSLDASIIWAMMQNKKTFTKPLA VIHHEAESKEKGPSMKEPNPISPPIFHGLDTLTVMGIAFAAFVIGAL LTGALWYIYSHTGETAGRQQVPTSPPASENSSAAHSIGSTQSTPCSS SSTA |
| SEQ ID NO: 3126 | Human TGFBR3 isoform 2 (Q03167-2) | GPEPGALCELSPVSASHPVQALMESFTVLSGCASRGTTGLPQEVHVL NLRTAGQGPGQLQREVTLHLNPISSVHIFIHKSVVFLLNSPHPLVWH LKTERLATGVSRLFLVSEGSVVQFSSANFSLTAETEERNFPHGNEHL LNWARKEYGAVTSFTELKIARNIYIKVGEDQVFPPKCNIGKNFLSLN YLAEYLQPKAAEGCVMSSQPQNEEVHIIELITPNSNPYSAFQVDITI DIRPSQEDLEVVKNLILILKCKKSVNWVIKSFDVKGSLKIIAPNSIG FGKESERSMTMTKSIRDDIPSTQGNLVKWALDNGYSPITSYTMAPVA NRFHLRLENNEEMGDEEVHTIPPELRILLDPGALPALQNPPIRGGEG QNGGLPFPFPPDISRRVWNEEGEDGLPRPKDPVIPSIQLFPGLREPEE VQGSVDIALSVKCDNEKMIVAVEKDSFQASGYSGMDVTLLDPTCKAK MNGTHFVLESPLNGCGTRPRWSALDGVVYYNSIVIQVPALGDSSGWP DGYEDLESGDNGFPGDMDEGDASLFTRPEIVVFNCSLQQVRNPSSFQ EQPHGNITFNMELYNTDLFLVPSQGVFSVPENGHVYVEVSVTKAEQE LGFAIQTCFISPYSNPDRMSHYTIIENICPKDESVKFYSPKRVHFPI |

TABLE 4-continued

Exemplary amino acid sequences of TGF-β polypeptides or TGF-β receptor polypeptides

| SEQ ID NO | Description | Amino acid sequence |
|---|---|---|
| | | PQADMDKKRFSFVFKPVFNTSLLFLQCELTLCTKMEKHPQKLPKCVP PDEACTSLDASIIWAMMQNKKTFTKPLAVIHHEAESKEKGPSMKEPN PISPPIFHGLDTLTVMGIAFAAFVIGALLTGALWYIYSHTGETAGRQ QVPTSPPASENSSAAHSIGSTQSTPCSSSSTA |
| SEQ ID NO: 3108 | Human TGFBR3 fragment 1 | GPEPGALCELSPVSASHPVQALMESFTVLSGCASRGTTGLPQEVHVL NLRTAGQGPGQLQREVTLHLNPISSVHIFIHKSVVFLLNSPHPLVWH LKTERLATGVSRLFLVSEGSVVQFSSANFSLTAETEERNFPHGNEHL LNWARKEYGAVTSFTELKIARNIYIKVGEDQVFPPKCNIGKNFLSLN YLAEYLQPKAAEGCVMSSQPQNEEVHIIELITPNSNPYSAFQVDITI DIRPSQEDLEVVKNLILILKCCKKSVNWVIKSFDVKGSLKIIAPNSIG FGKESERSMTMTKSIRDDIPSTQGNLVKWALDNGYSPITSYTMAPVA NRFHLRLENNAEEMGDEEVHTIPPELRILLDPGALPALQNPPIRGGE GQNGGLPFPFPDISRRVWNEEGEDGLPRPKDPVIPSIQLFPGLREPE EVQGSVDIALSVKCDNEKMIVAVEKDSFQASGYSGMDVTLLDPTCKA KMNGTHFVLESPLNGCGTRPRWSALDGVVYYNSIVIQVPALGDSSGW PDGYEDLESGDNGFPGDMDEGDASLFTRPEIVVFNCSLQQVRNPSSF QEQPHGNITFNMELYNTDLFLVPSQGVFSVPENGHVYVEVSVTKAEQ ELGFAIQTCFISPYSNPDRMSHYTIIENICPKDESVKFYSPKRVHFP IPQADMDKKRFSFVFKPVFNTSLLFLQCELTLCTKMEKHPQKLPKCV PPDEACTSLDASIIWAMMQNKKTFTKPLAVIHHEAESKEKGPSMKEP NPISPPIFHGLDTLTV |
| SEQ ID NO: 3192 | hCH1-hFc_Hole-3x4GS-TGFbR2 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVCTLP PSREEMTKNQVSLSCAVKGFYPSDIAVEWESNGQPENNYKTTPPVLD SDGSFFLVSKLTVDKSRWQQGNVFSCSVMHEALHNHYTQKSLSLSPG XGGGGSGGGGSGGGGSIPPHVQKSVNNDMIVTDNNGAVKFPQLCKFC DVRFSTCDNQKSCMSNCSITSICEKPQEVCVAVWRKNDENITLETVC HDPKLPYHDFILEDAASPKCIMKEKKKPGETFFMCSCSSDECNDNII FSEEYNTSNPD, where in X is K or absent |
| SEQ ID NO: 3193 | hCH1-hFc_Knob-3x4GS-TGFbR2 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PCREEMTKNQVSLWCLVKGFYPSDIAVEWESNGQPENNYKTTPPVLD SDGSFFLYSKLTVDKSRWQQGNVFSCSVMHEALHNHYTQKSLSLSPG XGGGGSGGGGSGGGGSIPPHVQKSVNNDMIVTDNNGAVKFPQLCKFC DVRFSTCDNQKSCMSNCSITSICEKPQEVCVAVWRKNDENITLETVC HDPKLPYHDFILEDAASPKCIMKEKKKPGETFFMCSCSSDECNDNII FSEEYNTSNPD, where in X is K or absent |
| SEQ ID NO: 3194 | hFc_Hole-3x4GS-TGFbR2 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVCTLPPSREEMTKN QVSLSCAVKGFYPSDIAVEWESNGQPENNYKTTPPVLDSDGSFFLVS KLTVDKSRWQQGNVFSCSVMHEALHNHYTQKSLSLSPGXGGGGSGGG GSGGGGSIPPHVQKSVNNDMIVTDNNGAVKFPQLCKFCDVRFSTCDN QKSCMSNCSITSICEKPQEVCVAVWRKNDENITLETVCHDPKLPYHD FILEDAASPKCIMKEKKKPGETFFMCSCSSDECNDNIIFSEEYNTSN PD, where in X is K or absent |
| SEQ ID NO: 3195 | hFc_Knob-3x4GS-TGFbR2 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPCREEMTKN QVSLWCLVKGFYPSDIAVEWESNGQPENNYKTTPPVLDSDGSFFLYS KLTVDKSRWQQGNVFSCSVMHEALHNHYTQKSLSLSPGXGGGGSGGG GSGGGGSIPPHVQKSVNNDMIVTDNNGAVKFPQLCKFCDVRFSTCDN QKSCMSNCSITSICEKPQEVCVAVWRKNDENITLETVCHDPKLPYHD FILEDAASPKCIMKEKKKPGETFFMCSCSSDECNDNIIFSEEYNTSN PD, where in X is K or absent |
| SEQ ID NO: 3196 | TGFbR2-3x4GS-hCH1-hFc_Hole | IPPHVQKSVNNDMIVTDNNGAVKFPQLCKFCDVRFSTCDNQKSCMSN CSITSICEKPQEVCVAVWRKNDENITLETVCHDPKLPYHDFILEDAA SPKCIMKEKKKPGETFFMCSCSSDECNDNIIFSEEYNTSNPDGGGGS GGGGSGGGGSASTKGPSVFPLAPSSKSTSGGTAALGCLVKDYFPEPV TVSWNSGALTSGVHTFPAVLQSSGLYSLSSVVTVPSSSLGTQTYICN VNHKPSNTKVDKRVEPKSCDKTHTCPPCPAPELLGGPSVFLFPPKPK DTLMISRTPEVTCVVVDVSHEDPEVKFNWYVDGVEVHNAKTKPREEQ |

TABLE 4-continued

Exemplary amino acid sequences of TGF-β polypeptides or TGF-β receptor polypeptides

| SEQ ID NO | Description | Amino acid sequence |
|---|---|---|
| | | YNSTYRVVSVLTVLHQDWLNGKEYKCKVSNKALPAPIEKTISKAKGQ PREPQVCTLPPSREEMTKNQVSLSCAVKGFYPSDIAVEWESNGQPEN NYKTTPPVLDSDGSFFLVSKLTVDKSRWQQGNVFSCSVMHEALHNHY TQKSLSLSPGX, where in X is K or absent |
| SEQ ID NO: 3197 | TGFbR2-3x4GS-hCH1-hFc_Knob | IPPHVQKSVNNDMIVTDNNGAVKFPQLCKFCDVRFSTCDNQKSCMSN CSITSICEKPQEVCVAVWRKNDENITLETVCHDPKLPYHDFILEDAA SPKCIMKEKKKPGETFFMCSCSSDECNDNIIFSEEYNTSNPDGGGGS GGGGSGGGGSASTKGPSVFPLAPSSKSTSGGTAALGCLVKDYFPEPV TVSWNSGALTSGVHTFPAVLQSSGLYSLSSVVTVPSSSLGTQTYICN VNHKPSNTKVDKRVEPKSCDKTHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQ PREPQVYTLPPCREEMTKNQVSLWCLVKGFYPSDIAVEWESNGQPEN NYKTTPPVLDSDGSFFLYSKLTVDKSRWQQGNVFSCSVMHEALHNHY TQKSLSLSPGX, where in X is K or absent |
| SEQ ID NO: 3198 | TGFbR2-3x4G5-hCLIg_v1 | IPPHVQKSVNNDMIVTDNNGAVKFPQLCKFCDVRFSTCDNQKSCMSN CSITSICEKPQEVCVAVWRKNDENITLETVCHDPKLPYHDFILEDAA SPKCIMKEKKKPGETFFMCSCSSDECNDNIIFSEEYNTSNPDGGGGS GGGGSGGGGSGQPKANPTVTLFPPSSEELQANKATLVCLISDFYPGA VTVAWKADGSPVKAGVETTKPSKQSNNKYAASSYLSLTPEQWKSHRS YSCQVTHEGSTVEKTVAPTECS |
| SEQ ID NO: 3199 | TGFβR2-3x4GS-hCLIg_vk | IPPHVQKSVNNDMIVTDNNGAVKFPQLCKFCDVRFSTCDNQKSCMSN CSITSICEKPQEVCVAVWRKNDENITLETVCHDPKLPYHDFILEDAA SPKCIMKEKKKPGETFFMCSCSSDECNDNIIFSEEYNTSNPDGGGGS GGGGSGGGGSRTVAAPSVFIFPPSDEQLKSGTASVVCLLNNFYPREA KVQWKVDNALQSGNSQESVTEQDSKDSTYSLSSTLTLSKADYEKFIK VYACEVTHQGLSSPVTKSFNRGEC |

Stromal Modifying Moieties

In other embodiments, the anti-NKp30 antibody molecule (e.g., the multispecific antibody molecule) further comprises one or more stromal modifying moieties. Stromal modifying moieties described herein include moieties (e.g., proteins, e.g., enzymes) capable of degrading a component of the stroma, e.g., an ECM component, e.g., a glycosaminoglycan, e.g., hyaluronan (also known as hyaluronic acid or HA), chondroitin sulfate, chondroitin, dermatan sulfate, heparin sulfate, heparin, entactin, tenascin, aggrecan and keratin sulfate; or an extracellular protein, e.g., collagen, laminin, elastin, fibrinogen, fibronectin, and vitronectin.

In some embodiments, the stromal modifying moiety is an enzyme. For example, the stromal modifying moiety can include, but is not limited to a hyaluronidase, a collagenase, a chondroitinase, a matrix metalloproteinase (e.g., macrophage metalloelastase).

Exemplary amino acid and nucleotide sequences for stromal modifying moieties are disclosed in WO 2017/165464, see e.g., pages 131-136, 188-193, incorporated herein by reference.

Nucleic Acids

Nucleic acids encoding the aforementioned antibody molecules, e.g., multispecific or multifunctional molecules. are also disclosed.

In certain embodiments, the invention features nucleic acids comprising nucleotide sequences that encode heavy and light chain variable regions and CDRs or hypervariable loops of the antibody molecules, as described herein. For example, the invention features a first and second nucleic acid encoding heavy and light chain variable regions, respectively, of an antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In certain embodiments, the nucleic acid can comprise a nucleotide sequence encoding a cytokine molecule, an immune cell engager, or a stromal modifying moiety disclosed herein.

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising the nucleotide sequences encoding a multispecific or multifunctional molecule described herein. In one embodiment, the vectors comprise nucleotides encoding a multispecific or multifunctional molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity Methods and conditions for culturing the resulting transfected cells and for recovering the antibody molecule produced are known to those skilled in the art, and may be varied or optimized depending upon the specific expression vector and mammalian host cell employed, based upon the present description.

Cells

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., $E.$ $coli$. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses

Methods described herein include treating a disorder, e.g., a cancer, an autoimmune or inflammatory disorder, or an infectious disorder, in a subject by using an anti-NKp30 antibody molecule, e.g., a multispecific molecule, described herein, e.g., using a pharmaceutical composition described herein. Also provided are methods for reducing or ameliorating a symptom of a disorder, e.g., a cancer, an autoimmune or inflammatory disorder, or an infectious disorder, in a subject, as well as methods for inhibiting the growth of a diseased cell, e.g., cancer cell, and/or killing or depleting one or more diseased cells, e.g., cancer cells. In embodiments, the methods described herein decrease the size of a tumor and/or decrease the number of cancer cells in a subject administered with a described herein or a pharmaceutical composition described herein.

In embodiments, the antibody molecule, e.g., multispecific molecules or pharmaceutical composition, is administered to the subject parenterally. In embodiments, the antibody molecule or pharmaceutical composition is administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319:1676, 1988) or an intravenous push. In embodiments, the cells are administered as an injectable depot formulation.

In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Cancers

In embodiments, the cancer is a hematological cancer, a solid tumor or a metastatic lesion thereof. In some embodiments, the anti-NKp30 antibody molecule used to treat the cancer further comprises a tumor targeting moiety, e.g., a tumor targeting moiety as described herein.

In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CIVIL), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sezary syndrome, Waldenström macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In certain embodiments, the cancer is an epithelial, mesenchymal or hematologic malignancy. In certain embodiments, the cancer treated is a solid tumor (e.g., carcinoid, carcinoma or sarcoma), a soft tissue tumor (e.g., a heme malignancy), and a metastatic lesion, e.g., a metastatic lesion of any of the cancers disclosed herein. In one embodiment, the cancer treated is a fibrotic or desmoplastic solid tumor, e.g., a tumor having one or more of: limited tumor perfusion, compressed blood vessels, fibrotic tumor interstitium, or increased interstitial fluid pressure. In one embodiment, the solid tumor is chosen from one or more of pancreatic (e.g., pancreatic adenocarcinoma or pancreatic ductal adenocarcinoma), breast, colon, colorectal, lung (e.g., small cell lung cancer (SCLC) or non-small cell lung cancer (NSCLC)), skin, ovarian, liver cancer, esophageal cancer, endometrial cancer, gastric cancer, head and neck cancer, kidney, or prostate cancer.

Examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In other embodiments, the multispecific molecule, as described above and herein, is used to treat a hyperproliferative disorder, e.g., a hyperproliferative connective tissue disorder (e.g., a hyperproliferative fibrotic disease). In one embodiment, the hyperproliferative fibrotic disease is multisystemic or organ-specific. Exemplary hyperproliferative fibrotic diseases include, but are not limited to, multisystemic (e.g., systemic sclerosis, multifocal fibrosclerosis, sclerodermatous graft-versus-host disease in bone marrow transplant recipients, nephrogenic systemic fibrosis, scleroderma), and organ-specific disorders (e.g., fibrosis of the eye, lung, liver, heart, kidney, pancreas, skin and other organs). In other embodiments, the disorder is chosen from liver cirrhosis or tuberculosis. In other embodiments, the disorder is leprosy.

In embodiments, the multispecific molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or multispecific molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the cancer is a myeloproliferative neoplasm, e.g., primary or idiopathic myelofibrosis (MF), essential thrombocytosis (ET), polycythemia vera (PV), or chronic myelogenous leukemia (CIVIL). In embodiments, the cancer is myelofibrosis. In embodiments, the subject has myelofibrosis. In embodiments, the subject has a calreticulin mutation, e.g., a calreticulin mutation disclosed herein. In embodiments, the subject does not have the JAK2-V617F mutation. In embodiments, the subject has the JAK2-V617F mutation. In embodiments, the subject has a MPL mutation. In embodiments, the subject does not have a MPL mutation.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

Inflammatory and Autoimmune Disorders

In some embodiments, the anti-NKp30 antibody molecules, e.g., the multispecific antibody molecules, disclosed herein can be used to treat inflammatory and autoimmune diseases, and graft vs. host disease (GvHD). In some embodiments, the antibody molecules, e.g., the multispecific antibody molecules, disclosed herein deplete autoreactive T cells, e.g., by directing an NK cell, e.g., an NKp30-expressing cell, to an autoreactive T cell. In some embodiments, the anti-NKp30 antibody molecule further comprises a binding specificity that binds to an autoreactive T cell, e.g., an antigen present on the surface of an autoreactive T cell that is associated with the inflammatory or autoimmune disorder.

As used herein, the term "autoimmune" disease, disorder, or condition refers to a disease where the body's immune system attacks its own cells or tissues. An autoimmune disease can result in the production of autoantibodies that are inappropriately produced and/or excessively produced to a self-antigen or autoantigen. Autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases. In some embodiments, the autoimmune disease is mediated by T cells, B cells, innate immune cells (e.g., macrophages, eosinophils, or natural killer cells), or complement-mediated pathways.

Examples of autoimmune disorders that may be treated by administering the antibodies of the present invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal aristeris/giant cell arteritis, transverse myelitis, ulcerative colitis, uveitis, vasculitides such as dermatitis herpetiformis vasculitis, vitiligo, and Wegener's granulomatosis. In some embodiments, the autoimmune disorder is SLE or Type-1 diabetes.

Examples of inflammatory disorders which can be prevented, treated or managed in accordance with the methods of the invention include, but are not limited to, asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Thus, the anti-NKp30 antibody molecules, e.g., multispecific molecules, of the present invention have utility in the treatment of inflammatory and autoimmune diseases.

Infectious Diseases

In some embodiments, the anti-NKp30 antibody molecules, e.g., the multispecific antibody molecules, disclosed herein can be used to treat infectious diseases. In some embodiments, the antibody molecules, e.g., the multispecific antibody molecules, disclosed herein deplete cells expressing a viral or bacterial antigen. In some embodiments, the anti-NKp30 antibody molecule further comprises a binding specificity that binds to an antigen present on the surface of an infected cell, e.g., a viral infected cell.

Some examples of pathogenic viruses causing infections treatable by methods include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. In one embodiment, the infection is an influenza infection.

In another embodiment, the infection is a hepatitis infection, e.g., a Hepatitis B or C infection.

Exemplary viral disorders that can be treated include, but are not limited to, Epstein Bar Virus (EBV), influenza virus, HIV, SIV, tuberculosis, malaria and HCMV.

Some examples of pathogenic bacteria causing infections treatable by methods of the invention include syphilis, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria. The anti-NKp30 antibody molecules can be used in combination with existing treatment modalities for the aforesaid infections. For example, Treatments for syphilis include penicillin (e.g., penicillin G.), tetracycline, doxycycline, ceftriaxone and azithromycin.

Diagnostic Uses

In one aspect, the present invention provides a diagnostic method for detecting the presence of a NKp30 protein in vitro (e.g., in a biological sample, such as a tissue biopsy, e.g., from a cancerous tissue) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as plasma, tissue, biopsy) or a control subject)); and (iii) detecting formation of a complex between the antibody molecule, and the sample or subject, or the control sample or subject, wherein a change, e.g., a statistically significant change, in the formation of the complex in the sample or subject relative to the control sample or subject is indicative of the presence of NKp30 in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids, or tissue samples.

Complex formation between the antibody molecule and NKp30 can be detected by measuring or visualizing either the binding molecule bound to the NKp30 antigen or unbound binding molecule. Conventional detection assays can be used, e.g., an enzyme-linked immunosorbent assays (ELISA), a radioimmunoassay (RIA) or tissue immunohistochemistry. Alternative to labeling the antibody molecule, the presence of NKp30 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of NKp30 in the sample is inversely proportional to the amount of labeled standard bound to the antibody molecule.

EXAMPLES

The Examples below are set forth to aid in the understanding of the inventions but are not intended to, and should not be construed to, limit its scope in any way.

Example 1: Immunization of Armenian Hamster to Generate Anti-NKp30 Antibodies

Briefly, armenian hamster were immunized with the extracellular domain of human NKp30 protein in complete Freund's adjuvant and boosted twice on day 14 and day 28 with NKp30 in incomplete Freund's adjuvant (IFA). On day 56 one more boost in IFA was given and the animals harvested three days later. Spleens were collected and fused with P3X63Ag8.653 murine myeloma cell line. 0.9×10^5 cells/well in 125 ul were seated in 96 well plate and fed with 125 μl of I-20+2ME+HAT (IMDM (4 g/L glucose) supplemented with 20% fetal bovine serum, 4 mM L-glutamine, 1 mM sodium pyruvate, 50 U penicillin, 50 μg streptomycin and 50 μM 2-ME in the absence or presence of HAT or HT for selection, and Hybridoma Cloning Factor (1% final) on days 7, 11 and thereafter as needed. At approximately 2 weeks after fusion (cells are about 50% confluent), supernatant was collected and assayed for binding.

Example 2: Hybridoma Screen for NKp30 mAbs

Expi293 cells were transfected with BG160 (hNKp30 cell antigen) 18 hours prior to screening. The day of screening, transfected cells were diluted to 0.05×10^6/mL and anti-Armenian hamster Fc Alexa Fluor 488 added to a final concentration of 0.4 ug/mL. 50 uL (2,500 cells) of this mixture was added to each well of a 384 well plate. The same density of untransfected 293 cells with secondary were used as a negative control. 5 uL of hybridoma supernatant was added to the cell mixture and the plate incubated for 1 hour at 37° C. The plates were then imaged on Mirrorball. Positive clones were identified and subcloned by serial dilution to obtain clonal selected hybridoma. After reconfirmation using the same protocols the hybridoma cells were harvested and the corresponding heavy and light chain sequences recovered. The DNA was subcloned into pcDNA3.4 for subsequent expression of the corresponding antibodies and further validation.

Example 3: Binding of NKp30 Antibodies to NK92 Cells

NK-92 cells were washed with PBS containing 0.5% BSA and 0.1% sodium azide (staining buffer) and added to 96-well V-bottom plates with 200,000 cells/well. Hamster NKp30 antibodies were added to the cells in 2.0 fold serial dilutions and incubated for 1 hour at room temperature. The plates were washed twice with staining buffer. The secondary antibody against hamster Fc conjugated to AF647 (Jackson, 127-605-160) was added at 1:100 dilution (1.4 mg/ml stock) and incubated with the cells for 30 minutes at 4° C. followed by washing with staining buffer. Cells were subsequently were fixed for 10 minutes with 4% paraformaldehyde at room temperature. The plates were read on CytoFLEX LS (Beckman Coulter). Data was calculated as the percent-AF747 positive population (FIG. 1).

Figure 2:
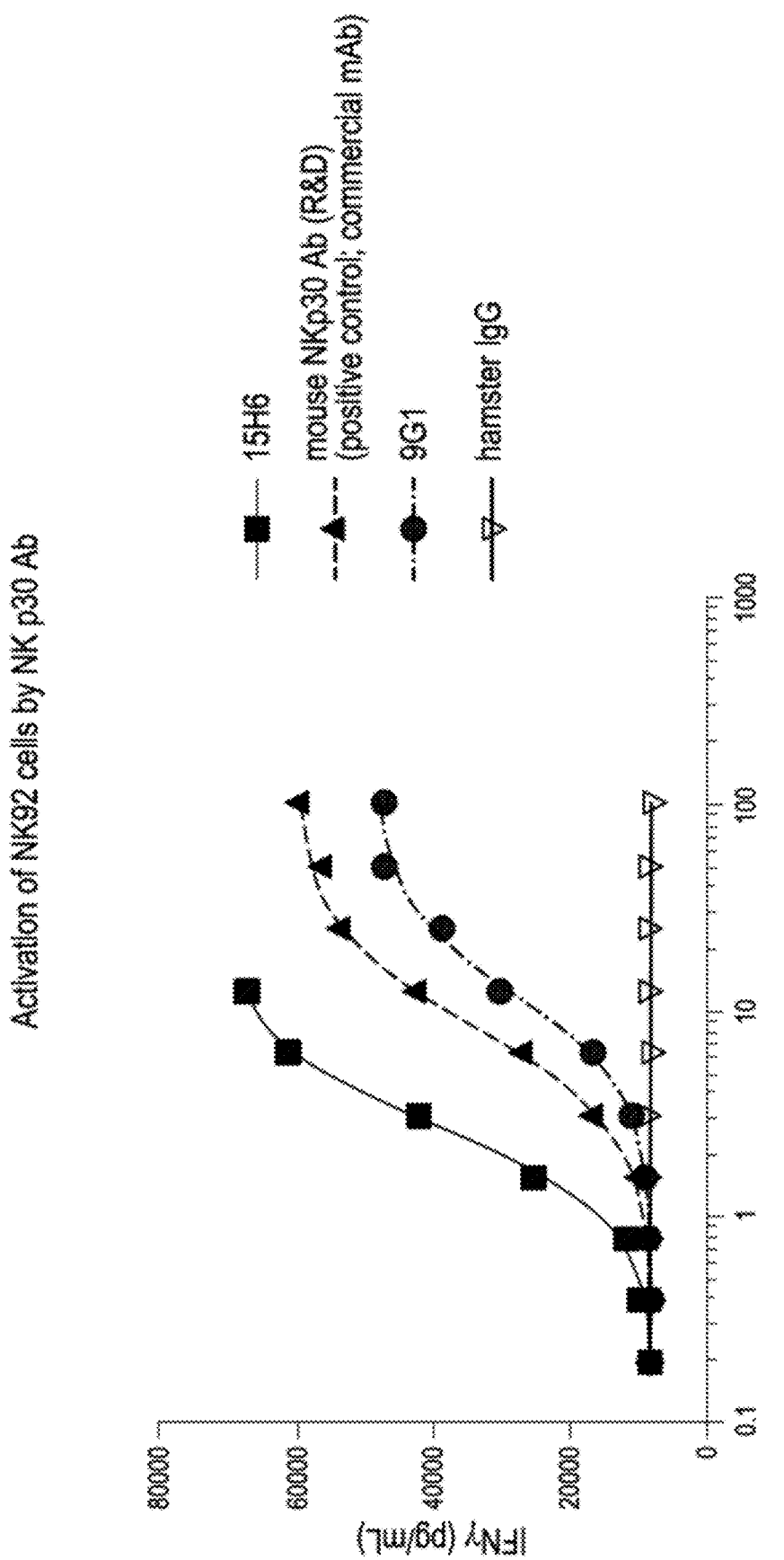
FIG. 2 is a graph showing activation of NK92 cells by NKp30 antibodies. Data were generated using hamster anti-NKp30 mAbs.

Example 4: Bioassay to Measure Activity of NKp30 Antibodies Using NK92 Cell Line NKp30 antibodies were three-fold serially diluted in PBS and incubated at 2-8° C. overnight in flat bottom 96 well plates. Plates were washed twice in PBS and 40,000 NK-92 cells were added in growth medium containing IL-2. Plates were incubated at 37° C., 5% $CO_2$, humidified incubator for 16-24 hours before supernatants were collected. IFNγ levels in supernatants was measured following MSD assay instructions (FIG. 2). Supernatant collected from cells incubated with hamster isotype IgG was used as negative control and supernatants from cells incubated with NKp30 monoclonal antibody (R&D, clone 210847) was utilized as a positive control. Data were generated using hamster anti-NKp30 mABs.

Example 5: Generation and Characterization of Humanized Anti-NKp30 Antibodies

A series of hamster anti-NKp30 antibodies were selected. These antibodies were shown to bind to human NKp30 and cynomolgus NKp30 and induce IFNγ production from NK-90 cells (data not shown). The VH and VL sequences of exemplary hamster anti-NKp30 antibodies 15E1, 9G1, 15H6, 9D9, 3A12, and 12D10 are disclosed in Table 9. The VH and VL sequences of exemplary humanized anti-NKp30 antibodies based on 15E1, 9G1, and 15H6 are also disclosed in Table 9. The Kabat CDRs of these antibodies are disclosed in Table 18 and Table 8.

Two humanized constructs based on 15E1 were selected. The first construct BJM0407 is a Fab comprising a heavy chain variable region comprising the amino acid sequence of SEQ ID NO: 7302 and a lambda light chain variable region comprising the amino acid sequence of SEQ ID NO: 7305. Its corresponding scFv construct BJM0859 comprises the amino acid sequence of SEQ ID NO: 7310. The second construct BJM0411 is a Fab comprising a heavy chain variable region comprising the amino acid sequence of SEQ ID NO: 7302 and a kappa light chain variable region comprising the amino acid sequence of SEQ ID NO: 7309. Its corresponding scFv construct BJM0860 comprises the amino acid sequence of SEQ ID NO: 7311. BJM0407 and BJM0411 showed comparable biophysical characteristics, e.g., binding affinity to NKp30 and thermal stability. The scFv constructs BJM0859 and BJM0860 also showed comparable biophysical properties.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An antibody or an antigen-binding portion thereof that binds to NKp30 comprising:
   (a) a heavy chain variable region (VH) comprising
      (i) a heavy chain complementarity determining region 1 (VHCDR1) amino acid sequence of SEQ ID NO: 7313,
      (ii) a VHCDR2 amino acid sequence of SEQ ID NO: 6001, and
      (iii) a VHCDR3 amino acid sequence of SEQ ID NO: 7315; and
   (b) a light chain variable region (VL) comprising
      (i) a light chain complementarity determining region 1 (VLCDR1) amino acid sequence of SEQ ID NO: 7326,
      (ii) a VLCDR2 amino acid sequence of SEQ ID NO: 7327, and
      (iii) a VLCDR3 amino acid sequence of SEQ ID NO: 7329.

2. The antibody or an antigen-binding portion thereof of claim 1, wherein
   (a) the VH comprises an amino acid sequence with at least 75% sequence identity to a sequence selected from the group consisting of SEQ ID NOs: 7298 and 7300-7304; and
   (b) the VL comprises an amino acid sequence with at least 75% sequence identity to a sequence selected from the group consisting of SEQ ID NOs: 7299 and 7305-7309.

3. The antibody or an antigen-binding portion thereof of claim 2, wherein
   (a) the VH comprises an amino acid sequence with at least 75% sequence identity to SEQ ID NO: 7302; and
   (b) the VL comprises an amino acid sequence with at least 75% sequence identity to SEQ ID NO: 7305.

4. The antibody or an antigen-binding portion thereof of claim 2, wherein
   (a) the VH comprises an amino acid sequence with at least 75% sequence identity to SEQ ID NO: 7302; and
   (b) the VL comprises an amino acid sequence with at least 75% sequence identity to SEQ ID NOs: 7305 or SEQ ID NO: 7309.

5. The antibody or antigen-binding portion thereof of claim 4, wherein
   (a) the VH comprises an amino acid sequence with at least 90% sequence identity to SEQ ID NO: 7302; and
   (b) the VL comprises an amino acid sequence with at least 90% sequence identity to SEQ ID NO: 7305 or SEQ ID NO: 7309.

6. The antibody or antigen-binding portion thereof of claim 5, wherein
   (a) the VH comprises the amino acid sequence of SEQ ID No: 7302; and
   (b) the VL comprises the amino acid sequence of SEQ ID No: 7305.

7. The antibody or antigen-binding portion thereof of claim 5, wherein
   (a) the VH comprises the amino acid sequence of SEQ ID No: 7302; and
   (b) the VL comprises the amino acid sequence of SEQ ID No: 7309.

8. The antibody or an antigen-binding portion thereof of claim 2, wherein the antibody or an antigen-binding portion thereof comprises an amino acid sequence with at least 75% sequence identity to SEQ ID NO: 7310 or SEQ ID NO: 7311.

9. A multispecific molecule comprising the antibody or an antigen-binding portion thereof of claim 2.

10. The multispecific molecule of claim 9, wherein the multispecific molecule further comprises
    (a) a tumor targeting moiety;
    (b) a cytokine molecule;
    (c) a T cell engager;
    (d) a stromal modifying moiety; or
    (e) any combination thereof.

11. The multispecific molecule of claim 9, wherein the multispecific molecule further comprises
    (a) a T cell engager that binds to an antigen present on the surface of an autoreactive T cell that is associated with an inflammatory or autoimmune disorder, or
    (b) a binding moiety that binds to an antigen present on the surface of a cell infected by a virus or a bacteria.

12. The multispecific molecule of claim 10, wherein the multispecific molecule comprises a linker between one or more of:
    (a) the targeting moiety and the cytokine molecule or the stromal modifying moiety,
    (b) the targeting moiety and the immune cell engager,
    (c) the cytokine molecule or the stromal modifying moiety,
    (d) the immune cell engager, the cytokine molecule or the stromal modifying moiety and the immunoglobulin chain constant region,
    (e) the targeting moiety and the immunoglobulin chain constant region, and
    (f) the immune cell engager and the immunoglobulin chain constant region.

13. The antibody or the antigen-binding portion thereof of claim 1, wherein the antibody or the antigen-binding portion thereof comprises an immunoglobulin chain constant region.

14. The antibody or the antigen-binding portion thereof of claim 13, wherein the immunoglobulin chain constant region is an IgGI chain constant region that comprises an amino acid substitution at a position selected from the group consisting of 347, 349, 350, 351, 366, 368, 370, 392, 394, 395, 397, 398, 399, 405, 407, 409, and any combination thereof.

15. The antibody or the antigen-binding portion thereof of claim 14, wherein the IgGI chain constant region comprises an amino acid substitution at a position selected from the group consisting of T366S, L368A, Y407V, T366W, and any combination thereof.

16. A polynucleotide comprising a sequence encoding the antibody or an antigen-binding portion thereof of claim 2.

17. A host cell comprising the polynucleotide of claim 16.

18. An expression vector comprising a polynucleotide sequence encoding the antibody or an antigen-binding portion thereof of claim 2.

19. A host cell comprising the expression vector of claim 18.

20. A method of making the antibody or an antigen-binding portion thereof of claim 2, comprising culturing the host cell of claim 17 under suitable conditions for gene expression and/or homo- or heterodimerization.

21. A pharmaceutical composition comprising the antibody or an antigen-binding portion thereof of claim 2; and a pharmaceutically acceptable carrier, excipient, or stabilizer.

22. A method of treating a disease or condition, wherein the disease or condition is cancer, an autoimmune or inflammatory disorder, an infectious disorder, or a hyperproliferative disorder, comprising administering to a subject in need thereof the antibody or an antigen-binding portion thereof of claim 2, wherein the antibody or antigen-binding portion thereof is administered in an amount effective to treat the disease or condition.

23. The method of claim 22, wherein the disease or condition is cancer, an autoimmune or inflammatory disorder, or an infectious disorder.

* * * * *